United States Patent
Seth et al.

(10) Patent No.: US 10,202,599 B2
(45) Date of Patent: *Feb. 12, 2019

(54) SELECTIVE ANTISENSE COMPOUNDS AND USES THEREOF

(75) Inventors: Punit P. Seth, Carlsbad, CA (US); Michael Oestergaard, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/238,441

(22) PCT Filed: Aug. 8, 2012

(86) PCT No.: PCT/US2012/050023
§ 371 (c)(1),
(2), (4) Date: Jun. 18, 2014

(87) PCT Pub. No.: WO2013/022990
PCT Pub. Date: Feb. 14, 2013

(65) Prior Publication Data
US 2014/0323707 A1 Oct. 30, 2014

Related U.S. Application Data

(60) Provisional application No. 61/522,659, filed on Aug. 11, 2011, provisional application No. 61/596,723, filed on Feb. 8, 2012, provisional application No. 61/603,196, filed on Feb. 24, 2012.

(51) Int. Cl.
| | |
|---|---|
| *C12N 15/11* | (2006.01) |
| *A61K 48/00* | (2006.01) |
| *C07H 21/02* | (2006.01) |
| *C07H 21/04* | (2006.01) |
| *C12N 15/113* | (2010.01) |

(52) U.S. Cl.
CPC .......... *C12N 15/113* (2013.01); *C12N 15/111* (2013.01); *C12N 2310/11* (2013.01); *C12N 2310/312* (2013.01); *C12N 2310/315* (2013.01); *C12N 2310/316* (2013.01); *C12N 2310/3125* (2013.01); *C12N 2310/321* (2013.01); *C12N 2310/3231* (2013.01); *C12N 2310/3341* (2013.01); *C12N 2310/341* (2013.01); *C12N 2310/351* (2013.01); *C12N 2320/34* (2013.01)

(58) Field of Classification Search
CPC .............. C12N 15/113; C12N 2310/11; C12N 2310/341; C12N 2310/325; C12N 2320/34
USPC ............................................... 536/24.5, 23.1
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Dinh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,367,066 A | 11/1994 | Urdea et al. |
| 5,432,272 A | 7/1995 | Benner |
| 5,457,187 A | 10/1995 | Gmeiner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,595,756 A | 1/1997 | Bally et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,700,922 A | 12/1997 | Cook |
| 5,750,692 A | 5/1998 | Cook et al. |
| 5,763,588 A | 6/1998 | Matteucci et al. |
| 5,801,154 A | 9/1998 | Baracchini et al. |
| 5,830,653 A | 11/1998 | Froehler et al. |
| 5,998,148 A | 12/1999 | Bennett et al. |
| 6,005,096 A | 12/1999 | Matteucci et al. |
| 6,043,060 A | 3/2000 | Imanishi |
| 6,147,200 A | 11/2000 | Manoharan et al. |
| 6,268,490 B1 | 7/2001 | Imanishi et al. |
| 6,525,191 B1 | 2/2003 | Ramasamy |
| 6,582,908 B2 | 6/2003 | Fodor et al. |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,320,965 B2 | 1/2008 | Sah et al. |
| 7,399,845 B2 | 7/2008 | Seth et al. |
| 7,427,672 B2 | 9/2008 | Imanishi et al. |
| 7,741,457 B2 | 6/2010 | Swayze et al. |
| 7,951,934 B2 | 5/2011 | Freier et al. |
| 8,084,437 B2 | 12/2011 | Freier et al. |
| 8,093,222 B2 | 1/2012 | Freier et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,679,750 B2 | 3/2014 | Hayden et al. |

(Continued)

FOREIGN PATENT DOCUMENTS

| | | |
|---|---|---|
| JP | 2008-513507 | 5/2008 |
| WO | WO 94/26764 | 11/1994 |

(Continued)

OTHER PUBLICATIONS

Seth et al. (J. Med. Chem, 2009 vol. 52:10-13).*

(Continued)

*Primary Examiner* — Terra C Gibbs
(74) *Attorney, Agent, or Firm* — McNeill Baur PLLC

(57) ABSTRACT

The present invention provides oligomeric compounds. Certain such oligomeric compounds are useful for hybridizing to a complementary nucleic acid, including but not limited, to nucleic acids in a cell. In certain embodiments, hybridization results in modulation of the amount activity or expression of the target nucleic acid in a cell.

18 Claims, No Drawings

Specification includes a Sequence Listing.

(56) References Cited

U.S. PATENT DOCUMENTS

| | | |
|---|---|---|
| 2001/0053519 A1 | 12/2001 | Fodor et al. |
| 2002/0081611 A1 | 6/2002 | O'Brien et al. |
| 2002/0187931 A1 | 12/2002 | Hayden et al. |
| 2003/0073123 A1 | 4/2003 | Shen et al. |
| 2003/0109476 A1 | 6/2003 | Kmiec et al. |
| 2003/0144242 A1 | 7/2003 | Ward et al. |
| 2003/0228597 A1 | 12/2003 | Cowsert et al. |
| 2004/0092465 A1 | 5/2004 | Dobie |
| 2004/0096880 A1 | 5/2004 | Kmiec |
| 2004/0137471 A1 | 7/2004 | Vickers et al. |
| 2004/0171570 A1 | 9/2004 | Allerson et al. |
| 2005/0042646 A1 | 2/2005 | Davidson |
| 2005/0096284 A1 | 5/2005 | McSwiggen |
| 2005/0130923 A1 | 6/2005 | Bhat et al. |
| 2005/0176045 A1 | 8/2005 | Federov et al. |
| 2005/0191638 A1 | 9/2005 | McSwiggen |
| 2005/0255086 A1 | 11/2005 | Davidson |
| 2005/0255487 A1 | 11/2005 | Khvorova et al. |
| 2006/0051769 A1 | 3/2006 | Barts |
| 2006/0063730 A1 | 3/2006 | Monia et al. |
| 2007/0031844 A1 | 2/2007 | Khvorova et al. |
| 2007/0099860 A1 | 5/2007 | Sah |
| 2007/0123484 A1 | 5/2007 | Bhat et al. |
| 2007/0161590 A1 | 7/2007 | Van Bilsen et al. |
| 2007/0287831 A1 | 12/2007 | Seth et al. |
| 2008/0015158 A1 | 1/2008 | Ichiro |
| 2008/0015162 A1 | 1/2008 | Bhanot et al. |
| 2008/0039418 A1 | 2/2008 | Freier |
| 2008/0039618 A1 | 2/2008 | Allerson et al. |
| 2008/0274989 A1 | 11/2008 | Davidson et al. |
| 2009/0012281 A1 | 1/2009 | Swayze et al. |
| 2009/0092981 A1 | 4/2009 | Swayze et al. |
| 2009/0318536 A1 | 12/2009 | Freier et al. |
| 2010/0069472 A1 | 3/2010 | Hung et al. |
| 2010/0299768 A1 | 11/2010 | Perrin et al. |
| 2011/0213010 A1 | 9/2011 | Hayden et al. |
| 2015/0051389 A1* | 2/2015 | Seth .................... C12N 15/113 536/24.5 |

FOREIGN PATENT DOCUMENTS

| | | |
|---|---|---|
| WO | WO 99/14226 | 3/1999 |
| WO | WO 2001/079283 | 10/2001 |
| WO | WO 2003/004602 | 1/2003 |
| WO | WO 2003/013437 | 2/2003 |
| WO | WO 2003/064625 | 8/2003 |
| WO | WO 2004/048601 | 6/2004 |
| WO | WO 2004/101787 | 11/2004 |
| WO | WO 2004/013280 | 12/2004 |
| WO | WO 2004/106356 | 12/2004 |
| WO | WO 2005/021570 | 3/2005 |
| WO | WO 2005/027980 | 3/2005 |
| WO | WO 2005/045032 | 5/2005 |
| WO | WO 2005/105995 | 11/2005 |
| WO | WO 2005/116204 | 12/2005 |
| WO | WO 2006/034348 A2 | 3/2006 |
| WO | WO 2007/027894 A2 * | 8/2006 |
| WO | WO 2007/002904 | 1/2007 |
| WO | WO 2007/131237 | 11/2007 |
| WO | WO 2007/134181 | 11/2007 |
| WO | WO 2008/005562 | 1/2008 |
| WO | WO 2008/018795 | 2/2008 |
| WO | WO 2008/049085 | 4/2008 |
| WO | WO 2008/066776 | 6/2008 |
| WO | WO 2008/101157 | 8/2008 |
| WO | WO 2008/147887 | 12/2008 |
| WO | WO 2008/147930 | 12/2008 |
| WO | WO 2008/150729 | 12/2008 |
| WO | WO 2008/154401 | 12/2008 |
| WO | WO 2009/006478 | 1/2009 |
| WO | WO 2009/135322 | 11/2009 |
| WO | WO 2010/048585 | 4/2010 |
| WO | WO 2011/097644 A2 * | 2/2011 |
| WO | WO 2011/097388 | 8/2011 |
| WO | WO 2012/109395 A1 * | 2/2012 |
| WO | WO 2012/109395 | 8/2012 |
| WO | WO 2013/022967 | 2/2013 |

OTHER PUBLICATIONS

Lombardi et al., "A majority of Huntington's disease patients may be treatable by individualized allele-specific RNA interference" Experimental Neurology (2009) 217(2): 312-319.

Schwarz et al., "Designing siRNA that distinguish between genes that differ by a single nucleotide" PLOS Genetics (2006) 2(9): p. e140.

European Search report for application EP 11740542.3 dated Aug. 14, 2014.

Abifadel et al., "Mutations and polymorphisms in the proprotein convertase subtilisin kexin 9 (PCSK9) gene in cholesterol metabolism and disease" Hum Mutat. (2009) 30(4): 520-529.

Albaek et al., "Analogues of a Locked Nucleic Acid with Three-Carbon 2',4'-Linkages: Synthesis by Ring-Closing Metathesis and Influence on Nucleic Acid Duplex Stability and Structure" J. Org. Chem. (2006) 71:7731-7740.

Altmann et al., "Second Generation Antisense Oligonucleotides—Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16:917-926.

Altmann et al., "Second Generation of Antisense Oligonucleotides: From Nuclease Resistance to Biological Efficacy in Animals" Chimia (1996) 50:168-176.

Altmann et al., "Second-generation antisense oligonucleotides: structure-activity relationships and the design of improved signal-transduction inhibitors" Biochem. Soc. Trans. (1996) 24:630-637.

Alves et al., "Allele-specific RNA silencing of mutant ataxin-3 mediates neuroprotection in a rat model of Machado-Joseph disease." PLoS One (2008) 3(10): e3341.

Anderson et al., "An Overview of Psychiatric Symptoms in Huntington's Disease" Current Psychiatry Reports (2001) 3:379-388.

Bennett et al., "Antisense oligonucleotides as a tool for gene functionalization and target validation" Biochimica Biophysica Acta (1999) 1489:19-30.

Boado et al., "Antisense-mediated down-regulation of the human huntington gene" *Journal of Pharmacology and Experimental Therapeutics* (2000) 295:239-243.

Boffa et al., "Isolation of active genes containing CAG repeats by DNA strands invasion by a peptide nucleic acid" PNAS (1995) 92: 1901-5.

Bonini et al., "Silencing Polyglutamine Degeneration with RNAi" Neuron (2005) 48:715-718.

Borovecki et al., "Genome-wide expression profiling of human blood reveals biomarkers for Huntington's disease" *Proc. Natl. Acad. Sci. USA* (2005) 102: 11023-11028.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brookes, "The essence of SNPs" Gene (1999) 234(2):177-186.

Bruijn et al., "Aggregation and Motor Neuron Toxicity of an ALS-Linked SOD1 Mutant Independent from Wild-Type SOD1" Science (1998) 281: 1851-1854.

Caplen et al., "Rescue of polyglutamine-mediated cytotoxicity by double-stranded RNA-mediated RNA interference" Human Molecular Genetics (2002) 11(2):175-184.

Carrell et al., "Alpha1—Antitrypsin Deficiency—A Model for Conformational Diseases" New Engl J Med (2002) 346: 45-53.

Carroll et al., "Potent and Selective Antisense Oligonucleotides Targeting Single-Nucleotide Polymorphisms in the Huntington Disease Gene / Allele-Specific Silencing of Mutant Huntingtin" Molecular Therapy (2011) 19(12):2178-2185.

Chan et al., "Antisense Oligonucleotides: From Design to Therapeutic Application" Clin. Exp. Pharmacol. Physiol. (2006) 33:533-540.

(56) References Cited

OTHER PUBLICATIONS

Chang et al., "Structural Analysis of Complementary DNA and Amino Acid Sequences of Human and Rat Androgen Receptors" PNAS (1988) 85:7211-7215.
Chen et al., "Allelic origin of the abnormal prion protein isoform in familial prion diseases." Nat. Med. (1997) 3(9): 1009-1015.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1: 1-50.
Crooke et al., "Pharmacokinetic Properties of Several Novel Oligonucleotide Analogs in mice" J. Pharmacol. Exp. Ther. (1996) 277(2):923-937.
Daiger et al., "Mutations in known genes account for 58% of autosomal dominant retinitis pigmentosa (adRP)." Adv Exp Med Biol (2008) 613: 203-219.
Davidson et al., "Molecular medicine for the brain: silencing of disease genes with RNA interference" Lancet Neurol. (2004) 3:145-149.
Dawson et al., "Rare genetic mutations shed light on the pathogenesis of Parkinson disease." J. Clin. Invest. (2003) 111(2): 145-151.
De Gobbi et al., "A regulatory SNP causes a human genetic disease by creating a new transcriptional promoter." Science (2006) 312(5777): 1215-1217.
Denovan-Wright et al., "RNAi: a potential therapy for dominantly inherited nucleotide repeat diseases" Gene Therapy (2006) 13(6):525-531.
Diaz-Hernandez et al., "Full Motor Recovery Despite Striatal Neuron Loss and Formation of Irreversible Amyloid-Like Inclusions in a Conditional Mouse Model of Huntington's Disease" J. Neurosci (2005) 25:9773-9781.
Dragatsis et al., "Inactivation of Hdh in the brain and testis results in progressive neurodegeneration and sterility in mice" Nat. Genet. (2000) 26:300-306.
Eder et al., "Inhibition of LNCaP Prostate Cancer Cells by Means of Androgen Receptor Antisense Oligonucleotides" Cancer Gene Therapy (2000) 7(7):997-1007.
Elayadi et al., "Application of PNA and LNA oligomers to chemotherapy" Curr. Opinions Invens. Drugs (2001) 2:558-561.
Ellis, "Spot-On SNP Genotyping" Genome Res. (2000) 10:895-897.
Englisch et al., "Chemically Modified Oligonucleotides as Probes and Inhibitors" Angewandte Chemie, International Edition (1991) 30(6): 613-629.
Ewart-Toland et al., "A gain of function TGFB1 polymorphism may be associated with late stage prostate cancer." Cancer Epidemiol Biomarkers Prey (2004) 13(5): 759-764.
Feng et al., "Allele-specific silencing of Alzheimer's disease genes: The amyloid precursor protein genes with Swedish or London mutations" Gene (2006) 371: 68-74.
Fluiter et al., "Tumor Genotype-specific Growth Inhibition in Vivo by Antisense Oligonucleotides against a Polymorphic Site of the Large Subunit of Human RNA Polymerase II" Cancer Res. (2002) 62:2024-2028.
Fontana et al., "P2Y12 H2 Haplotype Is Associated With Peripheral Arterial Disease" Circulation (2003) 108: 2971.
Freier et al., "The ups and downs of nucleic acid duplex stability: structure-stability studies on chemically-modified DNA:RNA duplexes" Nucleic Acids Res. (1997) 25:4429-4443.
Frieden et al., "Expanding the design horizon of antisense oligonucleotides with alpha-L-LNA" Nucleic Acids Research (2003) 21:6365-6372.
Gallo et al., "2'-C-Methyluridine phosphoramidite: a new building block for the preparation of RNA analogues carrying the 2'-hydroxyl group" Tetrahedron (2001) 57:5707-5717.
Gautschi et al., "Activity of a Novel bc1-2/bc1-xL-Bispecific Antisense Oligonucleotide Against Tumors of Diverse Histologic Origins" J. Natl. Cancer Inst. (2001) 93:463-471.

Gonzalez-Alegre et al., "Technology Insight: therapeutic RNA interference—how far from the neurology clinic?" Nature Clinical Practice 3:394-404.
Gossen et al., "Tight control of gene expression in mammalian cells by tetracycline-responsive promoters." PNAS (1992) 89:5547-5551.
Gray et al., "Full-Length Human Mutant Huntingtin with a Stable Polyglutamine Repeat Can Elicit Progressive and Selective Neuropathogenesis in BACHD Mice" J. Neurosc. (2008) 28(24):6182-6195.
Griffin et al., "Single-nucleotide polymorphism analysis by MALDI-TOF mass spectrometry" Trends Biotechnol. (2000) 18(2):77-84.
Gryaznov et al., "Oligodeoxyribonucleotide N3'->P5' Phosphoramidates Synthesis and Hybridization Properties" J Am. Chem. Soc. (1994) 116:3143-3144.
Gryk et al., "Local knowledge helps determine protein structures" PNAS (2008) 105: 4533-4534.
Guillerm et al., "Synthesis of 4'-fluoroadenosine as an inhibitor of S-adenosyl-L-homocysteine hydrolase" Bioorganic and Medicinal Chemistry Letters (1995) 5(14): 1455-1460.
Gutekunst et al., "Identification and localization of huntingtin in brain and human lymphoblastoid cell lines with anti-fusion protein antibodies" PNAS (1995) 92(19):8710-8714.
Hagemann et al., "Alexander Disease-Associated Glial Fibrillary Acidic Protein Mutations in Mice Induce Rosenthal Fiber Formation and a White Matter Stress Response" J. Neurosci. (2006) 26(43): 11162-11173.
Handley et al., "Pharmaceutical, cellular and genetic therapies for Huntington's disease" Clin. Sci. (2006) 110:73-88.
Haque et al., "Antisense gene therapy for neurodegenerative disease" Experimental Neurology (1997) 144:139-146.
Harlan et al., "Variants in Apaf-1 segregating with major depression promote apoptosome function" Mol Psychiatry (2006) 11:76-85.
Harper et al., "RNA interference improves motor and neuropathological abnormalities in a Huntington's disease mouse model" PNAS (2005) 102:5820-5825.
Harper et al., "Ten years of presymptomatic testing for Huntington's disease: the experience of the UK Huntington's Disease Prediction Consortium" J. Med. Genet. 37:567-571.
Harry-O'Kura et al., "A Short, Flexible Route toward 2'-C-Branched Ribonucleosides" J Org Chem (1997) 62(6) 1754-1759.
Hasholt et al., "Antisense downregulation of mutant huntingtin in a cell model" Journal of Gene Medicine (2003) 5:528-538.
Hersch et al., "Neuroprotection for Huntington's disease: Ready, set, slow" Neurotherapeutics (2008) 5(2):226-236.
Hersch et al., "Translating Therapies for Huntington's Disease from Genetic Animal Models to Clinical Trials" NeuroRX (2004) 1:298-306.
Hu et al., "Allele-specific silencing of mutant huntingtin and ataxin-3 genes by targeing expanded CAG repeats in mRNAs" Nature Biotechnology (2009) 27(5):478-484.
Hu et al., "Serotonin transporter promoter gain-of-function genotypes are linked to obsessive-compulsive disorder." Am J Hum Genet (2006) 78(5): 815-826.
Jacobson et al., "Methanocarba Analogues of Purine Nucleosides as Potent and Selective Adenosine Receptor Agonists" J. Med. Chem. Lett. (2000) 43(11): 2196-2203.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kabashi et al., "Gain and loss of function of ALS-related mutations of TARDBP (TDP-43) cause motor deficits in vivo." Hum Mol Genet (2010) 19(4): 671-683.
Kawasaki et al., "Uniformly Modified 2'-Deoxy-2'-fluoro Phosphorothioate Oligonucleotides as Nuclease-Resistant Antisense Compounds with High Affinity and Specificity for RNA Targets" J. Med. Chem. (1993) 36: 831-841.
Kordasiewicz et al., "Sustained Therapeutic Reversal of Huntington's Disease by Transient Repression of Huntingtin Synthesis" Neuron (2012) 74:1031-1044.

(56) References Cited

OTHER PUBLICATIONS

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.

Kroshwitz, The Concise Encyclopedia of Polymer Science and Engineering, Kroschwitz, J.I., Ed., John Wiley & Sons, 1990, 858-859.

Kumar et al., "The First Analogues of LNA (Locked Nucleic Acids): Phosphorothioate-LNA and 2'-Thio-LNA" Bioorg. Med. Chem. Lett. (1998) 8:2219-2222.

Landgraf, "The involvement of the vasopressin system in stress-related disorders." CNS Neurol. Disord. Drug Targets (2006) 5(2): 167-179.

Lee et al., "Ring-Constrained (N)-Methanocarba nucleosides as adenosine receptor agonists: independent 5'-Uronamide and 2'-deoxy modifications" Bioorganic and Medicinal Chemistry Letters (2001) 11: 1333-1337.

Letsinger et al., "Cholesteryl-conjugated oligonucleotides: Synthesis, properties, and activity as inhibitors of replication of human immunodeficiency virus in cell culture" PNAS (1989) 86:6553-6556.

Leumann, "DNA Analogues: From Supramolecular Principles to Biological Properties" Bioorganic & Medicinal Chemistry (2002) 10:841-854.

Li et al., "Gain-of-function polymorphism in mouse and human Ltk: implications for the pathogenesis of systemic lupus erythematosus" Hum Mol Gen (2004) 13(2): 171-179.

Liu et al., "Specific inhibition of Huntington's disease gene expression by siRNAs in cultures cells" Proceedings of the Japan Academy. Series B, Physical and Biological Sciences (2003) 79B:293-298.

MacDonald et al., "A novel gene containing a trinucleotide repeat that is expanded and unstable on Huntington's disease chromosomes" Huntington's Disease Collaborative Research Group, Cell (1993) 72(6):971-983.

Machida et al., "rAAV-mediated shRNA ameliorated neuropathology in Huntington disease model mouse" Biochem. Biophys. Res. Commun. (2006) 343:190-197.

MacMillan et al., "Molecular analysis and clinical correlations of the Huntington's disease mutation" Lancet (1993) 342:954-958.

Maher et al., "Comparative hybrid arrest by tandem antisense oligodeoxyribonucleotides or oligodeoxyribonucleoside methylphosphonates in a cell-free system" Nuc. Acid. Res. (1988) 16:3341-3358.

Manoharan et al., "Chemical Modifications to Improve Uptake and Bioavailability of Antisense Oligonucleotides" Ann. N.Y. Acad. Sci. (1992) 660:306.

Manoharan et al., "Cholic Acid-Oligonucleotide Conjugates for Antisense Applications" Bioorg. Med. Chem. Lett. (1994) 4:1053-1060.

Manoharan et al., "Introduction of a Lipophilic Thioether Tether in the Minor Groove of Nucleic Acids for Antisense Applications" Bioorg. Med. Chem. Lett. (1993) 3(12):2765-2770.

Manoharan et al., "Lipidic Nucleic Acids" Tetrahedron Lett. (1995) 36(21):3651-3654.

Manoharan et al., "Oligonucleotide Conjugates: Alteration of the Pharmacokinetic Properties of Antisense Agents" Nucleosides & Nucleotides (1995) 14(3-5):969-973.

Mantaring et al., "Genotypic variation in ATP-binding cassette transporter-1 (ABCA1) as contributors to the high and low high-density lipoprotein-cholesterol (HDL-C) phenotype" Transl Res (2007) 149(4): 205-210.

Margolis et al., "Expansion explosion: new clues to the pathogenesis of repeat expansion neurodegenerative diseases." Trends Mol. Med. (2001) 7: 479-482.

Martin et al., "38. Ein neuer Zugang zu 2'-O-Alkylribonucleosiden und Eigenschaften deren Oligonucleotide" Helv. Chim. Acta (1995) 78:486-504.

Marzolini et al., "A common polymorphism in the bile acid receptor farnesoid X receptor is associated with decreased hepatic target gene expression." Mol Endocrinol (2007) 21(8): 1769-1780.

Mishra et al., "Improved leishmanicidal effect of phosphorotioate antisense oligonucleotides by LDL-mediated delivery" Biochim. Biophys. Acta (1995) 1264:229-237.

Morita et al., "2'-O,4'-C-ethylene-bridged nucleic acids (ENA): highly nuclease-resistant and thermodynamically stable oligonucleotides for antisense drug" Bioorganic & Medicinal Chemistry Letters (2002) 12(1): 73-76.

Murray et al., "TricycloDNA-modified oligo-20-deoxyribonucleotides reduce scavenger receptor B1 mRNA in hepatic and extra-hepatic tissues—a comparative study of oligonucleotide length, design and chemistry" Nucleic Acids Res (2012) 40(13): 6135-6143.

Nasir et al., "Targeted disruption of the Huntington's disease gene results in embryonic lethality and behavioral and morphological changes in heterozygotes" Cell (1995) 81(5):811-823.

Nellemann et al., "Inhibition of Huntington synthesis by antisense oligonucleotides" Molecular and Cellular Neurosciences (2000) 16:313-323.

New England Biolabs 1998/99 Catalog (cover page and pp. 121 and 284).

Nguyen et al., "Clioquinol down-regulates mutant huntingtin expression in vitro and mitigates pathology in a Huntington's disease mouse model" PNAS (2005) 102:11840-11845.

Nikiforov et al., "The Use of Phosphorothioate Primers and Exonuclease Hydrolysis for the Preparation of Single-stranded PCR Products and their Detection by Solid-phase Hybridization" PCR Methods and Applications (1994) 3:285-291.

Oberhauser et al., "Effective incorporation of 2'-O-methyl-oligoribonucleotides into liposomes and enhanced cell association through modifications with thiocholesterol" Nucl. Acids Res. (1992) 20(3):533-538.

Orum et al., "Locked nucleic acids: A promising molecular family for gene-function analysis and antisense drug development" Curr. Opinion Mol. Ther. (2001) 3:239-243.

Owen et al., "4'-Substituted nucleosides. 3. Synthesis of some 4'-fluorouridine derivatives" J. Org. Chem. (1976) 41(18): 3010-3017.

Palazzolo et al., "The role of the polyglutamine tract in androgen receptor" J Steroid Biochem Mol Biol (2008) 108(3-5): 245-252.

Persichetti et al., "Differential expression of normal and mutant Huntington's disease gene alleles." Neurobiol Dis (1996) 3(3): 183-190.

Rajasekaran et al., "Human alpha B-crystallin mutation causes oxido-reductive stress and protein aggregation cardiomyopathy in mice" Cell (2007) 130(3): 427-439.

Reynolds et al., "Rational siRNA design for RNA interference" Nature Biotechnology (2004) 22(3):326-330.

Robertson et al., "Localized mutations in the gene encoding the cytoskeletal protein filamin A cause diverse malformations in humans." Nat Genet (2003) 33(4): 487-491.

Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.

Sanghvi et al., "Heterocyclic Base Modifications in Nucleic Acids and Their Applications in Antisense Oligonucleotides" Antisense Research and Applications (1993) pp. 273-288.

Scholefield et al., "Design of RNAi hairpins for mutation-specific silencing of ataxin-7 and correction of a SCA7 phenotype." PLoS One (2009) 4(9): e7232.

Sen et al., "Role of histidine interruption in mitigating the pathological effects of long polyglutamine stretches in SCA1: a molecular approach." Protein Sci. (2003) 12(5): 953-962.

Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.

Shashidharan etal., "TorsinA accumulation in Lewy bodies in sporadic Parkinson's disease" Brain Res. (2000) 877: 379-381.

(56) References Cited

OTHER PUBLICATIONS

Shea et al., "Synthesis, hybridization properties and antiviral activity of lipid-oligodeoxynucleotide conjugates" Nucl. Acids Res. (1990) 18(13):3777-3783.
Sheehan et al., "Biochemical properties of phosphonoacetate and thiophosphonoacetate oligodeoxyribonucleotides" *Nucleic Acids Research* (2003) 31:4109-4118.
Shiels et al., "CHMP4B, a Novel Gene for Autosomal Dominant Cataracts Linked to Chromosome 20q" Am J Hum Genet (2007) 81(3): 596-606.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Tang et al., "2'-C-Branched Ribonucleosides: Synthesis of the Phosphoramidite Derivatives of 2'-C-beta-Methylcytidine and Their Incorporation into Oligonucleotides." J Org Chem (1999) 64(3) 747-754.
Uhlmann et al., "Antisense oligonucleotides: a new therapeutic principle" *Chemical Reviews* (1990) 90:543-584.
Van Bilsen et al., "Identification and allele-specific silencing of the mutant huntingtin allele in Huntington's disease patient-derived fibroblasts" Human Gene Therapy (2008) 19:710-718.
Vezzoli et al., "R990G polymorphism of calcium-sensing receptor does produce a gain-of-function and predispose to primary hypercalciuria" Kidney Int. (2007) 71: 1155-1162.
Vickers et al., "Efficient Reduction of Target RNAs by Small Interfering RNA and Rnase H-dependent Antisense Agents. A comparative analysis." J Biol. Chem. (2003) 278:7108-7118.
Wahlestedt et al., "Potent and nontoxic antisense oligonucleotides containing locked nucleic acids" PNAS (2000) 97:5633-5638.
Wang et al., "Clinico-pathological rescue of a model mouse of Huntington's disease by siRNA" *Neurosci. Res.* (2005) 53:241-249.
Warby et al., "CAG expansion in the Huntington disease gene is associated with a specific and targetable predisposing haplogroup" The American Journal of Human Genetics (2009) 84(3):351-366.
Webster et al., "Mutation in the AChR ion channel gate underlies a fast channel congenital myasthenic syndrome." Neurology (2004) 62(7): 1090-1096.
Weinstein et al., "Genetic diseases associated with heterotrimeric G proteins" Trends Pharmacol Sci (2006) 27(5): 260-266.
Woolf et al., "Specificity of antisense oligonucleotide in vivo" PNAS (1992) 89:7305-7309.
Yen et al., "Sequence-specific cleavage of Huntingtin mRNA by catalytic DNA" Annals of Neurology (1999) 46(3):366-373.

Yu et al., "Structure, inhibitor, and regulatory mechanism of Lyp, a lymphoid-specific tyrosine phosphatase implicated in autoimmune diseases" PNAS (2007) 104(50): 19767-19772.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
European Search report for application EP 09741640.8 dated Dec. 11, 2012.
European Search report for application EP 11740543 dated Sep. 18, 2013.
International Search Report for application PCT/CA2009/000645 dated Aug. 25, 2009.
International Search Report for application PCT/US11/24103 dated Jul. 15, 2011.
International Search Report for application PCT/US11/24104 dated Jul. 20, 2011.
International Search Report for application PCT/US12/50015 dated Nov. 2, 2012.
International Search Report for application PCT/US12/50023 dated Oct. 16, 2012.
International Search Report for application PCT/US13/064666 dated Apr. 23, 2014.
Fluiter et al., "Killing cancer by targeting genes that cancer cells have lost: allele-specific inhibition, a novel approach to the treatment of genetic disorders," Cell. Mol. Life Sci. (2003) 60: 834-843.
Gagnon et al. "Allele-selective inhibition of mutant Huntingtin expression with antisense oligonucleotides targeting the expanded CAG repeat," Biochemistry (2010) 49:10166-10178.
Gow et al., "The unfolded protein response in protein aggregating diseases" NeuroMol. Med. (2003) 4(1-2):73-94.
Hizawa et al., "Functional single nucleotide polymorphisms of the CCL5 gene and nonemphysematous phenotype in COPD patients," Eur. Respir. J. (2008) 32(2):372-378.
McWhinney et al., "Intronic single nucleotide polymorphisms in the RET protooncogene are associated with a subset of apparently sporadic pheochromocytoma and may modulate age of onset," J. Clin. Endocrinol. Metab. (2003) 88(10):4911-4916.
Østergaard et al. "Rational design of antisense oligonucleotides targeting single nucleotide polymorphisms for potent and allele selective suppression of mutant Huntingtin in the CNS," Nucleic Acids Res. (2013) 41(21):9634-9650.
Pfister et al., "Five siRNAs targeting three SNPs in Huntingtin may provide therapy for three-quarters of Huntington's disease patients," Curr. Biol. (2009) 19(9):774-778.
Southwell et al. "Antisense oligonucleotide therapeutics for inherited neurodegenerative diseases," Trends Mol. Med. (2012) 18(11):634-643.
International Search Report for application PCT/US14/14722 dated Aug. 25, 2014.
Liu et al., "Linking SNP Identity to CAG Repeat Length in Huntington's Disease Patients," Nat Methods, 2008, 5(11):951-953.
Extended Search Report received in European Patent Application No. 17206749.8, dated Feb. 13, 2018, 9 pages.

\* cited by examiner

SELECTIVE ANTISENSE COMPOUNDS AND USES THEREOF

CROSS REFERENCED TO RELATED APPLICATIONS

This application is a U.S. National Phase filing under 35 U.S.C. § 371 claiming priority to International Serial No. PCT/US2012/050023 filed Aug. 8, 2012, which claims priority to U.S. Provisional Application 61/522,659, filed Aug. 11, 2011, U. S. Provisional Application 61/596,723, filed Feb. 8, 2012, and U.S. Provisional Application 61/603,196, filed Feb. 24, 2012, each of which is incorporated herein by reference in its entirety.

FIELD OF THE INVENTION

The present invention pertains generally to chemically-modified oligonucleotides for use in research, diagnostics, and/or therapeutics.

SEQUENCE LISTING

The present application is being filed along with a Sequence Listing in electronic format. The Sequence Listing is provided as a file entitled CORE0099USA2SEQ ST25.txt created on Feb. 5, 2014, which is 324 Kb in size. The information in the electronic format of the sequence listing is incorporated herein by reference in its entirety.

BACKGROUND OF THE INVENTION

Antisense compounds have been used to modulate target nucleic acids. Antisense compounds comprising a variety of chemical modifications and motifs have been reported. In certain instances, such compounds are useful as research tools, diagnostic reagents, and as therapeutic agents. In certain instances antisense compounds have been shown to modulate protein expression by binding to a target messenger RNA (mRNA) encoding the protein. In certain instances, such binding of an antisense compound to its target mRNA results in cleavage of the mRNA. Antisense compounds that modulate processing of a pre-mRNA have also been reported. Such antisense compounds alter splicing, interfere with polyadenlyation or prevent formation of the 5'-cap of a pre-mRNA.

SUMMARY OF THE INVENTION

In certain embodiments, the present invention provides oligomeric compounds comprising oligonucleotides. In certain embodiments, such oligonucleotides comprise a region having a gapmer motif. In certain embodiments, such oligonucleotides consist of a region having a gapmer motif.

The present disclosure provides the following non-limiting numbered embodiments:

Embodiment 1: A oligomeric compound comprising a modified oligonucleotide consisting of 10 to 30 linked nucleosides, wherein the modified oligonucleotide has a modification motif comprising:
  a 5'-region consisting of 2-8 linked 5'-region nucleosides, each independently selected from among a modified nucleoside and an unmodified deoxynucleoside, provided that at least one 5'-region nucleoside is a modified nucleoside and wherein the 3'-most 5'-region nucleoside is a modified nucleoside;
  a 3'-region consisting of 2-8 linked 3'-region nucleosides, each independently selected from among a modified nucleoside and an unmodified deoxynucleoside, provided that at least one 3'-region nucleoside is a modified nucleoside and wherein the 5'-most 3'-region nucleoside is a modified nucleoside; and
  a central region between the 5'-region and the 3'-region consisting of 6-12 linked central region nucleosides, each independently selected from among: a modified nucleoside and an unmodified deoxynucleoside, wherein the 5'-most central region nucleoside is an unmodified deoxynucleoside and the 3'-most central region nucleoside is an unmodified deoxynucleoside;
  wherein the modified oligonucleotide has a nucleobase sequence complementary to the nucleobase sequence of a target region of a target nucleic acid.

Embodiment 2: The oligomeric compound of embodiment 1, wherein the nucleobase sequence of the target region of the target nucleic acid differs from the nucleobase sequence of at least one non-target nucleic acid by 1-3 differentiating nucleobases.

Embodiment 3: The oligomeric compound of embodiment 1, the nucleobase sequence of the target region of the target nucleic acid differs from the nucleobase sequence of at least one non-target nucleic acid by a single differentiating nucleobase.

Embodiment 4: The oligomeric compound of embodiment 2 or 3, wherein the target nucleic acid and the non-target nucleic acid are alleles of the same gene.

Embodiment 5: The oligomeric compound of embodiment 4, wherein the single differentiating nucleobase is a single-nucleotide polymorphism.

Embodiment 6: The oligomeric compound of embodiment 5, wherein the single-nucleotide polymorphism is associated with a disease.

Embodiment 7: The oligomeric compound of embodiment 6, wherein the disease is Huntington's disease.

Embodiment 8: The oligomeric compound of embodiment 6, wherein the single-nucleotide polymorphism is selected from among: rs6446723, rs3856973, rs2285086, rs363092, rs916171, rs6844859, rs7691627, rs4690073, rs2024115, rs11731237, rs362296, rs10015979, rs7659144, rs363096, rs362273, rs16843804, rs362271, rs362275, rs3121419, rs362272, rs3775061, rs34315806, rs363099, rs2298967, rs363088, rs363064, rs363102, rs2798235, rs363080, rs363072, rs363125, rs362303, rs362310, rs10488840, rs362325, rs35892913, rs363102, rs363096, rs11731237, rs10015979, rs363080, rs2798235, rs1936032, rs2276881, rs363070, rs35892913, rs12502045, rs6446723, rs7685686, rs3733217, rs6844859, and rs362331.

Embodiment 9: The oligomeric compound of embodiment 8, wherein the single-nucleotide polymorphism is selected from among: rs7685686, rs362303 rs4690072 and rs363088

Embodiment 10: The oligomeric compound of embodiment 2 or 3, wherein the target nucleic acid and the non-target nucleic acid are transcripts from different genes.

Embodiment 11: The oligomeric compound of any of embodiments 1-10, wherein the 3'-most 5'-region nucleoside comprises a bicyclic sugar moiety.

Embodiment 12: The oligomeric compound of embodiment 11, wherein the 3'-most 5'-region nucleoside comprises a cEt sugar moiety.

Embodiment 13: The oligomeric compound of embodiment 11, wherein the 3'-most 5'-region nucleoside comprises an LNA sugar moiety.

Embodiment 14: The oligomeric compound of any of embodiments 1-13, wherein the central region consists of 6-10 linked nucleosides.

Embodiment 15: The oligomeric compound of any of embodiments 1-14, wherein the central region consists of 6-9 linked nucleosides.

Embodiment 16: The oligomeric compound of embodiment 15, wherein the central region consists of 6 linked nucleosides.

Embodiment 17: The oligomeric compound of embodiment 15, wherein the central region consists of 7 linked nucleosides.

Embodiment 18: The oligomeric compound of embodiment 15, wherein the central region consists of 8 linked nucleosides.

Embodiment 19: The oligomeric compound of embodiment 15, wherein the central region consists of 9 linked nucleosides.

Embodiment 20: The oligomeric compound of any of embodiments 1-19, wherein each central region nucleoside is an unmodified deoxynucleoside.

Embodiment 21: The oligomeric compound of any of embodiments 1-19, wherein at least one central region nucleoside is a modified nucleoside.

Embodiment 22: The oligomeric compound of embodiment 21, wherein one central region nucleoside is a modified nucleoside and each of the other central region nucleosides is an unmodified deoxynucleoside.

Embodiment 23: The oligomeric compound of embodiment 21, wherein two central region nucleosides are modified nucleosides and each of the other central region nucleosides is an unmodified deoxynucleoside.

Embodiment 24: The oligomeric compound of any of embodiments 21-23 wherein at least one modified central region nucleoside is an RNA-like nucleoside.

Embodiment 25: The oligomeric compound of any of embodiments 21-23 comprising at least one modified central region nucleoside comprising a modified sugar moiety.

Embodiment 26: The oligomeric compound of any of embodiments 21-25 comprising at least one modified central region nucleoside comprising a 5'-methyl-2'-deoxy sugar moiety.

Embodiment 27: The oligomeric compound of any of embodiments 21-26 comprising at least one modified central region nucleoside comprising a bicyclic sugar moiety.

Embodiment 28: The oligomeric compound of any of embodiments 21-27 comprising at least one modified central region nucleoside comprising a cEt sugar moiety.

Embodiment 29: The oligomeric compound of any of embodiments 21-28 comprising at least one modified central region nucleoside comprising an LNA sugar moiety.

Embodiment 30: The oligomeric compound of any of embodiments 21-29 comprising at least one modified central region nucleoside comprising an α-LNA sugar moiety.

Embodiment 31: The oligomeric compound of any of embodiments 21-29 comprising at least one modified central region nucleoside comprising a 2'-substituted sugar moiety.

Embodiment 32: The oligomeric compound of embodiment 31 wherein at least one modified central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)2SCH3$, $O$—$(CH2)2$-$O$—$N(Rm)(Rn)$ or $O$—$CH2$-$C(=O)$—$N(Rm)(Rn)$, where each Rm and Rn is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 33: The oligomeric compound of embodiment 32 wherein at least one modified central region nucleoside comprises a 2'-substituted sugar moiety comprising a 2' substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—$CH=CH_2$, $O(CH_2)_2$—$OCH_3$, $O(CH_2)_2$—$SCH_3$, $O(CH_2)_2$—$OCF_3$, $O(CH_2)_3$—$N(R_1)(R_2)$, $O(CH_2)_2$—$ON(R_1)(R_2)$, $O(CH_2)_2$—$O(CH_2)_2$—$N(R_1)(R_2)$, $OCH_2C(=O)$—$N(R_1)(R_2)$, $OCH_2C(=O)$—$N(R_3)$—$(CH_2)_2$—$N(R_1)(R_2)$, and $O(CH_2)_2$—$N(R_3)$—$C(=NR_4)[N(R_1)(R_2)]$; wherein $R_1$, $R_2$, $R_3$ and $R_4$ are each, independently, H or $C_1$-$C_6$ alkyl.

Embodiment 34: The oligomeric compound of embodiment 33 wherein the 2' substituent is selected from among: a halogen, $OCH_3$, $OCF_3$, $OCH_2CH_3$, $OCH_2CF_3$, $OCH_2$—$CH=CH_2$, $O(CH_2)_2$—$OCH_3$ (MOE), $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$, and $OCH_2$—$N(H)$—$C(=NH)NH_2$.

Embodiment 35: The oligomeric compound of any of embodiments 21-34 comprising at least one modified central region nucleoside comprising a 2'-MOE sugar moiety.

Embodiment 36: The oligomeric compound of any of embodiments 21-35 comprising at least one modified central region nucleoside comprising a 2'-OMe sugar moiety.

Embodiment 37: The oligomeric compound of any of embodiments 21-36 comprising at least one modified central region nucleoside comprising a 2'-F sugar moiety.

Embodiment 38: The oligomeric compound of any of embodiments 21-37 comprising at least one modified central region nucleoside comprising a 2'-(ara)-F sugar moiety.

Embodiment 39: The oligomeric compound of any of embodiments 21-38 comprising at least one modified central region nucleoside comprising a sugar surrogate.

Embodiment 40: The oligomeric compound of embodiment 39 comprising at least one modified central region nucleoside comprising an F-HNA sugar moiety.

Embodiment 41: The oligomeric compound of embodiment 39 or 40 comprising at least one modified central region nucleoside comprising an HNA sugar moiety.

Embodiment 42: The oligomeric compound of any of embodiments 21-41 comprising at least one modified central region nucleoside comprising a modified nucleobase.

Embodiment 43: The oligomeric compound of embodiment 42 comprising at least one modified central region nucleoside comprising a modified nucleobase selected from a 2-thio pyrimidine and a 5-propyne pyrimidine.

Embodiment 44: The oligomeric compound of any of embodiments 21-43, wherein the $2^{nd}$ nucleoside from the 5'-end of the central region is a modified nucleoside.

Embodiment 45: The oligomeric compound of any of embodiments 21-44, wherein the $3^{rd}$ nucleoside from the 5'-end of the central region is a modified nucleoside.

Embodiment 46: The oligomeric compound of any of embodiments 21-45, wherein the $4^{th}$ nucleoside from the 5'-end of the central region is a modified nucleoside.

Embodiment 47: The oligomeric compound of any of embodiments 21-46, wherein the $5^{th}$ nucleoside from the 5'-end of the central region is a modified nucleoside.

Embodiment 48: The oligomeric compound of any of embodiments 21-47, wherein the $6^{th}$ nucleoside from the 5'-end of the central region is a modified nucleoside.

Embodiment 49: The oligomeric compound of any of embodiments 21-48, wherein the $8^{th}$ nucleoside from the 3'-end of the central region is a modified nucleoside.

Embodiment 50: The oligomeric compound of any of embodiments 21-49, wherein the $7^{th}$ nucleoside from the 3'-end of the central region is a modified nucleoside.

Embodiment 51: The oligomeric compound of any of embodiments 21-50, wherein the $6^{th}$ nucleoside from the 3'-end of the central region is a modified nucleoside.

Embodiment 52: The oligomeric compound of any of embodiments 21-51, wherein the $5^{th}$ nucleoside from the 3'-end of the central region is a modified nucleoside.

Embodiment 53: The oligomeric compound of any of embodiments 21-52, wherein the $4^{th}$ nucleoside from the 3'-end of the central region is a modified nucleoside.

Embodiment 54: The oligomeric compound of any of embodiments 21-53, wherein the $3^{rd}$ nucleoside from the 3'-end of the central region is a modified nucleoside.

Embodiment 55: The oligomeric compound of any of embodiments 21-54, wherein the $2^{nd}$ nucleoside from the 3'-end of the central region is a modified nucleoside.

Embodiment 56: The oligomeric compound of any of embodiments 21-55, wherein the modified nucleoside is a 5'-methyl-2'-deoxy sugar moiety.

Embodiment 57: The oligomeric compound of any of embodiments 21-55, wherein the modified nucleoside is a 2-thio pyrimidine.

Embodiment 58: The oligomeric compound of any of embodiments 21-55, wherein the central region comprises no region having more than 4 contiguous unmodified deoxynucleosides.

Embodiment 59: The oligomeric compound of any of embodiments 21-55, wherein the central region comprises no region having more than 5 contiguous unmodified deoxynucleosides.

Embodiment 60: The oligomeric compound of any of embodiments 21-55, wherein the central region comprises no region having more than 6 contiguous unmodified deoxynucleosides.

Embodiment 61: The oligomeric compound of any of embodiments 21-55, wherein the central region comprises no region having more than 7 contiguous unmodified deoxynucleosides.

Embodiment 62: The oligomeric compound of any of embodiments 1-14 or 21-59, wherein the central region has a nucleoside motif selected from among: DDDDDDDDDD, DDDDXDDDDD; DDDDDXDDDDD; DDDXDDDDD; DDDDXDDDDDD; DDDDXDDDD; DDXDDDDDD; DDDXDDDDDD; DXDDDDDD; DDXDDDDDDD; DDXDDDDD; DDXDDDXDD; DDDDXDDDXDDD; DXDDDXDDD; DDXDDDXDD; DDXDDDDXDDD; DDXDDDDXDD; DXDDDDXDDD; DDDDXDDD; DDDDXDDD; DXDDDDDDD; DDDDXXDDD; and DXXDXXDXX; wherein
each D is an unmodified deoxynucleoside; and each X is a modified nucleoside.

Embodiment 63: The oligomeric compound of any of embodiments 1-14 or 21-59, wherein the central region has a nucleoside motif selected from among: DDDDDDDDD; DXDDDDDDD; DDXDDDDDD; DDDXDDDDD; DDDDXDDDD; DDDDDXDDD; DDDDDDXDD; DDDDDDDXD; DXXDDDDDD; DDDDDDXXD; DDXXDDDDD; DDDXXDDDD; DDDDXXDDD; DDDDDXXDD; DXDDDDDXD; DXDDDDDD; DXDDDDXDD; DXDDDDDXD; DXDXDDDDD; DDXDDDDXD; DDXDDDXDD; DDXDDXDDD; DDXDXDDDD; DDDXDDDXD; DDDXDDXDD; DDDXDXDDD; DDDDXDXDD; and DDDDDXDXD wherein each D is an unmodified deoxynucleoside; and each X is a modified nucleoside.

Embodiment 64: The oligomeric compound of any of embodiments 1-14 or 21-59, wherein the central region has a nucleoside motif selected from among: DDDDDDDD, DDDDXDDDD, DXDDDDDDD, DXXDDDDDD, DDXDDDDDD, DDDXDDDDD, DDDDXDDDD, DDDDDXDDD, DDDDDDXDD, and DDDDDDDXD.

Embodiment 65: The oligomeric compound of any of embodiments 1-14 or 21-59, wherein the central region has a nucleoside motif selected from among: DDDDDDDD, DXDDDDDD, DDXDDDDD, DDDXDDDD, DDDDXDDD, DDDDDXDD, DDDDDDXD, DXDDDDXD, DXDDDXDD, DXD-DXDDD, DXDXDDDD, DXXDDDDD, DDXXDDDD, DDXDXDDD, DXDDDXDD, DXDDDDXD, DDDXXDDD, DDDXDXDD, DDDXDDXD, DDDDXXDD, DDDDXDXD, and DDDDDXXD.

Embodiment 66: The oligomeric compound of any of embodiments 1-14 or 21-59, wherein the central region has a nucleoside motif selected from among: DDDDDDD, DXDDDDD, DDXDDDD, DDDXDDD, DDDDXDD, DDDDDXD, DXDDDXD, DXDDXDD, DXDXDDD, DXXDDDD, DDXXDDD, DDXDXDD, DDXDDXD, DDDXXDD, DDDXDXD, and DDDDXXD.

Embodiment 67: The oligomeric compound of any of embodiments 1-14 or 21-59, wherein the central region has a nucleoside motif selected from among: DDDDDD, DXDDDD, DDXDDD, DDDXDD, DDDDXD, DXXDDD, DXDXDD, DXDDXD, DDXXDD, DDXDXD, and DDDXXD.

Embodiment 68: The oligomeric compound of any of embodiments 1-14 or 21-59, wherein the central region has a nucleoside motif selected from among: DDDDDD, DDDDDDD, DDDDDDDD, DDDDDDDDD, DDDDDDDDDD, DXDDDD, DDXDDD, DDDXDD, DDDDXD, DXDDDDD, DDXDDDD, DDDXDDD, DDDDXDD, DDDDDXD, DXDDDDDD, DDXDDDDD, DDDXDDDD, DDDDXDDD, DDDDDXDD, DDDDDDXD, DXDDDDDDD; DDXDDDDDD, DDDXDDDDD, DDDDXDDDD, DDDDDXDDD, DDDDDDXDD, DDDDDDDXD, DXDDDDDDDD, DDXDDDDDDD, DDDXDDDDDD, DDDDXDDDDD, DDDDDXDDDD, DDDDDDXDDD, DDDDDDDXDD, and DDDDDDDDXD.

Embodiment 69: The oligomeric compound of embodiments 62-68, wherein each X comprises a modified nucleobase.

Embodiment 70: The oligomeric compound of embodiments 62-68, wherein each X comprises a modified sugar moiety.

Embodiment 71: The oligomeric compound of embodiments 62-68, wherein each X comprises 2-thio-thymidine.

Embodiment 72: The oligomeric compound of embodiments 62-68, wherein each X nucleoside comprises an F-HNA sugar moiety.

Embodiment 73: The oligomeric compound of embodiments 62-68, wherein the nucleobase sequence of the target region of the target nucleic acid differs from the nucleobase sequence of at least one non-target nucleic acid by a single differentiating nucleobase, and wherein the location of the single differentiating nucleobase is represented by X.

Embodiment 74: The oligomeric compound of embodiment 73, wherein the target nucleic acid and the non-target nucleic acid are alleles of the same gene.

Embodiment 75: The oligomeric compound of embodiment 73, wherein the single differentiating nucleobase is a single-nucleotide polymorphism.

Embodiment 76: The oligomeric compound of any of embodiments 1-75, wherein the 5' region consists of 2 linked 5'-region nucleosides.

Embodiment 77: The oligomeric compound of any of embodiments 1-75, wherein the 5' region consists of 3 linked 5'-region nucleosides.

Embodiment 78: The oligomeric compound of any of embodiments 1-75, wherein the 5' region consists of 4 linked 5'-region nucleosides.

Embodiment 79: The oligomeric compound of any of embodiments 1-75, wherein the 5' region consists of 5 linked 5'-region nucleosides.

Embodiment 80: The oligomeric compound of any of embodiments 1-75, wherein the 5' region consists of 6 linked 5'-region nucleosides.

Embodiment 81: The oligomeric compound of any of embodiments 1-80, wherein at least one 5'-region nucleoside is an unmodified deoxynucleoside.

Embodiment 82: The oligomeric compound of any of embodiments 1-80, wherein each 5'-region nucleoside is a modified nucleoside.

Embodiment 83: The oligomeric compound of any of embodiments 1-80 wherein at least one 5'-region nucleoside is an RNA-like nucleoside.

Embodiment 84: The oligomeric compound of any of embodiments 1-80 wherein each 5'-region nucleoside is an RNA-like nucleoside.

Embodiment 85: The oligomeric compound of any of embodiments 1-80 comprising at least one modified 5'-region nucleoside comprising a modified sugar.

Embodiment 86: The oligomeric compound of embodiment 80 comprising at least one modified 5'-region nucleoside comprising a bicyclic sugar moiety.

Embodiment 87: The oligomeric compound of embodiment 86 comprising at least one modified 5'-region nucleoside comprising a cEt sugar moiety.

Embodiment 88: The oligomeric compound of embodiment 85 or 86 comprising at least one modified 5'-region nucleoside comprising an LNA sugar moiety.

Embodiment 89: The oligomeric compound of any of embodiments 76-80 comprising of at least one modified 5'-region nucleoside comprising a 2'-substituted sugar moiety.

Embodiment 90: The oligomeric compound of embodiment 89 wherein at least one modified central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O-(CH_2)_2-O-N(R_m)(R_n)$ or $O-CH_2-C(=O)-N(R_m)(R_n)$, where each $R_m$ and $R_n$ is, independently, H, an amino protecting group or substituted or unsubstituted $C_1$-$C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 91: The oligomeric compound of embodiment 90 wherein at least one modified 5'-region nucleoside comprises a 2'-substituted sugar moiety comprising a 2'-substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2-CH=CH_2$, $O(CH_2)_2-OCH_3$ (MOE), $O(CH_2)_2-SCH_3$, $O(CH_2)_2-OCF_3$, $O(CH_2)_3-N(R_1)(R_2)$, $O(CH_2)_2-ON(R_1)(R_2)$, $O(CH_2)_2-O(CH_2)_2-N(R_1)(R_2)$, $OCH_2C(=O)-N(R_1)(R_2)$, $OCH_2C(=O)-N(R_3)-(CH_2)_2-N(R_1)(R_2)$, and $O(CH_2)_2-N(R_3)-C(=NR_4)[N(R_1)(R_2)]$; wherein $R_1$, $R_2$, $R_3$ and $R_4$ are each, independently, H or $C_1$-$C_6$ alkyl.

Embodiment 92: The oligomeric compound of embodiment 91, wherein the 2'-substituent is selected from among: a halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$, and $OCH_2-N(H)-C(=NH)NH_2$.

Embodiment 93: The oligomeric compound of any of embodiments 89-92 comprising at least one modified 5'-region nucleoside comprising a 2'-MOE sugar moiety.

Embodiment 94: The oligomeric compound of any of embodiments 89-92 comprising at least one modified 5'-region nucleoside comprising a 2'-OMe sugar moiety.

Embodiment 95: The oligomeric compound of any of embodiments 89-92 comprising at least one modified 5'-region nucleoside comprising a 2'-F sugar moiety.

Embodiment 96: The oligomeric compound of any of embodiments 89-92 comprising at least one modified 5'-region nucleoside comprising a 2'-(ara)-F sugar moiety.

Embodiment 97: The oligomeric compound of any of embodiments 82-96 comprising of at least one modified 5'-region nucleoside comprising a sugar surrogate.

Embodiment 98: The oligomeric compound of embodiment 97 comprising at least one modified 5'-region nucleoside comprising an F-HNA sugar moiety.

Embodiment 99: The oligomeric compound of embodiment 97 or 98 comprising at least one modified 5'-region nucleoside comprising an HNA sugar moiety.

Embodiment 100: The oligomeric compound of any of embodiments 1-99 comprising at least one modified 5'-region nucleoside comprising a modified nucleobase.

Embodiment 101: The oligomeric compound of embodiment 100, wherein the modified nucleoside comprises 2-thio-thymidine.

Embodiment 102: The oligomeric compound of any of embodiments 1-101, wherein the 5'-region has a motif selected from among:
ADDA; ABDAA; ABBA; ABB; ABAA; AABAA; AAABAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBB,
wherein each A is a modified nucleoside of a first type, each B is a modified nucleoside of a second type, each C is a modified nucleoside of a third type, and each D is an unmodified deoxynucleoside.

Embodiment 103: The oligomeric compound of any of embodiments 1-101, wherein the 5'-region has a motif selected from among:
AB, ABB, AAA, BBB, BBBAA, AAB, BAA, BBAA, AABB, AAAB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, AAAAA, BBBBAA, and AAABW wherein each A is a modified nucleoside of a first type, each B is a modified nucleoside of a second type, and each W is a modified nucleoside of a third type.

Embodiment 104: The oligomeric compound of any of embodiments 1-101, wherein the 5'-region has a motif selected from among: ABB; ABAA; AABAA; AAABAA; ABAB; ABADB; AAABB; AAAAA; AA; AAA; AAAA; AAAAB; ABBB; AB; and ABAB, wherein each A is a modified nucleoside of a first type, each B is a modified nucleoside of a second type, and each W is a modified nucleoside of a third type.

Embodiment 105: The oligomeric compound of embodiments 102-104, wherein each A nucleoside comprises a 2'-substituted sugar moiety.

Embodiment 106: The oligomeric compound of embodiment 105 wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O$—$(CH_2)_2$—$O$—$N(R_m)(R_n)$ or $O$—$CH_2$—$C(=O)$—$N(R_m)(R_n)$, where each $R_m$ and $R_n$, is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

Embodiment 107: The oligomeric compound of embodiment 102-106, wherein each A nucleoside comprises a 2'-substituted sugar moiety comprising a 2'-substituent selected from among: a halogen, $OCH_3$, $OCF_3$, $OCH_2CH_3$, $OCH_2CF_3$, $OCH_2$—$CH=CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$, and $OCH_2$—$N(H)$—$C(=NH)NH_2$.

Embodiment 108: The oligomeric compound of embodiment 107, wherein each A nucleoside comprises a 2'-substituted sugar moiety comprising a 2'-substituent selected from among: F, $OCH_3$, $O(CH_2)_2$—$OCH_3$.

Embodiment 109: The oligomeric compound of embodiments 102-106, wherein each A nucleoside comprises a bicyclic sugar moiety.

Embodiment 110: The oligomeric compound of embodiment 109, wherein each A nucleoside comprises a bicyclic sugar moiety selected from among: cEt, cMOE, LNA, α-LNA, ENA and 2'-thio LNA.

Embodiment 111: The oligomeric compound of any of embodiments 102-110, wherein each A comprises a modified nucleobase.

Embodiment 112: The oligomeric compound of embodiment 111, wherein each A comprises a modified nucleobase selected from among a 2-thio pyrimidine and a 5-propyne pyrimidine.

Embodiment 113: The oligomeric compound of embodiment 112, wherein each A comprises 2-thio-thymidine.

Embodiment 114: The oligomeric compound of embodiment 102-106, wherein each A nucleoside comprises an unmodified 2'-deoxyfuranose sugar moiety.

Embodiment 115: The oligomeric compound of embodiment 102-106, wherein each A nucleoside comprises an F-HNA sugar moiety.

Embodiment 116: The oligomeric compound of any of embodiments 102-115, wherein each B nucleoside comprises a 2'-substituted sugar moiety.

Embodiment 117: The oligomeric compound of embodiment 116, wherein at least one central region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O$—$(CH_2)_2$—$O$—$N(R_m)(R_n)$ or $O$—$CH_2$—$C(=O)$—$N(R_m)(R_n)$, where each $R_m$ and $R_n$ is, independently, H, an amino protecting group or substituted or unsubstituted $C_1$-$C_{10}$ alkyl; wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 118: The oligomeric compound of embodiment 117, wherein each B nucleoside comprises a 2'-substituted sugar moiety comprising a 2'-substituent selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 119: The oligomeric compound of embodiment 118, wherein each B nucleoside comprises a 2'-substituted sugar moiety comprising a 2'-substituent selected from among: F, OCH$_3$, O(CH$_2$)$_2$—OCH$_3$.

Embodiment 120: The oligomeric compound of any of embodiments 102-115, wherein each B nucleoside comprises a bicyclic sugar moiety.

Embodiment 121: The oligomeric compound of embodiment 120, wherein each B nucleoside comprises a bicyclic sugar moiety selected from among: cEt, cMOE, LNA, α-LNA, ENA and 2'-thio LNA.

Embodiment 122: The oligomeric compound of any of embodiments 102-115, wherein each B comprises a modified nucleobase.

Embodiment 123: The oligomeric compound of embodiment 122, wherein each B comprises a modified nucleobase selected from among a 2-thio pyrimidine and a 5-propyne pyrimidine.

Embodiment 124: The oligomeric compound of embodiment 123, wherein each B comprises 2-thio-thymidine.

Embodiment 125: The oligomeric compound of embodiment 102-106, wherein each B nucleoside comprises an unmodified 2'-deoxyfuranose sugar moiety.

Embodiment 126: The oligomeric compound of embodiment 102-115, wherein each B nucleoside comprises an F-HNA sugar moiety.

Embodiment 127: The oligomeric compound of any of embodiments 102-126, wherein each C nucleoside comprises a 2'-substituted sugar moiety.

Embodiment 128: The oligomeric compound of embodiment 127, wherein at least one central region nucleoside comprises a 2'-substituted sugar moiety comprising a 2' substituent selected from among: halogen, optionally substituted allyl, optionally substituted amino, azido, optionally substituted SH, CN, OCN, CF$_3$, OCF$_3$, O, S, or N(R$_m$)-alkyl; O, S, or N(R$_m$)-alkenyl; O, S or N(R$_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl; wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 129: The oligomeric compound of embodiment 128, wherein each C nucleoside comprises a 2'-substituted sugar moiety comprising a 2'-substituent selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 130: The oligomeric compound of embodiment 129, wherein each C nucleoside comprises a 2'-substituted sugar moiety comprising a 2'-substituent selected from among: F, OCH$_3$, O(CH$_2$)$_2$—OCH$_3$.

Embodiment 131: The oligomeric compound of any of embodiments 102-126, wherein each C nucleoside comprises a bicyclic sugar moiety.

Embodiment 132: The oligomeric compound of embodiment 131, wherein each C nucleoside comprises a bicyclic sugar moiety selected from among: cEt, cMOE, LNA, α-LNA, ENA and 2'-thio LNA.

Embodiment 133: The oligomeric compound of any of embodiments 102-126, wherein each C comprises a modified nucleobase.

Embodiment 134: The oligomeric compound of embodiment 133, wherein each C comprises a modified nucleobase selected from among a 2-thio pyrimidine and a 5-propyne pyrimidine.

Embodiment 135: The oligomeric compound of embodiment 134, wherein each C comprises 2-thio-thymidine.

Embodiment 136: The oligomeric compound of embodiment 102-126, wherein each C comprises an F-HNA sugar moiety.

Embodiment 137: The oligomeric compound of embodiment 102-126, wherein each C nucleoside comprises an unmodified 2'-deoxyfuranose sugar moiety.

Embodiment 138: The oligomeric compound of any of embodiments 102-138, wherein each W nucleoside comprises a 2'-substituted sugar moiety.

Embodiment 139: The oligomeric compound of embodiment 138, wherein at least one central region nucleoside comprises a 2'-substituted sugar moiety comprising a 2' substituent selected from among: halogen, optionally substituted allyl, optionally substituted amino, azido, optionally substituted SH, CN, OCN, CF$_3$, OCF$_3$, O, S, or N(R$_m$)-alkyl; O, S, or N(R$_m$)-alkenyl; O, S or N(R$_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl; wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 140: The oligomeric compound of embodiment 139, wherein each W nucleoside comprises a 2'-substituted sugar moiety comprising a 2'-substituent selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 141: The oligomeric compound of embodiment 139, wherein each W nucleoside comprises a 2'-substituted sugar moiety comprising a 2'-substituent selected from among: F, OCH$_3$, O(CH$_2$)$_2$—OCH$_3$.

Embodiment 142: The oligomeric compound of any of embodiments 102-137, wherein each W nucleoside comprises a bicyclic sugar moiety.

Embodiment 143: The oligomeric compound of embodiment 142, wherein each W nucleoside comprises a bicyclic sugar moiety selected from among: cEt, cMOE, LNA, α-LNA, ENA and 2'-thio LNA.

Embodiment 144: The oligomeric compound of any of embodiments 102-137, wherein each W comprises a modified nucleobase.

Embodiment 145: The oligomeric compound of embodiment 144, wherein each W comprises a modified nucleobase selected from among a 2-thio pyrimidine and a 5-propyne pyrimidine.

Embodiment 146: The oligomeric compound of embodiment 145, wherein each W comprises 2-thio-thymidine.

Embodiment 147: The oligomeric compound of embodiment 102-137, wherein each W comprises an F-HNA sugar moiety.

Embodiment 148: The oligomeric compound of embodiment 102-137, wherein each W nucleoside comprises an unmodified 2'-deoxyfuranose sugar moiety.

Embodiment 149: The oligomeric compound of any of embodiments 1-148, wherein the 3' region consists of 2 linked 3'-region nucleosides.

Embodiment 150: The oligomeric compound of any of embodiments 1-148, wherein the 3' region consists of 3 linked 3'-region nucleosides.

Embodiment 151: The oligomeric compound of any of embodiments 1-148, wherein the 3' region consists of 4 linked 3'-region nucleosides.

Embodiment 152: The oligomeric compound of any of embodiments 1-148, wherein the 3' region consists of 5 linked 3'-region nucleosides.

Embodiment 153: The oligomeric compound of any of embodiments 1-148, wherein the 3' region consists of 6 linked 3'-region nucleosides.

Embodiment 154: The oligomeric compound of any of embodiments 1-153, wherein at least one 3'-region nucleoside is an unmodified deoxynucleoside.

Embodiment 155: The oligomeric compound of any of embodiments 1-154, wherein each 3'-region nucleoside is a modified nucleoside.

Embodiment 156: The oligomeric compound of any of embodiments 1-153, wherein at least one 3'-region nucleoside is an RNA-like nucleoside.

Embodiment 157: The oligomeric compound of any of embodiments 1-154, wherein each 3'-region nucleoside is an RNA-like nucleoside.

Embodiment 158: The oligomeric compound of any of embodiments 1-153, comprising at least one modified 3'-region nucleoside comprising a modified sugar.

Embodiment 159: The oligomeric compound of embodiment 158, comprising at least one modified 3'-region nucleoside comprising a bicyclic sugar moiety.

Embodiment 160: The oligomeric compound of embodiment 159, comprising at least one modified 3'-region nucleoside comprising a cEt sugar moiety.

Embodiment 161: The oligomeric compound of embodiment 159, comprising at least one modified 3'-region nucleoside comprising an LNA sugar moiety.

Embodiment 162: The oligomeric compound of any of embodiments 1-162 comprising of at least one modified 3'-region nucleoside comprising a 2'-substituted sugar moiety.

Embodiment 163: The oligomeric compound of embodiment 162, wherein at least one central region nucleoside comprises a 2'-substituted sugar moiety comprising a 2' substituent selected from among: halogen, optionally substituted allyl, optionally substituted amino, azido, optionally substituted SH, CN, OCN, CF$_3$, OCF$_3$, O, S, or N(R$_m$)-alkyl; O, S, or N(R$_m$-alkenyl; O, S or N(R$_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl; wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 164: The oligomeric compound of embodiment 163 wherein at least one modified 3'-region nucleoside comprises a 2'-substituted sugar moiety comprising a 2'-substituent selected from among: a halogen, OCH$_3$, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH=CH$_2$, O(CH$_2$)$_2$—OCH$_3$ (MOE), O(CH$_2$)$_2$—SCH$_3$, O(CH$_2$)$_2$—OCF$_3$, O(CH$_2$)$_3$—N(R$_1$)(R$_2$), O(CH$_2$)$_2$—ON(R$_1$)(R$_2$), O(CH$_2$)$_2$—O(CH$_2$)$_2$—N(R$_1$)(R$_2$), OCH$_2$C(=O)—N(R$_1$)(R$_2$), OCH$_2$C(=O)—N(R$_3$)—(CH$_2$)$_2$—N(R$_1$)(R$_2$), and O(CH$_2$)$_2$—N(R$_3$)—C(=NR$_4$)[N(R$_1$)(R$_2$)]; wherein R$_1$, R$_2$, R$_3$ and R$_4$ are each, independently, H or C$_1$-C$_6$ alkyl.

Embodiment 165: The oligomeric compound of embodiment 164, wherein the 2'-substituent is selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 166: The oligomeric compound of any of embodiments 162-165 comprising at least one modified 3'-region nucleoside comprising a 2'-MOE sugar moiety.

Embodiment 167: The oligomeric compound of any of embodiments 162-166 comprising at least one modified 3'-region nucleoside comprising a 2'-OMe sugar moiety.

Embodiment 168: The oligomeric compound of any of embodiments 162-167 comprising at least one modified 3'-region nucleoside comprising a 2'-F sugar moiety.

Embodiment 169: The oligomeric compound of any of embodiments 162-168 comprising at least one modified 3'-region nucleoside comprising a 2'-(ara)-F sugar moiety.

Embodiment 170: The oligomeric compound of any of embodiments 162-169 comprising of at least one modified 3'-region nucleoside comprising a sugar surrogate.

Embodiment 171: The oligomeric compound of embodiment 170 comprising at least one modified 3'-region nucleoside comprising an F-HNA sugar moiety.

Embodiment 172: The oligomeric compound of embodiment 170 comprising at least one modified 3'-region nucleoside comprising an HNA sugar moiety.

Embodiment 173: The oligomeric compound of any of embodiments 1-172 comprising at least one modified 3'-region nucleoside comprising a modified nucleobase.

Embodiment 174: The oligomeric compound of any of embodiments 1-173, wherein each A comprises a 2'-substituted sugar moiety comprising a 2'-substituent selected from among: F, OCH$_3$, O(CH$_2$)$_2$—OCH$_3$, and each B comprises a bicylic sugar moiety selected from among: LNA and cEt.

Embodiment 175: The oligomeric compound of embodiment 174, wherein each A comprises O(CH$_2$)$_2$—OCH$_3$ and each B comprises cEt.

Embodiment 176: The oligomeric compound of any of embodiments 1-175, wherein the 3'-region has a motif selected from among: ABB, ABAA, AAABAA, AAAAABAA, AABAA, AAAABAA, AAABAA, ABAB, AAAAA, AAABB, AAAAAAAA, AAAAAAA, AAAAAA, AAAAB, AAAA, AAA, AA, AB, ABBB, ABAB, AABBB, wherein each A is a modified nucleoside of a first type, each B is a modified nucleoside of a second type.

Embodiment 177: The oligomeric compound of embodiments 1-175, wherein the 3'-region has a motif selected from among: ABB; AAABAA; AABAA; AAAABAA; AAAAA; AAABB; AAAAAAAA; AAAAAAA; AAAAAA; AAAAB; AB; ABBB; and ABAB, wherein each A is a modified nucleoside of a first type, each B is a modified nucleoside of a second type.

Embodiment 178: The oligomeric compound of embodiments 1-175, wherein the 3'-region has a motif selected from among: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB, wherein each A is a modified nucleoside of a first type, each B is a modified nucleoside of a second type, and each W is a modified nucleoside of a first type, a second type, or a third type.

Embodiment 179: The oligomeric compound of embodiments 176-178, wherein each A nucleoside comprises a 2'-substituted sugar moiety.

Embodiment 180: The oligomeric compound of embodiments 176-178, wherein at least one central region nucleoside comprises a 2'-substituted sugar moiety comprising a 2' substituent selected from among: halogen, optionally substituted allyl, optionally substituted amino, azido, optionally substituted SH, CN, OCN, CF$_3$, OCF$_3$, O, S, or N(R$_m$)-alkyl; O, S, or N(R$_m$)-alkenyl; O, S or N(R$_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl;

wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 181: The oligomeric compound of embodiment 180, wherein each A nucleoside comprises a 2'-substituted sugar moiety comprising a 2'-substituent selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 182: The oligomeric compound of embodiment 181, wherein each A nucleoside comprises a 2'-substituted sugar moiety comprising a 2'-substituent selected from among: F, OCH$_3$, O(CH$_2$)$_2$—OCH$_3$.

Embodiment 183: The oligomeric compound of embodiments 176-178, wherein each A nucleoside comprises a bicyclic sugar moiety.

Embodiment 184: The oligomeric compound of embodiment 183, wherein each A nucleoside comprises a bicyclic sugar moiety selected from among: cEt, cMOE, LNA, α-LNA, ENA and 2'-thio LNA.

Embodiment 185: The oligomeric compound of any of embodiments 176-178, wherein each B nucleoside comprises a 2'-substituted sugar moiety.

Embodiment 186: The oligomeric compound of embodiment 185, wherein at least one modified central region nucleoside comprises a 2'-substituted sugar moiety comprising a 2' substituent selected from among: halogen, optionally substituted allyl, optionally substituted amino, azido, optionally substituted SH, CN, OCN, CF$_3$, OCF$_3$, O, S, or N(R$_m$)-alkyl; O, S, or N(R$_m$)-alkenyl; O, S or N(R$_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl;

wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 187: The oligomeric compound of embodiment 185, wherein each B nucleoside comprises a 2'-substituted sugar moiety comprising a 2'-substituent selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 188: The oligomeric compound of embodiment 187, wherein each B nucleoside comprises a 2'-substituted sugar moiety comprising a 2'-substituent selected from among: F, OCH$_3$, O(CH$_2$)$_2$—OCH$_3$.

Embodiment 189: The oligomeric compound of any of embodiments 176-178, wherein each B nucleoside comprises a bicyclic sugar moiety.

Embodiment 190: The oligomeric compound of embodiment 189, wherein each B nucleoside comprises a bicyclic sugar moiety selected from among: cEt, cMOE, LNA, α-LNA, ENA and 2'-thio LNA.

Embodiment 191: The oligomeric compound of any of embodiments 176-190, wherein each A comprises a 2'-substituted sugar moiety comprising a 2'-substituent selected from among: F, OCH$_3$, O(CH$_2$)$_2$—OCH$_3$, and each B comprises a bicyclic sugar moiety selected from among: LNA and cEt.

Embodiment 192: The oligomeric compound of embodiment 191, wherein each A comprises O(CH$_2$)$_2$—OCH$_3$ and each B comprises cEt.

Embodiment 193: The oligomeric compound of any of embodiments 176-192, wherein each W nucleoside comprises a 2'-substituted sugar moiety.

Embodiment 194: The oligomeric compound of embodiment 193, wherein at least one central region nucleoside comprises a 2'-substituted sugar moiety comprising a 2' substituent selected from among: halogen, optionally substituted allyl, optionally substituted amino, azido, optionally substituted SH, CN, OCN, CF$_3$, OCF$_3$, O, S, or N(R$_m$)-alkyl; O, S, or N(R$_m$)-alkenyl; O, S or N(R$_m$)-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl; wherein each optionally substituted group is optionally substituted with a substituent group independently selected from among: hydroxyl, amino, alkoxy, carboxy, benzyl, phenyl, nitro (NO$_2$), thiol, thioalkoxy (S-alkyl), halogen, alkyl, aryl, alkenyl and alkynyl.

Embodiment 195: The oligomeric compound of embodiment 193, wherein each W nucleoside comprises a 2'-substituted sugar moiety comprising a 2'-substituent selected from among: a halogen, OCH$_3$, OCF$_3$, OCH$_2$CH$_3$, OCH$_2$CF$_3$, OCH$_2$—CH=CH$_2$, O(CH$_2$)$_2$—OCH$_3$, O(CH$_2$)$_2$—O(CH$_2$)$_2$—N(CH$_3$)$_2$, OCH$_2$C(=O)—N(H)CH$_3$, OCH$_2$C(=O)—N(H)—(CH$_2$)$_2$—N(CH$_3$)$_2$, and OCH$_2$—N(H)—C(=NH)NH$_2$.

Embodiment 196: The oligomeric compound of embodiment 195, wherein each W nucleoside comprises a 2'-substituted sugar moiety comprising a 2'-substituent selected from among: F, OCH$_3$, O(CH$_2$)$_2$—OCH$_3$.

Embodiment 197: The oligomeric compound of any of embodiments 176-192, wherein each W nucleoside comprises a bicyclic sugar moiety.

Embodiment 198: The oligomeric compound of embodiment 197, wherein each W nucleoside comprises a bicyclic sugar moiety selected from among: cEt, cMOE, LNA, α-LNA, ENA and 2'-thio LNA.

Embodiment 199: The oligomeric compound of any of embodiments 176-192, wherein each W comprises a modified nucleobase.

Embodiment 200: The oligomeric compound of embodiment 199, wherein each W comprises a modified nucleobase selected from among a 2-thio pyrimidine and a 5-propyne pyrimidine.

Embodiment 201: The oligomeric compound of embodiment 200, wherein each W comprises 2-thio-thymidine.

Embodiment 202: The oligomeric compound of embodiment 176-192, wherein each W comprises an F-HNA sugar moiety.

Embodiment 203: The oligomeric compound of embodiment 202, wherein each W nucleoside comprises an unmodified 2'-deoxyfuranose sugar moiety.

Embodiment 204: The oligomeric compound of embodiments 1-203, wherein the 5'-region has a motif selected from among: AB, ABB, AAA, BBB, BBBAA, AAB, BAA, BBAA, AABB, AAAB, ABBW, ABBWW, ABBB, ABBBB, ABAB, ABABAB, ABABBB, ABABAA, ABABAA, AAABB, AAAABB, AABB, AAAAB, AABBB, ABBBB, BBBBB, AAABW, AAAAA, and BBBBAA; wherein the 3'-region has a motif selected from among: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB; wherein the central region has a nucleoside motif selected from among: DDDDDD, DDDDDDD, DDDDDDDD, DDDDDDDDD, DDDDDDDDDD, DXDDDDDDD, DDXDDDDDD, DDDXDDDDD, DDDDXDDDD, DDDDDXDDD, DDDDDDXDD, DDDDDDDXD, DDDDDDDDX, DXXDDDDDD, DDDXXDDDD, DDDDXXDDD, DDDDDXXDD, DXDDDDXD, DXDDDDXDD, DXDDDXDDD, DXDDDXDDD, DXDDXDDDD, DXDXDDDDD, DDXDDDDXD, DDXDDDXDD, DDXDDXDDD, DDXDXDDDD, DDDXDDDXD, DDDXDDXDD, DDDXDXDDD, DDDDXDDXD, DDDDXDXDD, and DDDDDXDXD, DDDDDDDD, DXDDDDDD, DDXDDDDD, DDDXDDDD, DDDDXDDD, DDDDDXDD, DDDDDDXD, DXDDDDXD, DXDDDXDD, DXDDXDDD, DXDXDDDD, DXXDDDDD, DDXXDDDD, DDXDXDDD, DDXDDXDD, DXDDDDXD, DDDXXDDD, DDDXDXDD, DDDXDDXD, DDDDXXDD, DDDDXDXD, and DDDDDXXD, DXDDDDD, DDXDDDD, DDDXDDD, DDDDXDD, DDDDDXD, DXDDDXD, DXDDXDD, DXDXDDD, DXXDDDD, DDXXDDD, DDXDXDD, DDXDDXD, DDDXXDD, DDDXDXD, and DDDDXXD, DXDDDD, DDXDDD, DDDXDD, DXDDXD, DXDDDD, DXXDDD, DXDXDD, DDDXXD; and wherein each A is a modified nucleoside of a first type, each B is a modified nucleoside of a second type, each W is a modified nucleoside of a first type, a second type, or a third type, each D is an unmodified deoxynucleoside, and each X is a modified nucleoside or a modified nucleobase.

Embodiment 205: The oligomeric compound of embodiment 204, wherein the 5'-region has a motif selected from among:
AB, ABB, AAA, BBB, BBBAA, AAB, BAA, BBAA, AABB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, and BBBBAA; and wherein the 3'-region has a BBA motif.

Embodiment 206: The oligomeric compound of embodiment 204 or 205, wherein one of A or B comprises a bicyclic sugar moiety, another of A or B comprises a 2'-MOE sugar moiety, and W comprises a 2-thio-thymidine nucleobase.

Embodiment 207: The oligomeric compound of embodiment 204 or 205, wherein one of A or B comprises a bicyclic sugar moiety, another of A or B comprises a 2'-MOE sugar moiety, and W comprises FHNA.

Embodiment 208: The oligomeric compound of embodiment 204 or 205, wherein one of A or B comprises cEt, another of A or B comprises a 2'-modified sugar moiety, and W comprises a 2-thio-thymidine nucleobase.

Embodiment 209: The oligomeric compound of embodiment 204 or 205, wherein one of A or B comprises cEt, another of A or B comprises a 2'-modified sugar moiety, and W comprises FHNA.

Embodiment 210: The oligomeric compound of embodiment 204 or 205, wherein each A comprises MOE, each B comprises cEt, and each W is selected from among cEt or FHNA.

Embodiment 211: The oligomeric compound of embodiment 204 or 205, wherein each W comprises cEt.

Embodiment 212: The oligomeric compound of embodiment 204 or 205, wherein each W comprises 2-thio-thymidine.

Embodiment 213: The oligomeric compound of embodiment 204 or 205, wherein each W comprises FHNA.

Embodiment 214: The oligomeric compound of any of embodiments 1-213 comprising at least one modified internucleoside linkage.

Embodiment 215: The oligomeric compound of embodiment 214, wherein each internucleoside linkage is a modified internucleoside linkage.

Embodiment 216: The oligomeric compound of embodiment 214 or 215 comprising at least one phosphorothioate internucleoside linkage.

Embodiment 217: The oligomeric compound of any of embodiments 214 or 215 comprising at least one methylphosphonate internucleoside linkage.

Embodiment 218: The oligomeric compound of any of embodiments 214 or 215 comprising one methylphosphonate internucleoside linkage.

Embodiment 219: The oligomeric compound of any of embodiments 214 or 215 comprising two methylphosphonate internucleoside linkages.

Embodiment 220: The oligomeric compound of embodiment 217, wherein at least one of the $3^{rd}$, $4^{th}$, $5^{th}$, $6^{th}$ and/or $7^{th}$ internucleoside from the 5'-end is a methylphosphonate internucleoside linkage.

Embodiment 221: The oligomeric compound of embodiment 217, wherein at least one of the $3^{rd}$, $4^{th}$, $5^{th}$, $6^{th}$ and/or $7^{th}$ internucleoside from the 3'-end is a methylphosphonate internucleoside linkage.

Embodiment 222: The oligomeric compound of embodiment 217, wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 5'-end is a methylphosphonate internucleoside linkage, and wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 5'-end is a modified nucleoside.

Embodiment 223: The oligomeric compound of embodiment 217, wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 3'-end is a methylphosphonate internucleoside linkage, and wherein at least one of the $3^{rd}$, $4^{th}$, $5^{th}$, $6^{th}$, $7^{th}$, $8^{th}$, $9^{th}$, $10^{th}$, $11^{th}$, and/or $12^{th}$ internucleoside from the 3'-end is a modified nucleoside.

Embodiment 224: The oligomeric compound of any of embodiments 1-223 comprising at least one conjugate group.

Embodiment 225: The oligomeric compound of embodiment 1-223, wherein the conjugate group consists of a conjugate.

Embodiment 226: The oligomeric compound of embodiment 225, wherein the conjugate group consists of a conjugate and a conjugate linker.

Embodiment 227: The oligomeric compound of any of embodiments 1-226, wherein the nucleobase sequence of the modified oligonucleotide is 100% complementary to the nucleobase sequence of the target region of the target nucleic acid.

Embodiment 228: The oligomeric compound of any of embodiments 1-226, wherein the nucleobase sequence of the modified oligonucleotide contains one mismatch relative to the nucleobase sequence of the target region of the target nucleic acid.

Embodiment 229: The oligomeric compound of any of embodiments 1-226, wherein the nucleobase sequence of the modified oligonucleotide contains two mismatches relative to the nucleobase sequence of the target region of the target nucleic acid.

Embodiment 230: The oligomeric compound of any of embodiments 1-226, wherein the nucleobase sequence of the modified oligonucleotide comprises a hybridizing region and at least one non-targeting region, wherein the nucleobase sequence of the hybridizing region is complementary to the nucleobase sequence of the target region of the target nucleic acid.

Embodiment 231: The oligomeric compound of embodiment 230, wherein the nucleobase sequence of the hybridizing region is 100% complementary to the nucleobase sequence of the target region of the target nucleic acid.

Embodiment 232: The oligomeric compound of embodiment 230, wherein the nucleobase sequence of the hybridizing region contains one mismatche relative to the nucleobase sequence of the target region of the target nucleic acid.

Embodiment 233: The oligomeric compound of any of embodiments 230-232, wherein the nucleobase sequence of at least one non-targeting region is complementary to a portion of the hybridizing region of the modified oligonucleotide.

Embodiment 234: The oligomeric compound of embodiment 233, wherein the nucleobase sequence of at least one non-targeting region is 100% complementary to a portion of the hybridizing region of the modified oligonucleotide.

Embodiment 235: The oligomeric compound of embodiment 1-234 wherein the nucleobase sequence of the modified oligonucleotide comprises two non-targeting regions flanking a central hybridizing region.

Embodiment 236: The oligomeric compound of embodiment 235, wherein the two non-targeting regions are complementary to one another.

Embodiment 237: The oligomeric compound of embodiment 236, wherein the two non-targeting regions are 100% complementary to one another.

Embodiment 238: The oligomeric compound of any of embodiments 2-237, wherein the nucleobase sequence of the modified oligonucleotide aligns with the nucleobase of the target region of the target nucleic acid such that a distinguishing nucleobase of the target region of the target nucleic acid aligns with a target-selective nucleoside within the central region of the modified oligonucleotide.

Embodiment 239: The oligomeric compound of any of embodiments 3-237, wherein the nucleobase sequence of the modified oligonucleotide aligns with the nucleobase of the target region of the target nucleic acid such that the single distinguishing nucleobase of the target region of the target nucleic acid aligns with a target-selective nucleoside within the central region of the modified oligonucleotide.

Embodiment 240: The oligomeric compound of embodiment 238 or 239, wherein the target-selective nucleoside is the 5'-most nucleoside of the central region.

Embodiment 241: The oligomeric compound of embodiment 238 or 239, wherein the target-selective nucleoside is the $2^{nd}$ nucleoside from the 5'-end of the central region.

Embodiment 242: The oligomeric compound of embodiment 238 or 239, wherein the target-selective nucleoside is at the $3^{rd}$ nucleoside from the 5'-end of the central region.

Embodiment 243: The oligomeric compound of embodiment 238 or 239, wherein the target-selective nucleoside is at the $5^{th}$ nucleoside from the 5'-end of the central region.

Embodiment 244: The oligomeric compound of embodiment 238 or 239, wherein the target-selective nucleoside is at the $7^{th}$ nucleoside from the 5'-end of the central region.

Embodiment 245: The oligomeric compound of embodiment 238 or 239, wherein the target-selective nucleoside is at the 9' nucleoside from the 5'-end of the central region.

Embodiment 246: The oligomeric compound of any of embodiments 238 or 239, or 241-245, wherein the target-selective nucleoside is at the $2^{nd}$ nucleoside from the 3'-end of the central region.

Embodiment 247: The oligomeric compound of any of embodiments 238 or 239, or 241-245, wherein the target-selective nucleoside is at the $5^{th}$ nucleoside from the 3'-end of the central region.

Embodiment 248: The oligomeric compound of any of embodiments 1-247, wherein target-selective nucleoside is an unmodified deoxynucleoside.

Embodiment 249: The oligomeric compound of any of embodiments 1-247, wherein target-selective nucleoside is a modified nucleoside.

Embodiment 250: The oligomeric compound of embodiment 249, wherein the target-selective nucleoside is a sugar modified nucleoside.

Embodiment 251: The oligomeric compound of embodiment 250, wherein the target-selective nucleoside comprises a sugar modification selected from among: 2'-MOE, 2'-F, 2'-(ara)-F, HNA, FHNA, cEt, and α-L-LNA.

Embodiment 252: The oligomeric compound of any of embodiments 1-251, wherein the target-selective nucleoside comprises a nucleobase modification.

Embodiment 253: The oligomeric compound of embodiment 252, wherein the modified nucleobase is selected from among: a 2-thio pyrimidine and a 5-propyne pyrimidine.

Embodiment 254: The oligomeric compound of any of embodiments 1-253, wherein the oligomeric compound is an antisense compound.

Embodiment 255: The oligomeric compound of embodiment 254, wherein the oligomeric compound selectively reduces expression of the target relative to the non-target.

Embodiment 256: The oligomeric compound of embodiment 255, wherein the oligomeric compound reduces expression of target at least two-fold more than it reduces expression of the non-target.

Embodiment 257: The oligomeric compound of embodiment 256, having an $EC_{50}$ for reduction of expression of target that is at least least two-fold lower than its $EC_{50}$ for reduction of expression of the non-target, when measured in cells.

Embodiment 258: The oligomeric compound of embodiment 256, having an $ED_{50}$ for reduction of expression of target that is at least least two-fold lower than its $ED_{50}$ for reduction of expression of the non-target, when measured in an animal.

Embodiment 259: The oligomeric compound of embodiments 1-10, having an E-E-E-K-K-$(D)_7$-E-E-K motif, wherein each E is a 2'-MOE nucleoside and each K is a cEt nucleoside.

Embodiment 260: A method comprising contacting a cell with an oligomeric compound of any of embodiments 1-259.

Embodiment 261: The method of embodiment 260, wherein the cell is in vitro.

Embodiment 262: The method of embodiment 260, wherein the cell is in an animal.

Embodiment 263: The method of embodiment 262, wherein the animal is a human.

Embodiment 264: The method of embodiment 263, wherein the animal is a mouse.

Embodiment 265: A pharmaceutical composition comprising an oligomeric compound of any of embodiments 1-259 and a pharmaceutically acceptable carrier or diluent.

Embodiment 266: A method of administering a pharmaceutical composition of embodiment 265 to an animal.

Embodiment 267: The method of embodiment 266, wherein the animal is a human.

Embodiment 268: The method of embodiment 266, wherein the animal is a mouse.

Embodiment 269: Use of an oligomeric compound of any of embodiments 1-259 for the preparation of a medicament for the treatment or amelioration of Huntington's disease.

Embodiment 270: A method of ameliorating a symptom of Huntington's disease, comprising administering an oligomeric compound of any of embodiments 1-259 to an animal in need thereof.

Embodiment 271: The method of embodiment 270, wherein the animal is a human.

Embodiment 272: The method of embodiment 270, wherein the animal is a mouse.

In certain embodiments, including but not limited to any of the above numbered embodiments, oligomeric compounds including oligonucleotides described herein are capable of modulating expression of a target RNA. In certain embodiments, the target RNA is associated with a disease or disorder, or encodes a protein that is associated with a disease or disorder. In certain embodiments, the oligomeric compounds or oligonucleotides provided herein modulate the expression of function of such RNA to alleviate one or more symptom of the disease or disorder.

In certain embodiments, oligomeric compounds including oligonucleotides describe herein are useful in vitro. In certain embodiments such oligomeric compounds are used in diagnostics and/or for target validation experiments.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. DEFINITIONS

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position.

Unless otherwise indicated, the fluorine in a 2'-F nucleoside is in the ribo position (replacing the OH of a natural ribose).

As used herein, "2'-(ara)-F" refers to a 2'-F substituted nucleoside, wherein the fluoro group is in the arabino position.

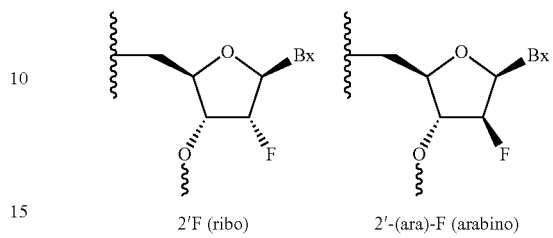

2'F (ribo)      2'-(ara)-F (arabino)

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH($CH_3$)—O-2' bridge.

As used herein, "locked nucleic acid nucleoside" or "LNA" means a nucleoside comprising a bicyclic sugar moiety comprising a 4'-$CH_2$—O-2' bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 3'-endo furanosyl nucleosides and RNA surrogates.

As used herein, "3'-endo-furanosyl nucleoside" means an RNA-like nucleoside that comprises a substituted sugar moiety that has a 3'-endo conformation. 3'-endo-furanosyl nucleosides include, but are not limitied to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a measurable activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound is intended to hybridize.

As used herein, "non-target nucleic acid" means a nucleic acid molecule to which hybridization of an antisense compound is not intended or desired. In certain embodiments, antisense compounds do hybridize to a non-target, due to homology between the target (intended) and non-target (un-intended).

As used herein, "mRNA" means an RNA molecule that encodes a protein.

As used herein, "pre-mRNA" means an RNA transcript that has not been fully processed into mRNA. Pre-RNA includes one or more intron.

As used herein, "object RNA" means an RNA molecule other than a target RNA, the amount, activity, splicing, and/or function of which is modulated, either directly or indirectly, by a target nucleic acid.

In certain embodiments, a target nucleic acid modulates splicing of an object RNA. In certain such embodiments, an antisense compound modulates the amount or activity of the target nucleic acid, resulting in a change in the splicing of an object RNA and ultimately resulting in a change in the activity or function of the object RNA.

As used herein, "microRNA" means a naturally occurring, small, non-coding RNA that represses gene expression of at least one mRNA. In certain embodiments, a microRNA represses gene expression by binding to a target site within a 3' untranslated region of an mRNA. In certain embodiments, a microRNA has a nucleobase sequence as set forth in miRBase, a database of published microRNA sequences found at http://microrna.sanger.ac.uk/sequences/. In certain embodiments, a microRNA has a nucleobase sequence as set forth in miRBase version 12.0 released September 2008, which is herein incorporated by reference in its entirety.

As used herein, "microRNA mimic" means an oligomeric compound having a sequence that is at least partially identical to that of a microRNA. In certain embodiments, a microRNA mimic comprises the microRNA seed region of a microRNA. In certain embodiments, a microRNA mimic modulates translation of more than one target nucleic acids. In certain embodiments, a microRNA mimic is double-stranded.

As used herein, "differentiating nucleobase" means a nucleobase that differs between two nucleic acids. In certain instances, a target region of a target nucleic acid differs by 1-4 nucleobases from a non-target nucleic acid. Each of those differences is referred to as a differentiating nucleobase. In certain instances, a differentiating nucleobase is a single-nucleotide polymorphism.

As used herein, "target-selective nucleoside" means a nucleoside of an antisense compound that corresponds to a differentiating nucleobase of a target nucleic acid.

As used herein, "allele" means one of a pair of copies of a gene existing at a particular locus or marker on a specific chromosome, or one member of a pair of nucleobases existing at a particular locus or marker on a specific chromosome, or one member of a pair of nucleobase sequences existing at a particular locus or marker on a specific chromosome. For a diploid organism or cell or for autosomal chromosomes, each allelic pair will normally occupy corresponding positions (loci) on a pair of homologous chromosomes, one inherited from the mother and one inherited from the father. If these alleles are identical, the organism or cell is said to be "homozygous" for that allele; if they differ, the organism or cell is said to be "heterozygous" for that allele. "Wild-type allele" refers to the genotype typically not associated with disease or dysfunction of the gene product. "Mutant allele" refers to the genotype associated with disease or dysfunction of the gene product.

As used herein, "allelic variant" means a particular identity of an allele, where more than one identity occurs. For example, an allelic variant may refer to either the mutant allele or the wild-type allele.

As used herein, "single nucleotide polymorphism" or "SNP" means a single nucleotide variation between the genomes of individuals of the same species. In some cases, a SNP may be a single nucleotide deletion or insertion. In general, SNPs occur relatively frequently in genomes and thus contribute to genetic diversity. The location of a SNP is generally flanked by highly conserved sequences. An individual may be homozygous or heterozygous for an allele at each SNP site.

As used herein, "single nucleotide polymorphism site" or "SNP site" refers to the nucleotides surrounding a SNP contained in a target nucleic acid to which an antisense compound is targeted.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity under stringent conditions. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "modification motif" means a pattern of chemical modifications in an oligomeric compound or a region thereof. Motifs may be defined by modifications at certain nucleosides and/or at certain linking groups of an oligomeric compound.

As used herein, "nucleoside motif" means a pattern of nucleoside modifications in an oligomeric compound or a region thereof. The linkages of such an oligomeric compound may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligomeric compound or a region thereof.

As used herein, "linkage motif" means a pattern of linkage modifications in an oligomeric compound or region thereof. The nucleosides of such an oligomeric compound may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleoside have "the same type of modification," even though the DNA nucleoside is unmodified. Such nucleosides having the same type modification may comprise different nucleobases.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substuent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)R$_{aa}$), carboxyl (—C(O)O—R$_{aa}$), aliphatic groups, alicyclic groups, alkoxy, substituted oxy (—O—R$_{aa}$), aryl, aralkyl, heterocyclic radical, heteroaryl, heteroarylalkyl, amino (—N(R$_{bb}$)(R$_{cc}$)), imino(=NR$_{bb}$), amido (—C(O)N(R$_{bb}$)(R$_{cc}$) or —N(R$_{bb}$)C(O)R$_{aa}$), azido (—N$_3$), nitro (—NO$_2$), cyano (—CN), carbamido (—OC(O)N(R$_{bb}$)(R$_{cc}$) or —N(R$_{bb}$)C(O)OR$_{aa}$), ureido (—N(R$_{bb}$)C(O)N(R$_{bb}$)(R$_{cc}$)), thioureido (—N(R$_{bb}$)C(S)N(R$_{bb}$)—(R$_{cc}$)), guanidinyl (—N(R$_{bb}$)C(=NR$_{bb}$)N(R$_{bb}$)(R$_{cc}$)), amidinyl (—C(=NR$_{bb}$)N(R$_{bb}$)(R$_{cc}$)

or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S—(O)$_2R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfminyls, aliphatic sulfminyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond.

An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "huntingtin transcript" means a transcript transcribed from a huntingtin gene.

B. OLIGOMERIC COMPOUNDS

In certain embodiments, the present invention provides oligomeric compounds. In certain embodiments, such oligomeric compounds comprise oligonucleotides optionally comprising one or more conjugate and/or terminal groups. In certain embodiments, an oligomeric compound consists of an oligonucleotide. In certain embodiments, oligonucleotides comprise one or more chemical modifications.

Such chemical modifications include modifications of one or more nucleoside (including modifications to the sugar moiety and/or the nucleobase) and/or modifications to one or more internucleoside linkage.

a. Certain Modified Nucleosides

In certain embodiments, provided herein are oligomeric compounds comprising or consisting of oligonucleotides comprising at least one modified nucleoside. Such modified nucleosides comprise a modified sugar moeity, a modified nucleobase, or both a modified sugar moiety and a modified nucleobase.

i. Certain Modified Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substitued sugar moieties. In certain embodiments, modified sugar moieties are sugar surrogates. Such sugar surogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, 2'-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)-alkynyl; O-alkylenyl-O-alkyl, alkynyl, alkaryl, O-alkaryl, O-aralkyl, O(CH$_2$)$_2$SCH$_3$, O—(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$SCH$_3$, O—(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'- CH$_2$-2', 4'-(CH$_2$)$_{2-2',4'}$-(CH$_2$)$_3$-2', 4'-(CH$_2$)—O-2' (LNA); 4'-(CH$_2$)—S-2'; 4'-(CH$_2$)$_2$—O-2' (ENA); 4'- CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008); 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et at, *J. Org. Chem.*, 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Ethylene(methoxy) (4'-(CH ($CH_2OMe$)-O-2') BNA (also referred to as constrained MOE or cMOE) as depicted below.

(A) 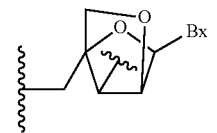

(B) 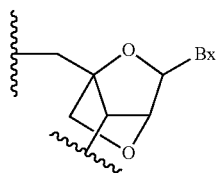

(C) 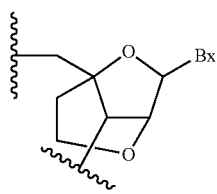

(D) 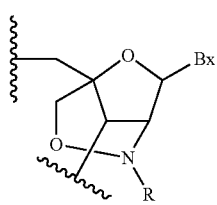

(E) 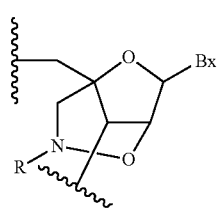

(F) 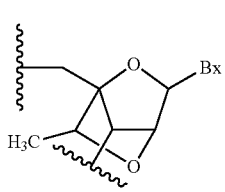

(G) 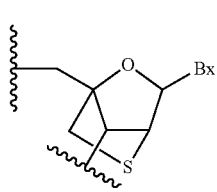

(H) 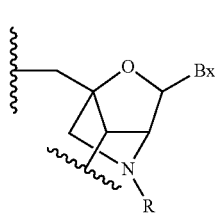

(I) 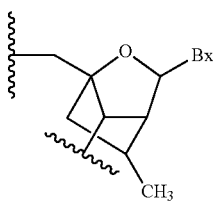

(J) 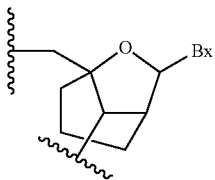

(K) 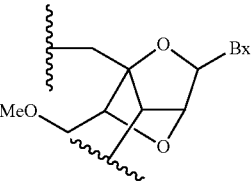

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 129(26) 8362-8379 (Jul. 4, 2007); Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research*, 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research*, 1997, 25(22), 4429-4443 and Albaek et al., *J. Org. Chem.*, 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

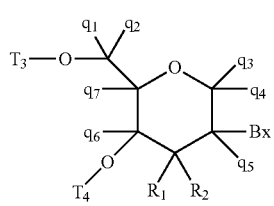

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodmients, oligonucleotides comprise one or more RNA-like nucleosides. In certain embodiments, oligonucleotides comprise one or more DNA-like nucleotides.

ii. Certain Modified Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

b. Certain Internucleoside Linkages

In certain embodiments, nucleosides may be linked together using any internucleoside linkage to form oligonucleotides. The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N'-dimethylhydrazine (—CH$_2$—N(CH$_3$)—N(CH$_3$)—). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-CH$_2$—N(CH$_3$)—O-5'), amide-3 (3'-CH$_2$—C(=O)—N(H)-5'), amide-4 (3'-CH$_2$—N(H)—C(=O)-5'), formacetal (3'-O—CH$_2$—O-5'), and thioformacetal (3'-S—CH$_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and CH$_2$ component parts.

i. 3'-Endo Modifications

In one aspect of the present disclosure, oligomeric compounds include nucleosides synthetically modified to induce a 3'-endo sugar conformation. A nucleoside can incorporate synthetic modifications of the heterocyclic base moiety, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric compounds having one or more nucleosides modified in such a way as to favor a C3'-endo type conformation.

Scheme 1

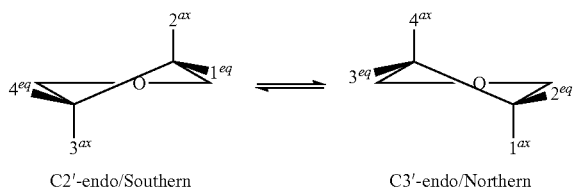

C2'-endo/Southern   C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as exemplified in Example 35, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun. (1998), 4, 455-456), and ethylene bridged nucleic acids (ENA, Morita et al, Bioorganic & Medicinal Chemistry Letters (2002), 12, 73-76.)

c. Certain Motifs

In certain embodiments, oligomeric compounds comprise or consist of oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar motif. Such sugar motifs include but are not limited to any of the sugar modifications discussed herein.

In certain embodiments, the oligonucleotides comprise or consist of a region having a gapmer sugar motif, which comprises two external regions or "wings" and a central or internal region or "gap." The three regions of a gapmer sugar motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap. In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric sugar gapmer). In certain embodiments, the sugar motifs of the 5'-wing differs from the sugar motif of the 3'-wing (asymmetric sugar gapmer).

ii. Certain Nucleobase Modification Motifs

In certain embodiments, oligonucleotides comprise chemical modifications to nucleobases arranged along the oligonucleotide or region thereof in a defined pattern or nucleobases modification motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, oligonucleotides comprise one or more nucleosides comprising a modified nucleobase. In certain embodiments, oligonucleotides having a gapmer sugar motif comprise a nucleoside comprising a modified nucleobase. In certain such embodiments, one nucleoside comprising a modified nucleobases is in the central gap of an oligonucleotide having a gapmer sugar motif. In certain embodiments, the sugar is an unmodified 2'deoxynucleoside. In certain embodiments, the modified nucleobase is selected from: a 2-thio pyrimidine and a 5-propyne pyrimidine In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

iii. Certain Nucleoside Motifs

In certain embodiments, oligonucleotides comprise nucleosides comprising modified sugar moieties and/or nucleosides comprising modified nucleobases. Such motifs can be described by their sugar motif and their nucleobase motif separately or by their nucleoside motif, which provides positions or patterns of modified nucleosides (whether modified sugar, nucleobase, or both sugar and nucleobase) in an oligonucleotide.

In certain embodiments, the oligonucleotides comprise or consist of a region having a gapmer nucleoside motif, which comprises two external regions or "wings" and a central or internal region or "gap." The three regions of a gapmer nucleoside motif (the 5'-wing, the gap, and the 3'-wing) form a contiguous sequence of nucleosides wherein at least some of the sugar moieties and/or nucleobases of the nucleosides of each of the wings differ from at least some of the sugar moieties and/or nucleobase of the nucleosides of the gap. Specifically, at least the nucleosides of each wing that are closest to the gap (the 3'-most nucleoside of the 5'-wing and the 5'-most nucleoside of the 3'-wing) differ from the neighboring gap nucleosides, thus defining the boundary between the wings and the gap. In certain embodiments, the nucleosides within the gap are the same as one another. In certain embodiments, the gap includes one or more nucleoside that differs from one or more other nucleosides of the gap. In certain embodiments, the nucleoside motifs of the two wings are the same as one another (symmetric gapmer). In certain embodiments, the nucleoside motifs of the 5'-wing differs from the nucleoside motif of the 3'-wing (asymmetric gapmer).

iv. Certain 5'-Wings

In certain embodiments, the 5'-wing of a gapmer consists of 1 to 6 linked nucleosides. In certain embodiments, the 5'-wing of a gapmer consists of 1 to 5 linked nucleosides. In certain embodiments, the 5'-wing of a gapmer consists of 2 to 5 linked nucleosides. In certain embodiments, the 5'-wing of a gapmer consists of 3 to 5 linked nucleosides. In certain embodiments, the 5'-wing of a gapmer consists of 4 or 5 linked nucleosides. In certain embodiments, the 5'-wing of a gapmer consists of 1 to 4 linked nucleosides. In certain embodiments, the 5'-wing of a gapmer consists of 1 to 3 linked nucleosides. In certain embodiments, the 5'-wing of a gapmer consists of 1 or 2 linked nucleosides. In certain embodiments, the 5'-wing of a gapmer consists of 2 to 4 linked nucleosides. In certain embodiments, the 5'-wing of a gapmer consists of 2 or 3 linked nucleosides. In certain embodiments, the 5'-wing of a gapmer consists of 3 or 4 linked nucleosides. In certain embodiments, the 5'-wing of a gapmer consists of 1 nucleoside. In certain embodiments, the 5'-wing of a gapmer consists of 2 linked nucleosides. In certain embodiments, the 5'-wing of a gapmer consists of 3 linked nucleosides. In certain embodiments, the 5'-wing of a gapmer consists of 4 linked nucleosides. In certain embodiments, the 5'-wing of a gapmer consists of 5 linked nucleosides. In certain embodiments, the 5'-wing of a gapmer consists of 6 linked nucleosides.

In certain embodiments, the 5'-wing of a gapmer comprises at least one bicyclic nucleoside. In certain embodiments, the 5'-wing of a gapmer comprises at least two bicyclic nucleosides. In certain embodiments, the 5'-wing of a gapmer comprises at least three bicyclic nucleosides. In certain embodiments, the 5'-wing of a gapmer comprises at least four bicyclic nucleosides. In certain embodiments, the 5'-wing of a gapmer comprises at least one constrained ethyl nucleoside. In certain embodiments, the 5'-wing of a gapmer comprises at least one LNA nucleoside. In certain embodiments, each nucleoside of the 5'-wing of a gapmer is a bicyclic nucleoside. In certain embodiments, each nucleoside of the 5'-wing of a gapmer is a constrained ethyl nucleoside. In certain embodiments, each nucleoside of the 5'-wing of a gapmer is a LNA nucleoside.

In certain embodiments, the 5'-wing of a gapmer comprises at least one non-bicyclic modified nucleoside. In certain embodiments, the 5'-wing of a gapmer comprises at least one 2'-substituted nucleoside. In certain embodiments, the 5'-wing of a gapmer comprises at least one 2'-MOE nucleoside. In certain embodiments, the 5'-wing of a gapmer comprises at least one 2'-OMe nucleoside. In certain embodiments, each nucleoside of the 5'-wing of a gapmer is a non-bicyclic modified nucleoside. In certain embodiments, each nucleoside of the 5'-wing of a gapmer is a 2'-substituted nucleoside. In certain embodiments, each nucleoside of the 5'-wing of a gapmer is a 2'-MOE nucleoside. In certain embodiments, each nucleoside of the 5'-wing of a gapmer is a 2'-OMe nucleoside.

In certain embodiments, the 5'-wing of a gapmer comprises at least one 2'-deoxynucleoside. In certain embodiments, each nucleoside of the 5'-wing of a gapmer is a 2'-deoxynucleoside. In a certain embodiments, the 5'-wing of a gapmer comprises at least one ribonucleoside. In certain embodiments, each nucleoside of the 5'-wing of a gapmer is a ribonucleoside. In certain embodiments, one, more than one, or each of the nucleosides of the 5'-wing is an RNA-like nucleoside.

In certain embodiments, the 5'-wing of a gapmer comprises at least one bicyclic nucleoside and at least one non-bicyclic modified nucleoside. In certain embodiments, the 5'-wing of a gapmer comprises at least one bicyclic nucleoside and at least one 2'-substituted nucleoside. In certain embodiments, the 5'-wing of a gapmer comprises at least one bicyclic nucleoside and at least one 2'-MOE nucleoside. In certain embodiments, the 5'-wing of a gapmer comprises at least one bicyclic nucleoside and at least one 2'-OMe nucleoside. In certain embodiments, the 5'-wing of a gapmer comprises at least one bicyclic nucleoside and at least one 2'-deoxynucleoside.

In certain embodiments, the 5'-wing of a gapmer comprises at least one constrained ethyl nucleoside and at least one non-bicyclic modified nucleoside. In certain embodiments, the 5'-wing of a gapmer comprises at least one constrained ethyl nucleoside and at least one 2'-substituted nucleoside. In certain embodiments, the 5'-wing of a gapmer comprises at least one constrained ethyl nucleoside and at least one 2'-MOE nucleoside. In certain embodiments, the 5'-wing of a gapmer comprises at least one constrained ethyl nucleoside and at least one 2'-OMe nucleoside. In certain embodiments, the 5'-wing of a gapmer comprises at least one constrained ethyl nucleoside and at least one 2'-deoxynucleoside.

In certain embodiments, the 5'-wing of a gapmer has a nucleoside motif selected from among the following: ADDA; ABDAA; ABBA; ABB; ABAA; AABAA; AAABAA; AAAABAA; AAAAABAA; AAABAA; AABAA; ABAB; ABADB; ABADDB; AAABB; AAAAA; ABBDC; ABDDC; ABBDCC; ABBDDC; ABBDCC; ABBC; AA; AAA; AAAA; AAAAB; AAAAAAA; AAAAAAAA; ABBB; AB; ABAB; AAAAB; AABBB; AAAAB; and AABBB, wherein each A is a modified nucleoside of a first type, each B is a modified nucleoside of a second type, each C is a modified nucleoside of a third type, and each D is an unmodified deoxynucleoside.

In certain embodiments, the 5'-wing of a gapmer has a nucleoside motif selected from among the following: AB, ABB, AAA, BBB, BBBAA, AAB, BAA, BBAA, AABB, AAAB, ABBW, ABBWW, ABBB, ABBBB, ABAB, ABABAB, ABABBB, ABABAA, AAABB, AAAABB, AABB, AAAAB, AABBB, ABBBB, BBBBB, AAABW, AAAAA, BBBBAA, and AAABW; wherein each A is a modified nucleoside of a first type, each B is a modified nucleoside of a second type, and each W is a modified nucleoside of either the first type, the second type or a third type.

In certain embodiments, the 5'-wing of a gapmer has a nucleoside motif selected from among the following: ABB; ABAA; AABAA; AAABAA; ABAB; ABADB; AAABB; AAAAA; AA; AAA; AAAA; AAAAB; ABBB; AB; and ABAB; wherein each A is a modified nucleoside of a first type, each B is a modified nucleoside of a second type, and each W is a modified nucleoside of either the first type, the second type or a third type.

In certain embodiments, an oligonucleotide comprises any 5'-wing motif provided herein. In certain such embodiments, the oligonucleotide is a 5'-hemimer (does not comprise a 3'-wing). In certain embodiments, such an oligonucleotide is a gapmer. In certain such embodiments, the 3'-wing of the gapmer may comprise any nucleoside motif.

In certain embodiments, the 5'-wing of a gapmer has a sugar motif selected from among those listed in the following non-limiting tables:

TABLE 1

Certain 5'-Wing Sugar Motifs

| Certain 5'-Wing Sugar Motifs | | | | |
|---|---|---|---|---|
| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |

TABLE 1-continued

Certain 5'-Wing Sugar Motifs

| | | | | |
|---|---|---|---|---|
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 2

Certain 5'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |
| BAABA | ACAA | BCBC | BAA | |
| BAABB | ACAB | BCCA | BAB | |
| BABAA | ACAC | BCCB | BAC | |
| BABAB | ACBA | BCCC | BBA | |
| BABBA | ACBB | CAAA | BBB | |
| BABBB | ACBC | CAAB | BBC | |
| BBAAA | ACCA | CAAC | BCA | |
| BBAAB | ACCB | CABA | BCB | |
| BBABA | ACCC | CABB | BCC | |
| BBABB | BAAA | CABC | CAA | |

TABLE 2-continued

Certain 5'-Wing Sugar Motifs

Certain 5'-Wing Sugar Motifs

| | | | |
|---|---|---|---|
| BBBAA | BAAB | CACA | CAB |
| BBBAB | BAAC | CACB | CAC |
| BBBBA | BABA | CACC | CBA |
| BBBBB | BABB | CBAA | CBB |
| AAAA | AACC | CCCC | CBC |
| AAAB | ABAA | AAAA | CCA |
| AAAC | ABAB | AAAB | CCB |
| AABA | ABAC | AABA | CCC |
| AABB | ABBA | AABB | AAA |
| AABC | ABBB | ABAA | AAB |
| AACA | ABBC | ABAB | ABA |
| AACB | ABCA | ABBA | ABB |

In certain embodiments, each A, each B, and each C located at the 3'-most 5'-wing nucleoside is a modified nucleoside. For example, in certain embodiments the 5'-wing motif is selected from among AB<u>B</u>, BB<u>B</u>, and CB<u>B</u>, wherein the underlined nucleoside represents the 3'-most 5'-wing nucleoside and wherein the underlined nucleoside is a modified nucleoside. In certain embodiments, the 3'-most 5'-wing nucleoside comprises a bicyclic sugar moiety selected from among cEt, cMOE, LNA, α-L-LNA, ENA and 2'-thio LNA. In certain embodiments, the 3'-most 5'-wing nucleoside comprises a bicyclic sugar moiety selected from among cEt and LNA. In certain embodiments, the 3'-most 5'-wing nucleoside comprises cEt. In certain embodiments, the 3'-most 5'-wing nucleoside comprises LNA.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises a F-HNA. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises a F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, OCH$_3$ and O(CH$_2$)$_2$—OCH$_3$ and each B comprises a bicyclic sugar moiety selected from among cEt, cMOE, LNA, α-L-LNA, ENA and 2'-thio LNA. In certain embodiments, each A comprises O(CH$_2$)$_2$—OCH$_3$ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me DNA, and 5'-(R)-Me DNA. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

v. Certain 3'-Wings

In certain embodiments, the 3'-wing of a gapmer consists of 1 to 6 linked nucleosides. In certain embodiments, the 3'-wing of a gapmer consists of 1 to 5 linked nucleosides. In certain embodiments, the 3'-wing of a gapmer consists of 2 to 5 linked nucleosides. In certain embodiments, the 3'-wing of a gapmer consists of 3 to 5 linked nucleosides. In certain embodiments, the 3'-wing of a gapmer consists of 4 or 5 linked nucleosides. In certain embodiments, the 3'-wing of a gapmer consists of 1 to 4 linked nucleosides. In certain embodiments, the 3'-wing of a gapmer consists of 1 to 3 linked nucleosides. In certain embodiments, the 3'-wing of a gapmer consists of 1 or 2 linked nucleosides. In certain embodiments, the 3'-wing of a gapmer consists of 2 to 4 linked nucleosides. In certain embodiments, the 3'-wing of a gapmer consists of 2 or 3 linked nucleosides. In certain embodiments, the 3'-wing of a gapmer consists of 3 or 4 linked nucleosides. In certain embodiments, the 3'-wing of a gapmer consists of 1 nucleoside. In certain embodiments, the 3'-wing of a gapmer consists of 2 linked nucleosides. In certain embodiments, the 3'-wing of a gapmer consists of 3 linked nucleosides. In certain embodiments, the 3'-wing of a gapmer consists of 4 linked nucleosides. In certain embodiments, the 3'-wing of a gapmer consists of 5 linked nucleosides. In certain embodiments, the 3'-wing of a gapmer consists of 6 linked nucleosides.

In certain embodiments, the 3'-wing of a gapmer comprises at least one bicyclic nucleoside. In certain embodiments, the 3'-wing of a gapmer comprises at least one constrained ethyl nucleoside. In certain embodiments, the 3'-wing of a gapmer comprises at least one LNA nucleoside. In certain embodiments, each nucleoside of the 3'-wing of a gapmer is a bicyclic nucleoside. In certain embodiments, each nucleoside of the 3'-wing of a gapmer is a constrained ethyl nucleoside. In certain embodiments, each nucleoside of the 3'-wing of a gapmer is a LNA nucleoside.

In certain embodiments, the 3'-wing of a gapmer comprises at least one non-bicyclic modified nucleoside. In certain embodiments, the 3'-wing of a gapmer comprises at least two non-bicyclic modified nucleosides. In certain embodiments, the 3'-wing of a gapmer comprises at least three non-bicyclic modified nucleosides. In certain embodiments, the 3'-wing of a gapmer comprises at least four non-bicyclic modified nucleosides. In certain embodiments, the 3'-wing of a gapmer comprises at least one 2'-substituted nucleoside. In certain embodiments, the 3'-wing of a gapmer comprises at least one 2'-MOE nucleoside. In certain embodiments, the 3'-wing of a gapmer comprises at least one 2'-OMe nucleoside. In certain embodiments, each nucleoside of the 3'-wing of a gapmer is a non-bicyclic modified nucleoside. In certain embodiments, each nucleoside of the 3'-wing of a gapmer is a 2'-substituted nucleoside. In certain embodiments, each nucleoside of the 3'-wing of a gapmer is a 2'-MOE nucleoside. In certain embodiments, each nucleoside of the 3'-wing of a gapmer is a 2'-OMe nucleoside.

In certain embodiments, the 3'-wing of a gapmer comprises at least one 2'-deoxynucleoside. In certain embodiments, each nucleoside of the 3'-wing of a gapmer is a 2'-deoxynucleoside. In a certain embodiments, the 3'-wing of a gapmer comprises at least one ribonucleoside. In certain embodiments, each nucleoside of the 3'-wing of a gapmer is a ribonucleoside. In certain embodiments, one, more than one, or each of the nucleosides of the 5'-wing is an RNA-like nucleoside.

In certain embodiments, the 3'-wing of a gapmer comprises at least one bicyclic nucleoside and at least one non-bicyclic modified nucleoside. In certain embodiments, the 3'-wing of a gapmer comprises at least one bicyclic nucleoside and at least one 2'-substituted nucleoside. In certain embodiments, the 3'-wing of a gapmer comprises at least one bicyclic nucleoside and at least one 2'-MOE nucleoside. In certain embodiments, the 3'-wing of a gapmer comprises at least one bicyclic nucleoside and at least one 2'-OMe nucleoside. In certain embodiments, the 3'-wing of a gapmer comprises at least one bicyclic nucleoside and at least one 2'-deoxynucleoside.

In certain embodiments, the 3'-wing of a gapmer comprises at least one constrained ethyl nucleoside and at least one non-bicyclic modified nucleoside. In certain embodiments, the 3'-wing of a gapmer comprises at least one constrained ethyl nucleoside and at least one 2'-substituted nucleoside. In certain embodiments, the 3'-wing of a gapmer comprises at least one constrained ethyl nucleoside and at least one 2'-MOE nucleoside. In certain embodiments, the 3'-wing of a gapmer comprises at least one constrained ethyl nucleoside and at least one 2'-OMe nucleoside. In certain embodiments, the 3'-wing of a gapmer comprises at least one constrained ethyl nucleoside and at least one 2'-deoxynucleoside.

In certain embodiments, the 3'-wing of a gapmer comprises at least one LNA nucleoside and at least one non-bicyclic modified nucleoside. In certain embodiments, the 3'-wing of a gapmer comprises at least one LNA nucleoside and at least one 2'-substituted nucleoside. In certain embodiments, the 3'-wing of a gapmer comprises at least one LNA nucleoside and at least one 2'-MOE nucleoside. In certain embodiments, the 3'-wing of a gapmer comprises at least one LNA nucleoside and at least one 2'-OMe nucleoside. In certain embodiments, the 3'-wing of a gapmer comprises at least one LNA nucleoside and at least one 2'-deoxynucleoside.

In certain embodiments, the 3'-wing of a gapmer comprises at least one bicyclic nucleoside, at least one non-bicyclic modified nucleoside, and at least one 2'-deoxynucleoside. In certain embodiments, the 3'-wing of a gapmer comprises at least one constrained ethyl nucleoside, at least one non-bicyclic modified nucleoside, and at least one 2'-deoxynucleoside. In certain embodiments, the 3'-wing of a gapmer comprises at least one LNA nucleoside, at least one non-bicyclic modified nucleoside, and at least one 2'-deoxynucleoside.

In certain embodiments, the 3'-wing of a gapmer comprises at least one bicyclic nucleoside, at least one 2'-substituted nucleoside, and at least one 2'-deoxynucleoside. In certain embodiments, the 3'-wing of a gapmer comprises at least one constrained ethyl nucleoside, at least one 2'-substituted nucleoside, and at least one 2'-deoxynucleoside. In certain embodiments, the 3'-wing of a gapmer comprises at least one LNA nucleoside, at least one 2'-substituted nucleoside, and at least one 2'-deoxynucleoside.

In certain embodiments, the 3'-wing of a gapmer comprises at least one bicyclic nucleoside, at least one 2'-MOE nucleoside, and at least one 2'-deoxynucleoside. In certain embodiments, the 3'-wing of a gapmer comprises at least one constrained ethyl nucleoside, at least one 2'-MOE nucleoside, and at least one 2'-deoxynucleoside. In certain embodiments, the 3'-wing of a gapmer comprises at least one LNA nucleoside, at least one 2'-MOE nucleoside, and at least one 2'-deoxynucleoside.

In certain embodiments, the 3'-wing of a gapmer comprises at least one bicyclic nucleoside, at least one 2'-OMe nucleoside, and at least one 2'-deoxynucleoside. In certain embodiments, the 3'-wing of a gapmer comprises at least one constrained ethyl nucleoside, at least one 2'-OMe nucleoside, and at least one 2'-deoxynucleoside. In certain embodiments, the 3'-wing of a gapmer comprises at least one LNA nucleoside, at least one 2'-OMe nucleoside, and at least one 2'-deoxynucleoside.

In certain embodiments, the 3'-wing of a gapmer has a nucleoside motif selected from among the following: ABB, ABAA, AAABAA, AAAAABAA, AABAA, AAAABAA, AAABAA, ABAB, AAAAA, AAABB, AAAAABAA, AAAAAAA, AAAAAA, AAAAB, AAAA, AAA, AA, AB, ABBB, ABAB, AABBB; wherein each A is a modified nucleoside of a first type, each B is a modified nucleoside of a second type. In certain embodiments, an oligonucleotide comprises any 3'-wing motif provided herein. In certain such embodiments, the oligonucleotide is a 3'-hemimer (does not comprise a 5'-wing). In certain embodiments, such an oligonucleotide is a gapmer. In certain such embodiments, the 5'-wing of the gapmer may comprise any nucleoside motif.

In certain embodiments, the 3'-wing of a gapmer has a nucleoside motif selected from among the following: BBA, AAB, AAA, BBB, BBAA, AABB, WBBA, WAAB, BBBA, BBBBA, BBBB, BBBBBA, ABBBBB, BBAAA, AABBB, BBBAA, BBBBA, BBBBB, BABA, AAAAA, BBAAAA, AABBBB, BAAAA, and ABBBB, wherein each A is a modified nucleoside of a first type, each B is a modified nucleoside of a second type, and each W is a modified nucleoside of either the first type, the second type or a third type.

In certain embodiments, the 3'-wing of a gapmer has a nucleoside motif selected from among the following: ABB; AAABAA; AABAA; AAAABAA; AAAAA; AABB; AAAAAAAA; AAAAAAA; AAAAAA; AAAAB; AB;

ABBB; and ABAB, wherein each A is a modified nucleoside of a first type, each B is a modified nucleoside of a second type, and each W is a modified nucleoside of either the first type, the second type or a third type.

In certain embodiments, the 3'-wing of a gapmer has a sugar motif selected from among those listed in the following non-limiting tables:

TABLE 3

Certain 3'-Wing Sugar Motifs

| | | | | |
|---|---|---|---|---|
| AAAAA | ABCBB | BABCC | BCBBA | CBACC |
| AAAAB | ABCBC | BACAA | BCBBB | CBBAA |
| AAAAC | ABCCA | BACAB | BCBBC | CBBAB |
| AAABA | ABCCB | BACAC | BCBCA | CBBAC |
| AAABB | ABCCC | BACBA | BCBCB | CBBBA |
| AAABC | ACAAA | BACBB | BCBCC | CBBBB |
| AAACA | ACAAB | BACBC | BCCAA | CBBBC |
| AAACB | ACAAC | BACCA | BCCAB | CBBCA |
| AAACC | ACABA | BACCB | BCCAC | CBBCB |
| AABAA | ACABB | BACCC | BCCBA | CBBCC |
| AABAB | ACABC | BBAAA | BCCBB | CBCAA |
| AABAC | ACACA | BBAAB | BCCBC | CBCAB |
| AABBA | ACACB | BBAAC | BCCCA | CBCAC |
| AABBB | ACACC | BBABA | BCCCB | CBCBA |
| AABBC | ACBAA | BBABB | BCCCC | CBCBB |
| AABCA | ACBAB | BBABC | CAAAA | CBCBC |
| AABCB | ACBAC | BBACA | CAAAB | CBCCA |
| AABCC | ACBBA | BBACB | CAAAC | CBCCB |
| AACAA | ACBBB | BBACC | CAABA | CBCCC |
| AACAB | ACBBC | BBBAA | CAABB | CCAAA |
| AACAC | ACBCA | BBBAB | CAABC | CCAAB |
| AACBA | ACBCB | BBBAC | CAACA | CCAAC |
| AACBB | ACBCC | BBBBA | CAACB | CCABA |
| AACBC | ACCAA | BBBBB | CAACC | CCABB |
| AACCA | ACCAB | BBBBC | CABAA | CCABC |
| AACCB | ACCAC | BBBCA | CABAB | CCACA |
| AACCC | ACCBA | BBBCB | CABAC | CCACB |
| ABAAA | ACCBB | BBBCC | CABBA | CCACC |
| ABAAB | ACCBC | BBCAA | CABBB | CCBAA |
| ABAAC | ACCCA | BBCAB | CABBC | CCBAB |
| ABABA | ACCCB | BBCAC | CABCA | CCBAC |
| ABABB | ACCCC | BBCBA | CABCB | CCBBA |
| ABABC | BAAAA | BBCBB | CABCC | CCBBB |

TABLE 3-continued

Certain 3'-Wing Sugar Motifs

| | | | | |
|---|---|---|---|---|
| ABACA | BAAAB | BBCBC | CACAA | CCBBC |
| ABACB | BAAAC | BBCCA | CACAB | CCBCA |
| ABACC | BAABA | BBCCB | CACAC | CCBCB |
| ABBAA | BAABB | BBCCC | CACBA | CCBCC |
| ABBAB | BAABC | BCAAA | CACBB | CCCAA |
| ABBAC | BAACA | BCAAB | CACBC | CCCAB |
| ABBBA | BAACB | BCAAC | CACCA | CCCAC |
| ABBBB | BAACC | BCABA | CACCB | CCCBA |
| ABBBC | BABAA | BCABB | CACCC | CCCBB |
| ABBCA | BABAB | BCABC | CBAAA | CCCBC |
| ABBCB | BABAC | BCACA | CBAAB | CCCCA |
| ABBCC | BABBA | BCACB | CBAAC | CCCCB |
| ABCAA | BABBB | BCACC | CBABA | CCCCC |
| ABCAB | BABBC | BCBAA | CBABB | |
| ABCAC | BABCA | BCBAB | CBABC | |
| ABCBA | BABCB | BCBAC | CBACA | |

TABLE 4

Certain 3'-Wing Sugar Motifs

| | | | | |
|---|---|---|---|---|
| AAAAA | BABC | CBAB | ABBB | BAA |
| AAAAB | BACA | CBAC | BAAA | BAB |
| AAABA | BACB | CBBA | BAAB | BBA |
| AAABB | BACC | CBBB | BABA | BBB |
| AABAA | BBAA | CBBC | BABB | AA |
| AABAB | BBAB | CBCA | BBAA | AB |
| AABBA | BBAC | CBCB | BBAB | AC |
| AABBB | BBBA | CBCC | BBBA | BA |
| ABAAA | BBBB | CCAA | BBBB | BB |
| ABAAB | BBBC | CCAB | AAA | BC |
| ABABA | BBCA | CCAC | AAB | CA |
| ABABB | BBCB | CCBA | AAC | CB |
| ABBAA | BBCC | CCBB | ABA | CC |
| ABBAB | BCAA | CCBC | ABB | AA |
| ABBBA | BCAB | CCCA | ABC | AB |
| ABBBB | BCAC | CCCB | ACA | BA |
| BAAAA | ABCB | BCBA | ACB | |
| BAAAB | ABCC | BCBB | ACC | |

TABLE 4-continued

Certain 3'-Wing Sugar Motifs

| Certain 3'-Wing Sugar Motifs | | | |
|---|---|---|---|
| BAABA | ACAA | BCBC | BAA |
| BAABB | ACAB | BCCA | BAB |
| BABAA | ACAC | BCCB | BAC |
| BABAB | ACBA | BCCC | BBA |
| BABBA | ACBB | CAAA | BBB |
| BABBB | ACBC | CAAB | BBC |
| BBAAA | ACCA | CAAC | BCA |
| BBAAB | ACCB | CABA | BCB |
| BBABA | ACCC | CABB | BCC |
| BBABB | BAAA | CABC | CAA |
| BBBAA | BAAB | CACA | CAB |
| BBBAB | BAAC | CACB | CAC |
| BBBBA | BABA | CACC | CBA |
| BBBBB | BABB | CBAA | CBB |
| AAAA | AACC | CCCC | CBC |
| AAAB | ABAA | AAAA | CCA |
| AAAC | ABAB | AAAB | CCB |
| AABA | ABAC | AABA | CCC |
| AABB | ABBA | AABB | AAA |
| AABC | ABBB | ABAA | AAB |
| AACA | ABBC | ABAB | ABA |
| AACB | ABCA | ABBA | ABB |

In certain embodiments, each A, each B, and each C located at the 5'-most 3'-wing region nucleoside is a modified nucleoside. For example, in certain embodiments the 3'-wing motif is selected from among A̲BB, B̲BB, and C̲BB, wherein the underlined nucleoside represents the 5'-most 3'-wing region nucleoside and wherein the underlined nucleoside is a modified nucleoside.

In certain embodiments, each A comprises an unmodified 2'-deoxyfuranose sugar moiety. In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH₃ and O(CH₂)₂—OCH₃. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises a 5'-substituted sugar moiety selected from among 5'-Me DNA, and 5'-(R)-Me DNA.

In certain embodiments, each B comprises an unmodified 2'-deoxyfuranose sugar moiety. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH₃ and O(CH₂)₂—OCH₃. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne uridine nucleoside. In certain embodiments, each B comprises an HNA. In certain embodiments, each B comprises an F-HNA. In certain embodiments, each B comprises a 5'-substituted sugar moiety selected from among 5'-Me DNA, and 5'-(R)-Me DNA.

In certain embodiments, each A comprises a 2'-substituted sugar moiety selected from among F, ara-F, OCH₃ and O(CH₂)₂—OCH₃ and each B comprises a bicyclic sugar moiety selected from among cEt, cMOE, LNA, α-L-LNA, ENA and 2'-thio LNA. In certain embodiments, each A comprises O(CH₂)₂—OCH₃ and each B comprises cEt.

In certain embodiments, each C comprises an unmodified 2'-deoxyfuranose sugar moiety. In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH₃ and O(CH₂)₂—OCH₃. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

vi. Certain Central Regions (gaps)

In certain embodiments, the gap of a gapmer consists of 6 to 20 linked nucleosides. In certain embodiments, the gap of a gapmer consists of 6 to 15 linked nucleosides. In certain embodiments, the gap of a gapmer consists of 6 to 12 linked nucleosides. In certain embodiments, the gap of a gapmer consists of 6 to 10 linked nucleosides. In certain embodiments, the gap of a gapmer consists of 6 to 9 linked nucleosides. In certain embodiments, the gap of a gapmer consists of 6 to 8 linked nucleosides. In certain embodiments, the gap of a gapmer consists of 6 or 7 linked nucleosides. In certain embodiments, the gap of a gapmer consists of 7 to 10 linked nucleosides. In certain embodiments, the gap of a gapmer consists of 7 to 9 linked nucleosides. In certain embodiments, the gap of a gapmer consists of 7 or 8 linked nucleosides. In certain embodiments, the gap of a gapmer consists of 8 to 10 linked nucleosides. In certain embodiments, the gap of a gapmer consists of 8 or 9 linked nucleosides. In certain embodiments, the gap of a gapmer consists of 6 linked nucleosides. In certain embodiments, the gap of a gapmer consists of 7 linked nucleosides. In certain embodiments, the gap of a gapmer consists of 8 linked nucleosides. In certain embodiments, the gap of a gapmer consists of 9 linked nucleosides. In certain embodiments, the gap of a gapmer consists of 10 linked nucleosides. In certain embodiments, the gap of a gapmer consists of 11 linked nucleosides. In certain embodiments, the gap of a gapmer consists of 12 linked nucleosides.

In certain embodiments, each nucleoside of the gap of a gapmer is a 2'-deoxynucleoside. In certain embodiments, the gap comprises one or more modified nucleosides. In certain embodiments, each nucleoside of the gap of a gapmer is a 2'-deoxynucleoside or is a modified nucleoside that is "DNA-like." In such embodiments, "DNA-like" means that the nucleoside has similar characteristics to DNA, such that a duplex comprising the gapmer and an RNA molecule is capable of activating RNase H. For example, under certain conditions, 2'-(ara)-F have been shown to support RNase H activation, and thus is DNA-like. In certain embodiments, one or more nucleosides of the gap of a gapmer is not a 2'-deoxynucleoside and is not DNA-like. In certain such embodiments, the gapmer nonetheless supports RNase H activation (e.g., by virtue of the number or placement of the non-DNA nucleosides).

In certain embodiments, gaps comprise a stretch of unmodified 2'-deoxynucleoside interrupted by one or more modified nucleosides, thus resulting in three sub-regions (two stretches of one or more 2'-deoxynucleosides and a stretch of one or more interrupting modified nucleosides). In certain embodiments, no stretch of unmodified 2'-deoxynucleosides is longer than 5, 6, or 7 nucleotides. In certain embodiments, such short stretches is achieved by using short gap regions. In certain embodiments, short stretches are achieved by interrupting a longer gap region.

In certain embodiments, the gap comprises one or more modified nucleosides. In certain embodiments, the gap comprises one or more modified nucleosides selected from among cEt, FHNA, LNA, and 2-thio-thymidine. In certain embodiments, the gap comprises one modified nucleoside. In certain embodiments, the gap comprises a 5'-substituted sugar moiety selected from among 5'-Me, and 5'-(R)-Me. In certain embodiments, the gap comprises two modified nucleosides. In certain embodiments, the gap comprises three modified nucleosides. In certain embodiments, the gap comprises four modified nucleosides. In certain embodiments, the gap comprises two or more modified nucleosides and each modified nucleoside is the same. In certain embodiments, the gap comprises two or more modified nucleosides and each modified nucleoside is different.

In certain embodiments, the gap comprises one or more modified linkages. In certain embodiments, the gap comprises one or more methyl phosphonate linkages. In certain embodiments the gap comprises two or more modified linkages. In certain embodiments, the gap comprises one or more modified linkages and one or more modified nucleosides. In certain embodiments, the gap comprises one modified linkage and one modified nucleoside. In certain embodiments, the gap comprises two modified linkages and two or more modified nucleosides.

In certain embodiments, the gap comprises a nucleoside motif selected from among the following: DDDDXDDDDD; DDDDDXDDDDD; DDDXDDDDD; DDDDXDDDDD; DDDDXDDDD; DDXDDDDDD; DDDXDDDDD; DXDDXDDD; DDDXDDDXDDD; DDXDDDDDD; DDXDDDXDD; DDDXDDDXDDD; DXDDDXDDD; DDXDDDXDD; DXDDDDXDDD; DDXDDDDXDD; DXDDDDXDD; DDDDXDDD; DDDXDDD; DXDDDDDD; DDDDXXDDD; and DXXDXXDXX; wherein each D is an unmodified deoxynucleoside; and each X is a modified nucleoside or a substituted sugar moiety.

In certain embodiments, the gap comprises a nucleoside motif selected from among the following: DDDDDDDDD; DXDDDDDDD; DDXDDDDDD; DDDXDDDDD; DDDDXDDDD; DDDDDXDDD; DDDDDDXDD; DDDDDDDXD; DXXDDDDDD; DDDDDDDXD; DDXXDDDDD; DDDXXDDDD; DDDDXXDDD; DDDDDXXDD; DXDDDDDXD; DXDDDDXDD; DXDDDXDDD; DXDDXDDDD; DDXDXDDDD; DDXDDXDDD; DDXDDDXDD; DDXDDDDXD; DDDXDXDDD; DDDXDDXDD; DDDXDDDXD; DDDDXDXDD; DDDDXDDXD; and DDDDDXDXD, wherein each D is an unmodified deoxynucleoside; and each X is a modified nucleoside or a substituted sugar moiety.

In certain embodiments, the gap comprises a nucleoside motif selected from among the following: DDDDXDDDD, DXDDDDDDD, DXXDDDDDD, DDXDDDDDD, DDDXDDDDD, DDDDXDDDD, DDDDDXDDD, DDDDDDXDD, and DDDDDDDXD, wherein each D is an unmodified deoxynucleoside; and each X is a modified nucleoside or a substituted sugar moiety.

In certain embodiments, the gap comprises a nucleoside motif selected from among the following: DDDDDDDD, DXDDDDDD, DDXDDDDD, DDDXDDDD, DDDDXDDD, DDDDDXDD, DDDDDDXD, DXDDDDXD, DXDDDXDD, DXDDXDDD, DXDXDDDD, DXXDDDDD, DDXXDDDD, DDXDXDDD, DXDDDXD, DDDXXDDD, DDDXDXDD, DDDXDDXD, DDDDXXDD, DDDDXDXD, and DDDDDXXD, wherein each D is an unmodified deoxynucleoside; and each X is a modified nucleoside or a substituted sugar moiety.

In certain embodiments, the gap comprises a nucleoside motif selected from among the following: DXDDDDD, DDXDDDD, DDDXDDD, DDDDXDD, DDDDDXD, DXDDDXD, DXDDXDD, DXDXDDD, DXXDDDD, DDXXDDD, DDXDXDD, DDXDDXD, DDDXXDD, and DDDXDXD, wherein each D is an unmodified deoxynucleoside; and each X is a modified nucleoside or a substituted sugar moiety.

In certain embodiments, the gap comprises a nucleoside motif selected from among the following: DXDDDD, DDXDDD, DDDXDD, DDDDXD, DXDDDD, DDXDDDD, DDDXDDD, DDDDXDD, DDDDDXD, DXDDDDDD, DDXDDDDD, DDDXDDDD, DDDDXDDD, DDDDDXDD, DDDDDDXD, DXDDDDDDD, DDXDDDDDD, DDDXDDDDD, DDDDXDDDDD, DDDDDXDDD, DDDDDDXDD, DDDDDDDXD, DXDDDDDDDD, DDXDDDDDDD, DDDXDDDDDD, DDDDXDDDDD, DDDDDXDDDD, DDDDDDXDDD, DDDDDDDXDD, and DDDDDDDDXD, wherein each D is an unmodified deoxynucleoside; and each X is a modified nucleoside or a substituted sugar moiety.

In certain embodiments, each X comprises an unmodified 2'-deoxyfuranose sugar moiety. In certain embodiments, each X comprises a modified sugar moiety. In certain embodiments, each X comprises a 2'-substituted sugar moiety. In certain embodiments, each X comprises a 2'-substituted sugar moiety selected from among F, (ara)-F, OCH$_3$ and O(CH$_2$)$_2$—OCH$_3$. In certain embodiments, each X comprises a 5'-substituted sugar moiety. In certain embodiments, each X comprises a 5'-substituted sugar moiety selected from among 5'-Me, and 5'-(R)-Me. In certain embodiments, each X comprises a bicyclic sugar moiety. In certain embodiments, each X comprises a bicyclic sugar moiety selected from among cEt, cMOE, LNA, α-L-LNA, ENA and 2'-thio LNA. In certain embodiments, each X comprises a modified nucleobase. In certain embodiments, each X comprises a modified nucleobase selected from among 2-thio-thymidine and 5-propyne uridine. In certain embodiments, each X comprises a 2-thio-thymidine nucleoside. In certain embodiments, each X comprises an HNA. In certain embodiments, each C comprises an F-HNA. In certain embodiments, X represents the location of a single differentiating nucleobase.

vii. Certain Gapmer Motifs

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among any of those listed in the tables above and any 5'-wing may be paired with any gap and any 3'-wing. For example, in certain embodiments, a 5'-wing may comprise AAABB, a 3'-wing may comprise BBA, and the gap may comprise DDDDDDD. For example, in certain embodiments, a gapmer has a 5'-wing, a gap, and a 3'-wing having features selected from among those listed in the following non-limiting table, wherein each motif is represented as (5'-wing)-(gap)-(3'-wing), wherein each number represents the number of linked nucleosides in each portion of the motif, for example, a 5-10-5 motif would have a 5'-wing comprising 5 nucleosides, a gap comprising 10 nucleosides, and a 3'-wing comprising 5 nucleosides:

TABLE 5

Certain Gapmer Sugar Motifs
Certain Gapmer Sugar Motifs

| | | | |
|---|---|---|---|
| 2-10-2 | 3-10-2 | 4-10-2 | 5-10-2 |
| 2-10-3 | 3-10-3 | 4-10-3 | 5-10-3 |
| 2-10-4 | 3-10-4 | 4-10-4 | 5-10-4 |
| 2-10-5 | 3-10-5 | 4-10-5 | 5-10-5 |
| 2-9-2 | 3-9-2 | 4-9-2 | 5-9-2 |
| 2-9-3 | 3-9-3 | 4-9-3 | 5-9-3 |
| 2-9-4 | 3-9-4 | 4-9-4 | 5-9-4 |
| 2-9-5 | 3-9-5 | 4-9-5 | 5-9-5 |
| 2-11-2 | 3-11-2 | 4-11-2 | 5-11-2 |
| 2-11-3 | 3-11-3 | 4-11-3 | 5-11-3 |
| 2-11-4 | 3-11-4 | 4-11-4 | 5-11-4 |
| 2-11-5 | 3-11-5 | 4-11-5 | 5-11-5 |
| 2-8-2 | 3-8-2 | 4-8-2 | 5-8-2 |
| 2-8-3 | 3-8-3 | 4-8-3 | 5-8-3 |
| 2-8-4 | 3-8-4 | 4-8-4 | 5-8-4 |
| 2-8-5 | 3-8-5 | 4-8-5 | 5-8-5 |

In certain embodiments, a gapmer comprises a 5'-wing, a gap, and a 3' wing, wherein the 5'-wing, gap, and 3' wing are independently selected from among those discussed above. For example, in certain embodiments, a gapmer has a 5'-wing, a gap, and a 3'-wing having features selected from among those listed in the following non-limiting tables:

TABLE 6

Certain Gapmer Nucleoside Motifs

| 5'-wing region | Central gap region | 3'-wing region |
|---|---|---|
| ADDA | DDDDDD | ABB |
| ABBA | DDDADDDD | ABAA |
| AAAAAAA | DDDDDDDDDD | AAA |
| AAAABB | DDDDDDDD | BBAAAA |
| ABB | DDDDADDDD | ABB |

TABLE 6-continued

Certain Gapmer Nucleoside Motifs

| 5'-wing region | Central gap region | 3'-wing region |
|---|---|---|
| ABB | DDDDBDDDD | BBA |
| ABB | DDDDDDDD | BBA |
| AABAA | DDDDDDDD | AABAA |
| ABB | DDDDDD | AABAA |
| AAABAA | DDDDDDDD | AAABAA |
| AAABAA | DDDDDDDD | AAB |
| ABAB | DDDDDDDD | ABAB |
| AAABB | DDDDDDD | BBA |
| ABADB | DDDDDDD | BBA |
| ABA | DBDDDDDD | BBA |
| ABA | DADDDDDD | BBA |
| ABAB | DDDDDDD | BBA |
| AA | DDDDDDD | BBBBBBBB |
| ABB | DDDDDD | ABADB |
| AAAAB | DDDDDDD | BAAAA |
| ABBB | DDDDDDDD | AB |
| AB | DDDDDDDD | BBBA |
| ABBB | DDDDDDDD | BBBA |
| AB | DDDDDDD | ABA |
| ABB | DDDDWDDDD | BBA |
| AAABB | DDDWDDD | BBAAA |
| ABB | DDDDWWDDDD | BBA |
| ABADB | DDDDDDD | BBA |
| ABBDC | DDDDDDD | BBA |
| ABBDDC | DDDDDD | BBA |
| ABBDCC | DDDDDD | BBA |
| ABB | DWWDWWDWW | BBA |
| ABB | DWDDDDDDD | BBA |
| ABB | DDWDDDDDD | BBA |
| ABB | DWWDDDDDD | BBA |
| AAABB | DDWDDDDDD | AA |
| BB | DDWDWDDDD | BBABBBB |
| ABB | DDDD($^N$D)DDDD | BBA |
| AAABB | DDD($^N$D)DDD | BBAAA |
| ABB | DDDD($^N$D)($^N$D)DDD | BBA |
| ABB | D($^N$D)($^N$D)D($^N$D)($^N$D)D($^N$D)($^N$D) | BBA |
| ABB | D($^N$D)DDDDDDD | BBA |
| ABB | DD($^N$D)DDDDDD | BBA |

TABLE 6-continued

Certain Gapmer Nucleoside Motifs

| 5'-wing region | Central gap region | 3'-wing region |
|---|---|---|
| ABB | D($^N$D)($^N$D)DDDDDD | BBA |
| AAABB | DD($^N$D)DDDDDD | AA |
| BB | DD($^N$D)D($^N$D)DDDD | BBABBBB |
| ABAB | DDDDDDDD | BABA |

TABLE 7

Certain Gapmer Nucleoside Motifs

| 5'-wing region | Central gap region | 3'-wing region |
|---|---|---|
| ABBW | DDDDDDD | BBA |
| ABB | DWDDDDDD | BBA |
| ABB | DDWDDDDD | BBA |
| ABB | DDDWDDDD | BBA |
| ABB | DDDDWDDD | BBA |
| ABB | DDDDDWDD | BBA |
| ABB | DDDDDDWD | BBA |
| ABB | DDDDDDD | WBBA |
| ABBWW | DDDDDDD | BBA |
| ABB | DWWDDDDD | BBA |
| ABB | DDWWDDDD | BBA |
| ABB | DDDWWDDD | BBA |
| ABB | DDDDWWDD | BBA |
| ABB | DDDDDWWD | BBA |
| ABB | DDDDDDWD | BBA |
| ABB | DDDDDDD | WWBBA |
| ABBW | DDDDDDD | WBBA |
| ABBW | DDDDDWD | BBA |
| ABBW | DDDDDWDD | BBA |
| ABBW | DDDDWDDD | BBA |
| ABBW | DDDWDDDD | BBA |
| ABBW | DDWDDDDD | BBA |
| ABBW | DWDDDDDD | BBA |
| ABB | DWDDDDDD | WBBA |
| ABB | DWDDDDWD | BBA |
| ABB | DWDDDWDD | BBA |
| ABB | DWDDWDDD | BBA |
| ABB | DWDWDDDD | BBA |

TABLE 7-continued

Certain Gapmer Nucleoside Motifs

| 5'-wing region | Central gap region | 3'-wing region |
|---|---|---|
| ABB | DWDWDDDD | BBA |
| ABB | DDWDDDDD | WBBA |
| ABB | DDWDDDDWD | BBA |
| ABB | DDWDDDWDD | BBA |
| ABB | DDWDDWDDD | BBA |
| ABB | DDWDWDDDD | BBA |
| ABB | DDWWDDDDD | BBA |
| ABB | DDDWDDDD | WBBA |
| ABB | DDDWDDDWD | BBA |
| ABB | DDDWDDWDD | BBA |
| ABB | DDDWDWDDD | BBA |
| ABB | DDDWWDDDD | BBA |
| ABB | DDDDWDDD | WBBA |
| ABB | DDDDWDDWD | BBA |
| ABB | DDDDWDWDD | BBA |
| ABB | DDDDWWDDD | BBA |
| ABB | DDDDDWDD | WBBA |
| ABB | DDDDDWDWD | BBA |
| ABB | DDDDDWWDD | BBA |
| ABB | DDDDDDWD | WBBA |

TABLE 8

Certain Gapmer Nucleoside Motifs

| 5'-wing region | Central gap region | 3'-wing region |
|---|---|---|
| ABBB | DDDDDDD | BBA |
| ABB | DBDDDDDD | BBA |
| ABB | DDBDDDDD | BBA |
| ABB | DDDBDDDD | BBA |
| ABB | DDDDBDDD | BBA |
| ABB | DDDDDBDD | BBA |
| ABB | DDDDDDBD | BBA |
| ABB | DDDDDDD | BBBA |
| ABBBB | DDDDDD | BBA |
| ABB | DBBDDDDD | BBA |
| ABB | DDBBDDDD | BBA |
| ABB | DDDBBDDD | BBA |
| ABB | DDDDBBDD | BBA |

TABLE 8-continued

Certain Gapmer Nucleoside Motifs

| 5'-wing region | Central gap region | 3'-wing region |
|---|---|---|
| ABB | DDDDDBBDD | BBA |
| ABB | DDDDDDBBD | BBA |
| ABB | DDDDDDD | BBBBA |
| ABBB | DDDDDDD | BBBA |
| ABB | DDDDDBD | BBA |
| ABBB | DDDDDBDD | BBA |
| ABBB | DDDBDDD | BBA |
| ABBB | DDDBDDDD | BBA |
| ABBB | DDBDDDDD | BBA |
| ABBB | DBDDDDDD | BBA |
| ABB | DBDDDDD | BBBA |
| ABB | DBDDDDBD | BBA |
| ABB | DBDDDDBDD | BBA |
| ABB | DBDDDBDD | BBA |
| ABB | DBDDBDDD | BBA |
| ABB | DBDBDDDD | BBA |
| ABB | DDBDDDD | BBBA |
| ABB | DDBDDDDBD | BBA |
| ABB | DDBDDDBDD | BBA |
| ABB | DDBDDBDDD | BBA |
| ABB | DDBDBDDDD | BBA |
| ABB | DDBBDDDD | BBA |
| ABB | DDDBDDD | BBBA |
| ABB | DDDBDDDBD | BBA |
| ABB | DDDBDDBDD | BBA |
| ABB | DDDBDBDDD | BBA |
| ABB | DDDBBDDDD | BBA |
| ABB | DDDDBDDD | BBBA |
| ABB | DDDDBDDBD | BBA |
| ABB | DDDDBDBDD | BBA |
| ABB | DDDDBBDDD | BBA |
| ABB | DDDDDBDD | BBBA |
| ABB | DDDDDBDBD | BBA |
| ABB | DDDDDBBDD | BBA |
| ABB | DDDDDDBD | BBBA |

TABLE 9

Certain Gapmer Nucleoside Motifs

| 5'-wing region | Central gap region | 3'-wing region |
|---|---|---|
| ABB | DDDDDDDD | BBA |
| AB | DBDDDDDDD | BBA |
| AB | DDBDDDDDD | BBA |
| AB | DDDBDDDDD | BBA |
| AB | DDDDBDDDD | BBA |
| AB | DDDDDBDDD | BBA |
| AB | DDDDDDBDD | BBA |
| AB | DDDDDDDBD | BBA |
| AB | DDDDDDDBD | BBA |
| AB | DDDDDDDDBD | BBA |
| AB | DDDDDDDD | BBBA |
| ABBB | DDDDDDD | BBA |
| AB | DBBDDDDDD | BBA |
| AB | DDBBDDDDD | BBA |
| AB | DDDBBDDDD | BBA |
| AB | DDDDBBDDD | BBA |
| AB | DDDDDBBDD | BBA |
| AB | DDDDDDBBD | BBA |
| AB | DDDDDDDBBD | BBA |
| AB | DDDDDDD | BBBBA |
| ABBBB | DDDDDDD | BBA |
| AB | DBBBDDDDD | BBA |
| AB | DDBBBDDDD | BBA |
| AB | DDDBBBDDD | BBA |
| AB | DDDDBBBDD | BBA |
| AB | DDDDDBBBD | BBA |
| AB | DDDDDDBBBD | BBA |
| AB | DDDDDDBBBD | BBA |
| AB | DDDDDD | BBBBBA |
| AB | DDDDDDDD | BBBA |
| AB | DDDDDDBD | BBBA |
| AB | DDDDDBDD | BBBA |
| AB | DDDDBDDD | BBBA |
| AB | DDDBDDDD | BBBA |
| AB | DDBDDDDD | BBBA |
| AB | DBDDDDDD | BBBA |
| AB | DDDDDBD | BBBBA |
| AB | DDDDBDD | BBBBA |
| AB | DDDBDDD | BBBBA |
| AB | DDBDDDD | BBBBA |
| AB | DBDDDDD | BBBBA |

TABLE 9-continued

Certain Gapmer Nucleoside Motifs

| 5'-wing region | Central gap region | 3'-wing region |
|---|---|---|
| AB | DDDDBD | BBBBBA |
| AB | DDDBDD | BBBBBA |
| AB | DDBDDD | BBBBBA |
| AB | DBDDDD | BBBBBA |

TABLE 10

Certain Gapmer Nucleoside Motifs

| 5'-wing region | Central gap region | 3'-wing region |
|---|---|---|
| AAAAAA | DDDDDDD | BABA |
| AAAAAB | DDDDDDD | BABA |
| AAAABA | DDDDDDD | BABA |
| AAABAA | DDDDDDD | BABA |
| AABAAA | DDDDDDD | BABA |
| ABAAAA | DDDDDDD | BABA |
| BAAAAA | DDDDDDD | BABA |
| ABAAAB | DDDDDDD | BABA |
| ABAABA | DDDDDDD | BABA |
| ABABAA | DDDDDDD | BABA |
| ABBAAA | DDDDDDD | BABA |
| AABAAB | DDDDDDD | BABA |
| AABABA | DDDDDDD | BABA |
| AABBAA | DDDDDDD | BABA |
| AAABAB | DDDDDDD | BABA |
| AAABBA | DDDDDDD | BABA |
| AAAABB | DDDDDDD | BABA |
| BAAAAB | DDDDDDD | BABA |
| BAAABA | DDDDDDD | BABA |
| BAABAA | DDDDDDD | BABA |
| BABAAA | DDDDDDD | BABA |
| BBAAAA | DDDDDDD | BABA |
| BBBAAA | DDDDDDD | BABA |
| BBABAA | DDDDDDD | BABA |
| BBAABA | DDDDDDD | BABA |
| BBAAAB | DDDDDDD | BABA |
| ABABAB | DDDDDDD | BABA |
| BBBBAA | DDDDDDD | BABA |
| BBBABA | DDDDDDD | BABA |
| BBBAAB | DDDDDDD | BABA |

TABLE 10-continued

Certain Gapmer Nucleoside Motifs

| 5'-wing region | Central gap region | 3'-wing region |
|---|---|---|
| BBBBBA | DDDDDDD | BABA |
| BBBBAB | DDDDDDD | BABA |
| AAABBB | DDDDDDD | BABA |
| AABABB | DDDDDDD | BABA |
| ABAABB | DDDDDDD | BABA |
| BAAABB | DDDDDDD | BABA |
| AABBBB | DDDDDDD | BABA |
| ABABBB | DDDDDDD | BABA |
| BAABBB | DDDDDDD | BABA |
| ABBBBB | DDDDDDD | BABA |
| BABBBB | DDDDDDD | BABA |
| BBBBBB | DDDDDDD | BABA |

TABLE 11

Certain Gapmer Nucleoside Motifs

| 5'-wing region | Central gap region | 3'-wing region |
|---|---|---|
| AAAAA | DDDDDDD | AAAAA |
| AAAAB | DDDDDDD | AAAAA |
| AAABA | DDDDDDD | AAAAA |
| AAABB | DDDDDDD | AAAAA |
| AABAA | DDDDDDD | AAAAA |
| AABAB | DDDDDDD | AAAAA |
| AABBA | DDDDDDD | AAAAA |
| AABBB | DDDDDDD | AAAAA |
| ABAAA | DDDDDDD | AAAAA |
| ABAAB | DDDDDDD | AAAAA |
| ABABA | DDDDDDD | AAAAA |
| ABABB | DDDDDDD | AAAAA |
| ABBAA | DDDDDDD | AAAAA |
| ABBAB | DDDDDDD | AAAAA |
| ABBBA | DDDDDDD | AAAAA |
| ABBBB | DDDDDDD | AAAAA |
| BAAAA | DDDDDDD | AAAAA |
| BAAAB | DDDDDDD | AAAAA |
| BAABA | DDDDDDD | AAAAA |
| BAABB | DDDDDDD | AAAAA |
| BABAA | DDDDDDD | AAAAA |
| BABAB | DDDDDDD | AAAAA |

TABLE 11-continued

Certain Gapmer Nucleoside Motifs

| 5'-wing region | Central gap region | 3'-wing region |
|---|---|---|
| BABBA | DDDDDDD | AAAAA |
| BABBB | DDDDDDD | AAAAA |
| BBAAA | DDDDDDD | AAAAA |
| BBAAB | DDDDDDD | AAAAA |
| BBABA | DDDDDDD | AAAAA |
| BBABB | DDDDDDD | AAAAA |
| BBBAA | DDDDDDD | AAAAA |
| BBBAB | DDDDDDD | AAAAA |
| BBBBA | DDDDDDD | AAAAA |
| BBBBB | DDDDDDD | AAAAA |
| AAAAA | DDDDDDD | BAAAA |
| AAAAB | DDDDDDD | BAAAA |
| AAABA | DDDDDDD | BAAAA |
| AAABB | DDDDDDD | BAAAA |
| AABAA | DDDDDDD | BAAAA |
| AABAB | DDDDDDD | BAAAA |
| AABBA | DDDDDDD | BAAAA |
| AABBB | DDDDDDD | BAAAA |
| ABAAA | DDDDDDD | BAAAA |
| ABAAB | DDDDDDD | BAAAA |
| ABABA | DDDDDDD | BAAAA |
| ABABB | DDDDDDD | BAAAA |
| ABBAA | DDDDDDD | BAAAA |
| ABBAB | DDDDDDD | BAAAA |
| ABBBA | DDDDDDD | BAAAA |
| ABBBB | DDDDDDD | BAAAA |
| BAAAA | DDDDDDD | BAAAA |
| BAAAB | DDDDDDD | BAAAA |
| BAABA | DDDDDDD | BAAAA |
| BAABB | DDDDDDD | BAAAA |
| BABAA | DDDDDDD | BAAAA |
| BABAB | DDDDDDD | BAAAA |
| BABBA | DDDDDDD | BAAAA |
| BABBB | DDDDDDD | BAAAA |
| BBAAA | DDDDDDD | BAAAA |
| BBAAB | DDDDDDD | BAAAA |
| BBABA | DDDDDDD | BAAAA |
| BBABB | DDDDDDD | BAAAA |
| BBBAA | DDDDDDD | BAAAA |
| BBBAB | DDDDDDD | BAAAA |
| BBBBA | DDDDDDD | BAAAA |
| BBBBB | DDDDDDD | BAAAA |
| AAAAA | DDDDDDD | BBAAA |
| AAAAB | DDDDDDD | BBAAA |
| AAABA | DDDDDDD | BBAAA |
| AAABB | DDDDDDD | BBAAA |
| AABAA | DDDDDDD | BBAAA |
| AABAB | DDDDDDD | BBAAA |
| AABBA | DDDDDDD | BBAAA |
| AABBB | DDDDDDD | BBAAA |
| ABAAA | DDDDDDD | BBAAA |
| ABAAB | DDDDDDD | BBAAA |
| ABABA | DDDDDDD | BBAAA |
| ABABB | DDDDDDD | BBAAA |
| ABBAA | DDDDDDD | BBAAA |
| ABBAB | DDDDDDD | BBAAA |
| ABBBA | DDDDDDD | BBAAA |
| ABBBB | DDDDDDD | BBAAA |
| BAAAA | DDDDDDD | BBAAA |
| BAAAB | DDDDDDD | BBAAA |
| BAABA | DDDDDDD | BBAAA |
| BAABB | DDDDDDD | BBAAA |
| BABAA | DDDDDDD | BBAAA |
| BABAB | DDDDDDD | BBAAA |
| BABBA | DDDDDDD | BBAAA |
| BABBB | DDDDDDD | BBAAA |
| BBAAA | DDDDDDD | BBAAA |
| BBAAB | DDDDDDD | BBAAA |
| BBABA | DDDDDDD | BBAAA |
| BBABB | DDDDDDD | BBAAA |
| BBBAA | DDDDDDD | BBAAA |
| BBBAB | DDDDDDD | BBAAA |
| BBBBA | DDDDDDD | BBAAA |
| BBBBB | DDDDDDD | BBAAA |
| AAAAA | DDDDDDD | BBBAA |
| AAAAB | DDDDDDD | BBBAA |

TABLE 11-continued

Certain Gapmer Nucleoside Motifs

| 5'-wing region | Central gap region | 3'-wing region |
|---|---|---|
| AAABA | DDDDDDD | BBBAA |
| AAABB | DDDDDDD | BBBAA |
| AABAA | DDDDDDD | BBBAA |
| AABAB | DDDDDDD | BBBAA |
| AABBA | DDDDDDD | BBBAA |
| AABBB | DDDDDDD | BBBAA |
| ABAAA | DDDDDDD | BBBAA |
| ABAAB | DDDDDDD | BBBAA |
| ABABA | DDDDDDD | BBBAA |
| ABABB | DDDDDDD | BBBAA |
| ABBAA | DDDDDDD | BBBAA |
| ABBAB | DDDDDDD | BBBAA |
| ABBBA | DDDDDDD | BBBAA |
| ABBBB | DDDDDDD | BBBAA |
| BAAAA | DDDDDDD | BBBAA |
| BAAAB | DDDDDDD | BBBAA |
| BAABA | DDDDDDD | BBBAA |
| BAABB | DDDDDDD | BBBAA |
| BABAA | DDDDDDD | BBBAA |
| BABAB | DDDDDDD | BBBAA |
| BABBA | DDDDDDD | BBBAA |
| BABBB | DDDDDDD | BBBAA |
| BBAAA | DDDDDDD | BBBAA |
| BBAAB | DDDDDDD | BBBAA |
| BBABA | DDDDDDD | BBBAA |
| BBABB | DDDDDDD | BBBAA |
| BBBAA | DDDDDDD | BBBAA |
| BBBAB | DDDDDDD | BBBAA |
| BBBBA | DDDDDDD | BBBAA |
| BBBBB | DDDDDDD | BBBAA |
| AAAAA | DDDDDDD | BBBBA |
| AAAAB | DDDDDDD | BBBBA |
| AAABA | DDDDDDD | BBBBA |
| AAABB | DDDDDDD | BBBBA |
| AABAA | DDDDDDD | BBBBA |
| AABAB | DDDDDDD | BBBBA |
| AABBA | DDDDDDD | BBBBA |
| AABBB | DDDDDDD | BBBBA |
| ABAAA | DDDDDDD | BBBBA |
| ABAAB | DDDDDDD | BBBBA |
| ABABA | DDDDDDD | BBBBA |
| ABABB | DDDDDDD | BBBBA |
| ABBAA | DDDDDDD | BBBBA |
| ABBAB | DDDDDDD | BBBBA |
| ABBBA | DDDDDDD | BBBBA |
| ABBBB | DDDDDDD | BBBBA |
| BAAAA | DDDDDDD | BBBBA |
| BAAAB | DDDDDDD | BBBBA |
| BAABA | DDDDDDD | BBBBA |
| BAABB | DDDDDDD | BBBBA |
| BABAA | DDDDDDD | BBBBA |
| BABAB | DDDDDDD | BBBBA |
| BABBA | DDDDDDD | BBBBA |
| BABBB | DDDDDDD | BBBBA |
| BBAAA | DDDDDDD | BBBBA |
| BBAAB | DDDDDDD | BBBBA |
| BBABA | DDDDDDD | BBBBA |
| BBABB | DDDDDDD | BBBBA |
| BBBAA | DDDDDDD | BBBBA |
| BBBAB | DDDDDDD | BBBBA |
| BBBBA | DDDDDDD | BBBBA |
| BBBBB | DDDDDDD | BBBBA |
| AAAAA | DDDDDDD | BBBBB |
| AAAAB | DDDDDDD | BBBBB |
| AAABA | DDDDDDD | BBBBB |
| AAABB | DDDDDDD | BBBBB |
| AABAA | DDDDDDD | BBBBB |
| AABAB | DDDDDDD | BBBBB |
| AABBA | DDDDDDD | BBBBB |
| AABBB | DDDDDDD | BBBBB |
| ABAAA | DDDDDDD | BBBBB |
| ABAAB | DDDDDDD | BBBBB |
| ABABA | DDDDDDD | BBBBB |
| ABABB | DDDDDDD | BBBBB |
| ABBAA | DDDDDDD | BBBBB |
| ABBAB | DDDDDDD | BBBBB |

TABLE 11-continued

Certain Gapmer Nucleoside Motifs

| 5'-wing region | Central gap region | 3'-wing region |
|---|---|---|
| ABBBA | DDDDDDD | BBBBB |
| ABBBB | DDDDDDD | BBBBB |
| BAAAA | DDDDDDD | BBBBB |
| BAAAB | DDDDDDD | BBBBB |
| BAABA | DDDDDDD | BBBBB |
| BAABB | DDDDDDD | BBBBB |
| BABAA | DDDDDDD | BBBBB |
| BABAB | DDDDDDD | BBBBB |
| BABBA | DDDDDDD | BBBBB |
| BABBB | DDDDDDD | BBBBB |
| BBAAA | DDDDDDD | BBBBB |
| BBAAB | DDDDDDD | BBBBB |
| BBABA | DDDDDDD | BBBBB |
| BBABB | DDDDDDD | BBBBB |
| BBBAA | DDDDDDD | BBBBB |
| BBBAB | DDDDDDD | BBBBB |
| BBBBA | DDDDDDD | BBBBB |
| BBBBB | DDDDDDD | BBBBB |

TABLE 12

Certain Gapmer Nucleoside Motifs

| 5'-wing region | Central gap region | 3'-wing region |
|---|---|---|
| AAAW | DDDDDDDD | BBA |
| AABW | DDDDDDDD | BBA |
| ABAW | DDDDDDDD | BBA |
| ABBW | DDDDDDDD | BBA |
| BAAW | DDDDDDDD | BBA |
| BABW | DDDDDDDD | BBA |
| BBAW | DDDDDDDD | BBA |
| BBBW | DDDDDDDD | BBA |
| ABB | DDDDDDDD | WAAA |
| ABB | DDDDDDDD | WAAB |
| ABB | DDDDDDDD | WABA |
| ABB | DDDDDDDD | WABB |
| ABB | DDDDDDDD | WBAA |
| ABB | DDDDDDDD | WBAB |
| ABB | DDDDDDDD | WBBA |
| ABB | DDDDDDDD | WBBB |

TABLE 12-continued

Certain Gapmer Nucleoside Motifs

| 5'-wing region | Central gap region | 3'-wing region |
|---|---|---|
| AAAWW | DDDDDDD | BBA |
| AABWW | DDDDDDD | BBA |
| ABAWW | DDDDDDD | BBA |
| ABBWW | DDDDDDD | BBA |
| BAAWW | DDDDDDD | BBA |
| BABWW | DDDDDDD | BBA |
| BBAWW | DDDDDDD | BBA |
| BBBWW | DDDDDDD | BBA |
| ABB | DDDDDDD | WWAAA |
| ABB | DDDDDDD | WWAAB |
| ABB | DDDDDDD | WWABA |
| ABB | DDDDDDD | WWABB |
| ABB | DDDDDDD | WWBAA |
| ABB | DDDDDDD | WWBAB |
| ABB | DDDDDDD | WWBBA |
| ABB | DDDDDDD | WWBBB |
| AAAAW | DDDDDDD | BBA |
| AAABW | DDDDDDD | BBA |
| AABAW | DDDDDDD | BBA |
| AABBW | DDDDDDD | BBA |
| ABAAW | DDDDDDD | BBA |
| ABABW | DDDDDDD | BBA |
| ABBAW | DDDDDDD | BBA |
| ABBBW | DDDDDDD | BBA |
| BAAAW | DDDDDDD | BBA |
| BAABW | DDDDDDD | BBA |
| BABAW | DDDDDDD | BBA |
| BABBW | DDDDDDD | BBA |
| BBAAW | DDDDDDD | BBA |
| BBABW | DDDDDDD | BBA |
| BBBAW | DDDDDDD | BBA |
| BBBBW | DDDDDDD | WAAAA |
| ABB | DDDDDDD | WAAAB |
| ABB | DDDDDDD | WAABA |
| ABB | DDDDDDD | WAABB |
| ABB | DDDDDDD | WABAA |
| ABB | DDDDDDD | WABAB |
| ABB | DDDDDDD | WABBA |

TABLE 12-continued

Certain Gapmer Nucleoside Motifs

| 5'-wing region | Central gap region | 3'-wing region |
|---|---|---|
| ABB | DDDDDDD | WABBB |
| ABB | DDDDDDD | WBAAA |
| ABB | DDDDDDD | WBAAB |
| ABB | DDDDDDD | WBABA |
| ABB | DDDDDDD | WBABB |
| ABB | DDDDDDD | WBBAA |
| ABB | DDDDDDD | WBBAB |
| ABB | DDDDDDD | WBBBA |
| ABB | DDDDDDD | WBBBB | wherein each A is a modified nucleoside of a first type, each B is a modified nucleoside of a second type and each W is a modified nucleoside or nucleobase of either the first type, the second type or a third type, each D is a nucleoside comprising an unmodified 2'deoxy sugar moiety and unmodified nucleobase, and $^N$D is modified nucleoside comprising a modified nucleobase and an unmodified 2'deoxy sugar moiety.

In certain embodiments, each A comprises a modified sugar moiety. In certain embodiments, each A comprises a 2'-substituted sugar moiety. In certain embodiments, each A comprises a 2'-substituted sugar moiety selected from among F, ara-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each A comprises an HNA. In certain embodiments, each A comprises an F-HNA. In certain embodiments, each A comprises a 5'-substituted sugar moiety selected from among 5'-Me, and 5'-(R)-Me.

In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each B comprises an HNA. In certain embodiments, each B comprises an F-HNA. In certain embodiments, each B comprises a 5'-substituted sugar moiety selected from among 5'-Me, and 5'-(R)-Me.

In certain embodiments, each C comprises a modified sugar moiety. In certain embodiments, each C comprises a 2'-substituted sugar moiety. In certain embodiments, each C comprises a 2'-substituted sugar moiety selected from among F, (ara)-F, OCH$_3$ and O(CH$_2$)$_2$—OCH$_3$. In certain embodiments, each C comprises a 5'-substituted sugar moiety. In certain embodiments, each C comprises a 5'-substituted sugar moiety selected from among 5'-Me, and 5'-(R)-Me. In certain embodiments, each C comprises a bicyclic sugar moiety. In certain embodiments, each C comprises a bicyclic sugar moiety selected from among cEt, cMOE, LNA, α-L-LNA, ENA and 2'-thio LNA. In certain embodiments, each C comprises a modified nucleobase. In certain embodiments, each C comprises a modified nucleobase selected from among 2-thio-thymidine and 5-propyne uridine. In certain embodiments, each C comprises a 2-thio-thymidine nucleoside. In certain embodiments, each C comprises an HNA. In certain embodiments, each C comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, OCH$_3$ and O(CH$_2$)$_2$—OCH$_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F—HNA. In certain embodiments, each W comprises a 2-thio-thymidine nucleoside.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F-HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety. In certain embodiments, a gapmer has a sugar motif other than: E-K-K-$(D)_9$-K-K-E; E-E-E-E-K-$(D)_9$-E-E-E-E-E; E-K-K-K-$(D)_9$-K-K-K-E; K-E-E-K-$(D)_9$-K-E-E-K; K-D-D-K-$(D)_9$-K-D-D-K; K-E-K-E-K-$(D)_9$-K-E-K-E-K; K-D-K-D-K-$(D)_9$-K-D-K-D-K; E-K-E-K-$(D)_9$-K-E-K-E; E-E-E-E-K-$(D)_9$-E-E-E-E-E; or E-K-E-K-E-$(D)_9$-E-K-E-K-E, E-E-E-K-K-$(D)_7$-E-E-K, E-K-E-K-K-K-$(D)_7$-K-E-K-E, E-K-E-K-E-K-$(D)_7$-K-E-K-E, wherein K is a nucleoside comprising a cEt sugar moiety and E is a nucleoside comprising a 2'-MOE sugar moiety.

In certain embodiments a gapmer comprises a A-$(D)_4$-A-$(D)_4$-A-$(D)_4$-AA motif. In certain embodiments a gapmer comprises a B-$(D)_4$-A-$(D)_4$-A-$(D)_4$-AA motif. In certain embodiments a gapmer comprises a A-$(D)_4$-B-$(D)_4$-A-$(D)_4$-AA motif. In certain embodiments a gapmer comprises a A-$(D)_4$-A-$(D)_4$-B-$(D)_4$-AA motif. In certain embodiments a gapmer comprises a A-$(D)_4$-A-$(D)_4$-A-$(D)_4$-BA motif. In certain embodiments a gapmer comprises a A-$(D)_4$-A-$(D)_4$-A-$(D)_4$-BB motif. In certain embodiments a gapmer comprises a K-$(D)_4$-K-$(D)_4$-K-$(D)_4$-K-E motif.

viii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif, as described above for nucleoside motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosphonate linkages. In certain embodiments, one methylphosphonate linkage is in the central gap of an oligonucleotide having a gapmer nucleoside motif.

ix. Certain Modification Motifs

Modification motifs define oligonucleotides by nucleoside motif (sugar motif and nucleobase motif) and linkage motif. For example, certain oligonucleotides have the following modification motif:

$A_sA_sA_sD_sD_sD_sD_s(^ND)_sD_sD_sD_sD_sB_sB_sB$;

wherein each A is a modified nucleoside comprising a 2'-substituted sugar moiety; each D is an unmodified 2'-deoxynucleoside; each B is a modified nucleoside comprising a bicyclic sugar moiety; $^ND$ is a modified nucleoside comprising a modified nucleobase; and s is a phosphorothioate internucleoside linkage. Thus, the sugar motif is a gapmer motif. The nucleobase modification motif is a single modified nucleobase at 8' nucleoside from the 5'-end. Combining the sugar motif and the nucleobase modification motif, the nucleoside motif is an interrupted gapmer where the gap of the sugar modified gapmer is interrupted by a nucleoside comprising a modified nucleobase. The linkage motif is uniform phosphorothioate. The following non-limiting Table further illustrates certain modification motifs:

TABLE 13

Certain Modification Motifs

| 5'-wing region | Central gap region | 3'-wing region |
|---|---|---|
| $B_sB_s$ | $_sD_sD_sD_sD_sD_sD_sD_sD_s$ | $A_sA_sA_sA_sA_sA_sA_sA$ |
| AsBsBs | DsDsDsDsDsDsDsDs | BsBsA |
| AsBsBs | DsDsDsDs($^ND$)sDsDsDsDs | BsBsA |
| AsBsBs | DsDsDsDsAsDsDsDsDs | BsBsA |
| AsBsBs | DsDsDsDsBsDsDsDsDs | BsBsA |
| AsBsBs | DsDsDsDsWsDsDsDsDs | BsBsA |
| AsBsBsBs | DsDsDsDsDsDsDsDs | BsBsAsBsB |
| AsBsBs | DsDsDsDsDsDsDsDs | BsBsAsBsB |
| BsBsAsBsBs | DsDsDsDsDsDsDsDs | BsBsA |
| AsBsBs | DsDsDsDsDsDsDsDs | BsBsAsBsBsBsB |
| AsAsBsAsAs | DsDsDsDsDsDsDsDs | BsBsA |
| AsAsAsBsAsAs | DsDsDsDsDsDsDsDs | BsBsA |
| AsAsBsAsAs | DsDsDsDsDsDsDsDs | AsAsBsAsA |
| AsAsAsBsAsAs | DsDsDsDsDsDsDsDs | AsAsBsAsAsA |
| AsAsAsAsBsAsAs | DsDsDsDsDsDsDsDs | BsBsA |
| AsBsAsBs | DsDsDsDsDsDsDsDs | BsAsBsA |
| AsBsAsBs | DsDsDsDsDsDsDsDs | AsAsBsAsAs |
| AsBsBs | DsDsDsDsDsDsDsDs | BsAsBsA |
| BsBsAsBsBsB | DsDsDsDsDsDsDsDs | BsAsBsA |
| AsAsAsAs | DsDsDsDsDsDsDsDs | AsAsAsAsA |
| AsAsAsAs | DsDsDsDsDsDs | AsAsAsAsA |
| AsAsAsAs | DsDsDsDsDsDsDsDs | BsBsAsBsBsBsB |

TABLE 13-continued

Certain Modification Motifs

| 5'-wing region | Central gap region | 3'-wing region |
|---|---|---|
| AsAsAsBsBs | DsDsDsDsDsDs | BsBsA |
| AsBsAsBs | DsDsDsDsDsDsDs | BsBsA |
| AsBsAsBs | DsDsDsDsDsDs | AsAsAsBsBs |
| AsAsAsAsBs | DsDsDsDsDsDs | BsAsAsAsA |
| BsBs | DsDsDsDsDsDs | AsA |
| AsAs | DsDsDsDsDsDs | AsAsAsAsAsAsA |
| AsAsAs | DsDsDsDsDsDs | AsAsAsAsAsA |
| AsAsAs | DsDsDsDsDsDs | AsAsAsAsA |
| AsBs | DsDsDsDsDsDs | BsBsBsA |
| AsBsBsBs | DsDsDsDsDsDsDs | BsA |
| AsBs | DsDsDsDsDsDsDs | BsBsBsA |
| AsAsAsBsBs | DsDsDs($^N$D)sDsDsDs | BsBsAsAsA |
| AsAsAsBsBs | DsDsDsAsDsDsDs | BsBsAsAsA |
| AsAsAsBsBs | DsDsDsBsDsDsDs | BsBsAsAsA |
| AsAsAsAsBs | DsDsDsDsDsDs | BsBsAsAsA |
| AsAsBsBsBs | DsDsDsDsDsDs | BsBsBsAsA |
| AsAsAsAsBs | DsDsDsDsDsDs | AsAsAsAsAs |
| AsAsAsBsBs | DsDsDsDsDsDs | AsAsAsAsAs |
| AsAsBsBsBs | DsDsDsDsDsDs | AsAsAsAsAs |
| AsAsAsAsAs | DsDsDsDsDsDs | BsAsAsAsAs |
| AsAsAsAsAs | DsDsDsDsDsDs | BsAsAsAsAs |
| AsAsAsAsAs | DsDsDsDsDsDs | BsBsBsAsAs |
| AsBsBs | DsDsDsDs(ND)s($^N$D)sDsDsDs | BsBsA |
| AsBsBs | Ds($^N$D)s($^N$D)sDs($^N$D)s($^N$D)sDs($^N$D)s($^N$D)s | BsBsA |
| AsBsBs | Ds($^N$D)sDsDsDsDsDsDs | BsBsA |
| AsBsBs | DsDs($^N$D)sDsDsDsDsDs | BsBsA |
| AsBsBs | Ds($^N$D)s($^N$D)sDsDsDsDsDs | BsBsA |
| AsBsBs | DsDs(D)zDsDsDsDsDs | BsBsA |
| AsBsBs | Ds(D)zDsDsDsDsDs | BsBsA |
| AsBsBs | (D)zDsDsDsDsDsDs | BsBsA |
| AsBsBs | DsDsAsDsDsDsDsDs | BsBsA |
| AsBsBs | DsDsBsDsDsDsDsDs | BsBsA |
| AsBsBs | AsDsDsDsDsDsDsDs | BsBsA |
| AsBsBs | BsDsDsDsDsDsDsDs | BsBsA |
| AsBsAsBs | DsDs(D)zDsDsDsDsDs | BsBsBsAsAs |
| AsAsAsBsBs | DsDs($^N$D)sDsDsDsDsDs | AsA |
| AsBsBsBs | Ds(D)zDsDsDsDsDsDs | AsAsAsBsBs |
| AsBsBs | DsDsDsDsDsDsDs(D)z | BsBsA |

TABLE 13-continued

Certain Modification Motifs

| 5'-wing region | Central gap region | 3'-wing region |
|---|---|---|
| AsAsBsBsBs | DsDsDsAsDsDsDs | BsBsBsAsA |
| AsAsBsBsBs | DsDsDsBsDsDsDs | BsBsBsAsA |
| AsBsAsBs | DsDsDsAsDsDsDs | BsBsAsBsBsBsB |
| AsBsBsBs | DsDsDsDs(D)zDsDsDsDs | BsA |
| AsAsBsBsBs | DsDsAsAsDsDsDs | BsBsA |
| AsBsBs | DsDsDsDs(D)zDsDsDs | BsBsBsA |
| BsBs | DsDs($^N$D)sDs($^N$D)sDsDsDsDs | BsBsAsBsBsBsB | wherein each A and B are nucleosides comprising differently modified sugar moieties, each D is a nucleoside comprising an unmodified 2'deoxy sugar moiety, each W is a modified nucleoside of either the first type, the second type or a third type, each $^N$D is a modified nucleoside comprising a modified nucleobase, s is a phosphorothioate internucleoside linkage, and z is a non-phosphorothioate internucleoside linkage.

In certain embodiments, each A comprises a modified sugar moiety. In certain embodiments, each A comprises a 2'-substituted sugar moiety. In certain embodiments, each A comprises a 2'-substituted sugar moiety selected from among F, (ara)-F, OCH$_3$ and O(CH$_2$)$_2$—OCH$_3$. In certain embodiments, each A comprises a bicyclic sugar moiety. In certain embodiments, each A comprises a bicyclic sugar moiety selected from among cEt, cMOE, LNA, α-L-LNA, ENA and 2'-thio LNA. In certain embodiments, each A comprises a modified nucleobase. In certain embodiments, each A comprises a modified nucleobase selected from among 2-thio-thymidine nucleoside and 5-propyne uridine nucleoside. In certain embodiments, each B comprises a modified sugar moiety. In certain embodiments, each B comprises a 2'-substituted sugar moiety. In certain embodiments, each B comprises a 2'-substituted sugar moiety selected from among F, (ara)-F, OCH$_3$ and O(CH$_2$)$_2$—OCH$_3$. In certain embodiments, each B comprises a bicyclic sugar moiety. In certain embodiments, each B comprises a bicyclic sugar moiety selected from among cEt, cMOE, LNA, α-L-LNA, ENA and 2'-thio LNA. In certain embodiments, each B comprises a modified nucleobase. In certain embodiments, each B comprises a modified nucleobase selected from among 2-thio-thymidine nucleoside and 5-propyne urindine nucleoside. In certain embodiments, each A comprises an HNA. In certain embodiments, each A comprises an F-HNA.

In certain embodiments, each W comprises a modified sugar moiety. In certain embodiments, each W comprises a 2'-substituted sugar moiety. In certain embodiments, each W comprises a 2'-substituted sugar moiety selected from among F, (ara)-F, OCH$_3$ and O(CH$_2$)$_2$—OCH$_3$. In certain embodiments, each W comprises a 5'-substituted sugar moiety. In certain embodiments, each W comprises a 5'-substituted sugar moiety selected from among 5'-Me, and 5'-(R)-Me. In certain embodiments, each W comprises a bicyclic sugar moiety. In certain embodiments, each W comprises a bicyclic sugar moiety selected from among cEt, cMOE, LNA, α-L-LNA, ENA and 2'-thio LNA. In certain embodiments, each W comprises a sugar surrogate. In certain embodiments, each W comprises a sugar surrogate selected from among HNA and F-HNA.

In certain embodiments, at least one of A or B comprises a bicyclic sugar moiety, and the other comprises a 2'-substituted sugar moiety. In certain embodiments, one of A or B is an LNA nucleoside and the other of A or B comprises a 2'-substituted sugar moiety. In certain embodiments, one of A or B is a cEt nucleoside and the other of A or B comprises a 2'-substituted sugar moiety. In certain embodiments, one of A or B is an α-L-LNA nucleoside and the other of A or B comprises a 2'-substituted sugar moiety. In certain embodiments, one of A or B is an LNA nucleoside and the other of A or B comprises a 2'-MOE sugar moiety. In certain embodiments, one of A or B is a cEt nucleoside and the other of A or B comprises a 2'-MOE sugar moiety. In certain embodiments, one of A or B is an α-L-LNA nucleoside and the other of A or B comprises a 2'-MOE sugar moiety. In certain embodiments, one of A or B is an LNA nucleoside and the other of A or B comprises a 2'-F sugar moiety. In certain embodiments, one of A or B is a cEt nucleoside and the other of A or B comprises a 2'-F sugar moiety. In certain embodiments, one of A or B is an α-L-LNA nucleoside and the other of A or B comprises a 2'-F sugar moiety. In certain embodiments, one of A or B is an LNA nucleoside and the other of A or B comprises a 2'-(ara)-F sugar moiety. In certain embodiments, one of A or B is a cEt nucleoside and the other of A or B comprises a 2'-(ara)-F sugar moiety. In certain embodiments, one of A or B is an α-L-LNA nucleoside and the other of A or B comprises a 2'-(ara)-F sugar moiety.

In certain embodiments, A comprises a bicyclic sugar moiety, and B comprises a 2'-substituted sugar moiety. In certain embodiments, A is an LNA nucleoside and B comprises a 2'-substituted sugar moiety. In certain embodiments, A is a cEt nucleoside and B comprises a 2'-substituted sugar moiety. In certain embodiments, A is an α-L-LNA nucleoside and B comprises a 2'-substituted sugar moiety.

In certain embodiments, A comprises a bicyclic sugar moiety, and B comprises a 2'-MOE sugar moiety. In certain embodiments, A is an LNA nucleoside and B comprises a 2'-MOE sugar moiety. In certain embodiments, A is a cEt nucleoside and B comprises a 2'-MOE sugar moiety. In certain embodiments, A is an α-L-LNA nucleoside and B comprises a 2'-MOE sugar moiety.

In certain embodiments, A comprises a bicyclic sugar moiety, and B comprises a 2'-F sugar moiety. In certain embodiments, A is an LNA nucleoside and B comprises a 2'-F sugar moiety. In certain embodiments, A is a cEt nucleoside and B comprises a 2'-F sugar moiety. In certain embodiments, A is an α-L-LNA nucleoside and B comprises a 2'-F sugar moiety.

In certain embodiments, A comprises a bicyclic sugar moiety, and B comprises a 2'-(ara)-F sugar moiety. In certain embodiments, A is an LNA nucleoside and B comprises a 2'-(ara)-F sugar moiety. In certain embodiments, A is a cEt nucleoside and B comprises a 2'-(ara)-F sugar moiety. In certain embodiments, A is an α-L-LNA nucleoside and B comprises a 2'-(ara)-F sugar moiety.

In certain embodiments, B comprises a bicyclic sugar moiety, and A comprises a 2'-MOE sugar moiety. In certain embodiments, B is an LNA nucleoside and A comprises a 2'-MOE sugar moiety. In certain embodiments, B is a cEt nucleoside and A comprises a 2'-MOE sugar moiety. In certain embodiments, B is an α-L-LNA nucleoside and A comprises a 2'-MOE sugar moiety.

In certain embodiments, B comprises a bicyclic sugar moiety, and A comprises a 2'-F sugar moiety. In certain embodiments, B is an LNA nucleoside and A comprises a 2'-F sugar moiety. In certain embodiments, B is a cEt nucleoside and A comprises a 2'-F sugar moiety. In certain embodiments, B is an α-L-LNA nucleoside and A comprises a 2'-F sugar moiety.

In certain embodiments, B comprises a bicyclic sugar moiety, and A comprises a 2'-(ara)-F sugar moiety. In certain embodiments, B is an LNA nucleoside and A comprises a 2'-(ara)-F sugar moiety. In certain embodiments, B is a cEt nucleoside and A comprises a 2'-(ara)-F sugar moiety. In certain embodiments, B is an α-L-LNA nucleoside and A comprises a 2'-(ara)-F sugar moiety.

In certain embodiments, at least one of A or B comprises a bicyclic sugar moiety, another of A or B comprises a 2'-substituted sugar moiety and W comprises a modified nucleobase. In certain embodiments, one of A or B is an LNA nucleoside, another of A or B comprises a 2'-substituted sugar moiety, and W comprises a modified nucleobase. In certain embodiments, one of A or B is a cEt nucleoside, another of A or B comprises a 2'-substituted sugar moiety, and C comprises a modified nucleobase. In certain embodiments, one of A or B is an α-L-LNA nucleoside, another of A or B comprises a 2'-substituted sugar moiety, and W comprises a modified nucleobase.

In certain embodiments, one of A or B comprises a bicyclic sugar moiety, another of A or B comprises a 2'-MOE sugar moiety, and W comprises a modified nucleobase. In certain embodiments, one of A or B is an LNA nucleoside, another of A or B comprises a 2'-MOE sugar moiety, and W comprises a modified nucleobase. In certain embodiments, one of A or B is a cEt nucleoside, another of A or B comprises a 2'-MOE sugar moiety, and W comprises a modified nucleobase. In certain embodiments, one of A or B is an α-L-LNA nucleoside, another of A or B comprises a 2'-MOE sugar moiety, and W comprises a modified nucleobase.

In certain embodiments, one of A or B comprises a bicyclic sugar moiety, another of A or B comprises a 2'-F sugar moiety, and W comprises a modified nucleobase. In certain embodiments, one of A or B is an LNA nucleoside, another of A or B comprises a 2'-F sugar moiety, and W comprises a modified nucleobase. In certain embodiments, one of A or B is a cEt nucleoside, another of A or B comprises a 2'-F sugar moiety, and W comprises a modified nucleobase. In certain embodiments, one of A or B is an α-L-LNA nucleoside, another of A or B comprises a 2'-F sugar moiety, and W comprises a modified nucleobase.

In certain embodiments, one of A or B comprises a bicyclic sugar moiety, another of A or B comprises a 2'-(ara)-F sugar moiety, and W comprises a modified nucleobase. In certain embodiments, one of A or B is an LNA nucleoside, another of A or B comprises a 2'-(ara)-F sugar moiety, and W comprises a modified nucleobase. In certain embodiments, one of A or B is a cEt nucleoside, another of A or B comprises a 2'-(ara)-F sugar moiety, and W comprises a modified nucleobase. In certain embodiments, one of A or B is an α-L-LNA nucleoside, another of A or B comprises a 2'-(ara)-F sugar moiety, and W comprises a modified nucleobase.

In certain embodiments, one of A or B comprises a bicyclic sugar moiety, another of A or B comprises a 2'-substituted sugar moiety, and W comprises a 2-thio-thymidine nucleobase. In certain embodiments, one of A or B is an LNA nucleoside, another of A or B comprises a 2'-substituted sugar moiety, and W comprises a 2-thio-thymidine nucleobase. In certain embodiments, one of A or B is a cEt nucleoside, another of A or B comprises a 2'-substituted sugar moiety, and W comprises a 2-thio-thymidine nucleobase. In certain embodiments, one of A or B is an α-L-LNA nucleoside, another of A or B comprises a 2'-substituted sugar moiety, and W comprises a 2-thio-thymidine nucleobase.

In certain embodiments, one of A or B comprises a bicyclic sugar moiety, another of A or B comprises a 2'-MOE sugar moiety, and W comprises a 2-thio-thymidine nucleobase. In certain embodiments, one of A or B is an LNA nucleoside, another of A or B comprises a 2'-MOE sugar moiety, and W comprises a 2-thio-thymidine nucleobase. In certain embodiments, one of A or B is a cEt nucleoside, another of A or B comprises a 2'-MOE sugar moiety, and W comprises a 2-thio-thymidine nucleobase. In certain embodiments, one of A or B is an α-L-LNA nucleoside, another of A or B comprises a 2'-MOE sugar moiety, and W comprises a 2-thio-thymidine nucleobase.

In certain embodiments, one of A or B comprises a bicyclic sugar moiety, another of A or B comprises a 2'-F sugar moiety, and W comprises a 2-thio-thymidine nucleobase. In certain embodiments, one of A or B is an LNA nucleoside, another of A or B comprises a 2'-F sugar moiety, and W comprises a 2-thio-thymidine nucleobase. In certain embodiments, one of A or B is a cEt nucleoside, another of A or B comprises a 2'-F sugar moiety, and W comprises a 2-thio-thymidine nucleobase. In certain embodiments, one of A or B is an α-L-LNA nucleoside, another of A or B comprises a 2'-F sugar moiety, and W comprises a 2-thio-thymidine nucleobase.

In certain embodiments, one of A or B comprises a bicyclic sugar moiety, another of A or B comprises a 2'-(ara)-F sugar moiety, and W comprises a 2-thio-thymidine nucleobase. In certain embodiments, one of A or B is an LNA nucleoside, another of A or B comprises a 2'-(ara)-F sugar moiety, and W comprises a 2-thio-thymidine nucleobase. In certain embodiments, one of A or B is a cEt nucleoside, another of A or B comprises a 2'-(ara)-F sugar moiety, and W comprises a 2-thio-thymidine nucleobase. In certain embodiments, one of A or B is an α-L-LNA nucleoside, another of A or B comprises a 2'-(ara)-F sugar moiety, and W comprises 2-thio-thymidine nucleobase.

In certain embodiments, one of A or B comprises a bicyclic sugar moiety, another of A or B comprises a 2'-MOE sugar moiety, and W comprises a 5-propyne uridine nucleobase. In certain embodiments, one of A or B is an LNA nucleoside, another of A or B comprises a 2'-MOE sugar moiety, and C comprises a 5-propyne uridine nucleobase. In certain embodiments, one of A or B is a cEt nucleoside, another of A or B comprises a 2'-MOE sugar moiety, and W comprises a 5-propyne uridine nucleobase. In certain embodiments, one of A or B is an α-L-LNA nucleoside, another of A or B comprises a 2'-MOE sugar moiety, and C comprises a 5-propyne uridine nucleobase.

In certain embodiments, one of A or B comprises a bicyclic sugar moiety, another of A or B comprises a 2'-F sugar moiety, and W comprises a 5-propyne uridine nucleobase. In certain embodiments, one of A or B is an LNA nucleoside, another of A or B comprises a 2'-F sugar moiety, and C comprises a 5-propyne uridine nucleobase. In certain embodiments, one of A or B is a cEt nucleoside, another of A or B comprises a 2'-F sugar moiety, and W comprises a 5-propyne uridine nucleobase. In certain embodiments, one of A or B is an α-L-LNA nucleoside, another of A or B comprises a 2'-F sugar moiety, and W comprises a 5-propyne uridine nucleobase.

In certain embodiments, one of A or B comprises a bicyclic sugar moiety, another of A or B comprises a 2'-(ara)-F sugar moiety, and W comprises a 5-propyne uridine nucleobase. In certain embodiments, one of A or B is an LNA nucleoside, another of A or B comprises a 2'-(ara)-F sugar moiety, and W comprises a 5-propyne uridine nucleobase. In certain embodiments, one of A or B is a cEt nucleoside, another of A or B comprises a 2'-(ara)-F sugar moiety, and W comprises a 5-propyne uridine nucleobase. In certain embodiments, one of A or B is an α-L-LNA nucleoside, another of A or B comprises a 2'-(ara)-F sugar moiety, and W comprises a 5-propyne uridine nucleobase.

In certain embodiments, one of A or B comprises a bicyclic sugar moiety, another of A or B comprises a 2'-MOE sugar moiety, and W comprises a sugar surrogate. In certain embodiments, one of A or B is an LNA nucleoside, another of A or B comprises a 2'-MOE sugar moiety, and W comprises a sugar surrogate. In certain embodiments, one of A or B is a cEt nucleoside, another of A or B comprises a 2'-MOE sugar moiety, and W comprises a sugar surrogate. In certain embodiments, one of A or B is an α-L-LNA nucleoside, another of A or B comprises a 2'-MOE sugar moiety, and W comprises a sugar surrogate.

In certain embodiments, one of A or B comprises a bicyclic sugar moiety, another of A or B comprises a 2'-F sugar moiety, and W comprises a sugar surrogate. In certain embodiments, one of A or B is an LNA nucleoside, another of A or B comprises a 2'-F sugar moiety, and W comprises a sugar surrogate. In certain embodiments, one of A or B is a cEt nucleoside, another of A or B comprises a 2'-F sugar moiety, and W comprises a sugar surrogate. In certain embodiments, one of A or B is an α-L-LNA nucleoside, another of A or B comprises a 2'-F sugar moiety, and W comprises a sugar surrogate.

In certain embodiments, one of A or B comprises a bicyclic sugar moiety, another of A or B comprises a 2'-(ara)-F sugar moiety, and W comprises a sugar surrogate. In certain embodiments, one of A or B is an LNA nucleoside, another of A or B comprises a 2'-(ara)-F sugar moiety, and W comprises a sugar surrogate. In certain embodiments, one of A or B is a cEt nucleoside, another of A or B comprises a 2'-(ara)-F sugar moiety, and W comprises a sugar surrogate. In certain embodiments, one of A or B is an α-L-LNA nucleoside, another of A or B comprises a 2'-(ara)-F sugar moiety, and W comprises sugar surrogate.

In certain embodiments, one of A or B comprises a bicyclic sugar moiety, another of A or B comprises a 2'-MOE sugar moiety, and W comprises a HNA sugar surrogate. In certain embodiments, one of A or B is an LNA nucleoside, another of A or B comprises a 2'-MOE sugar moiety, and W comprises a HNA sugar surrogate. In certain embodiments, one of A or B is a cEt nucleoside, another of A or B comprises a 2'-MOE sugar moiety, and W comprises a HNA sugar surrogate. In certain embodiments, one of A or B is an α-L-LNA nucleoside, another of A or B comprises a 2'-MOE sugar moiety, and W comprises a HNA sugar surrogate.

In certain embodiments, one of A or B comprises a bicyclic sugar moiety, another of A or B comprises a 2'-F sugar moiety, and W comprises a HNA sugar surrogate. In certain embodiments, one of A or B is an LNA nucleoside, another of A or B comprises a 2'-F sugar moiety, and W comprises a HNA sugar surrogate. In certain embodiments, one of A or B is a cEt nucleoside, another of A or B comprises a 2'-F sugar moiety, and W comprises a HNA sugar surrogate. In certain embodiments, one of A or B is an α-L-LNA nucleoside, another of A or B comprises a 2'-F sugar moiety, and W comprises a sugar HNA surrogate.

In certain embodiments, one of A or B comprises a bicyclic sugar moiety, another of A or B comprises a 2'-(ara)-F sugar moiety, and W comprises a HNA sugar surrogate. In certain embodiments, one of A or B is an LNA nucleoside, another of A or B comprises a 2'-(ara)-F sugar moiety, and W comprises a HNA sugar surrogate. In certain embodiments, one of A or B is a cEt nucleoside, another of A or B comprises a 2'-(ara)-F sugar moiety, and W comprises a HNA sugar surrogate. In certain embodiments, one of A or B is an α-L-LNA nucleoside, another of A or B comprises a 2'-(ara)-F sugar moiety, and W comprises a HNA sugar surrogate.

In certain embodiments, one of A or B comprises a bicyclic sugar moiety, another of A or B comprises a 2'-MOE sugar moiety, and W comprises a F-HNA sugar surrogate. In certain embodiments, one of A or B is an LNA nucleoside, another of A or B comprises a 2'-MOE sugar moiety, and W comprises a F—HNA sugar surrogate. In certain embodiments, one of A or B is a cEt nucleoside, another of A or B comprises a 2'-MOE sugar moiety, and W comprises a F-HNA sugar surrogate. In certain embodiments, one of A or B is an α-L-LNA nucleoside, another of A or B comprises a 2'-MOE sugar moiety, and W comprises a F-HNA sugar surrogate.

In certain embodiments, one of A or B comprises a bicyclic sugar moiety, another of A or B comprises a 2'-F sugar moiety, and W comprises a F-HNA sugar surrogate. In certain embodiments, one of A or B is an LNA nucleoside, another of A or B comprises a 2'-F sugar moiety, and W comprises a F-HNA sugar surrogate. In certain embodiments, one of A or B is a cEt nucleoside, another of A or B comprises a 2'-F sugar moiety, and W comprises a F-HNA sugar surrogate. In certain embodiments, one of A or B is an α-L-LNA nucleoside, another of A or B comprises a 2'-F sugar moiety, and W comprises a F-HNA sugar surrogate.

In certain embodiments, one of A or B comprises a bicyclic sugar moiety, another of A or B comprises a 2'-(ara)-F sugar moiety, and W comprises a F-HNA sugar surrogate. In certain embodiments, one of A or B is an LNA nucleoside, another of A or B comprises a 2'-(ara)-F sugar moiety, and W comprises a F-HNA sugar surrogate. In certain embodiments, one of A or B is a cEt nucleoside, another of A or B comprises a 2'-(ara)-F sugar moiety, and W comprises a F-HNA sugar surrogate. In certain embodiments, one of A or B is an α-L-LNA nucleoside, another of A or B comprises a 2'-(ara)-F sugar moiety, and W comprises a F-HNA sugar surrogate.

In certain embodiments, one of A or B comprises a bicyclic sugar moiety, another of A or B comprises a 2'-MOE sugar moiety, and W comprises a 5'-Me DNA sugar moiety. In certain embodiments, one of A or B is an LNA nucleoside, another of A or B comprises a 2'-MOE sugar moiety, and W comprises a 5'-Me DNA sugar moiety. In certain embodiments, one of A or B is a cEt nucleoside, another of A or B comprises a 2'-MOE sugar moiety, and W comprises a 5'-Me DNA sugar moiety. In certain embodiments, one of A or B is an α-L-LNA nucleoside, another of A or B comprises a 2'-MOE sugar moiety, and W comprises a 5'-Me DNA sugar moiety.

In certain embodiments, one of A or B comprises a bicyclic sugar moiety, another of A or B comprises a 2'-F sugar moiety, and W comprises a 5'-Me DNA sugar moiety. In certain embodiments, one of A or B is an LNA nucleoside, another of A or B comprises a 2'-F sugar moiety, and W comprises a 5'-Me DNA sugar moiety. In certain embodiments, one of A or B is a cEt nucleoside, another of A or B comprises a 2'-F sugar moiety, and W comprises a 5'-Me DNA sugar moiety. In certain embodiments, one of A or B is an α-L-LNA nucleoside, another of A or B comprises a 2'-F sugar moiety, and W comprises a 5'-Me DNA sugar moiety.

In certain embodiments, one of A or B comprises a bicyclic sugar moiety, another of A or B comprises a 2'-(ara)-F sugar moiety, and W comprises a 5'-Me DNA sugar moiety. In certain embodiments, one of A or B is an LNA nucleoside, another of A or B comprises a 2'-(ara)-F sugar moiety, and W comprises a 5'-Me DNA sugar moiety. In certain embodiments, one of A or B is a cEt nucleoside, another of A or B comprises a 2'-(ara)-F sugar moiety, and W comprises a 5'-Me DNA sugar moiety. In certain embodiments, one of A or B is an α-L-LNA nucleoside, another of A or B comprises a 2'-(ara)-F sugar moiety, and W comprises a 5'-Me DNA sugar moiety.

In certain embodiments, one of A or B comprises a bicyclic sugar moiety, another of A or B comprises a 2'-MOE sugar moiety, and W comprises a 5'-(R)-Me DNA sugar moiety. In certain embodiments, one of A or B is an LNA nucleoside, another of A or B comprises a 2'-MOE sugar moiety, and W comprises a 5'-(R)-Me DNA sugar moiety. In certain embodiments, one of A or B is a cEt nucleoside, another of A or B comprises a 2'-MOE sugar moiety, and W comprises a 5'-(R)-Me DNA sugar moiety. In certain embodiments, one of A or B is an α-L-LNA nucleoside, another of A or B comprises a 2'-MOE sugar moiety, and W comprises a 5'-(R)-Me DNA sugar moiety.

In certain embodiments, one of A or B comprises a bicyclic sugar moiety, another of A or B comprises a 2'-F sugar moiety, and W comprises a 5'-(R)-Me DNA sugar moiety. In certain embodiments, one of A or B is an LNA nucleoside, another of A or B comprises a 2'-F sugar moiety, and W comprises a 5'-(R)-Me DNA sugar moiety. In certain embodiments, one of A or B is a cEt nucleoside, another of A or B comprises a 2'-F sugar moiety, and W comprises a 5'-(R)-Me DNA sugar moiety. In certain embodiments, one of A or B is an α-L-LNA nucleoside, another of A or B comprises a 2'-F sugar moiety, and W comprises a 5'-(R)-Me DNA sugar moiety.

In certain embodiments, one of A or B comprises a bicyclic sugar moiety, another of A or B comprises a 2'-(ara)-F sugar moiety, and W comprises a 5'-(R)-Me DNA sugar moiety. In certain embodiments, one of A or B is an LNA nucleoside, another of A or B comprises a 2'-(ara)-F sugar moiety, and W comprises a 5'-(R)-Me DNA sugar moiety. In certain embodiments, one of A or B is a cEt nucleoside, another of A or B comprises a 2'-(ara)-F sugar moiety, and W comprises a 5'-(R)-Me DNA sugar moiety. In certain embodiments, one of A or B is an α-L-LNA nucleoside, another of A or B comprises a 2'-(ara)-F sugar moiety, and W comprises a 5'-(R)-Me DNA sugar moiety.

In certain embodiments, at least two of A, B or W comprises a 2'-substituted sugar moiety, and the other comprises a bicyclic sugar moiety. In certain embodiments, at least two of A, B or W comprises a bicyclic sugar moiety, and the other comprises a 2'-substituted sugar moiety.

d. Certain Overall Lengths

In certain embodiments, the present invention provides oligomeric compounds including oligonucleotides of any of a variety of ranges of lengths. In certain embodiments, the invention provides oligomeric compounds or oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, the invention provides oligomeric compounds which comprise oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligomeric compound or oligonucleotide is limited, whether to a range or to a specific number, the oligomeric compound or oligonucleotide may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents. In certain embodiments, a gapmer oligonucleotide has any of the above lengths.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

e. Certain Oligonucleotides

In certain embodiments, oligonucleotides of the present invention are characterized by their modification motif and overall length. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides. Herein if a description of an oligonucleotide or oligomeric compound is silent with respect to one or more parameter, such parameter is not limited. Thus, an oligomeric compound described only as having a gapmer sugar motif without further description may have any length, internucleoside linkage motif, and nucleobase modification motif. Unless otherwise indicated, all chemical modifications are independent of nucleobase sequence.

f. Certain Conjugate Groups

In certain embodiments, oligomeric compounds are modified by attachment of one or more conjugate groups. In general, conjugate groups modify one or more properties of the attached oligomeric compound including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligomeric compound, such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-5-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-tri-iodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides in oligomeric compounds. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligomeric compound. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide of an oligomeric compound. In certain embodiments, conjugate groups are near the 3'-end. In certain embodiments, conjugates are attached at the 3' end of an oligomeric compound, but before one or more terminal group nucleosides. In certain embodiments, conjugate groups are placed within a terminal group. In certain embodiments, the present invention provides oligomeric compounds. In certain embodiments, oligomeric compounds comprise an oligonucleotide. In certain embodiments, an oligomeric compound comprises an oligonucleotide and one or more conjugate and/or terminal groups. Such conjugate and/or terminal groups may be added to oligonucleotides having any of the motifs discussed above. Thus, for example, an oligomeric compound comprising an oligonucleotide having region of alternating nucleosides may comprise a terminal group.

C. ANTISENSE COMPOUNDS

In certain embodiments, oligomeric compounds provided herein are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid non-specific hybridization to any non-target nucleic acid sequences under conditions in which specific hybridization is desired (e.g., under physiological conditions for in vivo or therapeutic uses, and under conditions in which assays are performed in the case of in vitro assays).

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, such oligonucleotides are 90% complementary to the target nucleic acid.

In certain embodiments, such oligonucleotides are 85% complementary to the target nucleic acid. In certain embodiments, such oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

a. Certain Antisense Activities and Mechanisms

In certain antisense activities, hybridization of an antisense compound results in recruitment of a protein that cleaves of the target nucleic acid. For example, certain antisense compounds result in RNase H mediated cleavage of target nucleic acid. RNase H is a cellular endonuclease that cleaves the RNA strand of an RNA:DNA duplex. The "DNA" in such an RNA:DNA duplex, need not be unmodified DNA. In certain embodiments, the invention provides antisense compounds that are sufficiently "DNA-like" to elicit RNase H activity. Such DNA-like antisense compounds include, but are not limited to gapmers having unmodified deoxyfuronose sugar moieties in the nucleosides of the gap and modified sugar moieties in the nucleosides of the wings.

Antisense activities may be observed directly or indirectly. In certain embodiments, observation or detection of an antisense activity involves observation or detection of a change in an amount of a target nucleic acid or protein encoded by such target nucleic acid; a change in the ratio of splice variants of a nucleic acid or protein; and/or a phenotypic change in a cell or animal.

In certain embodiments, compounds comprising oligonucleotides having a gapmer nucleoside motif described herein have desirable properties compared to non-gapmer oligonucleotides or to gapmers having other motifs. In certain circumstances, it is desirable to identify motifs resulting in a favorable combination of potent antisense activity and relatively low toxicity. In certain embodiments, compounds of the present invention have a favorable therapeutic index (measure of activity divided by measure of toxicity).

b. Certain Selective Antisense Compounds

In certain embodiments, antisense compounds provided are selective for a target relative to a non-target nucleic acid. In certain embodiments, the nucleobase sequences of the target and non-target nucleic acids differ by no more than 4 differentiating nucleobases in the targeted region. In certain embodiments, the nucleobase sequences of the target and non-target nucleic acids differ by no more than 3 differentiating nucleobases in the targeted region. In certain embodiments, the nucleobase sequences of the target and non-target nucleic acids differ by no more than 2 differentiating nucleobases in the targeted region. In certain embodiments, the nucleobase sequences of the target and non-target nucleic acids differ by a single differentiating nucleobase in the targeted region. In certain embodiments, the target and non-target nucleic acids are transcripts from different genes. In certain embodiments, the target and non-target nucleic acids are different alleles for the same gene. In certain embodiments, the introduction of a mismatch between an antisense compound and a non-target nucleic acid may alter the RNase H cleavage site of a target nucleic acid compared to a non-target nucleic acid. In certain embodiments, the target and non-target nucleic acids are not functionally related to one another (e.g., are transcripts from different genes). In certain embodiments, the target and not-target nucleic acids are allelic variants of one another. In certain embodiments, the allelic variant contains a single nucleotide polymorphism (SNP). In certain embodiments, a SNP is associated with a mutant allele. In certain embodiments, a mutant SNP is associated with a disease. In certain embodiments, a mutant SNP is associated with a disease, but is not causative of the disease. In certain embodiments, mRNA and protein expression of a mutant allele is associated with disease.

Selectivity of antisense compounds is achieved, principally, by nucleobase complementarity. For example, if an antisense compound has no mismatches for a target nucleic acid and one or more mismatches for a non-target nucleic acid, some amount of selectivity for the target nucleic acid will result. In certain embodiments, provided herein are antisense compounds with enhanced selectivity (i.e. the ratio of activity for the target to the activity for non-target is greater). For example, in certain embodiments, a selective nucleoside comprises a particular feature or combination of features (e.g., chemical modification, motif, placement of selective nucleoside, and/or self-complementary region) that increases selectivity of an antisense compound compared to an antisense compound not having that feature or combination of features. In certain embodiments, such feature or combination of features increases antisense activity for the target. In certain embodiments, such feature or combination of features decreases activity for the target, but decreases activity for the non-target by a greater amount, thus resulting in an increase in selectivity.

Without being limited by mechanism, enhanced selectivity may result from a larger difference in the affinity of an antisense compound for its target compared to its affinity for the non-target and/or a larger difference in RNAse H activity for the resulting duplexes. For example, in certain embodiments, a selective antisense compound comprises a modified nucleoside at that same position as a differentiating nucleobase (i.e., the selective nucleoside is modified). That modification may increase the difference in binding affinity of the antisense compound for the target relative to the non-target. In addition or in the alternative, the chemical modification may increase the difference in RNAse H activity for the duplex formed by the antisense compound and its target compared to the RNase activity for the duplex formed by the antisense compound and the non-target. For example, the modification may exaggerate a structure that is less compatible for RNase H to bind, cleave and/or release the non-target.

In certain embodiments, an antisense compound binds its intended target to form a target duplex. In certain embodiments, RNase H cleaves the target nucleic acid of the target duplex. In certain such embodiments, there is a primary cleavage site between two particular nucleosides of the target nucleic acid (the primary target cleavage site), which accounts for the largest amount of cleavage of the target nucleic acid. In certain nembodiments, there are one or more secondary target cleavage sites. In certain embodiments, the same antisence compound hybridizes to a non-target to form a non-target duplex. In certain such embodiments, the non-target differs from the target by a single nucleobase within the target region, and so the antisense compound hybridizes with a single mismatch. Because of the mismatch, in certain embodiments, RNase H cleavage of the non-target may be reduced compared to cleavage of the target, but still occurs. In certain embodiments, though, the primary site of that cleavage of the non-target nucleic acid (primary non-target cleavage site) is different from that of the target. That is; the primary site is shifted due to the mismatch. In such a circumstance, one may use a modification placed in the antisense compound to disrupt RNase H cleavage at the primary non-target cleavage site. Such modification will result in reduced cleavage of the non-target, but will result little or no decrease in cleavage of the target. In certain embodiments, the modification is a modified sugar, nucleobase and/or linkage.

In certain embodiments, the primary non-target cleavage site is towards the 5'-end of the antisense compound, and the 5'-end of an antisense compound may be modified to prevent RNaseH cleavage. In this manner, it is thought that one having skill in the art may modify the 5'-end of an antisense compound, or modify the nucleosides in the gap region of the 5'-end of the antisense compound, or modify the 3'-most 5'-region nucleosides of the antisense compound to selectively inhibit RNaseH cleavage of the non-target nucleic acid duplex while retaining RNase H cleavage of the target nucleic acid duplex. In certain embodiments, 1-3 of the 3'-most 5'-region nucleosides of the antisense compound comprises a bicyclic sugar moiety.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to the target nucleic acid. The mismatch between the antisense compound and the non-target nucleic acid may destabilize the antisense compound non-target nucleic acid duplex, and consequently the cleavage site of RNaseH may shift upstream towards the 5'-end of the antisense compound. Modification of the 5'-end of the antisense compound or the gap region near the 5'-end of the antisense compound, or one or more of the 3'-most nucleosides of the 5'-wing region, will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more downstream, towards the 3' end of the antisense compound. Accordingly, modifications at the 5'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 3'-most nucleosides of the 5'-wing region comprises a bicyclic sugar moiety. In certain embodiments, one or more of the 3'-most nucleosides of the 5'-wing region comprises a bicyclic sugar moiety selected from cEt and LNA. In certain embodiments, one or more of the 3'-most nucleosides of the 5'-wing region comprises cEt. In certain embodiments, one or more of the 3'-most nucleosides of the 5'-wing region comprises LNA.

In certain embodiments, the introduction of a mismatch between an antisense compound and a target nucleic acid may alter the RNase H cleavage site of a target nucleic acid compared to a non-target nucleic acid by shifting the RNaseH cleavage site downstream from the mismatch site and towards the 3'-end of the antisense compound. In certain embodiments where the cleavage site of a target nucleic acid compared to a non-target nucleic acid has shifted downstream towards the 3'-end of the antisense compound, the 3'-end of an antisense compound may be modified to prevent RNaseH cleavage. In this manner, it is thought that one having skill in the art may modify the 3'-end of an antisense compound, or modify the nucleosides in the gap region near the 3'-end of antisense compound, to selectively inhibit RNaseH cleavage of the non-target nucleic acid while retaining RNase H cleavage of the target nucleic acid.

For example, in certain embodiments the target nucleic acid may have an allelic variant, e.g. a non-target nucleic acid, containing a single nucleotide polymorphism. An antisense compound may be designed having a single nucleobase mismatch from the non-target nucleic acid, but which has full complementarity to target nucleic acid. The mismatch between the antisense compound and the non-target nucleic acid may destabilize the antisense compound-non-target nucleic acid duplex, and consequently the cleavage site of RNaseH may shift downstream towards the 3'-end of the antisense compound. Modification of the 3'-end of the antisense compound, or one or more of the 5'-most nucleosides of the 3'-wing region, or the gap region of the antisense compound near the 3'-end will then prevent RNaseH cleavage of the non-target nucleic acid. Since the target nucleic acid is fully complementary to the antisense compound, the antisense compound and the target nucleic acid will form a more stabilized antisense compound-target nucleic acid duplex and the cleavage site of RnaseH will be more upstream, towards the 5' end of the antisense compound. Accordingly, modifications at the 3'-end of the antisense compound will prevent RNaseH cleavage of the non-target nucleic acid, but will not substantially effect RNaseH cleavage of the target nucleic acid, and selectivity between a target nucleic acid and its allelic variant may be achieved. In certain embodiments, one or more of the 5'-most nucleosides of the 3'-wing region comprises a bicyclic sugar moiety. In certain embodiments, one or more of the 5'-most nucleosides of the 3'-wing region comprises a bicyclic sugar moiety selected from cEt and LNA. In certain embodiments, one or more of the 5'-most nucleosides of the 3'-wing region comprises cEt. In certain embodiments, one or more of the 5'-most nucleosides of the 3'-wing region comprises LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside. In certain embodiments, the selectivity of antisense compounds having certain gaps, e.g. gaps of 7 nucleosides or longer, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

In certain embodiments, the selectivity of antisense compounds having certain gaps, e.g. gaps of 7 nucleosides or longer, may be improved by the addition of one or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two or more bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of one bicyclic nucleoside at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of two bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of three bicyclic nucleosides at the 3'-most 5'-wing nucleoside and the addition of one or more bicyclic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicylic nucleosides at the 5'-most 3'-wing nucleoside. In certain embodiments, the selectivity of antisense compounds having certain gaps, e.g. gaps of 7 nucleosides or longer, may be improved by the addition of four bicyclic nucleosides at the 3'-most 5'-wing nucleoside and the addition of one or more bicylic nucleosides at the 5'-most 3'-wing nucleoside.

In certain embodiments, the selectivity of antisense compounds having certain gaps, e.g. gaps of 7 nucleosides or shorter, may be improved by the addition of one or more bicyclic nucleosides at the 3'-most 5'-wing nucleoside. In certain embodiments, the selectivity of antisense compounds having certain gaps, e.g. gaps of 7 nucleosides or shorter, may be improved by the addition of two or more bicyclic nucleosides at the 3'-most 5'-wing nucleoside. In certain embodiments, the selectivity of antisense compounds having certain gaps, e.g. gaps of 7 nucleosides or shorter, may be improved by the addition of one bicyclic nucleoside at the 3'-most 5'-wing nucleoside. In certain embodiments, the selectivity of antisense compounds having certain gaps, e.g. gaps of 7 nucleosides or shorter, may be improved by the addition of two bicyclic nucleosides at the 3'-most 5'-wing nucleoside. In certain embodiments, the selectivity of antisense compounds having certain gaps, e.g. gaps of 7 nucleosides or shorter, may be improved by the addition of three bicyclic nucleosides at the 3'-most 5'-wing nucleoside. In certain embodiments, the selectivity of antisense compounds having certain gaps, e.g. gaps of 7 nucleosides or shorter, may be improved by the addition of four bicyclic nucleosides at the 3'-most 5'-wing nucleoside. In certain embodiments, the selectivity of antisense compounds having certain gaps, e.g. gaps of 7 nucleosides or shorter, may be improved by the addition of five bicyclic nucleosides at the 3'-most 5'-wing nucleoside. In certain embodiments discussed above, the bicyclic nucleosides at the 3'-most 5'-wing nucleoside are selected from among cEt, cMOE, LNA, α-LNA, ENA and 2'-thio LNA. In certain embodiments discussed above, the bicyclic nucleosides at the 3'-most 5'-wing nucleoside comprise cEt. In certain embodiments discussed above, the bicyclic nucleosides at the 3'-most 5'-wing nucleoside comprise LNA.

Antisense compounds having certain specified motifs have enhanced selectivity, including, but not limited to motifs described above. In certain embodiments, enhanced selectivity is achieved by oligonucleotides comprising any one or more of:

a modification motif comprising a long 5'-wing (longer than 5, 6, or 7 nucleosides);

a modification motif comprising a long 3'-wing (longer than 5, 6, or 7 nucleosides);

a modification motif comprising a short gap region (shorter than 8, 7, or 6 nucleosides); and a modification motif comprising an interrupted gap region (having no uninterrupted stretch of unmodified 2'-deoxynucleosides longer than 7, 6 or 5).

i. Certain Selective Nucleobase Sequence Elements

In certain embodiments, selective antisense compounds comprise nucleobase sequence elements. Such nucleobase sequence elements are independent of modification motifs. Accordingly, oligonucleotides having any of the motifs (modification motifs, nucleoside motifs, sugar motifs, nucleobase modification motifs, and/or linkage motifs) may also comprise one or more of the following nucleobase sequence elements.

ii. Alignment of Differentiating Nucleobase/Target-Selective Nucleoside

In certain embodiments, a target region and a region of a non-target nucleic acid differ by 1-4 differentiating nucleobase. In such embodiments, selective antisense compounds have a nucleobase sequence that aligns with the non-target nucleic acid with 1-4 mismatches. A nucleoside of the antisense compound that corresponds to a differentiating nucleobase of the target nucleic acid is referred to herein as a target-selective nucleoside. In certain embodiments, selective antisense compounds having a gapmer motif align with a non-target nucleic acid, such that a target-selective nucleoside is positioned in the gap. In certain embodiments, a target-selective nucleoside is the $1^{st}$ nucleoside of the gap from the 5' end. In certain embodiments, a target-selective nucleoside is the $2^{nd}$ nucleoside of the gap from the 5' end. In certain embodiments, a target-selective nucleoside is the $3^{rd}$ nucleoside of the gap from the 5'-end. In certain embodiments, a target-selective nucleoside is the $4^{th}$ nucleoside of the gap from the 5'-end. In certain embodiments, a target-selective nucleoside is the $5^{th}$ nucleoside of the gap from the 5'-end. In certain embodiments, a target-selective nucleoside is the $6^{rd}$ nucleoside of the gap from the 5'-end. In certain embodiments, a target-selective nucleoside is the $8^{th}$ nucleoside of the gap from the 3'-end. In certain embodiments, a target-selective nucleoside is the $7^{th}$ nucleoside of the gap from the 3'-end. In certain embodiments, a target-selective nucleoside is the $6^{th}$ nucleoside of the gap from the 3'-end. In certain embodiments, a target-selective nucleoside is the $5^{th}$ nucleoside of the gap from the 3'-end. In certain embodiments, a target-selective nucleoside is the $4^{th}$ nucleoside of the gap from the 3'-end. In certain embodiments, a target-selective nucleoside is the $3^{rd}$ nucleoside of the gap from the 3'-end. In certain embodiments, a target-selective nucleoside is the $2^{nd}$ nucleoside of the gap from the 3'-end.

In certain embodiments, a target-selective nucleoside comprises a modified nucleoside. In certain embodiments, a target-selective nucleoside comprises a modified sugar. In certain embodiments, a target-selective nucleoside comprises a sugar surrogate. In certain embodiments, a target-selective nucleoside comprises a sugar surrogate selected from among HNA and F-HNA. In certain embodiments, a target-selective nucleoside comprises a 2'-substituted sugar moiety. In certain embodiments, a target-selective nucleoside comprises a 2'-substituted sugar moiety selected from among MOE, F and (ara)-F. In certain embodiments, a target-selective nucleoside comprises a 5'-substituted sugar moiety. In certain embodiments, a target-selective nucleoside comprises a 5'-substituted sugar moiety selected from 5'-(R)-Me DNA. In certain embodiments, a target-selective nucleoside comprises a bicyclic sugar moiety. In certain embodiments, a target-selective nucleoside comprises a bicyclic sugar moiety selected from among cEt, and α-L-LNA. In certain embodiments, a target-selective nucleoside comprises a modified nucleobase. In certain embodiments, a target-selective nucleoside comprises a modified nucleobase selected from among 2-thio-thymidine and 5-propyne uridine.

iii. Mismatches to the Target Nucleic Acid

In certain embodiments, selective antisense compounds comprise one or more mismatched nucleobases relative to the target nucleic acid. In certain such embodiments, antisense activity against the target is reduced by such mismatch, but activity against the non-target is reduced by a greater amount. Thus, in certain embodiments selectivity is improved. Any nucleobase other than the differentiating nucleobase is suitable for a mismatch. In certain embodiments, however, the mismatch is specifically positioned within the gap of an oligonucleotide having a gapmer motif. In certain embodiments, a mismatch relative to the target nucleic acid is at positions 1, 2, 3, 4, 5, 6, 7, or 8 from the 5'-end of the gap region. In certain embodiments, a mismatch relative to the target nucleic acid is at positions 9, 8, 7, 6, 5, 4, 3, 2, 1 of the antisense compounds from the 3'-end of the gap region. In certain embodiments, a mismatch relative to the target nucleid acid is at positions 1, 2, 3, or 4 of the antisense compounds from the 5'-end of the wing region. In certain embodiments, a mismatch relative to the target nucleid acid is at positions 4, 3, 2, or 1 of the antisense compounds from the 3'-end of the wing region.

iv. Self Complementary Regions

In certain embodiments, selective antisense compounds comprise a region that is not complementary to the target. In certain embodiments, such region is complementary to another region of the antisense compound. Such regions are referred to herein as self-complementary regions. For example, in certain embodiments, an antisense compound has a first region at one end that is complementary to a second region at the other end. In certain embodiments, one of the first and second regions is complementary to the target nucleic acid. Unless the target nucleic acid also includes a self-complementary region, the other of the first and second region of the antisense compound will not be complementary to the target nucleic acid. For illustrative purposes, certain antisense compounds have the following nucleobase motif:

```
ABCXXXXXXXXXC'B'A';
ABCXXXXXXX(X/C')(X/B')(X/A');
(X/A)(X/B)(X/C)XXXXXXXXXXCXXC'B'A'
``` where each of A, B, and C are any nucleobase; A', B', and C' are the complementary bases to A, B, and C, respectively; each X is a nucleobase complementary to the target nucleic acid; and two letters in parentheses (e.g., (X/C')) indicates that the nucleobase is complementary to the target nucleic acid and to the designated nucleoside within the antisense oligonucleotide.

Without being bound to any mechanism, in certain embodiments, such antisense compounds are expected to form self-structure, which is disrupted upon contact with a target nucleic acid. Contact with a non-target nucleic acid is expected to disrupt the self-structure to a lesser degree, thus increasing selectivity compared to the same antisense compound lacking the self-complementary regions.

v. Combinations of Features

Though it is clear to one of skill in the art, the above motifs and other elements for increasing selectivity may be used alone or in combination. For example, a single antisense compound may include any one, two, three, or more of: self-complementary regions, a mismatch relative to the target nucleic acid, a short nucleoside gap, an interrupted gap, and specific placement of the selective nucleoside.

D. CERTAIN TARGET NUCLEIC ACIDS

In certain embodiments, antisense compounds comprise or consist of an oligonucleotide comprising a region that is complementary to a target nucleic acid. In certain embodiments, the target nucleic acid is an endogenous RNA molecule. In certain embodiments, the target nucleic acid is a non-coding RNA. In certain such embodiments, the target non-coding RNA is selected from: a long-non-coding RNA, a short non-coding RNA, an intronic RNA molecule, a snoRNA, a scaRNA, a microRNA (including pre-micro-RNA and mature microRNA), a ribosomal RNA, and promoter directed RNA. In certain embodiments, the target nucleic acid encodes a protein. In certain such embodiments, the target nucleic acid is selected from: an mRNA and a pre-mRNA, including intronic, exonic and untranslated regions. In certain embodiments, oligomeric compounds are at least partially complementary to more than one target nucleic acid. For example, antisense compounds of the present invention may mimic microRNAs, which typically bind to multiple targets.

In certain embodiments, the target nucleic acid is a nucleic acid other than a mature mRNA. In certain embodiments, the target nucleic acid is a nucleic acid other than a mature mRNA or a microRNA. In certain embodiments, the target nucleic acid is a non-coding RNA other than a microRNA. In certain embodiments, the target nucleic acid is a non-coding RNA other than a microRNA or an intronic region of a pre-mRNA. In certain embodiments, the target nucleic acid is a long non-coding RNA. In certain embodiments, the target RNA is an mRNA. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron. In certain embodiments, the target nucleic acid is selected from among non-coding RNA, including exonic regions of pre-mRNA. In certain embodiments, the target nucleic acid is a ribosomal RNA (rRNA). In certain embodiments, the target nucleic acid is a non-coding RNA associated with splicing of other pre-mRNAs. In certain embodiments, the target nucleic acid is a nuclear-retained non-coding RNA.

In certain embodiments, antisense compounds described herein are complementary to a target nucleic acid comprising a single-nucleotide polymorphism. In certain such embodiments, the antisense compound is capable of modulating expression of one allele of the single-nucleotide polymorphism-containing-target nucleic acid to a greater or lesser extent than it modulates another allele. In certain embodiments an antisense compound hybridizes to a single-nucleotide polymorphism-containing-target nucleic acid at the single-nucleotide polymorphism site. In certain embodiments, the target nucleic acid is a Huntingtin gene transcript. In certain embodiments, the target nucleic acid is a single-nucleotide polymorphism-containing-target nucleic acid of a Huntingtin gene transcript. In certain embodiments, the target nucleic acid is not a Huntingtin gene transcript. In certain embodiments, the target nucleic acid is a single-nucleotide polymorphism-containing-target nucleic acid of a gene transcript other than Huntingtin. In certain embodiments, the target nucleic acid is any nucleic acid other than a Huntingtin gene transcript.

a. Single-Nucleotide Polymorphism

In certain embodiments, the invention provides selective antisense compounds that have greater activity for a target nucleic acid than for a homologous or partially homologous non-target nucleic acid. In certain such embodiments, the target and non-target nucleic acids are not functionally related to one another (e.g., are transcripts from different genes). In certain embodiments, the target and not-targe nucleic acids are allelic variants of one another. Certain embodiments of the present invention provide methods, compounds, and compositions for selectively inhibiting mRNA and protein expression of an allelic variant of a particular gene or DNA sequence. In certain embodiments, the allelic variant contains a single nucleotide polymorphism (SNP). In certain embodiments, a SNP is associated with a mutant allele. In certain embodiments, a mutant SNP is associated with a disease. In certain embodiments a mutant SNP is associated with a disease, but is not causative of the disease. In certain embodiments, mRNA and protein expression of a mutant allele is associated with disease.

In certain embodiments, the expressed gene product of a mutant allele results in aggregation of the mutant proteins causing disease. In certain embodiments, the expressed gene product of a mutant allele results in gain of function causing disease. In certain embodiments, genes with an autosomal dominant mutation resulting in a toxic gain of function of the protein are the APP gene encoding amyloid precursor protein involved in Alzheimer's disease (Gene, 371: 68, 2006); the PrP gene encoding prion protein involved in Creutzfeldt-Jakob disease and in fatal familial insomnia (Nat. Med. 1997, 3: 1009); GFAP gene encoding glial fibrillary acidic protein involved in Alexander disease (J. Neurosci. 2006, 26:111623); alpha-synuclein gene encoding alpha-synuclein protein involved in Parkinson's disease (J. Clin. Invest. 2003, 111: 145); SOD-1 gene encoding the SOD-1 protein involved in amyotrophic lateral sclerosis (Science 1998, 281: 1851); atrophin-1 gene encoding atrophin-1 protein involved in dentato-rubral and pallido-luysian atrophy (DRPA) (Trends Mol. Med. 2001, 7: 479); SCA1 gene encoding ataxin-1 protein involved in spino-cerebellar ataxia-1 (SCA1) (Protein Sci. 2003, 12: 953); PLP gene encoding proteolipid protein involved in Pelizaeus-Merzbacher disease (NeuroMol. Med. 2007, 4: 73); DYT1 gene encoding torsinA protein involved in Torsion dystonia (Brain Res. 2000, 877: 379); and alpha-B crystalline gene encoding alpha-B crystalline protein involved in protein aggregation diseases, including cardiomyopathy (Cell 2007, 130: 427); alpha1-antitrypsin gene encoding alpha1-antitrypsin protein involved in chronic obstructive pulmonary disease (COPD), liver disease and hepatocellular carcinoma (New Engl J. Med. 2002, 346: 45); Ltk gene encoding leukocyte tyrosine kinase protein involved in systemic lupus erythematosus (Hum. Mol. Gen. 2004, 13: 171); PCSK9 gene encoding PCSK9 protein involved in hypercholesterolemia (Hum Mutat. 2009, 30: 520); prolactin receptor gene encoding prolactin receptor protein involved in breast tumors (Proc. Natl. Assoc. Sci. 2008, 105: 4533); CCL5 gene encoding the chemokine CCL5 involved in COPD and asthma (Eur. Respir. J. 2008, 32: 327); PTPN22 gene encoding PTPN22 protein involved in Type 1 diabetes, Rheumatoid arthritis, Graves disease, and SLE (Proc. Natl. Assoc. Sci. 2007, 104: 19767); androgen receptor gene encoding the androgen receptor protein involved in spinal and bulbar muscular atrophy or Kennedy's disease (J Steroid Biochem. Mol. Biol. 2008, 108: 245); CHMP4B gene encoding chromatin modifying protein-4B involved in progressive childhood posterior subcapsular cataracts (Am. J. Hum. Genet. 2007, 81: 596); FXR/NR1H4 gene encoding Farnesoid X receptor protein involved in cholesterol gallstone disease, arthrosclerosis and diabetes (Mol. Endocrinol. 2007, 21: 1769); ABCA1 gene encoding ABCA1 protein involved in cardiovascular disease (Transl. Res. 2007, 149: 205); CaSR gene encoding the calcium sensing receptor protein involved in primary hypercalciuria (Kidney Int. 2007, 71: 1155); alpha-globin gene encoding alpha-globin protein involved in alpha-thallasemia (Science 2006, 312: 1215); httlpr gene encoding HTTLPR protein involved in obsessive compulsive disorder (Am. J. Hum. Genet. 2006, 78: 815); AVP gene encoding arginine vasopressin protein in stress-related disorders such as anxiety disorders and comorbid depression (CNS Neurol. Disord. Drug Targets 2006, 5: 167); GNAS gene encoding G proteins involved in congenital visual defects, hypertension, metabolic syndrome (Trends Pharmacol. Sci. 2006, 27: 260); APAF1 gene encoding APAF1 protein involved in a predisposition to major depression (Mol. Psychiatry. 2006, 11: 76); TGF-beta1 gene encoding TGF-beta1 protein involved in breast cancer and prostate cancer (Cancer Epidemiol. Biomarkers Prev. 2004, 13: 759); AChR gene encoding acetylcholine receptor involved in congential myasthenic syndrome (Neurology 2004, 62: 1090); P2Y12 gene encoding adenosine diphosphate (ADP) receptor protein involved in risk of peripheral arterial disease (Circulation 2003, 108: 2971); LQT1 gene encoding LQT1 protein involved in atrial fibrillation (Cardiology 2003, 100: 109); RET protooncogene encoding RET protein involved in sporadic pheochromocytoma (J. Clin. Endocrinol. Metab. 2003, 88: 4911); filamin A gene encoding filamin A protein involved in various congenital malformations (Nat. Genet. 2003, 33: 487); TARDBP gene encoding TDP-43 protein involved in amyotrophic lateral sclerosis (Hum. Mol. Gene.t 2010, 19: 671); SCA3 gene encoding ataxin-3 protein involved in Machado-Joseph disease (PLoS One 2008, 3: e3341); SCA7 gene encoding ataxin-7 protein involved in spino-cerebellar ataxia-7 (PLoS One 2009, 4: e7232); and HTT gene encoding huntingtin protein involved in Huntington's disease (Neurobiol Dis. 1996, 3:183); and the CA4 gene encoding carbonic anhydrase 4 protein, CRX gene encoding cone-rod homeobox transcription factor protein, FSCN2 gene encoding retinal fascin homolog 2 protein, IMPDH1 gene encoding inosine monophosphate dehydrogenase 1 protein, NR2E3 gene encoding nuclear receptor subfamily 2 group E3 protein, NRL gene encoding neural retina leucine zipper protein, PRPF3 (RP18) gene encoding pre-mRNA splicing factor 3 protein, PRPF8 (RP13) gene encoding pre-mRNA splicing factor 8 protein, PRPF31 (RP11) gene encoding pre-mRNA splicing factor 31 protein, RDS gene encoding peripherin 2 protein, ROM1 gene encoding rod outer membrane protein 1 protein, RHO gene encoding rhodopsin protein, RP1 gene encoding RP1 protein, RPGR gene encoding retinitis pigmentosa GTPase regulator protein, all of which are involved in Autosomal Dominant Retinitis Pigmentosa disease (Adv Exp Med. Biol. 2008, 613:203)

In certain embodiments, the mutant allele is associated with any disease from the group consisting of Alzheimer's disease, Creutzfeldt-Jakob disease, fatal familial insomnia, Alexander disease, Parkinson's disease, amyotrophic lateral sclerosis, dentato-rubral and pallido-luysian atrophy DRPA, spino-cerebellar ataxia, Torsion dystonia, cardiomyopathy, chronic obstructive pulmonary disease (COPD), liver disease, hepatocellular carcinoma, systemic lupus erythematosus, hypercholesterolemia, breast cancer, asthma, Type 1 diabetes, Rheumatoid arthritis, Graves disease, SLE, spinal and bulbar muscular atrophy, Kennedy's disease, progressive childhood posterior subcapsular cataracts, cholesterol gallstone disease, arthrosclerosis, cardiovascular disease, primary hypercalciuria, alpha-thallasemia, obsessive compulsive disorder, Anxiety, comorbid depression, congenital visual defects, hypertension, metabolic syndrome, prostate cancer, congenital myasthenic syndrome, peripheral arterial disease, atrial fibrillation, sporadic pheochromocytoma, congenital malformations, Machado-Joseph disease, Huntington's disease, and Autosomal Dominant Retinitis Pigmentosa disease.

i. Certain Huntingtin Targets

In certain embodiments, an allelic variant of huntingtin is selectively reduced. Nucleotide sequences that encode huntingtin include, without limitation, the following: GENBANK Accession No. NT_006081.18, truncated from nucleotides 1566000 to 1768000 (replaced by GENBANK Accession No. NT_006051), incorporated herein as SEQ ID NO: 1, and NM_002111.6, incorporated herein as SEQ ID NO: 2.

Table 14 provides SNPs found in the GM04022, GM04281, GM02171, and GM02173B cell lines. Also provided are the allelic variants found at each SNP position, the genotype for each of the cell lines, and the percentage of HD patients having a particular allelic variant. For example, the two allelic variants for SNP rs6446723 are T and C. The GM04022 cell line is heterozygous TC, the GM02171 cell line is homozygous CC, the GM02173 cell line is heterozygous TC, and the GM04281 cell line is homozygous TT. Fifty percent of HD patients have a T at SNP position rs6446723.

TABLE 14

Allelic Variations for SNPs Associated with HD

| SNP | Variation | GM04022 | GM02171 | GM02173 | GM04281 | TargetPOP | allele |
|---|---|---|---|---|---|---|---|
| rs6446723 | T/C | TC | CC | TC | TT | 0.50 | T |
| rs3856973 | A/G | AG | AA | AG | GG | 0.50 | G |
| rs2285086 | A/G | AG | GG | AG | AA | 0.50 | A |
| rs363092 | A/C | AC | AA | AC | CC | 0.49 | C |
| rs916171 | C/G | GC | GG | GC | CC | 0.49 | C |
| rs6844859 | T/C | TC | CC | TC | TT | 0.49 | T |
| rs7691627 | A/G | AG | AA | AG | GG | 0.49 | G |
| rs4690073 | A/G | AG | AA | AG | GG | 0.49 | G |
| rs2024115 | A/G | AG | GG | AG | AA | 0.48 | A |
| rs11731237 | T/C | CC | CC | TC | TT | 0.43 | T |
| rs362296 | A/C | CC | AC | AC | AC | 0.42 | C |

TABLE 14-continued

Allelic Variations for SNPs Associated with HD

| SNP | Variation | GM04022 | GM02171 | GM02173 | GM04281 | TargetPOP | allele |
|---|---|---|---|---|---|---|---|
| rs10015979 | A/G | AA | AA | AG | GG | 0.42 | G |
| rs7659144 | C/G | CG | CG | CG | CC | 0.41 | C |
| rs363096 | T/C | CC | CC | TC | TT | 0.40 | T |
| rs362273 | A/G | AA | AG | AG | AA | 0.39 | A |
| rs16843804 | T/C | CC | TC | TC | CC | 0.38 | C |
| rs362271 | A/G | GG | AG | AG | GG | 0.38 | G |
| rs362275 | T/C | CC | TC | TC | CC | 0.38 | C |
| rs3121419 | T/C | CC | TC | TC | CC | 0.38 | C |
| rs362272 | A/G | GG | — | AG | GG | 0.38 | G |
| rs3775061 | A/G | AA | AG | AG | AA | 0.38 | A |
| rs34315806 | T/C | CC | TC | TC | CC | 0.38 | C |
| rs363099 | T/C | CC | TC | TC | CC | 0.38 | C |
| rs2298967 | T/C | TT | TC | TC | TT | 0.38 | T |
| rs363088 | A/T | AA | TA | TA | AA | 0.38 | A |
| rs363064 | T/C | CC | TC | TC | CC | 0.35 | C |
| rs363102 | A/G | AG | AA | AA | AA | 0.23 | G |
| rs2798235 | A/G | AG | GG | GG | GG | 0.21 | A |
| rs363080 | T/C | TC | CC | CC | CC | 0.21 | T |
| rs363072 | A/T | TA | TA | AA | AA | 0.13 | A |
| rs363125 | A/C | AC | AC | CC | CC | 0.12 | C |
| rs362303 | T/C | TC | TC | CC | CC | 0.12 | C |
| rs362310 | T/C | TC | TC | CC | CC | 0.12 | C |
| rs10488840 | A/G | AG | AG | GG | GG | 0.12 | G |
| rs362325 | T/C | TC | TC | TT | TT | 0.11 | T |
| rs35892913 | A/G | GG | GG | GG | GG | 0.10 | A |
| rs363102 | A/G | AG | AA | AA | AA | 0.09 | A |
| rs363096 | T/C | CC | CC | TC | TT | 0.09 | C |
| rs11731237 | T/C | CC | CC | TC | TT | 0.09 | C |
| rs10015979 | A/G | AA | AA | AG | GG | 0.08 | A |
| rs363080 | T/C | TC | CC | CC | CC | 0.07 | C |
| rs2798235 | A/G | AG | GG | GG | GG | 0.07 | G |
| rs1936032 | C/G | GC | CC | CC | CC | 0.06 | C |
| rs2276881 | A/G | GG | GG | GG | GG | 0.06 | G |
| rs363070 | A/G | AA | AA | AA | AA | 0.06 | A |
| rs35892913 | A/G | GG | GG | GG | GG | 0.04 | G |
| rs12502045 | T/C | CC | CC | CC | CC | 0.04 | C |
| rs6446723 | T/C | TC | CC | TC | TT | 0.04 | C |
| rs7685686 | A/G | AG | GG | AG | AA | 0.04 | G |

TABLE 14-continued

Allelic Variations for SNPs Associated with HD

| SNP | Variation | GM04022 | GM02171 | GM02173 | GM04281 | TargetPOP | allele |
|---|---|---|---|---|---|---|---|
| rs3733217 | T/C | CC | CC | CC | CC | 0.03 | C |
| rs6844859 | T/C | TC | CC | TC | TT | 0.03 | C |
| rs362331 | T/C | TC | CC | TC | TT | 0.03 | C |

E. CERTAIN INDICATIONS

In certain embodiments, provided herein are methods of treating an animal or individual comprising administering one or more pharmaceutical compositions as described herein. In certain embodiments, the individual or animal has Huntington's disease.

In certain embodiments, compounds targeted to huntingtin as described herein may be administered to reduce the severity of physiological symptoms of Huntington's disease. In certain embodiments, compounds targeted to huntingtin as described herein may be administered to reduce the rate of degeneration in an individual or an animal having Huntington's disease. In certain embodiments, compounds targeted to huntingtin as described herein may be administered regeneration function in an individual or an animal having Huntington's disease. In certain embodiments, symptoms of Huntingtin's disease may be reversed by treatment with a compound as described herein.

In certain embodiments, compounds targeted to huntingtin as described herein may be administered to ameliorate one or more symptoms of Huntington's disease. In certain embodiments administration of compounds targeted to huntingtin as described herein may improve the symptoms of Huntington's disease as measured by any metric known to those having skill in the art. In certain embodiments, administration of compounds targeted to huntingtin as described herein may improve a rodent's rotaraod assay performance. In certain embodiments, administration of compounds targeted to huntingtin as described herein may improve a rodent's plus maze assay. In certain embodiments, administration of compounds targeted to huntingtin as described herein may improve a rodent's open field assay performance.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual or animal in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

F. CERTAIN PHARMACEUTICAL COMPOSITIONS

In certain embodiments, the present invention provides pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligomeric compound which are cleaved by endogenous nucleases within the body, to form the active antisense oligomeric compound.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or poly-cationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents of the present invention to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives).

In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain.

G. ADMINISTRATION

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain enbodiments, the targeted tissue is brain tissue. In certain enbodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

H. CERTAIN COMBINATION THERAPIES

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligomeric compound having the nucleobase sequence "ATCGATCG" encompasses any oligomeric compounds having such nucleobase sequence, whether modified or unmodified, including, but not limited to, such compounds comprising RNA bases, such as those having sequence "AUCGAUCG" and those having some DNA bases and some RNA bases such as "AUCGATCG" and oligomeric compounds having other modified or naturally occurring bases, such as "AT$^{me}$CGAUCG," wherein $^{me}$C indicates a cytosine base comprising a methyl group at the 5-position.

EXAMPLES

The following examples illustrate certain embodiments of the present invention and are not limiting. Moreover, where specific embodiments are provided, the inventors have contemplated generic application of those specific embodiments. For example, disclosure of an oligonucleotide having a particular motif provides reasonable support for additional oligonucleotides having the same or similar motif And, for example, where a particular high-affinity modification appears at a particular position, other high-affinity modifications at the same position are considered suitable, unless otherwise indicated.

To allow assessment of the relative effects of nucleobase sequence and chemical modification, throughout the examples, oligomeric compounds are assigned a "Sequence Code." Oligomeric compounds having the same Sequence Code have the same nucleobase sequence. Oligomeric compounds having different Sequence Codes have different nucleobase sequences.

Example 1

Single Nucleotide Polymorphisms (SNPs) in the Huntingtin (HTT) Gene Sequence

SNP positions (identified by Hayden et al, WO/2009/135322) associated with the HTT gene were mapped to the HTT genomic sequence, designated herein as SEQ ID NO: 1 (NT_006081.18 truncated from nucleotides 1566000 to 1768000). Table 15 provides SNP positions associated with the HTT gene. Table 15 provides a reference SNP ID number from the Entrez SNP database at the National Center for Biotechnology Information (NCBI, http://www.ncbi.nlm.nih.gov/sites/entrez?db=snp), incorporated herein by reference. Table 15 furnishes further details on each SNP. The 'Reference SNP ID number' or 'RS number' is the number designated to each SNP from the Entrez SNP database at NCBI, incorporated herein by reference. 'SNP position' refers to the nucleotide position of the SNP on SEQ ID NO: 1. 'Polymorphism' indicates the nucleotide variants at that SNP position. 'Major allele' indicates the nucleotide associated with the major allele, or the nucleotide present in a statistically significant proportion of individuals in the human population. 'Minor allele' indicates the nucleotide associated with the minor allele, or the nucleotide present in a relatively small proportion of individuals in the human population.

TABLE 15

Single Nuclear Polymorphisms (SNPs) and their positions on SEQ ID NO: 1

| RS No. | SNP position | Polymorphism | Major allele | Minor allele |
|---|---|---|---|---|
| rs2857936 | 1963 | C/T | C | T |
| rs12506200 | 3707 | A/G | G | A |
| rs762855 | 14449 | A/G | G | A |
| rs3856973 | 19826 | G/A | G | A |
| rs2285086 | 28912 | G/A | A | G |
| rs7659144 | 37974 | C/G | C | G |
| rs16843804 | 44043 | C/T | C | T |
| rs2024115 | 44221 | G/A | A | G |
| rs10015979 | 49095 | A/G | A | G |
| rs7691627 | 51063 | A/G | G | A |
| rs2798235 | 54485 | G/A | G | A |
| rs4690072 | 62160 | G/T | T | G |
| rs6446723 | 66466 | C/T | T | C |
| rs363081 | 73280 | G/A | G | A |
| rs363080 | 73564 | T/C | C | T |
| rs363075 | 77327 | G/A | G | A |
| rs363064 | 81063 | T/C | C | T |
| rs3025849 | 83420 | A/G | A | G |
| rs6855981 | 87929 | A/G | G | A |
| rs363102 | 88669 | G/A | A | G |
| rs11731237 | 91466 | C/T | C | T |
| rs4690073 | 99803 | A/G | G | A |
| rs363144 | 100948 | T/G | T | G |
| rs3025838 | 101099 | C/T | C | T |
| rs34315806 | 101687 | A/G | G | A |

TABLE 15-continued

Single Nuclear Polymorphisms (SNPs) and their positions on SEQ ID NO: 1

| RS No. | SNP position | Polymorphism | Major allele | Minor allele |
|---|---|---|---|---|
| rs363099 | 101709 | T/C | C | T |
| rs363096 | 119674 | T/C | T | C |
| rs2298967 | 125400 | C/T | T | C |
| rs2298969 | 125897 | A/G | G | A |
| rs6844859 | 130139 | C/T | T | C |
| rs363092 | 135682 | C/A | C | A |
| rs7685686 | 146795 | A/G | A | G |
| rs363088 | 149983 | A/T | A | T |
| rs362331 | 155488 | C/T | T | C |
| rs916171 | 156468 | G/C | C | G |
| rs362322 | 161018 | A/G | A | G |
| rs362275 | 164255 | T/C | C | T |
| rs362273 | 167080 | A/G | A | G |
| rs2276881 | 171314 | G/A | G | A |
| rs3121419 | 171910 | T/C | C | T |
| rs362272 | 174633 | G/A | G | A |
| rs362271 | 175171 | G/A | G | A |
| rs3775061 | 178407 | C/T | C | T |
| rs362310 | 179429 | A/G | G | A |
| rs362307 | 181498 | T/C | C | T |
| rs362306 | 181753 | G/A | G | A |
| rs362303 | 181960 | T/C | C | T |
| rs362296 | 186660 | C/A | C | A |
| rs1006798 | 198026 | A/G | A | G |

Example 2

Modified Oligonucleotides Targeting Huntingtin (HTT) Single Nucleotide Polymorphism (SNP)

A series of modified oligonucleotides were designed based on the parent gapmer, ISIS 460209 wherein the central gap region contains nine 2'-deoxyribonucleosides. These modified oligonucleotides were designed by introducing various chemical modifications in the central gap region and were tested for their ability to selectively inhibit mutant (mut) HTT mRNA expression levels targeting rs7685686 while leaving the expression of the wild-type (wt) intact. The activity and selectivity of the modified oligonucleotides were evaluated and compared to the parent gapmer, ISIS 460209.

The modified oligonucleotides were created with a 3-9-3 motif and are described in Table 16. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e", "k", "y", or "z" are sugar modified nucleosides. A subscript "e" indicates a 2'-O-methoxyethyl (MOE) modified nucleoside, a subscript "k" indicates a 6'-(S)—CH$_3$ bicyclic nucleoside (e.g. cEt), a subscript "y" indicates an α-L-LNA bicyclic nucleoside and a subscript "z" indicates a F-HNA modified nucleoside. $^P$U indicates a 5-propyne uridine nucleoside and $^x$T indicates a 2-thio-thymidine nucleoside.

The number in parentheses indicates the position on the modified oligonucleotide opposite to the SNP position, as counted from the 5'-terminus.

Cell Culture and Transfection

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented below.

Analysis of IC$_{50}$'s

The half maximal inhibitory concentration (IC$_{50}$) of each oligonucleotide is presented in Table 17 and was calculated by plotting the concentrations of oligonucleotides used versus the percent inhibition of HTT mRNA expression achieved at each concentration, and noting the concentration of oligonucleotide at which 50% inhibition of HTT mRNA expression was achieved compared to the control. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

The parent gapmer, ISIS 460209 is marked with an asterisk (*) in the table and was included in the study as a benchmark oligonucleotide against which the activity and selectivity of the modified oligonucleotides targeting nucleotides overlapping the SNP position could be compared.

As illustrated in Table 17, modified oligonucleotides having chemical modifications in the central gap region at the SNP position exhibited similar activity with an increase in selectivity comparing to the parent gapmer, wherein the central gap region contains full deoxyribonucleosides.

TABLE 16

Modified oligonucleotides targeting HTT rs7685686

| ISIS NO | Sequence (5' to 3') | Gap chemistry | Wing chemistry 5' | Wing chemistry 3' | SEQ ID NO. |
|---|---|---|---|---|---|
| 460209* (8) | $T_eA_kA_k$ATTBTCATCA$_kC_kC_e$ | Full Deoxy | ekk | kke | 10 |
| 539560 (8) | $T_eA_kA_k$ATTG$^p$UCATCA$_kC_kC_e$ | Deoxy/ 5-Propyne | ekk | kke | 11 |
| 539563 (8) | $T_eA_kA_k$ATTG$^x$TCATCA$_kC_kC_e$ | Deoxy/ 2-Thio | ekk | kke | 10 |
| 539554 (8) | $T_eA_kA_k$ATTGU$_y$CATCA$_kC_kC_e$ | Deoxy/ α-L-LNA | ekk | kke | 11 |
| 542686 (8) | $T_eA_kA_k$ATTGT$_z$CATCA$_kC_kC_e$ | Deoxy/ F-HNA | ekk | kke | 10 | e = 2'-MOE, k = cEt

TABLE 17

Comparison of inhibition of HTT mRNA levels and selectivity of modified oligonucleotides with ISIS 460209 targeted to rs7685686 in GM04022 cells

| ISIS NO | Mut IC50 (μM) | Wt IC50 (μM) | Selectivity (mutGap vs wt) | Chemistry | Wing chemistry 5' | Wing chemistry 3' |
|---|---|---|---|---|---|---|
| 460209* (8) | 0.41 | 2.0 | 4.9 | Full Deoxy | ekk | kke |
| 539560 (8) | 0.29 | 1.1 | 3.8 | Deoxy/5-Propyne | ekk | kke |
| 539563 (8) | 0.45 | 3.1 | 6.9 | Deoxy/2-Thio | ekk | kke |
| 539554 (8) | 3.5 | >10 | >3 | Deoxy/α-L-LNA | ekk | kke |
| 542686 (8) | 0.5 | 3.1 | 6.0 | Deoxy/F-HNA | ekk | kke |

Example 3

Modified Oligonucleotides Comprising Chemical Modifications in the Gap Region Targeting Huntingtin (HTT) Single Nucleotide Polymorphism (SNP)

Additional modified oligonucleotides were designed in a similar manner as the antisense oligonucleotides described in Table 16. Various chemical modifications were introduced in the central gap region at the SNP position in an effort to improve selectivity while maintaining activity in reducing mutant HTT mRNA levels.

The modified oligonucleotides were created with a 3-9-3 motif and are described in Table 18. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "a", "e", "f", "h", "k", "l", "R", "w" are sugar modified nucleosides. A subscript "a" indicates a 2'-(ara)-F modified nucleoside, a subscript "e" indicates a 2'-O-methoxyethyl (MOE) modified nucleoside, a subscript "f" indicates a 2'-F modified nucleoside, a subscript "h" indicates a HNA modified nucleoside, a subscript "k" indicates a 6'-(S)—CH$_3$ bicyclic nucleoside (e.g. cEt), a subscript "l" indicates a LNA modified nucleoside, a subscript "R" indicates a 5'-(R)-Me DNA, a subscript "w" indicates an unlocked nucleic acid (UNA) modified nucleoside. $^D$T indicates an N3-ethylcyano thymidine nucleoside and $^b$N indicates an abasic nucleoside (e.g. 2'-deoxyribonucleoside comprising a H in place of a nucleobase). Underlined nucleoside or the number in parentheses indicates the position on the modified oligonucleotide opposite to the SNP position, as counted from the 5'-terminus.

Thermal Stability Assay

The modified oligonucleotides were evaluated in thermal stability ($T_m$) assay. The $T_m$'s were measured using the method described herein. A Cary 100 Bio spectrophotometer with the Cary Win UV Thermal program was used to measure absorbance vs. temperature. For the $T_m$ experiments, oligonucleotides were prepared at a concentration of 8 μM in a buffer of 100 mM Na+, 10 mM phosphate, 0.1 mM EDTA, pH 7. Concentration of oligonucleotides were determined at 85° C. The oligonucleotide concentration was 4 μM with mixing of equal volumes of test oligonucleotide and mutant or wild-type RNA strand. Oligonucleotides were hybridized with the mutant or wild-type RNA strand by heating duplex to 90° C. for 5 min and allowed to cool at room temperature. Using the spectrophotometer, $T_m$ measurements were taken by heating duplex solution at a rate of 0.5 C/min in cuvette starting @ 15° C. and heating to 85° C. $T_m$ values were determined using Vant Hoff calculations ($A_{260}$ vs temperature curve) using non self-complementary sequences where the minimum absorbance which relates to the duplex and the maximum absorbance which relates to the non-duplex single strand are manually integrated into the program.

Presented in Table 19 is the $T_m$ for the modified oligonucleotides when duplexed to mutant or wild-type RNA complement. The $T_m$ of the modified oligonucleotides duplexed with mutant RNA complement is denoted as "$T_m$ (° C.) mut". The $T_m$ of the modified oligonucleotides duplexed with wild-type RNA complement is denoted as "$T_m$ (° C.) wt".

Cell Culture, Transfection and Selectivity Analysis

The modified oligonucleotides were also tested in vitro. Heterozygous fibroblast GM04022 cell line was used Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN. The results in Table 19 are presented as percent of HTT mRNA expression, relative to untreated control levels and is denoted as "% UTC". Selectivity as was also evaluated and measured by dividing the percent of wild-type HTT mRNA levels vs. the percent of mutant HTT mRNA levels.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 19, improvement in selectivity was observed for antisense oligonucleotides comprising chemical modifications in the central gap region at the SNP site such as 5'-(R)-Me (ISIS 539558), HNA (ISIS 539559), and 2'-(ara)-F (ISIS 539565) in comparison to the parent full deoxy gapmer, ISIS 460209. Modified oligonucleotides comprising LNA (ISIS 539553) or 2'-F (ISIS 539570) showed comparable selectivity while UNA modification (ISIS 539556 or 543909) showed no selectivity. Modified oligonucleotides comprising modified nucleobase, N3-ethylcyano (ISIS 539564) or abasic nucleobase (ISIS 543525) showed little to no improvement in selectivity.

Modified oligonucleotides comprising chemical modifications in the central gap region

| ISIS NO | Sequence (5' to 3') | Gap chemistry | Wing chemistry 5' | 3' | SEQ ID NO. |
|---|---|---|---|---|---|
| 460209* (8) | $T_eA_kA_k$ATTG$\underline{T}$CATCA$_kC_kC_e$ | Full Deoxy | ekk | kke | 10 |
| 539553 (8) | $T_eA_kA_k$ATTGT$_l$CATCA$_kC_kC_e$ | Deoxy/LNA | ekk | kke | 10 |
| 539556 (8) | $T_eA_kA_k$ATTGU$_w$CATCA$_kC_kC_e$ | Deoxy/UNA | ekk | kke | 11 |
| 539558 (8) | $T_eA_kA_k$ATTGT$_R$CATCA$_kC_kC_e$ | Deoxy/5'-(R)-Me DNA | ekk | kke | 10 |
| 539559 (8) | $T_eA_kA_k$ATTGT$_h$CATCA$_kC_kC_e$ | Deoxy/HNA | ekk | kke | 10 |
| 539564 (8) | $T_eA_kA_k$ATTG"$\underline{T}$CATCA$_kC_kC_e$ | Deoxy/ deoxy with N3-Ethylcyano nucleobase | ekk | kke | 10 |
| 539565 (8) | $T_eA_kA_k$ATTGT$_a$CATCA$_kC_kC_e$ | Deoxy/2'-(ara)-F | ekk | kke | 10 |
| 539570 (8) | $T_eA_kA_k$ATTGT$_f$CATCA$_kC_kC_e$ | Deoxy/2'-F | ekk | kke | 10 |
| 543525 (8) | $T_eA_kA_k$ATTG$^b$NCATCA$_kC_kC_e$ | Deoxy/Deoxy-Abasic | ekk | kke | 12 |
| 543909 (5) | $T_eA_kA_k$AU$_w$TGTCATCA$_kC_kC_e$ | Deoxy/UNA | ekk | kke | 13 | e = 2'-MOE, k = cEt, d = 2'-deoxyribonucleoside

TABLE 19

Comparison of selectivity in inhibition of HTT mRNA levels and Tm of modified oligonucleotides with ISIS 460209 targeted to rs7685686 in GM04022 cells

| ISIS NO | Tm (° C.) mutant | Tm (° C.) wt | % UTC mutant | % UTC wt | Selectivity (wt vs mut) | Gap chemistry | Wing chemistry 5' | 3' |
|---|---|---|---|---|---|---|---|---|
| 460209* (8) | 53.7 | 52.2 | 23 | 57 | 2.4 | Full Deoxy | ekk | kke |
| 539553 (8) | 57.7 | 55.3 | 54 | 102 | 1.9 | Deoxy/LNA | ekk | kke |
| 539556 (8) | 43.7 | 44.1 | 90 | 105 | 1.2 | Deoxy/UNA | ekk | kke |
| 539558 (8) | 51.2 | 49.7 | 25 | 83 | 3.3 | Deoxy/5'-(R)-Me DNA | ekk | kke |
| 539559 (8) | 55.4 | 50.5 | 18 | 62 | 3.5 | Deoxy/HNA | ekk | kke |
| 539564 (8) | 42.8 | 43.1 | 86 | 135 | 1.6 | Deoxy/Deoxy N3-ethylcyano nucleobase | ekk | kke |
| 539565 (8) | 53.8 | 52.5 | 14 | 46 | 3.4 | Deoxy/2'-(ara)-F | ekk | kke |
| 539570 (8) | 54.4 | 51.8 | 25 | 50 | 2.0 | Deoxy/2'-F | ekk | kke |
| 543525 (8) | 43.1 | 43.8 | 87 | 97 | 1.1 | Deoxy/Deoxy Abasic | ekk | kke |
| 543909 (5) | 44.7 | 42.1 | 68 | 79 | 1.2 | Deoxy/UNA | ekk | kke | e = 2'-MOE, k = cEt, d = 2'-deoxyribonucleoside

Example 4

Chimeric Oligonucleotides Comprising Self-Complementary Regions Targeting Huntingtin (HTT) Single Nucleotide Polymorphism (SNP)

Chimeric oligonucleotides were designed based on the parent gapmer, ISIS 460209. These gapmers comprise self-complementary regions flanking the central gap region, wherein the central gap region contains nine deoxyribonucleosides and the self-complementary regions are complementary to one another. The underlined nucleosides indicate the portion of the 5'-end that is self-complement to the portion of the 3'-end.

The gapmers and their motifs are described in Table 20. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

The modified oligonucleotides were tested in vitro. Heterozygous fibroblast GM04022 cell line was used. Cultured GM04022 cells at a density of 25,000 cells per well were transfected using electroporation with a single dose at 2 µM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 21 are presented as percent of HTT mRNA expression, relative to untreated control levels and is denoted as "% UTC". Selectivity was also evaluated and measured by dividing the percent of wild-type HTT mRNA levels vs. the percent of the mutant HTT mRNA levels.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 21, improvement in selectivity was observed for chimeric oligonucleotides comprising 5-9-5 (ISIS 550913), 6-9-6 (ISIS 550912), 6-9-3 (ISIS 550907) or 3-9-7 (ISIS 550904) in comparison to the parent gapmer motif, 3-9-3 (ISIS 460209). The remaining gapmers showed moderate to little improvement in selectivity.

TABLE 20

Chimeric oligonucleotides comprising various wing motifs targeted to HTT rs7685686

| ISIS NO | Sequence (5' to 3') | Motif | Wing chemistry 5' | Wing chemistry 3' | SEQ ID NO. |
|---|---|---|---|---|---|
| 460209* | T$_e$A$_k$A$_k$ATTGTCATCA$_k$C$_k$C$_e$ | 3-9-3 | ekk | kke | 10 |
| 544838 | T$_e$A$_k$A$_k$ATTGTCATCA$_k$C$_k$C$_e$A$_k$ | 3-9-4 | ekk | kkek | 14 |
| 544840 | T$_e$A$_k$A$_k$ATTGTCATCA$_k$C$_k$C$_e$T$_k$T$_k$A$_k$ | 3-9-6 | ekk | kkekkk | 15 |
| 544842 | T$_e$A$_k$A$_k$ATTGTCATCA$_k$C$_k$C$_e$A$_k$T$_k$T$_k$A$_k$ | 3-9-8 | ekk | kkekkkkk | 16 |
| 550903 | T$_e$A$_k$A$_k$ATTGTCATCA$_k$C$_k$C$_e$T$_k$A$_k$ | 3-9-5 | ekk | kkekk | 17 |
| 550904 | T$_e$A$_k$A$_k$ATTGTCATCA$_k$C$_k$C$_e$TkT$_k$T$_k$A$_k$ | 3-9-7 | ekk | kkekkkk | 18 |
| 550905 | G$_k$T$_e$A$_k$A$_k$ATTGTCATCA$_k$C$_k$C$_e$ | 4-9-3 | kekk | kke | 19 |
| 550906 | G$_k$G$_k$T$_e$A$_k$A$_k$ATTGTCATCA$_k$C$_k$C$_e$ | 5-9-3 | kkekk | kke | 20 |
| 550907 | G$_k$G$_k$T$_k$T$_e$A$_k$A$_k$ATTGTCATCA$_k$C$_k$C$_e$ | 6-9-3 | kkkekk | kke | 21 |
| 550908 | G$_k$G$_k$T$_k$G$_k$T$_e$A$_k$A$_k$ATTGTCATCA$_k$C$_k$C$_e$ | 7-9-3 | kkkkekk | kke | 22 |
| 550909 | G$_k$G$_k$T$_k$G$_k$A$_k$T$_e$A$_k$A$_k$ATTGTCATCA$_k$C$_k$C$_e$ | 8-9-3 | kkkkkekk | kke | 23 |
| 550910 | G$_k$G$_k$C$_k$T$_e$A$_k$A$_k$ATTGTCATCA$_k$C$_k$C$_e$G$_k$C$_k$C$_k$ | 6-9-6 | kkkekk | kkekkk | 24 |
| 550911 | G$_k$C$_k$T$_e$A$_k$A$_k$ATTGTCATCA$_k$C$_k$C$_e$G$_k$C$_k$ | 5-9-5 | kkekk | kkekk | 25 |
| 550912 | T$_k$A$_k$A$_k$T$_e$A$_k$A$_k$ATTGTCATCA$_k$C$_k$C$_e$T$_k$T$_k$A$_k$ | 6-9-6 | kkkekk | kkekkk | 26 |
| 550913 | A$_k$A$_k$T$_e$A$_k$A$_k$ATTGTCATCAkC$_k$C$_e$T$_k$T$_k$ | 5-9-5 | kkekk | kkekk | 27 |
| 550914 | T$_k$C$_k$T$_k$T$_e$A$_k$A$_k$ATTGTCATCA$_k$C$_k$C$_e$A$_k$G$_k$A$_k$ | 6-9-6 | kkkekk | kkekkk | 28 |
| 550915 | C$_k$T$_k$T$_e$A$_k$A$_k$ATTGTCATCA$_k$C$_k$C$_e$A$_k$G$_k$ | 5-9-5 | kkekk | kkekk | 29 | e = 2'-MOE, k = cEt

TABLE 21

Comparison of selectivity in inhibition of HTT
mRNA levels of chimeric oligonucleotides with ISIS
460209 targeted to rs7685686 in GM04022 cells

| ISIS NO | % UTC mut | wt | Selectivity (wt vs. mut) | Motif | wing chemistry 5' | 3' |
|---|---|---|---|---|---|---|
| 460209* | 23 | 57 | 2.4 | 3-9-3 | ekk | kke |
| 544838 | 13 | 25 | 2.0 | 3-9-4 | ekk | kkek |
| 544840 | 17 | 31 | 1.8 | 3-9-6 | ekk | kkekkk |
| 544842 | 55 | 102 | 1.9 | 3-9-8 | ekk | kkekkkkk |
| 550903 | 13 | 36 | 2.7 | 3-9-5 | ekk | kkekk |
| 550904 | 23 | 67 | 3.0 | 3-9-7 | ekk | kkekkkk |
| 550905 | 21 | 51 | 2.4 | 4-9-3 | kekk | kke |
| 550906 | 23 | 67 | 2.9 | 5-9-3 | kkekk | kke |
| 550907 | 30 | 93 | 3.1 | 6-9-3 | kkkekk | kke |
| 550908 | 60 | 80 | 2.4 | 7-9-3 | kkkkekk | kke |
| 550909 | 42 | 101 | 2.4 | 8-9-3 | kkkkkekk | kke |
| 550910 | 57 | 102 | 1.8 | 6-9-6 | kkkekk | kkekkk |
| 550911 | 18 | 40 | 2.2 | 5-9-5 | kkekk | kkekk |

TABLE 21-continued

Comparison of selectivity in inhibition of HTT
mRNA levels of chimeric oligonucleotides with ISIS
460209 targeted to rs7685686 in GM04022 cells

| ISIS NO | % UTC mut | wt | Selectivity (wt vs. mut) | Motif | wing chemistry 5' | 3' |
|---|---|---|---|---|---|---|
| 550912 | 14 | 51 | 3.6 | 6-9-6 | kkkekk | kkekkk |
| 550913 | 8 | 36 | 4.5 | 5-9-5 | kkekk | kkekk |
| 550914 | 29 | 45 | 1.5 | 6-9-6 | kkkekk | kkekkk |
| 550915 | 13 | 28 | 2.1 | 5-9-5 | kkekk | kkekk | e = 2'-MOE, k = cEt

Example 5

Chimeric Antisense Oligonucleotides Comprising Non-Self-Complementary Regions Targeting Huntingtin (HTT) Single Nucleotide Polymorphism (SNP)

Additional gapmers are designed based on the most selective gapmers from studies described in Tables 61 and 62 (ISIS 550912 and 550913). These gapmers are created such that they cannot form self-structure in the effort to evaluate if the increased activity simply is due to higher binding affinity. Gapmers are designed by deleting two or three nucleotides at the 3'-terminus and are created with 6-9-3 or 5-9-3 motif.

The chimeric oligonucleotides and their motifs are described in Table 22. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

The gapmers, ISIS 550912 and ISIS 550913, from which the newly designed gapmers are derived from, are marked with an asterisk (*) in the table.

TABLE 22

Non-self-complementary chimeric oligonucleotides targeting HTT SNP

| ISIS NO | Sequence (5' to 3') | Motif | Wing chemistry 5' | 3' | SEQ ID NO. |
|---|---|---|---|---|---|
| 550912* | T$_k$A$_k$A$_k$T$_e$A$_k$A$_k$ATTGTCATCA$_k$C$_k$C$_e$T$_k$T$_k$A$_k$ | 6-9-6 | kkkekk | kkekkk | 26 |
| 550913* | A$_k$A$_k$T$_e$A$_k$A$_k$ATTGTCATCA$_k$C$_k$C$_e$T$_k$T$_k$ | 5-9-5 | kkekk | kkekk | 27 |
| 556879 | T$_k$A$_k$A$_k$T$_e$A$_k$A$_k$ATTGTCATCA$_k$C$_k$C$_e$ | 6-9-3 | kkkekk | kke | 30 |
| 556880 | A$_k$A$_k$T$_e$A$_k$A$_k$ATTGTCATCA$_k$C$_k$C$_e$ | 5-9-3 | kkekk | kke | 31 | e = 2'-MOE, k = cEt

Example 6

Chimeric Oligonucleotides Containing Mismatches Targeting Huntingtin (HTT) Single Nucleotide Polymorphism (SNP)

A series of chimeric antisense oligonucleotides were designed based on the parent gapmer, ISIS 460209, wherein the central gap region contains nine 2'-deoxyribonucleosides. These gapmers were designed by introducing modified nucleosides at both 5' and 3' termini. Gapmers were also created with a single mismatch shifted slightly upstream and downstream (i.e. "microwalk") within the central gap region and with the SNP position opposite position 5 of the parent gapmer, as counted from the 5'-gap terminus.

The gapmers and their motifs are described in Table 23. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides.

Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt). Underlined nucleosides indicate the mismatch position, as counted from the 5'-gap terminus.

These gapmers were evaluated for thermal stability ($T_m$) using methods described in Example 3. Presented in Table 24 are the $T_m$ measurements for chimeric antisense oligonucleotides when duplexed to mutant or wild-type RNA complement. The $T_m$ of chimeric antisense oligonucleotides duplexed with mutant RNA complement is denoted as "$T_m$ (° C.) mut". The $T_m$ of chimeric antisense oligonucleotides duplexed with wild-type RNA complement is denoted as "$T_m$ (° C.) wt".

These gapmers were also tested in vitro. Heterozygous fibroblast GM04022 cell line was used. Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 24 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 24, improvement in selectivity was observed for gapmers comprising a 4-9-4 motif with a central deoxy gap region (ISIS 476333) or a single mismatch at position 8 within the gap region (ISIS 543531) in comparison to the parent gapmer. The remaining gapmers showed moderate to little improvement in selectivity.

TABLE 23

Chimeric oligonucleotides containing a single mismatch targeting mutant HTT SNP

| ISIS NO | Sequence (5' to 3') | Mismatch position | Motif | Wing chemistry 5' | Wing chemistry 3' | SEQ ID NO. |
|---|---|---|---|---|---|---|
| 460209* | T$_e$A$_k$A$_k$ATTGTCATCA$_k$C$_k$C$_e$ | — | 3-9-3 | ekk | kke | 10 |
| 476333 | A$_e$TkA$_e$A$_k$ATTGTCATCA$_k$C$_e$C$_k$A$_e$ | — | 4-9-4 | ekek | keke | 32 |
| 543526 | A$_e$TkA$_e$A$_k$ATTCTCATCA$_k$C$_e$C$_k$A$_e$ | 4 | 4-9-4 | ekek | keke | 33 |
| 543527 | A$_e$TkA$_e$A$_k$ATAGTCATCA$_k$C$_e$C$_k$A$_e$ | 3 | 4-9-4 | ekek | keke | 34 |
| 543529 | A$_e$TkA$_e$A$_k$ATTGTGATCA$_k$C$_e$C$_k$A$_e$ | 6 | 4-9-4 | ekek | keke | 35 |
| 543530 | A$_e$TkA$_e$A$_k$ATTGTCTTCA$_k$C$_e$C$_k$A$_e$ | 7 | 4-9-4 | ekek | keke | 36 |
| 543531 | A$_e$TkA$_e$A$_k$ATTGTCAACA$_k$C$_e$C$_k$A$_e$ | 8 | 4-9-4 | ekk | keke | 37 |
| 543532 | T$_e$A$_k$A$_k$ATTCTCATCA$_k$C$_k$C$_e$ | 4 | 3-9-3 | ekk | kke | 38 |
| 543534 | T$_e$A$_k$A$_k$AATGTCATCA$_k$C$_k$C$_e$ | 2 | 3-9-3 | ekk | kke | 39 |
| 543535 | T$_e$A$_k$A$_k$ATTGTGATCA$_k$C$_k$C$_e$ | 6 | 3-9-3 | ekk | kke | 40 |
| 543536 | T$_e$A$_k$A$_k$ATTGTCTTCA$_k$C$_k$C$_e$ | 7 | 3-9-3 | ekk | kke | 41 |
| 543537 | T$_e$A$_k$A$_k$ATTGTCAACA$_k$C$_k$C$_e$ | 8 | 3-9-3 | ekk | kke | 42 | e = 2'-MOE, k = cEt

TABLE 24

Comparison of selectivity and $T_m$ of chimeric oligonucleotides with ISIS 460209 targeted to rs7685686 in GM04022 cells

| ISIS NO | Tm (°C.) mut | Tm (°C.) wt | % UTC mut | % UTC wt | Selectivity (wt vs mut) | Mismatch position | Motif | Wing chemistry 5' | Wing chemistry 3' |
|---|---|---|---|---|---|---|---|---|---|
| 460209* | 53.7 | 52.2 | 23 | 57 | 2.4 | — | 3-9-3 | ekk | kke |
| 476333 | 60.2 | 58.4 | 10 | 37 | 3.6 | — | 4-9-4 | ekek | keke |
| 543526 | 47.9 | 46.6 | 70 | 86 | 1.2 | 4 | 4-9-4 | ekek | keke |

TABLE 24-continued

Comparison of selectivity and $T_m$ of chimeric oligonucleotides with ISIS 460209 targeted to rs7685686 in GM04022 cells

| ISIS NO | Tm (°C.) mut | Tm (°C.) wt | % UTC mut | % UTC wt | Selectivity (wt vs mut) | Mismatch position | Motif | Wing chemistry 5' | Wing chemistry 3' |
|---|---|---|---|---|---|---|---|---|---|
| 543527 | 52.6 | 49.9 | 40 | 103 | 2.6 | 3 | 4-9-4 | ekek | keke |
| 543529 | 50.3 | 49.0 | 66 | 102 | 1.5 | 6 | 4-9-4 | ekek | keke |
| 543530 | 52.9 | 50.9 | 67 | 110 | 1.6 | 7 | 4-9-4 | ekek | keke |
| 543531 | 53.3 | 50.3 | 46 | 136 | 3.0 | 8 | 4-9-4 | ekk | keke |
| 543532 | 43.6 | 42.8 | 127 | 151 | 1.2 | 4 | 3-9-3 | ekk | kke |
| 543534 | 45.9 | 43.8 | 67 | 95 | 1.4 | 2 | 3-9-3 | ekk | kke |
| 543535 | 44.0 | 43.3 | 96 | 113 | 1.2 | 6 | 3-9-3 | ekk | kke |
| 543536 | 46.8 | 44.6 | 106 | 104 | 1.0 | 7 | 3-9-3 | ekk | kke |
| 543537 | 45.9 | 44.3 | 77 | 81 | 1.1 | 8 | 3-9-3 | ekk | kke | e = 2'-MOE, k = cEt

Example 7

Chimeric Oligonucleotides Comprising Mismatches Targeting Huntingtin (HTT) Single Nucleotide Polymorphism (SNP)

Additional chimeric antisense oligonucleotides are designed based on two gapmers selected from studies described in Tables 64 and 65 (ISIS 476333 and ISIS 460209) wherein the central gap region contains nine 2'-deoxyribonucleosides. These gapmers are designed by introducing a single mismatch, wherein the mismatch will be shifted throughout the antisense oligonucleotide (i.e. "microwalk"). Gapmers are also created with 4-9-4 or 3-9-3 motifs and with the SNP position opposite position 8 of the original gapmers, as counted from the 5'-terminus.

The gapmers and their motifs are described in Table 25. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH₃ bicyclic nucleoside (e.g. cEt). Underlined nucleosides indicate the mismatch position, as counted from the 5'-terminus.

The gapmers, ISIS 476333 and ISIS 460209, in which the newly designed antisense oligonucleotides are derived from, are marked with an asterisk (*) in the table.

TABLE 25

Chimeric oligonucleotides comprising mismatches targeting HTT SNP

| ISIS NO | Sequence (5' to 3') | Mismatch position | Motif | 5' | 3' | SEQ ID NO |
|---|---|---|---|---|---|---|
| 476333* | $A_eT_kA_eA_k$ATTGTCATCA$_kC_eC_kA_e$ | — | 4-9-4 | ekek | keke | 32 |
| 554209 | $\underline{T}_eT_kA_eA_k$ATTGTCATCA$_kC_eC_kA_e$ | 1 | 4-9-4 | ekek | keke | 43 |
| 554210 | $A_e\underline{A}_kA_eA_k$ATTGTCATCA$_kC_eC_kA_e$ | 2 | 4-9-4 | ekek | keke | 44 |
| 554211 | $A_eT_k\underline{T}_eA_k$ATTGTCATCA$_kC_eC_kA_e$ | 3 | 4-9-4 | ekek | keke | 45 |
| 554212 | $A_eT_kA_e\underline{T}_k$ATTGTCATCA$_kC_eC_kA_e$ | 4 | 4-9-4 | ekek | keke | 46 |
| 554213 | $A_eT_kA_eA_k\underline{T}$TTGTCATCA$_kC_eC_kA_e$ | 5 | 4-9-4 | ekek | keke | 47 |
| 554214 | $A_eT_kA_eA_k$ATTGTCAT$\underline{GA}_kC_eC_kA_e$ | 13 | 4-9-4 | ekek | keke | 48 |
| 554215 | $A_eT_kA_eA_k$ATTGTCATC$\underline{T}_kC_eC_kA_e$ | 14 | 4-9-4 | ekek | keke | 49 |
| 554216 | $A_eT_kA_eA_k$ATTGTCATCA$_k\underline{G}C_kA_e$ | 15 | 4-9-4 | ekek | keke | 50 |
| 554217 | $A_eT_kA_eA_k$ATTGTCATCA$_kC_e\underline{G}_kA_e$ | 16 | 4-9-4 | ekek | keke | 51 |
| 554218 | $A_eT_kA_eA_k$ATTGTCATCA$_kC_eC_k\underline{T}_e$ | 17 | 4-9-4 | ekek | keke | 52 |
| 460209* | $T_eA_kA_k$ATTGTCATCA$_kC_kC_e$ | — | 3-9-3 | ekk | kke | 10 |
| 562481 | $T_eA_kA_k\underline{G}$TTGTCATCA$_kC_kC_e$ | 4 | 3-9-3 | ekk | kke | 53 |
| 554482 | $T_eA_kA_kA\underline{G}$TGTCATCA$_kC_kC_e$ | 5 | 3-9-3 | ekk | kke | 54 |
| 554283 | $T_eA_kA_kAT\underline{G}$GTCATCA$_kC_kC_e$ | 6 | 3-9-3 | ekk | kke | 55 | e = 2'-MOE, k = cEt

Example 8

Short-Gap Chimeric Oligonucleotides Targeting Huntingtin (HTT) Single Nucleotide Polymorphism (SNP)

Chimeric antisense oligonucleotides were designed based on the parent gapmer, ISIS 460209, wherein the central gap region contains nine 2'-deoxyribonucleosides. These gapmers were designed by shortening the central gap region to seven 2'-deoxyribonuclosides. Gapmers were also created with 5-7-5 motif and with the SNP position opposite position 8 or 9 of the parent gapmer, as counted from the 5'-terminus.

The gapmers and their motifs are described in Table 26. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt). Underlined nucleoside or the number in parentheses indicates the position on the modified oligonucleotide opposite to the SNP position, as counted from the 5'-terminus.

The chimeric antisense oligonucleotides were tested in vitro. ISIS 141923 was included in the study as a negative control and is denoted as "neg control". A non-allele specific antisense oligonucleotide, ISIS 387916 was used as a positive control and is denoted as "pos control". ISIS 460209 was included in the study for comparison. Heterozygous fibroblast GM04022 cell line was used. Cultured GM04022 cells at a density of 25,000 cells per well were transfected using electroporation with 0.12, 0.37, 1.1, 3.3, and 10 µM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN and the results are presented in Table 27.

The IC$_{50}$ and selectivity were calculated using methods described previously in Example 2. As illustrated in Table 27, no improvement in potency and selectivity was observed for the chimeric antisense oligonucleotides as compared to ISIS 460209.

TABLE 27

Comparison of inhibition of HTT mRNA levels and selectivity of chimeric antisense oligonucleotides with ISIS 460209 targeted to rs7685686 in GM04022 cells

| ISIS NO | Mut IC$_{50}$ (µM) | Wt IC$_{50}$ (µM) | Selectivity (mut vs wt) | Motif | Wing chemistry 5'  3' |
|---|---|---|---|---|---|
| 460209* (8) | 0.41 | 2.0 | 4.9 | 3-9-3 | ekk  kke |
| 460085 (9) | 3.5 | >10 | >3 | 5-7-5 | eeeee  eeeee |
| 540108 (9) | 0.41 | — | — | 5-7-5 | eeekk  kkeee |
| 387916 (pos control) | 0.39 | 0.34 | 1.0 | 5-10-5 | eeeee  eeeee |
| 141923 (neg control) | >10 | >10 | — | 5-10-5 | eeeee  eeeee | e = 2'-MOE  k = cEt

Example 9

Short-Gap Chimeric Oligonucleotides Targeting Huntingtin (HTT) Single Nucleotide Polymorphism (SNP)

Additional chimeric antisense oligonucleotides were designed based on the parent gapmer, ISIS 460209, wherein the central gap region contains nine 2'-deoxyribonucleosides. These gapmers were designed with the central gap region shortened or interrupted by introducing various modifications either within the gap or by adding one or more modified nucleosides to the 3'-most 5'-region or to the 5'-most 3'-region. Gapmers were created with the SNP position opposite position 8 of the parent gapmer, as counted from the 5'-terminus.

The gapmers and their motifs are described in Table 28. The internucleoside linkages throughout each gapmer are phosphorothioate (P=S) linkages. All cytosine nucleobases throughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

TABLE 26

Chimeric antisense oligonucleotides targeting HTT rs7685686

| ISIS NO | Sequence (5' to 3') | Motif | Wing Chemistry 5'  3' | SEQ ID NO. |
|---|---|---|---|---|
| 460209* (8) | T$_e$A$_k$A$_k$ATTGTCATCA$_k$C$_k$C$_e$ | 3-9-3 | ekk  kke | 10 |
| 460085 (9) | A$_e$T$_e$A$_e$A$_e$A$_e$TTGTCATC$_e$A$_e$C$_e$C$_e$A$_e$ | 5-7-5 | eeeee  eeeee | 32 |
| 540108 (9) | A$_e$T$_e$A$_e$A$_k$A$_k$TTGTCATC$_k$A$_k$C$_e$C$_e$A$_e$ | 5-7-5 | eeekk  kkeee | 32 |
| 387916 (pos control) | T$_e$C$_e$T$_e$C$_e$T$_e$ATTGCACATTC$_e$C$_e$A$_e$A$_e$G$_e$ | 5-10-5 | eeeee  eeeee | 56 |
| 141923 (neg control) | C$_e$C$_e$T$_e$T$_e$C$_e$CCTGAAGGTTC$_e$C$_e$T$_e$C$_e$C$_e$ | 5-10-5 | eeeee  eeeee | 57 | e = 2'-MOE, k = cEt

The chimeric antisense oligonucleotides were tested in vitro. Heterozygous fibroblast GM04022 cell line was used. Cultured GM04022 cells at a density of 25,000 cells per well were transfected using electroporation with 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 29 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels. ISIS 460209 marked with an asterisk (*) in the table was included in the study for comparison.

As illustrated in Table 29, modifications to the 3'-most 5'-region nucleosides that shorten the gap from 9 to 7 or 8 nucleotides (ISIS 551429 and ISIS 551426) improved selectivity and potency comparing to the parent gapmer (ISIS 460209). The remaining chimeric antisense oligonucleotides showed moderate to little improvement in selectivity.

TABLE 28

Short-gap antisense oligonucleotides targeting HTT rs7685686

| ISIS NO | Sequence (5' to 3') | Motif | Wing Chemistry 5' | 3' | SEQ ID NO. |
|---|---|---|---|---|---|
| 460209* | T$_e$A$_k$A$_k$ATTGTCATCA$_k$C$_k$C$_e$ | 3-9-3 | ekk | kke | 10 |
| 551426 | T$_e$A$_k$A$_e$A$_k$TTGTCATCA$_k$C$_k$C$_e$ | 4-8-3 | ekek | kke | 10 |
| 551427 | T$_e$A$_k$A$_e$AT$_k$TGTCATCA$_k$C$_k$C$_e$ | 3-9-3 or 5-7-3 | eke or ekedk | kke | 10 |
| 551428 | T$_e$A$_k$A$_e$ATT$_k$GTCATCA$_k$C$_k$C$_e$ | 3-9-3 or 6-6-3 | eke or ekeddk | kke | 10 |
| 551429 | T$_e$A$_k$A$_e$A$_k$T$_k$TGTCATCA$_k$C$_k$C$_e$ | 5-7-3 | eeekk | kke | 10 | e = 2'-MOE, k = cEt, d = 2'-deoxyribonucleoside

TABLE 29

Comparison of selectivity in inhition of HTT mRNA levels of antisense oligonucleotides with ISIS 460209 targeted to rs7685686 in GM4022 cells

| ISIS NO | % UTC mut | % UTC wt | Selectivity (wt vs. mut) | Motif | Wing chemistry 5' | 3' |
|---|---|---|---|---|---|---|
| 460209* | 23 | 57 | 2.4 | 3-9-3 | ekk | kke |
| 551426 | 14 | 66 | 4.8 | 4-8-3 | ekek | kke |
| 551427 | 35 | 97 | 2.8 | 3-9-3 or 5-7-3 | eke or ekedk | kke |

TABLE 29-continued

Comparison of selectivity in inhition of HTT mRNA levels of antisense oligonucleotides with ISIS 460209 targeted to rs7685686 in GM4022 cells

| ISIS NO | % UTC mut | % UTC wt | Selectivity (wt vs. mut) | Motif | Wing chemistry 5' | 3' |
|---|---|---|---|---|---|---|
| 551428 | 61 | 110 | 1.8 | 3-9-3 or 6-6-3 | eke or ekeddk | kke |
| 551429 | 19 | 94 | 5.0 | 5-7-3 | eeekk | kke | e = 2'-MOE, k = cEt, d = 2'-deoxyribonucleoside

Example 10

Modified Oligonucleotides Targeting HTT SNP

A series of modified antisense oligonucleotides are designed based on the parent gapmer, ISIS 460209, wherein the central gap region contains nine 2'-deoxynucleosides and is marked with an asterisk (*) in the table. These modified oligonucleotides are designed by shortening or interrupting the gap with a single mismatch or various chemical modifications within the central gap region. The modified oligonucleotides are created with the SNP position opposite position 8 of the parent gapmer, as counted from the 5'-terminus.

The gapmers and their motifs are described in Table 30. The internucleoside linkages throughout each gapmer are phosphorothioate (P=S) linkages, except for the internucleoside linkage with a subscript "p", "pz" or "pw". Subscript "p" indicates methyl phosphonate internucleoside linkage. Subscript "pz" indicates (R)-methyl phosphonate internucleoside linkage. Subscript "pw" indicates (S)-methyl phosphonate internucleoside linkage. All cytosine nucleobases thoughout each gapmer are 5-methyl cytosines. $^x$T indicates a 2-thio thymidine nucleoside. Nucleosides without a subscript are β-D-2'-deoxyribonucleosides. Nucleosides followed by a subscript "e", "k" or "b" are sugar modified nucleosides. A subscript "e" indicates a 2'-O-methoxyethyl (MOE) modified nucleoside, a subscript "k" indicates a 6'-(S)—CH$_3$ bicyclic nucleoside (e.g. cEt) and a subscript "b" indicates a 5'-Me DNA modified nucleoside. Underlined nucleosides indicate the position of modification. Bold and underlined nucleosides indicate the mismatch position.

TABLE 30

Short-gap chimeric oligonucleotides targeting HTT SNP

| ISIS NO | Sequence (5' to 3') | Motif | Gap Chemistry | Wing Chemistry 5' | 3' | SEQ ID NO. |
|---|---|---|---|---|---|---|
| 460209* | $T_eA_kA_k$ATTGTCATCA$_kC_kC_e$ | 3-9-3 | — | ekk | kke | 10 |
| XXXX16 | $T_eA_kA_k$A$^x$TTGTCATCA$_kC_kC_e$ | 3-9-3 | Deoxy/2-thio | ekk | kke | 10 |
| XXXX17 | $T_eA_kA_k$AT$^x$TGTCATCA$_kC_kC_e$ | 3-9-3 | Deoxy/2-thio | ekk | kke | 10 |
| XXXX18 | $T_eA_kA_k$A$^x$T$^x$TGTCATCA$_kC_kC_e$ | 3-9-3 | Deoxy/2-thop | ekk | kke | 10 |
| XXXX19 (558257) | $T_eA_kA_k$ATT$_p$GTCATCA$_kC_kC_e$ | 3-9-3 | Deoxy/Methyl phosphate | ekk | kke | 10 |
| XXXX20 (558256) | $T_eA_kA_k$AT$_p$TGTCATCA$_kC_kC_e$ | 3-9-3 | Deoxy/Methyl phosphonate | ekk | kke | 10 |
| XXXX20a | $T_eA_kA_k$AT$_{pz}$TGTCATCA$_kC_kC_e$ | 3-9-3 | Deoxy/(R)-Methyl phosphonate | ekk | kke | 10 |
| XXXX20b | $T_eA_kA_k$AT$_{pw}$TGTCATCA$_kC_kC_e$ | 3-9-3 | Deoxy/(S)-Methyl phosphonate | ekk | kke | 10 |
| XXXX21 (558255) | $T_eA_kA_kA_z$TTGTCATCA$_kC_kC_e$ | 3-9-3 | Methyl phosphonate | ekk | kke | 10 |
| XXXX22 | $T_eA_kA_k$ATT$_b$GTCATCA$_kC_kC_e$ | 3-9-3 | 5'-Me-DNA | ekk | kke | 10 |
| XXXX23 | $T_eA_kA_k$AT$_b$TGTCATCA$_kC_kC_e$ | 3-9-3 | 5'-Me-DNA | ekk | kke | 10 |
| XXXX24 | $T_eA_kA_kA_b$TTGTCATCA$_kC_kC_e$ | 3-9-3 | 5'-Me-DNA | ekk | kke | 10 |
| XXXX25 | $T_eA_kA_k$GTTGTCATCA$_kC_kC_e$ | 4-8-3 | Mismatch at position 4 | ekk | kke | 53 |
| XXXX26 | $T_eA_kA_k$AGTGTCATCA$_kC_kC_e$ | 5-7-3 | Mismatch at position 5 | ekk | kke | 54 |
| XXXX27 | $T_eA_kA_k$ATGGTCATA$_kC_kC_e$ | 6-6-3 | Mismatch at position 6 | ekk | kke | 55 | e = 2'-MOE, k = cEt

Example 11

Short-Gap Chimeric Oligonucleotides Comprising Modifications at the Wing Regions Targeting Huntingtin (HTT) Single Nucleotide Polymorphism (SNP)

Additional chimeric antisense oligonucleotides were designed based on the parent gapmer, ISIS 460209, wherein the central gap region contains nine 2'-deoxynucleosides. These gapmers were designed by shortening the central gap region to seven 2'-deoxynucleosides and introducing various modifications at the wing regions.

The gapmers and their motifs are described in Table 31. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

The number in parentheses indicates the position on the chimeric oligonucleotide opposite to the SNP position, as counted from the 5'-terminus.

These gapmers were evaluated for thermal stability ($T_m$) using methods described in Example 3. Presented in Table 32 is the $T_m$ measurements for chimeric antisense oligonucleotides when duplexed to mutant or wild-type RNA complement. The $T_m$ of chimeric antisense oligonucleotides duplexed with mutant RNA complement is denoted as "$T_m$ (° C.) mut". The $T_m$ of chimeric antisense oligonucleotides duplexed with wild-type RNA complement is denoted as "$T_m$ (° C.) wt".

These gapmers were also tested in vitro. Heterozygous fibroblast GM04022 cell line was used. Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 32 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels. ISIS 460209 marked with an asterisk (*) in the table was included in the study for comparison.

As illustrated in Table 32, improvement in selectivity was observed for gapmers comprising 2-7-8 or 5-7-5 motifs having cEt subunits at the wing regions in comparison to the parent gapmer, ISIS 460209. The remaining gapmers showed moderate to little improvement in selectivity.

TABLE 31

Short-gap chimeric oligonucleotides comprising wing modifications

| ISIS NO | Sequence (5' to 3') | Motif | wing chemistry 5' | 3' | SEQ ID NO. |
|---|---|---|---|---|---|
| 460209* (8) | $T_eA_kA_k$ATTGTCATCA$_kC_kC_e$ | 3-9-3 | ekk | kke | 10 |
| 540103 (6) | $A_kA_k$TTGTCATC$_eA_eC_eC_eA_eG_eA_eA_e$ | 2-7-8 | kk | e8 | 58 |
| 540104 (6) | $A_eA_e$TTGTCATC$_eA_eC_eC_eA_eG_eA_eA_e$ | 2-7-8 | ee | e8 | 59 |
| 540105 (7) | $A_eA_eA_e$TTGTCATC$_eA_eC_eC_eA_eG_e$ | 3-7-7 | eee | e7 | 60 |
| 540106 (8) | $T_eA_eA_eA_e$TTGTCATC$_eA_eC_eC_eeG_e$ | 4-7-6 | eeee | e6 | 61 |
| 540107 (9) | $A_eT_eA_eA_eA_k$TTGTCATC$_kA_eC_eC_eA_e$ | 5-7-5 | eeeek | keeee | 32 |
| 540109 (10) | $A_eA_eT_eA_eA_eA_e$TTGTCATC$_eA_eC_eC_e$ | 6-7-4 | e6 | e4 | 62 |
| 540110 (11) | $T_eA_eA_eT_eA_eA_eA_e$TTGTCATC$_eA_eC_e$ | 7-7-3 | e7 | eee | 63 |
| 540111 (12) | $T_eT_eA_eA_eT_eA_eA_eA_e$TTGTCATC$_eA_e$ | 8-7-2 | e8 | ee | 64 |
| 540112 (12) | $T_eT_eA_eA_eT_eA_eA_eA_e$TTGTCATC$_kA_k$ | 8-7-2 | e8 | kk | 64 | e = 2'-MOE (e.g. e6 = eeeeee), and k = cEt

TABLE 32

Comparison of selectivity in inhibition of HTT mRNA levels of antisense oligonucleotides with ISIS 460209 targeted to RS7685686 in GM04022 cells

| | Tm (° C.) | | % UTC | | Selectivity | | wing chemistry | |
|---|---|---|---|---|---|---|---|---|
| ISIS NO | mut | wt | mut | wt | (wt vs mut) | Motif | 5' | 3' |
| 460209* (8) | 53.7 | 52.2 | 23 | 57 | 2.4 | 3-9-3 | ekk | kke |
| 540103 (6) | 57.6 | 56.4 | 23 | 74 | 3.3 | 2-7-8 | kk | e8 |
| 540104 (6) | 54.8 | 52.8 | 36 | 91 | 2.5 | 2-7-8 | ee | e8 |
| 540105 (7) | 54.2 | 52.2 | 53 | 135 | 2.6 | 3-7-7 | eee | e7 |
| 540106 (8) | 52.4 | 50.8 | 30 | 77 | 2.6 | 4-7-6 | eeee | e6 |
| 540107 (9) | 56.6 | 54.7 | 19 | 62 | 3.3 | 5-7-5 | eeeek | keeee |
| 540109 (10) | 49.1 | 47.3 | 78 | 127 | 1.6 | 6-7-4 | e6 | e4 |
| 540110 (11) | 42.8 | 41.2 | 89 | 112 | 1.3 | 7-7-3 | e7 | eee |
| 540111 (12) | 39.0 | 36.9 | 111 | 128 | 1.1 | 8-7-2 | e8 | ee |
| 540112 (12) | 44.2 | 42.4 | 86 | 102 | 1.2 | 8-7-2 | e8 | kk |

Example 12

Chimeric Oligonucleotides with SNP Site Shifting within the Central Gap Region

Chimeric antisense oligonucleotides were designed based on the parent gapmer, ISIS 460209 wherein the SNP site aligns with position 5 of the parent gapmer, as counted from the 5'-gap terminus. These gapmers were designed by shifting the SNP site upstream or downstream (i.e. microwalk) within the central gap region of the parent gapmer.

The gapmers and their motifs are described in Table 33. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt). Underline nucleosides indicate the position on the chimeric oligonucleotide aligns with the SNP site.

The SNP site indicates the position on the chimeric antisense oligonucleotide opposite to the SNP position, as counted from the 5'-gap terminus and is denoted as "SNP site".

The $IC_{50}$ and selectivity were calculated using the methods previously described in Example 2. As illustrated in Table 34, chimeric oligonucleotides comprising 4-9-2 (ISIS 540082) or 2-9-4 (ISIS 540095) motif with the SNP site at position 1 or 3 showed comparable activity and 2.5 fold selectivity as compared to their counterparts.

TABLE 33

Chimeric oligonucleotides designed by microwalk

| ISIS NO | Sequence (5' to 3') | Motif | SNP site | wing chemistry 5' | 3' | SEQ ID NO. |
|---|---|---|---|---|---|---|
| 460209* | T$_e$A$_k$A$_k$ATTGT̲CATCA$_k$C$_k$C$_e$ | 3-9-3 | 5 | ekk | kke | 10 |
| 540082 | A$_e$T$_k$T$_k$G$_k$T̲CATCACCAG$_k$A$_e$ | 4-9-2 | 1 | ekkk | ke | 65 |
| 540089 | T$_e$T$_k$A$_k$A$_k$TAAATTGT̲CA$_k$T$_e$ | 4-9-2 | 8 | ekkk | ke | 66 |
| 540095 | A$_e$T$_k$TGT̲CATCACC$_k$A$_k$G$_k$A$_e$ | 2-9-4 | 3 | ek | kkke | 65 | e = 2'-MOE, and k = cEt

TABLE 34

Comparison of inhibition of HTT mRNA levels and selectivity of chimeric oligonucleotides with ISIS 460209 targeted to HTT SNP

| ISIS NO | Mut $IC_{50}$ (μM) | Wt $IC_{50}$ (μM) | Selectivity (wt vs mut) | Motif | SNP site | Wing Chemistry 5' | 3' |
|---|---|---|---|---|---|---|---|
| 460209 | 0.41 | 2.0 | 4.9 | 3-9-3 | 5 | ekk | kke |
| 540082 | 0.45 | 5.6 | 12 | 4-9-2 | 1 | ekkk | ke |
| 540089 | >10 | >0 | — | 4-9-2 | 8 | ekkk | ke |
| 540095 | 0.69 | 8.4 | 12 | 2-9-4 | 3 | ed | kkke | e = 2'-MOE, and k = cEt

The chimeric oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN. ISIS 460209 marked with an asterisk (*) in the table was included in the study for comparison.

Example 13

Chimeric Oligonucleotides with SNP Site Shifting at Various Positions

Chimeric antisense oligonucleotides were designed based on the parent gapmer, ISIS 460209 wherein the SNP site aligns with position 8 of the parent gapmer, as counted from the 5'-terminus. These gapmers were designed by shifting the SNP site upstream or downstream (i.e. microwalk) of the original oligonucleotide.

The gapmers and their motifs are described in Table 35. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH₃ bicyclic nucleoside (e.g. cEt). Underline nucleosides indicate the SNP site.

The SNP site indicates the position on the chimeric antisense oligonucleotide opposite to the SNP position, as counted from the 5'-terminus and is denoted as "SNP site".

The chimeric oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. The results in Table 36 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels.

The parent gapmer, ISIS 460209 is marked with an asterisk (*) in the table and was included in the study as a benchmark oligonucleotide against which the selectivity of the modified oligonucleotides targeting nucleotides overlapping the SNP position could be compared.

As illustrated in Table 36, improvement in potency and selectivity was observed for chimeric oligonucleotides comprising 4-9-2 or 2-9-4 motif having the target SNP site at positions 3, 4, 6, 7 and 8 (ISIS540083, ISIS540084, ISIS 540085, ISIS 540094, ISIS 540096, ISIS 540097 and ISIS 540098) in comparison to position 8 of the parent gapmer (ISIS 460209). The remaining gapmers showed little to no improvement in potency or selectivity.

TABLE 35

Chimeric oligonucleotides designed by microwalk

| ISIS NO | Sequence (5' to 3') | SNP site | Motif | SEQ ID NO. |
|---|---|---|---|---|
| 460209* | T$_e$A$_k$A$_k$ATTGTCATCA$_k$C$_k$C$_e$ | 8 | 3-9-3 (ekk-d9-kke) | 10 |
| 543887 | T$_e$T$_k$G$_k$T$_k$CATCACCAGA$_k$A$_e$ | 4 | 4-9-2 (ekkk-d9-ke) | 67 |
| 540083 | A$_e$A$_k$T$_k$T$_k$GTCATCACCA$_k$G$_e$ | 6 | 4-9-2 (ekkk-d9-ke) | 68 |
| 540084 | A$_e$A$_k$A$_k$T$_k$TGTCATCACC$_k$A$_e$ | 7 | 4-9-2 (ekkk-d9-ke) | 69 |
| 540085 | T$_e$A$_k$A$_k$A$_k$TTGTCATCAC$_k$C$_e$ | 8 | 4-9-2 (ekkk-d9-ke) | 10 |

TABLE 35-continued

Chimeric oligonucleotides designed by microwalk

| ISIS NO | Sequence (5' to 3') | SNP site | Motif | SEQ ID NO. |
|---|---|---|---|---|
| 540087 | A$_e$A$_k$T$_k$A$_k$AATTGTCATC$_k$A$_e$ | 10 | 4-9-2 (ekkk-d9-ke) | 70 |
| 540090 | A$_e$T$_k$T$_k$A$_k$ATAAATTGTC$_k$A$_e$ | 13 | 4-9-2 (ekkk-d9-ke) | 71 |
| 540091 | T$_e$A$_k$T$_k$T$_k$AATAAATTGT$_k$C$_e$ | 14 | 4-9-2 (ekkk-d9-ke) | 72 |
| 540092 | G$_e$T$_k$CATCACCAGA$_k$A$_k$A$_k$A$_e$ | 2 | 2-9-4 (ek-d9-kkke) | 73 |
| 540093 | T$_e$G$_k$TCATCACCAG$_k$A$_k$A$_k$A$_e$ | 3 | 2-9-4 (ek-d9-kkke) | 74 |
| 540094 | T$_e$T$_k$GTCATCACCA$_k$G$_k$A$_k$A$_e$ | 4 | 2-9-4 (ek-d9-kkke) | 67 |
| 540096 | A$_e$A$_k$TTGTCATCAC$_k$C$_k$A$_k$G$_e$ | 6 | 2-9-4 (ek-d9-kkke) | 68 |
| 540097 | A$_e$A$_k$ATTGTCATCA$_k$C$_k$C$_k$A$_e$ | 8 | 2-9-4 (ek-d9-kkke) | 69 |
| 540098 | T$_e$A$_k$AATTGTCATC$_k$C$_k$C$_k$C$_e$ | 8 | 2-9-4 (ek-d9-kkke) | 10 |
| 540099 | A$_e$T$_k$AAATTGTCAT$_k$C$_k$A$_k$C$_e$ | 9 | 2-9-4 (ek-d9-kkke) | 75 |
| 540100 | A$_e$A$_k$TAAATTGTCA$_k$T$_k$C$_k$A$_e$ | 10 | 2-9-4 (ek-d9-kkke) | 70 |
| 540101 | T$_e$A$_k$ATAAATTGTC$_k$A$_k$T$_k$C$_e$ | 11 | 2-9-4 (ek-d9-kkke) | 76 |
| 540102 | T$_e$T$_k$AATAAATTGT$_k$C$_k$A$_k$T$_e$ | 12 | 2-9-4 (ek-d9-kkke) | 66 | e = 2'-MOE; k = cEt; d = 2'-deoxyribonucleoside

TABLE 36

Comparison of selectivity in HTT SNP inhibition of chimeric oligonucleotides with ISIS 460209

| ISIS NO | % UTC mut | % UTC wt | Selectivity (wt vs. mut) | SNP site | Motif |
|---|---|---|---|---|---|
| 460209* | 23 | 57 | 2.4 | 8 | 3-9-3 (ekk-d9-kke) |
| 543887 | 18 | 43 | 2.3 | 4 | 4-9-2 (ekkk-d9-ke) |
| 540083 | 18 | 67 | 3.7 | 6 | 4-9-2 (ekkk-d9-ke) |
| 540084 | 10 | 49 | 4.9 | 7 | 4-9-2 (ekkk-d9-ke) |
| 540085 | 21 | 86 | 4.1 | 8 | 4-9-2 (ekkk-d9-ke) |
| 540087 | 60 | 98 | 1.6 | 10 | 4-9-2 (ekkk-d9-ke) |
| 540090 | 129 | 137 | 1.1 | 13 | 4-9-2 (ekkk-d9-ke) |
| 540091 | 93 | 105 | 1.1 | 14 | 4-9-2 (ekkk-d9-ke) |

TABLE 36-continued

Comparison of selectivity in HTT SNP inhibition of chimeric oligonucleotides with ISIS 460209

| ISIS NO | % UTC mut | wt | Selectivity (wt vs. mut) | SNP site | Motif |
|---|---|---|---|---|---|
| 540092 | 28 | 55 | 2.0 | 2 | 2-9-4 (ek-d9-kkke) |
| 540093 | 18 | 62 | 3.4 | 3 | 2-9-4 (ek-d9-kkke) |
| 540094 | 13 | 45 | 3.4 | 4 | 2-9-4 (ek-d9-kkke) |
| 540096 | 17 | 68 | 4.0 | 6 | 2-9-4 (ek-d9-kkke) |
| 540097 | 8 | 35 | 4.2 | 8 | 2-9-4 (ek-d9-kkke) |
| 540098 | 12 | 45 | 3.9 | 8 | 2-9-4 (ek-d9-kkke) |
| 540099 | 62 | 91 | 1.5 | 9 | 2-9-4 (ek-d9-kkke) |
| 540100 | 80 | 106 | 1.3 | 10 | 2-9-4 (ek-d9-kkke) |
| 540101 | 154 | 152 | 1.0 | 11 | 2-9-4 (ek-d9-kkke) |
| 540102 | 102 | 106 | 1.0 | 12 | 2-9-4 (ek-d9-kkke) | e = 2'-MOE; k = cEt; d = 2'-deoxyribonucleoside

Example 14

Selectivity in Inhibition of HTT mRNA Levels Targeting SNP by Chimeric Oligonucleotides Designed by Microwalk A series of modified oligonucleotides were designed based on the parent gapmer, ISIS 460209, wherein the central gap region comprises nine 2'-deoxyribonucleosides. These gapmers were created with various motifs and modifications at the wings and/or the central gap region.

The modified oligonucleotides and their motifs are described in Table 37. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e", "k", "y", or "z" are sugar modified nucleosides. A subscript "e" indicates a 2'-O-methoxyethyl (MOE) modified nucleoside, a subscript "k" indicates a 6'-(S)—CH$_3$ bicyclic nucleoside (e.g. cEt), a subscript "y" indicates an α-L-LNA modified nucleoside, and a subscript "z" indicates a F-HNA modified nucleoside. $^P$U indicates a 5-propyne uridine nucleoside and $^x$T indicates a 2-thio-thymidine nucleoside. Underlined nucleosides indicate the mismatch position.

These gapmers were evaluated for thermal stability (T$_m$) using methods described in Example 3. Presented in Table 38 are the T$_m$ measurements for chimeric antisense oligonucleotides when duplexed to mutant or wild-type RNA complement. The T$_m$ of chimeric antisense oligonucleotides duplexed with mutant RNA complement is denoted as "T$_m$ (° C) mut". The T$_m$ of chimeric antisense oligonucleotides duplexed with wild-type RNA complement is denoted as "T$_m$ (° C.) wt".

These gapmers were also tested in vitro. ISIS 141923 was included in the study as a negative control and is denoted as "neg control". The non-allele specific antisense oligonucleotides, ISIS 387916 was used as a positive control and is denoted as "pos control". Heterozygous fibroblast GM04022 cell line was used Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. HTT mRNA levels were adjusted according to total RNA content, as measured by RIBOGREEN. ISIS 460209 marked with an asterisk (*) in the table was included in the study for comparison. The results in Table 38 are presented as percent of HTT mRNA expression, relative to untreated control levels and is denoted as "% UTC". Selectivity was also evaluated and measured by dividing the percent of wild-type HTT mRNA levels vs. the percent of mutant HTT mRNA levels.

As illustrated, several of the newly designed antisense oligonucleotides showed improvement in potency and/or selectivity in inhibiting mut HTT mRNA levels comparing to ISIS 460209.

TABLE 37

Modified oligonucleotides comprising various modifications targeting HTT SNP

| ISIS NO | Sequence (5' to 3') | Modification | Wing Chemistry 5' | 3' | SEQ ID NO. |
|---|---|---|---|---|---|
| 460209* | T$_e$A$_k$A$_k$ATTGTCATCA$_k$C$_k$C$_e$ | 3-9-3 (ekk-d9-kke) | ekk | kke | 10 |
| 539560 | T$_e$A$_k$A$_k$ATTG$^P$UCATCA$_k$C$_k$C$_e$ | 5-propyne in gap | ekk | kke | 11 |
| 539563 | T$_e$A$_k$A$_k$ATTG$^x$TCATCA$_k$C$_k$C$_e$ | 2-thio in gap | ekk | kke | 10 |
| 539554 | T$_e$A$_k$A$_k$ATTGU$_y$CATCA$_k$C$_k$C$_e$ | cc-L-LNA in gap | ekk | kke | 11 |
| 542686 | T$_e$A$_k$A$_k$ATTGT$_z$CATCA$_k$C$_k$C$_e$ | F-HNA in gap | ekk | kke | 10 |

TABLE 37-continued

Modified oligonucleotides comprising various modifications targeting HTT SNP

| ISIS NO | Sequence (5' to 3') | Modification | Wing Chemistry 5' | Wing Chemistry 3' | SEQ ID NO. |
|---|---|---|---|---|---|
| 540108 | $A_eT_eA_kA_k$TTGTCATC$A_kC_kC_e$ | 5-7-5 (eeekk-d7-kkeee) | eeekk | kkeee | 23 |
| 544840 | $T_eA_kA_k$ATTGTCATCA$C_kC_eT_kT_kA_k$ | 3-9-6 (ekk-d9-kkekkk) | ekk | kkekkk | 15 |
| 550904 | $T_eA_kA_k$ATTGTCATCA$C_kC_eT_kT_kT_kA_k$ | 3-9-7 (ekk-d9-kkekkkk) | ekk | kkekkkk | 18 |
| 540082 | $A_eT_kT_kG_k$TCATCACCAG$_kA_e$ | 4-9-2 (ekkk-d9-ke) | ekkk | ke | 65 |
| 540089 | $T_eT_kA_kA_k$TAAATTGTCA$_kT_e$ | 4-9-2 (ekkk-d9-ke) | ekkk | ke | 66 |
| 540095 | $A_eT_k$TGTCATCACC$_kA_kAG_kA_e$ | 2-9-4 (ek-d9-kkke) | ek | kkke | 67 |
| 543528 | $A_eT_kA_kA_k$A̲ATGTCATCA$_kC_eC_kA_e$ | Mismatch at position 2 counting from 5' gap | ekek | keke | 77 |
| 543533 | $T_eA_kA_k$ATAGTCATCA$_kC_kC_e$ | Mismatch at position 3 counting from 5' gap | ekk | kke | 78 |
| 387916 (pos control) | $T_eC_eT_eC_eT_e$ATTGCACATTC$_eC_eA_eA_eG_e$ | 5-10-5 | eeeee | eeeee | 56 |
| 141923 (neg control) | $C_eC_eT_eT_eC_e$CCTGAAGGTTC$_eC_eT_eC_eC_e$ | 5-10-5 | eeeee | eeeee | 57 | e = 2'-MOE; k = cEt; d = 2'-deoxyribonucleoside

TABLE 38

Comparison of selectivity in inhibition of HTT mRNA levels, and Tm of modified oligonucleotides with ISIS 460209 targeted to rs7685686 in GM04022 cells

| ISIS NO | Tm (° C.) mutant | Tm (° C.) wt | % UTC mut | % UTC wt | Selectivity (wt vs mut) | Modification | Wing Chemistry 5' | Wing Chemistry 3' |
|---|---|---|---|---|---|---|---|---|
| 460209* | 53.7 | 52.2 | 23 | 57 | 2.7 | 3-9-3 (ekk-d9-kke) | ekk | kke |
| 539560 | 54.1 | 50.8 | 13 | 32 | 2.4 | 5-propyne in gap | ekk | kke |
| 539563 | 53.8 | 49.1 | 13 | 40 | 3.2 | 2-thio in gap | ekk | kke |
| 539554 | 56.5 | 54.5 | 54 | 89 | 1.7 | a-L-LNA in gap | ekk | kke |
| 542686 | 56.1 | 50.4 | 26 | 62 | 2.4 | F-HNA in gap | ekk | kke |
| 540108 | 60.0 | 57.9 | 27 | 63 | 2.3 | 5-7-5 (eeekk-d7-kkeee) | eeekk | kkeee |
| 544840 | — | — | 19 | 40 | 2.1 | 3-9-6 (ekk-d9-kkekkk) | ekk | kkekkk |
| 550904 | — | — | 39 | 65 | 1.7 | 3-9-7 (ekk-d9-kkekkkk) | ekk | kkekkkk |
| 540082 | — | — | 21 | 62 | 3.0 | 4-9-2 (ekkk-d9-ke) | ekkk | ke |
| 540089 | — | — | 78 | 86 | 1.1 | 4-9-2 (ekkk-d9-ke) | ekkk | ke |
| 540095 | — | — | 22 | 66 | 3.1 | 2-9-4 (ek-d9-kkke) | ek | kkke |

TABLE 38-continued

Comparison of selectivity in inhibition of HTT mRNA levels, and Tm of modified oligonucleotides with ISIS 460209 targeted to rs7685686 in GM04022 cells

| ISIS NO | Tm (° C.) mutant | Tm (° C.) wt | % UTC mut | % UTC wt | Selectivity (wt vs mut) | Modification | Wing Chemistry 5' | Wing Chemistry 3' |
|---|---|---|---|---|---|---|---|---|
| 543528 | 50.5 | 49.1 | 44 | 90 | 2.1 | Mismatch at position 2 counting from 5' gap | ekek | keke |
| 543533 | 47.0 | 44.8 | 83 | 97 | 1.2 | Mismatch at position 3 counting from 5' gap | ekk | kke |
| 387916 (pos control) | — | — | 21 | 19 | 0.9 | 5-10-5 | eeeee | eeeee |
| 141923 (neg control) | — | — | 95 | 99 | 1.0 | 5-10-5 | eeeee | eeeee | e = 2'-MOE; k = cEt; d = 2-deoxyribonucleoside

Example 15

Chimeric Oligonucleotides Comprising Modifications at the SNP Site of HTT Gene

Additional gapmers are designed based on the gapmer selected from studies described in Tables 73 and 74 (ISIS 540108) and is marked with an asterisk (*). These gapmers are designed by introducing modifications at the SNP site at position 9 of the oligonucleotides, as counted from the 5'-terminus and are created with a 5-7-5 motif.

The gapmers are described in Table 39. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "a", "b", "e", or "k" are sugar modified nucleosides. A subscript "a" indicates 2'-(ara)-F modified nucleoside, a subscript "b" indicates a 5'-Me DNA modified nucleoside, a subscript "e" indicates a 2'-O-methoxyethyl (MOE) modified nucleoside, and a subscript "k" indicates a 6'-(S)—CH$_3$ bicyclic nucleoside (e.g. cEt). $^X$T indicates a 2-thio-thymidine nucleoside. Underline nucleoside or the number in parentheses indicates the position on the oligonucleotides opposite to the SNP position, as counted from the 5'-terminus.

Example 16

Chimeric Oligonucleotides Comprising Modifications at the Wing Regions Targeting HTT SNP Additional gapmers are designed based on the gapmer, ISIS 540107 selected from Example 11 and is marked with an asterisk (*). These gapmers are designed by introducing bicyclic modified nucleosides at the 3' or 5' terminus and are tested to evaluate if the addition of bicyclic modified nucleosides at the wing regions improves the activity and selectivity in inhibition of mutant HTT SNP.

The gapmers comprise a 5-7-5 motif and are described in Table 40. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e", or "k" are sugar modified nucleosides. A subscript "e" indicates a 2'-O-methoxyethyl (MOE) modified nucleoside, and a subscript "k" indicates a 6'-(S)—CH$_3$ bicyclic nucleoside (e.g. cEt).

TABLE 39

Modified oligonucleotides targeting HTT SNP

| ISIS NO | Sequence (5' to 3') | Gap Chemistry | Wing chemistry 5' | Wing chemistry 3' | SEQ ID NO. |
|---|---|---|---|---|---|
| 540108* (9) | A$_e$T$_e$A$_e$A$_k$A$_k$TTG<u>T</u>CATC$_k$A$_k$C$_e$C$_e$A$_e$ | Deoxy | eeekk | kkeee | 32 |
| XXXX28 (9) | A$_e$T$_e$A$_e$A$_k$A$_k$TTG$^x$<u>T</u>CATC$_k$A$_k$C$_e$C$_e$A$_e$ | Deoxy/2-thio | eeekk | kkeee | 32 |
| XXXX29 (9) | A$_e$T$_e$A$_e$A$_k$A$_k$TTG<u>T</u>$_a$CATC$_k$A$_k$C$_e$C$_e$A$_e$ | Deoxy/2'-(ara)-F | eeekk | kkeee | 32 |
| XXXX30 (9) | A$_e$T$_e$A$_e$A$_k$A$_k$TTG<u>T</u>$_b$CATC$_k$A$_k$C$_e$C$_e$A$_e$ | Deoxy/5'-Me-DNA | eeekk | kkeee | 32 | e = 2'-MOE, k = cEt

TABLE 40

Modified oligonucleotides targeting HTT SNP

| ISIS NO | Sequence (5' to 3') | Motif | wing chemistry 5' | wing chemistry 3' | SEQ ID NO. |
|---|---|---|---|---|---|
| 540107* | $A_eT_eA_eA_eA_k$TTGTCATC$_kA_eC_eC_eA_e$ | 5-7-5 (eeeek-d7-keeee) | eeeek | keeee | 32 |
| XXXX31 | $A_eT_eAkA_kA_k$TTGTCATC$_kA_kC_kC_eA_e$ | 5-7-5 (eekkk-d7-kkkee) | eekkk | kkkee | 32 |
| XXXX32 | $A_eT_eA_eA_eA_k$TTGTCATC$_eA_eC_eC_eA_e$ | 5-7-5 (eeeek-d7-eeeee) | eeeek | eeeee | 32 |
| XXXX33 | $A_eT_eA_eA_kA_k$TTGTCATC$_eA_eC_eC_eA_e$ | 5-7-5 (eeekk-d7-eeeee) | eeekk | eeeee | 32 |
| XXXX34 | $A_eT_eAkA_kA_k$TTGTCATC$_eA_eC_eC_eA_e$ | 5-7-5 (eekkk-d7-eeeee) | eekkk | eeeee | 32 |
| XXXX35 | $A_eT_eA_eA_eA_e$TTGTCATC$_kA_eC_eC_eA_e$ | 5-7-5 (eeeee-d7-keeee) | eeeee | keeee | 32 |
| XXXX36 | $A_eT_eA_eA_eA_e$TTGTCATC$_kA_kC_eC_eA_e$ | 5-7-5 (eeeee-d7-kkeee) | eeeee | kkeee | 32 |
| XXXX37 | $A_eT_eA_eA_eA_k$TTGTCATC$_kA_kC_kC_eA_e$ | 5-7-5 (eeeee-d7-kkkee) | eeeee | kkkee | 32 | e = 2'-MOE; k = cEt; d = 2'-deoxyribonucleoside

Example 17

Chimeric Oligonucleotides Comprising Wing and Central Gap Modifications Targeting HTT SNP Additional gapmers are designed based on the parent gapmer, ISIS 460209, wherein the central gap region comprises nine 2'-deoxyribonucleosides and is marked with an asterisk (*) in the table. These gapmers were designed by introducing modifications at the wings or the central gap region and are created with a 3-9-3 motif.

The gapmers are described in Table 41. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e", or "k" are sugar modified nucleosides. A subscript "e" indicates a 2'-O-methoxyethyl (MOE) modified nucleoside, and a subscript "k" indicates a 6'-(S)—CH$_3$ bicyclic nucleoside (e.g. cEt). $^P$T indicates a 5-propyne thymidine nucleoside. $^P$C indicates a 5-propyne cytosine nucleoside. Underline nucleoside or the number in parentheses indicates the position on the oligonucleotides opposite to the SNP position, as counted from the 5'-terminus.

TABLE 41

Modified oligonucleotides targeting HTT SNP

| ISIS NO | Sequence (5' to 3') | Modification | wing chemistry 5' | wing chemistry 3' | SEQ ID NO |
|---|---|---|---|---|---|
| 460209* (8) | $T_eA_kA_k$ATTG<u>T</u>CATCA$_kC_kC_e$ | Deoxy gap (3-9-3) | ekk | kke | 10 |
| 552103 (8) | $T_eA_kA_k$ATTG<u>T</u>CATCA$_kC_kC_k$ | Deoxy gap (3-9-3) | eee | kkk | 10 |
| 552104 (8) | $T_eA_kA_k$ATTG<u>T</u>CATCA$_eC_eC_e$ | Deoxy gap (3-9-3) | kkk | eee | 10 |
| 552105 (8) | $T_eA_kA_k$ATTG$^P$<u>T</u>$^P$CATCA$_kC_kC_e$ | Deoxy/5-Propyne | ekk | kke | 10 |
| 552106 (8) | $T_eA_kA_k$A$^P$T$^P$TG$^P$<u>T</u>$^P$CA$^P$T$^P$CA$_kC_kC_e$ | Deoxy/5-Propyne | ekk | kke | 10 | e = 2'-MOE; k = cEt

Example 18

Modified Oligonucleotides Comprising F-HNA Modification at the Central Gap or Wing Region Targeting HTT SNP A series of modified oligonucleotides were designed based on ISIS 460209, wherein the central gap region contains nine 2'-deoxyribonucleosides. These modified oligonucleotides were designed by incorporating one or more F-HNA(s) modification within the central gap region or on the wing regions. The F-HNA containing oligonucleotides were tested for their ability to selectively inhibit mutant (mut) HTT mRNA expression levels targeting rs7685686 while leaving the expression of the wild-type (wt) intact. The activity and selectivity of the modified oligonucleotides were evaluated and compared to ISIS 460209.

The modified oligonucleotides and their motifs are described in Table 42. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). Nucleosides followed by a subscript "z" indicate F-HNA modified nucleosides. $^m$C indicates a 5-methyl cytosine nucleoside. Underlined nucleoside indicates the position on the oligonucleotides opposite to the SNP position, which is position 8 as counted from the 5'-terminus.

The gap-interrupted antisense oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 43.

The IC$_{50}$ and selectivity were calculated using methods previously described in Example 2. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

The parent gapmer, 460209 is marked with an asterisk (*) in the table and was included in the study as a benchmark oligonucleotide against which the activity and selectivity of antisense oligonucleotides targeting nucleotides overlapping the SNP position could be compared.

As illustrated in Table 43, oligonucleotides comprising F-HNA modification(s) showed improvement in selectivity while maintaining activity as compared to the parent gapmer, ISIS 460209.

TABLE 42

Gap-interrupted antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209* | T$_e$A$_k$A$_k$ATTG$\underline{T}$$^m$CAT$^m$CA$_k$$^m$C$_k$$^m$C$_e$ | 3-9-3 | Full deoxy | ekk | kke | 10 |
| 566266 | T$_e$A$_k$A$_k$A$_z$TTG$\underline{T}$$^m$CAT$^m$CA$_k$$^m$C$_k$$^m$C$_e$ | 3-9-3 or 4-8-3 | Deoxy/F-HNA | ekk or ekkz | kke | 10 |
| 566267 | T$_e$A$_k$A$_k$AT$_z$TG$\underline{T}$$^m$CAT$^m$CA$_k$$^m$C$_k$$^m$C$_e$ | 3-9-3 or 5-7-3 | Deoxy/F-HNA | ekk or ekkdz | kke | 10 |
| 566268 | T$_e$A$_k$A$_k$ATT$_z$G$\underline{T}$$^m$CAT$^m$CA$_k$$^m$C$_k$$^m$C$_e$ | 3-9-3 or 6-6-3 | Deoxy/F-HNA | ekk or ekkddz | kke | 10 |
| 566269 | T$_e$A$_k$A$_k$ATTG$_z$$\underline{T}$$^m$CAT$^m$CA$_k$$^m$C$_k$$^m$C$_e$ | 3-9-3 or 7-5-3 | Deoxy/F-HNA | ekk or ekkdddz | kke | 10 |
| 567369 | T$_e$A$_k$A$_k$A$_z$T$_z$TG$\underline{T}$$^m$CAT$^m$CA$_k$$^m$C$_k$$^m$C$_e$ | 3-9-3 or 5-7-3 | Deoxy/F-HNA | ekk or ekkzz | kke | 10 | e = 2'-MOE, k = cEt, d = 2'-β-deoxyribonucleoside, z = F-HNA

TABLE 43

Comparison of inhibition of HTT mRNA levels and selectivity of gap-interrupted antisense oligonucleotides with ISIS 460209 targeting HTT SNP

| ISIS NO | Mut | Wt | Selectivity (wt vs mut) | Motif | Gap chemistry | Wing Chemistry 5' | Wing Chemistry 3' |
|---|---|---|---|---|---|---|---|
| 460209* | 0.28 | 3.1 | 11 | 3-9-3 | Full deoxy | ekk | kke |
| 566266 | 0.20 | >10 | >50 | 3-9-3 or 4-8-3 | Deoxy/F-HNA | ekk or ekkz | kke |
| 566267 | 0.90 | >9.9 | >11 | 3-9-3 or 5-7-3 | Deoxy/F-HNA | ekk or ekkdz | kke |

TABLE 43-continued

Comparison of inhibition of HTT mRNA levels and selectivity of gap-interrupted antisense oligonucleotides with ISIS 460209 targeting HTT SNP

| ISIS NO | Mut | Wt | Selectivity (wt vs mut) | Motif | Gap chemistry | Wing Chemistry 5' | 3' |
|---|---|---|---|---|---|---|---|
| 566268 | 1.0 | >10 | >10 | 3-9-3 or 6-6-3 | Deoxy/F-HNA | ekk or ekkddz | kke |
| 566269 | 1.7 | >10.2 | >6 | 3-9-3 or 7-5-3 | Deoxy/F-HNA | ekk or ekkdddz | kke |
| 567369 | 0.82 | >9.8 | >12 | 3-9-3 or 5-7-3 | Deoxy/F-HNA | ekk or ekkzz | kke | e = 2'-MOE, k = cEt, d= 2'-β-deoxyribonucleoside, z = F-HNA

Example 19

Modified Oligonucleotides Comprising cEt Modification(s) at the Central Gap Region Targeting HTT SNP A series of modified oligonucleotides were designed in the same manner as described in Example 18. These modified oligonucleotides were designed by replacing F-HNA(s) with cEt modification(s) in the central gap region while maintaining the wing configuration. The modified oligonucleotides were tested for their ability to selectively inhibit mutant (mut) HTT mRNA expression levels targeting rs7685686 while leaving the expression of the wild-type (wt) intact. The activity and selectivity of the modified oligonucleotides were evaluated and compared to ISIS 460209.

The modified oligonucleotides and their motifs are described in Table 44. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). $^m$C indicates a 5-methyl cytosine nucleoside. Underlined nucleoside indicates the position on the oligonucleotides opposite to the SNP position, which is position 8 as counted from the 5'-terminus.

The gap-interrupted antisense oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented below.

The IC$_{50}$ and selectivity were calculated using methods previously described in Example 2. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 45, some of the newly designed antisense oligonucleotides (ISIS 575006, 575007, and 575008) showed improvement in potency and/or selectivity in inhibiting mut HTT mRNA levels comparing to ISIS 460209.

TABLE 44

Gap-interrupted antisense oligonucleotides targeting HTT SNP

| ISIS NO. | Sequence (5' to 3') | Motif | Gap chemistry | Wing chemistry 5' | 3' | SEQ ID NO. |
|---|---|---|---|---|---|---|
| 460209* | T$_e$A$_k$A$_k$ATTG$\underline{T}$$^m$CAT$^m$CA$_k$$^m$C$_k$$^m$C$_e$ | 3-9-3 | Full deoxy | ekk | kke | 10 |
| 575006 | T$_e$A$_k$A$_k$A$_k$TTG$\underline{T}$$^m$CAT$^m$CA$_k$$^m$C$_k$$^m$C$_e$ | 4-8-3 | Full deoxy | ekkk | kke | 10 |
| 575007 | T$_e$A$_k$A$_k$AT$_k$TG$\underline{T}$$^m$CAT$^m$CA$_k$$^m$C$_k$$^m$C$_e$ | 3-9-3 or 5-7-3 | Full deoxy or Deoxy/cEt | ekk or ekkdk | kke | 10 |
| 575133 | T$_e$A$_k$A$_k$ATT$_k$G$\underline{T}$$^m$CAT$^m$CA$_k$$^m$C$_k$$^m$C$_e$ | 3-9-3 or 6-6-3 | Full deoxy or Deoxy/cEt | ekk or ekkddk | kke | 10 |
| 575134 | T$_e$A$_k$A$_k$ATTG$_k$$\underline{T}$$^m$CAT$^m$CA$_k$$^m$C$_k$$^m$C$_e$ | 3-9-3 or 7-5-3 | Full deoxy or Deoxy/cEt | ekk or ekkdddk | kke | 10 |
| 575008 | T$_e$A$_k$A$_k$A$_k$T$_k$TG$\underline{T}$$^m$CAT$^m$CA$_k$$^m$C$_k$$^m$C$_e$ | 5-7-3 | Deoxy | ekkkk | kke | 10 | e = 2'-MOE, k = cEt, d= 2'-β-deoxyribonucleoside

TABLE 45

Comparison of inhibition of HTT mRNA levels and selectivity of gap-interrupted antisense oligonucleotides with ISIS 460209 targeting HTT SNP

| ISIS NO | IC$_{50}$ (μM) Mut | IC$_{50}$ (μM) Wt | Selectivity (wt vs mut) | Motif | Gap chemistry | Wing Chemistry 5' | Wing Chemistry 3' |
|---|---|---|---|---|---|---|---|
| 460209* | 0.28 | 3.1 | 11 | 3-9-3 | Full deoxy | ekk | kke |
| 575006 | 0.27 | 3.8 | 14 | 4-8-3 | Full deoxy | ekkk | kke |
| 575007 | 0.67 | >10.1 | >15 | 3-9-3 or 5-7-3 | Full deoxy or Deoxy/cEt | ekk or ekkdk | kke |
| 575133 | 3.0 | >9 | >3 | 3-9-3 or 6-6-3 | Full deoxy or Deoxy/cEt | ekk or ekkddk | kke |
| 575134 | 2.6 | >10.4 | >4 | 3-9-3 or 7-5-3 | Full deoxy or Deoxy/cEt | ekk or ekkdddk | kke |
| 575008 | 0.18 | >9.9 | >55 | 5-7-3 | Deoxy | ekkkk | kke | e = 2'-MOE, k = cEt d= 2'-β-deoxyribonucleoside

Example 20

Modified Oligonucleotides Comprising F-HNA Modification at the 3'-End of Central Gap Region Targeting HTT SNP A series of modified oligonucleotides were designed based on ISIS 460209, wherein the central gap region contains nine 2'-deoxyribonucleosides. These modified oligonucleotides were designed by incorporating one F-HNA modification at the 3'-end of the central gap region. The F-HNA containing oligonucleotides were tested for their ability to selectively inhibit mutant (mut) HTT mRNA expression levels targeting HTT SNP while leaving the expression of the wild-type (wt) intact. The activity and selectivity of the modified oligonucleotides were evaluated and compared to ISIS 460209.

The modified oligonucleotides and their motifs are described in Table 46. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). Nucleosides followed by a subscript "z" indicate F-HNA modified nucleosides. $^m$C indicates a 5-methyl cytosine nucleoside. Underlined nucleoside indicates the position on the oligonucleotides opposite to the SNP position, which is position 8 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C$_{13}$ 2229297_10 which measures at dbSNP rs362303. The HTT mRNA levels were adjusted according to total RNA content, as measured by RIBOGREEN and the results are presented in Table 47.

The IC$_{50}$ and selectivity were calculated using methods previously described in Example 2. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 47, a couple of the newly designed antisense oligonucleotides (ISIS 575833 and 575834) showed improvement in selectivity while maintaining potency as compared to ISIS 460209. ISIS 575836 showed an increase in potency without improvement in selectivity while ISIS 575835 showed comparable selectivity without improvement in potency.

TABLE 46

Modified oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209* | T$_e$A$_k$A$_k$ATTG$\underline{T}$$^m$CAT$^m$CA$_k$$^m$C$_k$$^m$C$_e$ | 3-9-3 | Full deoxy | ekk | kke | 10 |
| 575833 | T$_e$A$_k$A$_k$ATTG$\underline{T}$$^m$C$_z$AT$^m$CA$_k$$^m$C$_k$$^m$C$_e$ | 3-9-3 or 3-5-7 | Deoxy/F-HNA | ekk | kke or zdddkke | 10 |
| 575834 | T$_e$A$_k$A$_k$ATTG$\underline{T}$$^m$CA$_z$T$^m$CA$_k$$^m$C$_k$$^m$C$_e$ | 3-9-3 or 3-6-6 | Deoxy/F-HNA | ekk | kke or zddkke | 10 |
| 575835 | T$_e$A$_k$A$_k$ATTG$\underline{T}$$^m$CAT$_z$$^m$CA$_k$$^m$C$_k$$^m$C$_e$ | 3-9-3 or 3-7-5 | Deoxy/F-HNA | ekk | kke or zdkke | 10 |

TABLE 46-continued

Modified oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 575836 | $T_eA_kA_k$ATTG$\underline{T}^mCA T^mC_eA_k^mC_k^mC_e$ | 3-9-3 or 3-8-4 | Deoxy/F-HNA | ekk | kke or zkke | 10 | e = 2'-MOE, k = cEt, d = 2'-β-deoxyribonucleoside, z = F-HNA

TABLE 47

Comparison of inhibition of HTT mRNA levels and selectivity of modified oligonucleotides with ISIS 460209 targeting HTT SNP

| ISIS NO | Mut | Wt | Selectivity (wt vs mut) | Motif | Gap chemistry | Wing Chemistry 5' | Wing Chemistry 3' |
|---|---|---|---|---|---|---|---|
| 460209* | 0.28 | 3.1 | 11 | 3-9-3 | Full deoxy | ekk | kke |
| 575833 | 0.22 | 4.2 | 19 | 3-9-3 or 3-5-7 | Deoxy/F-HNA | ekk | kke or zdddkke |
| 575834 | 0.30 | 6.3 | 21 | 3-9-3 or 3-6-6 | Deoxy/F-HNA | ekk | kke or zddkke |
| 575835 | 0.89 | 9.8 | 11 | 3-9-3 or 3-7-5 | Deoxy/F-HNA | ekk | kke or zdkke |
| 575836 | 0.09 | 0.4 | 4.6 | 3-9-3 or 3-8-4 | Deoxy/F-HNA | ekk | kke or zkke | e = 2'-MOE, k = cEt, d = 2'-β-deoxyribonucleoside, z = F-HNA

Example 21

Short-Gap Chimeric Oligonucleotides Targeting Huntingtin (HTT) Single Nucleotide Polymorphism (SNP)

Additional chimeric antisense oligonucleotides were designed based on ISIS 460209 and ISIS 540094 wherein the central gap region contains nine 2'-deoxynucleosides. These gapmers were designed with the central gap region shortened by introducing cEt modifications to the wing regions, or interrupted by introducing cEt modifications at the 3'-end of the central gap region. The modified oligonucleotides were tested for their ability to selectively inhibit mutant (mut) HTT mRNA expression levels targeting HTT SNP while leaving the expression of the wild-type (wt) intact. The activity and selectivity of the modified oligonucleotides were evaluated and compared to ISIS 460209 and 540094.

The gapmers and their motifs are described in Table 48. The internucleoside linkages throughout each modified oligonucleotide are phosphorothioate linkages (P=S). Nucleosides without a subscript are 3-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). $^mC$ indicates a 5-methyl cytosine nucleoside. Underlined nucleoside indicates the position on the oligonucleotides opposite to the SNP position, which is position 4 or 8 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 49.

The IC$_{50}$ and selectivity were calculated using methods previously described in Example 2. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 49, the newly designed antisense oligonucleotides (ISIS 575003) showed improvement in selectivity while maintaining potency as compared to ISIS 460209.

TABLE 48

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209* | $T_eA_kA_k$ATTG$\underline{T}^mCAT^mCA_k^mC_k^mC_e$ | 3-9-3 | Full deoxy | ekk | kke | 10 |
| 540094* | $T_eT_kG\underline{T}^mCAT^mCA^mC^mCA_kG_kA_kA_e$ | 2-9-4 | Full deoxy | ek | kkke | 67 |

TABLE 48-continued

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 575003 | $T_eT_kG\underline{T}^mCAT^mCA^mC^mC_kA_kG_kA_kA_e$ | 2-8-5 | Full deoxy | ek | kkkke | 67 |
| 575004 | $T_eT_kG\underline{T}^mCAT^mCA^mC_k^mCA_kG_kA_kA_e$ | 2-9-4 or 2-7-6 | Full deoxy or Deoxy/cEt | ek | kkke or kdkkke | 67 |
| 575005 | $T_eT_kG\underline{T}^mCAT^mCA^mC_k^mC_kA_kG_kA_kA_e$ | 2-7-6 | Full deoxy | ek | kkkke | 67 | e = 2'-MOE  k = cEt,  d = 2'-deoxyribonucleoside

TABLE 49

Comparison of inhibition of HTT mRNA levels and selectivity of modified oligonucleotides with ISIS 460209 targeting HTT SNP

| | $IC_{50}$ (μM) | | Selectivity | | | Wing Chemistry | |
|---|---|---|---|---|---|---|---|
| ISIS NO | Mut | Wt | (wt vs mut) | Motif | Gap chemistry | 5' | 3' |
| 460209* | 0.34 | 3.3 | 9.7 | 3-9-3 | Full deoxy | ekk | kke |
| 540094* | 0.17 | 2.4 | 14 | 2-9-4 | Full deoxy | ek | kkke |
| 575003 | 0.40 | 10 | 25 | 2-8-5 | Full deoxy | ek | kkkke |
| 575004 | 1.2 | >9.6 | >8 | 2-9-4 or 2-7-6 | Full deoxy or Deoxy/cEt | ek | kkke or kdkkke |
| 575005 | >10 | >100 | >10 | 2-7-6 | Full deoxy | ek | kkkke | e = 2'-MOE  k = cEt,  d = 2'-deoxyribonucleoside

Example 22

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 and 17-mer, ISIS 476333 wherein the central gap region contains nine 2'-deoxynucleosides. These gapmers were designed with the central gap region shortened at the 5'-end of the central gap region. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209 and ISIS 476333.

The gapmers and their motifs are described in Table 50. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH₃ bicyclic nucleosides (e.g. cEt). $^mC$ indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 51.

The $IC_{50}$ and selectivity were calculated using methods previously described in Example 2. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 51, a couple of the newly designed antisense oligonucleotides (ISIS 571036 and 571037) showed improvement in potency and selectivity in inhibiting mut HTT mRNA levels as compared to ISIS 460209 and 476333.

TABLE 50

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209* | $T_eA_kA_kATTG\underline{T}^mCAT^mCA_k^mC_k^mC_e$ | 3-9-3 | Full deoxy | ekk | kke | 10 |
| 476333* | $A_eT_kA_eA_kATTG\underline{T}^mCAT^mCA_k^mC_e^mC_kA_e$ | 4-9-4 | Full deoxy | ekek | keke | 32 |

TABLE 50-continued

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 571036 | $A_eT_kA_eA_kA_eT_kTGT^mCAT^mCA_k^mC_e^mC_kA_e$ | 6-7-4 | Full deoxy | ekekek | keke | 32 |
| 571037 | $A_eT_eA_eA_eAkT_kTGT^mCAT^mCA_k^mC_e^mC_kA_e$ | 6-7-4 | Full deoxy | eeeekk | keke | 32 |
| 571038 | $A_eT_kA_eA_kA_eT_eTGT^mCAT^mCA_k^mC_e^mC_kA_e$ | 6-7-4 | Full deoxy | ekekee | keke | 32 | e = 2'-MOE k = cEt, d = 2'-deoxyribonucleoside

TABLE 51

Comparison of inhibition of HTT mRNA levels and selectivity of modified oligonucleotides with ISIS 460209 targeting HTT SNP

| ISIS NO | IC$_{50}$ (μM) Mut | IC$_{50}$ (μM) Wt | Selectivity (wt vs mut) | Motif | Gap chemistry | Wing Chemistry 5' | Wing Chemistry 3' |
|---|---|---|---|---|---|---|---|
| 460209* | 0.34 | 3.3 | 9.7 | 3-9-3 | Full deoxy | ekk | kke |
| 476333* | 0.32 | 1.5 | 4.7 | 4-9-4 | Full deoxy | ekek | keke |
| 571036 | 0.17 | >10.0 | >59 | 6-7-4 | Full deoxy | ekekek | keke |
| 571037 | 0.11 | >9.9 | >90 | 6-7-4 | Full deoxy | eeeekk | keke |
| 571038 | 1.5 | >10.5 | >7 | 6-7-4 | Full deoxy | ekekee | keke | e = 2'-MOE, k = cEt, d = 2'-deoxyribonucleoside

Example 23

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 wherein the central gap region contains nine 2'-deoxynucleosides. These gapmers were designed by having the central gap region shortened to seven 2'-deoxynucleosides. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209.

The gapmers and their motifs are described in Table 52. The internucleoside linkages throughout each modified oligonucleotide are phosphorothioate linkages (P=S). Nucleosides without a subscript are (β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH$_3$ bicyclic nucleosides (e.g. cEt). $^m$C indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 μM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 53.

The IC$_{50}$ and selectivity were calculated using methods previously described in Example 2. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 53, each of the newly designed antisense oligonucleotides (ISIS 540108 and 571069) showed improvement in potency and/or selectivity in inhibiting mut HTT mRNA levels as compared to ISIS 460209.

TABLE 52

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209 | $T_eA_kA_kATTGT^mCAT^mCA_k^mC_k^mC_e$ | 3-9-3 | Full deoxy | ekk | kke | 10 |
| 540108 | $A_eT_eA_eA_kA_kTTG\underline{T}^mCAT^mCk_kk^mC_e^mC_eA_e$ | 5-7-5 | Full deoxy | eeekk | kkeee | 32 |

TABLE 52-continued

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 571069 | $A_eT_eA_eA_eA_kT_kTGT\underline{T}^mCAT^mCA_k^mC_k^mC_eA_e$ | 6-7-4 | Full deoxy | eeeekk | kkee | 32 |
| 571173 | $A_eT_eA_kA_kATTGT\underline{T}^mCAT_k^mC_kA_e^mC_e^mC_eA_e$ | 4-7-6 | Full deoxy | eekk | kkeeee | 32 |
| 572773 | $T_eA_eA_kA_kTTGT\underline{T}^mCAT^mC_kA_k^mC_e^mC_e$ | 4-7-4 | Full deoxy | eekk | kkee | 10 | e = 2'-MOE, k = cEt, d = 2'-deoxyribonucleoside

TABLE 53

Comparison of inhibition of HTT mRNA levels and selectivity of modified oligonucleotides with ISIS 460209 targeting HTT SNP

| ISIS NO | $IC_{50}$ (µM) Mut | $IC_{50}$ (µM) Wt | Selectivity (wt vs mut) | Motif | chemistry | Wing Chemistry 5' | Wing Chemistry 3' |
|---|---|---|---|---|---|---|---|
| 460209 | 0.34 | 3.3 | 9.7 | 3-9-3 | Full deoxy | ekk | kke |
| 540108 | 0.20 | >10 | >50 | 5-7-5 | Full deoxy | eeekk | kkeee |
| 571069 | 0.29 | >9.9 | >34 | 6-7-4 | Full deoxy | eeeekk | kkee |
| 571173 | 1.0 | >10 | >10 | 4-7-6 | Full deoxy | eekk | kkeeee |
| 572773 | 0.71 | >7.8 | 11 | 4-7-4 | Full deoxy | eekk | kkee | e = 2'-MOE, k = cEt, d = 2'-deoxyribonucleoside

Example 24

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 and 17-mer, ISIS 540108 wherein the central gap region contains nine and seven 2'-deoxynucleosides, respectively. These gapmers were designed by introducing one or more cEt modification(s) at the 5'-end of the central gap region. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209 and ISIS 540108.

The gapmers and their motifs are described in Table 54. The internucleoside linkages throughout each modified oligonucleotide are phosphorothioate linkages (P=S). Nucleosides without a subscript are (β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH₃ bicyclic nucleosides (e.g. cEt). $^mC$ indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 55.

The $IC_{50}$ and selectivity were calculated using methods previously described in Example 2. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 55, most of the newly designed oligonucleotides showed improvement in selectivity while maintaining potency as compared to 460209.

TABLE 54

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209 | $T_kA_kA_kATTGT\underline{T}^mCAT^mCA_k^mC_k^mC_e$ | 3-9-3 | Full deoxy | ekk | kke | 10 |
| 540108 | $A_eT_eA_kA_kA_kTTG^mT\underline{T}^mCAT^mC_kA_k^mC_e^mC_eA_e$ | 5-7-5 | Full deoxy | eeekk | kkeee | 32 |

TABLE 54-continued

Short-gap antisense oligonucleotides targeting HTT SNP

| ISIS NO. | Sequence (5' to 3') | Motif | Gap chemistry | Wing chemistry 5' | 3' | SEQ ID NO. |
|---|---|---|---|---|---|---|
| 556872 | $A_eT_eA_eA_eA_k$TTG$\underline{T}$$^mCAT^mC_eA_e^mC_e^mC_eA_e$ | 5-7-5 | Full deoxy | eeeek | eeeee | 32 |
| 556873 | $A_eT_eA_eA_kA_k$TTG$\underline{T}$$^mCAT^mC_eA_e^mC_e^mC_eA_e$ | 5-7-5 | Full deoxy | eeekk | eeeee | 32 |
| 556874 | $A_eT_eA_kA_kA_k$TTG$\underline{T}$$^mCAT^mC_eA_e^mC_e^mC_eA_e$ | 5-7-5 | Full deoxy | eekkk | eeeee | 32 |
| 568877 | $A_eT_kA_kA_kA_k$TTG$\underline{T}$$^mCAT^mC_eA_e^mC_e^mC_eA_e$ | 5-7-5 | Full deoxy | ekkkk | eeeee | 32 |
| 568878 | $A_kT_kA_kA_kA_k$TTG$\underline{T}$$^mCAT^mC_eA_e^mC_e^mC_eA_e$ | 5-7-5 | Full deoxy | kkkkk | eeeee | 32 | e = 2'-MOE, k = cEt, d = 2'-deoxyribonucleoside

TABLE 55

Comparison of inhibition of HTT mRNA levels and selectivity of modified oligonucleotides with ISIS 460209 targeting HTT SNP

| ISIS NO | $IC_{50}$ (µM) Mut | Wt | Selectivity (wt vs mut) | Motif | chemistry | Wing Chemistry 5' | 3' |
|---|---|---|---|---|---|---|---|
| 460209 | 0.45 | 2.3 | 5.1 | 3-9-3 | Full deoxy | ekk | kke |
| 540108 | 0.25 | 9.5 | 38 | 5-7-5 | Full deoxy | eeekk | kkeee |
| 556872 | 1.0 | 9.9 | 9.9 | 5-7-5 | Full deoxy | eeeek | eeeee |
| 556873 | 0.67 | 3.4 | 5.1 | 5-7-5 | Full deoxy | eeekk | eeeee |
| 556874 | 0.38 | 1.9 | 5.0 | 5-7-5 | Full deoxy | eekkk | eeeee |
| 568877 | 0.44 | 6.2 | 14 | 5-7-5 | Full deoxy | ekkkk | eeeee |
| 568878 | 0.41 | 8.6 | 21 | 5-7-5 | Full deoxy | kkkkk | eeeee | e = 2'-MOE, k = cEt, d = 2'-deoxyribonucleoside

Example 25

Short-Gap Chimeric Oligonucleotides Targeting Huntingtin (HTT) Single Nucleotide Polymorphism (SNP)

Additional chimeric antisense oligonucleotides were designed based on 15-mer, ISIS 460209 and 17-mer, ISIS 540108 wherein the central gap region contains nine and seven 2'-deoxynucleosides, respectively. These gapmers were designed by introducing one or more cEt modification(s) at the 3'-end of the central gap region. The gapmers were tested for their ability to selectively inhibit mutant (mut) HTT mRNA expression levels targeting HTT SNP while leaving the expression of the wild-type (wt) intact. The activity and selectivity of the gapmers were evaluated and compared to ISIS 460209 and ISIS 540108.

The gapmers and their motifs are described in Table 56. The internucleoside linkages throughout each modified oligonucleotide are phosphorothioate linkages (P=S). Nucleosides without a subscript are β-D-2'-deoxyribonucleosides. Nucleosides followed by a subscript "e" indicate 2'-O-methoxyethyl (MOE) modified nucleosides. Nucleosides followed by a subscript "k" indicate 6'-(S)—CH₃ bicyclic nucleosides (e.g. cEt). $^mC$ indicates a 5-methyl cytosine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used. Cultured GM04022 cells at a density of 25,000 cells per well were transfected using electroporation with 0.12, 0.37, 1.1, 3.3 and 10 µM concentrations of modified oligonucleotides. After a treatment period of approximately 16 hours, RNA was isolated from the cells and mRNA levels were measured by quantitative real-time PCR using ABI assay C_2229297_10 which measures at dbSNP rs362303. The HTT mRNA levels were adjusted according to total RNA content, as measured by RIBOGREEN and the results are presented in Table 57.

The $IC_{50}$ and selectivity were calculated using methods previously described in Example 2. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 57, each of the newly designed oligonucleotides showed improvement in selective inhibition of mutant HTT mRNA levels compared to ISIS 460209. Comparable potency was observed for ISIS 568879 and 568880 while a slight loss in potency was observed for ISIS 556875, 556876 and 556877.

TABLE 56

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209 | T$_e$A$_k$A$_k$ATTG$\underline{T}$$^m$CAT$^m$CA$_k$$^m$C$_k$$^m$C$_e$ | 3-9-3 | Full deoxy | ekk | kke | 10 |
| 540108 | A$_e$T$_e$A$_k$A$_k$A$_k$TTG$\underline{T}$$^m$CAT$^m$C$_k$A$_k$$^m$C$_e$$^m$C$_e$A$_e$ | 5-7-5 | Full deoxy | eeekk | kkeee | 32 |
| 556875 | A$_e$T$_e$A$_e$A$_e$A$_e$TTG$\underline{T}$$^m$CAT$^m$C$_k$A$_e$$^m$C$_e$$^m$C$_e$A$_e$ | 5-7-5 | Full deoxy | eeeee | keeee | 32 |
| 556876 | A$_e$T$_e$A$_e$A$_e$A$_e$TTG$\underline{T}$$^m$CAT$^m$C$_k$A$_k$$^m$C$_e$$^m$C$_e$A$_e$ | 5-7-5 | Full deoxy | eeeee | kkeee | 32 |
| 556877 | A$_e$T$_e$A$_e$A$_e$A$_e$TTG$\underline{T}$$^m$CAT$^m$C$_k$A$_k$$^m$C$_k$$^m$C$_e$A$_e$ | 5-7-5 | Full deoxy | eeeee | kkkee | 32 |
| 568879 | A$_e$T$_e$A$_e$A$_e$A$_e$TTG$\underline{T}$$^m$CAT$^m$C$_k$A$_k$$^m$C$_k$$^m$C$_k$A$_e$ | 5-7-5 | Full deoxy | eeeee | kkkke | 32 |
| 568880 | A$_e$T$_e$A$_e$A$_k$A$_k$TTG$\underline{T}$$^m$CAT$^m$C$_k$A$_k$$^m$C$_k$$^m$C$_k$A$_k$ | 5-7-5 | Full deoxy | eeeee | kkkkk | 32 | e = 2'-MOE, k = cEt, d = 2'-deoxyribonucleoside

TABLE 57

Comparison of inhibition of HTT mRNA levels and selectivity of modified oligonucleotides with ISIS 460209 targeting HTT SNP

| ISIS NO | IC$_{50}$ (µM) Mut | IC$_{50}$ (µM) Wt | Selectivity (wt vs mut) | Motif | Gap chemistry | Wing Chemistry 5' | Wing Chemistry 3' |
|---|---|---|---|---|---|---|---|
| 460209 | 0.45 | 2.3 | 5.1 | 3-9-3 | Full deoxy | ekk | kke |
| 540108 | 0.25 | 9.5 | 38 | 5-7-5 | Full deoxy | eeekk | kkeee |
| 556875 | 1.9 | >9.5 | >5 | 5-7-5 | Full deoxy | eeeee | keeee |
| 556876 | 0.99 | >9.9 | >10 | 5-7-5 | Full deoxy | eeeee | kkeee |
| 556877 | 1.0 | >10 | >10 | 5-7-5 | Full deoxy | eeeee | kkkee |
| 568879 | 0.44 | >10.1 | >23 | 5-7-5 | Full deoxy | eeeee | kkkke |
| 568880 | 0.59 | >10 | >17 | 5-7-5 | Full deoxy | eeeee | kkkkk | e = 2'-MOE, k = cEt, d = 2'-deoxyribonucleoside

Example 26

Modified Oligonucleotides Targeting Huntingtin (HTT) Single Nucleotide Polymorphism (SNP)

A series of modified oligonucleotides were designed based on the parent gapmer, ISIS 460209 wherein the central gap region contains nine 2'-deoxyribonucleosides. These modified oligonucleotides were designed by introducing various chemical modifications in the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to the parent gapmer, ISIS 460209.

The modified oligonucleotides were created with a 3-9-3 motif and are described in Table 58. The internucleoside linkages throughout each gapmer are phosphorothioate (P=S) linkages, except for the internucleoside linkage having a subscript "p" which indicates a methyl phosphonate internucleoside linkage (—O—P(CH$_3$)(=O)—O—). Nucleosides without a subscript are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). $^m$C indicates a 5-methyl cytosine nucleoside. $^x$T indicates a 2-thio-thymidine nucleoside. Underlined nucleoside indicates the position on the oligonucleotides opposite to the SNP position, which is position 8 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented in Table 59.

The $IC_{50}$ and selectivity were calculated using methods previously described in Example 2. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 59, improvement in selectivity with a slight decrease in potency was observed for the newly designed oligonucleotides as compared to ISIS 460209.

The modified oligonucleotides and their motifs are described in Table 60. The internucleoside linkages throughout each gapmer are phosphorothioate (P=S) linkages, except for the internucleoside linkage having a subscript "p" which indicates a methyl phosphonate internucleoside linkage (—O—P(CH$_3$)(=O)—O—). Nucleosides without a subscript are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). $^m$C indicates a 5-methyl cytosine nucleoside. $^x$T indicates a 2-thio-thymidine nucleoside. Underlined nucleo-

TABLE 58

Short-gap antisense oligonucleotides targeting HTT SNP

| ISIS NO. | Sequence (5' to 3') | Gap chemistry | Wing chemistry 5' | Wing chemistry 3' | SEQ ID NO. |
|---|---|---|---|---|---|
| 460209 | T$_e$A$_k$A$_k$ATTG$\underline{T}^m$CAT$^m$CA$_k^m$C$_k^m$C$_e$ | Full deoxy | ekk | kke | 10 |
| 556845 | T$_e$A$_k$A$_k$A$^x$TTG$\underline{T}^m$CAT$^m$CA$_k^m$C$_k^m$C$_e$ | Deoxy/2-Thio | ekk | kke | 10 |
| 556847 | T$_e$A$_k$A$_k$A$^x$T$^x$TG$\underline{T}^m$CAT$^m$CA$_k^m$C$_k^m$C$_e$ | Deoxy/2-Thio | ekk | kke | 10 |
| 558257 | T$_e$A$_k$A$_k$ATT$_p$G$\underline{T}^m$CAT$^m$CA$_k^m$C$_k^m$C$_e$ | Deoxy/Methyl Phosphonate | ekk | kke | 10 |
| 571125 | T$_e$A$_k$A$_k$A$^x$TT$_p$G$\underline{T}^m$CAT$^m$CA$_k^m$C$_k^m$C$_e$ | Deoxy/2-Thio/Methyl Phosphonate | ekk | kke | 10 | e = 2'-MOE  k = cEt, d = 2'-deoxyribonucleoside

TABLE 59

Comparison of inhibition of HTT mRNA levels and selectivity of modified oligonucleotides with ISIS 460209 targeting HTT SNP

| | IC$_{50}$ (μM) | | Selectivity | | Wing Chemistry | |
|---|---|---|---|---|---|---|
| ISIS NO | Mut | Wt | (wt vs mut) | Gap chemistry | 5' | 3' |
| 460209 | 0.56 | 3.8 | 6.8 | Full deoxy | ekk | kke |
| 556845 | 0.98 | >9.8 | >10 | Deoxy/2-Thio | ekk | kke |
| 556847 | 1.3 | >10.4 | >8 | Deoxy/2-Thio | ekk | kke |
| 558257 | 1.7 | >10.2 | >6 | Deoxy/Methyl Phosphonate | ekk | kke |
| 571125 | 1.8 | >10.8 | >6 | Deoxy/2-Thio/Methyl Phosphonate | ekk | kke | e = 2'-MOE, k = cEt, d = 2'-deoxyribonucleoside

Example 27

Modified Oligonucleotides Comprising Chemical Modifications in the Central Gap Region Targeting Huntingtin (HTT) Single Nucleotide Polymorphism (SNP)

Additional chimeric antisense oligonucleotides were designed in the same manner as the antisense oligonucleotides described in Example 26. These gapmers were designed by introducing various modifications in the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to the parent gapmer, ISIS 460209.

side indicates the position on the oligonucleotides opposite to the SNP position, which is position 8 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 μM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented in Table 61.

The $IC_{50}$ and selectivity were calculated using methods previously described in Example 2. The $IC_{50}$ at which each oligonucleotide inhibits the mutant HTT mRNA expression is denoted as 'mut $IC_{50}$'. The $IC_{50}$ at which each oligonucleotide inhibits the wild-type HTT mRNA expression is denoted as 'wt $IC_{50}$'. Selectivity was calculated by dividing the $IC_{50}$ for inhibition of the wild-type HTT versus the $IC_{50}$ for inhibiting expression of the mutant HTT mRNA.

As illustrated in Table 61, some of the newly designed oligonucleotides showed improvement in selectivity while maintaining potency as compared to 460209.

TABLE 60

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209 | $T_eA_kA_kATTG\underline{T}^mCAT^mCA_k{}^mC_k{}^mC_e$ | 3-9-3 | Full deoxy | ekk | kke | 10 |
| 551429 | $T_eA_eA_eA_kT_kTG\underline{T}^mCAT^mCA_k{}^mC_k{}^mC_e$ | 5-7-3 | Full deoxy | eeekk | kke | 10 |
| 571122 | $T_eA_eA_eA_k{}^xTTG\underline{T}^mCAT^mCA_k{}^mC_k{}^mC_e$ | 4-8-3 | Deoxy/2-Thio | eeek | kke | 10 |
| 571123 | $T_eA_eA_eA_kT_kT_pG\underline{T}^mCAT^mCA_k{}^mC_k{}^mC_e$ | 5-7-3 | Deoxy/Methyl Phosphonate | eeekk | kke | 10 |
| 571124 | $T_eA_eA_eA_k{}^xTT_pG\underline{T}^mCAT^mCA_k{}^mC_k{}^mC_e$ | 4-8-3 | Deoxy/2-Thio/Methyl Phosphonate | eeek | kke | 10 |
| 579854 | $T_eA_eA_eA_kTT_pG\underline{T}^mCAT^mCA_k{}^mC_k{}^mC_e$ | 4-8-3 | Deoxy/Methyl Phosphonate | eeek | kke | 10 |
| 566282 | $T_eA_kA_kA_{dx}T_{dx}T_dG_dT_d{}^mC_dA_dT_d{}^mC_dA_k{}^mC_k{}^mC_e$ | 3-9-3 | Deoxy/Methyl Phosphonate | ekk | kke | 10 | e = 2'-MOE, k = cEt, d = 2'-deoxyribonucleoside

TABLE 61

Comparison of inhibition of HTT mRNA levels and selectivity of modified oligonucleotides with ISIS 460209 targeting HTT SNP

| ISIS NO | $IC_{50}$ (μM) Mut | $IC_{50}$ (μM) Wt | Selectivity (wt vs mut) | Motif | Gap chemistry | Wing Chemistry 5' | Wing Chemistry 3' |
|---|---|---|---|---|---|---|---|
| 460209 | 0.56 | 3.8 | 6.8 | 3-9-3 | Full deoxy | ekk | kke |
| 551429 | 0.50 | >10 | >20 | 5-7-3 | Full deoxy | eeekk | kke |
| 571122 | 1.8 | >10.8 | >6 | 4-8-3 | Deoxy/2-Thio | eeek | kke |
| 571123 | 0.96 | >9.6 | >10 | 5-7-3 | Deoxy/Methyl Phosphonate | eeekk | kke |
| 571124 | 2.3 | >9.2 | >4 | 4-8-3 | Deoxy/2-Thio/Methyl Phosphonate | eeek | kke |
| 579854 | 0.63 | >10.1 | >16 | 4-8-3 | Deoxy/Methyl Phosphonate | eeek | kke |
| 566282 | 0.51 | 6.3 | 12.4 | 3-9-3 | Deoxy/Methyl Phosphonate | ekk | kke | e = 2'-MOE, k = cEt

Example 28

Modified Oligonucleotides Comprising Chemical Modifications in the Central Gap Region Targeting Huntingtin (HTT) Single Nucleotide Polymorphism (SNP)

Additional chimeric antisense oligonucleotides were designed in the same manner as the antisense oligonucleotides described in Example 26. These gapmers were designed by introducing various modifications to the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to the parent gapmer, ISIS 460209.

The modified oligonucleotides and their motifs are described in Table 62. The internucleoside linkages throughout each gapmer are phosphorothioate (P=S) linkages, except for the internucleoside linkage having a subscript "p" which indicates a methyl phosphonate internucleoside linkage (—O—P(CH$_3$)(=O)—O—). Nucleosides without a subscript are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). $^m$C indicates a 5-methyl cytosine nucleoside. $^x$T indicates a 2-thio-thymidine nucleoside. Underlined nucleoside indicates the position on the oligonucleotides opposite to the SNP position, which is position 8 or 9 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented in Table 63.

The IC$_{50}$ and selectivity were calculated using methods previously described in Example 2. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 63, all but one of the newly designed oligonucleotides showed improvement in selectivity while maintaining potency as compared to ISIS 460209.

TABLE 62

Short-gap antisense oligonucleotides targeting HTT SNP

| ISIS NO. | Sequence (5' to 3') | Motif | Gap chemistry | Wing chemistry 5' | Wing chemistry 3' | SEQ ID NO. |
|---|---|---|---|---|---|---|
| 460209 | T$_e$A$_k$A$_k$ATTG<u>T</u>$^m$CAT$^m$CA$_k$$^m$C$_k$$^m$C$_e$ | 3-9-3 | Full deoxy | ekk | kke | 10 |
| 476333 | A$_e$T$_k$A$_k$A$_k$ATTGT$^m$CAT$^m$CA$_k$$^m$C$_e$$^m$C$_k$A$_e$ | 4-9-4 | Full deoxy | ekek | keke | 32 |
| 571039 | A$_e$T$_k$A$_k$A$^x$TTGT$^m$CAT$^m$CA$_k$$^m$C$_e$$^m$C$_k$A$_e$ | 4-9-4 | Deoxy/2-Thio | ekek | keke | 32 |
| 571171 | A$_e$T$_k$A$_k$A$_k$ATT$_p$GT$^m$CAT$^m$CA$_k$$^m$C$_e$$^m$C$_k$A$_e$ | 4-9-4 | Deoxy/Methyl Phosphonate | ekek | keke | 32 |
| 571041 | A$_e$T$_k$A$_k$A$^x$TT$_p$GT$^m$CAT$^m$CA$_k$$^m$C$_e$$^m$C$_k$A$_e$ | 4-9-4 | Deoxy/2-Thio/Methyl Phosphonate | ekek | keke | 32 | e = 2'-MOE, k = cEt, d = 2'-deoxyribonucleoside

TABLE 63

Comparison of inhibition of HTT mRNA levels and selectivity of modified oligonucleotides with ISIS 460209 targeting HTT SNP

| | IC$_{50}$ (µM) | | Selectivity | | Wing Chemistry | |
|---|---|---|---|---|---|---|
| ISIS NO | Mut | Wt | (wt vs mut) | Gap chemistry | 5' | 3' |
| 460209 | 0.56 | 3.8 | 6.8 | Full deoxy | ekk | kke |
| 476333 | 0.56 | 3.4 | 6.1 | Full deoxy | ekek | keke |
| 571039 | 0.34 | >9.9 | >29 | Deoxy/2-Thio | ekek | keke |
| 571171 | 0.54 | >10.3 | >19 | Deoxy/Methyl Phosphonate | ekek | keke |

TABLE 63-continued

Comparison of inhibition of HTT mRNA levels and selectivity of modified oligonucleotides with ISIS 460209 targeting HTT SNP

| ISIS NO | IC$_{50}$ (µM) Mut | Wt | Selectivity (wt vs mut) | Gap chemistry | Wing Chemistry 5' | 3' |
|---|---|---|---|---|---|---|
| 571041 | 0.75 | >9.8 | >13 | Deoxy/2-Thio/Methyl Phosphonate | ekek | keke | e = 2'-MOE, k = cEt, d = 2'-deoxyribonucleoside

Example 29

Selectivity in Inhibition of HTT mRNA Levels Targeting SNP by Gap-Interrupted Modified Oligonucleotides Additional modified oligonucleotides were designed based on the parent gapmer, ISIS 460209 wherein the central gap region contains nine 2'-deoxyribonucleosides. These modified oligonucleotides were designed by introducing one or more modified nucleobase(s) in the central gap region and were tested for their ability to selectively inhibit mutant (mut) HTT mRNA expression levels targeting SNP while leaving the expression of the wild-type (wt) intact. The activity and selectivity of the modified oligonucleotides were evaluated and compared to ISIS 460209.

The modified oligonucleotides were created with a 3-9-3 motif and are described in Table 64. The internucleoside linkages throughout each gapmer are phosphorothioate (P=S) linkages. Nucleosides without a subscript are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). $^m$C indicates a 5-methyl cytosine nucleoside. $^x$T indicates a 2-thio-thymidine nucleoside. Underlined nucleoside indicates the position on the oligonucleotides opposite to the SNP position, which is position 8 as counted from the 5'-terminus.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The IC$_{50}$ and selectivity were calculated using methods previously described in Example 2. The IC$_{50}$ at which each oligonucleotide inhibits the mutant HTT mRNA expression is denoted as 'mut IC$_{50}$'. The IC$_{50}$ at which each oligonucleotide inhibits the wild-type HTT mRNA expression is denoted as 'wt IC$_{50}$'. Selectivity was calculated by dividing the IC$_{50}$ for inhibition of the wild-type HTT versus the IC$_{50}$ for inhibiting expression of the mutant HTT mRNA.

As illustrated in Table 65, ISIS 556845 showed improvement in selectivity and potency as compared to ISIS 460209. ISIS 556847 showed improvement in selectivity with comparable potency while ISIS 556846 showed improvement in potency with comparable selectivity.

TABLE 64

Gap-interrupted modified oligonucleotides targeting HTT SNP

| ISIS NO. | Sequence (5' to 3') | Gap chemistry | Wing chemistry 5' | 3' | SEQ ID NO. |
|---|---|---|---|---|---|
| 460209 | T$_e$A$_k$A$_k$ATTGT$^m$CAT$^m$CA$_k$$^m$C$_k$$^m$C$_e$ | Full deoxy | ekk | kke | 10 |
| 556845 | T$_e$A$_k$A$_k$A$^x$TTGT$^m$CAT$^m$CA$_k$$^m$C$_k$$^m$C$_e$ | Deoxy/2-Thio | ekk | kke | 10 |
| 556846 | T$_e$A$_k$A$_k$AT$^x$TGT$^m$CAT$^m$CA$_k$$^m$C$_k$$^m$C$_e$ | Deoxy/2-Thio | ekk | kke | 10 |
| 556847 | T$_e$A$_k$A$_k$A$^x$T$^x$TGT$^m$CAT$^m$CA$_k$$^m$C$_k$$^m$C$_e$ | Deoxy/2-thio | ekk | kke | 10 | e = 2'-MOE k = cEt, d = 2'-deoxyribonucleoside

TABLE 65

Comparison of inhibition of HTT mRNA levels and selectivity of gap-interrupted modified oligonucleotides with ISIS 460209 targeting HTT SNP

| ISIS NO | IC$_{50}$ (µM) Mut | Wt | Selectivity (wt vs mut) | Gap chemistry | Wing Chemistry 5' | 3' |
|---|---|---|---|---|---|---|
| 460209 | 0.30 | 0.99 | 3.3 | Full deoxy | ekk | kke |
| 556845 | 0.13 | 10.01 | >77 | Deoxy/2-Thio | ekk | kke |
| 556846 | 0.19 | 0.48 | 2.5 | Deoxy/2-Thio | ekk | kke |
| 556847 | 0.45 | 9.9 | >22 | Deoxy/2-Thio | ekk | kke | e = 2'-MOE, k = cEt, d = 2'-deoxyribonucleoside

Example 30

Evaluation of Modified Oligonucleotides Targeting HTT SNP—In Vivo Study

Additional modified oligonucleotides were selected and tested for their effects on mutant and wild type HTT protein levels in vivo targeting various SNP sites as illustrated below.

The gapmers and their motifs are described in Table 66. The internucleoside linkages throughout each gapmer are phosphorothioate (P=S) linkages. All cytosine nucleobases thoughout each gapmer are 5-methyl cytosines. Nucleosides without a subscript are β-D-2'-deoxyribonucleosides. Nucleosides followed by a subscript "e" or "k" are sugar modified nucleosides. A subscript "e" indicates a 2'-O-methoxyethyl (MOE) modified nucleoside and a subscript "k" indicates a 6'-(S)—CH$_3$ bicyclic nucleoside (e.g. cEt).

The gapmer, ISIS 460209 was included in the study as a benchmark oligonucleotide against which the potency and selectivity of the modified oligonucletides could be compared. A non-allele specific oligonucleotide, ISIS 387898, was used as a positive control.

Hu97/18 mice, the first murine model of HD that fully genetically recapitulates human HD were used in the study. They were generated in Hayden's lab by cross bred BACHD, YAC18 and Hdh (−/−) mice.

Hu97/18 mice were treated with 300 µg of modified oligonucleotides by a single unilateral intracerebroventricular (ICV) bolus injection. This treatment group consisted of 4 animals/oligonucleotide. The control group received a 10 µl bolus injection of sterile PBS and consisted of 4 animals.

Animals were sacrificed at 4 weeks post-injection. The second most anterior 2 mm coronal slab for each brain hemisphere was collected using a 2 mm rodent brain matrix. The remaining portion of the brain was post-fixed in 4% paraformaldehyde, cryoprotected in 30% sucrose and sectioned into 25 µm coronal sections for immunohistochemical analysis.

The HTT protein levels were analyzed by high molecular weight western blot (modified from Invitrogen's NuPAGE Bis-Tris System Protocol). The tissue was homogenized in ice cold SDP lysis buffer. 40 µg of total protein lysate was resolved on 10% low-BIS acrylamide gels (200:1 acrylamide:BIS) with tris-glycine running buffer (25 mM Tris, 190 mM Glycince, 0.1% SDS) containing 10.7 mM β-mercaptoethanol added fresh. Gels were run at 90V for 40 min through the stack, then 190V for 2.5 h, or until the 75 kDa molecular weight marker band was at the bottom of the gel. Proteins were transferred to nitrocellulose at 24V for 2 h with NuPage transfer buffer (Invitrogen: 25 mM Bicine, 25 mM Bis-Tris, 1.025 mM EDTA, 5% MeOH, pH 7.2). Membranes were blocked with 5% milk in PBS, and then blotted for HTT with MAB2166 (1:1000, millipore). Anti-calnexin (Sigma C4731) immunoblotting was used as loading control. Proteins were detected with IR dye 800CW goat anti-mouse (Rockland 610-131-007) and AlexaFluor 680 goat anti-rabbit (Molecular Probes A21076)-labeled secondary antibodies, and the LiCor Odyssey Infrared Imaging system.

The results in Table 67 are presented as the average percent of HTT protein levels for each treatment group, normalized to PBS-treated control and is denoted as "% UTC". The percent of mutant HTT protein levels is denoted as "mut". The percent of wild-type HTT protein levels is denoted as "wt". Selectivity was also evaluated and measured by dividing the percent of wild-type HTT protein levels vs. the percent of the mutant HTT protein levels.

As illustrated in Table 67, treatment with the newly designed oligonucleotides, ISIS 476333 and 460085 showed improvement in potency and selectivity in inhibiting mutant HTT protein levels as compared to the parent gapmer, 460209. Comparable or a slight loss in potency and/or selectivity was observed for the remaining oligonucleotides.

TABLE 66

Modified oligonucleotides targeting HTT rs7685686, rs4690072 and rs363088 in Hu97/18 mice

| ISIS NO | Sequence (5' to 3') | Motif | Wing Chemistry 5' | 3' | SEQ ID NO. |
|---|---|---|---|---|---|
| 387898 | C$_e$T$_e$C$_e$G$_e$A$_e$CTAAAGCAGGA$_e$T$_e$T$_e$T$_e$C$_e$ | 5-10-5 | e5 | e5 | 79 |
| 460209 | T$_e$A$_k$A$_k$ATTGTCATCA$_k$C$_k$C$_e$ | 3-9-3 | ekk | kke | 10 |
| 435879 | A$_e$A$_e$T$_e$A$_e$A$_e$ATTGTCATCA$_e$C$_e$C$_e$A$_e$G$_e$ | 5-9-5 | e5 | e5 | 80 |
| 476333 | A$_e$T$_k$A$_e$A$_k$TTGTCATCA$_k$C$_e$C$_k$A$_e$ | 4-9-4 | ekek | keke | 32 |
| 435874 | C$_e$A$_e$C$_e$A$_e$G$_e$TGCTACCCAA$_e$C$_e$C$_e$T$_e$T$_e$ | 5-9-5 | e5 | e5 | 81 |
| 435871 | T$_e$C$_e$A$_e$C$_e$A$_e$GCTATCTTCT$_e$C$_e$A$_e$T$_e$C$_e$ | 5-9-5 | e5 | e5 | 82 |
| 460085 | A$_e$T$_e$A$_e$A$_e$A$_e$TTGTCATC$_e$A$_e$C$_e$C$_e$A$_e$ | 5-7-5 | e5 | e5 | 32 | e = 2'-MOE (e.g. e5 = eeeee), k = cEt

TABLE 67

Effects of modified oligonucleotides on mutant and wild type HTT protein levels in Hu97/18 mice

| ISIS NO | SNP site | Dosage (µg) | % UTC mut | wt | Selectivity (wt vs mut) |
|---|---|---|---|---|---|
| PBS | — | 300 | 100 | 100 | 1 |
| 387898 | — | 300 | 23.76 | 25.66 | 1 |
| 460209 | rs7685686 | 300 | 18.16 | 48.99 | 2.7 |
| 435879 | rs7685686 | 300 | 41.48 | 73.11 | 1.8 |
| 476333 | rs7685686 | 300 | 6.35 | 22.05 | 3.5 |
| 460085 | rs7685686 | 300 | 2.9 | 40.1 | 13.8 |
| 435874 | rs4690072 | 300 | 44.18 | 76.63 | 1.7 |
| 435871 | rs363088 | 300 | 33.07 | 89.30 | 2.7 |

Example 31

Evaluation of ISIS 435871 in Central Nervous System (CNS) Targeting HTT rs363088—In Vivo Study A modified oligonucleotide from Example 29, ISIS 435871 was selected and tested for its effects on mutant and wild type HTT protein levels in the CNS in vivo targeting rs363088.

Hu97/18 mouse was treated with 300 µg of ISIS 435871 by a single unilateral intracerebroventricular (ICV) bolus injection. The animal was sacrificed at 4 weeks post-injection. Regional CNS structures were then micro-dissected including bilateral samples from the most anterior portion of cortex (Cortex 1), an intermediate section of cortex (Cortex 2), the most posterior section of cortex (Cortex 3), the striatum, the hippocampus, the cerebellum, and a 1 cm section of spinal cord directly below the brain stem. Tissue was homogenized and assessed for mutant and wild-type HTT levels by Western blotting using the procedures as described in Example 30. The results are presented below. As no untreated or vehicle treated control is shown, HTT intensity of each allele is expressed as a ratio of calnexin loading control intensity. The ratio of the mutant HTT to the wt HTT in the treated animal was determined and is denoted as "wt/mut". Having a ratio higher than 1 is indicative of allele-specific silencing.

As illustrated in Table 68, a single unilateral ICV bolus injection of the modified antisense oligonucleotide showed selective HTT silencing throughout the CNS except in the cerebellum, where the antisense oligonucleotide did not distribute evenly.

TABLE 68

Effects of ISIS 435871 on mutant and wild type HTT protein levels in CNS targeting rs363088 in Hu97/18 mice

| Tissue | HTT intensity/calnexin intensity | | |
|---|---|---|---|
| | wt | mut | wt/mut |
| Cortex 1 | 0.032 | 0.014 | 2.29 |
| Cortex 2 | 0.027 | 0.009 | 3 |
| Cortex 3 | 0.023 | 0.007 | 3.29 |
| Striatum | 0.030 | 0.012 | 2.5 |
| Hippocampus | 0.016 | 0.006 | 2.67 |
| Cerebellum | 0.023 | 0.019 | 1.21 |
| Spinal Cord | 0.014 | 0.007 | 2 |

Example 32

Evaluation of Modified Oligonucleotides Targeting HTT rs7685686—In Vivo Study

Several modified oligonucleotides from Examples 43, 51, 52, 53 and 66 were selected and tested for their effects on mutant and wild type HTT protein levels in vivo targeting HTT rs7685686.

The gapmer, ISIS 460209 was included in the study as a benchmark oligonucleotide against which the potency and selectivity of the modified oligonucletides could be compared.

Hu97/18 mice were treated with 300 μg of modified oligonucleotides by a single unilateral intracerebroventricular (ICV) bolus injection. This treatment group consisted of 4 animals/oligonucleotide. The control group received a 10 μl bolus injection of sterile PBS and consisted of 4 animals.

Animals were sacrificed at 4 weeks post-injection. The second most anterior 2 mm coronal slab for each brain hemisphere was collected using a 2 mm rodent brain matrix. The HTT protein levels were analyzed in the same manner as described in Example 30 and the results are presented below.

The results in Table 69 are presented as the average percent of HTT protein levels for each allele and treatment group, normalized to PBS-treated control and is denoted as "% UTC". The percent of mutant HTT protein levels is denoted as "mut". The percent of wild-type HTT protein levels is denoted as "wt".

As shown in Table 69, each of the newly designed oligonucleotides showed improvement in selective inhibition of mutant HTT protein levels as compared to ISIS 460209. ISIS 550913 and 540095 showed improvement in potency while the remaining modified oligonucleotides showed comparable or a slight decrease in potency as compared to the parent gapmer.

TABLE 69

Effects of modified oligonucleotides on mutant and wild type HTT protein levels targeting rs7685686 in Hu97/18 mice

| ISIS NO | % UTC | | Motif | Wing chemistry | | Gap chem-istry | SEQ ID NO |
|---|---|---|---|---|---|---|---|
| | mut | wt | | 5' | 3' | | |
| PBS | 100 | 100 | — | — | — | — | — |
| 460209 | 18.16 | 48.99 | 3-9-3 | ekk | kke | Full deoxy | 10 |
| 550913 | 9.31 | 34.26 | 5-9-5 | kkekk | kkekk | Full deoxy | 27 |
| 540095 | 12.75 | 106.05 | 2-9-4 | ek | kkke | Full deoxy | 65 |
| 551429 | 19.07 | 108.31 | 5-7-3 | eeekk | kke | Full deoxy | 10 |
| 540094 | 24.68 | 87.56 | 2-9-4 | ek | kkke | Full deoxy | 67 |
| 540096 | 24.89 | 98.26 | 2-9-4 | ek | kkke | Full deoxy | 68 |
| 540108 | 28.34 | 85.62 | 5-7-5 | eeekk | kkeee | Full deoxy | 23 | e = 2'-MOE, k = cEt

Example 33

Evaluation of Modified Oligonucleotides Targeting HTT rs7685686—In Vivo Study

Several modified oligonucleotides selected from Examples 57, 58, 61 and 62 were tested and evaluated for their effects on mutant and wild type HTT protein levels in vivo targeting HTT rs7685686.

Hu97/18 mice were treated with 300 μg of modified oligonucleotides by a single unilateral intracerebroventricular (ICV) bolus injection and the control group received a 10 μl bolus injection of sterile PBS. Each treatment group consisted of 4 animals.

Animals were sacrificed at 4 weeks post-injection. The second most anterior 2 mm coronal slab for each brain hemisphere was collected using a 2 mm rodent brain matrix. The HTT protein levels were analyzed in the same manner as described in Example 30. The in vivo study for ISIS 575008 and 571069 marked with an asterisk (*) was performed independently and the results are presented below.

The results in Table 70 are presented as the average percent of HTT protein levels for each allele and treatment group, normalized to PBS-treated control and is denoted as "% UTC". The percent of mutant HTT protein levels is denoted as "mut". The percent of wild-type HTT protein levels is denoted as "wt".

As illustrated in Table 70, selective inhibition of mut HTT protein levels was achieved with the newly designed oligonucleotide treatment as compared to PBS treated control.

TABLE 70

Effects of modified oligonucleotides on mutant and wild type HTT protein levels targeting rs7685686 in Hu97/18 mice

| ISIS NO | % UTC mut | % UTC wt | Motif | Wing chemistry 5' | Wing chemistry 3' | Gap chemistry | SEQ ID NO |
|---|---|---|---|---|---|---|---|
| PBS | 100 | 100 | — | — | — | — | — |
| 575007 | 26.9 | 104.5 | 3-9-3 | ekk | kke | Deoxy/cEt | 10 |
| 575008* | 21.7 | 105.9 | 5-7-3 | ekkkk | kke | Deoxy/cEt or full deoxy | 10 |
| 566267 | 32.8 | 109.3 | 3-9-3 | ekk | kke | Deoxy/F-HNA | 10 |
| 571036 | 30.3 | 103.3 | 6-7-4 | ekekek | keke | Full deoxy | 32 |
| 571037 | 32.8 | 111.9 | 6-7-4 | eeeekk | keke | Full deoxy | 32 |
| 571069* | 29.4 | 109.8 | 6-7-4 | eeeekk | kkee | Full deoxy | 32 | e = 2'-MOE, k = cEt

Example 34

Evaluation of Modified Oligonucleotides Targeting HTT rs7685686—In Vivo Dose Response Study ISIS 476333, 435871, 540108, 575007 and 551429 from previous examples were selected and evaluated at various doses for their effect on mutant and wild type HTT protein levels in vivo targeting HTT rs7685686.

Hu97/18 mice were treated with various doses of modified oligonucleotides as presented in Table 71 by a single unilateral intracerebroventricular (ICV) bolus injection. This treatment group consisted of 4 animals/oligonucleotide. The control group received a 10 μl bolus injection of sterile PBS and consisted of 4 animals.

Animals were sacrificed at 4 weeks post-injection. The second most anterior 2 mm coronal slab for each brain hemisphere was collected using a 2 mm rodent brain matrix. The HTT protein levels were analyzed in the same manner as described in Example 30. The dose response study was performed independently for each modified oligonucleotide and the results are presented below.

The results in Table 71 are presented as the average percent of HTT protein levels for each allele and treatment group, normalized to PBS-treated control and is denoted as "% UTC". The percent of mutant HTT protein levels is denoted as "mut". The percent of wild-type HTT protein levels is denoted as "wt".

As illustrated in Table 71, selective inhibition of mut HTT protein levels was achieved in a dose-dependent manner for the newly designed oligonucleotides.

TABLE 71

Dose-dependent effect of modified oligonucleotides on mutant and wild type HTT protein levels targeting rs7685686 in Hu97/18 mice

| ISIS NO | Dosage (μg) | % UTC mut | % UTC wt | Motif | SEQ ID NO |
|---|---|---|---|---|---|
| PBS | 0 | 100 | 100 | — | 32 |
| 476333 | 50 | 48.7 | 115 | 4-9-4 (ekek-d9-keke) | 32 |
| | 150 | 23.1 | 53.3 | | |
| | 300 | 8.8 | 36.7 | | |
| 435871 | 75 | 114 | 118 | 5-9-5 (e5-d9-e5) | 82 |
| | 150 | 47.3 | 80.3 | | |
| | 300 | 33 | 89.3 | | |
| | 500 | 36 | 97.5 | | |
| 540108 | 75 | 30.5 | 71.7 | 5-7-5 (eeekk-d7-kkeee) | 32 |
| | 150 | 22 | 81 | | |
| | 300 | 8.6 | 59.6 | | |
| 575007 | 150 | 41.5 | 110.7 | 3-9-3 (ekk-d-k-d7-kke) (deoxy gap interrupted with cEt) | 10 |
| | 300 | 29 | 119.4 | | |
| 551429 | 75 | 58 | 101.3 | 5-7-3 | 10 |
| | 150 | 36.2 | 110.4 | | |
| | 300 | 19.7 | 107.8 | | | e = 2'-MOE (e.g. e5 = eeeee), k = cEt, d = 2'-deoxyribonucleoside

Example 35

Modified Oligonucleotides Targeting Huntingtin (HTT) Single Nucleotide Polymorphism (SNP)

A series of modified oligonucleotides was designed based on a parent gapmer, ISIS 460209, wherein the central gap region contains nine β-D-2'-deoxyribonucleosides. The modified oligonucleotides were designed by introducing a 5'-(R)-Me DNA modification within the central gap region. The 5'-(R)-Me DNA containing oligonucleotides were tested for their ability to selectively inhibit mutant (mut) HTT mRNA expression levels targeting rs7685686 while leaving the expression of the wild-type (wt) intact. The potency and selectivity of the modified oligonucleotides were evaluated and compared to ISIS 460209.

The position on the oligonucleotides opposite to the SNP position, as counted from the 5'-terminus is position 8.

The modified oligonucleotides were created with a 3-9-3 motif and are described in Table 72. The internucleoside linkages throughout each gapmer are phosphorothioate (P=S) linkages. Nucleosides followed by a subscript "d" are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). Nucleosides followed by a subscript "z" indicates a 5'-(R)-Me DNA. "$^m$C" indicates a 5-methyl cytosine nucleoside.

The modified oligonucleotides were tested in vitro. Heterozygous fibroblast GM04022 cell line was used Cultured GM04022 cells at a density of 25,000 cells per well were transfected using electroporation with a single dose at 2 μM concentration of the modified oligonucleotide. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2xPCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The $IC_{50}$s and selectivities as expressed in "fold" were measured and calculated using methods described previously in Example 2. As illustrated in Table 73, treatment with the newly designed oligonucleotides showed comparable or a slight increase in potency and/or selectivity as compared to ISIS 460209.

TABLE 72

Gap-interrupted oligonucleotides comprising 5'-(R)-Me DNA targeting HTT SNP

| ISIS NO. | Sequence (5' to 3') | Gap chemistry | Wing chemistry 5' | 3' | SEQ ID NO. |
|---|---|---|---|---|---|
| 460209 | $T_eA_kA_kA_dT_dT_dG_dT_d{}^mC_dA_dT_d{}^mC_dA_k{}^mC_k{}^mC_e$ | Full deoxy | ekk | kke | 10 |
| 556848 | $T_eA_kA_kA_dT_dT_dG_dT_d{}^mC_dA_dT_d{}^mC_dA_k{}^mC_k{}^mC_e$ | Deoxy/ 5'-(R)-Me DNA | ekk | kke | 10 |
| 556849 | $T_eA_kA_kA_dT_zT_dG_dT_d{}^mC_dA_dT_d{}^mC_dA_k{}^mC_k{}^mC_e$ | Deoxy/ 5'-(R)-Me DNA | ekk | kke | 10 |
| 556850 | $T_eA_kA_kA_dT_dT_zG_dT_d{}^mC_dA_dT_d{}^mC_dA_k{}^mC_k{}^mC_e$ | Deoxy/ 5'-(R)-Me DNA | ekk | kke | 10 | e = 2'-MOE, k = cEt

TABLE 73

Comparison of inhibition of HTT mRNA levels and selectivity of gap-interrupted oligonucleotides with ISIS 460209 targeting HTT SNP

| ISIS NO. | $IC_{50}$ (µM) Mut | $IC_{50}$ (µM) Wt | Selectivity (wt vs mut) | Gap chemistry | Wing chemistry 5' | 3' |
|---|---|---|---|---|---|---|
| 460209 | 0.30 | 0.99 | 3.3 | Full deoxy | ekk | kke |
| 556848 | 0.15 | 0.6 | 4.0 | Deoxy/ 5'-(R)-Me DNA | ekk | kke |
| 556849 | 0.16 | 0.46 | 2.9 | Deoxy/ 5'-(R)-Me DNA | ekk | kke |
| 556850 | 0.33 | 0.96 | 2.9 | Deoxy/ 5'-(R)-Me DNA | ekk | kke | e = 2'-MOE, k = cEt

Example 36

Modified Oligonucleotides Comprising 5'-(R)— or 5'-(S)-Me DNA Modification Targeting HTT SNP A series of modified oligonucleotides was designed based on a parent gapmer, ISIS 460209, wherein the central gap region contains nine β-D-2'-deoxyribonucleosides. The modified oligonucleotides were designed by introducing 5'-(S)— or 5'-(R)-Me DNA modification slightly upstream or downstream (i.e. "microwalk") within the central gap region. The gapmers were created with a 3-9-3 motif and were tested for their ability to selectively inhibit mutant (mut) HTT mRNA expression. The potency and selectivity of the modified oligonucleotides were evaluated and compared to ISIS 460209.

The position on the oligonucleotides opposite to the SNP position, as counted from the 5'-terminus is position 8.

The modified oligonucleotides and their motifs are described in Table 74. The internucleoside linkages throughout each gapmer are phosphorothioate (P=S) linkages. Nucleosides followed by a subscript "d" are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—$CH_3$ bicyclic nucleoside (e.g. cEt). Nucleosides followed by a subscript "v" indicates a 5'-(S)-Me DNA. Nucleosides followed by a subscript "z" indicates a 5'-(R)-Me DNA. "$^mC$" indicates a 5-methyl cytosine nucleoside.

The modified oligonucleotides were tested in vitro. Heterozygous fibroblast GM04022 cell line was used. Cultured GM04022 cells at a density of 25,000 cells per well were transfected using electroporation with 0.1, 0.4, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 uL 2×PCR buffer, 101 uL primers (300 uM from ABI), 1000 uL water and 40.4 uL RT MIX. To each well was added 15 uL of this mixture and 5 uL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN and the results are presented below.

The $IC_{50}$s and selectivities as expressed in "fold" were measured and calculated using methods described previously in Example 2. The results in Table 75 demonstrated that each of the newly designed oligonucleotides comprising 5'-(S)— or 5'-(R)-Me DNA within the central gap region achieved improvement in potency and selectivity as compared to the parent gapmer, ISIS 460209.

TABLE 74

Gap-interrupted oligonucleotides comprising 5'-(S)- or 5'-(R)-Me DNA targeting HTT SNP

| ISIS NO | Sequence (5' to 3') | Motif | Gap Chemistry | Wing Chemistry 5' | 3' | SEQ ID NO |
|---|---|---|---|---|---|---|
| 460209 | $T_eA_kA_kA_dT_dT_dG_dT_d{}^mC_dA_dT_d{}^mC_dA_k{}^mC_k{}^mC_e$ | 3-9-3 | Full deoxy | ekk | kke | 10 |
| 589429 | $T_eA_kA_kA_dT_vT_dG_dT_d{}^mC_dA_dT_d{}^mC_dA_k{}^mC_k{}^mC_e$ | 3-9-3 | Deoxy/5'-(S)-Me DNA | ekk | kke | 10 |

TABLE 74-continued

Gap-interrupted oligonucleotides comprising
5'-(S)- or 5'-(R)-Me DNA targeting HTT SNP

| ISIS NO | Sequence (5' to 3') | Gap Motif | Chemistry | Wing Chemistry 5' | Wing Chemistry 3' | SEQ ID NO |
|---|---|---|---|---|---|---|
| 589430 | $T_eA_kA_kA_dT_dT_vG_dT_d{}^mC_dA_dT_d{}^mC_dA_k{}^mC_k{}^mC_e$ | 3-9-3 | Deoxy/5'-(S)-Me DNA | ekk | kke | 10 |
| 589431 | $T_eA_kA_kA_dT_dG_dT_v{}^mC_dA_dT_d{}^mC_dA_k{}^mC_k{}^mC_e$ | 3-9-3 | Deoxy/5'-(S)-Me DNA | ekk | kke | 10 |
| 589432 | $T_eA_kA_kA_dT_dG_dT_d{}^mC_dA_dT_v{}^mC_dA_k{}^mC_k{}^mC_e$ | 3-9-3 | Deoxy/5'-(S)-Me DNA | ekk | kke | 10 |
| 594588 | $T_eA_kA_kA_dT_vT_vG_dT_d{}^mC_dA_dT_d{}^mC_dA_k{}^mC_k{}^mC_e$ | 3-9-3 | Deoxy/5'-(S)-Me DNA | ekk | kke | 10 |
| 556848 | $T_eA_kA_kA_zT_dT_dG_dT_d{}^mC_dA_dT_d{}^mC_dA_k{}^mC_k{}^mC_e$ | 3-9-3 | Deoxy/5'-(R)-Me DNA | ekk | kke | 10 |
| 556849 | $T_eA_kA_kA_dT_zG_dT_d{}^mC_dA_dT_d{}^mC_dA_k{}^mC_k{}^mC_e$ | 3-9-3 | Deoxy/5'-(R)-Me DNA | ekk | kke | 10 |
| 556850 | $T_eA_kA_kA_dT_dT_zG_dT_d{}^mC_dA_dT_d{}^mC_dA_k{}^mC_k{}^mC_e$ | 3-9-3 | Deoxy/5'-(R)-Me DNA | ekk | kke | 10 |
| 539558 | $T_eA_kA_kA_dT_dG_dT_z{}^mC_dA_dT_d{}^mC_dA_k{}^mC_k{}^mC_e$ | 3-9-3 | Deoxy/5'-(R)-Me DNA | ekk | kke | 10 |
| 594160 | $T_eA_kA_kA_dT_dG_dT_d{}^mC_zA_dT_d{}^mC_dA_k{}^mC_k{}^mC_e$ | 3-9-3 | Deoxy/5'-(R)-Me DNA | ekk | kke | 10 |
| 594161 | $T_eA_kA_kA_dT_dG_dT_d{}^mC_dA_zT_d{}^mC_dA_k{}^mC_k{}^mC_e$ | 3-9-3 | Deoxy/5'-(R)-Me DNA | ekk | kke | 10 |
| 589433 | $T_eA_kA_kA_dT_dG_dT_d{}^mC_dA_dT_z{}^mC_dA_k{}^mC_k{}^mC_e$ | 3-9-3 | Deoxy/5'-(R)-Me DNA | ekk | kke | 10 |
| 594162 | $T_eA_kA_kA_dT_dG_dT_d{}^mC_dA_dT_d{}^mC_zA_k{}^mC_k{}^mC_e$ | 3-9-3 | Deoxy/5'-(R)-Me DNA | ekk | kke | 10 |
| 594589 | $T_eA_kA_kA_zT_zG_dT_d{}^mC_dA_dT_d{}^mC_dA_k{}^mC_k{}^mC_e$ | 3-9-3 | Deoxy/5'-(R)-Me DNA | ekk | kke | 10 | e = 2'-MOE; k = cEt

TABLE 75

Comparison of inhibition of HTT mRNA levels and selectivity of gap-interrupted oligonucleotides with ISIS 460209 targeting HTT SNP

| ISIS NO. | IC$_{50}$ (µM) Mut | IC$_{50}$ (µM) Wt | Selectivity (wt vs. mut) | Gap Motif | Chemistry | Wing Chemistry 5' | Wing Chemistry 3' |
|---|---|---|---|---|---|---|---|
| 460209 | 1.2 | 1.4 | 1.2 | 3-9-3 | Full deoxy | ekk | kke |
| 589429 | 0.22 | 3.3 | 15 | 3-9-3 | Deoxy/5'-(S)-Me DNA | ekk | kke |
| 589430 | 0.22 | >10 | >45.5 | 3-9-3 | Deoxy/5'-(S)-Me DNA | ekk | kke |
| 589431 | 0.16 | 1.9 | 11.9 | 3-9-3 | Deoxy/5'-(S)-Me DNA | ekk | kke |
| 589432 | 0.23 | >10 | >43.5 | 3-9-3 | Deoxy/5'-(S)-Me DNA | ekk | kke |
| 594588 | 0.81 | >10 | >12.3 | 3-9-3 | Deoxy/5'-(S)-Me DNA | ekk | kke |
| 556848 | 0.16 | 1.8 | 11.3 | 3-9-3 | Deoxy/5'-(R)-Me DNA | ekk | kke |
| 556849 | 0.14 | 1.1 | 7.9 | 3-9-3 | Deoxy/5'-(R)-Me DNA | ekk | kke |
| 556850 | 0.22 | 1.7 | 7.7 | 3-9-3 | Deoxy/5'-(R)-Me DNA | ekk | kke |
| 539558 | 0.38 | 3.8 | 10 | 3-9-3 | Deoxy/5'-(R)-Me DNA | ekk | kke |
| 594160 | 0.28 | 3.3 | 11.8 | 3-9-3 | Deoxy/5'-(R)-Me DNA | ekk | kke |

TABLE 75-continued

Comparison of inhibition of HTT mRNA levels and selectivity of gap-interrupted oligonucleotides with ISIS 460209 targeting HTT SNP

| ISIS NO. | IC$_{50}$ (µM) Mut | Wt | Selectivity (wt vs. mut) | Motif | Gap Chemistry | Wing Chemistry 5' 3' |
|---|---|---|---|---|---|---|
| 594161 | 0.28 | >10 | >35.7 | 3-9-3 | Deoxy/ 5'-(R)-Me DNA | ekk kke |
| 589433 | 0.27 | 4.4 | 16.3 | 3-9-3 | Deoxy/ 5'-(R)-Me DNA | ekk kke |
| 594162 | 0.27 | 3.5 | 13.0 | 3-9-3 | Deoxy/ 5'-(R)-Me DNA | ekk kke |
| 594589 | 0.48 | 4.4 | 9.2 | 3-9-3 | Deoxy/ 5'-(R)-Me DNA | ekk kke | e = 2'-MOE; k = cEt

Example 37

Inhibition of HTT mRNA Levels Targeting SNP by Modified Oligonucleotides

Additional modified oligonucleotides were designed in a similar manner as the antisense oligonucleotides described in Example 36. Various chemical modifications were introduced slightly upstream or downstream (i.e. "microwalk") within the central gap region. The gapmers were created with a 3-9-3 motif and were tested for their ability to selectively inhibit mutant (mut) HTT mRNA expression. The position on the oligonucleotides opposite to the SNP position, as counted from the 5'-terminus is position 8. The potency and selectivity of the modified oligonucleotides were evaluated and compared to ISIS 460209.

The modified oligonucleotides and their motifs are described in Table 76. The internucleoside linkages throughout each gapmer are phosphorothioate (P=S) linkages. Nucleosides followed by a subscript "d" are β-D-2'-deoxyribonucleosides. Nucleosides followed by a subscript "e" indicates a 2'-O-methoxyethyl (MOE) modified nucleoside. Nucleosides followed by a subscript "k" indicates a 6'-(S)—CH$_3$-bicyclic nucleoside (e.g. cEt). Nucleosides followed by a subscript "b" indicates a 5'-(R)-allyl DNA. Nucleosides followed by a subscript "c" indicates a 5'-(S)-allyl DNA. Nucleosides followed by a subscript "g" indicates a 5'-(R)-hydroxyethyl DNA. Nucleosides followed by a subscript "i" indicates a 5'-(S)-hydroxyethyl DNA. "$^m$C" indicates a 5-methyl cytosine nucleoside.

The modified oligonucleotides were tested in vitro using heterozygous fibroblast GM04022 cell line. The transfection method and analysis of HTT mRNA levels adjusted according to total RNA content, as measured by RIBOGREEN were performed in the same manner as described in Example 37. The IC$_{50}$s and selectivities as expressed in "fold" were measured and calculated using methods described previously and the results are shown below. As presented in Table 77, several modified oligonucleotides achieved greater than 4.5 fold selectivity in inhibiting mutant HTT mRNA levels and, therefore, are more selective than ISIS

TABLE 76

Gap-interrupted oligonucleotides comprising 5'-substituted DNA targeting HTT SNP

| ISIS NO. | Sequence (5' to 3') | Motif | Gap Chemistry (mod position) | Wing Chemistry 5' 3' | SEQ ID NO |
|---|---|---|---|---|---|
| 460209 | T$_e$A$_k$A$_k$A$_d$T$_d$T$_d$G$_d$T$_d$$^m$C$_d$A$_d$T$_d$$^m$C$_d$A$_k$$^m$C$_k$$^m$C$_e$ | 3-9-3 | Full deoxy | ekk kke | 10 |
| 589414 | T$_e$A$_k$A$_k$A$_d$T$_b$T$_d$G$_d$T$_d$$^m$C$_d$A$_d$T$_d$$^m$C$_d$A$_k$$^m$C$_k$$^m$C$_e$ | 3-9-3 | Deoxy/5'-(R)-allyl DNA (pos 5) | ekk kke | 10 |
| 589415 | T$_e$A$_k$A$_k$A$_d$T$_d$T$_b$G$_d$T$_d$$^m$C$_d$A$_d$T$_d$$^m$C$_d$A$_k$$^m$C$_k$$^m$C$_e$ | 3-9-3 | Deoxy/5'-(R)-allyl DNA (pos 6) | ekk kke | 10 |
| 589416 | T$_e$A$_k$A$_k$A$_d$T$_d$T$_d$G$_d$T$_b$$^m$C$_d$A$_d$T$_d$$^m$C$_d$A$_k$$^m$C$_k$$^m$C$_e$ | 3-9-3 | Deoxy/5'-(R)-allyl DNA (pos 8) | ekk kke | 10 |
| 589417 | T$_e$A$_k$A$_k$A$_d$T$_d$T$_d$G$_d$T$_d$$^m$C$_d$A$_d$T$_b$$^m$C$_d$A$_k$$^m$C$_k$$^m$C$_e$ | 3-9-3 | Deoxy/5'-(R)-allyl DNA (pos 11) | ekk kke | 10 |
| 589418 | T$_e$A$_k$A$_k$A$_d$T$_c$T$_d$G$_d$T$_d$$^m$C$_d$A$_d$T$_d$$^m$C$_d$A$_k$$^m$C$_k$$^m$C$_e$ | 3-9-3 | Deoxy/5'-(S)-allyl DNA (pos 5) | ekk kke | 10 |
| 589419 | T$_e$A$_k$A$_k$A$_d$T$_d$T$_c$G$_d$T$_d$$^m$C$_d$A$_d$T$_d$$^m$C$_d$A$_k$$^m$C$_k$$^m$C$_e$ | 3-9-3 | Deoxy/5'-(S)-allyl DNA (pos 6) | ekk kke | 10 |
| 589420 | T$_e$A$_k$A$_k$A$_d$T$_d$T$_d$G$_d$T$_c$$^m$C$_d$A$_d$T$_d$$^m$C$_d$A$_k$$^m$C$_k$$^m$C$_e$ | 3-9-3 | Deoxy/5'-(S)-allyl DNA (pos 8) | ekk kke | 10 |
| 589421 | T$_e$A$_k$A$_k$A$_d$T$_d$T$_d$G$_d$T$_d$$^m$C$_d$A$_d$T$_c$$^m$C$_d$A$_k$$^m$C$_k$$^m$C$_e$ | 3-9-3 | Deoxy/5'-(S)-allyl DNA (pos 11) | ekk kke | 10 |
| 589422 | T$_e$A$_k$A$_k$A$_d$T$_g$T$_d$G$_d$T$_d$$^m$C$_d$A$_d$T$_d$$^m$C$_d$A$_k$$^m$C$_k$$^m$C$_e$ | 3-9-3 | Deoxy/5'-(R)-hydroxyethyl DNA (pos 5) | ekk kke | 10 |

TABLE 76-continued

Gap-interrupted oligonucleotides comprising 5'-substituted DNA targeting HTT SNP

| ISIS NO. | Sequence (5' to 3') | Motif | Gap Chemistry (mod position) | Wing Chemistry 5' | Wing Chemistry 3' | SEQ ID NO |
|---|---|---|---|---|---|---|
| 589423 | $T_eA_kA_kA_dT_dG_dT_d{}^mC_dA_dT_d{}^mC_dA_k{}^mC_k{}^mC_e$ | 3-9-3 | Deoxy/5'-(R)-hydroxyethyl DNA (pos 6) | ekk | kke | 10 |
| 589424 | $T_eA_kA_kA_dT_dG_dT_g{}^mC_dA_dT_d{}^mC_dA_k{}^mC_k{}^mC_e$ | 3-9-3 | Deoxy/5'-(R)-hydroxyethyl DNA (pos 8) | ekk | kke | 10 |
| 589437 | $T_eA_kA_kA_dT_dG_dT_d{}^mC_dA_dT_g{}^mC_dA_k{}^mC_k{}^mC_e$ | 3-9-3 | Deoxy/5'-(R)-hydroxyethyl DNA (pos 11) | ekk | kke | 10 |
| 589426 | $T_eA_kA_kA_dT_iG_dT_d{}^mC_dA_dT_d{}^mC_dA_k{}^mC_k{}^mC_e$ | 3-9-3 | Deoxy/5'-(S)-hydroxyethyl DNA (pos 5) | ekk | kke | 10 |
| 589427 | $T_eA_kA_kA_dT_dG_iT_d{}^mC_dA_dT_d{}^mC_dA_k{}^mC_k{}^mC_e$ | 3-9-3 | Deoxy/5'-(S)-hydroxyethyl DNA (pos 6) | ekk | kke | 10 |
| 589428 | $T_eA_kA_kA_dT_dG_dT_i{}^mC_dA_dT_d{}^mC_dA_k{}^mC_k{}^mC_e$ | 3-9-3 | Deoxy/5'-(S)-hydroxyethyl DNA (pos 8) | ekk | kke | 10 |
| 589425 | $T_eA_kA_kA_dT_dG_dT_d{}^mC_dA_dT_i{}^mC_dA_k{}^mC_k{}^mC_e$ | 3-9-3 | Deoxy/5'-(S)-hydroxyethyl DNA (pos 11) | ekk | kke | 10 | e = 2'-MOE; k = cEt

TABLE 77

Comparison of inhibition of HTT mRNA levels and selectivity of gap-interrupted oligonucleotides with ISIS 460209 targeting HTT SNP

| ISIS NO | IC$_{50}$ (µM) Mut | IC$_{50}$ (µM) Wt | Selectivity (wt vs. mut) | Gap Chemistry (mod position) | Motif | Wing Chemistry 5' | Wing Chemistry 3' |
|---|---|---|---|---|---|---|---|
| 460209 | 0.47 | 2.1 | 4.5 | Full deoxy | 3-9-3 | ekk | kke |
| 589414 | 1.0 | 7.6 | 7.6 | Deoxy/5'-(R)-Allyl DNA (pos 5) | 3-9-3 | ekk | kke |
| 589415 | 1.4 | >10 | >7.1 | Deoxy/5'-(R)-Allyl DNA (pos 6) | 3-9-3 | ekk | kke |
| 589416 | 2.7 | >10 | >3.7 | Deoxy/5'-(R)-Allyl DNA (pos 8) | 3-9-3 | ekk | kke |
| 589417 | 5.4 | >10 | >1.9 | Deoxy/5'-(R)-Allyl DNA (pos 11) | 3-9-3 | ekk | kke |
| 589418 | 1.2 | >10 | >8.3 | Deoxy/5'-(S)-Allyl DNA (pos 5) | 3-9-3 | ekk | kke |
| 589419 | 1.1 | >10 | >9.1 | Deoxy/5'-(S)-Allyl DNA (pos 6) | 3-9-3 | ekk | kke |
| 589420 | 3.2 | >10 | >3.1 | Deoxy/5'-(S)-Allyl DNA (pos 8) | 3-9-3 | ekk | kke |
| 589421 | 2.0 | >10 | >5.0 | Deoxy/5'-(S)-Allyl DNA (pos 11) | 3-9-3 | ekk | kke |
| 589422 | 0.73 | 3.2 | 4.4 | Deoxy/5'-(R)-Hydroxyethyl DNA (pos 5) | 3-9-3 | ekk | kke |
| 589423 | 0.92 | 9.2 | 10 | Deoxy/5'-(R)-Hydroxyethyl DNA (pos 6) | 3-9-3 | ekk | kke |
| 589424 | 0.21 | 4.4 | 21 | Deoxy/5'-(R)-Hydroxyethyl DNA (pos 8) | 3-9-3 | ekk | kke |

TABLE 77-continued

Comparison of inhibition of HTT mRNA levels and selectivity of gap-interrupted oligonucleotides with ISIS 460209 targeting HTT SNP

| ISIS NO | IC$_{50}$ (µM) Mut | Wt | Selectivity (wt vs. mut) | Gap Chemistry (mod position) | Wing Chemistry Motif 5' 3' |
|---|---|---|---|---|---|
| 589437 | 0.73 | >10.2 | >14 | Deoxy/5'(R)- Hydroxyethyl DNA (pos 11) | 3-9-3 ekk kke |
| 589426 | 0.91 | 5.1 | 5.6 | Deoxy/5'-(S) Hydroxyethyl DNA (pos 5) | 3-9-3 ekk kke |
| 589427 | 0.91 | >10 | >11 | Deoxy/5'-(S) Hydroxyethyl DNA (pos 6) | 3-9-3 ekk kke |
| 589428 | 1.1 | >11 | >10 | Deoxy/5'-(S) Hydroxyethyl DNA (pos 8) | 3-9-3 ekk kke |
| 589425 | 1.5 | >10.5 | >7 | Deoxy/5'-(S) Hydroxyethyl DNA (pos 11) | 3-9-3 ekk kke | e = 2'-MOE; k = cEt

Example 38

Modified Oligonucleotides Comprising Methyl Phosphonate Internucleoside Linkage Targeting HTT SNP—In Vitro Study ISIS 558255 and 558256 from Example 10 were selected and evaluated for their effect on mutant and wild type HTT mRNA expression levels targeting rs7685686. ISIS 46020 was included in the study for comparison. The position on the oligonucleotides opposite to the SNP position, as counted from the 5'-terminus is position 8.

Heterozygous fibroblast GM04022 cell line was used for the in vitro assay (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 µL 2×PCR buffer, 101 µL primers (300 µM from ABI), 1000 µL water and 40.4 µL RT MIX. To each well was added 15 µL of this mixture and 5 µL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The IC$_{50}$s and selectivities as expressed in "fold" were measured and calculated using methods described previously in Example 2. As illustrated in Table 78, improvement in selectivity and potency was achieved with the modified oligonucleotides comprising methyl phosphonate internucleoside linkage as compared to ISIS 460209.

TABLE 78

Comparison of selectivity in inhition of HTT mRNA levels of antisense oligonucleotides with ISIS 460209 targeted to rs7685686 in GM4022 cells

| ISIS NO | IC$_{50}$ (µM) Mut | Wt | Selectivity (wt vs mut) | Motif | Gap Chem-istry | Wing Chem-istry 5' 3' | SEQ ID NO |
|---|---|---|---|---|---|---|---|
| 460209 | 0.30 | 0.99 | 3.3 | 3-9-3 | Full deoxy | ekk kke | 10 |
| 558255 | 0.19 | 1.3 | 6.8 | 3-9-3 | Deoxy/ Methyl phosphate | ekk kke | 10 |
| 558256 | 0.20 | 1.3 | 6.5 | 3-9-3 | Deoxy/ Methyl phosphate | ekk kke | 10 | e = 2'-MOE (e.g. e5 = eeeee), k = cEt

Example 39

Modified Oligonucleotides Comprising Methyl Phosphonate or Phosphonoacetate Internucleoside Linkage(s) Targeting HTT SNP A series of modified oligonucleotides were designed based on ISIS 460209 wherein the gap region contains nine β-D-2'-deoxyribonucleosides. The modified oligonucleotides were synthesized to include one or more methyl phosphonate or phosphonoacetate internucleoside linkage modifications within the gap region. The oligonucleotides with modified phosphorus containing backbone were tested for their ability to selectively inhibit mutant (mut) HTT mRNA expression levels targeting rs7685686 while leaving the expression of the wild-type (wt) intact. The potency and selectivity of the modified oligonucleotides were evaluated and compared to ISIS 460209.

The position on the oligonucleotides opposite to the SNP position, as counted from the 5'-terminus is position 8.

The modified oligonucleotides and their motifs are described in Table 79. Each internucleoside linkage is a phosphorothioate (P=S) except for the internucleoside linkage having a subscript "x" or "y". Each nucleoside followed by a subscript "x" indicates a methyl phosphonate internucleoside linkage (—P(CH$_3$)(=O)—). Each nucleoside followed by a subscript "y" indicates a phosphonoacetate internucleoside linkage (—P(CH$_2$CO$_2$)(=O)—). Nucleosides followed by a subscript "d" is a β-D-2'-deoxyribonucleoside. Nucleosides followed by a subscript "e" indicates a 2'-O-methoxyethyl (MOE) modified nucleoside. Nucleosides followed by a subscript "k" indicates a 6'-(S)—CH$_3$ bicyclic nucleoside (e.g. cEt). "$^m$C" indicates a 5-methyl cytosine modified nucleoside.

The modified oligonucleotides were tested in vitro. Heterozygous fibroblast GM04022 cell line was used (from Coriell Institute). Cultured GM04022 cells at a density of 25,000 cells per well were transfected using electroporation with 0.12, 0.37, 1.1, 3.3 and 10 µM concentrations of modified oligonucleotides. After a treatment period of approximately 24 hours, cells were washed with DPBS buffer and lysed. RNA was extracted using Qiagen RNeasy purification and mRNA levels were measured by quantitative real-time PCR using ABI assay C_2229297_10 which measures at dbSNP rs362303. RT-PCR method in short; A mixture was made using 2020 µL 2×PCR buffer, 101 µL primers (300 µM from ABI), 1000 uL water and 40.4 µL RT MIX. To each well was added 15 µL of this mixture and 5 µL of purified RNA. The mutant and wild-type HTT mRNA levels were measured simultaneously by using two different fluorophores, FAM for mutant allele and VIC for wild-type allele. The HTT mRNA levels were adjusted according to total RNA content, as measured by RIBOGREEN.

The $IC_{50}$s and selectivities as expressed in "fold" were measured and calculated using methods described previously in Example 2. As illustrated in Table 80, most of the newly design oligonucleotides achieved improvement in selectivity while maintaining potency as compared to ISIS 460209.

TABLE 79

Modified oligonucleotides comprising methyl phosphonate or phosphonoacetate internucleoside linkage(s) targeting HTT SNP

| ISIS NO | Sequence (5' to 3') | Motif | Chemistry | Wing Chem-istry 5' 3' | SEQ ID NO |
|---|---|---|---|---|---|
| 460209 | $T_eA_kA_kA_dT_dT_dG_dT_d{}^m$ $C_dA_dT_d{}^mC_dA_k{}^mC_k{}^mC_e$ | 3-9-3 | Full deoxy | ekk kke | 10 |
| 566276 | $T_eA_kA_kA_dT_dT_dG_{dx}T_d{}^m$ $C_dA_dT_d{}^mC_dA_k{}^mC_k{}^mC_e$ | 3-9-3 | Deoxy/ Methyl phosphonate | ekk kke | 10 |
| 566277 | $T_eA_kA_kA_dT_dT_dG_dT_{dx}{}^m$ $C_dA_dT_d{}^mC_dA_k{}^mC_k{}^mC_e$ | 3-9-3 | Deoxy/ Methyl phosphonate | ekk kke | 10 |
| 566278 | $T_eA_kA_kA_dT_dT_dG_dT_d{}^m$ $C_{dx}A_dT_d{}^mC_dA_k{}^mC_k{}^mC_e$ | 3-9-3 | Deoxy/ Methyl phosphonate | ekk kke | 10 |
| 566279 | $T_eA_kA_kA_dT_dT_dG_dT_d{}^m$ $C_dA_{dx}T_d{}^mC_dA_k{}^mC_k{}^mC_e$ | 3-9-3 | Deoxy/ Methyl phosphonate | ekk kke | 10 |
| 566280 | $T_eA_kA_kA_dT_dT_dG_dT_d{}^m$ $C_dA_dT_{dx}{}^mC_dA_k{}^mC_k{}^mC_e$ | 3-9-3 | Deoxy/ Methyl phosphonate | ekk kke | 10 |
| 566283 | $T_eA_kA_kA_dT_{dx}T_dG_d$ $T_d{}^mC_dA_dT_d{}^mC_d$ $A_k{}^mC_k{}^mC_e$ | 3-9-3 | Deoxy/ Methyl phosphonate | ekk kke | 10 |
| 573815 | $T_eA_kA_kA_dT_{dy}T_dG_dT_d{}^m$ $C_dA_dT_d{}^mC_dA_k{}^mC_k{}^mC_e$ | 3-9-3 | Deoxy/ Phos-phono-acetate | ekk kke | 10 |
| 573816 | $T_eA_kA_kA_dT_dT_{dy}G_dT_d{}^m$ $C_dA_dT_d{}^mC_dA_k{}^mC_k{}^mC_e$ | 3-9-3 | Deoxy/ Phos-phono-acetate | ekk kke | 10 |

TABLE 79-continued

Modified oligonucleotides comprising methyl phosphonate or phosphonoacetate internucleoside linkage(s) targeting HTT SNP

| ISIS NO | Sequence (5' to 3') | Motif | Chemistry | Wing Chem-istry 5' 3' | SEQ ID NO |
|---|---|---|---|---|---|
| 573817 | $T_eA_kA_kA_dT_dT_dG_dT_{dy}{}^m$ $C_dA_dT_d{}^mC_dA_k{}^mC_k{}^mC_e$ | 3-9-3 | Deoxy/ Phos-phono-acetate | ekk kke | 10 |
| 573818 | $T_eA_kA_kA_dT_dT_dG_dT_d{}^m$ $C_dA_dT_{dy}{}^mC_dA_k{}^mC_k{}^mC_e$ | 3-9-3 | Deoxy/ Phos-phono-acetate | ekk kke | 10 | e = 2'-MOE, k = cEt

TABLE 80

Comparison of selectivity in inhition of HTT mRNA levels of antisense oligonucleotides with ISIS 460209 targeted to rs7685686 in GM4022 cells

| ISIS NO | Mut $IC_{50}$ (µM) | Select-ivity (wt vs mut) | Motif | Chemistry | Wing Chem-istry 5' 3' | SEQ ID NO |
|---|---|---|---|---|---|---|
| 460209 | 0.15 | 9.4 | 3-9-3 | Full deoxy | ekk kke | 10 |
| 566276 | 0.76 | 12.8 | 3-9-3 | Deoxy/ Methyl phosphonate | ekk kke | 10 |
| 566277 | 0.20 | 17 | 3-9-3 | Deoxy/ Methyl phosphonate | ekk kke | 10 |
| 566278 | 0.25 | 8.9 | 3-9-3 | Deoxy/ Methyl phosphonate | ekk kke | 10 |
| 566279 | 0.38 | — | 3-9-3 | Deoxy/ Methyl phosphonate | ekk kke | 10 |
| 566280 | 0.27 | 47 | 3-9-3 | Deoxy/ Methyl phosphonate | ekk kke | 10 |
| 566283 | 0.8 | >100 | 3-9-3 | Deoxy/ Methyl phosphonate | ekk kke | 10 |
| 573815 | 0.16 | 18.8 | 3-9-3 | Deoxy/ Phos-phonoacetate | ekk kke | 10 |
| 573816 | 0.55 | 18.1 | 3-9-3 | Deoxy/ Phos-phonoacetate | ekk kke | 10 |
| 573817 | 0.17 | 22.5 | 3-9-3 | Deoxy/ Phos-phonoacetate | ekk kke | 10 |
| 573818 | 0.24 | 13.5 | 3-9-3 | Deoxy/ Phos-phonoacetate | ekk kke | 10 | e = 2'-MOE, k = cEt

We claim:

1. An oligomeric compound comprising a modified oligonucleotide consisting of 10 to 30 linked nucleosides, wherein the modified oligonucleotide has a modification motif comprising:
   a 5'-region consisting of 5-8 linked 5'-region nucleosides, each independently selected from among a modified nucleoside and an unmodified deoxynucleoside, wherein the 5'-region comprises an AAABB motif, wherein each A is a non-bicyclic modified nucleoside and each B is a bicyclic nucleoside, and wherein the 3'-most 5'-region nucleoside is the second B of AAABB;
   a 3'-region consisting of 2-8 linked 3'-region nucleosides, each independently selected from among a modified nucleoside and an unmodified deoxynucleoside, provided that at least one 3'-region nucleoside is a modified nucleoside and wherein the 5'-most 3'-region nucleoside is a modified nucleoside; and
   a central region between the 5'-region and the 3'-region consisting of 6-12 linked unmodified deoxynucleosides;
   wherein the modified oligonucleotide has a nucleobase sequence complementary to the nucleobase sequence of a target region of a nucleic acid associated with a huntingtin transcript, and wherein the nucleobase sequence of the target region of the target nucleic acid differs from the nucleobase sequence of at least one non-target nucleic acid by 1-3 differentiating nucleobases, and wherein the target nucleic acid and the non-target nucleic acid are alleles of the huntingtin gene.

2. The oligomeric compound of claim 1, wherein the single differentiating nucleobase is a single-nucleotide polymorphism.

3. The oligomeric compound of claim 2, wherein the single-nucleotide polymorphism is selected from among: rs6446723, rs3856973, rs2285086, rs363092, rs916171, rs6844859, rs7691627, rs4690073, rs2024115, rs11731237, rs362296, rs10015979, rs7659144, rs363096, rs362273, rs16843804, rs362271, rs362275, rs3121419, rs362272, rs3775061, rs34315806, rs363099, rs2298967, rs363088, rs363064, rs363102, rs2798235, rs363080, rs363072, rs363125, rs362303, rs362307, rs362310, rs10488840, rs362325, rs35892913, rs363102, rs363096, rs11731237, rs10015979, rs363080, rs2798235, rs1936032, rs2276881, rs363070, rs35892913, rs12502045, rs6446723, rs7685686, rs3733217, rs6844859, and rs362331.

4. The oligomeric compound of claim 2, wherein the single-nucleotide polymorphism is selected from among: rs7685686, rs362303, rs362307, rs4690072 and rs363088.

5. The oligomeric compound of claim 4, wherein the 3'-most bicyclic nucleoside of the 5'-region is selected from among a cEt sugar moiety and an LNA sugar moiety.

6. The oligomeric compound of claim 5, wherein the central region consists of 6-10 linked nucleosides.

7. The oligomeric compound of claim 6, wherein the central region consists of 7 linked nucleosides.

8. The oligomeric compound of claim 4, wherein at least one non-bicyclic modified 5'-region nucleoside comprises a 2'-substituted sugar moiety comprising a 2' substituent selected from among: halogen, optionally substituted allyl, optionally substituted amino, azido, optionally substituted SH, CN, OCN, $CF_3$, $OCF_3$, O, S, or $N(R_m)$-alkyl; O, S, or $N(R_m)$-alkenyl; O, S or $N(R_m)$-alkynyl; optionally substituted O-alkylenyl-O-alkyl, optionally substituted alkynyl, optionally substituted alkaryl, optionally substituted aralkyl, optionally substituted O-alkaryl, optionally substituted O-aralkyl, $O(CH_2)_2SCH_3$, $O-(CH_2)_2-O-N(R_m)(R_n)$ or $O-CH_2-C(=O)-N(R_m)(R_n)$, where each $R_m$ and $R_n$ is, independently, H, an amino protecting group or substituted or unsubstituted $C_1-C_{10}$ alkyl;

wherein each optionally substituted group is optionally substituted with a substituent group independently selected from among: hydroxyl, amino, alkoxy, carboxy, benzyl, phenyl, nitro ($NO_2$), thiol, thioalkoxy (S-alkyl), halogen, alkyl, aryl, alkenyl and alkynyl.

9. The oligomeric compound of claim 4, wherein at least one non-bicyclic modified 5'-region nucleoside comprises a 2'-substituted sugar moiety comprising a 2'-substituent selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2-CH=CH_2$, $O(CH_2)_2-OCH_3$ (MOE), $O(CH_2)_2-SCH_3$, $O(CH_2)_2-OCF_3$, $O(CH_2)_3-N(R_1)(R_2)$, $O(CH_2)_2-ON(R_1)(R_2)$, $O(CH_2)_2-O(CH_2)_2-N(R_1)(R_2)$, $OCH_2C(=O)-N(R_1)(R_2)$, $OCH_2C(=O)-N(R_3)-(CH_2)_2-N(R_1)(R_2)$, and $O(CH_2)_2-N(R_3)-C(=NR_4)[N(R_1)(R_2)]$; wherein $R_1$, $R_2$, $R_3$ and $R_4$ are each, independently, H or $C_1-C_6$ alkyl.

10. The oligomeric compound of claim 9, wherein the 2'-substituent is selected from among: a halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$, and $OCH_2-N(H)-C(=NH)NH_2$.

11. The oligomeric compound of claim 7, wherein each non-bicyclic modified 5'-region nucleoside of the AAABB motif comprises a 2'-MOE sugar moiety.

12. The oligomeric compound of claim 11, comprising at least one modified 3'-region nucleoside comprising a bicyclic sugar moiety.

13. The oligomeric compound of claim 12, comprising at least one modified 3'-region nucleoside comprising a cEt sugar moiety.

14. The oligomeric compound of claim 13, comprising at least one modified 3'-region nucleoside comprising a 2'-substituted sugar moiety.

15. The oligomeric compound of claim 14, wherein the 2'-substituent is selected from among: a halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$, and $OCH_2-N(H)-C(=NH)NH_2$.

16. The oligomeric compound of claim 14, comprising at least one modified 3'-region nucleoside comprising a 2'-MOE sugar moiety.

17. The oligomeric compound of claim 11, wherein each B of the AAABB motif is a cEt sugar moiety.

18. The oligomeric compound of claim 17, wherein the 3'-region comprises a BBA motif, wherein each B is a cEt sugar moiety and A is a 2'-MOE sugar moiety.

* * * * *

SEQUENCE LISTING

<160> NUMBER OF SEQ ID NOS: 82

<210> SEQ ID NO 1
<211> LENGTH: 202001
<212> TYPE: DNA
<213> ORGANISM: Homo sapiens

<400> SEQUENCE: 1

| | | | | | |
|---|---|---|---|---|---|
| gcccagcagg | tgtcagcctc | attttacccc | gcccctattc | aagatgaagt | tgttctggtt | 60 |
| ccaacgcctc | tgacatatta | gctgcatcat | tttacatttc | tttttttttt | ttccttttaa | 120 |
| atggggtctt | gctctgtcac | ccaggctgga | gtgctgtggt | atgatctcgg | ctcactgcaa | 180 |
| tctccacctc | cgaggttcca | gcgattctct | tgcctcagcc | tcccgagtag | ctgggactac | 240 |
| aggcacccac | catcatactg | gctaattttt | tgtgttttta | gtagagatgg | ggtttcccca | 300 |
| tgttgcccag | gctgatctca | aactcctggg | cttaagcaat | acagccgcgt | tggcctccca | 360 |
| aagtgttggg | attacaagca | tgagctaccc | cacccagctc | attttacatt | tccacttgtt | 420 |
| aaactgaaaa | ctggcccgag | aaagcttctg | tactgccatc | cttgcgtcct | tgcagatgaa | 480 |
| tcgtaaccta | gcatagtagg | taggcagact | gaaaacctaa | cttagcagta | ggcttctgta | 540 |
| acaacagctg | tgtctcagcc | agttcctgca | gccagacttc | aaccactcac | aggccgcaaa | 600 |
| ctgttcaaac | tgtgttcgga | gaaggcgaat | tcatctggct | gttaacgtgc | ctcacttctg | 660 |
| ctttctgtgg | ccactttccc | ttttctgtcc | ataaatttgc | tttgaccaca | cagcatccct | 720 |
| agagtctccc | tgaatctgct | gtgattctgg | gacctgcacc | atttgtgaat | tgttttttt | 780 |
| ttccttgatc | agctaaactc | tgttcaattc | aatttgttgg | aagttttaa | cataccaatg | 840 |
| gtgcaccaag | gttccaattt | ctccacttcc | tcataaataa | gtcattttaa | atggcttttc | 900 |
| agtattccaa | tatttggaag | tattaatgtt | tctaccaatt | ttctattttt | ggacattgag | 960 |
| gttgtttcat | ttttttttc | tttttttgag | acagagtctc | gctccgtcac | ccaggctgga | 1020 |
| gtgcagtggc | ctgatcccgg | cccactgcaa | cctccacctc | cctcctcagc | ctcctgagta | 1080 |
| gctgggatta | caggtgcatg | caccaccaca | cccagctaat | ttttgtattt | ttagtagaga | 1140 |
| tggggtttca | ccatgttggt | caggctggtc | tcaaactcct | gacctcaggt | ggtccacctg | 1200 |
| ccttggcctc | ccaaaatgct | gggattacag | gcctgagcca | ctgcgcctgg | cctcatcttc | 1260 |
| ttgatattaa | tgttgcttta | acatctttgt | ccctgtgttt | tttgttttt | ttttgagac | 1320 |
| ggagtctcat | tcattctgtc | acccaggctg | gagttcagtg | gcgtgatctc | agctcactgc | 1380 |
| aacctctgtc | tcctgggttc | cagtgattct | cctgcgtcgg | tctcctgagt | agctgtgttc | 1440 |
| ctgggtcttt | cgatggttat | ttaatacttc | cctacagtaa | tgccctgtgc | gtacatgcta | 1500 |
| agtgtgatga | atggttggc | acagttaaat | cttttgaaag | acattgccaa | gtcactcttc | 1560 |
| agaaaagtga | taggaggtca | tagcaatttt | aagaagtcct | catttctaca | tttccttact | 1620 |
| aatctcggtt | ggtgtctctt | caatctttcc | tcacactttt | cttgggtttt | tcctgaatca | 1680 |
| tgagtctact | acatttacac | attttaaagc | atctttagaa | acaggatctc | attttgttgc | 1740 |
| ccaggctaga | gtttggtggc | atgattatag | ctcctcatac | tcctgggctc | aagtgatcct | 1800 |
| tccacctctg | aaaccccaaa | atttgagaaa | ggtctcattt | aatttagaaa | gtttattttg | 1860 |
| ccaaggttga | gggtgcacac | ctgtgatgat | atacgagtta | aaagaaatt | atttaggcag | 1920 |
| atactgaggg | taagaaagtc | ctcggtaagg | ttttcttttc | aatgaaaagc | agcccccaag | 1980 |
| cattttcttt | tctaacaaag | agcagcctgt | aaaatcgagc | tgcagacata | cacaagcaag | 2040 |
| ctggaagctt | gcacaggtga | atgctggcag | ctgtgccaat | aagaaaaggc | tacctggggc | 2100 |

```
caggcagatc caacatggcg gctccatctt ccctttcctt gtcaaccatg tgcacagtaa    2160
ggagcaggca acatagtgtc ccccgagtag agaccaattt gcataataaa aggtgagggt    2220
agggtgggca gcttctttgc atgctatgta aacattatgc ctggtccaac caatctttgg    2280
gccctgtgta aattagacac cacctcctca agcctgtcta taaaaccctg tccattctgc    2340
cgcaggctgg aagacccact ggggcacccc tctctctcta taggagacag ctattcattt    2400
ttctctttct ttcacctatt aaagctccac tcttaacccc actccgtgtg tatctatgtt    2460
cttgatttcc ttggcatgag gcaatgaacc ttgggtatta ccccagaacc ttgggtatta    2520
tgccacttca gtgacacagc ctcaggaaat cctgatgaca tgttcccaag atggtcgggg    2580
cacagcttgg ttttatacat tttagggaga catgagacgt caattcatat atgtaagaag    2640
tacattggtt ccgtccagaa aggcgcgggac aacttgaggc aggagagag cttctaggtc    2700 acaggtagac aaatggttgc attcttttga atctccgata agcctttcca aaggaggcaa    2760
tcagaatatg cgtctattga ctgggcgcag tggctcatgc ctgtaatgcc agcactttgg    2820
gaggcggagg tgggtggatc acctgaggtc aggagtttga gagcagcccg gccaacatgg    2880
tgaaaccctg tctctactaa aaatacaaaa aattagctgg gcgtggtggc gggcgcctgt    2940
aatcccagct actcgggagg ctgaggcagg agaatagctt gaacccagaa ggaagaggtt    3000
gcagtgagct gagatggtgc cattgcactc cagcctgggc aacaagagtg aaactccatc    3060
tcagaaaaaa aaaaaaaagg cctgggcaaa gtggctcacg cctgtaatcc cagcactttg    3120
ggaagccgag gcgggcaggt cacaaagtca ggagattgag accatcctgg ctaacatgat    3180 gaaacccat ctctactaaa aaatacaaaa aactagctgg gtgtggtggc gagcacctgt    3240
agtcccagct actcggcagg ctgaggcagg agaatggcgt gaaccgggga ggcggagctt    3300
gcagtgagcc gagatcacac cactgcactc cagcccggac gacagggcaa gactctatct    3360
caaattaaaa aaaaaaaaa aaaaaaaaaa aagagagag agaatatgca tctatctcag    3420
tgagcagaag gatgactttg aatggaatgg gagcagttcc tagcttgaac ttccccttta    3480
gcttcagtga tttgggggct caaggtatgt tcctttcaca tacctcagcc tcccaagtag    3540
ctgggaccac aagtgcatgc caccacacgt ggctaatgtt ttattttttt tgtaggaata    3600
gggtctcact atgtgtccag gctggtctaa aaccctgag ctcaaatggt cctcccgcct    3660
cagcctcccg aaatgctggg attacaggca tgagccagca tgcccggcct agtctacatt    3720
tttataaatt gctaattcaa agttccctct ccaaaacctc atggttttcc ctgttctcat    3780
cccctgcacc ctcccttccc ctggagtact cacctggcct tggaggtctg gtgtgagccc    3840
ggacttcgat tctaggcaca gcatgtgatg agcgcccca ggtcaaacac ctcccctctg    3900
cggcctgtgc ttcaccgcct tgacagtgag aaaggtctcc cttcggctca ttctcgaagt    3960
ctcaaacttc acttctcctg tgcgctgatt ctgaattcag ccccgtcca aggtcctggc    4020 ccctttctct tctgcttggc gtgttgttca tcaccactgt gcactgctga gggtaagtgc    4080
ggttctctgg acctctgctt tatcattaga acagactctt gcggtttccc acgacattcc    4140
tttcacttct cacttggaag atgagccgtg aggaaatcct gtgttgtgtg gtatgtgggc    4200
tgtgcttctg cttgacttga gggccaagca gcattgcaag ccatggtttt aaataagaaa    4260
gaacatttct aaccttcatc ttctagtaag gaaacaagtg ggctttagag ttcttgctca    4320
ggaaagacct atgtcccagt ccaaccggac cttttactaa agagatcttc ctgatcctcc    4380
tccccaggcc aggggagggg tcctccctgg ggttggagcc tttagtaggg ggtcggagac    4440
```

```
acgacgtagc cttcatgaca ttcatagtct agttacacga tccctgtaag ggtcagttga   4500
agtaagtgct acaaaggaag ggaggtgctc agtggagagg gctctctttt atgtattata   4560
tttctttcat ggggagggat atggatcagg gatcagcaga ggtgtttcag tcccgaggga   4620
aagaaagtca gcgtggcttg ggagttggga gcagcaagac agtggctcaa gatatcttaa   4680
gactagtgga gtacaccttg catgttaaaa gccttgctca gggctgcctg gttcttgtag   4740
gacgacagag atggcctagc tctgcatact gcaccccag gggctcagaa cagtgcaaat   4800
gtcagtctat ctgtcagtgg cagagccagc cttggagcag gggtgcaagg aggtctctgc   4860
actggccagg catgcagaac attctgttca gtagcactgg acagaaggcc ccatctagat   4920
gagacagagc tggtggggca ggacaaagac tcctggcagc tcaaacggcc tggcagatgc   4980
ttggagagag ggggcttctt gagacagcac catttctggg aagagagtca cctgggaggg   5040
atgaggccac gctccggctt ggaggtgaag agaggggctg ctgcaagaaa gaattagaga   5100
catgccagcc tttgctgtgt tgcccaggct ggtcatgaac tcttggcctc aagcaatctt   5160
cccacctcag cctccccaag cgctgggatt atagacatga gcccccatgc tggccaataa   5220
aagatgattt tatggagggg atggtggtga aggttgtggg tggtatgaaa tagtaagaaa   5280
tatatattgg tctgcaccca gttcctgcca cagagctcct aaaatcctga gaacttcctg   5340
ggtgagcatc ttttgttcta atgaggtgac tcttggtggc tcctggatag gagtgaatca   5400
ccagaaagat caagccagag ttagaagcag aaagtgctgg ctataacaca ggaaagctgt   5460
aacacaaata ataaagtttt ttttttttt tttgagatgg agcctcactc tgttgcccag   5520
gctggagtgc aatggtgcaa tctcagctca ctacaagctc tgcctccag gttcaagtga   5580
ttctcctgcc tcagcctcct gagcagttgg gactacaggt gtgtgccacc acatctggct   5640
aattttgta ttttttagcag agacggggtt tcaccatatt aaccaggctg gcctcaaact   5700
ccttaccttg tgatccgcct gcctcagcct cccaaagtgc tgggattaca ggcatgagcc   5760
accgtgcctg gccaaaagac attgttctta aagaatcaa ctaactaacc aaataaataa   5820
aaatctaacc taattaagaa actaaaaata cacaaaaatt aatttcaagg ggagaaaaat   5880
catgtaaaga gagaaagata atgaatactt tgcagaaatt tatgaacata acataaaaac   5940
ttggatgaaa tgcatttcta ggaaaacata atttatcaaa actaaccaca agtaaaatag   6000
aagcctaaat aggatatttt caagagaaga agtaaagttg tcaaagtgct acccttcaaa   6060
aaaacaccag gctcaaacaa tctgacatgg gaatgttagc acaccttaga gagcaaataa   6120
aactttgaat gggcttgaaa tattccagac tctagaaaaa caaaacttcc caattctttt   6180
tataaagcaa gtataaattg ataccaaaat cttataaaga ccttatacaa aacttcatac   6240
caatctcttt tatgaataca aaacccttaa taaagtatta ccagacagaa cccaacaata   6300
cataaaaatg tcacatcata acatagtggg gtttatttca ataatgcatg gatggttcaa   6360
tacaaggaaa ttcagtaaca caatataata gatcatgtga atatacccaa agaaaaaata   6420
gattattttc atagatgctg taaaggcatt tgaccaaatt caacacctac ttttaggtg   6480
gtcaataaaa taaattagtt actccttctt tagcatgata aaatatattt atcagcccag   6540
aaggcatcat tttacccgat aagggcacac gctggaggga ataatgttaa aattaggaat   6600
aagaggatag ctagtttctt tcttcttttt ttttttgag acggagtctt gctctgttgc   6660
caggctggag tgcagtggtg caatgttggc tcactgcacg ccccccgcct cccaggttca   6720
agcgattctc ctgcctcagc ctcccgagta gctgggacta caggcgcgca ccaccatgcc   6780
cggctaattt ttttttgtat tttagtagag atggggtttc accatgttgg tcaggctggt   6840
```

```
cttgaactcc caacctcacg tactgggatt accggtgtga gccaccacgc cagcccaact    6900
actttcaaca ttatccttaa tactgatgct tattgactta ctatggggtt acctctagat    6960
aaatccataa taagttgaaa atataagtaa aaaatgccct taatacacct aacctaccaa    7020
acatcatagc tgagcccagc ctgccttagc tatgctcaga cactgacgtc agcctacaat    7080
tggcaaaatc acacagcagc acagtctact gcagagcatc tgctgtttgc ccttgtgact    7140
gcgtggctgc ctgggagctt cccagcttca caagacagta ttacgtagca catcactagc    7200
ctggggaaag atcaaagttg aaaatttgaa gtgtggtttc cattgaatgt gtactgcttt    7260
tgcaccatca tcaagtcaaa aattttagt tgaaccagcc taagtttggg accatcttta    7320
ttttcaggag gaacttccat gtacattgat gacggacgat agaatccgtt tctatcatcc    7380
taatgaacat aatgaataaa tccagacaaa cataaacatt aacagagtaa gcagctttcg    7440
gggctggaag ccagaagagg gtgggagcgc agagagagag gccaaacacc agggctgctt    7500
ctgctttgcg ggtatttgct gatctggaca aggtatctgg aaggctgagc taagcctcct    7560
ttttttttga ggtggcgtct cactctgttg ccaggctgga gtgcaatggt gcgatctcag    7620
ctcactgcaa cctccacctc cctggttcaa gcgattctcc tgcctcagcc tcccgagtag    7680
ctgggattac aggctcccgc cactacaccc agctgatttt tgtaatttta gtagagacgg    7740
ggtttcacca tgttggccag gatggtctcg atctcttgac gtcatgatct gtccacctcg    7800
gcctcccaaa gtgctgggat tataggcgtg acccaccgtg ccccgtctga gctaagcctc    7860
ttgagcatag gggactaaaa atgaaatcta gcgcatgcca agtttagggt cccaggcaat    7920 tccttttccac tttggggtcc actttggggt ccaccccacc caagaagaag gatgacttgg    7980 aagtaaaacca gctctgaaat atggatggtc ctctgggacc ataccaatcc cttcatatca    8040
accacatcca gttcctcaaa actggaactt ggattaagat ggcctaggac ttctagtgtc    8100
ccaggagcct ggcattgcaa acaaaaatcc tctccggaag aagataatac cttaagcttc    8160
aaatgactct ctaataaatt tcaaatacaa tgtccagcac acaaacacaa attaccagga    8220
acgtgatatg aggcctgatg gatgggaatt agcagaaact tcaggcatga gaaacatacc    8280
ctcagaggcc tagaatctat ctagtgtcta gataatggag atatgaaata cagacactta    8340
aacaactatg tttcccatgt tcaaagagga aatttgcaaa acttgaaagt gttggcagga    8400
aatcagaaac tataaaatgt gacaacagca tactttagag tcagtataaa ttacggtccc    8460
gaaaactgca gaattccaga acttaatggt aaagcaaggg tttaacagca gaatagaaat    8520
agccagagag aactaggaag taagtcagat gacactaccc agaataaggc actgagaggc    8580
caaggaatgg aaaatgcaga agaaaggata tggtgagagg atctaatata catttatttg    8640
gagtaccagg gagagagaga aggagaagaa cagaagccgt gtttcaagga cggtgactga    8700
gaggcttcga aactgatgaa agccatcagt tcacaaattc aaagcccagt gaattccaag    8760
gagaaaaaaa gaaatcccata ctgtgaaagc aagtccagac aatgacaaac accatcaaca    8820
atacacagga caggcataag atgcatttaa tggggacact cagaggcaga gggttatcag    8880
aaggaggcac ttctctccca agttctcatc atcccaggggc cagggacagc tggtcacacc    8940
ttagggagtt cactaggaga gggatctggc ttccttgtcat tctgggtatt tgtagggaaa    9000
ttggaaggga accgagagca cctagccaat cgcatagcaa tgggagattt caggctgtgg    9060
ggaatgtctt tgctggtgaa aagaacatcc tgacccttaga aatctttcac cgaggggggat    9120 ctgcgttcca gaacttctgg agctggtata ggtaaggctt tgagctttcc tactgagcca    9180
```

```
gcctgttgct aggttaccaa aggggacctc gagggccatc tggccaacaa gcagacttgt    9240
ctctccttac acccccagac gtatcactgc aaaactacag aaaaccaaag acagagaaaa    9300
tcttaaaagc agccagattt aaaaaatggc atattagttt caaagcagca gccatgaaat    9360
tgacagctga tgtctcaaca gcaagaatga aaagtggaag acaggccagg tgtggtggct    9420
caggcctgta atcccagcac tttgggaggc cgaggcgggt ggatcacgag gtcaggagac    9480
caagaccatc ctggctaaca tggtgaaacc ccgtctctac taaaaataca aaaaattag    9540
tcgggcatgg tggtgggtgc ctgtagtccc agctactcgg gaggctgagg caggagaatg    9600
gcgtgaaccc gggaggcgga gcttgcagtg agccgagatt gtgccactgc actccagcct    9660
gggtgacaga gcaagactct gtctcaaaaa aaaaaaaaa aaaaaaaaa aaagggtgac    9720
gaagcttcaa tctcctgaaa ggaagcaact gccgcctttg attcgatacc caccaaaatc    9780
cgtgaagaag aaggcaaaa taaaaacact tcctgattga actggaaaga tttccgcaat    9840
agaagaccca ctgtccaagg aattctaaag gatgctttcc aggcagaaga aaatgacccc    9900
agaggaagat cagagattca ggaaagaaat ggagagtgat aaaaatgaaa aattcggggg    9960
ccaatttaaa caaagctga ctgctctaca actgttgtgt ctctatcttt tgtaacatat   10020
atgtgtgtgt agcttttttt ttttttttg tcaagatgga ttctcactct gtcgcccagg   10080
ctacagtgaa atggcacggt ctcggctcac tgcaacctct gccccttggg ctcaaatgat   10140
tctcttgcct cagcctcctg agtagctgag attacaggtg cctggcacaa tgcctggcta   10200
atttttgtat ttttactaga gatgggattt ctccatgttg gccaggctgg tcttgaacac   10260
ctgacctcag gtgatccacc tgcctgggcc tcccaaagtg ctaggattac aggcgcgagc   10320
cactgcatct ggcctatgtg tgtgtttata tggaattaaa acacatggca ataatccct   10380
ccaaattggg agaaaccaaa aatagcattt aaatgttgta agctccctgc ataatcaaga   10440
agagaataga tttacgttag atttttgatac ctggaggatg aatgttgtaa tttctagggt   10500
gaccatgaaa agaggagaca acggtgtatg ttttttttt tttgagatgg agtctcactt   10560
tgtcacccag gctggagtgt tgtggtgtga tcttggctca ctgcaacctc ctcctcttgg   10620
gttcaggcca tcctcccacc taggcctcca gagtaggtgg gatcacaggc acctgccacc   10680
acacctggct aatttttttt ttttttaaa tatttagtag agatgggggtt tcaccatgtt   10740
ggccaggctg tcttgaact cctgacctca ggcgatctgc ctacctctgc ctctcaaagt   10800
gctgggatta caggtgtgag ccatcgcgcc cggccaacag tgatcacttt caaactaaca   10860
gaggttcaaa aataaaatca gacttaacca aaaaccaggt aacagagctg gtaggatata   10920
cagaaagact gacctcacgt atatcaacga ttacagttaa tattaatgaa ggaaatgctc   10980
tagtttaaaa acgagggttg tcaaagaccc cacataagaa gctccttacc agcggtgcac   11040
ctagaaccta aggaaacagg acagatgaag gaggacgcgc cccgccgct gtcctgcgcc   11100
tcagccatcc tatgagacgg gaaaggtttc tgtctgcagc tgggcccgtg ctctttacca   11160
gctcctggct ttcttctctg gaaggttcct gcctgttttg ccctcacacc tgctcctctc   11220
tcagccctct caggggtggg gctggaggcc accaaagagc ctcctctgct ctccagttgc   11280
tcgactgctc ctcatttccc cctggggtct gcgtcagggt ttccttcttt tccagcccca   11340
ccccgcgtgc atcccacctg gtctcgggtc ggggctgctc ccgcttactg cccctgccc    11400
aggctggtgt gcacccctc tggctgcttt caaggcctct tctctcttct cggcaggaca   11460
ggcacaggca ggtggccagg tgtcatgctt agctccccgc ccagtgagat tctttcattt   11520
aacaatcttc ccctgaatag ttcatgttca ttgctgaaaa tttgaaaaat atggaaaagc   11580
```

```
acaaagatta agatataaac cgccctcaat tcccctgccc agagagagtc actgctatga   11640
cttggtgact aggaacctta tttctctctc gctcttttt tttttttga dacagagtct     11700
tgctctgtca cccaggctgg agtgcagtgg ctcgatctca gctcactgca acctccgcct   11760
cctgggttca agcgattctc ctgcctcagc ctcttgagta gctgggatta caggcacctg   11820
ccaccatgcc cggctaattt ttgtattttt agttgagaga gggtttcatc ttgttggtca   11880
ggcggacttg aactcctgac ctcaggtgat cagcccacct cggcctccca aagtgctggg   11940
attacaggtg tgagccactg cgccttcatc tctcttctgt gtatgtgtac gctgttttt     12000
ctttagaatg ggggacgtta tcaggctcta catggtgtgt agtcggctag catgttgtaa   12060
gcctttccct gtgtcacaag tgctcatctg aacaggatt ctaatgactg cctgtggcta    12120
tgttgggatt cctttaactc agctccttct gcccagcatc tatctttttt ccatcttttg   12180
tcctaagtgt tgctataata aatcattgat cacacatgcc tgactgtttg cataggataa   12240
attacgggaa atgttttgc tgttcaggga ctgtgcccat ttttaggcct cagagacacc    12300
atgccagact gcccagtatt gatctttact cttttagat gatgccaaac ttttctgtga    12360
actttaaaaa cctgtgtctt gacagtccat ttctgtaagt cttcacatt agatttcctg    12420
tcaggatgat agtcaattct aggcagatga tgttttctca gccatggctg aagcagttgt   12480
gatttgttgt ggccatgtaa agtcccgatg atccattgcc tccctggatg ggttggaata   12540
atttggtttg ggagcatata acagaatgac ctggagtcac agcagctcag acggaagtgt   12600
atttctccct tacagatgaa agaattccag gccaggctgg aatgacaact gcacacagtc   12660
atctgggccc cctccttcca gctcccatca ccccaggatg tggctttat gcagatgatc    12720
caaaatggct gctcaagtcc cagccaacac atcccattcc agggagcagg aaaaggtgt    12780
gtctttccct tcatttatg tgattccttt ctagaagtac tactcattac ttctgcttgc    12840
atctccctgg ctagcactta cttagttata tggccatagc tagctgaagg aaggacaggg   12900
actgtcatac actagctaag aggcaaactg cttagataaa aaggtctcta aagaaggtca   12960
gagcggctgc tagggtgcaa ctctattact tattgttatg ggacgaactg tgtccctcat   13020
tcaggttgat gtcctaagcc ccagaacctc agaatgggat tgtatttgga dacaggttct   13080
ttaaggaggt aaggaggcta aaatgagatc attagggtgg gccataatcc gactgatgtc   13140
ttacaagaag agattaggac acggacatgc tcagagggac ggccacgtga ggacaccaag   13200
aaaggcagct gtctgcaagt caaggacagg gctcagggga aaccaacctt gccaacacct   13260
tcatctcgga cttctagcct ctaggaccat gagaagatac atttctgttg tttaagctgc   13320
ccggtctgtg gtactttgtt atggcagccc aagtaaacaa atacagtcat ctgctgctgg   13380
aacaaatcac cccagcactg tggcttggca gcacacatgt ctagtcatag agttatatgt   13440
agttacgtgt agagccatat gtatcgtcac acgttctgtg ggtcaggaat ttggacccag   13500
cttaaccagc tccacttctc gccagggttc agtcaaatac cagctgcctc ccacctgaga   13560
gctcagccgg ggaagggtcc cttttccaatc tcacgtggtg ttggcaggat ccagttcctc   13620
atggcctgct ggactgagaa cctcagttct cactgcctgt tggccagagg ccgcctttat   13680
gtcctcgcca tgtgggcctc tccaacatgg cagctgactt catcagagca tccatgccaa   13740
gaaggcaaca gagagggcca gggagactga agtcataccc ttttgcgacc tagtcatggg   13800
gtgacattcc atcacctttg cccattggtt agaagcaggc caccaggtac agcccaagct   13860
cacggggagg ggtcatacaa gggtgtcaat accaggaggt gaggggtgct ggggccatct   13920
```

-continued

```
tatgagtctg cccactgagg taactaacaa ccttgaggcc tgacacagtg gacaaaggcc   13980
cttattaaca gcagagaact gggaactttta tttatttatt tattttttgag acagagtctc   14040
actcttgtca cccaggctgg agtgcaatgg catgatcttg gctcactgca acctccacct   14100
cccaggttca gcaattctg cctcagcctc cggaatagct gggactacag gcatgcacca   14160
ctacacccgg ctaattttg tattttttagt agagacaggg tttcgccatg ttggccaggc   14220
tggtctcgaa ctcctgacct ctggtgatct gcctgcctg gcctcccaaa gtgctgggat   14280
tacaggcgtg agccaccgca cctcgctgga acttaatttt tttagagaca gtgtcgctct   14340
atcacccaag ctggagtgca gtggtgcaat cctagctcac ttgcagcctc aaattcctgg   14400
gttcaggtga tcctcccaca tcagcctccc aagaactggg aactaacagc tgtttctctg   14460
ctgtccttct caagaaaagg gaggctactg ctaccccact ggggacaatg ctgggtttcc   14520
cttaggaca ggctctgaga caaggcggag gtgctgtttg tggccacaga gcaggggact   14580
ctgggttgca ggtgtggcct ggctaaagta ggctttactg ggctcctctc tgcctgcatc   14640
accccccggc tgggcggttg tctctgaggc caaccttact ccctgctggg caggctggac   14700
agctgccctc tccgttttgcc cctctaccac ccaaaaggca ggaggctctg gagaccagga   14760
ccctgcccgc cacggcctgt gtcccaggcg tgagggggtg cccacagac ctctgctgag   14820
ctgctgctga atgacgcccc ttggggtcc tgccggaagg tcagagcagg ggtgcactcc   14880
cataaagaaa cgcccccagg tcgggactca ttcctgtggg cggcatcttg tggccatagc   14940
tgcttctcgc tgcactaatc acagtgcctc tgtgggcagc aggcgctgac cacccaggcc   15000
tgccccagac cctctcctcc cttccggggc gctgcgctgg gaccgatggg gggcgccagg   15060
cctgtggaca ccgccctgca ggggcctctc cagctcactg ggggtggggt gggggtcaca   15120
cttgggtcc tcaggtcgtg ccgaccacgc gcattctctg cgctctgcgc aggagctcgc   15180
ccaccctctc ccgtgcaga gagccccgca gctggctccc cgcagggctg tccgggtgag   15240
tatggctctg gccacgggcc agtgtggcgg gagggcaaac cccaaggcca cctcggctca   15300
gagtccacgg ccggctgtcg ccccgctcca ggcgtcggcg gggatccttt tccgcatggg   15360
cctgcgcccg cgctcggcgc ccccctccacg gccccgcccc gtccatggcc ccgtccttca   15420
tgggcgagcc cctccatggc cctgcccctc cgcgcccac cctccctcg ccccacctct   15480
caccttcctg ccccgccccc agcctcccca ccctcaccg gccagtcccc tccctatcc   15540
cgctccgccc ctcagccgcc ccgcccctca gccggcctgc ctaatgtccc cgtccccagc   15600
atcgccccgc ccgccccg tctcgcccg ccctcaggc ggcctccctg ctgtgccccg   15660
ccccggcctc gccacgcccc tacctcacca cgccccccgc atcgccacgc ccccgcatc   15720
gccacgcctc ccttaccatg cagtcccgcc ccgtcccttc ctcgtcccgc ctcgccgcga   15780
cacttcacac acagcttcgc ctcaccccat tacagtctca ccacgccccg tccctctcc   15840
gttgagcccc cgcgccttcgc ccgggtgggg cgctgcgctg tcagcggcct tgctgtgtga   15900
ggcagaacct gcgggggcag gggcgggctg gttccctggc cagccattgg cagagtccgc   15960
aggctagggc tgtcaatcat gctggccggc gtggccccgc ctccgccggc gcggccccgc   16020
ctccgccggc gcagcgtctg ggacgcaagg cgccgtgggg gctgccggga cgggtccaag   16080
atggacggcc gctcaggttc tgcttttacc tgcggcccag agcccccatc attgcccccgg   16140
tgctgagcgg cgccgcgagt cggcccgagg cctccgggga ctgccgtgcc gggcgggaga   16200
ccgccatggc gaccctggaa aagctgatga aggccttcga gtccctcaag tccttccagc   16260
agcagcagca gcagcagcag cagcagcagc agcagcagca gcagcagcag cagcaacagc   16320
```

```
cgccaccgcc gccgccgccg ccgccgcctc ctcagcttcc tcagccgccg ccgcaggcac    16380
agccgctgct gcctcagccg cagccgcccc cgccgccgcc cccgccgcca cccggcccgg    16440
ctgtggctga ggagccgctg caccgaccgt gagtttgggc ccgctgcagc tccctgtccc    16500
ggcgggtccc aggctacggc ggggatggcg gtaaccctgc agcctgcggg ccggcgcacac   16560
gaaccccgg ccccgcagag acagagtgac ccagcaaccc agagcccatg agggacaccc     16620
gccccctcct ggggcgaggc cttccccac ttcagccccg ctccctcact tgggtcttcc     16680
cttgtcctct cgcgagggga ggcagagcct tgttgggcc tgtcctgaat tcaccgaggg     16740
gagtcacggc ctcagccctc tcgcccttcg caggatgcga agagttgggg cgagaacttg    16800
tttcttttta tttgcgagaa accagggcgg gggttctttt aactgcgttg tgaagagaac    16860
ttggaggagc cgagatttgc tcagtgccac ttccctcttc tagtctgaga gggaagaggg    16920
ctgggggcgc gggacacttc gagaggaggc ggggtttgga gctggagaga tgtgggggca    16980
gtggatgaca taatgctttt aggacgcctc ggcgggagtg gcggggcagg ggggggcgg     17040
ggagtgaggg cgcgtccaat gggagatttc ttttcctagt ggcacttaaa acagcctgag    17100
atttgaggct cttcctacat tgtcaggaca tttcatttag ttcatgatca cggtggtagt    17160
aacacgattt taagcaccac ctaagagatc tgctcatcta agcctaagtt ggtctgcagg    17220
cgtttgaatg agttgtggtt gccaagtaaa gtggtgaact tacgtggtga ttaatgaaat    17280
tatcttaaat attaggaaga gttgattgaa gttttttgcc tatgtgtgtt gggaataaaa    17340
ccaacacgtt gctgatgggg aggttaattg ccgagggatg aatgaggtgt acatttttacc   17400
agtattccag tcaggcttgc cagaatacgg ggggtccgca gactccgtgg gcatctcaga    17460
tgtgccagtg aaagggtttc tgtttgcttc attgctgaca gcttgttact ttttggaagc    17520
tagggggtttc tgttgcttgt tcttggggag aattttttgaa acaggaaaag agagaccatt  17580
aaaacatcta gcggaacccc aggactttcc ctggaagtct gtgtgtcgag tgtacagtag    17640
gagttaggaa gtactctggt gcagttcagg cctttctctt acctctcagt attctatttc    17700
cgatctggat gtgtcccaga tggcatttgg taagaatatc tctgttaaga ctgattaatt    17760
tttagtaata tttcttgttc tttgtttctg ttatgatcct tgtctcgtct tcaaagttta    17820
attagaaaat gattcggaga gcagtgttag cttatttgtt ggaataaaat ttaggaataa    17880
attattctaa aggatggaaa aacttttttgg atatttggag aaattttaaa acaatttggc    17940
ttatctcttc agtaagtaat ttctcatcca gaaatttact gtagtgcttt tctaggaggt    18000
aggtgtcata aaagttcaca cattgcatgt atcttgtgta aacactaaac agggctcctg    18060
atgggaagga agaccttttct gctgggctgc ttcagacact tgatcattct aaaaatatgc    18120
cttctctttc ttatgctgat ttgacagaac ctgcatttgc ttatcttcaa aatatggta     18180
tcaagaaatt tcctttgctg ccttgacaaa ggagatagat tttgtttcat tactttaagg    18240
taatatatga ttaccttatt taaaaaattt aatcaggact ggcaaggtgg cttacacctt    18300
taatccgagc actttgggag gcctaggtgg acgaataccc tgaggtcagg agtttgagac    18360
cagcctggct aacatggtga aaccctgtct ctactaaaaa tacaaaaatt agctggtcat    18420
ggtggcacgt gcctgtaatc caagctacct gggaggctga ggcaggaaaa tcgcttgaac    18480
ccgggaggca gagtctgcag tgagttgaga tcacgccact gcactccagc ctgggtgaca    18540
gagcgagact ctatctcaaa aaaaattttt tttaatgtat tattttttgca taagtaatac   18600
attgacatga tacaaattct gtaattacaa aagggcaata attaaaatat cttccttcca    18660
```

```
ccccttttcct ctgagtacct aactttgtcc ccaagaacaa gcactatttc agttcctcat   18720
gtatcctgcc agatataacc tgttcatatt gtaagataga tttaaaatgc tctaaaaaca   18780
aaagtagttt agaataatat atatctatat attttttgag atgtagtctc acattgtcac   18840
ccaggctgga gtgcagtgat acaatctcgg ctcactgcag tctctgcctc ccaggttcaa   18900
atgcttctcc tgcctcagcc ttctgagtag ctgggattac aggcgcccac caccatgtcc   18960
agctaatttt tgtattttta gtagagatgg ggtttcacca tgttggccag ctggtcttg    19020 aactcctgac cttgtgatct gtccacctcg gcctcccaaa gtgctgggat tacaggtgtg   19080
agccaccatg cctggctaga ataataactt ttaaaggttc ttagcatgct ctgaaatcaa   19140
ctgcattagg tttatttata gttttatagt tattttaaat aaaatgcata tttgtcatat   19200
ttctctgtat tttgctgttg agaaaggagg tattcactaa ttttgagtaa caaacactgc   19260
tcacaaagtt tggattttgg cagttctgtt cacgtgcttc agccaaaaaa tcctcttctc   19320
aaagtaagat tgatgaaagc aatttagaaa gtatctgttc tgtttttatg gctcttgctc   19380
tttggtgtgg aactgtggtg tcacgccatg catgggcctc agtttatgag tgtttgtgct   19440
ctgctcagca tacaggatgc aggagttcct tatgggctg gctgcaggct cagcaaatct    19500
agcatgcttg ggagggtcct cacagtaatt aggaggcaat taatacttgc ttctggcagt   19560
ttcttattct ccttcagatt cctatctggt gtttccctga ctttattcat tcatcagtaa   19620
atatttacta aacatgtact atgtgcctgg cactgttata ggtgcagggc tcagcagtga   19680
gcagacaaag ctctgccctc gtgaagcttt cattctaatg aaggacatag acagtaagca   19740
agatagataa gtaaaatata cagtacgtta atacgtggag gaacttcaaa gcagggaagg   19800
ggatagggaa atgtcagggt taatcgagtg ttaacttatt tttattttta aaaaaattgt   19860
taagggcttt ccagcaaaac ccagaaagcc tgctagacaa attccaaaag agctgtagca   19920
ctaagtgttg acatttttat tttattttgt tttgttttgt ttttttgag acagttcttg    19980 ctctatcagc caggctggag tgcactagtg tgatcttggc tcactgcaac ctctgcctct   20040
tgggttcaag tgattctcat gcctcagcct cctgtttagc tgggattata gacatgcact   20100
gccatgcctg ggtaattttt tttttttccc ccgagacgga gtcttgctct gtcgcccagg   20160
ctggagtgca gtggcgcgat ctcagctcac tgcaagctcc gcttcccgag ttcacgccat   20220
tctcctgcct cagtctccca gtagctggg actacaggcg cctgccacca cgtccagcta    20280 attttttgt attttaata gagacggggt ttcaccgtgt tagccaggat gatcttgatc     20340
tcctgacctc gtcatccgcc gaccttgtga tccgcccacc tcggcctccc aaagtgctgg   20400
gattacaggc atgagccact gtgcccggcc acgcctgggt aattttgta ttttagtag     20460 agatggggtt ttgccatgat gagcaggctg gtctcgaact cccggcctca tgtgatctgc   20520
ctgccttggc ctcccaaagt gctaggatta caggcatgag ccaccatacc tggccagtgt   20580
tgatatttta aatacggtgt tcagggaagg tccactgaga agacagcttt tttttttttt   20640 tttttttgggg ttgggggca aggtcttgct ctttaaccca ggctggaatg cagtatcact   20700
atcgtagctc acttcagcct tgaactcctg ggctcaagtg atcctcccac ctcaacctca   20760
caatgtgttg ggactatagg tgtgagccat cacacctggc cagatgatgg cttttgagta   20820
aagacctcaa gcgagttaag agtctagtgt aagggtgtat gaagtagtgg tattccagat   20880
ggggggaaca ggtccaaaat cttcctgttt caggaatagc aaggatgtca ttttagttgg   20940
gtgaattgag tgaggggac atttgtagta agaagtaagg tccaagaggt caagggagtg   21000
ccatatcaga ccaatactac ttgccttgta gatggaataa agatattggc atttatgtga   21060
```

```
gtgagatggg atgtcactgg aggattagag cagaggagta gcatgatctg aatttcaatc    21120
ttaagtgaac tctggctgac aacagagtga aggggaacac cggcaaaagc agaaaccagt    21180
taggaagcca ctgcagtgct cagataagca tggtgggttc tgtcagggta ccggctgtcg    21240
gctgtgggca gtgtgaggaa tgactgactg gattttgaat gcggaaccaa ctgcacttgt    21300
tgaactctgc taagtataac aatttagcag tagcttgcgt tatcaggttt gtattcagct    21360
gcaagtaaca gaaaatcctg ctgcaatagc ttaaactggt aacaagcaag agcttatcag    21420
aagacaaaaa taagtctggg gaaattcaac aataagttaa ggaacccagg ctctttcttt    21480
tttttttttt tgaaacggag tttcgctctt gtcacccggg ctggagtgca atgatgtgat    21540
ctcagctcac taaaacctct acctcctggg ttcaagtgat tcttctgcct cagcctccca    21600
agtaactggg attacaggcg tataccacca tgcccagcta attttgtgt ttttagtaga    21660 gatggggttt caccatgttg gccaggctgg tctcgaactt ctgacctcag gtgatccact    21720
cgcctcagcc tgccaaagtg ctgggattac aggtttgggc cactgcaccc ggtcagaacc    21780
caggctcttt cttatactta ccttgcaaac ccttgttctc atttttttccc tttgtatttt    21840 tattgttgaa ttgtaatagt tctttatata ttctggatac tggattctta tcagatagat    21900
gatttgtaaa aactctccct tcctttggat tgtcttttta ctttcttgat agtgtctttt    21960
gaagtgtaaa agttttaat tttgatgaag tcgagtttat ctatttttgtc tttggttgct    22020 gtgcttcaag tgtcatatct aagaaatcat tgtctaatcc aaagtcaaaa aggtttactc    22080
ctatgttttc ttctaagaat tttagagttt tacatttaag tctgatccat tttgagttaa    22140
tttttatata tggttcaggt agaagtccaa ctttattctt ttccatgtgg ttattcagtt    22200
gtcccagcac tgtttgttga agagactatt cttcccccat ggaattatct tagtaccctt    22260
gttgaaaatt aatcgtcctt aattgtataa atttatttct agactgtcag ttctacctgt    22320
tggtctttat gtcgatcctg tgccagtacc atacagtctt gattactgaa gtttgtgtca    22380
cagtttaaat tcatgaaatg tgagttctcc aactttgttc cttttcaaga ttgatttggc    22440
catgctgggt cccttgcatt tccgtacgaa ttgtaggatc agcttgtcag tttcaacaaa    22500
gaagccaagt aggattctga gagggattgt gttgaatctg tagatcaact tggggagtat    22560
tcgcatctta acaatattgt cttccaccta tgaacatggg caaactttgt gtaaatggtc    22620
agattgtaag tatttcgggc tgtgtgggca cagtgtctct gtcacagcta cgcggctctg    22680
ccattgtagc atgaaagtag ccataagcaa tatgtatgag tgtctgtgtt ccaatagaat    22740
tttattaatg acaaggaagt ttgaatttca tataatttc acctgtcatg agatagtatt    22800
tgattatttt ggtcaaccat ttaaaaatgt aaaaacattt cttagcttgt gaactagcca    22860
aaaatatgca ggttatagtt ttcccactcc taggttaaaa tatgatagga ccacatttgg    22920
aaagcatttc ttttttttt tttttttttt ttttgagac ggagtttcac tcttgttgcc    22980
caggctggag tgcagtggcg cgatctcggc tcactgcaac ctctgcctcc caggttcaag    23040
acattctcct gcacggcctc cctagtagct gggattacag gcatgcgcca ccacacccag    23100
ctaattttgt attttagta gagacggggt ttctccatgt tggtcaggct ggtcttgaac    23160
tcctgacctc aggtgatcca cccgcctcag cctcccaaag tgctgggatt acagggtgtg    23220
agccaccaca ccctgctgga aagcatttct ttttggctg ttttgtttt tttttaaac    23280 tagttttgaa aattataaaa gttacacata tacattataa aaatatcttc aagcagcaca    23340
gatgaaaaac aaagcccttc ttgcaagtct gtcatctttg tctaacttcc taagaacaaa    23400
```

```
agtgtttctt gtgtcttctt cccagatttt aatatgcata tacaagcatt taaatgtgtc    23460 atttttgtt tgcttgactg agatcacatt acatatgtat ttttttactt aacaatgtgt    23520
catagatatt gttccatagc agtacctgta attcttatta attgctatgt aatattttag    23580
aatttctttt taaaagagga cttttggaga tgtaaaggca aaggtctcac attttttgtgg   23640 ctgtagaatg tgctggtgac atattctctc taccttgaga agtccccatc cccatcacct    23700
ccatttcctg taaataagtc aaccacttga taaactacct ttgaatggat ccacactcaa    23760
aacatttagt cttattcaga caacaaggag gaaaaataaa ataccttata aagcactgtt    23820
taatattgta ttaaattgga tcaatttggg ggctagaatg tatgttagag acatgatatg    23880
tccataggtc cttgctatca cagtgaggtc tcaggacag tcgtttggta tcatttggga    23940
tctcataagc agactctctc tgcttgacct gacaaatcag agtctgtgtt ttaacaggtt   24000
cagtgagtga cttacatgca cattggagtt tgggaagctc cactgtaggt gcttagacct   24060
tacctttgtt gttgctaata acaatgcaag catttgggag gaagacctgt gttgctcata   24120
tgtgtccagg tgtagctgag gtggccttgc ttatctgctg tagggccgtt gagcatttct   24180
gtagctgtga tgagtgagct gaggtgagcc tgcggagagc tcccagccat tggtagtggg   24240
actcgcttag atgaactgga aggaccctt catctgagca gccactatgg agaaaaacaa   24300
ccgaatgagg ggagagacaa tgtgcaattt tatttagggc acaaaggaga gctgtggtta   24360
gaaggtgaca tttgagtgga aagggggcaa gccatgtgta tagcgggaga agagaggtcc   24420
aggcagagtt aacagaaggc agaaatgctt tccatgtttg agaaccagta aggaggccag   24480
tggctgaagt aaggtgaagg gcagaaataa ggatgaggct gcgagagatg agaggttaga   24540
gacgagcgtc ttgtgcacca agataagctt gtgtggtcaa aacaagtagt ttaatttatg   24600 ttttaaaag atcattttgg ctgggcacaa tggttcatgc ctgtaatacc agtagtttga    24660
gacggtgtgg tgggaggatt gcctgaggcc agacgaccag catagccaac atagcagcac   24720
ctataaggtc tctacaaaaa actttaaaaa attagctggg catagtggtg tgtgcctgta   24780
gtcccagcta ctcaggaggc tgaggaggct ggaggattgc ttgagtccag agtttgagg    24840 ctgcagtgag ctatgattat gccactacac tacaacctgg gcaagagagt gagaccctgt   24900
ctctaaatat acacacacac acacacacac acacacacac acacacacac acacacacac   24960
acacacatat atatgtatat atatgcattt agatgaaaag atcactttga caataccaca   25020
tgctggtgag gatttagaaa aactaggtca cttattgctg gtgggaatat aatatagtac   25080
ggccactctg gaaaacagtt tggcagtttg tcataaaact gaacataccg ttagtataca   25140
gcccagcagc aactacaatc ctgggcatta atcctagaga aatgaaacct taatgttcac   25200
ataaaaacct atactcaagt atgcatagca gctttacccca taatatctaa gaactggaat   25260
cagctcagat gtccttcaac aggtgaatgg ttaaactact cagtaataaa aaggaatgag   25320
ctactgatag catgcaacag tttaggtgaa gttatgctaa tgaaaaaagc caatcccaaa   25380
aggttataca tactgtatga ttctatgttt ttttgcaatg gcacagtttt agggatggag   25440
aatagattag tggttgcctg gggttagaga tggggtagta gagtaggtta gtggtggcag   25500
aggagagaaa agagagggag gtgaatgtgg ttataaaagg acaacacagg ggaatacttg   25560
taatggaaat gctttgtctt ttttttttt tttttttttt tggcgacaga gtcttgctct   25620
gttgcccagg ctggagtgca gtggcatgat cttttctcac tgcaacctct gcctcctggg   25680
ttcaagtgat acttgtgtct cagtctccca tgttcagagt gaaacaaacc agaggtaatg   25740
ttcatccaaa taatccaaca cacatgacat taaaacatca agatcaggtc ggacgtggtg   25800
```

```
gctcatgcct gtaatcccag cacttttggg aggccaaggt gggcagatca cttgaggtca    25860
ggagttcgag accagccggg ccaacatgat gaaaccccat cttgactaaa aatacaaaaa    25920
ttagccgggc atggtggtgt gcacctgtag tcccagctac ttgggaggct gaggcaagag    25980
aactgcttga acccgagggg cagaggttgc agtgagctga gagtgcgcca ttgcacttca    26040
gcctgtgtga cagagtaaga ctccatctcc aaaaaaaaaa aaccaagatc aattaaaata    26100
cagcattact gggccgggtg tggtggctca cacctgtaat cccagcactt tgggaggccg    26160
agatgggcag atcacgaggt caggagatcc agaccatccc ggctaacacg gtgaaacccc    26220
gtctctacta aaaatacaa aaaattagcc gggtatagtg gtgggtgcct gtagtcccag    26280
ctacttggga ggctgaagca ggagaatggt gtgaacccgg gaggcagagc tggcagtgag    26340
ctgagatcgc gccactgcac tccagcctgg gcgacagagc aagactccgt ctcggggaa    26400 aaaaaaaat aaataaatag aatgctgtag tgtccttgag tttacatgcc cctccttacg    26460
cttgtgtgcc cgtgcagatt gcttgattac acaattagag gaggctggcg gaggattgtt    26520 ttaattttt tttttttgag acagtctggc tctgttcccc aggctagagt gcaatggcgc    26580
aatcttggtg cactgcaacc tctgcctcct gggttcaagc agttcttctg ccgcagcctc    26640
ccgagtagct gggattatag gcgcccgcca ccacgcccaa ctattttttg tattttagt    26700 agagcagcgt ttcaccatgc tggccaggct ggtctcgaac tcctgacctc agatgatctg    26760
ctgccccagc ctcccaaagt gctgggatta caggcgtgag ccacacctgg ccgtttgttt    26820
taattttgaa ggtgaagtga aagtgactac atttaccaaa agtgattgaa aagccaggac    26880
tgttcttacc ctgttttttcc agttcttgct cagagcaagg tggtttcttt ttcacttaat    26940
caccatactt acttttcatg tagaacaagt cagtttgagt tatcagttca tcatcttaac    27000
taaattccat gggggaagga attagtttta gtttcttaaa cttccaggtt tgcttattgg    27060
acaaaatgag atagcaaggc agtgttttta agttagattt tttatttctt tggtaataca    27120
attttctcag aaacttagta gtcttttagt ttagttgttt ttagttggtc ctatgttttg    27180
gatcacccct ctctacttta ttttgatagt gccaactgtg aagacatctg aagccatagg    27240
tttggatggg aaggaggcat ctttagcctg atcatcttcg ccaggctgtt tatctccttt    27300
tgcttggctg agaagtctta ataggaggct tattcccagc tatttgggga catagaagca    27360
gttagccatt gcttatattt tactgaggtc tgtgtggtat gttgattgta gtcagttaac    27420
gattttgaga actgaaggca gcctggtata tatagagtag gtattagact gtgtttcttc    27480
taattgaatt tcccatctct tgtaatctat gccatcatct tctgtactgc tgagaaagaa    27540
agaaagtttc taatcaaact ataccactgg ttgtaagatg cagtttggct ttagtgatgt    27600
taacacatga ttcaaacgtg aaattgattg agtattggtg aaatacagag gagatttaaa    27660
gccagaagac ctgggtttaa atgctggctg tatgacttca tatctgtgtg atcttgggca    27720
tgtcatggtt ggcacttcaa tttcttctct ctataatggg ggaagtgagg ccagtcatgg    27780
tggctcatac ctataatccc agtgctttgg gaggccaaga tgggaagatc gcttgaggcc    27840
aggagtttga gcaattgggc aacatcgtga ggccccgtct ctacaaaata tttgaaaaa    27900 attagccagg cccagtggtg cgtgcctgtg gtccgcgcca ctcaggaggc tgagacggga    27960
ggatcctttc agcctaggag tttaaggcta aagtgagcca tgattgtgct atcgtactcc    28020
agcctgggca gcagagcaag atcctgactc taaaaaaaag taaaataaag taaaatgggg    28080
gaaatgaact gctttagtaa catcatctgt tttttctgtg agcagcgtag cttgacagcc    28140
```

```
attggtgaac tcgtgccctg tgcttccctg tccagatccc cattctgccc gcaacatgga   28200
gtataacggt ttattcatag tagtcgagaa acactcactg aatgaatgaa tgaggtgtag   28260
aactaagtgg agtgggtaat tcaacacata ttaatttcct tctttttttt attttttagaa  28320 agaaagaact ttcagctacc aagaaagacc gtgtgaatca ttgtctgaca atatgtgaaa   28380
acatagtggc acagtctgtc aggtaattgc actttgaact gtctagagaa aataagaact   28440
ttgtatattt tcagtcttaa tgggctagaa tattctttgt gtcccagcta ttttaaatgg   28500
attcagaaat ccatttaaga tgaagaagga ccctttccc atatttctgg ctatatacaa    28560
ggatatccag acactgaaat gaataatgtt cccttttgt aatcttttat gcaaaaatta    28620
aaaccattat ggtaattgaa caacatgttt atgtttagtt aacacccta gcaactatag    28680 ttattttaaa accatctatg gtttgatatt tttgcatttg ttgcaatagt aggaacagca   28740
caagacagtt cagtttgtct ctcttatttg cttttttcttg gcagtttgct gtcctattgt   28800
acctctgctc ctagcagtgg ctggagccca ctcctctgtg cttcgggatt agtggggatc   28860
gtggggcatt gactgtaggt cagcttcct tgcttgatct ttctcactgg gatgaactag    28920
cagcaccttc ttttgtagct gctttgcttt tgactatctt tctgaccgtt gttcctagta   28980
gctgtagatg gtaaatatat ttaggcctgt ttccaatggc tcagtaggag acatattcac   29040
ctatgatatc tgaattctgt tacccacatg ggcatgcgtg aaatagttgc cttgccttac   29100 tttccccttgg aataaataat tcatgttatt ctcctggtag aagctagaaa aagctttat   29160 agtcagtcag aaaaaatttt ttagacaaat aatcttgatt ttagtactga caaaaacgtg   29220
tggtgattct ttttttaatt ttttttgag acggagtttc actcttgttg cccaggctgg   29280
agtgcaatgg cgtgatctcg gctcactgca acctctgcct cctgggttca agtgattctc   29340
ctgcctcagc ctcccaagta gctggagtta caggcatgtg ctactgtgcc cagctaattt   29400
tgtattttta gtagagatgt tggtcaggct gatctcgaac tcccaacctt aggtgatctg   29460
cccgcctcag cctcccaaag tgctgggatt acaggcgtga gccagggcgc ccggtgattc   29520
atttgttttt tcaaaaaatt tcctcttggc cattgctttt cacttttgtt tttttttttt    29580
ttttgagacg gagtcacgat ctgtcaccca ggctggagtg cagtggcatg atcttggctt   29640
actgcaagct ctgcctccca ggttcacgcc attctcctgc ttcagcctgg cgagtagctg   29700
ggactacagg tgctcgccac cacacccggc taatttttg tattttagt agagatgggg    29760 tttcaccgtg gtcttgatct cctgacctca tgacccgctc aactcagcct cccaaagtgc   29820
tgggattaca ggcgtgagcc accgcgcccg gccctctctt gtcttttat tgtggtaaaa    29880 tgcacataaa attgactgtc ttaaccattt ttaggggtac agttcagtat atatattcgt   29940
aatgttgtac agccatcact gccatctact tcataagttt ttcttctgtc aaaactgaac   30000
atctgtcttc attaaactcc ctatcatcca ttctttcctg tagtcccttt ctactttctg   30060
tctgtatgag tgtaactgct ctggagacct catgtaagtg gattcctaca ggatttgtgt   30120
tttttttttg gtgatctgct tattttaat gcctctgtgc atttgtatta tatctttca    30180 aagtgatttc acaaaaccgt ttcattttag gttaactcat ttctgttgtt tgtgaaatac   30240
tgtgtatgat tctgttctgt ttctgtctaa tttgtggaaa tgttgtggga agaaaatgaa   30300
ataacaaatg agcatatgtc ctgaaaataa aaatataaaa attctaagtt agcatgctat   30360
tgtagaatac aacgctatga taaaagtagg aaaaaaaaag gtttgaattc tatctctgct   30420
acctgtgtaa gctgggtgac tttagataag ctgtaacgtg tttgagcctt actggctcat   30480
ttttgaaatg taatccctag ttacacagtt cttgtgggat cagatggtac atgtgaaaca   30540
```

```
ctgtgaaaaa gcaactgcat agatatgttc attagccacc tgagcgggaa gcgtatccca    30600
ttgcgatgcc catcatccaa agctatatgt tatctttact ttttttttt tgagacagag     30660
tcttgctctg ttgcccaggc tagagtgcag tggtgcaatc tcagctcact gcaagctcca    30720
cctcccgggt tcacgctatt ctcctgcccc agcctcccaa gtagctggga ctacaggcac    30780
ccgccaccat gcctggctaa attttttgtat tttagtaga gatggggttt caccgtgtta    30840
gccaggatgg tcttgatctc ctgacctcgt gatccgcccg cctcggcctc ccaaagtgct    30900
gggattacag gcgtgagcca ctgcccctgg ccatctttac ttttttttgtg aaatgacttt   30960
aaatacttgg caaacatttg gtcattgttc atctgatctc caccatccag gtctcagaga    31020
acataatttc tctctgaaag cttattgacc caggaaataa gatctctttc aatctgagtg    31080
cgtcaggctt tattcttgtc attttgtctt ttgataattt tcaaatggaa ttcatggaat    31140
gttggcttat attcatatat tagtaaagta tgttgagaca tcttaagatt gatttgtggt    31200
tctatatgcc atattaaatc aaaataatag ctgttaatgg ttttcacatt agtctgtctc    31260
ttgtttttat ggagtaatgc tgagagttca ttatgcttgt tctacagaag agcatgttaa    31320
aaggagtttt tggagtcaga gaggttattc ttggtttcat aggatacact ctatactttt    31380
tagggatttc agagtatata gctgaaggtg atattttatg taaatatgtt ttatggaaac    31440
ttattgctca tcgctgtttc ctgttaactc tcctaaaata taattaaact tttgaacttt    31500
ttttatagct tttgtgctag actaattttt gtctctaatg aggttatata aatggcagct    31560
tctgacgttt tcaatgtagg aagtcattta aaacttcatg tatattgtga aaatgtagtc    31620
tgctttaagc tctctaaagt ggtctaagtt actggttcct aagtatggat gagcatcaaa    31680
atcatctgga aaatttgtta aaaatacagt aatgaaggca cctcactgtc ctttttccca    31740
aacatacttc tgcattctgt ttgagtaggt agggactaca cattttttcac aagtatcctc   31800
ttgggaatac ccaggaatgc ttacttgagc aacctcttac taatatgtac cttgataagg    31860
tggctaggta aacataaata tacaaaaatc catagatctc ccatatatta gcataaatca    31920
gctagaaaat ataacgttta aagatctagt tcacagtagc accaatatat cgaactctaa    31980
ggaatcgata aatatgcaaa aactttataa aaacttctgt taatgtttct gaaagatata    32040
ggtgaccact ttctagatag gaagatttta tattactaag ttgaatttc tctaaattaa     32100
cacagaaatt taaaataatc ttgatcaaaa ttctagtaga ggtattttg aacttgttca     32160
ctgcaagaat aaatacataa ttgcaaagaa tatctcaaaa tcatcaccag gcctggtgtg    32220
gtggcccatg cctgtaatcc cagcactttg ggaggctgag gcaggcagat cacctgaggt    32280
caagagtttg agaccagctg gaccagtgcg gtgaaacact gcctctacta aaaatacaaa    32340
aattagctgg gtgtggtggt gcatgcctgt agtcccagct acttgggagg ctgaggcagg    32400
agaattgctt gaacccagga ggtacaggtt gcggtgagcc tagatcgcac cactgcattc    32460
cagcctgggc gacaagagca aaattctgtc tcaagaaaaa agagaaaaaa gaaaagaaa     32520
tcaacactaa tatggtgaga cttaatgtat gtgacattaa aatagtgatt ggatgttaaa    32580
acaggtatag aacagaaaga agagtgtatg tgtgtatctg tatgaattta tgatgggtgt    32640
aacatatatg tattagggaa atgagggaaa tgatacattt ctctgacttt gggagaacat    32700
tatatctcta cctcatattg caaacaaaca taaagttcag attaattacc taaatgtgaa    32760
aaaatgaaat aatttcttta aaaaatgtaa tcttagtttg aggaaggtta acattataaa    32820
ggaaaaaact gttttgagtg gaatatagtt caatatgtca aaatccacct tcaacaaaat    32880
```

```
tgaaagtaaa ttgaacttgg ggaaagtatt gacagcatat agatcaaagg ttactagcct    32940
gtgtaaagag cagttataaa tatcgttaag aaaaacactg tcgacctgtc ggcaccttgt    33000
tctccgactc ccagcctcca gaactgtgac gagtaagtgc ttattgttta aaccacccag    33060
tctgtatgtg gtattttgtt atagaaactc aagctgatta ggacactagt aatcagtaga    33120
ctgaaactga aacaaaaata agaaccettt ttacctgtca aattggcaaa cattaagaat    33180
attcagattt ttgtcagagg tgatacaacc ttctaagaag gcaatttggg aaaatataaa    33240
gctttagatt attatatgtc tgacctagca gttttacctc tagggtgctt acccctagga    33300
aagtgtgtaa tgatattggt gcagtgccct tcatcccatt agaaaattaa aaataacctt    33360
aatggcctac cactaaaagg ggattgaaaa tttaagatat atttatttat gtgtttattg    33420
agatggagtc ttgcactgtc cgcctgggcc agagtgcaat ggtgcgatct cggctcactg    33480
caacctctgc ttcccggggtt catgtgattc tcctgcctca gcctcctgag tagctgggat    33540
tacaggctca caccaccgca cccggctaat ttttgtatt tttagtagag atggggtttc    33600
actgtgttgg ccagactggt ctcgaactcc tgacctcatg atccgcgccc ctcggcctcc    33660
cagtgttggg attacaggtg tgagccactg cgcctggcca gatacattta tacaagagaa    33720
tgttagttaa cattcataga tatttatatt ttgtttactt tttattaaaa aaattttttt    33780
tagagacagg atcttactct gtcacccagg caggatgcag ttgcacaatc atagcccact    33840
gcagcctgaa ctcctgggct taagtgatcc ttctgcctca gccttttgag tacctgggggg   33900 actttaggca gtgctactat acctggctaa tttttaaatg ttttatagat gagatcttgc    33960
tgtattgccc aggctggtct agaattcctg ggcccaagtg atcctcccac cttggcctcc    34020
caaagcgctg agattacagg catgagccac cacttctgac caatagatat ttatatttgt    34080
gactggaaaa tatattaaca atgtgttaaa aaattcagtt aaaaaataat gaaagatttt    34140
tgcttctggc taagatagaa taacaaggac agcatttatc ttcttgcctt gaaatagttg    34200
aaaacggaag aaatatatgt aacagtggtt ttcaagttat tgggcatcag gcaaagaaga    34260
atagttatcc caggaaaatg aatgtggaga gccctacaat ttccttacat tactgcctgg    34320
tcatggcaag aggaaaaact gagaggagac tgaggctgag ccagtggttt gctgggttga    34380
ggaggcagag ctgggagtgc agagatgcaa ggtggtgaga gcccatatgg aagaatacca    34440
gggaagagag ctgcagaggg agctccggag acctgcaccc tgccctctca gtaccctgtc    34500
atgtgtgtag ctgagtactg acgagcactt gcttgtgcgg aaatgaccca gggctggagg    34560
tagagccacc tgaaaggatt agaaggaaca gttgctgaaa gtcacacagg gccaggaaga    34620
atttctaatc acaccagttg gagtggaaaa cctcagctct catagagcag gtagggtact    34680
cagaagggtt tgcccaccta gccccagact aagtttcgtt actctgaccc tacctaatat    34740 taaaagaga ttaattaaat tgttcgcaac aaaaataata tatttcagtg tttgtaacac     34800
gtagaagtga attgtatgac aatagcataa aggctggaag agcagaaatt gacatgtatt    34860
tgcgctgggc agaataatgc tcccctcttt ccccaaaaga tatcaagtcc taatccctgg    34920
agcctgtaaa tattacttta tatggaaaat tgttttatga tgtgattaaa ttcaggatct    34980
tgagatgagg gggctatctt ggatgatctg ggtaggcact aaatgcaatc acatatatat    35040
aaaaaggagg cagagggaga ttttacacac agagagaagg ccctgtgaag atggaacaga    35100
aagatttgaa ggtgctggcc ttgaaaattg gagtgatgaa gctataagcc aaggaatgca    35160
gcagccacca aagctggaag aggcacggag cagttctcat ttagagccta ctccagaggg    35220
aatgtggtgc tgccaattcc ttttttttt ttttttttaa gatatcattt acccctttaa     35280
```

```
gttggttttt ttttttttttt ttttttttta gtatttattg atcattcttg ggtgtttctt   35340 ggagagggggg atttggcagg gtcataggac aatagtggag ggaaggtcag cagataaaca   35400
tgtaaacaaa ggtctctggt tttcctaggc agagggccct gccacgttct gcagtgtttg   35460
tgtccctggg tacttgagat tagggagtgg tgatgactct taacgagtat gctgccttca   35520
agcatctgtt taacaaagca catcttgcac cgcccttaat ccatttaacc cttagtggac   35580
acagcacatg tttcagagag cacggggttg ggggtaaggt tatagattaa cagcatccca   35640
aggcagaaga attttctta gtacagaaca aaatggagtg tcctatgtct acttctttct   35700
acgcagacac agtaacaatc tgatctctct ttcttttccc acatttcctc cttttctatt   35760
cgacaaaact gccaccgtca tcatggactg ttctcaatga gctattgggt acacctccca   35820
gatggggtgg cggccgggca gagggctcc tcacttccca gatggggcgg ccgggcagag   35880
gcgcccccca acctcccaga cggggcggcg gctgggcggg ggctgccccc cacctcccgg   35940
acggggcggg tggccgggcg ggggctgccc accacctccc ggacggggcg gctggccggg   36000
cgggggctgc ccccccacctc ccggacgggg cgggtggccg ggcgggggct gccccccacc   36060
tcccggacgg ggcggctggc cgggcggggg ctgcccccca cctcccggac ggagcggctg   36120
ccgggcggag gggctcctca cttcccggac ggggcggctg ctgggcggag gggctcctca   36180
cttctcagac ggggcggctg gtcagagacg ctcctcacct cccagacggg gtggcagtgg   36240
ggcagagaca ttcttaagtt cccagacgga gtcacggccg ggcagaggtg ctcttcacat   36300
ctcagacggg gcggcgggc agaggtgctc cccacttccc agacgatggg cggccgggca   36360
gagatgctcc tcacttccta gatgggatga cagccgggaa gaggcgctcc tcacttccca   36420
gactgggcag ccaggcagag gggctcctca catcccagac gatgggcggc caggcagaaa   36480
cgctcctcac ttcctagacg gggtggcggc tgggcagagg ccgcaatctt ggcactttgg   36540
gaggccaagg caggcggctg ggaggtgaag gttgtagtga cccgagatca cgccactgca   36600
ctccagcctg ggcaacactg agcactgagt gagcgagact ccgtctgcaa tcccggcacc   36660
tcgggaggcc gaggctggca gatcacttgc agtcaggagc tggagaccag cccgcccaac   36720
acggcgaaac cccgtctcca ccaaaaaaca cgaaaaccag tcagacatgg cggtgcgtgc   36780
ctgcaatccc aggcacttgg caggctgagg caggagaatc aggtaggag gttgcagtga   36840 gtagagatgg tggcagtaca gtccagcctt ggctcggcat cagagggaga ctgtgcgagg   36900
gcgagggcga gggcgaggga attccttaat ttcagtttag tgatactaat tttggactct   36960
ggcctctaaa actgtgaaag aaaaaattt ttgtttgttt gtttctttta agccacatag   37020
tttgtggtaa tttgttacag cagctgcagg aaactaattt atgctgcatg tgaaatggtg   37080
taataaggta gattgtgatg aagatacata gtataaacaa ttaagcaaca actaaaagca   37140
caacaaggaa ttatagctaa tgaaccaaaa aaggagatta gaataataaa aatggtgaat   37200
cccaaagaag ccagaaatag gggaagaggc aaataaagga agaaagagc ttgatggtag   37260 atttcaacct aactatgtca aaaaggacat tacatgtaaa aggcagcgat ttttcagatt   37320
gaatggaaaa gtaagactcg gtatatgctg ctgcctgcaa gaaacacatt ctaaatataa   37380
aggcaaaaat aacctacagg taacagaacg gaaagaagtt cactgtgctt acaagaatta   37440
gatgcaagct agactggttc tgttaatatc agacaaagtg gatttcaaag caaaggctct   37500
tgcccaggat gagatggtca tttcataatg atgaagggga ttcgttcatc agcctggcat   37560
agcaagctga aatgtttatg caccggacta cagagctaaa atacatgaag caaagcctga   37620
```

```
cagaactaca agtagaaaca gacaaatcca cagtgataga gatttcagta gccgctctca   37680
atgatttgta gaacacgtag ccataatatc tggatctaga acacttgacc aacactgtcc   37740
cctgtgcaac ctcattggca tttacaggac actccaccca gcaccagcag aagagacact   37800
ctctcaagtg ctcacagaat gtttgccaag atagagcaga tgctgggcca taaaacaagt   37860
ctctaaatta aaagcattca aattattcag agtatgtttt ctgacctcag tatcattaag   37920
ttggaatata ttataggaag ataacctgga aaagcctcag atatgtggaa aaacccattt   37980
ccacatggcc catgggtcag aagtgaagtc aaaagggaaa tttgaaagtc ttttggattg   38040
actgatataa aaacaataga tttctaaact tgtggggtgc tgttacagca tagtaaatgg   38100
aaatttctag cattaaatgc ctgttttagg aaagaaagat ttcaaatcaa tgacctcagc   38160
ttctaccttt ggaaacttga aaatgacaag caaatggaat ccagagttac agaagggcc    38220 aggtacggtg gcttatgcct gcagttctgc cactttggga ggccgaggca ggtggattgt   38280
ttgagactgg cagttgaaga ccagcctggg cagcctaggg agaccccata tctacaaaaa   38340
acaaaaaaat tagccaggtg tggtggcatg tgcctgtagt cccagctaac caggagtcta   38400
aggtgggagg attgcttgag tctgggaggt tgaggctgca gtgaactgtg attgtgccac   38460
tgtgttccat cctgggcaac agaatgagac cctgtctcaa aaacaaaaac agttactaga   38520
agaatggaca tcataaagat aggagcagaa gtcagtaaaa tagaaaacaa aaatacatag   38580
gaaatcaata aaaccaaaag ctggttcatc aagaacatca ataaattggt aaagctgata   38640
ggaaaaacag tgaagtcaca aattagcaat atcaggaatg agggagatga cagtagtata   38700
gattatatag atattaaaag gactgtatga ggcaggtgtg gtggttcacg cctgtaatcc   38760
cagcaccttg ggaggccgag gtggacagat cacctgaggt caggagtttg gaccagcct    38820 ggccaacatg gtgaaactct gtctctacta aaaatacaaa aattagttgg tcgtggtgct   38880
gtgtgcctgt aatcccagct acttgggagg ctgaggcagg agaattgctt gaacctggga   38940
ggcggaggtt gcagtgagct gagattgtgc cgttgcactc cagcctgggt gacagagcaa   39000
gactccatct caaaacaaat aaataaataa aaaggactat atggtaatat tatgaacaac   39060
tttatgccaa taaatttgac aacttataga tgaaatggat gagttccttg aaagacacag   39120
aaactattaa agctctctca agaagatata gataagctga ttagccctat atctatttta   39180
ttgaatttaa atgtaaaaat caatatttag ttactggaaa acttttaagt gtggttggaa   39240
atggtatacg aacttttttca actgaatttt atgaagtcta atcacaggta aaggttttct   39300
gatgaaaatt tagtgtctga attgagatat actgtaaaaa atgttatata tcttaattat   39360
ttcttcacat taattacatg ttgaaataat actttgggtg tattgggtta aattaaatat   39420
tatgaaaatc ttgcctgttt tcttttact tttgatgcgt cagctaggaa atataaaagt    39480
gtagctcaca ttctgtttct gttgacagta ctgctttgga gcacagtgtt tgaatgatct   39540
atcatttcaa agacctttcc tcagttcgtt attcatggct gtctgtattc cacatagata   39600
aggtctgaaa tactgctaag tggcatgttt tgttttatgc ttttataagt tgttgatca    39660 ttactgatgt ggacttttgg tgcctcttag gctcattgct atcttccaac cattgtttgc   39720 aattttacc tagagataaa gagaaagaga catttggttt cagagtagtt agattgggat    39780
catgaaagag caacctcatt ttgatgcttc aaaaatagca catccccgt attactggga    39840 tttgctattc ttgggattac ttcaagaaca tccttgtgtt actggtttgg atgcttctga   39900
atgctgtgaa gtcagtttca tgtacatggc tcatcagttt agctctctct tggctttgtt   39960
tagacagttg gagcatgatg gcctaaacag cttcttttcaa ttaaacatttt taaaatagtt   40020
```

```
tacaaatagt aaacaaactc cagttttttgt gactctttgt ctcgcacaac aaaaacacaa   40080
tctgaccatg atcatctggc atcttagggt gaaatatgtg tatactttgg cccataccga   40140
aagcaagatt aaaaaggggc aggagagata gactgctgaa ctgattttca aggttccaag   40200
aatattgtag gttaagagta aaagtaaact tttggtagaa agcagtgggt tgtctaggat   40260
tgaagtatct gaagttttta aacgaaaatt taaaaagaaa aatgagaatt gccttacaag   40320
tacaatctct tctttttttaa aaaataaact ttattttgaa atagtttag atttatagaa   40380 aaaaattaga tagggtagga agttttcata tacctacat ccagttaccc cagttattat   40440
catcctaatt tagtgtgaga cattttcatg tttaatgaat caatattgat atgctattaa   40500
cttaagtcca gactttattc agattttctt aatttctatg taatgtcctt tttctgttcc   40560
agaattccat gcaggacacc ggatacctca ttacatttca ttgtcatgtc accttaggct   40620
cctcttgaca gtttctcttc tttttttgct tagaaattct ccagaatttc agaaacttct   40680
gggcatcgct atggaaccttt ttctgctgtg cagtgatgac gcagagtcag atgtcaggat   40740
ggtggctgac gaatgcctca acaaagttat caaagtaaga accgtgtgga tgatgttctc   40800
ctcagagcta tcattgttgt aggctgagag aagaagcgat cattgagtgt tcttctgttt   40860
tgagtccctg aggatgtctg cactttttttc ctttctgatg tatggttttgg aggtgctctg   40920 ttgtatggtt tggaggtgct ctgttgtatg gtttggaggt gctctattgt atggtttgga   40980
ggtgctctgt tgtatggttt ggaggtgctc ttgtatggtt tggaggtgct cttgtatggt   41040
ttggaggtgc tctgttgtat ggtttggagg tggtcttgta tggtttgcag gtgctctatt   41100
gcatggtttg caggtgctct attgtatggt ttggaagtgc tcttgtatgg tttggaggtg   41160
ctcttgtatg gtttggagat gctctattgt atggtttgca ggtgctctat tgtatggttt   41220
ggaagtgctc ttgtatggtt tggaggtgct cttgtatggt ttggaggtgc tctgttgtat   41280
ggtttggagg tgctctgttg tatgtttggg aggtgctctt gtatggtttg gaggtgctct   41340
attgtatggt ttggagatgc tctggtatct gcctgcattg cttgccacac ctgcccggtc   41400
agaaggcgct atgttgacaa ttgtgcctgc acggtgccta ggtcaatgaa gggaaccgat   41460
ggtagccact ggatgctcct gggaaaatgt cactacaggc accagagaag ccagagctat   41520
gcccaaattt ctatgagtct cagttttctt aaccataaaa tgggatcaat gttttttgtgg   41580 catgtgtatg agtgtgtgtc tgtgtatgtg tgaggattaa attgtgtatg tgtgaggact   41640
aattgccact actggatcct caaagtggta agaagtgttc ttattaataa tgacatcctt   41700
acactcttac ccagcaagat tgatgggtgt ggcactgctt ctcttttcc atcacatggt   41760 ttccatggta tccttttgcc cagggaatct ttgctttgtg gctagcactt tgttgtttgg   41820
ctaatcacgc tttctgtggt caggacgctg gcttctctgg agccatggga ttctagctcc   41880
ctgtcttgtc cctagagtgg tcactgtctt ctctctccgc ttgcaattcc tgctttgctc   41940
gcatctcact tatgcagtga cgtatatcag tttcaccttg ttctccgtgc ctgctgatca   42000
ttggcaccac ttgcatggtg ccatttaggg cctgcttcca gttaagcttg cttctccaca   42060
ggcctaaata tccttgcttg cttcttttat tctcactggc aggaccaggg cggtctgtct   42120
ttgcatgaga cagggtctcg ctcagtcacc caggctggag tgcagtggct gatcacggct   42180
cattgcagcc ttgagctacc gggctcaagc tatcctcctg gcttggcccc ttgagtagct   42240
gggactacag gcgtgcacca ccatgcccag ctaattttta aaattatttg tagagatggg   42300
atctcgccag gttgcccagg ctggtcttga acgcctgggc tcaagtgatc ctccctcctt   42360
```

```
ggtttcccaa agtgctggga tcacaggtgt gagccactgt gcctggccct tgatgtttca   42420
gttcttgata tttgatcctc agagtcagaa aatctaaaaa gagggctatc ccaggttgcc   42480
ttggttcatg gcaaatggga cgttaagagg gcagagagaa tatgaacaga aactgttcta   42540
atattggtca tttaatgtgt aagtattgtt cttttttaaa cctccttcat tttttttcca   42600
ggaattgctg gacacagtgg cttggtgtgt gtctgaggac tgtaggccat ggccctaggt   42660
tgtggtttta ggtctcaggt gctcttcctg gctgtctcct tgcttctttc ccatgtcctc   42720
ttctttgttt ccagccattt ctcccttatg cttaagtttg gtgcagcagg gtttggctgc   42780
tctcagattc ctgcttcctc agatgctgta gttgtcaggc ccagcgggct ggcagcggga   42840
tcaggatctg gctaggtttg ctctcactgt ggcagagtag ggggaggcgt gggagagcac   42900
gtgtgacccc aggccagctg tagggagcat aggcatggtc acgtagcctt caggtcctag   42960
actttgtctt ctcatgagta tggctgtgtg tgtatggtga aaactaggtt ctacttagcc   43020
caagaaaatg ggcacatttt gcatgtggtt tctgtagaga aatgcactgg gtatctgaca   43080
tagcctggca gcatgcctcc ctcaggtagg ttagtctcag gcggtgaagc acgtgtgtcc   43140
agcaagaact tcatatgtgg cataaagtct ccgttctgtg aggtgctggc aaatcaccac   43200
caccgtcaag aggctgaagt gattttttgtc tagggaggca ggaaaggctt cctggagtca   43260
gcagccagta ggtgaaagag tagattggag accttcttaa tcatcaccgc ctcttgtctc   43320 aagggggtgcc aggaagctgt ggaggctgaa cccatcttat gctgccagag agtgggacac   43380
catgagggtc aggtcaaggg gttgtacctt gtttggtaga gaattagggg ctcttgaaga   43440
ctttggatgt ggtcagggga gtgtatcatt taggaagagt gacccggtga ggacgtgggg   43500
tagaggagga caggtgggag ggagtccagg tgggagtgag tagacccagc aggagtgcag   43560
ggcctcgagc caggatggtg gcagggctgt gaggagaggc agccacctgt gtgtctgcgg   43620
aagcaggggc aagagggaag aggccagcag cgtgctgcca tcacccagcg actggcgtag   43680
attgtgagag accattccct gctcttagga ggggctgagt tttagttttc tcttgttata   43740
caataagctt ggtatttgtt tacaaaacat ttgtaaagct aaatcaaggt ttgataaggc   43800 ttctagttttt atttaagaag taatgttgaa ataaatgttt gtccaattcg ctttgctcat   43860
ttaaggactt tcagtacaaa ctgcaacaac aggattagga tttaaacgtt tctgagatgt   43920
ttttactcct cagaatttcc cagaatgtga tctggttttg attttcaagc ttgctgaccc   43980
aataggttaa cccacaagtt ttacgaagac catctcagtc cacttacatc aactgcccat   44040
gccacggtta aagagatcat cgactgatgt ttggcacagc ttcctccctc ttgggtgggc   44100
aagcatttgg aagagaaggc tcctatgggt gagagtgggg caccaaagtc ttccctgtcc   44160
catcccctag cttgagaagc ccttctctaa tgtggacttt gtgccgttag catcgttact   44220
agcttgaagt tgaccatctg gacgtacttt ctggtttagc ctcacaagtg agcaaggagg   44280
gttgagagat gtgctgtgag gaatgtgggg ccccagctgg cagcaggctc tgggtcaggg   44340
gggcagggac cacgggcata cctgacagtg aggaggggcc acacctgcag aaaaggatgc   44400
aggactccgc cttgggaagt gttctaggcc agagcgaggg tctgtggttt ataagtacac   44460
ccacagtgct cggacccctg cagatgtcca gggtgccgtc tgagcccgta tcatccaaca   44520
gaatgttctg ctagtgaaga ttaaagattt actccagggg ctttaggatt tattatatat   44580
atataaatcc tatatatata atttttttttt tttttttttt tgagatggag tttcgctctt   44640
gttgcccagg ctggagtgca atggcgtgat cttggctcac tgcaacctcc gcctcccggg   44700
ttcaaactat tctcctgcct cagcctctcg agtagctggg attacaggcg cccaccacca   44760
```

-continued

```
cacccggcta attttttgtat tttttagtag agacggagtt tctccatgtt ggtcaggctg    44820
gtcttgaact cctgacctca ggtgatctgc ccgccttggc ctcccaaagt gctgggatta    44880
caggcatgag ccaccccacc tggccaggat ttattgtatt tgaaccatct accatttttaa   44940 ttttgatgtt atgtagtatt tgatgataat gaaagttaaa ttgttttttct ttccattttt   45000 ctgtttaagt gaatgacctg tatctagttt attcagtaac ttcctgcata tatttgtttc    45060
tttcattctt aatgaatata ttcttaattt agttgctatt atgttttgct ttgccccaaa    45120
attgaaatct tagtttcctt ttagctcgtt ttagaactag tgatgggatg tgtcttccat    45180
aaatctcttg tgatttgttg taggctttga tggattctaa tcttccaagg ttacagctcg    45240
agctctataa ggaaattaaa aaggtgggcc ttgcttttct tttttaaaaa tgttttaaat    45300
tttaaatttt tataggtaca cgtatttgt aggtacatgt aaatgtatat atttatgggg     45360
tacatgagat attttgatac aggtatacaa tacataataa tcacaccatg gaaagttgga   45420
tatccatgcc ctcaagcatt tatcctttgt gttacaaaca atccagttac atgctttact    45480 tatttttattt tattttttgag acagagtctt gctttcaccc atgctagagt acagtggcat   45540
gaccttggct cactgcaacc tccgcctccc gggttcaacc gaactttggg ctggtctcaa    45600
actcctgacc tcaggtgatc cgcccgcctc ggcctcccaa agtgttggga ttacaggcgt    45660
gagccactgt gccgggcctg attgtacatt ttaaaataac taaaacagtc agggcacagt    45720
ggctcatgcc tgtaatccca gcattttggg aggctgaggc aggtgatcac ctgagatcag   45780
gagttcgaga ccagcctggc caacatggag aaaccctgtc tctactaaaa atacaaaaat   45840
tagccaagtg tggtggcggg cgcctgtaat cctggctact cgggaggctg aggtagggga    45900
atcgcttgaa cctgggggtg gaggttgcag tgagccgaga tcacgccact gcattccagc    45960
ctgagcgaca gagtgagact ttgtctcaaa aaataaaaat gaaataaaat tgggccgggt    46020
gtggtggctc acaccttagt cccagcactt tgggaacctg aggcaggtgg atgcttgaga    46080
ccaggagttt gagaccagca tgggcaacat ggcaaaacgc tgtctgtaca gaaattagct    46140
gggtgtggtg gtgcacaact atagtctcag ctacttggga gattgaggtg ggaggattaa    46200
ttgagcctgg aaggttgaat ctataggtag ctgagattgt gccactgccc ttcagcctgg    46260
gcgaccaagt gagaccctgt ctcaaaagaa aacaaaaaaa acaaaaaaca aaccactatt   46320
atcgactata tattattgtc tatgatccct ctgctgtgct gtcgaatacc aggtcttggg    46380
cccttatttc catcactgag caaacttcac tctgttaagc agcaggtgtg ggatttcatc    46440
gttattcagt aattcacaat gttagaagga atgctgtttt ggtagacgat tgctttactt   46500
ttcttcaaaa ggttactctt tattagatga gatgagaatt aaaaatggta acttacttta    46560
tatctttata attgaagccc actagacctt aaagtagtta ccagatgttt tatgcattta   46620
aatggccttt tctctaaaat tagaaagtaa caaggaaaga aaatgcttcg tttctatgca    46680
accctcttgg tgactagtat gtgactctta atgcaaccct cattgcaccc ctcagaatg    46740 gtgcccctcg gagtttgcgt gctgccctgt ggaggtttgc tgagctggct cacctggttc    46800
ggcctcagaa atgcaggtaa gttgtacact ctggatgttg gtttttgtcg ggggccagct    46860
gctactgatc ctttatgtct cagctcagat gtcatttcaa aagtctgctc tgccctctcc    46920
aaattgcagt cgaccttgcc ctgtttatgt ttccctcata gcactaatcc atgtcagaaa   46980
ttgtcacgta cagtctatct gtgtgcttgt ttattttcta tcccacccctt ccgcaagaga   47040 cttatgggat gtgtgcccca ggacagcagg ggtcttactg tcttatgctc tgttgcagcc    47100
```

```
cagcagcgat aacagtgtct gcacatagta cttgcttaaa agatacttgc caaattgttg   47160
aaggttgagg taccaatttc attattgctg actataggag ttatagcaaa atatccattt   47220
gtctgttaca tgagttaaaa atatggttgt tgcactgtga atagtttggt ttagtcaaaa   47280
cagttgtatc ttaacggatt gagaaacaaa agcaggacca cttttcatca gctccctcct   47340
tctccttaac cagcaataca tgctgatgct gatatcccat agaccctcag ctccatcctg   47400
agtcactggg aatgtggtct aaaccctcac tattaatatg aactgagttt caataagaat   47460
cttatatggg tcgggcatag tggctcatac ctttgatccc agcacttcag gaggccaagg   47520
caggtggatt gcttgaccca gactaggcaa catggtgaaa cgccgcctct acaaaaaata   47580
caaaacttag ccaggcatgg tggtgcgtgc ctgtggtcac agccactcga gaggctgagg   47640
tgggaggatc acttgagcct gggaggtgga ggtcgtgttg agccaagatc gcaccactgc   47700
actccagcct gggcaacaga gtgagacctg tctcaaaaaa accaaaatcc agaaaagaac   47760
ttatatggct gcagaggtat aatcactaag gaaatttcct tttgtataat cttttttctt   47820
ttactatcat ttaaaaaaat gtgttatatt tctgaagcaa cacatccagg ttctgcacat   47880
agcagccaaa gtgaccttaa agaatataac tgggtcttgt cattcccttá tttaaactct   47940 tgtacccatt tcccagtgcc gtttagatag agattccaga ctcgtcaatg gctctgtcac   48000
ctcagacacc ctgcattgac tcattagtct gattagagtc aggttttttct tcctcctgat   48060 ggtttttttt tcccccttag ttctcagcgg aacagtcact tccttaggga ggtttcccca   48120
gccaccctct gaggccgtgc ttgttgccag actctgccac tagagggcag ggctgcacca   48180
ctcctggcac ctcgcacccg gcctgccctg tcactctgtg tgttgggtga attcctgtga   48240
tctgtgactc actgctctgt gtcctacaca ttcggctttt cttctctccc cacaacccca   48300
ttttataatt ctccttttc aggaaagctt tattcccatt taaaaatttt tgtttttaaa    48360
atggtatttt cttacactta ttttctaatt aaaaatgagt gttttaagaa gtattatgat   48420
ttactgcaaa taatttttaa acccagcctt ttagatcctc tgtgatcata agagaaatga   48480
aggatgtctc ccaacacttg agcttcatcc acatttcatc ctcctgttct ttcagctgag   48540
ttttccccat cccattaggg actgttggaa tataaaactg gcttttccct aacagggaat   48600
gaattgcttc tgtttctcct gaaggagagc tggaagaatg acttgcgttc ttttgcatac   48660
acaggcctta cctggtgaac cttctgccgt gcctgactcg aacaagcaag agacccgaag   48720
aatcagtcca ggagaccttg gctgcagctg ttcccaaaat tatggcttct tttggcaatt   48780
ttgcaaatga caatgaaatt aaggtatgat tgttgcctca ggtcacaaac atgcgagtga   48840
tgctgtgagt gagtctgtgg agggtgaggg cttctgaaca gggagtcctg tgggagtgct   48900 tcttgggta tgttgtatgt cgtaatttag actaccatca tttgtgttat ttttgaggca   48960
cctaaggact tctttccact tctcatttct tactgtgggg tgaagagttg aattgggaga   49020
tggtttctag atgcaaattg aaaaggcatt tttccagagc agatttgttt tcggcgtact   49080
agagtgactc tttaacctag ctgcgggaag atgactgtgc caagactgca ggtaggagaa   49140
agctcactga cgaggccttg tgggtctgaa cgtcctgcag ctatcagagc ctgttggctt   49200
cctgttgtgc attccaacaa atcatcttca aacccacttt agtgttttgt ttataatgtc   49260
cagaaatagt gaccctgtca catgctctac agattacagg attcttagcc tcttcctttt   49320
tggtaggtca gtcctgggtt tgagcccaag tgaccctcct gggaggtgat gatacacact   49380
gggtagagtg gaatcagatg gacttggatt agaattctgt cctctttact agttattttc   49440
ctctaggcaa actgcccaac agctctaagc tatttccttc gtattctgaa aaataagcct   49500
```

```
taatgggacc catatagggc aactctgaga gtaaaataaa ggaatatgtg ttagagtgta    49560
gcatagtcac ccacgggaag ggcttagatg ttagctgcta ctgctcttat tagctgaatg    49620
atttggaata aactgttagc ctctctcatg ttttttctct tgagcttcga agttttcttg    49680
ttaatactaa ggagatattc aaactagtca tggggttttg gaatgacgaa gggagatgat    49740
gaatctaaag aatttagtgt aatatttctt catgctcagt aaatggtagt ttctgctgct    49800
gttattttta ttaccatctc tttggaatgg gagtaggtgc tcctttgtgg tcagaggctg    49860
tgagagctcc acagcgccag tttgcccatc tgtacactgg ggtctgttga aggcagtccc    49920
ctctgtgata tctctggctg tcagagctca gatgatagat ggtattttg tactcttagt    49980 tctcatcatt ttcatgattt cgatcaccat ttgagtatga tgatgctaac actttgttga    50040
acgtagaatc cgttaattac ttccttcctg aacctttggc attaaaaaaa atctattctg    50100
ctacctctct gctcatttat ggttattcaa atttattatc aagagcctgg tacagtggct    50160
tgtgcctata attgtagcta cttgggaggc tgaggtagga ggattgcttg aggccaggag    50220
tttgagacca gcctgggcaa gatagtgaga ccctatctct aaaaaaactg aaaaaaaatt    50280
agctggacat gatggcatgt gcctgtggtc ctagctactc aggaggctga gacaggaggc    50340
tcggttgagc ccaggagttg gagttcgagg ctacactgag ctgtgattgt gccaccacac    50400
tccagcatgg gtggtaaaac aagatgccat ttcttaaaaa aaaaaaatat atatatat    50460 attatcaatg aaattcagta gtaccaacag gattataaac aaagatagta gttcccttcc    50520 tacttttct cttaatcctt gtgtctcaca ggcaaacata actcttagta tttcttccaa    50580
tatttacttt catgtttctt tctttctttc tttttttttc tttgagatgg agttttgctc    50640
ttgttgccaa ggctggagtg caatgacgca atcttggctc accacaacct ctgtctcccg    50700
ggttcaagcg attctcctgc ctcagcctcc tagtagctgg gattacaggc atgcatcacc    50760
acgctcggct aattttgtac ttttagtaga tgggggtttt ctccggggttg gtcaggctgg    50820 tctcgaactc ctgacctcag gtgatcctcc cacctcagcc tcccaaagtg ctgggattac    50880
aggcgtgagc cactgcgccc agcaacttcc acatttctaa ataacatgct tctactgcta    50940 ttttttttt caattttaga cattttttta ctttcactat agttctatca gaattcagtg    51000
tgtacgttat tatgcctaag taaatagtca tggttgctta cgtattatat ttctttgatt    51060
gtgtttctta tttgatgaga aagctgtgtt ttttgctctg ggttgaaact ggagagagga    51120
cctggggagg aggaggagga cagatgaagt tggtgactgt accttcatgg ccatagctgg    51180
gttctcagca cccgggatc tgctgatcac ctactcatag gccaggcccc tatcgaagtt    51240
ctaggtgacc cagtgctggg gacggggggg ccacctgcaa ggtctaatca tggaggtggg    51300
ggctacagtg ttggcttgtg ctggggccag catccttagg aaggcatctt ggaggtggag    51360
gagacagccg cccacttctt gattggggcc ttcagcagca ccagcttctt gggcaggctg    51420
gtgctggctt tcatcaccat gtcgtgttca atcttcttcc agatcctgac ttctaggttc    51480
agctttcctc agaccctggt tcctttcaga ggccattgct gctgccttgc tctttgctgg    51540
cttgtgcctt gattatatgt ctttgtacaa cttttttgttt tcctggagtt aatcttcaca    51600
tctgttttct tggagttaat cgttacctct atatcgcttg cttattattc tttggccttt    51660
ttgtcttctc acaccttcca acttctttgt aatatgtgtt tagtacaatt tttcatgaca    51720
ggtagtttac tgaatcagtt ttttccccagt gtggtcatcc aacttgagtt atccagctct    51780
ctgccccagt ctgggcaggt tgatcttcag gtctgtagta cacttgtatc ctaggacttc    51840
```

```
tctttgccat tagcctggaa tttcctttgc agttctcccg ttggatgccc agttcctaga   51900
tgccatatgt ttttctatcg tctagtagct tcctgagaga agatgaatgg gagggaaatt   51960
gtatgaggtt ttgcattcat aaaaatgcca ttttttttcc tgtacacttg gctgggtatg   52020
gtgttctggg gtagaaatca ttttcccctca gaaatgcaaa gtctttgccc tgttgtctta   52080
aaatctccaa cgtgacccga ttccttaacc tatgaatgta cttttctttg gaagctttcc   52140 attttttgggg aggtgaagtg ctaggtactt agtaggcctt ttaatttgga aacttacatc   52200
ccttcagttc tgggaaaatt ttcttaacat ttctctgaga agttcttgcc ttttatttttc   52260 tgtgttctct cctgaaattg gttagttgga tgttggtcct cctagattga ctcacatctt   52320
acctttttct tttctttttc tggtacttttt tagatatcca tctcaaactc ttctattcat   52380
tgttatgttt ttaacttctt tctttttcttt gtctcttgat ggggtcttgc cctgttgccc   52440
aggttgtggt gcagtggtgc gatcatagct cactgcagcc tcaaattcct gggctcaagc   52500
agctgttctg cctcaccctc ccaagtagtt gggactacag gtatgcacca ccacgtccag   52560
ctatttcttt tactttttttt tttttttttt tgagatggag tcctactctg tcgcccaggc   52620
tagagtgcgg tggtgggatt ttggctcact taagcctctg cctcccaggt tcaagcagtt   52680
ctcctgcctc agcctctcaa gtagctggga ttacaggtgt gcaccaccat gcccggctaa   52740
tttttgtatt tttagtagag ccagagtttc accatgttgg ccaggctggt ctcgaacgcc   52800
tgacctcagg tgatccgcct gccttggcct ccgaaagtgc cgggattaca ggcgtgagcc   52860
catcattaga tctttaaata ccagtatcta taagtctttt cctcttgagt cagctagtat   52920
ccctggaagg aaaattactca ttttcctgct tggaggctat aagcttggct atgtttatcc   52980
tgcaaccggg gactggaagg gaggggactg acagtgttgc tggtcagggt gccctcttac   53040 ttttttgtttt ctgtgtgcat ctcacgtctg tcctcagcct atgtaaacac ctcttgagat   53100
tatccctctc aatctttgcc ggaggtgggg gaggggctgc ttcctgggct gccttggatt   53160
ggagggaaga cctcaggtga gtgggtggga atttgcccaa ggagccatga gaccagccac   53220
tatttcaccc tctccatccc tccactttca gatgtatgtg gcgcctccaa agcccgagct   53280
cttcttggcg tctgtggctt caataagctt gcttttttgct ggtatccctc ctaccctccc   53340
ctgtccccag caaagcttgc atttgaactt cttcctacgg gctaacaaat cagtcagtta   53400
tgtagctctt gttactttttt agcttccgaa gttttgttga cacccgtagt ctgctaatgt   53460
ccctgttctg ttctttctgt tcgtgtaaat atatgcttta tacaacttct ttacatgatt   53520
tttgtggggt ttctgggtag cagagcttca caagttcaat ccagcgtgtt ggattagaaa   53580
tctcccaccc tctggtttat tcttattctc aaaattacct gccaaacact gatactccct   53640 tgttttttcct tttcctgaca ggaaatgtac ataccataca ggacagaaat cattagtgta   53700
tcccttggtg aataaccaca aagtgaactt aaccctggta accgccaccc aggtcaagac   53760
agaatattac caagcactca gaagcctctc ccctattccc ccgtcactgc tcctgccttc   53820
ctccccaagg tcatgactgc tggcttctaa ttccagagtc tgttttaaa ttctgtgtac   53880 atagaccatg gattaagtgt tctttttgtc tggtttattt tggtcgacat taagttcatg   53940
agagtcttct atattatcgt gtgtattagt attcctgtag ttttaggagc ttcatagcat   54000
tccattgtag ggatatacca cagtttattc attgtattat cactgggttg tttctagttc   54060
ttggctattg cgagcagtgc tactgtgacc actcttaggt gtgtcttttg gagtacatgt   54120
gcaggtttcc atcttgcaca gctagaggtg gagttgttgg gtgatagggt gtgtgcatct   54180
cagctgcagt agaaactgcc aaatagcttt ccttgagtgc ttgtaccagc tcacccttt   54240
```

```
gccactgtgt atggggattc caggagctct ggtcctcgct agcacttgga attgctgatg   54300
cttttactct tagccttcct gatgggtgtt ttctggaatc acattatgat tttaatttcc   54360
attccttaaa gtaccttgg  ctctgaagtt taatgattca tgcatctctt cccttttgaa   54420
gtactcttac aggtatgttg tgcatgtgtt gaaaagtggc actatctatt ctaaaataca   54480
gtatgcctcc tctgtgtttg aacagttgta gcgtggcctt ggggcctcct gttagctggc   54540
ttggagaagg gattcttggg attgtagaga ttagacctga ggaggcccct tggagctctc   54600
tgactaaatt ttattctttta ttattccaaa ctatttaagc tcaccgtgtg ctgactcatc   54660
ataataatga gtagctctca ttgtgcttgt ctatttggac tcatacaatg attttttttt   54720
tttctttgag acagagtctt gctctgttgc ctaggctgga gtgcagtggc acaatctcgg   54780
ctcactgcag cctccacctc ccaggttcaa gtgattcttg tgcctcagct tctcaagtag   54840
ctgagactgc aggtgcgtac caccatgcct ggctaatgtt tgtatttta  gtagagacgg   54900 ggtttcacca tgttggccag gttggtctca aactcctgac ctcaagtgat ctgccttctt   54960
cagcctccca aagtgctggg attacaggtg tgagccactg agcttggcca aagtagtttt   55020
ttaagatgtt agtatctttt cttgcagcta aaaaagtttg tcagagatga ttctactttg   55080
ttctccaggt gttttctcag ggagaaattg gaggcagtaa gccactgggg gagtcctgtg   55140 gctgggggt  gggtagtcc  tgtggctcct tgtcagggag tcctgtggct ggcaaggaga   55200
gaagtcctgt ggctgggttg ggagggagtc ctgtggctgg ggtctcatcc tgtgcctaac   55260
agtgtccaga ggtgccgaga ccagctcagt cggggagacc ctaacccagc agcgctagag   55320
gaattaaaga cacacacaca gaaatataga ggtgtgaagt gggaaatcag gggtctcaca   55380
gcctttagag ctgagagccc tgaacagaga tttacccaca tatttattaa tagcaaacca   55440
gtcattagca ttgtttctat agatgttaaa ttaactaaaa gtatcccctta tgggaaacga   55500 ggggatgggc cgaattaaaa gaagaggttg ggctagttaa ccgcagcagg agcatgtcct   55560
taaggcacag atcgctcatg ctattgtttg tggcttaaga atgcctttaa gcggttttcc   55620
accctgggtg ggccaggtgt tccttgccct cattcctgtc aacccacaac cttccagtgt   55680
gggcattagg gccattatga acatgttaca gtgcttcaga gattttgttt atggccagtt   55740
ttggggccag tttatggcca gattttgggg ggcctgctcc caatacagag gtctcgtgta   55800
aattccctgg gaggcgataa gcctctgaga aacagactat gctaaccacg ccatgaaaga   55860
gaaacttatt tataaatcag atgccagtta ctagtttact gcttatttgc ccaggcgtag   55920
ctctgacaga gtccccgact catagtgctt gctcagtgca tgctgaacaa tgattggaat   55980
caagtcatgg ctcagagcat agttttgaat aatgggaaat ggatgttctt aagtaacata   56040
gtcaccaaga taatgcgact agctgggtca ccccttttca attttaggat attttttatca   56100 agatttaaat ggccatcatt agagttatag cactttctcc tttggattgt cctagaggcc   56160
catgagaaag tattccctaa tttcttagga gaacagtttg tgggtagtat gcggtcatgt   56220
ccagttaaat tgcagatatt tccgatcgaa gatgttccag tcctgagaac ttcgtgacat   56280
tagcaggact tctacaagcc atctcttagg gtggggcatt tactgcagtt ggctagtact   56340
cttttctcct taactttgtc atttgttgat ttttttttaa ctgtccccaa atactgtggg   56400
cagagtgtat ctagaattga ggcctccacc attgcggaga ggacatggat gctgagcagt   56460
cccctgagtg aaggttataa agaagcaaat agactacaca tgtctgtaaa ctgctcttga   56520
gtgtcccaaa tttggggtac ttcagttcag ctgtaggaaa agcctcaaac tgtttatact   56580
```

```
ttgcaagaat tggaaacttc taattcacgt taagttttat gtaatacatg ataagcttca    56640
taggagcttc atcttttatc tacttggact tttgcttccg taggttttgt taaaggcctt    56700
catagcgaac ctgaagtcaa gctcccccac cattcggcgg acagcggctg gatcagcagt    56760
gagcatctgc cagcactcaa gaaggacaca atatttctat agttggctac taaatgtgct    56820
cttaggtaag gtggaggcat atgagtggaa gagtctccag catgtactca agatagacct    56880
ttgaaataaa taaaaccaga tgatccctca gcttctagac caggctattt ggcactggtt    56940
gattgaatgt gaactgcact ggggctgctg tgagcccgca tgggtctctg tgaccctgca    57000
gatgcagccg tgcccaggga ctgggcagtg ggtgtgggct ggtgtgagcc ctgtctgcca    57060
cccagggcct ggccctctgt ctgtgtcggc catgactatg gtgagtcttg taggcttgag    57120
actgtgcctc gggttcctgc gggttctctg taggtcagtt gacagtttct cctgttgttt    57180
gggtaactgt ggaaacgaac actggcaagt gctgaagcga gcatgtggac gtgcgatatg    57240
aaataacgac ctggctttca aaggcagtga ggctctctgg aaaggacctt gctgagctag    57300
ggatgtgggt gtgtagccat tcccagtggg cctcatggcg tactcgttca tgatcatgtt    57360
tgtgccatct tgatctctca ggatctcttc ttttttaaca gattaagccg ggaatctcca    57420
aacagtgagt cagatgttaa gatgtcttgc ttccaccccc acaggcttac tcgttcctgt    57480
cgaggatgaa cactccactc tgctgattct tggcgtgctg ctcaccctga ggtatttggt    57540
gcccttgctg cagcagcagg tcaaggacac aagcctgaaa ggcagcttcg gagtgacaag    57600
gaaagaaatg gaagtctctc cttctgcaga gcagcttgtc caggtaggag cacagggttt    57660
actctaggcc ctgcatgtga atgactgaca ttcaaagaac cgattaattt ggaagagaag    57720
cggcagaacc gagagttaga ggtgtggact ctggagctgc gctgctcgtt tccaacccta    57780
ggtgctgacc tctagctgtc ttccctctgt atgtccctgt caccgtgagt caaatgcggg    57840
tgatgcctcc tcaggtgccg tgttacctaa gcctctcaga gaccactgct accctgtttc    57900
taaaaccaga ggtcacgata tgtgttcatc cacccagtaa atactgattg agcacccact    57960
gtgtgctagg ctctgggata ggggctgggt atacaatggt gagtatttca gctgcagctt    58020
ctgccccgtg gaggctgtgg cctagcacac tggtctaggc acggtggtat atgctcactc    58080
aaggagatag ggacgtggtc gtttggggtg tcggaacaaa atgtcggaac ttctctttcc    58140
aatgcagaga aaccttgcag taattctaat gtactgtgat tggcagttga cttcagttct    58200
ttgtagcacg cttactcagg ttatttcact aactatgtaa ccatgcagcc tcattttaag    58260
caattggatt ttttgaactt tacttaaaat gttatgtcag ggttttttatt gtgcttaatg    58320
tgtgccattt agctaagttt tgtaggatac gaaattgtaa gtggcttaaa atgattctta    58380
atagaatcat gaattgaaga taatgctaat aatttaagca ctgagttagg tagtgtttgt    58440
aaaatgctta gaatgcttcc tggcacatgt taaggccatg taagtgctgc gtgttgataa    58500
acagctgagc aaaagtggac tcttaagaaa gtattgggc tgagagttct gttccaacca    58560
gctgcccttt ggttattttt cagaataaaa gcagagtctc atgggatatg acatttatat    58620
ttccttcaca aaaaacactg ctgagtgttt tgttgagtaa aaagggtgta gccatggtaa    58680
taatacattt aaaatatagt ttatttcatc tttaccttgc cttgtttttt ttttaagcta    58740
gctttttatt gagaattcca cacatacaaa agtatcaact catgaccagt tatatttcat    58800
ttataatcct acttctcct ttttttatta tttgaaagca aacccaatt atcctcttat    58860
ttcatctata agtatttcag tatctctata gatgaggact cttctttatt tttaaaactt    58920
tatttttaaa atgatggtca gatgcagtgt tcatgcctgt aatcccagaa ctttgggagg    58980
```

```
ccaagctggg cggatcactt gaacctggga gtttgagacc agcccgggaa acatggcgaa    59040
accccatgtc ttaaagaaaa aaatcagcca agtgtggtga tgcatgcctg tagtcccagc    59100
tacttgggag gctgagatgg gagggtcaca tgagcctgga agatcaaggc tgcagtgatc    59160
catgattgta ccactgcact ccatcctggg tgatggagca agattctgtc tcaaaaaaac    59220
aaaactgcaa aacaacgtca caaaacagtg ccattgttag acctgaaaat attaaacatt    59280
tcctacatca aatacccacc aactcattat caattttttct ctctactctt ttggaatcag    59340
catctaaata aaattggtcg ataaggattg taaatctctt tgatgaactg gttccctcc     59400 atcccagttt ttttcccctta gagttcattt attgagaaac cagattgttt gtcttctaag    59460
ttttcctgtg gtctgatata ctgcttccat ctccactgtg taaattaaca ccttttttctc    59520 ttctctgtat ttcctgtaaa tcaataattg gaggaaaagc cttgtcagat ttagtgtata    59580
ttttatatct gagtccagta tttcttatat aatattttaa gataagtgta ctcttttaaa    59640
aagtattgaa actatatgct caattttttt taactgatgc ttttaagaag gctgcttgat    59700
cataaaagtt tagagatcat tggtctgatg ggaaaagcaa ataattacta aaccgtttag    59760
caaggttgag gtgcacatgg tggggcctgg agaagttcag tcatgagccg tcacttatgg    59820
gcacgtggaa tctgacccgg cacagagttg ggagaagaca ggagctttat agacagaaaa    59880
tgtggtcttt gctaagtccc aggagtgaaa gggtgagaca gtgctcacag cacacgagtg    59940
tgggtgcgta gacagagcaa gggtgggtcc tgaaaaggcc tgcaggcttt ctcatagatt    60000
agcaagagtg ctggttacgg aggtttctaa catttgtgaa cagatcgaaa ctgtgttaaa    60060
ttgggattgc agtaatcctg gaaggacagg gatagagggt gaaggggaaa aagggtatg     60120 gatgtgagac ttaattgctg attttcttaa gacctttctc caaagtaaat aaatgatgtg    60180
gcacattttt gaactggcaa attctaaact ctagatatga ttatctctat aacatatctt    60240
actccatctt cttttgacta aaaactgttc ttaattaaat taccatgaga cgttcaattc    60300
agcaaatgta gtttggctaa ccatatttaa ttagaattta atataatcct aggcctggcc    60360
aaactattaa gcaagtgtgg gcaaaatatt gataattta gatatgcagg aacttagttt      60420
gctttccatg tgtgctttc gaaaaaggaa taaattgaaa aatagaggaa gccctgaaat      60480
ccaagaagca aactctctca cctaggcatg cagtaaaagc aattctagga tgattgctgt    60540
ttggcgcgta gttcgtatta gaaaccattc ttccttgaata aatagtatgt ttaagaagct    60600
gggcagaggg aaggcatatg catatattat caacaaggag ggagaaaaag gcaattagta    60660
accatccata ggagggtcag caagatttat aaaggaaatt tgtgatccaa gtatgaagca    60720
aaataaggtg cagaataaat tttaagcaag taatagatta gagtaagaga acccatttga    60780
ccattaacct tgggacattc tctttcaaat gacatggagt agtactgaaa tctttctttc    60840
tttctgagtc taggttattg tgactggact cagaaagaaa tatttcatta ttgcagtgaa    60900
taacatttgt gaacattatt gttcataaat tatgcagtga ataacattta tgaacacgtg    60960
atgtgtaaga tacatactgt ttattttag ttaagttttt tggctcaact tctaggcaga     61020
gaacattaaa tgtaaatagt gttacctagg agcatgtaaa tggaaatctc catagtatga    61080
aagcagtgct gttgctaaca gaattaggga gggggcagat gaggtgaagg aaatgtgggt    61140
gctgatttcc ttattacatt gagaggagcc aggagattct tgttcaaaa tggatggctt     61200 aagaagtcaa agtataagct gattacgtag agcaggtacc caaaaatgtt ttgtgtaagg    61260
ggccagatag taaatatttt cagtcttgca ggccatccca agtctgtggc agctactcaa    61320
```

```
cactacctttt gtagcatgaa agcagccaca ggcagcccat aaatgtggct ctgttccggt    61380
gaaactttag gtacaaaagc aggtgcaggc cagacctgac ctgtgcactg tggtttgctg    61440
acctgggatt cagggtata gaagttacca tcagaagagc taaaagtgag acttttact     61500 ttatactctt ctacactgtc tgattttgaa aaaagaaac atgtatttta taatattaaa    61560
gatagggttg gcaaatagca aataaaaata cagaatacca gtgaaatttg aacttcagat    61620
acattatgag taattttatg gtgtaagtat attccaaatc atgtgggaca tacttacact    61680
acaaaattat ttgttgtttg tttacagttt aaatttgagt gccttgtatt ttatctggca    61740
actgtaatta aagggaaaaa gaataaaattc attatgttca tataatgtga tatagcaggg    61800
gtccccaacc cccaggctgc agagtggtac tggtccatgg gtccccaacc cccaggctgc    61860
agagcggtat tggtccatgg cctgttagga accaggctgc ccagcaggaa gtgagcagca    61920
ggtgagctgg cattcccacc tgagcaccgc ctcctgtcag atcagtggca gcattagatt    61980
cccataggag tgcaaaccct attgtgaact gcacatgtga ggggtctagg ttgtgcgctc    62040
cttatgagaa tctaatgcct gatgatctga ggtggaacag tctcgtcttg aaaccatccc    62100
ctggccctgt ggaaaaattg tctcccatga aaccagtctc tggtgccaga aaggttgggt    62160
agcactgtga tatagtatta aaagtgctaa taaatatggc atactgcctt taaaatgtct    62220
ggtagctctt tctcagtggc actcataata gtgttttttg atttttaaat gtgtgtcaag    62280
ctgactctcc cctccgtgta tgctgggctt tattttccct ttcctagtca ccagttttgg    62340
gaaatagaga tcttcattct catgctgctc ctctagtgca agtgctccat ttattttaa     62400 ggaattaata taacaaaaaa tcatgggaat ttagaaaaca acatggaagc taatgatcac    62460
attggtggaa gtgatagga aatatttagg gggagaagtt aaggtataaa ctttgtcaat    62520
gaagtcctat taaaaacaac aaaaaagtga agcttaggat gcattttata aactctgacc    62580
agaacacctg tgtttctctg tttctaggtt tatgaactga cgttacatca tacacagcac    62640
caagaccaca atgttgtgac cggagccctg gagctgttgc agcagctctt cagaacgcct    62700
ccacccgagc ttctgcaaac cctgaccgca gtcgggggca ttgggcagct caccgctgct    62760
aaggaggagt ctggtggccg aagccgtagt gggagtattg tggaacttat aggcaagtta    62820
ttagcaaggt ctactcttac aattaacttt gcagtaatac tagttacact ctattgatta    62880
tgggcctgcc ctgtgctaag cagtctgcat tccatcttcc ttgccaaaac ttataataca    62940
aatttcatct ttattttata aatagggag ttgggctggg tgtggtggct cacgcctgta    63000
atttcagcac tttggaagga tcgcttcagc ccaggagttt gagacaacct ggccaagtga    63060
gaccctgtct ctacaaaaaa aaaaaaaaa aaaaaattag ctgggcatgg tggcacatgc    63120
ctgtagtccc agctgctttg gaggctgagg tggtaggatt gcttaagccc aagaggttga    63180
ggctgcagtg aatcttgatg gcagctgcac tgagcctggt gacagagcaa gatgctgtct    63240
caaaataaat ttaaaaataa aataagagaa ttaaagttta gcaggttggg tggcaaaatg    63300
aggccacaca tttaaagccc ctcctcctga ttcttttctc tgccttggct gcctcctgtg    63360 gcatttagg tgctgagaaa tgaaaacagt agggaaaata gttccaggat cctcatgtta    63420
atttgccaga aatggcatct tcaagtcgtc agagggatct gagagttcct tcctggcctg    63480
acttgagaaa atccgtctgt cccagctct gcgtctgcct ccactgccca gtcacctcct    63540
ctccatgctc ttggggctgg gccctacccc accatgcagt gctgccctgg agcagtgagc    63600
ttggtgggtc ctgtctggca tgagagctgc ctttgggagc tggatcccag cctctaccac    63660
tgggtctggt gcctagcagg ctatggataa acttctgctg actccggcct ctcctaagcc    63720
```

```
actgcaacgt ggtcggtgta gtgcacagtg tgtgtgcagc gtggccttac tcacagcctc   63780
cacattagag agaatctgac tgaagtctta ctgctgcctc gtgtgaacat aaatgtttgc   63840
cagaaccatg agcaggaaat gttaatctgc cttgtttcct gtcctttaca cggaagaatt   63900
tttttctgta tggaatgcgt gccttacaaa taatgagtgg aaatacccat cgctaatgaa   63960
aagttatact tgactgttag tcagctaaat aatctgagat ttctaatact tttaatttgg   64020
cttttacaat gcaatttatc ttagcttttt tgatttctta ggtcatatct ttagaactat   64080
atatttgaat gttaatgtaa ttttcatatt gaattaaaa tgttgaactg cgatgttaag    64140
tgtttcctgt ggaaaaacgt tcacatttc tctagtttta aagttgaatc aagctgtttg    64200
aagattttca catttcttct agattttatc agcttgttac tttatctgtc actttctgtg   64260
atttgcagct ggagggggtt cctcatgcag ccctgtcctt tcaagaaaac aaaaggtga    64320 ttatttcaga aatcagagtc ttgtgttgaa tcttactgat tttcttgtat ttctgtaatg   64380
taatgtatct tgtatttctt gtaatactgt attggactct gtgtatatct cttctcagat   64440
gagtgattat atgtgtgaat gttgctggaa tctgataacc aggcctgaat agttttgtag   64500
ggtggctttt aaaaattact ttcatatcag aattgctttg tcataaattt tgaacgcatc   64560
ataaatttct aatgttcggg gtcagcagac tttttttgta aagggacaga gtgtaaacat   64620
cttagcttta tgggccatat ggtctctttt gcaacattca gctctgccct gtgacaggaa   64680
tgcagttgta aagacatgag ctactggcca gctatgttcc agtagaactt tacttacaga   64740
aacagacagg ctgtagtttg ccaatacctg ccttagggaa tgtgttgtta tattttgtga   64800
gttaccttct cagtaaattt tatttagtat tagtcaggaa tattattaag tagcttcttt    64860
tccagcctgg tcaacatagt gagacccggt ctctaccaaa acaaaacaaa acaaaaaaac   64920
agccacgcat gtggcatgtg cctgtagcct cagctgctgc tcagggggct gaggcaagag   64980
gattgtttga gcccaggagt ttgaggtcac agtgagctgt agtcatgcca ctgcactcca   65040
gcctaggcaa cagaatgaga ccttgtgtct taaaaaaaaa aagtttcctt tgttgggtta   65100
ttttaatttg gacctggtta tcattttca gccatattta actttgtaca tatcagaatg   65160
ttctgataaa acttaacttt tattaaagtg tttgtgtat aatctgctag ttttggtaca    65220
cattatcttt tgcaatgcca gttatttct tttccagtgt gggtttgcat aggaaaagaa    65280
ttgctgtcac tttctatttt gaaatcttaa aagactgatc cttttttgtg tcatgatttg   65340
agtatttaat tgagagccta atgcctaata ttatttgcag tattaaatgg gatcttaaca   65400
ggaatagcat tctagccttc attgaattaa gtaaacattt cttaagagaa cttggaatct   65460
ataatatttg cgtcatcata gtatgagata cttaatcaag tttgagattt tagtgaaaca   65520
ttgtttagaa gccaaaagga ttctaggaaa aattaatgtc tatattcttg aattaggaga   65580
gattttggga cgtgtgacta agttacgctg acacttgttt gtttcttagt cgcttttcc    65640 agtggcggtg agaacgaaga tgactgattc acattgctca gatgagttta tcctcttctg   65700
gctgggacat gggatatatc ctgtctcttt taagccttt tggtatttt ccccccattga    65760 gagctgtgtc ttcaaactct tctgttatag ctggaaaatc cttttaagt gaaatctgcc    65820 caaattataa gacagatgaa ggtagagttg tgttggatat aggattaggg tgaaagtagt   65880
gggggtgtcc tggagcctct cttctggtgg cagcctagct cttgtgcctt tgaggaaatt   65940
accctgggga cggctctgtg gaacatattt gcaaaccact gatttggaag atagagatgg   66000
cttttgttaa gatctgaatt cacctttttg gcattttatt tgatttctca aggtaaagaa   66060
```

```
cttattttgt aataaagttt cctattattt agtagatagg ccaagttgct gtgttaattc    66120
catgtagatt tgggtttcc tttgctcatt ttttcactct taatctcaca tcattgtaag    66180
tttatggaag ttatcatact tctgactttt tctttgaaga gcagaaatta gaaattccca    66240
ataattattt tgatagtgtc atttaatgac actcacatgt gatgtagcca caaagattta    66300
atgagttcag ttttaaatca tattaagact gttggtttca tttgttctca ttaatgtaat    66360
tctgaagatg aacaataaaa tgtatttta gaactttcaa atgaaatatt atttcatcct    66420
tccagatcat ataatgctta agttctgatt gttaatcata aagtctagaa aattaaaaga    66480
taataaaatg aaagtgactt ttaggtatta gagttttatt ataaattctg gtgtgtcatt    66540
ggagctatga catgaatatt tcaaaggcca atagcattgg atctttacag ttataactta    66600
ccatttttaa gtttaagtag taatatagat tatttaataa tcaaaatcaa taaatattaa    66660
ttattaaaat gttttgtggt atagtttgag aatcattgct tttaactttt tccatatagg    66720
tttattgact ttaatagcat tctaaacata acatctctac attctttgtg tttaatactg    66780
tggaggtata aaaatactta tatatgatga taaactatat tagagtaaat taaatattct    66840
tatgagtttc attttagagt gcatttactt aattttgaag tccttatttt tagcaaacta    66900
aaaggaatgt tggtacatta tttactaggc aaagtgctct taggagaaga agaagccttg    66960
gaggatgact ctgaatcgag atcggatgtc agcagctctg ccttaacagg tagttctcac    67020
tagttagccg ctggtgtgga ccttcactgt ctgccttcca cccctgccc ttcctgctcg    67080 tcccctgca cctggtggac agcacgactg ggggcagcag tggagccagg ttgcttaaat    67140
ggggcatatt cgggcttctt ttataatact tactctgaag cttgtgtgtc tgtggtgttt    67200
gcatcatata tttgttgttt tccatggttt aggctgtttt aaaattaggt ttatggcttg    67260
agcatagggc tttgtgagta ggggatggca ggtcgaaaca tctcatgagt tggatgggtt    67320
atgctggggg ttgggaaatg ggatgaaaaa ttatgggatg aaaaattgcc tatggatagt    67380
ttaacttgaa agaatctgcc tttgtttaca gatagttatc tttttctttt ttgagatag    67440 agtctcacac tgtcacccag tgcagatacc cagtgtcact ggagtgcagt ggtgtgctct    67500
tggtgcactg cagcctccgc cttctgggtt ccagcgattc tcctgcctca gcctcccaag    67560
tagctgggac tacaggtgcc cgccaccacg cttggctaat ttttgtattt ttttgtggag    67620
acggtttttt gccatgttgg tcaggctggt cttgaactcc tgacctcaag tgatctgcct    67680
gcctcagcct cccacagtgc cgggattaca ggagtgagcc actgtgcccg gccagttaca    67740
gatacttatc taatgaaatt ctctgtgtac tttataaaag atgaggatta actgaaggta    67800
ctaataactg gattatatga gggtggtttt ggttgtataa tcctatctaa aagaatattt    67860
tagctataac tgaaagtaag acttaaatat ttagagagga aaatctgaat aattctagta    67920
gtaattattt atttacaaaa taaaaataga tttttttttg attacacaaa ttaaacaaca    67980
ataaaacatc acagcaatcc ggatactata aagctcacat gcttaccgac ccaactgccc    68040
caggagtgac cactgccaac agcttcatgt cgaccttttt gccataattt ttatatagcc    68100 tttttgttt ttaaatggta atttagaaag tcaactagga aaatgtgtta caggtttatc    68160
ttccaggaga ataggactgg agtcgagatc ttgaatgtgg cttggaagaa ggcaagccca    68220
ccccagagag atgagttgac agttgtttct gaccactgct tgcttagagg gcctgcgtgt    68280
ctgtgaccgc ctagctttgc gcccctgact aggctgcccc ttaattacaa atgtctttat    68340
atattgctcc agctaaggct tggagtagtc ggttaagaac ttgaacttcg gttttgcag    68400 tgaaacagca tttgagaata tcaccttctg ataagcctta ttttataagg tgggtactgt    68460
```

```
agtgggaggc agtgtgagag atgcttgaag gatgcactgc tgtcctgcat ttcagcatct   68520
tcaggatgct gtgcagctga acatttgat aacggtggaa ctgttcgtta ttttgcaagc   68580
ctgtgattcc ctattgaatg ttttctctcg ccatttgaca aatgagtgtt tctctgtctt   68640
cagcctcagt gaaggatgag atcagtggag agctggctgc ttcttcaggg gtttccactc   68700
cagggtcagc aggtcatgac atcatcacag aacagccacg gtcacagcac acactgcagg   68760
cggactcagt ggatctggcc agctgtgact tgacaagctc tgccactgat ggggatgagg   68820
aggatatctt gagccacagc tccagccagg tcagcgccgt cccatctgac cctgccatgg   68880
acctgaatga tgggacccag gcctcgtcgc ccatcagcga cagctcccag accaccaccg   68940
aagggcctga ttcagctgtt accccttcag acagttctga aattgtaagt gggcagaggg   69000
gcctgacatc ttttttttta tttttattt gagacagagt ctcactccat agtgcagtgg   69060
aggccgggca caggggctca tgcctgtaat cccagcactt gggagactg aggcaggcgg   69120
atcacttgag gtcaggagtt cgagaccagc ctggccaaca tggtgaaacc ctgtctctac   69180
taaaaataca aaaattagtt gggcgtggtg gcacatgtct gtagtcccag ctgttaggga   69240
ggctgaggca ggagaattgc ttgagcctgg gaggcagagg ttgcaatgag ccagatcgt   69300
gacactgcac tccagcccgg gcaacagagc aagactccat ttcaaaaaaa ataaaaaat   69360
aaagtgcagt ggctcgttct cagcccactg caacttctgc ctcccaggct cgagcgattc   69420
tcccgcctca gcctcctgag taggtgggat tacaggtggg caccaccaca ctcagctaat   69480
gtttgtattt tcagtagaga cagggtttca ccatgttggc caggctggtc tcaaactcct   69540
gaccttagat gatccaccca ccttggcctc ctaaagtatt gggattatag ttgtgagcca   69600
ccatgcccgg ccctgccacc tgccatcttt tgagttcttc cctggagacc tagacctgaa   69660
ccctcctgct tgttctcttg ttatctaata cccctattga cagcgcagct tagatcatta   69720
atggagagct tgacctcatc tgataccttc actgaaggaa acaacttagt gtcttttgtg   69780
ttgaacactg aggtaaaaaa ttggaatagt tgattatatg aactctgcta aaattgagtg   69840
cattttacat ttttttaaggc cttgttgggc cctggttaaa taattatttt taaaaatcct   69900
taaggagcct attataaaca gatctgtggt cttaatgaaa tgtgattaat actgtgcatt   69960
atttttaagaa cttttgactt tcaaaaaac ttttacaaca tttcccattt gatagcggca   70020
taggtttaag cacttctcat ctctaagtta gtggacaaaa aaccctcatg gatagtctaa   70080
taatgtttgc tacaagtcca tgttgagttt tatactccat tttatttttca gttttaaaaa   70140
ctgtggttaa atatgtgtaa cataaaattt atgttcttaa ccattttttg cgtatacagt   70200
tcgctggtat taaatacatt taaataatgt catggaatca ttgctaccac ccatctctgt   70260
aaccttttga tcatgtaaca ctgaagctct gttcccattg aactctattc ctcctttccc   70320
gccaagtccc tggcaaccac gattcttctt tctgtcttct gaatttgact actttgggtt   70380
ctcatatact ttaggagtca cacagtattt gttttactta gcataatgtc cccaaagctc   70440
atgcatgttg tagcctatgt tagaacttcc taatgtttca ggccaaatac tattccattg   70500
tatggatagg ccacattttg cttttccatt cctctgtcca tggacacttg tattgcttca   70560
tgttttagcc attgtgaatc atgctgttat gaacgtgggt gtacagatag ctcctggaga   70620
ctctgctttc cattttttg gctaaatacc cagaaatgga gttgcttta cattccaatt   70680
ttaatttaaa acattcatat cattgagtgt tttacttaat agtatagtag ttaacaaact   70740
taataaaata gtattttggt aataaatttgc tggtagtcca ttgttcagtt ttttaggta   70800
```

```
aattacacag gacatttcaa gtggacatga aacatcttgt gatgtggaat catgccccaa    70860
gctgatggct aaacatatga aataccatac cctaaattta gtagatttag tctttgcaat    70920
ttaggagata acctgttata ttgttaggtt tttgtcgaaa agctttgtcc tcatatttcc    70980
aacttgctgt aaaatttgtt tgtgaagaca aatattttg tatgggtttt ttcttttca     71040 tattaaaaag aaatgtccac attggaattt ttttggagtt tttagagcta atagagcttt    71100
tcataatgta gtgggaatga gtgatcagta agctcttagc agtttccatg cgtgcatttc    71160
tgtgccttga aataaatgac agatgagtac atttgtgttc tgtgtgtaaa atgtgctctt    71220
tcctcattgc acttccatgt tggagggctt gtctcttggt gatcacactt caaaattctc    71280
acagcccccc ttgaaccgtt taggtgttag acggtaccga caaccagtat ttgggcctgc    71340
agattggaca gccccaggat gaagatgagg aagccacagg tattcttcct gatgaagcct    71400
cggaggcctt caggaactct tccatgggta tgtggactac aggtgatgcg ctacaaagtg    71460
gtttgtattc agacctggac atcttaatta tatctttgct tccaagaaga agtcctttga    71520
tactgttttc tgagttctga atagctgatg aaaatgacca attgaggaat aatcatactt    71580
tttcttgatc taaatcttat acttttgagt tatcttagca taaatgtata attgtatttt    71640
aagtggaaat ttgtcactta atcttgattt ctctgttttt aaagcccttc aacaggcaca    71700
tttattgaaa aacatgagtc actgcaggca gccttctgac agcagtgttg ataaatttgt    71760
gttgagagat gaagctactg aaccgggtga tcaagaaaac aaggtgaggg acataggctt    71820
gagacgactt ggtgtttctg agcttgtgtg aggatttaaa atcgccctgg ctactgtcta    71880
ctttattgct ttcccatccc tgggccttta aatttcccct ttaaatacca gctcttccca    71940
ggcctgttgt tttctgcctt tccaggtact acccacagcc ttgagaattg cctgagttct    72000
gcctcctttg agagtgtgcc ccagacaaat ctattctgta ctgaatgttt ccttgtctga    72060
tttcttggat cattcatttg atggttgcgt atggcctgca acgtttcttg ttttggttct    72120
actgaactgt tctaaaagtc tctcttcata ttatcttttt acatgtaaat gtaactgtct    72180
tcacttttaa ttcctcaagg acaaggaata gcgtttcaca gttcgtccca tcaatcagaa    72240
ttatagcctt tggcatctcc ctatctacca ggcccacttc ctcttagatt tgggcttccc    72300
caggctgttg cctttcccca gtagcttct gcttgtcctg tagaagacct ttcatgcttt     72360
gcttctgcag cagccgttcc tgaatgccta gtgtcaactg ccttcttacc acgcccaccc    72420
tccctgcatg ctgcatttat cccctgccac agccctgtga ccctgtgtcc tgctgcctct    72480
gacttgtctg tttctgcttg gccatggtct ctgtgaggtc aggtgtgcat atgggcacaa    72540
accagggcat ctctttatcc ccagcacctg gcttaagtgc tgctctggaa ctatctgttg    72600
aatgaactaa tgcatgaatg tattgttgag tatgagacaa acaagtgtca ttgtctcctt    72660
tctagccttg ccgcatcaaa ggtgacattg gacagtccac tgatgatgac tctgcacctc    72720
ttgtccattg tgtccgcctt ttatctgctt cgttttgct aacaggggga aaaaatggtg      72780
agtacaaaag gggatgtgca cagttgaagg aaataactag gtttcagagg tcagcttggt    72840
ggcctgtttt tgccttgcgt gcagcagagg aagtagaatc tgaggatgag tttggttttc    72900
actagccgag gggagggagg aaatgatggg agcaggtagg ttattgggtc tggttttgtt    72960
catttgaaaa caatctgttg tttgaggctg aaggtggctt gggtgatttc ttggcagtgc    73020
tggttccgga cagggatgtg agggtcagcg tgaaggccct ggccctcagc tgtgtgggag    73080
cagctgtggc cctccacccg gaatctttct tcagcaaact ctataaagtt cctcttgaca    73140
ccacggaata ccctggtatg ttaaaagttc acatcttatt ttctcagatt taatcattat    73200
```

-continued

```
tgtaaaaact atttcagtat tgactatttt agttttagag cagtaagtgt tttgagttca    73260
tttgggatat ttgacctgcg ttgtagctct tcagaaaaca catgaatagt gaagttcttt    73320
gtttcatggg ttcccttag atgaaaccca tagaggagaa agtagaaac ctcagcacgt      73380 aagagccaac atatatacac atcggattta aacctaaagc acaaattgtg cctggtcgca    73440
gtggcgctga gtcgcactca gccaggccag gcattcacac tcagggtgag tgggaaccag    73500
gactggctga ggcagcagtg gacccaagtc tccatcgcgc ccatgcttac tatggagcct    73560
tctcgttctc tcttttctt tgggtgagag ggtacacttg tgtttttgaa tttatatgag    73620
gtaagtgtgt aatagggttt tttctaatct tttttaagtg gaatctggaa ttttaatcag    73680
atttattatc tgcaaccta gaattataat ccagaaagtc tgtggtattg aggacatatt    73740
ggcaatatga tgaatctcta attcttaaat cctgaaactt ttttttttt aatcacttag     73800 ggttattata gtgaagtcat ttctgaattt ggatcttctc ttcacacctc tttttctctt    73860
tcctgagaat taagcttttg tttcgagtta gaaagttgat agtagggaat tgttccatgg    73920
ctgagcaatt tatctccaca gaggaacagt atgtctcaga catcttgaac tacatcgatc    73980
atggagaccc acaggttcga ggagccactg ccattctctg tgggaccctc atctgctcca    74040
tcctcagcag gtcccgcttc cacgtgggag attggatggg caccattaga accctcacag    74100
gtaacggcca gttttcagc tgtgtttttt ctagttatgc ttactaaggt ttaagtttag     74160
atgatgatgt ttgttgcttg ttcttctggt taggaaatac attttctttg gcggattgca    74220
ttcctttgct gcggaaaaca ctgaaggatg agtcttctgt tacttgcaag ttagcttgta    74280
cagctgtgag ggtgagcata atcttctgtg gaaccatttc ttcacttagt ggacatttta    74340
tcattgctac aattaaaatt ggagcttaat aggaaatatt tccatgcact ctaaagctgt    74400
aaccagtaat acccaccatg tatccatctc tcagctttag aaagaaaacg ttgccagtaa    74460
agttaatgct tcataaactt cagtttaagt tctaattctc agaatatttg tttgaaatag    74520
acctcttcct aaaggatata tttagaaata acctatcatt aagtgtaaag tctgttgaat    74580
atgctgggca cggtgactca cacctgtaat ctgaccactt tgggaggcca aggtggaagg    74640
attgcttgag cccaggagtt caagactatg ggcaacatag ttgaccctgt ccctacagaa    74700
aattaaaaaa aaaaaaaaaa aaagtagctg ggtatggtgg tgcatacctg tagtctcagc    74760
tactcgggaa gctgaggtgg aggggggatt gcttgagccc cagagatcaa ggctgcagta    74820
aggcgtggtt acaccactgc cctctagcct gggcaacaga gtgagactgt ctcaaaaata    74880
atagtaataa taatcagttg aattaaaaaa aaaaaaaaa aaaccactgt gctaggccca    74940
tagtatggta agagttaaag tgagccttag ggattattta ctcaacctct gtttctgtat    75000
aaagtggaat aggctcaatt ctttaagtga tagcatgttg aacctttcca taccaactgg    75060
ctcataagtc acaactggcc agtcaacaag agtaaaaatt aactggtaaa aatcaaagca    75120
aaaaacctac aattgtcaaa tttgtgggat aactcccct tttaaatgt catgcctgac       75180 agtaatttct ctctagtttc caggttttca gtcagttgtg tcttttttga gcagaaggaa    75240
gcatgctaag agctcaatct tgtggctagc tgggggtctt tgtgtcagcc atgcatgtga    75300
tggtgcccct gggtgcttgg ggctgcaggg gaggggtaca gcagtagggg cctgttctgt    75360
tctctcgtgc tgtggagtac atagtgacat agtggggtgg tccttggtgt aggtcccttg    75420
ttcctacccc tgggtctgag atttatttag aagtggtgtt ggggctgtgc ggcaggcccc    75480
tctgtaactg atcaatgttt gtgaagttgc tgtttgagag ttgaaaccat gacataagca    75540
```

```
gaaatggaag gaagaaagaa ccagttatgt gaaagggaca catttacttt taagcttgta    75600
tttactgaga taaagtattc ttaatcaatg ttcttgagag gtgtgggaaa aatgcaacat    75660
cctggttgca gttaaaccca gaacattgtg tgttgaagag tgacggttct caaaccgtca    75720
agacgcgggt actgagtggg actaacctgc tgtcctcttg ccttggacct tgtgttccag    75780
aactgtgtca tgagtctctg cagcagcagc tacagtgagt taggactgca gctgatcatc    75840
gatgtgctga ctctgaggaa cagttcctat tggctggtga ggacagagct tctgaaaacc    75900
cttgcagaga ttgacttcag gtaagtgagt cacatccatt agatttcatg aactaagctc    75960
aattgaaagt tctgggatca cttgatgcaa ggaatgatgt tatcaagtac cctgtccatc    76020
agaaatccga gtggtttagg tagatgacag tgattttctc ctcccagtgg cttttgctg     76080 aactttgccc tatgcttgga atttattttt atttattat ttatttagag acaagatctt     76140
gctctgtcgc ccaggcttga atgcagtagc acaatcatag ctcactgaag ctttgaactc    76200
taggactcaa gtggtcctcc tgcctcagcc tcccgattag ctaggagaat aggtgtgtgc    76260
cgtcacactg gctaatattt tttgtagaaa tggggtcttg ctatgttgcc caggctggtc    76320
tcaaactcct gggcttgatt gatcctccat cttggcctcc caaagtgctg ggattacagg    76380
catgagccac tgtgcctggc ctagaatttt aaaatataag tagaagagta gatttttttt    76440
tttggtagtc ctcgtcattt aagtattctg gatagtggga ataaaagagc ttagaatttt    76500
tcatctttgt cttaaacttt taaaaaaatg tagcttatat taattctgct tgtttaaaaa    76560
gaatatactc ttcattatac tgaacctagg taagacagct ggtttatatt ttgttgcaat    76620
taaaaaacgt gagctgtggt tgcagtgagc caagattgtg gccattgcac ttcagcctgg    76680
caacagagtg agacttggcc tcaaaaaaaa aaaataaca tgagctgtgt tggcactttc    76740
attttctaag agtagttttg gctggagaag ttttctttca gtactttctt ttagaaggga    76800
aattttcctt tataatttag ggtttgtttt ttttttttcc aagccacctt ttatagagcc    76860
cttgtgggtt atttcattta atccttagaa tgttataaaa tctgggcttg ttctcggctc    76920
cacccacaga tagggacgct gagcgtgcat gagtgggcag caagatagca ggttatggag    76980
ggcccagctc accccttctg tggcttgagc caatttttata gggcacttac agagtctttt    77040
gaaatagtat ttattttgaa gaaaaagaaa aacagtttac tgagtactgt cttattgagt    77100
ctggaattgt gagaggaatg ccacctctat ttatttaaag ccattggcct ttttgttgt    77160 tttgagtaag tgctgcccaa ggtccttcca gggcacctgg atgagcctgc tctggagcaa    77220
gctggcggta agtgtttact gagtaactaa atgatttcat tgttaaatgt gctcttttgt    77280
taggctggtg agcttttggg aggcaaaagc agaaaactta cacagagggg ctcatcatta    77340 tacagggta agcggtttat ttttgtgaga tgctgtttta ccttcaagaa ggtgaaagtg     77400
aggctttcct tgtggaattt ctctaaatgc attcgtcatg ttttagatgt ttatttcaca    77460
gtttatatca tgaaagttat aatcttgtca tatggattta agtctagtaa tgttgagttc    77520
tttctcacta gctttccaaa atatcttacc taaaatttag tcaaatacaa gattatgttt    77580 attttttatta tccttctctc taaagctttt aaaactgcaa gaacgagtgc tcaataatgt    77640
tgtcatccat ttgcttggag atgaagaccc cagggtgcga catgttgccg cagcatcact    77700
aattaggtat ttaccaatat tttatctctt ttccttttt ggttgaagta ctaaaagata     77760
cgagaatgga aagagaggga agaattcaaa ggatgtagag cagtattcct gaatctgagc    77820
tcatttcagc cattctattc ttaaactata atgaaaaaaa aatccaaaaa agtctaaaat    77880
tataattaaa aaaacaacaa aatactaact gtccattgta aaaagtaatg cactttcatt    77940
```

```
gtaaaaattt tggactatag agaatagtac taagaagaaa aaaaaaatca ccttcaattc    78000
tgctgccacc tggaggtaat cactgttaat attttgctat atactctatg agtttcttgt    78060
tcaaaatcag gtcaaaatta catgcaattt tgtaatctga caatttccac ttaatatttt    78120
attagcattt tcctgttatg aaacagtaat tttagttatg ggtcgttgtt ttgctatgcg    78180
gttgggataa aattttatat actttttttg gcaattactt attatacata aatgtttgtg    78240
tatagttttc ttttctgag aattcctgga agttgagtta ccaggccgg ctttgaattt     78300 ttttttttat tttttttttg agacagagtc ctgctctatt gtccaggtgc tatctcggct    78360
cactgcaacc tctgtctccc tggttcaagc gattctcctg cctcagcctc ccgagtagct    78420
gggattacag gggcacacca ccacgcccaa ttaattttg tattttagt agagacaggg       78480 tttcacgata ttggccaggc tggtctcgaa cttctgaccc cgtgatccac ctgcattggc    78540
ctcccaaagt gctgggatta caggcgtgag ccatggcgcc tggccaggct ttaaatttaa    78600
aacaaatctt ctaatagctt tatggaggtt ataatttaca tttcttgaaa tgtactcact    78660
ttgagtgtat agtaaactcc aattttatca catttctgtc accccaaatg tatccttgtg    78720
cccatttgct gtaacctccg gttcctgccc caactcctag gcagccactc atctattttc    78780
tgtcccttaa gatttgtgtt ttcgccaggc gctcatgcct gtaatcccag cactttggga    78840
ggccgaggtt ggtggatcac ttgaggtcag gagttcgaga ccagcctggc caacatggtg    78900
aaaccttgtc tctactaaaa atacaaaaat tagtcggatg tggtggcaca cgcctgtaat    78960
cccagctact cgggaggctg aggcaggaga atcacttgaa cctgggaggc ggaggttgca    79020
gtgagcagag atcgcgccac tgccttccaa cctgggcaac agagagagac tgtctcaaaa    79080
caaacaaaga tttgtatttt ctggacattt tatagtactg gggtcatagt atagatggac    79140
ttttgcattt ggcttctttt acttaattgt gagattggtt cttgttgtag catgtatcag    79200
tagtttgttc attttttatg gcgaaagtat tctattatat gaataatacc atattttatc    79260
tatccatcag atggatatta tagagttcat gttttggcta atttatgaat tatggtactg    79320
tgaacatttg cctgcaagat tttgtgtaga catgtcttca tttctcttga gtagatcacc    79380
tagaagtgga tttttaaata attttggtac ttactgtgaa actgctcttc aaaaacatac    79440
cattgttcct tccttccttc cttccttcct tccttccttc tttccttcct ccctcctcc    79500 ctccttccc tacttccctc tccctttccc tttcccttcc ccttttccct tccccttccc    79560
gcctgcctgc ctgcctgcct tccttccttc cttccttcgt ttctttctac atatacacat    79620 tttttttaaat ttcaatggtt tttggggtac aagtggttttt tggttacatg gctgaatttt     79680
ggttacatgg tgaagtctga gattttagta cacctgtcac ccgagtagtg taccttgtac    79740
ccaatatgta gttttttgtc cctcaccttc cagccttccg ccttgtgagt ctccaatgtc    79800
cattatacca cactgtatgc ccttgcgtac ccacagctca gctcccactt ctgagaacat    79860
atagcagaaa catgccaaag tatactccca ctaccagaat gtgattgtgc ctgattcttc    79920
tcaccagtac aaatatttca aaaaagtta aatatgtatc agttttttgg gcagaagttg     79980
atacttctct ttatttattt attttttttg agatagggtc tcattctatg atgcccaggc    80040
tggagtgtgg tggtgcgatc tcggctcact gcagtctctg cctcccaggt tcaagtgatt    80100
cccacgtcag cctcccagga agctggaatt acaggcgagg gccaccactg ccagctaatt    80160
tttgtatttt ttggtagaga tggggttcca ccatgttggc cagactggtc tcaagctcct    80220
gacctcaagt gatccacctg ccttggcctt ccaaagtgct gggattacag gcgtgagcta    80280
```

```
ccacacccgg ctgatatttc tttttaaaat aacttacctt cttttgaaag taatacatgt   80340
ttaatgaaca gaatttaagg aaaatataaa aaaacgaaat aatctttgta atcaaactac   80400
tgaaaagaaa accaaagtta cattttggtg catattcttt ttcattttca tcattgtaat   80460
ttgcatttct ttgattactt gtgagacact cctttcattt acttaatagg tttatatgac   80520
ttgcctattc agagattttg cagctttacc attttctgca aatgatagca acttcttttt   80580
gtttgtttgt ttgtggagac agagtctcgc tctgtcactc aggcaggaat gcagtggtgg   80640
aatcttggct cattgcaact attgcctcct gggttcaagc gattttcctg cctcagcctc   80700
ccaagtagct gggattacag gagtgtgcca ccatgcccgg ctaattttg tatctttagt   80760 agagatgggg ttttgccatg ttggccgggc tgatcttgaa ctcctggcct caagcggtcc   80820
ccctgtctcg gcctcccaaa gtgctgggat tacaggcgtg agccaccgta cccagccagt   80880
agttacttct tatattctag aaaaaattct actcatgatc aagtctccat gaggaaagag   80940
actttaattg aagatcatgg ggcttgcaga ccaatatgat aaaatagttc attgtttcta   81000
aaagtattac tgagtgttga tggcagatat gaacccttt gttttgtag aaaatgtta   81060 cccgtattct ccatttgaat tcagtttaga tttgttagga atcgcagctt aagctttgcc   81120
atctgggagt gtttgggaca gttttgcaga caaaattgca aaagtgccta aggaatgcag   81180
ctggcattca gacctgctct gtgctcagta ctctgtggac agacactgtt cagcacttgt   81240
tgatcagaag gtttagaaag agaactttca aagttggttt ttaattaaag catttaatag   81300
tgtaaataga aagggattaa attttatgac agacaaaaga aagtacagca cccagctggg   81360
cgtgggggct cacgcctgta atccagcact atggggggct gaggtgggtg gatcacgagg   81420
tcaggagttc aagagttcaa gaacagcctg gccaaggtga tgaaaccctg tctctactaa   81480
aactacaaaa attagccggg cgcggtggca ggcgcctgta atcccagcta ctcaggaggc   81540
tgaggcagga gaatcacttg aacctggacg gcagaggttg cagtgagcca agattgcacc   81600
attgtactcc ggcctgggcc acagagtgac attctgtctc aaaaaaaaaa aaaaagaaa   81660 aaagaaagt acagcaccca gttatgtccg agtgggtgca tgagagtgac cctgagattg   81720
gagacaacgc tgtcacgtgc ttgaagaacg ccacctgaga aagggggcga gaagtggtgt   81780
ccgctggtaa ccagaggtgt tggcttagcc atctgcaggg aggagggtgg tctatcacag   81840
gtgagtttca tctactttct taagcaaatt aaccttactt ttgtgttagg cttgtcccaa   81900
agctgtttta taaatgtgac caaggacaag ctgatccagt agtggccgtg caagagatc   81960 aaagcagtgt ttacctgaaa cttctcatgc atgagacgca gcctccatct catttctccg   82020
tcagcacaat aaccaggtat gctgacccag tggcatcttc acattgtcgg gaaaatgccc   82080
tttcctgatg ccttctctta ggctttaatt gaaacatttt tattttctag aaaaaagctt   82140
cagctcagga tgtttgagtg taggtcagtc ctttgatagg atattatcat tttgaggatt   82200
gaccacacca cctctgtatt taagctctgc cacaatcact cagctgtgac actgtaaatc   82260
tcttaatagt ttattacatt ccatgtgctg acagttgtat ttttgtttgt gacacttacg   82320
tattatctgt taaaacattt tcactttagt tgtgttacct ttaaagagga ttgtattcta   82380
tcatgcctgt tgatttttg gtgagcgggc tattaaagtc agtgttattt agggttatcc   82440
actagttcag tgatttgcga gattatcatt cacatttatt gtggagcttt tgaatatcgt   82500
gtcaaatggc cacatatatc ccattcttat ctgcttctta ggtgagtggg acacagtgct   82560
ttaatgaagc tataatcttc agaattctag cttgcagaga agattgcaga agtgataaga   82620
cttgtgcttt ttaattttgt cttttaaatg ttattttaaa aattggcttt atatgatact   82680
```

```
cttttttttct gctgagtaac agtgttttac aaaacttgga ctaaatgact tctaagctta    82740
aatgatcact tgatgctttt tttctgaatt aggaactcag cttatcaaat atcaaagtca    82800
taattcctga ataaataacg tcttttttca tgtaaagact gctttaaaaa acacatggaa    82860
ggctgggtgc ggtggctcac gcctgtaatc ctaacacttt gggaggccca ggtgggcagg    82920
tcgcttgagc tcaggggttc aagaccaccc agggcaacat ggcaaaaccc acctctactc    82980
aaatacaaaa aattagccag gcgtggtggc gggcccctgt aatcccagct actcgggagg    83040
ctgagggatg agaatcactt gagccccgga ggcagaggtt gcagtgagcc aagattgtgc    83100
cattgcactc ccagcttggg ctacagagtg agactctgtc tcaaaaaaag acacacacac    83160
aaacaaaaaa aacatggaga cattttttg gccaccttaa tatttcccct cagataattt    83220
cctttgttta aactcagaac tggcattttc tctcttggag aagattcagg acaaatactc    83280
ctttaagata agtagaagca gtgaaagagg atttgattat caggaatttg ataagcttag    83340
aataaattgt tgcttcttaa tgtcatttca gaagatgaat atttattaat agatgccaac    83400
tgagatatca ttaaaattga ttactaacta ctacttggaa aagtctccca gttccaaact    83460
tcagcaggcc tcttgacaat tcagctgtgg tcaattgggt cttgcgtgat agatacaatg    83520
accaattgtg cagcagagtg tgctgcttag ctgcctattc tgttagcatt catgtgttaa    83580
cttaaaatca taatctcctt agttttgttg agtgtctccg tggacaagac actgtgaggg    83640
atacaaaatc agattggctt tattcaaacc actggggtat tataattcat ttataattta    83700 ttttatttt tgccttttt ccatgtgttc taaaggaatt agagtttgta tataactata    83760
atgggggata gaaattgaca tgtgccatga agggaatgca aaaagtgcc gtgggagatg    83820 agaagtggag aaaggaattt cttttttctt ggaagcagga ataacttcat gaagcatgta    83880
tttcaactta aacagatagt aggcaacgct gtaagggag tatggctgca gcaaaagtgt    83940
tcggggcaga ctgggaggaa gggagggaat aaattcagcc attgttatgg aataatgatc    84000
aaaatttatt ttcagcccgt ttcacttaaa agttgagact gcttaacttt ttttaatctt    84060
taatcttaaa cttttaaatg ccatttgatc tttaaaaata tatgttttaa tagtgtattt    84120
taagtctcta tattttgtt attagaatat atagaggcta taacctacta ccaagcataa    84180
cagacgtcac tatggaaaat aacctttcaa gagttattgc agcagtttct catgaactaa    84240
tcacatcaac caccagagca ctcacagtaa gtctctttct tgatcggtct tactgacatt    84300
gtaatagttt ttggtagctt gtatggccag ttagttgtat ggtcatctta cggtgaggtg    84360
cttgtcttac agctcttact tatccatgag gcttgctaag aaattgtgct tctgtgaaaa    84420
gaatctcagc ttactccagg aatgtaaatg actatgtttt ttctgattat taaagtaata    84480
cacgcccaaa ataaaaaaat tcagccaatt taggaagaca caacaattaa aataagccag    84540
gcatggtggc tcatgcctgt aatcccagca ctttgggagg ccaaggttgg gggctcactt    84600
gaggtcagga gtcggatacc agcctggcca acgtggtgaa accccatctc tactaaaaat    84660
acaaaaatta gctgggcgtg gtggcgggcg cctgtaatcc cagctactca ggaggctgag    84720
gcaggagaat cgcttgaacc tgggaggtag aggttgcagt gagctgaggt caagccactg    84780
cactccagcc tgtgcaatag agcgagactc tgtctcaaaa aaaaaaaaaa aaaagaaaa    84840 gaaaaaagta aactactgtc acctgcattg gtaatgtatc agaagtttaa aatgtctaga    84900
ttataattaa ctcagtgacc tggtaatata tactaaggga aaaatattta taatttacat    84960
ttttacattt ttattttttt aattttatta ttttttttt gagacagagt tttgctcttg    85020
```

```
ttgcccaggc tggagtgcaa tggcatgatc tcagctcacc acaacctcca cctcccgggt    85080
tcaagcaatt ctcctgcctc agcctcctga gtagctggga ttacaggcat gcaccaccat    85140
gcccggctaa ttttgtattt ttagtagaga cagggtttct ccatgttggt caggctggtc    85200
tcaaactccc aacctcaggt gatccgccct cctcgacccc ccaaagtgct gggattacag    85260
gtgtgagcca ccatgcctgg ccttacattt ttataataag aatttatgtt gctgacatta    85320
gaaaagaacc ataatatcca agaatccaag aataattaaa ttatgtacat atgctagtat    85380
atagtgtgat gctttggaga attttttaaca atatggagat gtataatctg gattgtaata    85440
ttgagtgaaa aaaggcagaa tacaaacctg gtgggggtat agtcggattt cagttaagaa    85500
aaataatatt tacatatata catttctcac actggcagat aatcaccaag ataaattttg    85560
ggattgtgga tgattttttt cttctttata ttttcagat attctcaaat tttctaaaat    85620
gagcaagtat aacttttgtt atcagaaaaa aataatatac aaaagtaatg ttaatttgct    85680
ggtgaccagg ttaaaccttt ttattttat tttgagat ggaatctcac tctgttgccc    85740
aggctagagc acagtggcat gatcttggct cactgcagcc tccgcttcct gggttcaaat    85800
gattctctgg ccccagcctc ctgagtggct ggaattacag gcgtgtggca ccacacctgg    85860
ctaatttttg tattttagt agaggtaggg tttcaccagg ttggtcaggc tggtctcgaa    85920
ctcctgacct cgtgatccac ccacctcggc ctcccaaagt gctgggatta caggcgtgag    85980
ctactgcgcc cagccagacc ttttattt atttgacaaa agaaatactt ccatgttata    86040
gaagactaaa tattgtttgg gctgtctgca gtatggtctt cccttgattt gttcaaaata    86100
tcgtaaactt tgcttattta ttttattgt ggccgactgt gtcgggcact gttgtaggct    86160
tgggatggaa aaacaggatt cctgccctta gggtttctgc aggctggtca gggagacgat    86220
gtggtaagct ggagctcagc tcctaaggat gtgcaggggc agttgagagg cggaagggtg    86280
ggagatcatt ccagggtgtg ggcagcacag gaacctctct tcattgggat ataattgcca    86340
ttctgataac acgtgtttga ggtgtctaaa gtaggaagtt gtaccatggt gggacagata    86400
tcctgtggtt atcatacaca gatctcagtt ttcttctcat tgtttgtact ttttataaag    86460
ggtaacagga gatataattc aataaaacctt tgtggtgttt gggtgtgatt ttattgtttc    86520
tttcttctca gtttggatgc tgtgaagctt tgtgtcttct ttccactgcc ttcccagttt    86580
gcatttggag tttaggttgg cactgtgggt atgtattttc ctcagtatat attaatagtt    86640
gtctacaaca gtatgacata aacatagtta ttaggatgcc cttttctctt cttttaagt    86700 cttttatcaa tttggctttt tggaaaaata tctgatggaa tacttgtttc tgctatatta    86760
gctgtgtgag actagtgaca ggagctgtgg gaaatgaatg ccaaatgttc ttaggcattg    86820
atgggaattt cagggtgtgg tcttcaagtt catttaaggg aattttcata tgctggcaaa    86880
aggcttttct cattagcttg actctttcca aaattatttg ctgtgaatta aagtttagg    86940 aaccttttt cacttaattg tgacctagca tacgaaatgg tgatgattta ggaactactg    87000
ttcttgtatt aacagctttt atttaaaaat gattttcctc cagtagatgg ccctactagc    87060
atctgggaaa taatttcaag tcttctccag cattcaggaa taggctttca ttttgtgtat    87120
caattactga gaatgatttt ggtgactcac atcacatttg agaagtaaac ctgcagattt    87180
cttgtgtgtg tcagcaaatg accaactgat atttgcttga agtggattac attatctgct    87240
ctagaatgat tgctttccca ccttcctcac atacagactg agcagctacg gtttctaatc    87300
ataggtctgg cactagactt cacttctggg caacttggc attggagtaa aatgtattaa    87360
tttaaagaaa gttaaaaatc cgttcaagta aacatacagt tctaatactt tttacaattt    87420
```

```
aaaatataga tttaaatgat aaaataaaaa agaaaatatg ggtagacacc ataatcctcg   87480
tttctgcatc tgttcacaag gggttgatat ttatgagttc tattctccat atccattcta   87540
tgttctctta atgctcagtc agcacctcag gtggttggag ttcaatgctt ggtagtttga   87600
cttacactgt cttttctagg ggattgagcc ctgggtagtc ctgcttattt gaggttgcaa   87660
tttgtctttc aataacttt actacaagat atggcgtgtt aaaggatacc attggggaac    87720
caacataata atatcaggaa aactaaccac gtcagacctg ccccattgtg tatcaagtac   87780 actattttc catagtaata aagagttcac cccagccaat tctcttttat tttgtgcctg    87840
tttactcaat ggcattaaca tgcccaaatg tctgggtagc tgtctcatct ccagttcagc   87900
agaaccattg tcatatgccc tagtaaaagc attccttcat tggacactta ggccccaata   87960 cttcattca gatctactac ctgatttcat ttctcaaatg atttttatgg agctctgatt    88020
tataggaaag atgttagttg attaaaaata aaacaatttc tgagctggta taaaatgtat   88080
tgtgacatgc cttcctcttg gaattgcaag agaaaggaag actgttgttt gcttaaaaat   88140
tgtctataat ttgactttgc aaatgtctgc ttccagagtg cctccactga gtgcctcaga   88200
tgagtctagg aagagctgta ccgttgggat ggccacaatg attctgaccc tgctctcgtc   88260
agcttggttc ccattggatc tctcagccca tcaagatgct ttgattttgg ccggaaactt   88320
gcttgcaggt actggtactg agttgaaaca gggactccag gacttggatt ttgatttcct   88380 taggggaat ggggtggtg agcatatgag gggaaaatac tataaggtca ttgccagtga    88440
tggcttgtcc ctttagtcaa atttcagatg ttacctatat gcataaacac atgcagttgg   88500
cagctgttct gtgctgagta ttttaaagta gcctcttccc aatatagccc ctcagttaac   88560
tacaagtaaa ctcattttga atttcatttt aatgggcacc atatgccagt actccctcgg   88620
gcactgggat gttaagaaag tataatgtat ggacttcatt ctcaagttag ttttagatta   88680 gaggggata cacgtaaaca aaagtgcagt ggtcacacag agtggcccta atcactctcc    88740
ttgggcagat ttatgggctg gtaggaaaga gcacaacacg gagagggtgt agcaccttgg   88800
cgatgataat ggaggatgtg gccagcaagg aagacggagt ccattgaaat tgattttggg   88860
agaagttgcc aatctccatg aaagaattgg ggcctgtgct atttgcttca gggggctata   88920
ggagagtttc gtgaaaggga ctaaaagatg agtattttaa taagatcatt catccaactt   88980
gaacatgggc tggaggagaa ggtagggaga ctcaggagat taatgttgat gctaaggcaa   89040
gataatggct ttgggactgt agggaagaca ctgattgtaa gagaatgaag gaggcagaat   89100
tgccaggcct ggttccaccaa ctgaacttcg gttgtgaaga caaagaaacc tgggatgact   89160
tcacatcctg ggcaggtgtg tggtggtgac agtcatggaa attgggaaca cagatttgtg   89220
cgggaaacat cagtttcagt ttgagtttgg cttatcagtt gaatatcagg cacagatgtc   89280
tggccaactc tcaacatagg gtcttaaatg acttcagttc cccaagcaat ttgtccttcc   89340
catgctattg gggtggagag gtaatgtctg tgcccatatc acagccagtg ctcccaaatc   89400
tctgagaagt tcatgggcct ctgaagaaga agccaaccca gcagccacca agcaaggaga   89460
ggtctggcca gccctggggg accgggcct ggtgccatg gtggagcagc tcttctctca     89520
cctgctgaag gtgattaaca tttgtgccca cgtcctggat gacgtggctc ctggaccgc    89580 aataaggta atgtcccact tgggtgctgg attcatacag ccttaatgac tatgggtttc    89640
cagactacct ttgtttagta atctgtccct tctttattct ctttttgctt taaatgaaca   89700
aaattgctca gattgtgaca ctaaatttaa catcaaaatg tgaccatgtg gatgggtgca   89760
```

```
gtggctcgtg cctgttattc cagcactttg ggagactgag gcaagtggat cacttgaggc    89820
caagagttcg agaccagcct gggcaacatc acgaaacccc ctctctacta aaaatacaaa    89880
aaattagatg ggttgggccg ggcgtggtgg ctcaagcctg taatcccagc actttgggag    89940
gccgaggtgg gcggatcacg aggtcaagag atcaagacca tcctggctaa cacagtgaaa    90000
ccccgtctct actaaaaata caaaaaaatt atctgagcat ggtggcgggc gcctgtagtc    90060
ccagctgctc gggaggctga ggcaggagaa tggcgtgaat ccgggaggcg gagcttgcag    90120
tgagccgaga tcgtgccact gcactccagc ctgggtgaca gagcgagact ccgtctcaaa    90180
aaaaaaatta gatgggcatg gtggtgcgtg cctgtaatcc cagctacttg ggaggctgag    90240
gcaagagagt tgcttgaacc tgggaggcgg agtttgcagt aagccttgat tgtgccgctg    90300
cactccagcc tgggtgacag agtcagactc tttccaaaag aagaaaaaaa tgtgaccatg    90360
tgttttatag ctctttagt atcatcagtc actgttatcc ctaagaggga aatacctagc    90420
tttagtttta ggtttccagc attagccaag aaagctcaga attgatgttc ctggccaagt    90480
acctcattgc tgtctcctta aatcttggtt aatggctact gtcctggcta gcatagttat    90540
ggagcatttc catggttgta gaatgttctg ccaatctcag ggacagtttt gcttttctgt    90600
gaagcaataa aatcaacttc aaaacaaatg ttaactattt gtacaatgga tttaagatag    90660
accagttcac atactttttt tttttttttt ttttgagatg gagtttcatt cttgttgcct    90720
gggctggagt gcaatggtgt gatctcagct cactgcaact tctgcctcct gggttcaaac    90780
gattcttctg cctcagcctc tcgaggcaga ttacagctgg gattacaggc atgcaccacc    90840
acacccagct aatttttttg tagttttagt agagacgggg tttcaccatg ttggtcaggt    90900
tggtctcaaa ctcctgacct gaagtgatct atccgcttcg gcctcccaaa gtgttgggat    90960
tacgggcatg agccaccacg cccagcctaa gatagaccag ttcacttact gtttatatct    91020
gattactctc tctttgcctt gtcttctacc tttaaaaatc tccctactaa cttcccattc    91080
tcctttagct gccatcagtc ttctcccttc tctgcaaaca tctctggaga gtcccagcct    91140
cagcccacag agcttcccac tgctctgagg tggaccttgt ttgcaaggct tctttggctc    91200
tcttggcctg gaccctgtct actacttcag ccatccttcc ttaacccctg ctggtggttt    91260
ctgttgccac actccatagc agcgtttccc gcccagatca tgtctttaca tctctgggca    91320
ctgctctggt cctgcctgcc tttccctctt tgtatcctgc aggctgctac ccccatcttg    91380
agtgtcctct tcagttggct ttcagagggc ctcctgggtg ttcccttacc cacttgccac    91440
tccccagtca ctgggttcag tccttcctgc ccaccagcac atgctttcta ggctctgtcc    91500
taggccgtct tctctctttg tagtctctgg gccagtgctg ttctagagag tggcagaatt    91560
ttctataacc atggcagtgc tccatagcta tgccaggcaa gacagtagcc actaaacaca    91620
tatagctgtt gagcccttga aatgcagcta gtgtgactga agaactgaac cccgattcgg    91680
tttaattttc attaaattta aatttaaata accttatgtg ggtagtggct ccagtattgg    91740
gcagggcagc ctgagagtcg gggctgttct cctgtcttca gtgtctagat gagggacctc    91800
agaggacctg tctctggagc tgcagttcaa tgtagccagc tgccccgtga cacttacata    91860
tagctgattt gtggatatgt cagacacggt gtgatgagct cagctttctg tcctcctccc    91920
cacatctgcc cctgccccat ttaccccact tgtgtcttta tcaagctaga aacaggtcac    91980
cacaagtctt catttccact caccaagtct tttgtttccc ctactaaata ttttgcgaga    92040
agaaagtgtg taccttttgta ttcacataca tgtacatgca catatacatg cacatatgca    92100
ggggtcccca acctctgtta aaaaccggac tgcaggccgt gcgtggtggc tcacgcctgt    92160
```

```
aattccagaa ctttgggagg ccgagaccag tgcatcacaa ggtcaggaga tcgagaccat    92220
tccggctcac acggtgaaac cccgtctcta ctaaaaatac aaaaaaaaat tagccgggtg    92280
tggtggcggg cgcccatagt cccagctacc tgggaggctg atgcaggaga acggcgtgaa    92340
cctgggaggc ggagcttgca gtgagccgag attgtgccat tgcactccag cctgggcgac    92400
agagcgagac tctgtctcaa aaacaaaaca aaacaaaaaa aaaaaaaacc aggctgcaca    92460
ggaagaagtg agcaagcatt accatctgag ctctatctcc tctcaggcca gtggtggcat    92520
tagattctca taggagcgtg tatgagttcg ttctcacact tctgtaaaga catacctgag    92580
acatataaag aaaagaggtt taattggctc acagttctgc aggctgtaca ggcttctgtt    92640
tctgggaagg cctcaggaaa cttgcagtca tggcagaagg tgaaggggaa gtaggcacat    92700
cttcacatgg cccacaggaa aaagagagaa ggagagagag agagagacag agagagagag    92760
agaaaaagaa agattgagag ggagagagga gggagaaagg agagtgcctg tagggggagt    92820
tgctacacaa aggagcacca gggggatggt gctcaaccat tagaaactac ccccatgatc    92880
caatcacctc ccaccaggcc ccacctccga cactggagat tacaattcag catgagattt    92940
gggtggggac acagagccaa accatatcag agcatgaacc ctattgtgaa ctgcacattt    93000
gagggatcta ggttgcatgc tccttatgag aatctaatgc ctgatgatga tttgaggtgg    93060
aacagtttca tcccgaaacc atcccccgcc aaccctggtt tgtggaaaaa ttgtcttcca    93120
cagaaccggt ccctggtgcc aaaaagtttg gggacctctg cacatatgca tgcacctgta    93180
catggacaca taatacatgt acatatgcat actttatatt ctctgccact tctggtccag    93240
actgatatac tatctcattt ggattactgc actagccttt tgttttggaa acagcatttt    93300
ttaaaaaatt taatttaatt tttttgagat agggtgtcat tctgttgccc agcttggagt    93360
gcagtgtcat gatcatagct cactgcggcc tcgatctccc aggctcaagt gatccttctg    93420
cctcagcctt ctcagtagtt gggactacag gcatacccac catgcccagc taattttttg    93480 atttttttt tttttgaga cagagtctca gcctgtcgcc caggctggag tgggttggcg    93540
cgatctcagc tcactgcaac ttctgcctcc caggttcaag tgattctcct gcctcagcct    93600
cccgagtagt tgggattaca ggcgcctgcc accacaccca gctaactttt tgtatttta    93660 gtagagacgg ggtttcacca tgttggccag gctggtctcg aacttgtgac ctcgtgatta    93720
gcccgcctcg gcctcccaaa gtgctgggat tacaggcgtg agctaccgct cccagccagg    93780
aaacagcatt cttgagataa ttcatataat tcacccattt aaagtatata attcattctc    93840
tttagtatgc ccacagagtt gtacagccat caccagaatc agttttagaa cccataaagg    93900
aactctgtac tctttaccca aaacctccat gcctccagct gcaggcagcc actaacctgc    93960
cttctgtctc tgtgactcta cgtcttctgg acattactgt ggatgggctc atacagtcag    94020
tgagcttgtg actggtgcct tctaccaagc agggttttca gtgtagcagc ctctctgttt    94080 ttctttttt tttaaattgt gacggaactt ctgcctccg ggttcaagcg attctcctgc    94140
ctcagcctcc cgagtggctg ggactacagg cccatgtcac catgcctggc taattttttt    94200
tttttttttt tttagtagag atgggttttca acatgttagc cagggtggtc tcgatctcct    94260
gacttcatga tccgcctgcc tcggcctccc aaagtgctgg gattacaggc gtgagccacc    94320
atgcccggct aacctttcat ttactgtctg catttcttcc ctgatgcctt ccagtccatg    94380
cacccgattg tagccattca tcctattatg gtttaaggtg actgtcttag tcagcatggg    94440
ttgccataac aaaataccat agcctgggtg gcttcaacaa cagaatttac ttctcacact    94500
```

```
tctggaggtt gggaagtcca agatccagga ctttcgcctt gccctcatgt ggtgagggggg   94560
tgaggaagct ctgtggggcc tcttatatat ggatgctaat ctcattcatg agggtctgc    94620
cctcatgacc cagtcacctc ccaaaggccc cacctcctaa taccatcacc ctggtaatta   94680
agtttcagtg tataaatttg ggggactata gacattgaaa ccataacaag cacttttcta   94740
agatcaggga gtgagtaagt agcagagcta ggacctcaat tccacatgtc agtcatcttg   94800
ccttcactct gctccatgat ggctgcctcc tagagcattg ggagtctcga tgttctatat   94860
gctctcatgt gttgtgtatt ggagatagtt gaggctttat gaatacatct ggatttgttg   94920
acttctagct ttgctggtaa ccagctgtga ccttgaataa gttacttcat ctctgagcct   94980
gtttcctctt ttagaaacag gagtttaaaa tgctgctttg ggttgggcac ggtggctcat   95040
gcctgtaatt ccagcacttt gggaggctga gatgggagga tcactggagc ttggagttcg   95100
agaccagcct gggcatcata gtgtgagatc ctgtctcctc aagaaattaa aaaattagct   95160
gggtgatgtg gcgtgtgcct gtggtcccat ctactctgga ggctgaggtg ggaggattgc   95220
ttgagcccag gaggttgagg ctacaatgaa atatgattgc accccatcct gggtgacgag   95280
tgagaccctg tctcaaaaaa gaaaaaaaaa atgctgcttt gtaccccttt catgtcatgg   95340
cgtcatggcc aacatagaat gccctggttg tttgctgttg gagggcatgg gcctgggggc   95400
tccctgaggg ctccttccat cttcaactca ttctctgtgc acctgttagg aagttgtggg   95460
ccagtcccta ccatgtatca ttgtgtgggt aaaagtaaat aaaatgtgta cagtgtctga   95520
actgtacata tcagggtcca agaacaaaat gagtgacatg ggttagctct ttttaataaa   95580
tggtaaaacc aaatattcta attttcagtt ttgttatact tccatcacat gttttgtttt   95640
ttttgttttt tgttttgtt tttctatttt aggcagcctt gccttctcta acaaaccccc    95700
cttctctaag tcccatccga cgaaagggga aggagaaaga accaggagaa caagcatctg   95760
taccgttgag tcccaagaaa ggcagtgagg ccagtgcagg taggaaacag cgtggggaag   95820
ggagggacat gagtgcagca tctgtcatgt agaaacatag gatttaagta acttggtgtt   95880
ttagagaaat aaatataata cacatcagta aagtgagaga agtttctcc aggtgcggtt    95940
caagatatta gaaactaatg actgatgtac acagaccacc ttttggtctg aagcatttct   96000
aagtgccact ggctgacatg cagcccctac agcctccagg cttccagccc tagcatggag   96060
catcactctc ctatgcttcc ctggttgcag gtgatggctg gagaggcctc ctgatttca    96120
gtaagggaag tggtgtagat gcttaggaat agatgtagtg agtgaaaaaa ctgattctga   96180
tatgtcaaaa attctgattg gaaatggaat atttacattt ggaagagcta aaggcgagag   96240
aaagtgggga taaagtcatc tgagttggag gagcttaaac cattcacaag tttggaggac   96300
cttttttac ccatgaaaag gtcagaacag aaggggctag gatttaggtg tgactgcagt    96360
ttattgaatt cccatccata ctgctctcgg tgggcagtgg cagggcagg agaggagcct    96420
ggcaaagcat gaagtgactg ctgctgcctc tgctatctgg gacgcctggc cacctgtctg   96480
tacagtctcc ctccagaccc attctcacgc tgtctcttgg cacccagggg ccagtgatgg   96540
ttctcccatt tgttttgtgt atatagcatt tatatcaagg ctatttattt atttatttat   96600
tttatttatt tattttttg agacagagtc tcactctgtc acccaggctg gagtgcagtg    96660
gtgcaatctc ggctcagtgc aagctctgcc tcctgggttc aagcaattct cctgcctcag   96720
cctcctgagt agctgggact acaggtgtgc accaccacac ctggctaatt ttttgtattt   96780
tttattagtg gagacggggt ttcaccttgt tggccaggat ggtcttgatc tcctgacctc   96840
gtgatccgtc cacctcagcc tctcaaagtg ctgggattac aggcatgagt cactgtaccc   96900
```

```
ggcctattta tttatttta  attgacaaaa  ttgtatatat  ctgtaatata  caacatgatg   96960
tttgaaatat gtgtacattg  gccaggcgtg  gtggctcaca  cctgtaatcc  cagcactttg   97020
ggaggctgag gtgggcggat  cacgaggtcg  ggagttcaag  accaaactgg  ccagcatggt   97080
gaaatcctgt ctctactaaa  aataccacaa  aaaaaaaaaa  aaaaaaaaaa  agccgggcat   97140
ggtggctcgc gccagtcgtc  ccagctactt  gggaggctga  ggcaggagaa  ttgcttgaat   97200
ctggcaggtg gaggttgcag  tgagctgagt  tcatgccact  gcactctagc  ctgggcgata   97260
gagcgagact ccgtctcaaa  aaaaaaaaaa  aagaagaaa   tacatatgca  ttgtggaatg   97320
gctaattaac ctgtgcatca  cctcacgtat  cattgttttg  tggtgagaac  acttaaaatc   97380
tactctttca gtgatttct   tgcatatggt  acattgctat  taactgcagt  caccatgcta   97440
tacagtagat ctcttgaact  cattcctcct  gtctataaat  gaaattttgt  atccttgacc   97500
aacacattca aggtttttt   tgagatggag  tcttcttcac  ccaggctgga  gtaccatggc   97560
acgatctcat ctcactgcaa  cctccgcctc  ccaggttcaa  gcaattctcc  tgcctcagcc   97620
tcctgagtag ctgggattac  aggcacatgc  tactgcacct  ggctaatttt  tgtatttta   97680 gtagaagtgg agtttcacca  tgttggccag  gctggtctcg  aactcctgac  ctcaagtgat   97740
ccgcctgcct tggcctgcca  aagtgctggg  attacaggtg  tgagccactg  cacccggcct   97800
caagcgtttt aaaagatgct  cttttctaag  gattgactgt  agtacaggag  gaagattgac   97860
ctgttgaaaa gcctcagcct  ttacaagtgt  aaaattatca  gtatattact  atcatctttc   97920
tgatgaatta aataaactaa  ggactccaag  tcaaaagtct  tcaaactgaa  gtagaatagt   97980
tgtatatagt gcttggcact  ttaatattta  gtatcggttt  aatgataatg  tttgtgcctt   98040
tgccgtcttt aaaacatttt  tacatcatcc  ctgtttgatt  acttggtgtg  ctcatgaagt   98100
tgttggccac taaggaatct  taggctcaga  gaggttctgg  aattggccag  tggtccttga   98160
atcagctgct cctatgattc  tctaactgat  ttctcacaaa  gcaaacaagc  aatcataaca   98220
aaacaactgt gcacactgct  cttcttattt  tgttatttaa  aaagtactta  ggctctactt   98280
atgtttgtta gtcaatttct  cattacttct  agttaatcaa  aaggtcagag  gaaatacttg   98340
aatattttca tactagaata  cttaaaaaa   tcatgatttc  cagtaatctc  tttaaaactt   98400
ggcaagttat tttgatctaa  aagtttatct  tttgtgtgca  tatttttaaa  gcttctagac   98460
aatctgatac ctcaggtcct  gttacaacaa  gtaaatcctc  atcactgggg  agtttctatc   98520
atcttccttc atacctcaaa  ctgcatgatg  tcctgaaagc  tacacacgct  aactacaagg   98580
tatgggcctc tgcatctttt  aaaaatatat  atgcacacat  acttacgtct  aatggatagt   98640
tgatgttttt cttatgattt  gtaggatgta  taagcccttt  gagatatgag  ttacatttag   98700 tttttcaag tttgtttgtc   tttcagcttt  gtttatgata  gcttctatca  tacaggtgtt   98760
ttggattttc atattgtttg  tactcacagc  taagattgat  tacagtgaca  gagctaggat   98820
gtgcagccag gttataggg   gaagtggccc  tggtggagtc  tggagggatc  cgtgtacagg   98880
cttccttccc tcccgtgagg  ctcacacaaa  aatacagcaa  catgctggtc  ctgcaggtac   98940
cctctgccta acatgagcca  caattccaga  ctcacagaag  aaaagcaggt  gttcggcata   99000
aaccatgtgt ttcaaatagt  ctgggcatgg  tgagccactt  gttatcagct  agggaaagtt   99060
tatgtcagcg taagaaactg  ttcaccagat  accccaaga   gccagccttt  ctgtctaggg   99120
atgttttagt ttttagttc   attttttttt  ttaactttaa  aattttctgt  tcatctgcaa   99180
tttgttagat atgaagtatg  tgtctaattt  aattttgtt   tttggttgtc  cccaataatg   99240
```

```
tttacagaag aatttttctg cactaattgg cttgagttac ttacattctc atagttctct    99300
agtttcagta gtttcatttta ttattttgtt atatcaatct atctgtctgc tcatctatta    99360
gaagcatcct tgttttttttt ttttcttttt tagacagagt cttgctctgt ccccaggttg    99420
gagtgcagtg gtgcaaccat gcctccctgc agtctcaggg ctcaagtgat cctcccacct    99480
cagctcctga gtacctggga ctaccggcat gtgccaccac acccagctaa ttttttacatt    99540
ttttgtagag acagggtctc cctaagttgc ctgggctggt ctcaagctcc tggcttaagt    99600
aatcctccct ccttggcctc ccaaagtgct gggattacag gtgtgagcaa ctgcacccgg    99660
ctacaagtat acttcttaat tattgtagct taatggtatt tatgagggga tcagttcccc    99720
tgttgttctt tagaattttc tggatattct tctttattga ttttgggatg tgaacaatag    99780
aatcaacttc tacttgtaga ttgatttagg gagaacttat acctcagatg ttaagtcacc    99840
ctgtccagaa tgtgggatgc tttcctattt gttcagaact tttaaatta cctcagaagc    99900
acatgaaatt taaaggattt taaaaaaaac ttaaagatta tttcacatag ctcttgcaca    99960
tttcttgata aatgaatcct caggtattcc tctgttttg ttactaatag ttacttctta    100020
tgggttttt ttcccctgaa aatcatttat caaacgtatg tggcttattt tctgaaggat    100080
gtttgataat tttggaagat atgaaagtct tcatattta caaggtttga ggtctcttta    100140
agctgcatgg ttctcatgtc agctcccaaa gcagaagacg gcatgttgaa aaatgccgta    100200
gagaagatac ttcttttcca cctgttttca actcatatca tcttgaattt cagggcacct    100260
ttccatgctc ctagtgcttg ctatctgttt attatttttcc ttcctgaata ccctgaactc    100320
cagcatgttc tgctgtaatt ctggcctccc tggcatcttg gactcctgtt tcctttgctc    100380
tgtcatcccc gcggtcagct cctgctgcgc agcttctcag ctgaagtgcg tttggagtgc    100440
ctggcgtgtc ttgctggatc tttgagtatt gcctctggtt tccttggttc cttctgctga    100500
gttgctcagc gtctccactc cccatttctt gtgtggccct tcctgcactc ctctgattcc    100560
ttttgtcttc cctggtttct tgctttggtt tcgagtctcc acagaacttt tgcagctctt    100620
ctgaagacct ggaagctttt tcatcttaat tctcatctca tgacctcttt tcccttcttt    100680
gagagctaga acttcccatg gtgaacttct ctttccagaa ttccatgcct tcttttccct    100740
cccacttacc tgttgtccag gagaggtcag attgctgtgc atattggagg agaacccttt    100800
cttccctggg ctcttcatct cacatgacat caccacatca cctcgttcct tggaccctca    100860
gtggtgtcac tgctggattt ttcttttcctt tggctggcct tagggcacac ccaggttgac    100920
tagcgtagtc atggtattta gatccactca catttttcagt ttctgtgtct gtctcttgcc    100980
tgcttctgac ttcgcccaga gaaagcttct cttttcacaag ggttcttaga tttatgttca    101040
ctgagcacct tcttttctga ggcagtgttt taccaatatt tattttccta gtcagtctcg    101100
ccttaccttt cttgttatgc atgtctttgg tcctgaccca ttctctgagt ctgtaaaata    101160
gaattgctgt ataatttaat tacatgaaat cctttagaat cttaacacat cttacacctg    101220
atttaatatt ttattgtatc caaattgaac caaccctatg tgaatttgac agtgattct    101280
cccagggatc ctagtgtata aggaatagga cttagtattt tctatttttt gatataccac    101340
ataccagata ctgattatga tggacattta acccttttt ctcattatga aagaaagtta    101400
ggaattattt cttccagtag cgccagtgta acctgaaagc ctttgaaaga gtagttttg    101460
tatagctatc tgaaaggaat ttcttttccaa aatattttc cagtgctgac aacaaacacg    101520
cagacacacc ctgcaaggtg agtgtacggc gccgcacagt ggaggcatct gctgcagccg    101580
tcgatgtttg tgtctttggt tgtacattat gagatcgtga cagggccagt aaccgtgtgt    101640
```

```
tctctccttc accttcccaa ggtcacgctg gatcttcaga acagcacgga aaagtttgga   101700
gggtttctcc gctcagcctt ggatgttctt tctcagatac tagagctggc cacactgcag   101760
gacattggga aggtttgtgt cttgttttt ctccttgggt tgtggctggc acacttgatg    101820
tgcgtcttct gggctgagtt catctaggat ggagcctggt tctccagggt gcctccggga   101880
gactcctccc tgccccacgt gcttgcgtca caggacccaa gtctgactct gccttagcca   101940
tgaagtttag ggggaagttt ctatttgtat tctattttg tctgttatca tgtattagct     102000
tagacccagt ttagtttgga aaatcagtgg gtttcaaaat gtgtttgtag agtcctttat   102060
ttcttaactt gacctttca agtggaaagg ggcaaaacag acgggtaagg gggcggggcg    102120
ggaggtgtga cttgctcttt tgtgcctgag gaagtaacag agctggggtt gacagtcata   102180
ttctctgaca cagatagtct ctgacttatc tcacagaaag tcagcggcag agcctgagtt   102240
aaaagtctcg tagatttct ttttcttttt tttggtggct aatttcagtt ttatttatat    102300 ttgttatt atttattata ctttaagttc tgggttacat gtgcagaatg tgcagttttg    102360
ttacataggt atacacgtgc catgatggtt tgctgcaccc atcaacccat cacctacatt   102420
aggtatttct cctaatgtta tccctccccc agtcccctca ctcccatgg gccccggtgt     102480 gtgatgttct cctccctgtg cccatgtgtt ctcattgttc aatttccact tgtgagtgag   102540
aacatgcggt gtttggtttt ctgatcttgt gatagtttgc tgagaatgat ggtttccagc   102600
atcatccatg tgcctgcaaa ggacatgaac tcatcctttt ttatggctgt atagtattcc   102660
atggtgtata tgtgccacat tttcttaatc cagtctatca ttgatggaca ttcgggttgg   102720
ttccaagtct ttgctattgt gactagtgcc acaataaaca tacatgtgca tgtgtcttta   102780
tcgtagaatg atttataatc ctttgggtat atgcccagta atgggattgc tgggtcaaat    102840
ggtatttcta gttctagacc tttgaggaat cgccagactg tcttccacaa tagttgaact   102900
aatttacact cccaccaaca gtgtaaaagt gttcctattt ttccacaacc tctccagcat   102960
ctgttgtttc gtgactttt aacgatcgcc atcctaactg gcgtgagatg gtatctcatt    103020
gtgattttga tctgcatttc tctaatgacc agtggtgatg agcatttttt cgtatgtctg   103080
ttggctgcat aaatgtcttc ttttgcgaag tgtctgttca tatcctttgt ccatttttg    103140 atggggttgt ttgctttttt ttcgtaaatt tgtttaagtt ctttgtagat tctggatgtt   103200
aatcttttgt cagatgggta gattgcaaaa attttatccc attctgtagg ttgcctgttc   103260
actctgatga tagtttcttt tgctatgcag aagctcttta gtttaattag atcccgttg    103320 tcaattttgg cttttgttgc cattgctttt ggtgttttag acatgaagtc tttgcctatg   103380
cctatgtcct gaatgttatg gcccaggttt tcttctagga ttttatggt cctaggtctt    103440 atgtttaagt ctttgatcca tcttgagttg attttgtgt aaggtataag gaaggggtcc   103500
agtttcagtt ttctgcatgt ggctagccag ttttcccaac accatttatt aaatagggaa   103560
tcttttcccc attgcttatg tgtgtcaggt ttgtcaaaga tcagatgatt gtagatgtgt   103620
ggtggtattt ctgaggcctc tgttctgttc cattggtcta tatatctgtt ttggtaccag   103680
taccatgcag ttttggttac tgtagtgttg tagtatagtt tgaagtcagg tagtgtgatg   103740
cctccagctt tgttcttcta gcccaggatt gtcttggcta tgcaggctct ttttggttc    103800 catatgaagt ttaaaatagt tttttccaat tctgtgaaga aagtcagtga tagcttgatg   103860
gggggatagc attgaatcta taaattactt tgggcagcaa ggccattttc acgatattga   103920
ttcgtcctat ccatgaacat ggaatgtttt tctatttgtt tgtgtcctct cttatttcct   103980
```

```
tgagcagtgg tttgtagttc tccttgaaga ggtccttcac atcccttgta agttgtcttc   104040
ctaggtgttt cattcccttta gtagcatttg tgaatgggag ttcactcatg atttggctct   104100
ctgtttgtct gttattggtg tataggaatg cttgtgattt ttgcacattg attttgtatc   104160
ctgagacttt gctgaagttg ctaatcagct taaggagatt ttgagctgaa ccaatagggt   104220
tttctaaata tacaatcatg tcatctgcaa acagggacag ttttacttcc tctcttccta   104280
tttgaatacc ctttattgct ttctcttgcc tgattgcgct ggccagaact tccaatacta   104340
tgttgaatag gagtggtgag agagggcatc cttgtcttgt gccggttttc gaagggaatg   104400
cttccagttt ttgcccattc agtatgatat tagctgtggg tttgtcataa atagctctta   104460
ctatgttgag atacgttcca tcgataccta gtttattgag agtttttagc atgaaaggct   104520
gttgaatttt gtcaaaggcc ttttctgcat ctgttgagat aatcatatgg tttttgttgt   104580
tggttctgtt tatgtgatgg attacgttta ttgatttgcg tatgttgaac cagccttgca   104640
ttccagggat gaagctgact tgattgtggt ggataagctt tttgatgtgc tgctggattc   104700
agtttgccag tattttattg aggattttca catcgatgtt catcagggat attggcctaa   104760
aattctcttt ttttgttgtg tctctgccag gctttggtat caggatgatg ctggcctcat   104820
aaaatgagtt agggaggatt ctctcttttt ctattgattg aatagtttc agaaggaatg   104880 gtaccatctc ctctttgtac ctctggtaga attcggctgt gaatccatcc tggactttt   104940 ttggttagta ggctattaac tattgcctca agtttagaac ctgttatcag tctattcaga   105000
gattcagctt ttttctggtt tagtcttggg agggtgtatg tgtccaggaa tttatccatt   105060
tcttctagat tttctagttt atttgggtag agatgtttat agtattctct gatggtagtt   105120
tgtatttctg tgggatcggt ggtgatatcc cctttatcgt ttttattgag tctatttgat   105180
tcttctctct tttcttcttt attagtcttg ctagcggtct acctattta ttgatctttt   105240 caaaaaacca gcacctggat tcattgattt ttttggagg gttttttttc gtgtctctat   105300
ctccttcagt tctgctctga tcttagttat tttttgtctt ctgctagctt ttgaatttgt   105360
ttgctcttgc ttttctagtt cttttaattg tgatgttagg gtgttaattt tagatctttt   105420
ctgctttctc ttgtgggcat ttagtgctat aaatttccct ctacacactg ctttaaatgt   105480
gtcccagaga ttctggtatg ttgtgtcttc gttctcattg gtttccaaga aaatttttat   105540
ttctgccttc atttcgttat ttacccagta gtcattcaag agcaggttgt tcagtttcca   105600
tgtagttgtg tggttttgag tgagattctc aatcctgagt tctaatttga ttgcactgtg   105660
gtctgacaga cagtttgttg tgatttctgt tcttttacat ttgctgagga gtgttttact   105720
tccaactatg tggtcagttt tagaataagt gcaatgtggt gctgagaaga atgtatgttc   105780
tgttgatttg gggtgcagag ttctgtagat gtctattagg tccgcttggt ccagtgctga   105840
gttcaagtcc tggatatcct tgttaatttt ctggctcatt gatctgccta atattgacag   105900
tggggtgtta aagtctccca ctattaccgg gtggagtct ctttgtaggt ctctaagaac   105960
ttgcttcatg aatctgggtg ctcctgtatt gggggcgtgt atatttagga tagttagctc   106020
ttcttgttga attgatccct ttaccattat gtaatggcct tctttgtctc ctttgaactt   106080
tgttgattta aagtctgttt tatcagagac taggattgca atccctgctt ttttttttgct   106140 ttccatttgc ttgttagatc ttcctccatc cctttatttt gagccaatga gtgtctttgc   106200
atgtgagatg ggtctcctga atacagcaca ccaatgggtc ttgactcttt atccaatttg   106260
ccagtctgtg tcttttaatt ggggcattta gcccatttac atttaaggtt aatattgcta   106320
tgtgtgaatt tgatcctgtc attatgatcc tagttggtta ttttgcccgt taactgatgc   106380
```

```
agtttcttca tagcgtcagt agtctttaca atttggcatg tttttgcagt ggctggtact   106440
ggttgttcct ttccatgttt agtgcttcct tcaggagctc ttgtaaggca ggcctggtgg   106500
tgacaaaatc tctgcatttg cttgtctgta aaggatttta tttctcgttc acttatgaag   106560
cttagtttgg ctggatatga aattctgggt tgaaaatact ttttttaaag aatgttgaat   106620
attggctccc actctttttct ggcttgtagg atttctgcag agagatctgc tgttagtctg   106680
atgggcttcc ctttgtgggt aacccgacct ttctctctgg ctgcccttct cttcatttca   106740
atcttggtgg atctgatgat tatgtgtctt ggggttgctc ttctcgagga gtatctttgt   106800
ggtgttctct gtatttcctg aatttgaatg ttggtctgcc ttgctaggtt ggggaagttc   106860
tcctggataa tatcctgaag agtgttttct aacttggttc tattctcccc atcactttca   106920
ggtacaccaa tcaaacgtag atttggtctt ttcacatagt cccatatttc ttggaggctt   106980
ggttcatttc ttttcactct tttttctcta atcttgtctt ctcgctttat ttcattaatt   107040
tgatcttcaa tcactgatat cctttcttct gcttgattga atcggctgtc gaagcttgtg   107100
tatacttcac aaaattctcg ttctgtggtt tttagctcca tcaggtcatt taagctcttc   107160
tctcactgg ttattctagc cattagtcta acatttttttt caaggttttt agcttccttg   107220
tgatgggtta aacatgctc ctttagctcg gagaagtttg ttattaccga ccttctgaag   107280
cctacttctg tcaattcatc aaactcattc tccatccagt tttgttccct tgctggtgag   107340
gagttgtgat cctttggagg agaagaggtg ttctggtttt tggaattttc agcctttctg   107400
ctatggtttc tccccatcat tgtggtttta tctacctttg gtctttgatg ttggtgacct   107460
acggatgggg ttttggtgtg ggtgtccttt ttgttgatgt tgatgctatt cctttctgtt   107520
tgttagtttt ccttctaaca gacaggcccc tcagctgcag gtctgttgga gtttgctgga   107580
ggtccactcc aggccctgtt tgcctgggca tcaccagcag aggctgcaga acagcaaata   107640
ttgctgcctg atccttcctc tggaaacatc gtcccagagc acgaaggtgt ctgcctgtat   107700
gaggtgtttg ttggccccta ctgggaggtg tctcccagtc aggctacatg ggggtcaggg   107760
acccacttga ggcagtctgt tcattatcgg agcttgaatg ccgtaccggg agaaccactg   107820
ctctcttcag agctgtcagg cacgtatgtt taaatctgga gaagctgtct gctgcctttt   107880
gttcagatgt gcccttcccc cagaggtgga atctagagag gcagtaggcc ttgctgagct   107940
gcagtgggct ctgcccagtt cgagcttccc tgctgctttg tttacactgt gagcatagaa   108000
ccacctactc tagcctcagc agtggtggac acccctcccc cagccaagct cctgcatccc   108060
aggtcgattt cagagtgctg cgctagcagt gagcaaggcc ccatgggcgt gggacccgct   108120
gagccaggca caggagagaa tctcctggtc tgctggttgt gaagactgtg ggaaaagtgc   108180
agtatttggg caggagtgta ctgctccttc aggtacagtc actcatggct tcctttggct   108240
tggaaaggga agtcccccga ccccttgtgc ttcccaggtg aggcaacacc ccgccctgct   108300
tcggcttgcc ctccgtgggc tgcacccact gtccagcaag tcccagtgag atgaactagg   108360
tacctcagtt ggaaatgcag aaatcacctg tcttctgtgt cgatctcact gggagctgta   108420
gactggagct gttcctattc ggccattttg gaagcatccc ttgttttttg aggtggagtc   108480
ttgctctgtc gcccaggctg acgtgcatcg gcacaatctc ggcccactgc aacctttgcc   108540
tcctggtttc aagcgattct cctacctcag cctccggagt agctgggatt acaggcacct   108600
gccaccatgc ctggctaatt ttttgtattt ttagtggaga tggggtttca ccacattggc   108660
caggctagtc tcgaactcct gaccttgtga tccacccacc tcagcctcct agagtgctgg   108720
```

```
gatcacaggt gtcagccacc acgcccagcc atattttcag atctccctct ctttgccta    108780
aaccactgtg cttaataagt agtttttagt ggccagcagt ctccatgtat aacacatttt    108840
agcaaaatgg aaaatactat atgttttaaa tttgaacgtg agattatact gaaataaaaa    108900
tcatctaact gggattcttt aaatagtaag attttctttt ttgtatgtgg gttttttttt    108960
aaccttatta ttatgactgt catatataga aatggctgtt tttcagttac agtcagtgaa    109020
tgtatcaaat gctgccttat ccaaataata aaagtaaatt attaataagt cacaatttaa    109080
tgaagattga tgttagttga tctttatatt cttgaaatca gccatatggt tgtgtgtgta    109140
tgtatatatt tttaaaggta cataaagata ataagctcat ctctgaaaat ttttacattt    109200
ggcataagaa taactggata attaagcatc ttattctctg gcctgtgtct ttacagttaa    109260
aggtagattt actcacctct ccttttttgt ttttctaagt tcatcttttt tgctgtttca    109320
agacagaggc ccattttagc tttctcgcat atccttttgt ttgtactttg gaagcctcac    109380
ctgcttaatt gttgagtttt tatccgtggt cttttagagg gggatatgta gggtagaagc    109440
tttcacaggt tcttgtttgc acttggcccc tgactgtttt gaggaatctc cctcactgac    109500
tcacagcatg gcaaggtttc agatctcttt ctgccacaca gcagttctga ggcagctgga    109560
aagatatcca gatgcttaga ttgtcaggcc aggcttgaga tatacaaact attgagcctt    109620
atctgtgacc ttgcttaggt gaaggcatca gagcccctgc accaacatgc ataggcctct    109680
gcatgtgtgc ggggctgggt gttgaggtct gagcacaagt gtagctggag aggtgagctt    109740
gatgtggcga cgggtatgag caggttttct tcagacttct gtgagtttac ctagttccag    109800
gatttaaagg cacagagact ttagaattaa aatagaatca ttttcttttt ctaaatagca    109860
acactaggaa taaaaaataa taattccaca ttcttgacag gtaatgtttt ttcttgtctt    109920
ctaatcctta tttattccat actcattttt atacataatt gaaatgtatt atgcattgga    109980
ttttctttt gcattatatt atagacgatt tttcatgtaa ctccttactg ttccatttta    110040
tatgtttgt ctggtttaag actttatctg caaaccggga aactgtctct acaaaaagaa    110100
aaacaaaaat agttggccgc agtggcatgc gtctgtggtc ccagctactc ggggctgagg    110160
tgggaggatt gcttgagcct tgggaggttg aggctgcaaa gagccatgat catgccattg    110220
cactccagca tgggtgacag actttatact gtctgttttg ggtgatttga taatgatatg    110280
ccctgatgta gttttttttat atctgtgtt tcttgtgcct gggtttattg aggttgggtc    110340
tgtggcttca tagtattttt aaagtttgga aaattttagg ccattctttc tttctttctt    110400
tcttttttt tttttgaga cagtgtctcg ctctgtcgcc tgcgttggag tgcagtgaca    110460
ctatcttggc tcactgcaag ctctgcctcc tgggttcacg ccattctcct gcctcagcct    110520
cctgagtagc tgggactaca ggcgcctgcc accacgcctg gctaattttt tgtatttta    110580
gtagagacga ggtttcactg tgttagccag gatggtctca atctcctgac ctcgtgatct    110640
gcccgcctgg gcctcccaaa gtgctgggat tacaggcgtg agccactgca cccagctagg    110700
ccattatttc ttcaaagatt ttttttctgc cctgcctccc tccttttttc cctctcttaa    110760
aggggctgtg atttcctgaa tgattgctta gtgttgtccc atagcttact gatgctcttt    110820
tcagtgtttg attgttttat gtgttttctg ttttgtatag tttctattat tgtgtttca    110880
agttctctga tcttttcttc tacagtgtct actctgttgt taatctgtta atctgttgtt    110940
aatcctgtcc agcgtatttt ttttttgtt tttgaaacag tctcactctg ttgcccaggc    111000
tggagtttag tggtgcgata tcagctcact gcaacctcca cctcccaggc tcaagcaatt    111060
cttctgcctc agcctcccga gtagctggga ctataggcac gtgccaccac acctggctaa    111120
```

```
tttgtgtatt tttattagag atggggtttc accatgttgg ccaaactggc cttgaactcc    111180
tgacctcagg tgattcatcc gcctcggtct cccaaagtgt tgggattata ggcatgagcc    111240
accgtgtctg gcccctgttc agtgtatatc actaattttg ttttatctc tagaagtttg     111300 atttaggtct tttaaaaatg tctccctgtg tttctgttta gctttgtgaa cacaattgta    111360
ataactgttt taatatcctt ctctgctagt tctaagatct tctaataact tcccagttct    111420
tggtgtttct cattggttga ttgatactcc tcgttttggg ttgtattttc ctgcctcttt    111480
gtatggctgc caatttttta ttggatgccc aaccttgtga attttacttt gttggatgct    111540 atatatttt gtgttcccat agatcttctt gagctttgtt ctgaggttag ttgagttaca     111600
tatagatggt ttactctttt gggtcttgct ttataatttg tcagatgggt tggagcagtg    111660
cttagtttag gactaatttt tttttggac taattattcc tctttaggaa taattaggta     111720
ccatgcttag gaggcaagac catcctgagt actctaccta atgaaccaga aagtttgggt    111780
tttccagtcc gcctgctgag aacagtgact ttctagccct gtgtgagcgc tgagctctgc    111840
tccttctaat cctttccaat gcttcttttcc ctggcctcag ggagttttct cacacacata   111900
tctctgctga gtactcgaga gggaccttcc ccagatctcc agagctctct ctgtcttgtt    111960
ttctcttctc tggtgctctg tcttatgaac tgtggctgtc ttggtctcct tagattctca    112020
gcacctcttc aattcagagg gttgcctgtc cctcctcctt gtgccacagc ctaggaactc    112080
tctcaaagca gcgagttggg gcagccatag gctgactta gtctctcgtc tcccagggat     112140
cactgtcctt cattgctcat gtccagtgtc ttgaggactc tgggttttgt ctgttttgtt    112200
ttttggtttg ctttggttgt ctcaggcagg agggtaaacc cagtccctca ccctcattgt    112260
gctcagtagt ggaagtctca ctctattaca ttagatatta gtatttgtag cagagccctg    112320
gttccctggt acttggggag ctcttgaaag gccagaaaca gcatgctttc tcacctttc     112380 cagggcttca gtttctggtg cacatcaagc attccataca catttgttaa agtcctttgt    112440
tagacaagta gtgattcaca ggttctattt gtaattttt cagttaacat gtattgggta     112500
tctgctggga gctagtaaaa acaaaaagtg gtgtgtgaca aattcaattc tgacaagaac    112560
aaccttaaac acttagaata tactttgagc atatcagaat tttaaaaatg tgtggccctt    112620
gagtatttga aaccaacaag aatctattgc ttattagtag aggatatttt gttaaacaag    112680
tggagagaga ggcattttca gtctaattgg tgttggcttt tagcagctga tggaaaccag    112740
ttcgtgatta gccaggcagt ggtgaaacag gctgtgcatt ctgaatgcct aggtatctag    112800
gcattcagaa tggtggcgct ctttgagtta gcatcttctt cttcttgat tctttttttt     112860 ttttttttga gatggacttt cgctcttgtt gcccaggtaa caactccagt gcaatggcgc    112920
catctcggct cactgtaacc tctgcctccc tggttcaagc gattctcctg cctcagcctc    112980
tcaagtagct gggattacag gtgtgcgcca ccacgcctgg ctaattttgt attttggta     113040 gagatggggt ttcactatat tggtcaggct ggtcttgaac tcctgacctc aagtgatgca    113100
cctgcctcga tctcccaaaa tgctgggatt acaggcgtga gccaccactc ccagccccttt   113160 cttgattctt gaaaggaca ttgggtgctg tacatctcgt tatagatgtt gataaaaatg     113220
cttgtgagaa gagtaacatt aaggtagtta tttggtcatt tttgcagatt attttaagac    113280
aattctagga ctgatttgtg gtaaatcaca cattgctgta tcatagttgt gttcactgaa    113340
catattcagg ggctctacag atgcagggct cttagctgct ttgcacactt ctgaattcct    113400
gccctgcgaa caggactgga tacctaatag acaacaggta cttgataaca gtttattgaa    113460
```

-continued

```
ttaatgagtg aatgaacaga tacataaatg catgaaagaa tggttgtaat gtatataact   113520
tggatttcaa gacttttttac tgactgttca aaataagaaa ttgaaaactt tcctctgatt   113580
ttcctctact atttacacaa tttaaatgga agttatcttg taccttcaat ttctgtctag   113640
gattcgtaca ataacgggtc atctctgagt cgcttaatgt ctcacttgtc tttctacagt   113700
gtgttgaaga gatcctagga tacctgaaat cctgctttag tcgagaacca atgatggcaa   113760
ctgtttgtgt tcaacaagta agagcttcat tcttttcctc ttctgttaag acgttcgggt   113820
atgacagcaa aacgctgcta ctccttaaga ggcaggcgct gttggcataa tcagctggga   113880
ggattgtggg gtccagcgca gcacttttttg gctcagtcca tgattgagcc aagaggccat   113940
ccttcccttc actccccagg aggacgaggt ctgtcactgt ggagggcaga ggacaccaga   114000
agctcctctg caacctcgct agttaacttc cagtccctcg gagtttctgt ttagaatgct   114060
caatctcatt tagaattgca aggaaaccca aaacgcctat ttaaggtaca aacagcactt   114120
catacaatat ctcatgaggt attaatagtg attcacagga agaatttcac gctgtgagtc   114180
tttgctaaca tatccagtta tttacagatg gatttgatat ttgtgtggga gattcttaaa   114240
agtgttgttc acgccacatt gttgatgcct cattttttttc actgtagttg ttgaagactc   114300
tctttggcac aaacttggcc tcccagtttg atggcttatc ttccaacccc agcaagtcac   114360
aaggccgagc acagcgcctt ggctcctcca gtgtgaggcc aggcttgtac cactactgct   114420
tcatggcccc gtacacccac ttcacccagg ccctcgctga cgccagcctg aggaacatgg   114480
tgcaggcgga gcaggagaac gacacctcgg ggtaacagtt gtggcaagaa tgctgtcgtt   114540
ggtgaagca cgaaagagca agcaggaaat actttgtaaa agaataaaaa cgaaaaatgt   114600
tagcgaacat cttctaatag tctgctgtat tcagagaact ctaggagata tatatggttg   114660
atgcaaagat gatttaaggc atagcccggc cttccaagaa gtgtgtggcc agtgagtgag   114720
atgggcttgg gacttacaca tctcagaggt gggggtagag gaggaggaac actgagtggg   114780
ctgagaagca gccagctctc attgccaaag tgtgtcagca aaccagaatg cagttcataa   114840
tgtcccacc cattcaaagc acaggacctg tagagtggtg tggcatgtgt tggtggcact   114900
tttcaggcct gtaacaagga tgaaagaaca gcttcatagc agcacagtag tgctggtgtt   114960
cagaggtgtg tgaaggccat agaagcatct tggatatatt accttgtgtt ttgtcagctt   115020
tatgactaga agtctctttt cacttaaatt tgtttttttt ttttttgaga cggagtcttg   115080
ctctgtcgcc caggctggag tgcagtggtg caatctcagc tcactgcaag ctctgcatcc   115140
tgggttcatg ccattctcct gcctcagcct cccgagtagc tgggactaca ggcgcctgcc   115200
atcacgcctg gctaactttt ttttgtattt ttagtagaga cggggtttca ccatgttagc   115260
caggatggtc tcgatctcct gacctcgtga tctgcccgtc ccggcctccc aaagtgctgg   115320
gattacaggc gtgagccacc gcgcccggcc tcttttcact taaatttatg tttgtgtttt   115380
taatgcctag tatacaggac ttcttaaatt gccttaagta tgaacaggta tttgagttgc   115440
taatctgtat agtagcaata atagaatccc ttgttttttcc ttttataaat ttagcgatta   115500
aatagctaca attaaaacac tagagtcagg agtcaaggaa aatacccatg ttccaggctg   115560
tatgttagtg atgtacttac tatatattgg agtttcagga gtaagtctgt ttcaatgctt   115620
tctgtaacca tttgggggtat taataagcat gtgagtgtgt gcatgtttgg gttaatttca   115680
tatatgtttc ttagaaggga tatcattgat gtaaatattt taaaggcttg tcctccaaaa   115740
aaatcatgta atttcttcta aattactgat ctttttaaatg accttcacct ttctctcaaa   115800
tctcacttaa gactgggctg agtagtcagt ttcctgtagc agaaaaaagc tcagacttga   115860
```

```
gtagccttct gcgagtgagg agacttgatg gctgtcaggc agctgtaaac tctaaataga    115920
gtgtcattat ctgaagaggg cgatgctgcc acactgagtg gcctttcaag ttgtttctca    115980
atctgacacg ttctgatcgt gtgaatgtga aattggtttg agcaggagta tatctgagtg    116040
cagaggagat tatttaaaga tattctcatt ctctgcttcc cttttattcc catttggcag    116100
atggtttgat gtcctccaga aagtgtctac ccagttgaag acaaacctca cgagtgtcac    116160
aaagaaccgt gcagataagg taaatggtgc cgtttgtggc atgtgaactc aggcgtgtca    116220
gtgctagaga ggaaactgga gctgagactt ccaggtatt ttgcttgaag cttttagttg     116280
aaggcttact tatggattct ttcttctttt ttttctttt tatagaatgc tattcataat     116340
cacattcgtt tgtttgaacc tcttgttata aaagctttaa aacagtacac gactacaaca    116400
tgtgtgcagt tacagaagca ggttttagat ttgctggcgc agctggttca gttacggggtt   116460
aattactgtc ttctggattc agatcaggtt tgtcacttt atctttcatc catcatacct     116520
gttcctaatt tagtacaaat taccctaaaa gacactgaaa tctactttaa agaaatgtgg    116580
tctgcatgtt tccctcatca gttgctgctg cttatctttt tcatgcacct agctggtgca    116640
gaaggcctgg ggcatagcca gcctcagcaa gtcagcatcc ttgccccagc tccctggact    116700
caaggctaac ctggggttgg ctgttaggga tttccaaagg tttgtcccat ccacttgcct    116760
ccctccaaa ataagtttga atttaaattg tgagatacaa ttaagattta ttgtttgggg     116820
aacattttg caaaatctag agttagttta aacagattat caattattac cataaattgat    116880
catctgcagt ttcaagctat ctaacaggtt cacttacctc tttaaaaagg aatggaattt    116940
agcaggacag taactgagac ccgtgctcct ggagtccatg tgggagctgt gtggctctgc    117000
acaagcattt gcacgcttcc cctcttgact gcattacctt cctcctatag ttgctgtggg    117060
caccagattc tggctagtcc tgtcccttca tgatgcacat tttcctcaag attcgtccca    117120
gttaaatcac tgcagatgaa actgcctttt catcgtcaaa atttaactgt cattttttgag   117180
ccgtgatctt gggctacttt cttatgtggg gtaggaatat ttgtgagtta gaaatattac    117240
acttctctat ttccttctag acgtaaatct gttaatcctg tcagcactgt tactcacctg    117300
aaagggtctg tttccctagg agaactgagg gcactcggtc aacactgatt ttccacagtg    117360
ggtattgggg tggtatctgc ttgttttttt tgttgttgtt gtttgttttt ttttgttttt    117420
tttttgagat ggagtctcgc tctgtcaccc aggctggagt gcaggggtgc gatctcggct    117480
cactgccagc tccgcctcag aggttcacgc cattctcctg cctcagcctc ccgagtagct    117540
gggactacag gcacccacca ctacgccagg ctaattttt gtattttag tagagacgag      117600
gtttcactgt gttagccagg atggtctcca tctcctgacc tcgtgatctg cccgcctcgg    117660
cctcccaaag tgctgggatg acaggcgtga gccaccgcgc ccggcctggg gtctgctttt    117720
aatgaaggag gcatcaaggg gtgggctttg cgttggcctg atgctttcat ctttctttca    117780
caaaacctgt ccgaagaaaa tccgtctaaa tgggccattg ctctcctcag gaaatagtca    117840
ttgggaactt cttttccttt cctttgacac taggaggctg actggggaga gccctggtc     117900
tatggctgtg ggcagcaggg gctgagagga gcaggctctc aggggggcac gggtaccca     117960
agggaagcca gagccctgat ttgttccatt ctagtaagaa caaagactgc tctggtttca    118020
tgtttgttct gattgccttt catcaaccgg tcccctttct cccagttctt aagattcagt    118080
acagtgacag ttttatgaac aagaatagaa cactagaaca gacaaaccat tgaactctat    118140
gctgataaag atttattgag ctcctgctgt atgtttgcat tctgcccaga ggctctgaga    118200
```

```
aaaccaggcc atatgctcca tgctttatcc atggaagctc cccgtcaggt tgggaaagct 118260
gacagctgca gggaatacag tgtgacacaa aactggctcc catgcagccc ttacgtgtcg 118320
cctctcagat ggttggggga cgaaggtcga ctcctttggg tatcttatta ctaaaccagt 118380
ttcagggaat ctgtgccacc ctatctgcca ttaacgtgaa cagatgagtc cccaaggtgt 118440
aattttgggt attgtctgat gtctcttgga atttattatt tgttttcca atgagatttc 118500 acctcagggt atagtaaagt tgttgagggg attcctggat gtgttctgca attatctagg 118560
ctgatttcag aatagagtta tgcttatagt caaatttatc agctgtcaag aattttattt 118620
aaaatttatg cagataagca ggaggaaaag aagcctggtt tttacatttt aatcctatta 118680
ttgatgtgaa attttatttt ccttcctgta ggtgtttatt ggctttgtat tgaaacagtt 118740
tgaatacatt gaagtgggcc agttcaggta atagcatttt attatttag attttttct 118800 tcttcttgtg tacttacatg taatttaggt tattaagtga atgtttaaac tactgttagg 118860 cattttgct gttttcttta aatggaaatc tgactaacat actgtgcatt tttgcttctc 118920
ttaaaaatta atgtatatct caagacttgt ttggaagtag ttatgtatct gaaaattcca 118980
tatgttgtca gtattcattg cacatttcaa agcatttaat tgtgttgaca gatggtggaa 119040
tgaaatcttg tggtggagca ctagttttta aatcttctta gagaaagcag ttttatataa 119100
tgttgtcttt agtaattatt atgcatttgt attctctgca gctttttctt gctagatgtt 119160
gaggttttaa tacttcttgc tagtccatta caggtttata attattaaaa gttaaaattc 119220
ttttagtacc taaatgctt aataaacatt gtaattagga aaatttagtg cagaaggaaa 119280
gtgttcccag attccctggg gtctggaaac atagtgttta ttctaattac atgcacactc 119340
cactgtgttt tggggcaagt tactgtttct cttttgagtt tcaatttctt caagagcaaa 119400
gaggcagagg agagctagga agatcgtagc tgctgtgccc ctgtgccgtc gggtgccttc 119460
tacctgctgc ctccgaacct ttacacatgt ccctgctctg cgcgagggca cagatgggat 119520
gcactgtggc aggggtgggg ttagagtaga tcacggacac ctgttagctt gatgtgtgct 119580
tgctgtcaag gttgaatcat gaattatttt atgttgctta tattgatatg tatcttaatt 119640
ttaaaagaaa ggtctaaatg gatgttttg tttttaggga atcagaggca atcattccaa 119700
acatcttttt cttcttggta ttactatctt atgaacgcta tcattcaaaa cagatcattg 119760
gaattcctaa aatcattcag ctctgtgatg gcatcatggc cagtggaagg aaggctgtga 119820
cacatggtaa cgggacacac ctttcactgt cgtcttcggt gtcgtgatgt gcttggcagt 119880
gttcgttttc atatacccac tttgaacgtt gtcagtggca gccatgtgct tctcaggctc 119940
tgcatgtgtg tctgtgtatg tgaaggtact ggttagagac gtttcaaaag agaagagagc 120000 atattctta ctctcagcaa tttgtaatct tctcagggaa aaaaattcaa gaaacagtaa 120060
gataacctaa ggtacagata gattctgaat ataaagttcc tgttcattca catgaaacgc 120120
taaaagttct tcacttgatc ttagccaaaa ggccaagaag cgatgcaaca ctaaaaattc 120180
ttaaatcgaa cttgccgtga attaaatttt gatctctcat ccagtggtat tggagatata 120240
gtttgacttg ggttcagggc tttctgtttt gcctgatgat tttgctggag cttaaataag 120300
gaacccagga gatggccagc tgtgcaagcc cccagcctgt ggaaggagct agtgtggttt 120360
tatgaatgag ttgcaaatct ttctttgagc tttttgaact gatcttccag cattgcccta 120420
ttgacccctc cctgactcct ttgctggaat ctgtaggctt ttgaactttg acagggacac 120480
atcctaagac ccttgcaaac tcccagatgt gagaatggca ctactactta gagtcttttc 120540
gactcagcgt gtgtgcagaa gagcatcaac cgggctgtgt tgcgaggcag ggccttggct 120600
```

```
gacctctcag tgtttacata gctaagccag ttagtgtttg ccacggcctc acaagggctt   120660
cagattcaca cagccaaagt atagattatt aaaggcatag gtgtttggtt tcctggactt   120720
ggagggtctt tggacagaaa atcagtaggc aaccacaccc agtactttgt gctgggaagc   120780
ttggtcatct gtgagagggt cagagagtat acccatgcgt gcatgccacc gaagggtcag   120840
tgagtattcc tgtgtgtgca tgtctcaggg ccggagagag tatgtgtcac tgagaggtca   120900
gagtgttcgt gtgtgtgtca aagagggttg cattgtgccc ttcactgagg ggtcagaggg   120960
tgcctcgcgt gtgtgtgtgt gtacgtgtgt gtgtgtcact gaggggtcag agtgtgcctg   121020
tgtgtgtgct tgtgtgtgcg tacatgtcac tgaggggtca gagtgtgcct ctgtgtgtgt   121080
gctcatgtgt gtgcatacgt gtcactgagg ggtcagagtg tgcctctgtg tgtgctcatt   121140
tgtgagcgta tgtgtcactg aggggggtcag agtgtgcctc tgtgtgtgtg ctcatgtgtg   121200
agcgtatgtg tcactgaggg ggtcagagtg tgcctctgtg tgtgtgctca tgtgtgagcg   121260
tatgtgtcac tgaggggtca gtgttcctat gtgctcatga cattgagggt cagagtgtgc   121320
ctgtgtgcca atgaaaggca tttcttatat ttttttatat gtggtcatag tagaccagtt   121380
aatttatttt gactcctgtg ttagaccaaa ataagacttg ggggaaagtc ccttatctat   121440
ctaatgacag agtgagttta cttaaaaaag cataataatc cagtggcttt gactaaatgt   121500
attatgtgga agtctttatt gtcttttcag atgaatcaag tagattattc ttgagaccag   121560
gaatgttgct gttttggtta tttggaaagt tttatcattt tcaaattgac ttttgaattt   121620
gagtcacctt ttttcagaag tggtgttaaa ttataggagc cctaggtttt ttttctttt   121680 ttagaagtca tcacaaaatg atcagtgttc agaggaagag ctttgacctt ccacatggta   121740
taatgattga taaccttaat tcatctctta ccataaacca agtatgtgta agggttttct   121800
ttatttcttg aaagcatttt gtagatgttg agagcagttt tccaaatgta atttccatga   121860
aatgcctgat aagggtaccc ttttgtcccc acagccatac cggctctgca gcccatagtc   121920
cacgacctct ttgtattaag aggaacaaat aaagctgatg caggaaaaga gcttgaaacc   121980
caaaaagagg tggtggtgtc aatgttactg agactcatcc agtaccatca ggtaagagga   122040
atgtatgttg gaactgtcgt ggatacttta ttgacccgtg cagatggaag gaagtgccat   122100
gtggtaacgc tcactgttaa ctgtgttact ttgaaccagg tttgggcttt ctggggcctg   122160
ggtagatgcc ggtgcagggg gatggggagg gaggcggggg gtgggggggt gtggtggagt   122220
tggggaggtg cagtggcagg aggtgttgtt ggtgtgtatc ctttttttt tttgagatg     122280 gagtctctct ccgtcgccca ggctggagtg tggtggcacg atcttggctc attgcaagct   122340
ccacctcccg ggtttaagca attctcctgc ctccacctcc cgagtagctg ggattacagg   122400
catgcaccac catgcccagc aaatttttt ttttgtattt ttagtagaga tggggtttca   122460
ccatgatggc caagctgttt cgaactcctg acctcaagtg atcctcctgc cttggcctcc   122520
caaagtgcta ggattacagg cgtgagccac catgcccagc ctggtgttta tctttaaagt   122580
gggcacagcc acaggagttc acctgactcc tggtctgaga gtcacgagat cgttcaagat   122640
agtgaggccc tcttttccaa aacgaggacc aaaaatcaat tgacagtgtt ggtcaagatg   122700
gtagaaacct taaaatgata gaaatctcaa ctctgaaata aaaactttat ttgtatattt   122760
atttaccact attttgacat agggctaagg tcttttttctt tgagctgatt tctggttttg   122820
ttttcttaaa gtggcataag aattcaaaga cattttgagg aaggctgagt gcagaaatct   122880 ctcttttaa atgacttctc ctttcttttta acttgcactg ttgtctagcc ctcacttatt   122940
```

```
ttgtcaattc ttttttagctg tttgtctttg aatcttcata aagccatagc tttttctcata  123000
agaagcagca ctttctttgt tcattcatat tttaatgaac ccctgtagta tttaattaaa   123060
tacttaatgc ctaattaaat cacataattg caatgcaaaa gtacatgtat cataaagagg   123120
tctgaaaatg agcaactggc aagcaggtgg tggcaggcag agctgcttgg gtgggtgggt   123180
gtcatggaga ggagttcatc agccacatgt tcagtgagct ctggatatgt ctgtttagaa   123240
atgatcacta ataaacttgt gctcaaccat gtatacctct gggaagcagg tgctcttcag   123300
tagattgcct ctgcagagaa cacagaattg aagtgaatgt ccacaaaggc aatgagccac   123360
ctgcagaata gtttagtcaa ggctgtgttt gaagtttgcc aaagattaat atacatttga   123420
ttttcatgtt gtgcctttc tctgattgtg aaatattaca aattctatac aaataacaat   123480
gatggcaaat cctcctgagc aaagtgtgca ccttgtatgt gccctagagg aacttgtgtt   123540
tcgttctgat tcccctacat ttctcatgtc atagagtggg ggttgcatta gtgtccccct   123600
gtcctcgctg ggatcacatc tgtttggatc ctagagtctt ccagctgaac tgggacaagt   123660
ataacagacg gacacgtagg ggtggaaagg cgtctcttgg cagcagactt tctaattgtg   123720
cacgctctta taggtgttgg agatgttcat tcttgtcctg cagcagtgcc acaaggagaa   123780
tgaagacaag tggaagcgac tgtctcgaca gatagctgac atcatcctcc caatgttagc   123840
caaacagcag gtttgtcccc gcagccttgg cttgttgttg catagtgatg gtagcttaag   123900
gtccttgtga aaggtgggtg gctggaatca gctcttcctt cagtcctaat ctgtgccttg   123960
atagcagttc tccgtgctag tcatgggaca gctgacttca tttcttctca caatgccatc   124020
tcaggttggt attgcccacc tactttacag gggggatccc acagctccga gaggttatgg   124080
aggtgatcag gcagcacaca gctttagagt gctggggtga gggcgggcca aggctaactc   124140
taaagcccga acccttacct cctacactgc ctcctgcatt ctggtcaacc cagtgtttta   124200
tttggtggtt agatttttgt ttttgttacc ttactgcttg taatttagca gttttccttt   124260
cctttccctt cctttccttt ccgacagggt ctcactctgt cacccaggct agagtgcagt   124320
cgtgtaatct cactgcaaca acctctgcct cccaggttca accaattctc ccacctcagc   124380
ctcctgagta gcaaggacca caggtgtgca ccactacgcc tggctagttt tttgtatttt   124440
tagtagagat gaggtctcgc tgtgttgccc aggctggttt taaactcctg ggcgcaagtg   124500
atccaccaac cttggcctgc caaagtgctg gcattacagg tgtgagccac ctcgcctggc   124560
ctattcatca ctaatcagaa tttctatgat caaatgacat gaatcattgt ttccacaact   124620
gcagtggaag gaaatggcct ggcagtgcca gtttcagaag cagcctgccc ccagtcaggc   124680
acaggccact gtgcccccag tgtagcagca cctctgtagc tcacagagaa gggtggtggg   124740
gacctccttg aggcagctct gccagaaaat ctcatgagct gcctggcaca gcttgaggtt   124800
gccttttaag tggactcagc aaatacatgt ttgttcatct tgattataca caataaacaa   124860
ctactctgta tagtacgagt agtccgtggt ttttggcatt tgatttaaac ttagaggcat   124920
gtgatattga tgttactgcc ttcatgactg cacccccatt ctgatttcat aatggaatgt   124980
tatcttgaga ccagttagac aacaggacag ggatcttggc ttctggtgag attgacagca   125040
gttttagtgt ggtcagggtc tccctgccta cagatggttt tagaatggtg ccctggaagc   125100
tttatcccat tctttttctgt gcgtaatctg agtagagtgg agatcgaagg cctgaataca   125160
tagtaaatac ctgacttaat atctgccgca atggaaattg tgtgatacaa catttatgaa   125220
acgcttagtg cagcacctgc caggtagctc accacaggtg catgttgcat tcagaagtag   125280
tgctagatac tatcctgtta ctggcagtgc atacatcagt gatcaaagca gattaaagaa   125340
```

```
agaccccctg ccttcttgga gtgaagattt tgttgggatg cgggtaaggg gacagacaat  125400
agaaaagcaa gtgagtgaag tctataccat ggcggctgat caggaacacc gtacagaaga  125460
atccaggagg gaagagagtt aggtggtgtc tgcggtggga gtggcattgt tcagctggtg  125520
atgagaagaa gctttggtga tctggtgaca tttgagtgaa tttgcagaaa ggaaagatac  125580
aagcctagga gatacctggg gaaggaacat tccaggcaga gcaaatagca gtgcaaaggc  125640
cctggcgggg ggcggacatg ctgttagggt acaagcaatg agggtggagg agtggggcag  125700
ccatggggag ggaagggagt gaggcctggt ggggtgaggc cagtgtggag gagccttgag  125760
agggtttgcg ctgatgtggt gtaggtttta gcaggatcat tcttattcct gagttgagaa  125820
tagccttgag ggggaggtga gggcagagca gggccaccca tgtgagaccc ggcactggag  125880
tggaatggcc caagtcagca tcccttggca gcatgaaagc aaaaccagca aggtttgctg  125940
gtggcttaga tgtggcatgt gagagagagc agggctttgg gggtgatttc agggtgagga  126000
cagggtggct gtgacaagg tagggcagac attgggggca gcaggaggtc agagcctgtc  126060
tggatgtagc agttgagacc ccataggtgc ctaatgaggt gaggccagca tcaggtgtat  126120
gagcctggag ttgtcgagag actgtggggc aggggggtcag catctgagat gtccactcac  126180
agtggaccca gactggctgg agaggaggag gagcttgaat accgagcctg ctgagtccca  126240
gctccaaggt caggtaggtg aggggagcca gtgctgggc aggggagta ggcaggtgtg  126300
gggttcctaa agccaagatt ttttttaagg cattttgtgc aggagggcga catctgctgt  126360
cagcaccttg ggaacttggc ccaggtttgg cagcaccgag ggcactgatg agtgcttttg  126420
gaggagcaaa gggagccaaa ccctaatggg aatgtgttcc tgaaaggaca ggagagagac  126480
ttgggaaaag gtttttacttg aagagggaac ggagaaatag ggcagtagcc agaggaggag  126540
aggagtcggc aatgggttaa gttggcagaa atgaaggcct gtttacgcac tgagggcaga  126600
agcaacaggg aggatcagtt catgacacag gagacacaaa tcgccgttgt ggtgttcaca  126660
gacatgggtt aggattggct gcatggatga cagagcactg tgggttctcc cagagttgct  126720
ggggaggagg cagagttggt gagcacaggc gagggtccag gatgcaggaa tcctggagct  126780
caagtcagtt gttcccttgt tgtaagatgt ggccagtgtt gtgagcttca catctgtgcc  126840
ttgaaaaaca ccacatctgt ttgcagagtt gtttactatg tatacacact cagtagaaac  126900
aaaaattgga aacagtcagt gcccaccatc aataagtaat ggttgaacac actgtggtat  126960
aagcttagac tattttagct tgggctattt tgcatgatta aaaatgttct ggccaggtgt  127020
ggtggctcat gcctgtaatc ccagcacttt ggggaggccaa ggcaggcaga ttgcttgagc  127080
tcaggagttt gagaccagcc tgggcaacat ggtgaaaccc tgtctctact agaaatacaa  127140
aaagtagctg ggtgtggtgg tgtgcgcctg tagtcctggc taactcagga ggctgaggtg  127200
ggaggatcac ttgagcccat tcgtgcgcca ctgcactcct ggggcacaga gtgagactct  127260
gttagaaaga gagagagaga aagaagagag agggagggag gaaggaagga aggaaataaa  127320
tggaagaaat ggaagggagg aaggggaggg aggaaggaag aaaggaagtt cagccagttg  127380
ccttgggagt tctccattgc actgggttaa gtgagaagag cagagacgtt tatgattttt  127440
caaaacaact aaaacaaaac ctctgtgggt gagggggcaa ggatatggct ataggaacat  127500
ggggcagatt aagaaaggga tatacacaca ccacttagca tttgttacaa ctgttgtggg  127560
agggatggag tgcagaaaaa gaaaaaaaaa agtgcacacc atcccatgta tgtgtataca  127620
aagggacgct tggaagactg gtccccaaaa tgttggtaat gattgtgtca gggtgctgca  127680
```

```
gtgctagttg attttttttc acacttttgt atatttgagt cttttacaga aagcatttat 127740
tatttatgta ataaaaatct aaatgacaag atttctgtta tgggaaaaat gtagctatac 127800
agtgttgttg taaaaatgtt tgcttggttc accactgaac ttaaaatgct tttaaatgag 127860
ggaaggtgac gatgagatga ttatgatgat ttgcccttga gttacatagc tggtgtacag 127920
gaagctgtcg tttcttttgg cttacgtaga aatgtttgtg gtgtctaatt ccacagatgc 127980
acattgactc tcatgaagcc cttggagtgt taaatacatt atttgagatt ttggccectt 128040
cctccctccg tccggtagac atgcttttac ggagtatgtt cgtcactcca aacacaatgg 128100
tgagtctctc gcctggctca gcagatgaat ctggacggct tgttcaggct ctgattactg 128160
ggaccaccec cagaatgtct gagtcagtca gtttgggtag ggcttcttga gagtttgctt 128220
ttttttttt tttttttttt ggtgtggggg tggtgcggaa cagagtctca ctctgtcgcc 128280
caggctggag tacagtgtca tgatctcggc tcactgcaag ctctgccttc cagcttcaca 128340
ccattctcct gcctcagcct cccgagttgc tgggactaca gcgcccacc accacgcccg 128400
gctaattttt ttgtatttt agtagagatg gggtttcacc gtgttagcca ggatggtctt 128460
gatctcctga cctcgtgacc cgcccatctc agcctcccaa agtgctggga ttacaggcgt 128520
gagccaccgc acccggcctt tttattttt ttggagatgg agccttgctc tgtcacccag 128580
gctggagtac agtggcgcta cctcgactca ctgcaacctc cgcctccgg gttcaagcaa 128640
ttttcctgcc tcagcctccc gagtagctgg gactacaggt gcgtgccact gtgcccggct 128700
aattttttgt attttagta gagacggggt ttcactgtgt tagccaggat ggtcgcgatc 128760
tcctgacctt gtgatccgcc cgcctcggcc tcccaaagtg ttgggattac aggtggctct 128820
cgcaccaagc caagagtttg catttttagc aaattcccag gtgaaactaa tgcctgcttt 128880
tctgggagca cactttggga ctcagtgata gagaggttta ttggtaggat agtaaaatag 128940
gagttatttt ctttcacaaa attggcaatt gggggaaatt taatcttcct ttttcttca 129000
gctgtgactt atgtattatg tttatttag gcgtccgtga gcactgttca actgtggata 129060
tcgggaattc tggccatttt gagggttctg atttcccagt caactgaaga tattgttctt 129120
tctcgtatc aggagctctc cttctctccg tatttaatct cctgtacagt aattaatagg 129180
ttaagagatg gggacagtac ttcaacgcta gaagaacaca gtgaagggaa acaaataaag 129240
aatttgccag aagaaacatt ttcaaggtat gctttctatc tgagcctata actaacccat 129300
gccttttggg aagtcacgtg atgtttcaca gtcagtaagt ctggaataat acctggtctt 129360
gcttcacttc tgagttgggt aaagaagtct gtatcagtgt aattttctaa tccgtcctgc 129420
attatctatg gctcttggtt catacctgtc ttgaagttct gtcatgttct gtctcttgtc 129480
ctcagtagag atgctacagc agtggctcgc ctcaggcagg gcagggcagt ggggtggctg 129540
tcctggggc aggcagtagg ggcacgctga cgtcaggaa gttgaaaccc aagagaagcc 129600
agtaaaagtg agtctcagat tgtcaccatg tgctggcagt tttacacgct gtcagtaata 129660
aaagtcttct ccctgcaggg cagcctgcct ccaataaata cgtgtagtat caaatcctgt 129720
cttccctcat aaattgtttg gaagctcccc aaggacagtg atgaggcact cgtaagtgct 129780
tgctgcctag atgggtccct ctccacctt gctagattct gagcattcac tgagttagag 129840
ctgcttctgc aaatgtgctg cttctgctaa gtggctgtga cttcatgcag ccttcacttg 129900
gtttgtcatc agtggagatg ccctgtgttg tcgaaggaga taagcccagt aagcctgctg 129960
ggcacctttt ggtttgcagg ttcagcaggc agcccatggc tttccctgtg tcgcattgaa 130020
gcagctggct aaaattgatg atacattaaa ttcctgtgac agatgatcag cttgtatttg 130080
```

-continued

```
tgtaatggtg tacagttcac aaagcttaaa aaaatgctac ctgccatttc atcctcagtg 130140
aggaaggtga tacacagaga gaccaagtga ctgtgtccac ggcgacggcg ctctgcattt 130200
cactttagcg gttaatgtac tctacctata tttttacttt atatttacca tatatctttt 130260
catgtatact tggcgtaagt gctttatagt agtcacctaa ttcactgtca tctttttgt 130320 ttcttggaag gtttctatta caactggttg gtattctttt agaagacatt gttacaaaac 130380
agctgaaggt ggaaatgagt gagcagcaac atactttcta ttgccaggaa ctaggcacac 130440
tgctaatgtg tctgatccac atcttcaagt ctggtaggtg aatcacatta gtcttcctgg 130500
agtgtctcgt tccccattct gcactataca ctctcagagt gtaggagctg tgctgcccgt 130560
tagaaactct gccttgccca gtgtgccagt tgaaaatatt tgttgctgta agagtacacc 130620
tgataccatg tgacccagca gttccactct tgggtatata cccaaaagaa tggaaagcag 130680
ggtggtgaaa agatatttgc atgccagcat tcatagcagc attattcacg atagctaaaa 130740
tgtggaacca actgaagtgt ccctcgatgg atgaatggat aagcaaaatc tggtgtatat 130800
ttacagtgga atattattca gccttaaaaa aaggacattc tgacacatgc tacaacatgg 130860 gtgacccta aggacattat gctaaatgaa ataagccagt cacaaaagga caaatactat 130920
gtgattccac ttacatgagg gacctggagt agttaattca tagatataga aagtagaatg 130980
gtggttgcca ggggctgcag gggagggggag ttatttttac aagatgaaga gagttattct 131040
agaaatgaat ggtggtgatg gttgtataac attatgaatg tacttaatgc tactgaactg 131100
tacagttaaa aatagttaag aggaccaggt gtcatggctc atgcctgaaa tccaagcact 131160
ttgagaggcc aaggcaggag gattgcttga gccaaggagt ttgagaccag cctcagcaac 131220
atggtaggac cccatctgta caaacaaact agccggggat agtggtgtgc atgtggtccc 131280
agctactcag gagactgagg ctggaggatc gcttgagccc aggaggttaa gtctctagtg 131340
agatgtgttc atgccactgc actccagcct cggctataga gtaagaccct gcctcaaaaa 131400
aacaaaacaa aacaagacaa gagccaaaaa tggttaagat gggccaatca cagtggctta 131460
tgcctgtaat cccaacactt tgggaggtca aggtaaaagg atcacttgaa gccaggagct 131520
tgggaccagc ctgagcaaca tatcgagacc cctatctcta caaagaaaat caaaaactag 131580
ctagatatgg tgggcacatg cctgtagtcc cagctacttg ggaggctgag gtgggaggat 131640
ctcttgagct caggagttcg aggctgcagg gagctattat tgcactccag cctgggctac 131700
agaatgatac cctgcctctt attaaaaaaa aatccaaaaa aaaaaaaaag taaacctgag 131760
agcttcctcc tcctgtgtta aatttggagg ccaagatgtt tttgttactt ttacaaatga 131820
tcaaggacgg tgaaggttgg gcatggtagc tcacacctga atcccagca ctttgggagg 131880 ctgaggcggg gtgatcgctt gagcttgaga ccagcctgga caacatagca agagacccca 131940
tctccacaaa aataaaaaaa taaaaaaaaa tagccaggag tagtggcatg agcctgagcc 132000
caggaggtca agctgtagtg agccatgatc atgccactgc actccagcct gggcgagatc 132060
gagaccatgt ctctagagaa agaaaatgac aaggacagtg aacccaagaa agtcataaga 132120
tgccagctgt gcagcaagca tggaaagcag ccagtccaaa ttaggacagt gtgttttcca 132180
agaagaacga tcgtttgtaa tgagaatgct ttgctttaaa taaatgacta aatagctaga 132240
agcctagttc tagggggatag gcacgtcttt cttctctcaa gaaaatagaa aggcaattct 132300
aatttctagt aacagcaaac agcattaagt catggtccaa atatgaggca aaccaaaatg 132360
tggcttgatt gttcagcagt tgatctgttg gaagcccttg atattaaaaa ggttctcctt 132420
```

```
taagcggctt aggagtcacg atcaaagacc tatagaaaga gatgccatcc ttctaggatc   132480
cttggctctc ttgggaacta gattcagata gtcataatgt aaatactgct tgagctttct   132540
ttctttcttt ctttctttct tttttttttt gagacagagt ttcactcttg ttgcccatcc   132600
tggagtgcaa tggtgccatc tcggctcacc gcaacctctg cctcccaggt tcaagcaatt   132660
ctcctgcctc agcctcccga gtagctggga ttacgggcat gcaccaccac gcctggctaa   132720
ttttttgtat ttttagtaga cagggtttt ctccatgttg aggctggtct cgaactcctg   132780
acctcaggtg atccacccgc ctcggcctcc caaagtgctg ggattacagg tgtgagccac   132840
cgcacccggc ccgagctttc attttttgaaa tcaatgtatg actgaaacac tgaagactta   132900
ctgacttaat tatggtttca gaacagaatg aaaatgtctt cggttctgat gaatataaaa   132960
ggaaaactaa ccaagttaat ttggcaagta gatggtagag atagaggtgg ggagtggaag   133020
gggaactaaa atcttcacct agcattgttg ggattatatg gttacatcat ctgaagttga   133080
cagaccaaaa tatagaggct tcagaggtct ccaaatagaa ctaaacatgt aattcagatt   133140
gttaggaggt agtataaatg agctaaatct catctttatt acggtagagt taatgggtga   133200
tgtctaaagt tgtctgaagt ctataaatca tgacaaatta tgatgtggtg attgtattca   133260
acagtctttc agttgcaggg ataaaacccc agtttaaact agagtaagag aaagaatgtg   133320
ttggtttaag ctcctggaaa gtgcaggcaa gggtagttgg taggactgca tctagtgttg   133380
taattctgtg gtctgcattg tatatttatg catctcagct ctgctttctt cttttcattt   133440
atataatttt taaattttat tttaaagata gggtctcact ttgtcgccta ggctgaagtg   133500
cagtggcatg aagtgcagtg cgaggctcac tctagcctcg aactcctggg ctctagagtt   133560
cttcctgcct cagccttcta agtagctgag acaataggca tgtaccaaca tgcctggata   133620
ggttttaaaa tttttttgta gaaatggaag tcttgctgtg ttgcccaggc gggtctttaa   133680
ctcttagctt caggcgatcc tcctgcctct gcctcccaaa atgctgaggt tataggtgtc   133740
acccaccacg cccagtctca tctctgcttc ctgtgttagt tttgttctct ggtgggctgt   133800
tttcacatga ccgaagatga cctctagcag gctgtgttct cagcccctca gtaggcctta   133860
tgtgattggc cttgcatgag taatatgggt gaccataaac ccctgaatgc tctggtccac   133920
atgggccaaa tgggagactg gacagcattc cattgatgag gaggtgggc tggtctccgg   133980 gagtaaggga gaggagcaca tgcagtaact gatggtctgc tgcaagggat agcagcacag   134040
cagttagaat tttggaggta actaccagaa ctgaaaacag aaatgataac aagtagttgc   134100
cttaaaaagg gatgggagca gggtgctttt gtgatcaaag ctccttctc ttactggatt   134160 tttgtacaca ttttgcatac atatcttaga gtaaaagata gcattttcag ccttggtcca   134220
tttgaggata ctcttggcgt ggcccgcctc catgctagca ggctctggtt gtgccaagtt   134280
cagttgagca tcctggctct tgcctgcacg gaacttccag tcagtgcgtc agtatcacaa   134340
gtcttgatat ttcctatgaa gaagaacagt agtgcagtga cagacgaaat gggtgggcag   134400
gcagaggcag gatttctgag ggagagaagt agctagcttt ttgcagagaa gagttccggc   134460
acccaagaga gcagctgaga gtacaggcag gcaggcagga tgccggtagg gcccggccgc   134520
acggcgccac agaatcctgg agaaagggc ctcttcatgg cctctgcatt cagctgctgt   134580
caccctccgc acaggccatg gccaaaattt aattttcata gtggactcta gttttgagc   134640 cttacttgct attattgaaa taattttctt gtttcttttt aaagatcttc ggattatgct   134700
tcactgacca ctgtaataag tttaaagttg agaaaatatg gcttgttaat gaatgatagg   134760 tcaatttag tatgttggtc attttaatat tttgccacca gttggtttgg atttgatgcc   134820
```

```
aggaggagac agcctcattt ctaaggacta gtcttgcctt tgtgggataa gggtggtgtg   134880
ttctgtgtcc ttctacatgt ccgagcgatc tctgtgcagc tcaaatgtgg tcactgtctt   134940
attgcgctga tttcctctcc ttccatctca caattgaggc aaaatattgt tactgttgaa   135000
gtgttgtcca ataggacttc cagcagagac aggatgtctg cactgtctaa tttagttgcc   135060
tttagccaca tgtggtgttc tgtacctgaa atgtggctgg tctgattgga tagcttaatt   135120
tataatttta tttaattta attaacttaa atttaaacag ctctgtgtgg atagtggctc   135180
ctgtatgaga cagtgcaggt ctgttgagaa gcagctttac tggtgggagt ggagggcttg   135240
gagagggcac gtgggtttcc tgctggtatc ttttgacctt atttaatctg cccaacattt   135300
gcaagtaagt tgtgtgtgtg tgtatatata aatgtgtgtt tctgtcttct tgtttccttt   135360
gactgcattt atttgaaaga cactaggtgg cagaattact gtatttgatt ggtttcaaga   135420
taagagttga aataattcat ctcgtgtttt tatataagta aggtgtgttt agcatgtaaa   135480
attggtaata tgtattcacg tactgcttaa acaaaggcta tgaattccac ccataaaccg   135540
aaaatgaaga cctttaaatt tgtccatttc aggcgtgggt acttcttaaa taatacctgg   135600
ttcaggaact agtcagaatg gcacccttga cttttttgttt cctgcttttc ctcttgttgg   135660
gagaggaggg tattcatccc aaagtggttt gcctatttca cattccatct aggataagca   135720
gaatagccaa gaaagatagc tgtcctcctg tttacaacat tgggggtaac cagcatccct   135780
ctcttttggt ccaagataga ctggtttaga aacagatgat ggcaccagag gcccaggagg   135840
tggaaacatc agctttgttt gttgtccatg tggctgaatt agagctgtct ggccttgtag   135900
cctcaacacg gccttccagc tttgctcacc gtgattttca aggacacatc ttgtgctctt   135960
ccctgcctgc catccagact atcccagtc agggtggcag gagctgctgc cccttcctcc   136020
ctgagtcctg gtcgtgggtg gtggagatgt gccatgacgc tcacggaggc atgctcaccc   136080
cttcctctgt ggcagagggg atggctgcac gacagctctt ccctgtcctt tccaaagcgt   136140
ctgtggttcc acttttttggg gcaaagcagg aatactggaa gagagagaaa gtggtccttt   136200
ctatagtaat aaagttgaca ttgattcaag ttcatgcttg gggaaaggac agggctacta   136260
acaattataa tgctgggagc aatggaattt tctcatgggt atgtggtagg tttaattta   136320 attatcccag ttaattctta gaactgctct gtgaagtatt tcccgctttg tgcttaagtt   136380 ctaaagatc ctgtgccaaa accaagaatg aaaacccaag cattctttct tgcccatcga   136440 tcttttctctc atcaggccac ttcttgggtt gatagtggtg agtgtagccg ctgccacttt   136500
cagaataccc accatgggcc ccagtcactg tgtggcgtgg agaagagatg gttctctctg   136560
tgtcatagct gaacaagccc agcccagaga ggtttctgcc ctaggagctc tcgatggtgg   136620
aattgggatg cgatcccaca tcctgcctgt tttgaaaaca gcattcttta tttccaattc   136680
ctgcttccat tgttcctttt aatatttctt tgtttagctc acaaaaacac ggcttgcgga   136740
gctgctgcgt gcagctgtag ctgtttctct gggtgcagcc tgcatccgcc ttcctgcccg   136800
cctcctttcc tgcactgcca tcgtggtctc cgggcacttg gtccctttct cttcccctga   136860
gtccctttgg ctcccctgtg ccaccttgt gatccacagg ctctgccttc tttctgtctc   136920
agactgctgc tcatcactac tcgggaccct aggaagggag gttccaccga gaagcatctt   136980
ctcatctcag ccacgttctc agtgccactg ttgtctttgt taggtaatgg tagctactgt   137040
aacaaataaa ccaacatttc catggcttca caccagagaa ggttgtttct tggtttatg   137100 acaatgtatt gagggtgttc ttggttcacg gatggttttc ctccatgtgg gaattcgggg   137160
```

```
acccaggctc ctttccttct tttggttctg ttctccaggc cttcacatcc tctgtgtctg    137220
gttggggaca aggagaggga aggtaaagaa ggctttgtgg ccttggataa gtgacaggca    137280
tgcctttgct ggtgttctct cgtggtgaca ggtcacagcc ccaccctgta aaggggact    137340 gagagacgtc gtcctgctgc ttcccagcag cagcactgtg gtctctgatg tgttttctgt    137400
gaggataaaa acaggtgatt ccaggatgag gaaagtcagg gaaacccttg gaaggagggg    137460
accaggcggg tgtcaccatg ggattagtgg tggcttcaga atgagctgca gcgagtgcca    137520
tgccttctaa agcttttgct attctgatat gcccacacca tgcccagcag gtgtctgcct    137580
tgctctccgc agagagagtg atgaatcctt ctcatgagcc tctgtccagt tgttcctccc    137640
tccacctgga agggaccctg ggttcctcat aacatcccag cggaacaggg gaccttctat    137700
cctgtcccca agttcatcct catcctcctg ccggcttcct ggcccctctt atgtctgctt    137760
cctgacgcca catccttctg gattctctgg aattgaattt tgcctttgat gcttatttaa    137820
aaatatccat tgcaggccag gtgtggtggc tcacacctgt aatcctgtgc actttgggaa    137880
gccaaggtgg gcagattgct tgagcccagg agtttgagat tagcctgagc aacatgttga    137940
aatcctgttt ctatagaaaa tacaaaaatt agctgggcat ggtggcgcac acctatactc    138000
ccagctactc aggaacctga gacaggagga tcaattgagc cccggaggcc aaagctacag    138060
tgggctgtga tcgtgccact gtactccagt ctggtcaaac agagtgagac cctgtctgaa    138120
aaaaaaaaaa aaatccattg catacttcac cgtagcgaaa catgtatgtc ttacctttcc    138180
tttcctgcct gtagctgctc ttttacactt aacagccaca ctaagccagc cttaaatgaa    138240
aaacaaacca gcacttcctg tgccctcctg cttccttcat gaggggtccc tccctctgtg    138300
tacactccat tctcattgcc catggtggtt tgtttccctc ttgtttctca agccatggca    138360
gcctgcctct tgccctcttt actaaaaagg cctttgcaga ggctgcctgt gttctttctt    138420
tctaggtctc tctcatccta ggccctccag cttgattctg tggagctgcc ctcttgtcac    138480
tcagtagctt gtgggtctt ctctgtctag ccacttaatt gattgtgttc ctcgagttgc    138540
tgtccatggt ctctcgttac tgttttctct gtgtttctgc ctctctcctt ggccttggta    138600
ggtccatccc ctttgtgacc ttggctgttg ctctcatgga caactttctc ttgctggtcc    138660
ttgtagtcct ggcatccagc ttctcgacac gggacttgtc ctgccagtac ctcagacttg    138720
cacttaaaat tgaactagca ccactgtcac tctccagggc ctcttcttgt taattagatc    138780
attagggatg ttcagaatcc cagcatcata gtatgttcct cctcccgcta ccccaggaac    138840
cctaacctta cctcctcctc tctatctact aggaggtggc cctcagagtc cgtctcatct    138900
tccacctgaa cttccctaat aggctccagc agctgccacc ccgggggctg agtacttcct    138960
ccatgccttg tgcagtgctg agccctttac ctgggttctc ctgtttgctc cttattacag    139020
ccctgcgaac agatactgct cttaattcca tcttacacct aaggaagctg aggccccagg    139080
taaggtgcat ccaaggtcac ccaggtagta gacagtagag ccacgatctg aaccaggcag    139140
tctgattcag agcctgtgtt gacactcagc cacctagaac acagcttgga ttgtgggttt    139200
ctattacctg ttcaaaaccc ctacatcccg ggtctgtccc tgcacgtgct ctgtggcctg    139260
gctgcatctt ccttgaaggc agtgcatgcc tcttcactca gggggcccat gcaggaacag    139320 agggcccac agaaggatga ggccagtgca gaatgggctg gaggggacaa tgctgaccag    139380
gaagcaagtg tagagaaatc ccaggaaacc tggaggagcc agagacaagg cattagaact    139440
cctcgtcgtg acctggtctg cattctctga gtgtgctgct tctgttagct cgcttccttg    139500
gtctcaggtt atagtttaag gcattgtgga gccctaaaaa gcctgtactc tgttttacc    139560
```

```
tgttttagga ccctttcact ttggggatgt gttgatttt ttttttttt tttttttttt    139620
tttgagatag agtctcgctc cattgcccag gctagagtgc agtggcacga tcttggccac   139680
tgctgccct  gcctcctggg ttcaagcaat tcttgtgctc ccgcctccca ataccctggg   139740
attacaggca cccgccacca cactcggcca attttgtat  ttttagtgga gacagggttt   139800
taccatgttg gtcaggctgg tctcgaactc ctgacctcaa gtgatctgcc caccttggcc   139860
tcccaaagtg ctgtgattat aggcgtgagc caccacaccc ggcctgaaat ttaaatcaga   139920
aataaaattt tgatcccaac agtgatgcca ggcagcccag atctggggga gagggtggcc   139980
ttggccagct gggcctttct ctgtttccca agtcttgctg cctctccctg ctgggctttg   140040
cagcctgtgc atgtctctgt gcctttgacc ttgtttatcc aaaggagagg atagaatgaa   140100
gtcatgattc ctggagccct gagaaggatg ctgtggagaa atttgccggt agaatctagc   140160
tgagtgtgtt gctgaggtgc cagcattgtg tgtggggagg ctgaccgctt ggcctgccta   140220
ggcccaggat gctccatggc cgggcacaga ggccacttgg ctgtcaggtg tcaggagcct   140280
gcagagggca cacagagcct ggaccgcagg ggggtcctgc tttctcacct ggcctccttc   140340
agcatttctg tccctcagtc cttagcaagc ccaggagctg ttgagtttgg caggtgccga   140400
gtgctgttcc tgcctgtgta gctgtggctc agtcctgtgg gggcccgct  gtggcccgag   140460
tgcagtgatt cgaggcgctg agtgttccct gactccttct ccaggagctg tgttcagact   140520
ttcgcagctc ttggcttgga gctcctggag gcttggcat  tgccgaccaa tgtggaggtc   140580
gacagtgaga gaggaggaat gctagctttc ttgaccagtc cattaaataa gtgggatatt   140640
ggccaggcac ggcggctcac gccttaatcc cagcactttg ggaggctgag gcgggtggat   140700
cacgagctca ggagttcaag accagcctgg ccaacatggt gaaaccccct ctatactaaa   140760
aatacaaata ttagctgggc gtggtggcag gcgcctgtaa tcctagctac ttgggaggct   140820
gaggcaggag aacagcttga aaccggaagg tggagtttgc agtgagccaa gattgcgcca   140880
ctgcactcca acctgggcaa caagagcaaa actctatctc aaaaaaaaaa aaaaaagtag   140940
gatatctgtt tctgcttaga aaaatcagaa ttttctaaat gccaggtgtt ctgaatacgt   141000
aagtatggga gacgactcag cctgtttcat ttttatgtaa aatcttcgcg tagccatgtg   141060
gcactggacc gagatgaaag caaagacatt tctccttaac tttgtttcta ggaatgttcc   141120
ggagaatcac agcagctgcc actaggctgt tccgcagtga tggctgtggc ggcagttcct   141180
acaccctgga cagcttgaac ttgcgggctc gttccatgat caccacccac ccggccctgg   141240
tgctgctctg tgtcagata  ctgctgcttg tcaaccacac cgactaccgc tggtgggcag   141300
aagtgcagca gaccccgaag taggttcata atgccccaca gcccagggcg ccagcccagc   141360
accctgtcct gagactccca gtaacctgag ctttggccac cgttaaagca ttttcatttt   141420
ccatttttg  tgagggcttg tgaaatttct gctgcatatt aatattcctt tcatggacag   141480
catattattg ggacaaacat gcggtccagc taaaggcatt caaatagca  gttgcttct    141540
aaatgcgatt ttctttggca ggttctttga caccattgca tcttgtggga tatgcttgtc   141600
atgctctgtg gctcctacta agttctagtc cttaaattgg ttccatagcc agacatgttg   141660
caatgtctta acctcattat aaagtaaatg tggttctggt tatccttaga taatgaagta   141720
acagtgtagc aaatttcaaa acctcttgga aatgttattt taccattcaa aaaggcttac   141780
taaggttctc gttatgggtg gccctctttt tgcaaaaggt tttcaggctt aagctccatt   141840
tctaggtgct ccaacactcc attatttgta tatgtatgga aataaaagct gtgaccaccc   141900
```

-continued

```
ccaaccctgg cccccgccca gctgaatcct cagcacagta tttctggaag gctcaagatc  141960
ccacgctggg gaaaagaagt tctggagaca aaagagggca ggtgctgccg tgcctctctg  142020
ctcagtatgg atactggacc ttgtgctgcc agggctccca gtagggccag ttcatggcac  142080
tcagctggaa agtccactgt tgggaggcat tcttaaccat ccactctgtg ccgtatgtag  142140
tggggtctgg tcattctgtt ggaggagaca gaccagtgac gacatttgaa atgcttggtg  142200
gatgtcttag gcctgttacg atgactgagc actgtggggg caggagacag aaagtcagtg  142260
tctcctagtt ctgtgctgct ttaacgtgca tagaaatcag ctgcggattc agcagatcac  142320
tcctttctg acagatgggc ctgcttactc tgatgttata tcagaaagct ctgaatctgg  142380
gaattgtgtc ccctgaattg gagtaacaga aatgcttaga tgatgagtgt ttaaaagaaa  142440
taaaccaaag gtaaatttag tttggaattc agcaagcgtc ttcattcagc cctctgaggg  142500
caaactacag cttttttgtaa atgtaggtaa attctgtgac tgtttcgtga cccctctga  142560
tccagttttc ctttataacc ttctgtattg ttccttctat tatcctgaaa taacattaat  142620
agattaggct gggcgtggtg gctcatgcct ataatcccag caccttggga agccaaggcg  142680
ggcagatcac ctgaggccag gacttcgaga ccagcctggc caacatgatg aaatgctgtc  142740
tctactgaaa ataacaaaaa ttagccgagc atggtgacag gtgcctgtag tccctgctac  142800
tcagaaggct gaggcgggag aatcgcttga acctaggagg aaaaggttgc agtgagctga  142860
gatcgcgcca ctgcactcta gcctgggtga cagagtgaga ctccatctca aaaaaaaaa  142920
aaaaaaaaa aaattaatgg atcaatggat ttttaaccta ataattaaat ttcaaaaaat  142980
atcgttcttt aatggtaatg taaaggtaaa attaagataa tatgtaacaa gcatgtgagt  143040
gtctaaggtg tccccgtggt ggaaggaaaa aataaatccc cataagtgtc caagatgccc  143100
atagagagca gagctgttct ggtttaaacc cctgctctta gcactgtgtt tttccagctg  143160
tgggtggtgg gggatgagta tcttttttatt tccatgagat gagaaaatg aattactaga  143220
agtgtgaaat acaaaacaca gctgctcttt ttttagccat agactcagca gccataaaat  143280
tgctgtatcc agttgcagaa attcctgctg cttactcttg accctctctc ggtttgtgtg  143340
catctcctct caggctggct cccagatggg agctggctcc aggcgacact gggtgctctg  143400
ctccaggagg tccttatgtg ggtcctgccc tagcctagcc cctctcttat ggactctgtc  143460
actgtgggtt tatgattcac tctcaatctg tcttacctct tggtgaactg ttagagtcct  143520
gcctatactt tggcgcttgt gggtgtgttg tggtacacat gatgtgttgg tcacttccca  143580
gctcatcttt ttctgagtca ccctagattt gggacattca ttcgccacca gtaccgggcg  143640
gtgtatggcc tgagatttgg gggggcttgt gctgctacaa attggggctg aatttgagtt  143700
gacagtggac cttctttatg tctactgctc atatttgaat tgcaaatact gcctcttctc  143760
tttcagaggc tcattaccct atagctgtat tattgcaaag tgcacaatta cagcttgagt  143820
gtaagtcaca ctgcgctggc aggacggccc actgagaaag gcacgtttc ctgttcgtta  143880
gttttcacat tgacacataa tttacaatac agtaaaatgt acttttctat caactgtagt  143940
cagtaacagc cccctcccc caaccacatc aagatataga ggagtgctgt cacttcaaac  144000
agttccctct tcctctgcca catcctgccc ctccccaggt ctaaccacca atccgtgctc  144060
tgtccctctg ttcagcccat tgcagaaggc catagaaata gaatctatag gctaggtgtg  144120
gtggctcatg cctgtaatcc cagtattttg agaggctgaa gtgggaggat gacttgaggc  144180
tgggagttca agactagcct gggctgccta gcaagacccc atctccagaa aaaaaaaatt  144240
taaaaattac aatcacgtcc ctgtagttca gctgcttggg aggctgaggc aggaggatca  144300
```

```
cttgagctca ggagttagag gttacagtga gctatgatcg tgccactgtg ctccagccta    144360
ggtgacacag caagacgttg tctctgggga aaaagaaag aaacggaacc acgcggtgtg     144420
cagccttctg agtctggccc ctttcggtga gcagtgtcta aagttctgtc gcgtgttgcc    144480
cacgcgtcgg tggctcgctc cttgcaactg ctgagcattg tatggctagg ctgtagtttg    144540
ttttcacttc accagttggg aaacagagaa aaggcacttt ttaaaaagtt taaatctgta    144600
gaattttggt ttttaccagt tctcttctaa atcctgaggg attacaggaa aagttgttgt    144660
atttcagaat attcttagct tgatgtgacc tctgtccccg ttaaggccct ttgccgcaat    144720
gggaaggacg tcgctcggtc agaccctgaa ggtcagaggg gcagtttggg agtgtgtcaa    144780
cattttaact gtatggacta gagccaagag tctcaaggtt tataattccc acgtattcaa    144840
aaagaaaaaa acaataaagt gagaagtcag tgtagagtga aataacctgt gttagtgggg    144900
aagaagtgtt tttaaacagg atttccataa cgtataacat caacatgttt agagtggtga    144960
tgtttcattg ggaaacgaac agtaaaacat gaaagcaggg aggttttcat tctggcagtt    145020
ggcaactttc acggcagatg gagaatttca aaagcaattg ctcaattatc aaacatagcc    145080
agtgtgagtt ctgaaataaa ggtgctgatt gaatgtgcag ctttatggtg gattttgcta    145140
ttcaggcaag cattttaatt ttctgcctgt taaattctgt tttctttagt ttttcatatg    145200
tggtttattg tagcttagga atagataact gagagtatat attacacata caacattctg    145260
atatggcaat atttaaaaca acttgtctgt tttagaacta gaattaaaca taatcatctt    145320
cagtattttg caaataagct cactgccatc cagaaacatt gtcaatgcat ctgttgctcc    145380
ttctagaaga cacagtctgt ccagcacaaa gttacttagt ccccagatgt ctggagaaga    145440
ggaggattct gacttggcag ccaaacttgg aatgtgcaat agagaaatag tacgaagagg    145500
ggctctcatt ctcttctgtg attatgtcgt aagtttgaaa tgcctgtaaa cggggttgag    145560
ggaggtgggg accaggagaa catcctgtgt agatgacact tgcatggacc ctctggaacc    145620
cagaccgccc ggtgtcctgc caagctccat cgaaactaaa tctagaatga atgtttactt    145680
ctgctgtgac atataattgg agaccaggcc tggccttcca gtcactggat tctaagttgg    145740
actgtgagag tttttgcagc tgactcattt atcaaatgcc cggctattgg ctcacgccta    145800
catgatgctg ggtatgtttg ttaatttgag ggaagcaatg gaataataat aactaatgat    145860
ttaaaaaaca aagtaagtgc attgactgta gtggggttct gattttaaat tttttttaaaa   145920 attaatacca ggagcagtgg cttatgccta aattccagca actcgagagg ctgaggtagg    145980
aagatcactt gagcccagga gtttgagaca agcctgggct atggtgtgag acacccatct    146040
ctaaaaaaat aaaaaataaa aaattatcca agtgtggtgg ctcgtgcctg taatcacagc    146100
tctttgagaa gctgagggcg gaggatggct tgagcctggg agttcgagac cagcctggca    146160
acacagagaa accctgcctc taccaaaaaa agaaagagag gaagaaagaa aaattagcct    146220
ggcgtggtgg tgcatgcctg tggtcccagc cacctgagag actgagaagg gaggattgct    146280
tgagcccaga gtttgaggc tgcagtgagc tgtgactgtg tcactgcact ccggcctggg     146340
tgacaaggcg agaccctgc tctaaaataa ttttttaag ttaatttgta gaaaaggtgt       146400
tagatgttct ttgtcacatt ttatgatgga ttcctgttta aatgccgttc tctttaaaga    146460
aaaaaaaata acttgtggga gtttttaacc ataaaactag catcacatat ttaccatgga    146520
gaatttacaa aaaaacaaat aaacggagga aaataaaacc tcctgtaatc atactactca    146580
gagataactt gctgttagat tttggtctag atttaatact ttttctatat ttatattaaa    146640
```

```
aatatttaaa acatatgcat ttctttgtca caaacatggt atcttataga tactactgtc  146700
acatagcaaa acagtgttaa atattctgaa tcagaaaagg aagccgactc tccaactgaa  146760
agaggtgtta tcctagagac ttttttctggt gatgacaatt tattaatagt cacttttttgc 146820 tttactttct ctattgaagt agttttctcta ttttgttcta cttttaagga taatataatt  146880
tataatgctg ttttttcacag aaatataaga aaaagatac taattttata agttaataaa  146940
gtttgatcat cccaaatcca aaaatctgaa atccaaaatg ctccaaattc tgaagctttt  147000
tgagtgctga cattatgttc aaaggaaatg ttcattggaa ggtttcagat tttcggattt  147060
agggagctca acaaataagt ataatgcaca tatttcaaaa cctgaaaaaa atcctaaatt  147120
cagaatactt ctgatcccaa acatttcaga taagggttat tcaacctgta ctgtcagatg  147180
atcccaaatg aaaatattta atcgttaacc aaatatcaag gaattgatca cattttacag  147240
tttctgccta ggattatgaa tcaagatgaa aaggctctgc atgtttaaaa atatatattt  147300 ttatttctt ataaatctta aatatctaca cttaagattt atttgatatg tgggatccat  147360
tcatattttg gattcaacag ttctgtcaaa actgtggcag tgatagggga ttctttttttt  147420 cccactgaac tatcacaaaa ttggaaaaag agtaattgga gaaccccact ggcttagccg  147480
gcccgaagcc cgggagaggg caggcagtgc tgtggatggg gtcatcccag cgcaacgctg  147540
cccctgctac ctgcggatct cgctgaggcc tgcctttgtc ctttgaccct tggccatttg  147600
ttagtgtctc tgagagctgg actgctgtac cctacttccc caggggggcct aacttcacac  147660 agcctctgcc gcagtgcgtg gttggaggtg acggccttgg taaatcgagt ttcctacctc  147720
ctcaattatt tgtgctcata cactgtatat ttttagtgag gttatatttt gggatgtgtt  147780
ttctccttct taccctttct ggcctttcta tggcattaat acctggtctc ttcttgtgta  147840
cttgaaaatg aatctctcat catatttttc cttagtgtca gaacctccat gactccgagc  147900
acttaacgtg gctcattgta aatcacattc aagatctgat cagccttttcc cacgagcctc  147960 cagtacagga cttcatcagt gccgttcatc ggaactctgc tgccagcggc ctgttcatcc  148020
aggcaattca gtctcgttgt gaaaaccttt caactgtacg tcttcatcct gccgactatt  148080
gccagttgca gttttcccctg ccttaaaaat ggagtattga aattttttaac tttaatttct  148140 gatttgcaaa atagtcatct tttgttcttt tccttcttgc tgttagccaa ccatgctgaa  148200
gaaaactctt cagtgcttgg aggggatcca tctcagccag tcgggagctg tgctcacgct  148260
gtatgtggac aggcttctgt gcacccctttt ccgtgtgctg gctcgcatgg tcgacatcct  148320
tgcttgtcgc cgggtagaaa tgcttctggc tgcaaattta caggtattgg gaagagaaac  148380
cctgatattg atttatattg aaaatttagc aggccaagca aaacaggtgg ctggcttttt  148440
cctccgtaag tatggtcttg acatggtcac cgatagaaac atggaaacat ctgcaaactt  148500
gccgttactc gtgtgtccga tctgactgtt tcttgtattt ttttctagtc tgcccttact  148560
aggatgaact gtacacatca gttcatcctt tttaaatgag catgaggtta ttttgggttg  148620
ttaggtgtta caaacacact aatgtgtttt tgtctattag agcagcatgg cccagttgcc  148680
aatggaagaa ctcaacagaa tccaggaata ccttcagagc agcgggctcg ctcagaggta  148740
atgctgaaaa cacaggtcgt ccttgtgtta ggacaaccca ggatataaag gatatagatt  148800
tgtacgggaa taaattcaca ggacaagaaa tcgatgtgcc ttataggtgg gtttactgca  148860
gaagtgccat aatagaacct tcctacttttt aaaacaacca gatctcactt tctaaagagt  148920
aaaggatgac cggcaggatc acgtctgtga cgtgagtgga ggcagtttgc actcctggtg  148980
gctgtttgag aggtagcatt tagaatgcct gtattcactg tcctgtgatg agtgggaaaa  149040
```

```
taggttatca ggtttatctt agcaaaatca aagcatgtca tctaattgct aaacaagagt 149100
tggcaaatct gagagacatt actcaatcct tggcatgcag gacttacatc tgcatcctgt 149160
tgccatttta tgtcttcaaa gcatttaatc atttagttgt gtttgcaaag tctttgagaa 149220
gcctttgtca gaaatccta catctcctat gtgagtgtat ttccatgact gcagaataag 149280
ttaaactttt acctttttcc ttcccttgcg gggcggggtg ggggcaggg attgtgtgtg 149340 tgagagggag agagagacag cagagaagga gaatataatt atcatgctgt gtactttgag 149400
ctgaaactgc aaaaaaggaa aaacacacaa aaattattat gcttttcagt ctttagagta 149460
ccttgtctat tatgcttttc agtctttaga gtaccttgtt gatggtgttt ttaaatggga 149520
ttgggcacaa ttaggtggac agtttgggat gattttcag tctgtagggc caagctcttt 149580
tgtaatttgc attatgaagt tgtcactctc atagcagatg gcgggagata aactattatt 149640 acttttgac cctagactta gtcttcagtc cagatgaggg agattaaaag attataaata 149700
tcttgtgcca gatgaggtga ttttattttg aaatgaccat gaattcctat cagttgtctt 149760
actgggatat ttgatagtgg aatttgtgca tttgagtctt agatgatctg ttttacattt 149820
attaagaaag ccttttattag cttttatact gtgtattgcc tgttgcagtg tttgagtata 149880
aatgaaattt ctggaaaata ttaatggagt acaaactgtg atacttaaaa gtaaactagg 149940
gcctgcattt gtatcatgac ctgtttgagt attgatgaga agagcgt gaagaaaaag 150000 gtttaaacaa gtgtatttc cttaagaag ccactaatag tgcatctcct tagagtgtat 150060
atttctagaa tcctagtgtg cagagtttag actaagacta aaaaaaaaa aaacaaatt 150120 atactgtaat ttcattttta tttgtatttt agacaccaaa ggctctattc cctgctggac 150180
aggtttcgtc tctccaccat gcaagactca cttagtcct ctcctccagt ctcttcccac 150240
ccgctggacg gggatgggca cgtgtcactg gaaacagtga gtccggacaa agtaagtgtc 150300
cagcgtgtct gcatgggagg cacagggcgc tgagtgcctc tgtcacctgt ggcagataca 150360
gagagtgcag aggaggtgcc gtggacccaa ggagttctgg cgctcggctc ggctcagtga 150420
agctgtggtt agagacgtgg ggggccatca aggtctgagg gagccaagca gtgctgatgt 150480 gggaccctt tggtaggagt gtggggtgag tagttagtgg gtgaatcaag gaatagtcgg 150540
ccgtggcctg caggcccctg actgcacagg ccttcaagca catgtcaatg ccgttagcct 150600
ccctccatct cctcatacct tctggccacc tgtgagttgc actgccactg ccagccattc 150660
tggtatgttg tcagcacctc cactgctcat acctcatggt tagggaccac ctggagcctt 150720
ggtagagcct tggtagagcc ttggtactct actttcctgg acaaagttca gcttatgaat 150780
atgaatttag atttcaaaaa ccagcagccc aagtataaga agcgaaggt tcagtcctgc 150840 cttcttaggc tctattcgct aagcacctgc cctgccctgg ttgctgggga gagatgagta 150900
aagcagacaa cccaggagag gatggcaaag gggccgctaa cccttagtgg tttagctata 150960 tttgaaggc ctattggaag ttcaccaggt gaaggggag gctgtgaggg tgcccaggca 151020
ggtaacagaa gtccaaaggg gaaaaccctgt ggtgtggtga gccgtatagc cacagcctgc 151080
cggccggcag ccctctcagc ctagtgcggt gttcccaagc actggcctag gcctgtagct 151140
ccagggatgt gaagtcccct tgaacgccgc ccatcatgtt ccccttatcc atttttttct 151200
tcccaggact ggtacgttca tcttgtcaaa tcccagtgtt ggaccaggtc agattctgca 151260
ctgctggaag gtgcagagct ggtgaatcgg attcctgctg aagatatgaa tgccttcatg 151320
atgaactcgg tacgggggga gcagtggagg caaggaatcc tcagcttttc ttgtgacttc 151380
```

```
caagtgggat tgtctcatc atcatgtgac ccacttgttg acaacacatg ttggggactc    151440
cagtctgggc agggacggga tgtcggagag actccactct gaatgggcc gggaagtggg    151500 gaggactcca tttcagatgg ggtcgggaca tgggggttat gctgatcgag acagaaaagc    151560
acattgtttc agccacatta gaatccacgg aggtgttgtt ttgaaatcca gctggcccca    151620
aggctgggtg tatggtttgg gatgagaact atctggcctc cactggagga acaaacacag    151680
gatgttatca tctaagctcc atggccaaga cagaatggaa gtcaaggttg cgtatttgcc    151740
gtagacttca acacagtgtc gtaatgcgtg acgtcaataa cttgtttcta gtgtcttgga    151800
agttgatctt tagtcgtaaa agagacccct tggatgcagcg agatttcctc tactcacacc    151860
tctgttagat gtagtgaggt tcttcacccc ccaaccccag atgtcagagg gcaccctgcg    151920
cagagctagg aggccatgca aagccttggt gtccctgtcc ctcacccgtg ggcaggtcct    151980
gtgagcagtg ggggggccac ctcttgggta tggtgcagcc atggcccaag cagggcttct    152040
tctcagacct actaggacgg gagaaacctc ctggtgcttt agccctgcgt tgatatgcag    152100
caaatgggag ggaagtgggc acctggggag acaaatgcct gtagaggccg ggagtgacgg    152160
caggtgttca tgaaaagaga ccttgtgggg agggcaacac aacagtgtgt tctgatgtac    152220
tgaagagctc aactgaaaac aacaggagaa ttagcccaaa atccatttac taaaattgtt    152280
tatctttttt tttttttttg agacaaagtc tcgctgttgt cccccaggct ggagtgcaat    152340
ggcgctatct tggctcactg caacctccgc ctcctgggtt catacgattc tcctgcctca    152400
gcctcccaaa tagctggtat taacaggcat gcaccaccac gcccggctaa ttttttgtatt    152460 tttagtagag acgggatttc accatgttgg ccaggctggt ctcaaactcc tgacctcagg    152520
tgatccgccc acctcggcct cccaaagtgc tgggattata ggcctgagcc accacgcccg    152580
gcctaaaatt gtttatctta agattcatgc agtgaaagct aacttactga gtgataaatt    152640
tgcttagtga tctgtttatt aggttttcca aatttgctaa ttgggctttg aacagctgta    152700
aaagttctga ctgtaaaaga aagcttcaac ttttggcatt catgatgctt ttctgagtat    152760
taaactaaga tagatgtttt acctgaagga tcggccacca atctttaaat ggctaaacaa    152820
aagggttgct aaaacataat ccaaattgac ataagaaata ccattttcc aaccaaaatt    152880 ttggcattca tatggctact tttacgtatt tcagctgcat ttgaacatct tttcaaact    152940 ttagggtggt tggtgtatca ctgaggtctt ggatgacact ttagctttga ttttgttttt    153000
atgaattaaa attgtcatac caaaattttt atttcaagca aatccaagag cataaaaaat    153060
taaaatatta cttaaaatac taagagagaa cagatatata ttttactaag catatgttga    153120
atgaaattgt tcaaatattt ataacaggca tagagtagaa ttttcttaaa aatatttttg    153180
atggtatacc aatttgtatt ttctcagaaa catttgcctt attcttttt ctgttgtgtt    153240 tttcttacct gattgaaagc tcataatctg ttgttattgt ttgttaacct ttaatgctct    153300
gatttcagga gttcaaccta agcctgctag ctccatgctt aagcctaggg atgagtgaaa    153360
tttctggtgg ccagaagagt gcccttttg aagcagcccg tgaggtgact ctggcccgtg    153420
tgagcggcac cgtgcagcag ctccctgctg tccatcatgt cttccagccc gagctgcctg    153480
cagagccggc ggcctactgg agcaagttga atgatctgtt tggtaattaa aattaaaatt    153540
tatcttattt ttaaaaagca ttccagggcc agtatagtac tttgcaccaa gtaaatgtac    153600
aataaaggca gtggatctaa tacattgaaa gcgtttacag aggtagctaa agagcagcac    153660
gggtgtcctc ggctcagaat tcttcctgt gtgtttgcca ctttgccatt cattgacatg    153720
gtcatggaca tagggctcta agcccttgag gaaggctggg ccagacctca ggggagatgc    153780
```

```
agccccaaac cacgtgcagt cctgtggacg gatgtgtaga gtgccactg aggaacaatg   153840 tcttgagctt tcatcagatt ctcagagaat tgcttgactg cctttcgaag ttgatgcatc   153900
tgtgctcacg tttgcaccca cccacgaggt ccttctgttt caggggatgc tgcactgtat   153960
cagtccctgc ccactctggc ccgggccctg gcacagtacc tggtggtggt ctccaaactg   154020
cccagtcatt tgcaccttcc tcctgagaaa gagaaggaca ttgtgaaatt cgtggtggca   154080
acccttgagg taagaggcag ctcgggagct cagtgttgct gtggggaggg ggcatggggc   154140
tgacactgaa gagggtaaag cagttttatt tgaaaagcaa gatctctgac cagtccagtc   154200
acttttccat ctcagcctgg cagtaagtct tgtcaccgtc aagttattgt agccatcctt   154260
caccctcacc tcgccactcc tcatggtggc ctgtgaggtc agccaggtcc ccttctcatc   154320
tgcacctacc atgttaggtg gatcctaatt ttagagacat gaaaaataat catctggaag   154380
tactttatgt cttaagttgg cctggacatg tcagccaagg aatacttact tggtttgtgt   154440
tagtgcttgt aattcgcccc cagaatgtgt acacgttctg gatgcattaa agtctggcct   154500
gtatccttaa agggccatcg ctgtgctgcc tgccctcagc aaggacacac tttgcagacc   154560
cacagaggct ccgcctccac ctcacaccaa agaaagggag gagtccaaag ggcatcagtg   154620
ccattactca caaaatgata aatacaccct tattctgaac cacgtggagt catatggttt   154680
gtgatccctg tccttcaggt ttcagcttag tggggaagtg ggaaagtcag cgtgtgatca   154740
cagcacaggg tgattgctgc tgattatatt atgtgcctgc tgtatgcagg atgaaatact   154800
ttatatgcgt catcttattt gactctcaca accccctgtg agataggctc tgttactccc   154860
atttgacagg tgaggaaagc aaggcttaga gaatttcagt gacttgccca ggtcctctga   154920
gctaggaagt agccattctg gcatttgaac ccaaggcctg ctatccctag aacccacgct   154980
ctcaaattca acctatgaca gaggcaagcc ctggtgctgt gggagcccca aggaagagcc   155040
tctggcctgg tggccacgta gcccaggaga gatttctaca ggagcccaca gcgctgaagg   155100
agagagaggc agcagagtaa gggggctttg tggcagagag gggactggca ctttggggaa   155160
taggtgggtc aggactgaat gtaatggagc catgtcagag ctgtccttct ggaagggcaa   155220
gggcacctgg acgcgctgcc cctcagtgct ttggacggtt ccacaactgt gattcacacg   155280
gcttccccaa acgaaggtac acgagtgggc attctgtgac tcggtacttc cctttaggcc   155340
ctgtcctggc atttgatcca tgagcagatc ccgctgagtc tggatctcca ggcagggctg   155400
gactgctgct gcctggccct gcagctgcct ggcctctgga gcgtggtctc ctccacagag   155460
tttgtgaccc acgcctgctc cctcatctac tgtgtgcact tcatcctgga ggccggtgag   155520
tccccgtcca tgaacggtgg gttcctatca tagttcctgt ctgcttcacc atgttttat    155580 tttgtgctgc ctgtttgcca ggtactaagc taggaattgg ggatggagag gtagataaaa   155640
tatgcatcag gaagggctgg gccccatctc ttactctcca atatattgga gtctacactg   155700
gaatttaact ggaatttgct tttttagtca ttttatttag attttgaagt ttcagctttc   155760
atcaaaaata cctctaaact ttatgtctct gtgatctttg gtcttagctg ttttatgtat   155820
ttagtcttat atgatcataa gattaataac attacattca gaagattatt tgttttctgt   155880
cagagttaaa atgtttgttt ttatactgca ttgtaatatt aacgtactgt aaaataaaag   155940
tggcttgttc ttttcaagga acagtatcct caacaagggt cattagccac aattttaaa    156000 aaattggacg tcatagttta catgttagag ggcgttttga agctttgtat ttttaaatta   156060
aatgttatag agtgatgttt tcatgtttca taattgtttt catctgtgca tttgtagcca   156120
```

```
acttgaaaac aaagatccag ggattactac ttaaaagcca gacttcttgg aggttatagt    156180
gatgattttg atagtatctt gagccgtctc ataataacct cagggtgaga gatggccaac    156240
aggagacagt cgagggactt agaaatctga atgaaatctg aagttcaaat cttcagacat    156300
ataccactaa ccaagagatt ggtacctcag tctagtattg tctgtttgtc taaaattggt    156360
tctaaggaat ctaggctagt ctgtctatcc ctttcaactt ttgtgaggct gcacaaatgt    156420
aaaatgttga ataaaaagca ctgatggaag tgtgtagaaa ttcttctctt tgttctgttg    156480
taattttagt tgcagtgcag cctggagagc agcttcttag tccagaaaga aggacaaata    156540
ccccaaaagc catcagcgag gaggaggagg aagtagatcc aaacacacag agtaagtctc    156600
aggacccatt tttttcttac atgttgttcc tccaggactt aaaaatcatt cacagagacg    156660
tgcaccgcgg tgagtgtgga ctcctggaag cgcaccgtag ctccgctgtg tcctgctgct    156720
cctccctagc tgtcagggag gctgtagtcc attgctttgc cagctctttt gtttccgagt    156780
gaacacctta tccgtacaca tgcggctgtc tctgacccta cagaccagct gggatgccac    156840
tgggggagcg ctcccttccc cccgcacttc ccacactctg cagttattct gagatccttg    156900
agggcaggga acaggtttgt cttctttgtg ttctcagaaa ttaatgctcg gcctctggtc    156960
agcaagcaac aaccttttgt tgagtgataa tgaataaata aatgtttccc acatgagtat    157020
tcagtaacct cagtgtcagg ttcagccatc tgttttggtg atatttaaa  agaaaattcc    157080
gcttttccta cagaaaaaaa aaaaaatcca atcccagtg  atttaagcca gttatagact    157140
tagacatata ctacggcttt tcatgcactt tcctcccaat tctagagtag gtattttact    157200
aggaaaatgg tggcagtgcc tgttgggagg aagattcttt ggccaagtgt cttttgttct    157260
tgccagggcc cctaggctgc tggggtgctt cagcttcttt agcccagtgt ctggtgggga    157320
atggcccctg ttgcctgtcc cacagaggtg ggggtgcctc acctggagcc tgtccacaca    157380
ttttacacag cacgcttacc tggagcatca ggcatctttt ccatgctctg tggctcagga    157440
aacacgcctt ttcaatcatg agtgcaccag tgcttttggg cttttttctcc ccgcttttgt   157500
gcaatcctgg ttgtggatgg agttttcctg tctttagtct tctgcatagt acttttctct    157560
tctggttccc ggttcaaggt tttgtaatta gagaatgacc cagaagcaat ggcattttaa    157620
tgcacagcca aggacttctc tgaatttgta tctcaaacct ctgtgggtcc ttcaggcttc    157680
agtttgtgat ttcatgattt cttgttgcta cctaaggaat atgaaaacac ccacctccct    157740
actctgcatc ttccagccga gtggcacctc aggctgtgga tcctgtgctt ctgtggtgag    157800
gataagaata gtgccaaccg tgtggattga aatcaatcag ttaatccctc catgtaaagc    157860
acctggaacg gatgacagtc ttgttatgaa tactcaacaa atgctatcat gattttagt     157920
tagatttcca ttgctttaaa acagttgaga catcttggcg gtttgagtta gagcaacggg    157980
ccctgaagtg ggttctgttt gggtgaagat gattatgctt attccccatg gccctcttta    158040
ggcaagagtg ggaagctttc tttgtttttt taatcacctc gataggacgt tacttcttaa    158100
aggtcatcca ataaatatta ataggccggg cgcggtggct cacgcctgta atcccagcac    158160
tttgggaggc cgaggcgggc ggatcacgag gtcaggagat cgagaccatc ccagctaaaa    158220
cggtgaaacc ccgtctctac taaaaataca aaaaattagc cgggcgtagt ggcgggcgcc    158280
tgtagtccca gctacttggg aggctgaggc aggagaatgg cgtgaacccg ggaggcggag    158340
cttgcagtga gccgagatcc cgccactgca ctccagcctg ggcgacagag caagactccg    158400
tctcaaaaaa aaaaaaaaat attaataaag ccaactcgtt agcgtggggc ttaattgctt    158460
aagtccaatg agaagtcctt ctctatccta ggaagttgcc caaactgtag aatctcgtgg    158520
```

```
cctgtgggta atagccacgt aatacacact cactgcctca acaaatcata ttttagtagg 158580
tatgatattc tagactcaag acaccattct gtggatcttc ccaagggtgt gaagtgtcca 158640
cagcgtctgc cttgggagtt tccatgccca ccagaaccat gccccaagcc cctcaagcac 158700
tctgacctag gaaagccagt gaagcaagga tgacaacatg gcccttgat actagctgag 158760
ggacagacac aggtcctggg agaccagaga aagacgaggg gcagaggagg tgtcctaaag 158820
gaagtctgag gctgaggagc cacaggatgg cttccagctg tcacaggctg ctgctggcct 158880
tatcacagag agtgggccag agggctggga accaaggcca gagctcaggt tcaggaccat 158940
tccagcaatc ccagcagaaa atggggagaa ttgtatggta taggcggata tgaaggtaga 159000
atctgcaggc cttcagtggc caactcagag tctaagtgga ttccacagtt acagcttgag 159060
cagctggttg taggtcatgc tttctacact gggcatatag gatgtgtttt ttaaaaagtc 159120
ctctcttaac cgttgcttgt ttagatccta agtatatcac tgcagcctgt gagatggtgg 159180
cagaaatggt ggagtctctg cagtcggtgt tggccttggg tcataaaagg aatagcggcg 159240
tgccggcgtt tctcacgcca ttgctaagga acatcatcat cagcctggcc cgcctgcccc 159300
ttgtcaacag ctacacacgt gtgccccac tggtgagtct gctcgttcct tgcagaagac 159360
caagtacggt gaaaggcacc ggtaggccct gggctgggca cacgtgagag ggcgggacag 159420
aatccccgca gcccagaggc tgcctgctgt ggttctggtg cccactgtgg ttctggtgcc 159480
aggctgcttt cctcaggcac cacgtgtgga ggtcgctagt agaaatactg ggttttctaa 159540
aatgaactga ggcccctacat ccctaagaga ttagtgttag acctgattct agagcaacta 159600
gaccactttg cttaatagca gaccagaaac cacaccccct cgagtgagtg agattttcct 159660
ttggagataa ttcatgtttt tctacacagt tttgcagttg tcttcagaat tggtttaaag 159720
taggtgttat tgccaggcgc agtagctcat gcctgtaatc ccagcacttt gggaagccaa 159780
ggtgggcgga tcacttgagg tcaggatttc gagaccagcc tggccaacat ggtgaaaccc 159840
catctctact aaaaatataa aaattagcca ggtgtggtgg tgtacgcctg taatcccagc 159900
tactcaggag actgagacag gagaatcgct tgaacccagg aggcgaaggt tgcagtaagc 159960
cgagatcgcg ccactgcact ctagcctggg caacagagca agactccgtc tcaaaaaaaa 160020
aaaaggtagg tgttattgat cagaaccctt gtttcagata acatgaggag cttagcttga 160080
ggagagtgag ggttgatgga gggggactga cttctgccca gtgaaatggc atcatctccc 160140
accagcccgc tgaaataaga tgatggggcc tgttccttag ggcctgcagc atcctcaggc 160200
aggaaagaaa ggccgacctg gcagggtgtg agccagcagg tgtaggtcag ggagaatgga 160260
gccaggtccc agggaagagg cttgtggctg cctgagaagg gtgcgtgcct gcctgtgtgt 160320
gtgtgtgcac gtgtgtgtat gtatgctgga gagtctaggg aggcttgctc caaggacgca 160380
gtattgtttg atcctgagag ataaggattc tgccgcaggg aatgaaggta ttccagatgg 160440
cgggcttatt ccgaagaaga ggccagtgcc tggcggtgct ggaagcagtt gcagaacagg 160500
gagttgtagg cttcctggg aagagagcag cagggtgct ggagaagcag gccacacttg 160560
ctgcatgggg ttgctctcgg ccccactctt ggtgcacagc gagtcactgt gggttcatta 160620
gcatctggtt atgagacagt aactgctcct ttggagggc tcgtggagac catgcaggag 160680
ggcacggtct tgaggtcatg ccgtccagag cacacctgag gataggccag gacgggctgc 160740
acgctgtagg taaaattcct ccagcaagct cttcactggc attgaggagt tccctgagtg 160800
cggtcatctg gaaggcagct gtaacaggca ctgcagtctc tccctgggtg ggtaccagag 160860
```

```
aggagcatag gggagcataa ccgatttaaa gagagggctt tcctgtggtg aggtaagaga   160920
ttagctggtc attatcatag agccccctct gcctttgtgc agatgggctg tgggaatcct   160980
ggggttccgt tgggtccttt gtcacctcac tgaaggcatg taagctgagc tggccagacc   161040
gtgagctgat cctgccactt gaacagcatc aagcctgcct ctggattctt ctgtgcatgg   161100
cacttgtctg agcacctcac gcacagagaa ctggacttca gagtttacag aaataagctg   161160
tatggttcat tttcatgcct gcttgccaat aaacatatct gagctgaacc tcattgaacg   161220
cctgccttta ttctagcaca gcacctgctg tttgtgggcg aggggtgctg tctctaactc   161280
ctgcctgctt ctcccagcac tccctgagtg gggtgtgcca gcagcctcag gatgaggaca   161340
ggaagtggga gggcagagca gatttgggag ggccacttga tggggaagga agtcccagga   161400
agcagttgga gctgttttct gggggagaag gtgccagctc tgggacagtg ttggggtagt   161460
gaggagggag cccagtggag agaagtcggg cttcctgctt cctcacagta tgtctgtcct   161520
gactcaactc ggatgatgtc acttcctttt catcttctca ggtgtggaag cttggatggt   161580
cacccaaacc ggggagggat tttggcacag cattccctga gatccccgtg gagttcctcc   161640
aggaaaagga agtctttaag gagttcatct accgcatcaa cacactaggt actcttgggg   161700
cctctccttc aggtcaccat tgtcggacat ctaccgggag gaaatccaga gcccccagta   161760
ctgggatctt ctcatttgac tccagaaaag atttaagcat gataataata caaacctatg   161820
tgaatacatt ttgcagtgtt ggcaaaactc cttttatact gagaaaatag atcccagttc   161880
ctgtgttttg tggcttgaat cccagctttg tgtattccgg gcttgtttga agtcaggaaa   161940
ggttcatgtg tagtggacaa cgtgagacca aattctgcct tagattttgc atttaggcta   162000
aacagtggca gcacttgtct cagaatgttt tcttgtgttc accagtctga tcctgttgtg   162060
tctcagtggt ccattttctc atatgggaac aagcagacgg gagcagatgg agtcaggttt   162120
cttggcactc gccttcccca gagcctagag gcagcatggg gagaaagcag gcttggggct   162180
cagacagtcc tggtctgctt ccagccctcc tacctgagca gcgcagggca agtccgtcta   162240
acctctagag accctcagtt ttgtcatatg taaaatgggg gtcgtgtcta tttcatagaa   162300
ttgttgcaga tttagaaatt acatttctaa acaaatgtta ccccttattt ctaaataagt   162360
gtctaaatga ataagtcacc acttttgccc ctatttgatg gcaagaggtg tgatcttgtg   162420
gtgggactgt aatcagtcag ttctcagtga ctgtgccctg ctgtggtgtt tcctggaatg   162480
ttcctgtctt gtcctagaaa gtctggcagg ggcaccctga ctccactgtc cagtcctctc   162540
cccagtccct cgggcttctg cagatttgag gcttgtttgg atcccagaag gttgtggcag   162600
gagacacctt gcctctactt tccccttat aattcaatgt ccaaagagag ccctgagcag   162660
gtacctcacg ccagctgcct cacggagctc ctcctcttcc tggctgtgag gatcggtatc   162720
agtggcctcc tgctctctcc cccttgccta acacgagcac ctttgcttac ttgggtgccc   162780
ttgctcttga actgcccatc ggacgtgcgt gacccaagac tgtgccgcag tccttgcctt   162840
gtctgtgctc attttctttg ttcatttttt tccctgtaac gtaaattgtt atatttgtct   162900
gtatctgtgt ctgaatcagt cctgcacgct ctccttctct ctgtctcttg ttctttcttt   162960
accccgttta tcacgggac cccgatgtcc attgctctag ttctcctgtc ctaagcaccc   163020
catcccgtct ctctggcctt accacaagtg gcgtggctgc ctcagacatc atgatgggga   163080
catgaagcac agctgtcaga aacaactgtt cgttagatac actcgaatgc agctcatcaa   163140
tagggatgga gggtctgtcg gatgtatttt cactgaatcc ccgttcctac cttgatacac   163200
tcttttaat ctattcttct agacaggtca gaggaaccat tactttgact tttaaatttt   163260
```

```
tagcagcttt attgaggtag aattcacata ctacagattt cacccactct aagcggacag  163320
cttggtggcc attagtttta tccacagagt tgtgcagcca gctgcacagt ctcagggctg  163380
gactccaggg aagattttag cccatttagt gagtggggca gaagtggccc tggccctgca  163440
cgaggttgcc tgcatgggcg tccctgccct gtccctgtgt ctgctccact gggggttgac  163500
caggctgcca gggccgactt gggcctgtgc cacctgcctc tcatgtgtct cggacagtgc  163560
agccgatgtc tatacttcgg tttcctcaat gatgaaatgg aggggatagt gttccccgca  163620
tcatagaact gtgtgaggtt taagggactc actgcccttg gcgtggagcc ttctccaggg  163680
gccgtgctgt gtcggcgtag ctgtcagctc tccgttacag gcttgagaag ggttgacact  163740
ctctcatgta acatttatat ttctaggctg gaccagtcgt actcagtttg aagaaacttg  163800
ggccaccctc cttggtgtcc tggtgacgca gcccctcgtg atggagcagg aggagagccc  163860
accagaagta aggccacacc ctgtgctggt tggcacatgg gcagttatgg ccgcttgcag  163920
gcctttggtg gggaataaaa taaggcagca agctggtgtt cttttttttct cttaccttat  163980
ttttgaaaga gtagctgaat ggtgtcttga ctgatattcc agagcaggga caaagcctgc  164040
tgaggtctgg gggctgcgat taccaatggc tggaatgcat tttattacgg tgcattccat  164100
gttaaggatc aatacgattg tgcccttttct ggaaaatatc ttttagttta tcaatattca  164160
gaggagtgta ggttgaatta aaatgaaaag gcactttata aaggccatga gtagtacctg  164220
gtttcatttt tctaatgtct tgcagagatt ttatcaggct tcttgaagtg ttcacgtaca  164280
ttacgctaac acgatattaa taataactgt gctctggtac agcggagcca gcagaatggg  164340
aagttgtgga atgcaggccc ttgattctga tagaaggtgt ggtttgaact cacagaaatg  164400
acagtttgga gggtagacat atgtcacaag tcatcaagat tgtctttaaa ttcatgcata  164460
gaagctaaca gggtgtcata agcaaggcct gtaaaatgta tgagggaatt caaagataat  164520
ttattaaaaa gtaattcatg tttggagttt tgtgcccaaa ggagtccttg atttgaaaaa  164580
tgggcttttg cccatcagat tgtttcaggg cccgtgtgtg cggaggccct gccttgtgcc  164640
ccgtgagctc agcctgacag aaatcctttg gtagcactta aggctcctct tcctcccatt  164700
gaggcaggga agactctggg ttctgcaggc agaggtggtt gtgggtgtct tgctgctctt  164760
gttgacatgt gggctctcct tccaggaaga cacagagagg acccagatca acgtcctggc  164820
cgtgcaggcc atcacctcac tggtgctcag tgcaatgact gtgcctgtgg ccggcaaccc  164880
agctgtaagc tgcttggagc agcagccccg gaacaagcct ctgaaagctc tcgacaccag  164940
gtttgcttga gttcccacgt gtctctggga catagcaggt gctggggaca gtgggttccc  165000
cgctgaagcg tccagcagct tcaaccaggc cgttttcctt cattgctaga attgaaaaca  165060
ccgtccgtgt ggcctgtgca ggagatgcag acccaaaggt ggcctcctgg tcagtgagaa  165120
gctggaaacg tgacaggaac tgacgtgggg ttattgagca tttagggaa gacgttagca  165180
gagcaggaat gagcaggcaa ctagtagaac acccacttaa gggctcacgg acaggtgctc  165240
acttaggaag tgagtttcat ttggtattac accaggttcc tttaggcaaa gcggagggaa  165300
agttctggtg tttttcactt gtaagatttt gaaggaaaca aaacactctt tacctttttt  165360
ctaaaatgta ggtttgggag gaagctgagc attatcagag ggattgtgga gcaagagatt  165420
caagcaatgg tttcaaagag agagaatatt gccacccatc atttatatca ggcatgggat  165480
cctgtccctt ctctgtctcc ggctactaca ggtacctgag ggaaagggtg cgggggagcg  165540
gttgtacttg ggctagaatg agagaagact ggcatgctca ccacaccagt gatgcgggaa  165600
```

```
gacctgagtg tggtctgagt tggaggctgt ggtgctaaat acgctgcccc tttcataagc  165660
aggagtctta gtcaggccca gggaggaagt aaaatctgga aatgaatgag aagcattctc  165720
tcctgccagt caagaaatga gaagcgaaag aattctcacg ggctgtaaga ccagcaggat  165780
ttaaaagttg aattagttgc ttatgttaag aactcaacca agttcatcta cacaagctga  165840
atctccagct tttcctaaga aaccatgtgt ggcagtggct gcagggcagg gcacagctgg  165900
gcctgagcac cccgctccct gcacctctcc cctccctggg ccctgcctgt cactgcccac  165960
tctcccacca agccttccgg ttgtgtgcct gccctatcac aggcatcgga gcttgtcacc  166020
tggtttaaaa gaagagagtt gtgtgggat ttgggatgca cgttttcac tcaaaagtat  166080 tttagcgtag agctctgtga ttccgtagct atttaggagt ttaagcacct tgaaggcttt  166140
aattgcagaa agttctatgt ggacgtgcaa tgtgttatac gcagtgtcta tgagactcaa  166200
atgtttatta gggcgttgaa gtaaactgag cacttggagg gccatggatc cagccttcaa  166260
ggagctcata agtcaggagg acccaggagc aatgacctgt catagaaggc agaaaagagg  166320
ggcacagagg tgggtgggag gcatacacag gcagctcctg gagctccaag gggagcaagt  166380
gcttccaggg aaggggggcgt ggaggcccct ttggaggagg caagttgatc tggggtctgg  166440
cagagggtta gctggggaca tttagcggga ggctggtgcc cgggaattgg ggggatgccc  166500
agcagaaaga catgaggagg ctggcctggg gcgtgggggg gtgtgaaagg ttaagtgggg  166560
gcattatcct gctcccgctc ctgccggctg tatctggtca gcctgggcac cgaggtgggg  166620
ttctggaagg cactgttcac caaaatgctt atctgggtcc cccagagagc ttgcctgcct  166680
ggactgtcgg ctcgcctgca actgctgact cctaagcttt tgcagctcag cccacaacca  166740
gttcctattc acagaggtgg gagctgaggg gtgacaagtg actgctgcag tcttatttgt  166800
catagagaaa aagtgacaga gtccagcttg cccactggcc ctgccagctt aactggttat  166860
aaagtgacaa atccccaaga cccacagggc tctgcacaac ctgggccctc ctgccagtgg  166920
cggcgagggc aggtggctca cggctgggtg cctgtctggg caggagctgg gctggtatgg  166980
ggtgggcctg cggccctgcc cccctgtgca gatcaagact cagggtgctg gtgttcacag  167040
gtgccctcat cagccacgag aagctgctgc tacagatcaa ccccgagcgg gagctgggga  167100
gcatgagcta caaactcggc caggtcagtc tcgcgccccc gccgcctggc ctctgtccgt  167160
ttctgtcctc agactttggc gcttgacaca cccaggagaa aagctcagtg cacttttaa  167220 atgaaaggaa gttttccttt ttttaaaaa aaaatttaat gttcattgtt tttatctgtt  167280
ttattcctag gtcccgcaag cagaggaagc attagttttg ttttatttta tgttctgtat  167340
tccagaaagt agttaagaga cctcacatgt agcgatagag atgtgtgtaa gagacagtga  167400
gagggcgtga cttggactta agcaaggacc gtgagacaca aaaagggggg tgaggacaga  167460
gtggagtcag ctgaaatgct caggaggaag tagacgccat gaagggccat ggtatggggg  167520
gccgcaggcg tggccgtgag tgtccctggg gccagctctt ggggggctcc ctgagtgtcc  167580
ctgtccctgt ggccagttct gggtgggagc cccgtgtgca ggcagacagc tcggccactt  167640
cctagcaggt cacattggtc tgtgcttctg tttcctcctc agataagtga agggattcaa  167700
gggtctgggt gtggtggcta acacctgtaa tctataacat tttaggaggc tgaggcagga  167760
ggcttacctg agctcaggag gttgaggctg cagtgagcca tgattgcacc actgcactcc  167820
agcctgggca acagaccagt actctgtccc ttaaaaaaaa atgtaaacag aaacgtaggg  167880
ccatttgcat atgatggcac atggcgtgga gccctacagg tgtatgctgg gcggggcccg  167940
gctgtgctgg ccgacttgca ccttttccctc caccccggtg ctgtgtcttt cgctcaccgg  168000
```

```
gttcctgatt tagtgaaagc agttgtgcag gacagttctc tttgtagctt ttgtttctgt   168060
ggaaatgggt cagaatatgg tgtttagaaa cacttatgag ctctgagagt ttcctcttct   168120
gagttcctgg cctgcagcct tcacagcaga acccctgtga tgtcacaagc ctgtttctgt   168180
tccctgctct ctgcctgtac tgtcctgttt tgtgcctgcc ggtttcagtg acaggaagca   168240
gggagctact ggaccagcct gtattttttct agacatagtt ggaaaaagaa gtcccactct   168300
tctgtccttt ccacctttgac agatgttccc accccaagat aagtgaaaat gaccaatagg   168360
atgcactgta ttttcatga aagtgtttct gaagggcagg ctgagagtga gaggcctggg   168420
gctcactggg tgcctctggc cttgtcctgg gcccagggac actggtctgt gcccgaggta   168480
ttccctatcc ccccaacccc gctgcatttg ccacatcct tcaatgtttg cgttgtgtcc   168540
agcgtccgca aaccaactgt catgggatca tactggggct gaagtacggt cccacccctg   168600
ccctgtctgg ggctgaagta cagtgccacc cctgccctgt ctgggctga aggacagtgc   168660 caccctgcc ctgtctgggg ctgaagtaca gtgccacccc tgccctgtct ggggctgaag   168720
gacagtgcca cccttccct gtctggggct gaaggacagt gccacccctg ccctgtctgg   168780
ggctgaagga cagtgccacc cctgccctgt ctggggctga aggacagtgc cacccctgcc   168840
ctgtctgggg ctgaaggaca gtgccacccc tgccctgtct ggggctgaag acagtgcca   168900 ccctgccct gtctgggct gaaggacagt gccacccctg ccctgtctgg ggctgaagga   168960
cagtgccacc cctgccctgt ctggggctga aggacagtgc cacccctgcc ctgtctgggg   169020
ctgaaggaca gtgccacccc tgccctgtct ggggctgaag acagtgcca ccctgccct   169080 gtctgggct gaaggacagt gccacccctg ccctgtctgg ggctgaagga cagtgccacc   169140
cctgccctgt ctggggctga aggacagtgc cacccctgcc ctgtctgggg ctgaaggaca   169200
gtgccacccc tgccctgtct gggatgttta gcccctagat gccactggac tgagccgcta   169260
cttgcttttg ggaaagaggg gtgggggtta ggggtctggg cgaggggagt gcaggggctc   169320
ctccttggcc tgagagctgt tcatacagac tcctcgccca ctccctgcag ggtgctgggt   169380
cccagggggg aaatggccct tggtgccaag aacgtgagtt ggggctagtg ccagtgatga   169440
tggagaacag cttttatgg gcacacagcc cacagcactg tgccaagtgc tcgaggcttc   169500
ccgagaacca ggcagaaagg aggacagtcg aggtgtgctg actgcgtggt ggctgcgtga   169560
tctagagcgc gggtcacaaa ggcgcgaggg agctctggcc ttgggtttac cgcaatgact   169620
gccagtgcgg gagactggaa aaggaatctc acgtattggt tccgtgtttt ggggactcca   169680
ttcagatgtc acttaggagt gaaagcatcc cttcgtagag cctctttctg tgtcaccctc   169740
ctcagctgct cctggggttg actggcccct gattcatgcc tttagcatgt gctggagctt   169800
cccagcagct gtccagcccc tgccccaccc tctctgtggg ctcccttgcc cgtaacctgg   169860
ggtgtctgaa cgaccttgc taaggggcag actgttagac ggtaggcatg tgctgagtcc   169920
cagtggccac acccacccac caggagcctg gcactgtggc cgcagcactg agcagtgccc   169980
cgtttctgtg gcaggtgtcc atacactccg tgtggctggg aacagcatc acaccctga   170040 gggaggagga atgggacgag gaagaggagg aggaggccga cgcccctgca ccttcgtcac   170100
cacccacgtc tccagtcaac tccaggtttt ccaatggcct ttttcttttt aacagaaatt   170160 tgaaattct tatcagtcat ttgatttgtt tgaggtgctt cttgaaatga gcctctcatc   170220
tcatgtactt ggaaaatacc catctcgcat attccacagg aaacaccggg ctggagttga   170280
catccactcc tgttcgcagt ttttgcttga gttgtacagc cgctggatcc tgccgtccag   170340
```

```
ctcagccagg aggaccccgg ccatcctgat cagtgaggtg gtcagatccg taagtgagcc   170400
ttcccattcc cctcacacct gcacgtgcca cacgcaccac acacgccaca caccccacac   170460
acacacaccg cccacacaca tgccacttgc acacacaccc ctcatgcatg caacacacac   170520
acaggccaca cgcaccatag acaccacaca cacatgccac atgcacacac atacacggca   170580
tgcaccatac acacaacaca cacagcacac atgccacaca cacgccac accacatgca     170640 ccacacacat gccacatgca cacacactcc acatgcatgc accacacaca cacacacaca   170700
ccacacacac cacatgcacc acaccacaca ggttacatgc acaaacaca cacatgccac     170760 gtgcacacac cccacacacc acatgtatgt gccacacaca gcacaaacc acacacatgc     170820 accacacaca tgccacatgt gcatgcacca gacacatggc acacactaca cacacgccac   170880
gtgcacacac cccacacaca tgtacgcacc acacacatgc cacacacaca tgcaccacac   170940
acatgccaca tgtacacaca tgtatataca caccccacac cacacacaca ccacttgcac   171000
accacgcaca cacaccacat gcgcacacac acaccacata cgccacatgt acacaccata   171060
cacacaccat acatgcacca cgtgtaccac gcacccacac agacacagca cacgcataca   171120
ccacacacac acgcacacat gcgtcccgca cagtaatgtc tcttgggtgt aagaacacga   171180
cttgccagta gtagcgttct ggatgcgttg cctggattct aacagcgcga ttctcccctt   171240
gccctcctgg ttttccacat ctccagcttc tagtggtctc agacttgttc accgagcgca   171300
accagtttga gctgatgtat gtgacgctga cagaactgcg aagggtgcac ccttcagaag   171360
acgagatcct cgctcagtac ctggtgcctg ccacctgcaa ggcagctgcc gtccttggga   171420
tggtaagtga caggtggcac agaggtttct gtgctgaagc cacgggggcc catctgcctt   171480
gggacctggt gttggccaga ggtgccgggt gcggctgcct ccttccaaga gttgacccga   171540
accggactcc acgcccacg tgagctgcag tgcttctcag atggaggggg ttcagcgacg    171600
gtcagtgcca ttcacaggtc actgtgatgt gggttgtggc ggccaagcca tggtttgggg   171660
tcccgtatcc ctgggcttat gacatcattg tagtagccca tccccacaga accacggtgt   171720
gtggtggcgc tgaggcatcg tagatggtgg aaatgctact ggcttcccca tgctctgccc   171780
tgaggcctga ctgcctcact ccccttctca gttatgttcc aggcccccg agcttcctgg    171840 ctggacagct tctctcctgg gggccgtttt gtcacagtga ccctgtgttt ctagtcccaa    171900
atctgggtgc tatagtctct ttttagcgtg gtggttgtct tagtcttttt tggctgctac   171960
cacaagttac cttagactgg gtaatttata aacagtggaa atttacttct caccgttctg   172020
ggggctggaa gttttcatgg tcaaggtgcc agcagatttg gtgtgtgatg agggctgctc   172080
tctgcttcat agatggcatc ttctggctgg gtcctcacgg tggaaggagt gaacaagctc   172140
cctcaggcct tttagaaggg ccccaatcca caagggctct cccatcatga cctcatcacc   172200
tcccaaggcc ccaccttctt gtactgtggc actgcaaatt aggtgtcagt gtaggagttt   172260
caggagggat agaaacattc agaccatccc agcggtcaag tgttcatcct cttgagttcc   172320
tccttattct gcttctggtt tatcaggatt cagccagtgc agcatggtac ctgtattctg   172380
tggcacatca ccacatggta tttgccaagt atccatcacc tgcacacgtg aaatcattgc   172440
ccgtgggtcc cgacatctgg cgaagcatat tcaaggatgg cagaactgtc agagctggca   172500
cctctggttc cttgtcatgt ggcattacct agtaatccat tttatgatag caatggaaac   172560
tcatttcttc aacaaacacc tgagtggctg ccgtgtgcca gccgtctggg gcccttggtg   172620
agaatggcat ggtggtgccc atcagggcct gcctagcccg tgctctggac gggctcctgt   172680
gtgtcaggaa cgacaatgct gtcatgacgg tgaatgattt tttttttgc catcactcca    172740
```

-continued

```
gccgctaaca tttgcggagc tcttcctccc gcaccccac ctgacaaggc caagggtgac 172800
cttggcccca ccctaggcgg ccaaggtcag aggttagctg gcttgtctgg gtcacacaaa 172860
atgcagcaga ggttgaggtg agcacatgtc cgtgacctgg agcctgactc cctctctgcg 172920
agtcttgact gctcttgcct agactctgtc ctccccgagc ccaaacgcca gtcatcttcc 172980
cttgtgggtg tccttcagcc tggtgccatg ctggtgactc agcagccgtc cagggagtgg 173040
aaacaattga gtgtgtgggt tccctgtgtg ggcatctctc ttcacggcga acaccctctg 173100
ggtgttgccc acacgatgtc aaagcggctc ttggaagggg tccttctcct tgtgggaag 173160
tttcagctgc tgggctaact tgaattgtaa ctgtggtttt gtgctcaggc ccagatcccc 173220
ctaggcaagt gttgtgccat cagtaatcaa atgagaaata atcattttga aaagcagatc 173280
ctaaggcagg atggtcatgg acactcactc ccagctcttt gtgcactcat gcttctgga 173340
agatggccat cctctgtgaa ggttttcagc gcgtcatgct tggtacccac gtatccagag 173400
catgtcgttt tgaggtattt gcccaccgtt gtgaaatccg tgccacccga gagcaggtcc 173460
tgatgtgggg ctttcagaag tgggacctgg ggccgtacgc agtccttagg gagggccgt 173520
gtggcgttgt gcgtgtgagg ggatagcaca gggtgaggtg ggggcccaag aaggaagtga 173580
cccacaaaga acagcctcct cttttggtcc ttgttcctgg gatggctggg agtggcttct 173640
gtgtcgtccg gccatttccc ctgcggagag gctcctacca ctgccgagaa cctcatcatt 173700
ccacaaaaac aagaggccgc ctggccatcc agcgctccat gggaattctg tgtccccata 173760
gtcttgggct gaaggagggt gacattcctt gctgacttct gcaggggtct cctcactgtt 173820
aaagagcaga ttgaaagtga agaacgtggg ctaagtgttt aggtcgatat ttaaccctgc 173880
taggttttgg atactaagtg aaattgaggc cattttggtt gaagttgaca gaaaccacta 173940
tcagggatcc ccaagactac cccaggcttt tctagaaaga ctctcagcta agatgtgtta 174000
tggtaaaagc acacaaaaca aaatcagcaa agaaaattag caagggcaga ggcccatggg 174060
gcgatgtccc gaggacacca ggcttgagct tccagaatcc tctcccagcg gggtcgtgca 174120
ggacgcactt aactccccgc acagtgagcc gtgacagcgc gtgtgcagtg tcgtcgccag 174180
gaaagcacac tagagactcg gtgccagggt ttttactggg ggctgggcac atgggcaccc 174240
tctgcctgcc tcgtgcccag actctggact cccggaggga aggcaagttc tcagcaccaa 174300
ccctggtgcc cacacaagca gctgagcaca gggagcccct cctcagtgag gatggtgggc 174360
accgtcccaa caccagccag gggccagcct tgcacacagg cctctcagga tggtctccgg 174420
cctgctgtgt agtctcttct gcacacaagc gtgagggcag cgccccgcc tcggctgtgg 174480
ggaggagcca ctgggacgtg agctctggtg gcatgcagca gcttttgtct gtgtgtgcct 174540
aggacaaggc cgtggcggag cctgtcagcc gcctgctgga gagcacgctc aggagcagcc 174600
acctgcccag cagggttgga gccctgcacg gcgtcctcta tgtgctggag tgcgacctgc 174660
tggacgacac tgccaagcag ctcatcccgg tcatcagcga ctatctcctc tccaacctga 174720
aagggatcgc ccagtgagtg ggagcctggc tggggctggg gcggggggtct cagaatgagc 174780
tgtgaaggaa gcagcatcac cctctccaag tgcccaggct cctggccaga tggcaggcca 174840
ggtatcagtg ggaacccagg tgggtgccat ggctgaggtc agtgagacgc aagagcacag 174900
gtgcgtccta gaggcttcct cgggcacctc cagcgagctg gagctctcgc ctctgctgct 174960
gtctcatgtg gcgcttagca cactctccca cgtgcccatt cctgactctg ctctcgaggc 175020
catcggctct cattctctgc tcccagaacc ctgttattac ccaggctagc ctcctctctg 175080
```

```
caccttcccc gccctggccc agtacctccc tcttgtttcc actgtgattc cgacctcacc   175140
ttatcttaaa gctgctggac ggcaggttct gtacacacgt gtccttgaca aagcacggct   175200
ggtgccgcaa cccctcagcg agcaagtcaa gctcttcaca gcgatgtctt acaagcgcag   175260
agggctctgt gacaccctgg tctcaccgcc actcttccaa agtcgcagag gctttagcag   175320
agatgggccc agcctctctg agtcataggc ttctgcacac gggagctgtc tttagaggga   175380
gggtggaatt tcatcagcca cccacatggg ggagttgagg gcaagaatta ggagcaaaga   175440
tgggaagggg tctgggagga atggccagtg atccccttttg acaagtgggc aggaaacggg   175500
ggctaggtca aagttgagtg gaagacctgg agggagacgg gaaggtctct gtaggcacag   175560
ttcagacagg agggaggtgt gagccagggc acatgccggt ggccgtctgg caggatttgg   175620
gacatgctgg agcagggaca gcggctcatc aggggccatt gccctcatcc aggccagagt   175680
gtcacaagcc cgtggggagg ccttctcgc ctgtcatcct tgctgggcag tgggtgctgt   175740
gctagcagga caggcggacg gctggcaact gtctctgcat ccctggagcc tggcataggg   175800
ccaagtcaca cggggcacag gcctgcaaat caggcacata tgttggtgca gtgacgtgat   175860 tttgggggc agccccagaa caggccccag acacaggcca aagccctgcc tgtgctggtg   175920 tgtttgggctg ttctatggct cttgctgtgg gcatggagga ctcagggaag gagagttgag   175980
gtggtccagg agttgcgttt gggatgcaga gagcttgtgg catccaggta gaaatggtgc   176040
gtggggctga cctcagcacc atgggcagag gggccgtgtc acgtgcctcc gaggtggagg   176100
tgggaccacg tggtgacaga tatacgcatc actgggcacg ttttgtggg tgttgggggg   176160 catcgtattg gctcctctgt tcacagtggc cactcattca gtccctggct accaggtcct   176220
cactgtgcca tggggaaggc cggcgctgtc ggggatcac agaaggcagc acgtcatgat   176280
ggcatgtgcc atgaaggaaa agcacagggc actcaggaag tagaggggac tggcctgggg   176340
tgtgggaatc tagggcctcg ttgagggaca gagagaggaa gtgtgtggtg gccagcatgg   176400
aggtggccac aggggaggct gagttaggcc gagagggcag ggcgttgggg aggtagacgg   176460
gctcagccac tcagggagtg gtcaagcaga ggctgaaggg tcaggccagg ttgcaggggc   176520
ctgggggagc cactcagggt aggcgctccc gggagcccgc ctggcccata gctctacact   176580
cccgcgtggg gccggacatg ctgtgaagcc ctctccacgt tggatggggg tggctgagcc   176640
tggatgctgt ctcccgtttt cagctgcgtg aacattcaca gccagcagca cgtactggtc   176700
atgtgtgcca ctgcgttta cctcattgag aactatcctc tggacgtagg gccggaattt   176760
tcagcatcaa taatacaggt gagtgggccc tggctgtctt cctctgcaca cggggagtgg   176820
gcttcccttc tctttcctt gcaggatcat accagtgggc cagttttgac ttggtcggga   176880
ggaggcatga acacctgaga ctgtgcagcg attctttgac acagaggcct ttctccctgt   176940
gcagatgtgt ggggtgatgc tgtctggaag tgaggagtcc acccctcca tcatttacca   177000 ctgtgccctc agaggcctgg agcgcctcct gctctctgag cagctctccc gcctggatgc   177060
agaatcgctg gtcaagctga gtgtggacag agtgaacgtg cacagcccgc accgggccat   177120
ggcggctctg ggcctgatgc tcacctgcat gtacacaggt gagcatgtac acggtgccca   177180
taaggccagc ccaagtcctg ttcaaggag gcaggagcat gctcactcaa gggacctcga   177240
ctaggtgccc tctgatttca cacttctggt gttgccccaa gccggcccca tcaccttgca   177300
agaaaggctc tggagccccc agggctggag tacctggtca gggttgaccg tccctgtggt   177360
cactcatccc atgtgctga gctggctgg gtcctgggca agcaagggc tgatatcacc   177420 tgctttcaga tctccaggga ctcactggac ccctgtgtac aaagcactgt ctacagagcc   177480
```

```
tattgggttg tatagaggta accttcgtac tgaacacttt tgttacagga aaggagaaag   177540
tcagtccggg tagaacttca gaccctaatc ctgcagcccc cgacagcgag tcagtgattg   177600
ttgctatgga gcgggtatct gttctttttg ataggtaaga agcgaagccc catccctcag   177660
ccgttagctt ccctagaact ttggcctgaa gctgtgcttt tgtgtgtgtc tgctgatccc   177720
ctggcgctgt tgctggagtc ctgccagtga ttccccacca cagcctgacc atgggctgcc   177780
ttggctcagg gttccactgg cgagctggtg gtccttggac cccagcactc aggtgtagcg   177840
ttgaccagtt ccaaggttgt cccagtgcct gcccatctct cctgagggct cagggacagt   177900
acctggcagt tgggggtgtg gcaggggggca ggaatgacca gcctctggga gggtggggca   177960
gaagcctgta cagtgaggag gagctggctc agcctggctg cctatcgtga gagggagcc    178020 cacggggctg tgggaggggg gccgtggtgc ctgtgagcag ggtgaggagc agcggcagga   178080
ggatgaaggt ggaacccaca catgcatctt tgagacccgt gtggtcagtg cttctgccc    178140 cccaccaccc cccactgctg tgcgtgcata gaattggctt ccctcacctg ctctggaagt   178200
gggttaggag cttggtaggg cttttttctca aggacaaggg cccctgattt gctctcaggc   178260
ctcagtcctg gcgacatggt ggatctggag ccttgttgca ctgccttgcc tgtgctctcc   178320
aatcagggtg gccagtgggg agccatttgg cttttctcaa gagcatactc aggtggacct   178380
tgctccactg tttgaccaga tgaggcattc tgaacagcca agcctgtgct ggtctgtttt   178440
catgttgatt ttttttttc ttttcttttt gagatggagt ttttcccttg tcacccaggc    178500
tggagtgcaa tggtgtgatc tcggctcact gcaacctccg cctcccgggt tcaagtgatt   178560
ctcctgcctc agcctcccta gtagctggga ttacaggcac acaccaccat gcccagctaa   178620
tttttgtgtt tttagtagag acggggtttc accgtgttgg ctgggctggt ctcgaactcc   178680
tgaactcaag tgatccaccc tccttggcct cccaaagtgc tgggattgca ggcgtgagcc   178740
actgcgcccg gcccccatgt cgattttaaa atgcacctct gcatcgttct tcagtcccca   178800
tatgctcact gagcaccact gcgactggca gacgggcaca gggaggcgcc acgaccagtc   178860
ctggccttca aggggcttgt ggtctagtgg gcccaatgct aggtggcgag tgctccaaag   178920
agtgtggtgc acgccttccg cttgaccgct tccagacgc cacagggagg cacctcgcag    178980
ctgaccacag atttctctct gtggagcagt gtcttcagag cggctgccat gccactgctg   179040
ggcgagggtc tgcgggcggg tagagccagg agcacctgtg aggaagtgca ctgccatttt   179100
cgtagctgct tcccgtgtgt ctcagttaca cacggctggc atgtgtgcac tgatgagacg   179160
ggaacgtgat ggttgctttt cagcactgaa agggatactg ctcaggggc gtgtttcagg    179220 atctggttag ggaagaagca gcgagagcac agatggggcc ctgtgtggta acaagaaaaa   179280
agtcctggtt gacaacagtg ccacgaagcg ttagaacaca tagggatgtt tgtggagcat   179340
ttgcatgtgg aaagcagcaa aaacataatg ggaacgggtt cttttgttat gatttttaaa   179400
aatctctttt gtaacatcct tcccgctgcg ccgtttctgc atattccttt atgtagcttt   179460
caaactcctc ttaggagttc tggtccctac agggcgtggg agcccaggct ttacgtagct   179520
ttcaaactcc tcttaggagt tctggtccct acagggtgtg ggagcccagg cctgtgccg    179580 agcagcctgc ctccacgagc tagacagagg aagggctggg gttttgcctt tttagtctca   179640
aaattcgtac tccagttgct taggctctga cttcccccac ttggaaagtc cctcacggcc   179700
gagggtccct cccagccctg atttcacatc ggcatttcc ccagtattag agccaaggcc    179760
ctccgcgggc aggtggggca gctgtgggag ctggtgccag tctctgacct gcgtccctcc   179820
```

```
tcccaggatc aggaaaggct ttccttgtga agccagagtg gtggccagga tcctgcccca   179880
gtttctagac gacttcttcc cacccccagga catcatgaac aaagtcatcg gagagtttct   179940
gtccaaccag cagccatacc cccagttcat ggccaccgtg gtgtataagg tgaggttgca   180000
tgtgggatgg ggatggagtg ggaaagcctg gaggtggagt tgcctccgac ttcccagcag   180060
attcgccagc agagcccagc tcctccgctt taaagcagca atgcctctgg cccccacccc   180120
accccgcca cccaggcgca gcaggtgctt cccgtccccc cagccctgac actcaggcac   180180
ctgcttgctc cttgcaggtg tttcagactc tgcacagcac cgggcagtcg tccatggtcc   180240
gggactgggt catgctgtcc ctctccaact tcacgcagag ggcccggtc gccatggcca   180300
cgtggagcct ctcctgcttc tttgtcagcg cgtccaccag cccgtgggtc gcggcgatgt   180360
atcctctctg ggtccctggt gctgcccccg tttcccttgt caacaccgag gctcatgttt   180420
catgataagg ttttgaaacc taacctttgc aaaaacccca cagatgccag ggtgacaggc   180480
cctcagcccc agggaagtaa aatgctgaca ggggtacaga aaggagcacg tccagacatt   180540
tgctgaccag ggcctctcag aggggccggt gtatggcagg agggtcgcag ctgagggggcc   180600
tttctgtgga gggcctgggt gaggggagcg agggtgggcg gtggtctctg cagacgtccc   180660
gcccactcgc gggctctgtg tggctgggct tctcctgaca ctgcttctca ttagctttgg   180720
tcattgtgcc tcgatcgccc tctcggggaa aggcttaagt aaagatccag ttcccacccc   180780
cagatgctgg ctgccaggag tttcccttc cacagcccctt ccccaagaca gaccacaaga   180840
gcctccaagc agcacagttg tcctggtgct gacagcacag ccttgcccgg cgtgcctggc   180900
acggctctgc cctcactgca ttggagcagg gctagtggag gccagcggaa gcaccggcca   180960
ccagcgctgc acaggagcca ggccaggtga gtgctgccga gtgggtgccc tgcctgcagg   181020
gcatccagcc agccaagggt tgcaggaatg gaggtggagg cgctgatgca gctggaggca   181080
tccaggtggc ccttccgggg ctctgctcgc tctccaggct ccctggaccc ctttgtagac   181140
tgtttcagga gaggaactcc caggtgagga cagggaggca gcattcccct catttgccgg   181200
cctttttcct taactcctgc accagcctcc cacatgtcat cagcaggatg ggcaagctgg   181260
agcaggtgga cgtgaacctt ttctgcctgg tcgccacaga cttctacaga caccagatag   181320
aggaggagct cgaccgcagg gccttccagt ctgtgcttga ggtggttgca gccccaggaa   181380
gcccatatca ccggctgctg acttgtttac gaaatgtcca caaggtcacc acctgctgag   181440
cgccatggtg ggagagactg tgaggcggca gctggggccg gagcctttgg aagtctgcgc   181500
ccttgtgccc tgcctccacc gagccagctt ggtccctatg ggcttccgca catgccgcgg   181560
gcggccaggc aacgtgcgtg tctctgccat gtggcagaag tgctctttgt ggcagtggcc   181620
aggcaggag tgtctgcagt cctggtgggg ctgagcctga ggccttccag aaagcaggag   181680
cagctgtgct gcacccccatg tgggtgacca ggtcctttct cctgatagtc acctgctggt   181740
tgttgccagg ttgcagctgc tcttgcatct gggccagaag tcctccctcc tgcaggctgg   181800
ctgttggccc ctctgctgtc ctgcagtaga aggtgccgtg agcaggcttt gggaacactg   181860
gcctgggtct ccctggtggg gtgtgcatgc cacgccccgt gtctggatgc acagatgcca   181920
tggcctgtgc tgggccagtg gctggggggtg ctagacaccc ggcaccattc tcccttctct   181980
ctttctcttct caggatttaa aatttaatta tatcagtaaa gagattaatt ttaacgtaac   182040
tctttctatg cccgtgtaaa gtatgtgaat cgcaaggcct gtgctgcatg cgacagcgtc   182100
cggggtggtg gacagggccc ccggccacgc tccctctcct gtagccactg gcatagccct   182160
cctgagcacc cgctgacatt tccgttgtac atgttcctgt ttatgcattc acaaggtgac   182220
```

```
tgggatgtag agaggcgtta gtgggcaggt ggccacagca ggactgagga caggccccca    182280
ttatcctagg ggtgcgctca cctgcagccc ctcctcctcg gcacagacg actgtcgttc    182340 tccacccacc agtcagggac agcagcctcc ctgtcactca gctgagaagg ccagccctcc    182400
ctggctgtga gcagcctcca ctgtgtccag agacatgggc ctcccactcc tgttccttgc    182460
tagccctggg gtggcgtctg cctaggagct ggctggcagg tgttgggacc tgctgctcca    182520
tggatgcatg ccctaagagt gtcactgagc tgtgttttgt ctgagcctct ctcggtcaac    182580
agcaaagctt ggtgtcttgg cactgttagt gacagagccc agcatcccctt ctgccccgt    182640 tccagctgac atcttgcacg gtgacccctt ttagtcagga gagtgcagat ctgtgctcat    182700
cggagactgc cccacggccc tgtcagagcc gccactccta tccccaggcc aggtccctgg    182760
accagcctcc tgtttgcagg cccagaggag ccaagtcatt aaaatggaag tggattctgg    182820
atggccgggc tgctgctgat gtaggagctg gatttgggag ctctgcttgc cgactggctg    182880
tgagacgagg caggggctct gcttcctcag ccctagaggc gagccaggca aggttggcga    182940
ctgtcatgtg gcttggtttg gtcatgcccg tcgatgtttt gggtattgaa tgtggtaagt    183000
ggaggaaatg ttggaactct gtgcaggtgc tgccttgaga ccccaagct tccacctgtc    183060 cctctcctat gtggcagctg gggagcagct gagatgtgga cttgtatgct gcccacatac    183120
gtgaggggga gctgaaaggg agcccctcct ctgagcagcc tctgccaggc ctgtatgagg    183180
cttttcccac cagctcccaa cagaggcctc ccccagccag gaccacctcg tcctcgtggc    183240
ggggcagcag gagcggtaga aaggggtccg atgtttgagg aggcccttaa gggaagctac    183300
tgaattataa cacgtaagaa aatcaccatt ccgtattggt tgggggctcc tgtttctcat    183360
cctagctttt tcctggaaag cccgctagaa ggtttgggaa cgaggggaaa gttctcagaa    183420
ctgttggctg ctccccaccc gcctcccgcc tcccccgcag gttatgtcag cagctctgag    183480
acagcagtat cacaggccag atgttgttcc tggctagatg tttacatttg taagaaataa    183540
cactgtgaat gtaaaacaga gccattccct tggaatgcat atcgctgggc tcaacataga    183600
gtttgtcttc ctcttgttta cgacgtgatc taaaccagtc cttagcaagg ggctcagaac    183660
accccgctct ggcagtaggt gtcccccacc cccaaagacc tgcctgtgtg ctccggagat    183720
gaatatgagc tcattagtaa aaatgacttc acccacgcat atacataaag tatccatgca    183780
tgtgcatata gacacatcta taatttaca cacacacctc tcaagacgga gatgcatggc    183840
ctctaagagt gcccgtgtcg gttcttcctg gaagttgact ttccttagac ccgccaggtc    183900
aagttagccg cgtgacggac atccaggcgt gggacgtggt cagggcaggg ctcattcatt    183960
gcccactagg atcccactgg cgaagatggt ctccatatca gctctctgca gaagggagga    184020
agactttatc atgttcctaa aaatctgtgg caagcaccca tcgtattatc caaatttgt    184080 tgcaaatgtg attaatttgg ttgtcaagtt ttggggtgg gctgtgggga gattgctttt    184140
gttttcctgc tggtaatatc gggaaagatt ttaatgaaac cagggtagaa ttgtttggca    184200
atgcactgaa gcgtgtttct ttcccaaaat gtgcctccct tccgctgcgg gcccagctga    184260
gtctatgtag gtgatgtttc cagctgccaa gtgctctttg ttactgtcca ccctcatttc    184320
tgccagcgca tgtgtccttt caaggggaaa atgtgaagct gaaccccctc cagacaccca    184380
gaatgtagca tctgagaagg ccctgtgccc taaaggacac ccctcgcccc catcttcatg    184440 gaggggggtca tttcagagcc ctcggagcca atgaacagct cctcctcttg gagctgagat    184500
gagccccacg tggagctcgg gacggatagt agacagcaat aactcggtgt gtggccgcct    184560
```

```
ggcaggtgga acttcctccc gttgcggggt ggagtgaggt tagttctgtg tgtctggtgg    184620
gtggagtcag gcttctcttg ctacctgtga gcatccttcc cagcagacat cctcatcggg    184680 cttttgtccct cccccgcttc ctccctctgc ggggaggacc cgggaccaca gctgctggcc   184740
agggtagact tggagctgtc ctccagaggg gtcacgtgta ggagtgagaa gaaggaagat    184800
cttgagagct gctgagggac cttggagagc tcaggatggc tcagacgagg acactcgctt    184860
gccgggcctg ggcctcctgg gaaggaggga gctgctcaga atgccgcatg acaactgaag    184920
gcaacctgga aggttcaggg gccgctcttc ccccatgtgc ctgtcacgct ctggtgcagt    184980
caaaggaacg ccttcccctc agttgtttct aagagcagag tctcccgctg caatctgggt    185040
ggtaactgcc agccttggag gatcgtggcc aacgtggacc tgcctacgga gggtgggctc    185100
tgacccaagt ggggcctcct tgtccaggtc tcactgcttt gcaccgtggt cagagggact    185160
gtcagctgag cttgagctcc cctggagcca gcagggctgt gatgggcgag tcccggagcc    185220
ccacccagac ctgaatgctt ctgagagcaa agggaaggac tgacgagaga tgtatattta    185280 atttttttaac tgctgcaaac attgtacatc caaattaaag gaaaaaaatg gaaaccatca    185340
gttgttgctg tgtgaggctt gctttgcttc atgagaacct agaccttgct gagctggagt    185400
cttaggaagc agtctcctaa gtgcttctcc agcaggggca gaaactgtcc caccagctaa    185460
catctggcat tatggagggt ccccaggca gctgccagca gggacaggcc ccgtgttttc     185520
tgtagccagg gatgaggaag tggccccagg gcatgggcct ggctgggtgc ttctgcaagg    185580
gccttcccaa accacagtac aggtggtctt cctgccctgc agatgggagc tgtgggagct    185640
gctggagctg ctggagcctt catggtcaag tgacatcata agcttatatg acatacacaa    185700
gcctcaggac ttggcccatg gcactgaagc aggtcatcag gcccagcaca gagactagag    185760
ctgtgttctc acagggccca ccaccttcc acctccttgg ccattgacac ctgcgtccct     185820
ggcccagctg ctcccaggta acccccaaag cagctggcac atcccacctc tggtgtggcc    185880
ggggctgctg tgtgtccgca gggcctgccc cgtctattct agcttgtttg tcctgtctga    185940
accagcgcct actccaagaa gcctctgctc agcccagcgg ggatgcttct aagctccgga    186000
cgagcctctc ggaagccttg gtgattggtg gtgtagtcat cttgggatgc agatgtctta    186060
ccaacctgca agaacaaaaa ccctgtggct tcctctggtg cagggtattt agtcaatgtt    186120
tgctgaggtc ccgtctggtt ctggctaatt ggcaggggtc gtccacccat tctttccctg    186180
ctctgctgtc tgtgccagga gagacggggg ccagtcggcc aaggggccag ctcctgctgc    186240
ctgctcctct tgggcacgtg cggggcccc ctttctctga gcaggatag ggatcagtct      186300 gccggaggga tgtggtggac aggcctaaag catttggggc ggggcatgcc acttgagctc    186360
cctaaatctg tctcctcata ggtgacaccg ctccagggcc cccagtggc ctctcctttc     186420 agagctacct aaattctggt cacttcagag aaatggagca ccccttctc cctggtccag     186480 gtgtggacag cctggcacac tgagcacacc tggcatggct ggtaatttca gaaagaagag    186540
gggccggggt ccagtgggaa gcagcggtga acccctcgtg agtgggcttt gcagtccctc    186600
cccatgccac ggcagagctg ccctcaacac agccttcctc ttcctcatcg gagagcacac    186660 cctgtccct tgccgagctg tgccctgtgc cttcggtggt atttgattt ggctgctact      186720 ggctttgttg ggatctggaa gtcgcttccc ctgcgtggtg cgtggagcac tgtaagtcag    186780
atgagggaag tagccagggt gaggtgagta ccgggtggag ccgccactga agggactggg    186840 tagggggggcc ttgcctctac atgatgtgac acagccaacc gaggacagag gaagcccgt    186900 tcctgggggt gtggggtgca cccctcaggg aagcctgcag tggggcctga ggaaaggcat    186960
```

```
cctccgcgag cccacgagtc tggtccatga gcaccgtgac agtgtctgtg ggtagaggtg    187020
gacccggcct tgtgtcatca ccaggacctc ttttgggaaa ccatgtggac atcgcttgcg    187080
ggtcccccag gctctgcagc cccagcagcc tggctgcctt ttgggcaagt ggcttgagcc    187140
acagaggacc cagtcctgtt gcagccacat cctctggggg ggcccgccag tgtggccggc    187200
tttctccacc ctacaccagg cctccaggtg tcctggtcgg gggtgtctgg gccctgggtg    187260
ggccctgtgg acctgtgagg tcagggtcag ggcatcactg gaggcagagg gctgaagttg    187320
tgggtctggg ttccccttgt gtgcacaggc ccctgccctc catgcttggt caggcagcta    187380
cccccaaaac tgctaggaca ggctggtcct gaggtggatc ctggcccctg taccctctgg    187440
acagcccacc cgcccaacct tctaccctgc cccagcggcg gcagtgttgg ccacatcctt    187500
cccctcctgg ccccaattgc tctggggaag tccaggctcc ggagcctgcc caggggcccc    187560
ccgtgatttg ggcccaggac tccacgtggt tctctgcctt cacccaagcc ctgaactcct    187620
cagctgccaa atccccaccc atctgcacag gctgtgctca ccactgctgc tcctggaagg    187680
tgcccctcag tgggacgccc acctcctctc tgggcttctg tgtttgggag ccctgctgcc    187740
cccacccttg gtcagtcccc atgtcctgct ggcctgtcag gcagggcaga aaatccaccc    187800
agaaatgctg agcaggatga gagtctagtt gggcccagcc tcattattta aagggatgg    187860
aggcctaggg agcatgcttc tagcctgagc ccagcagggc cccgcccatg tcccaggtct    187920
gcaccaggga cagctcctgc cgaggcctga cctgccccct ctccctcagg tgctgctggt    187980
tgaccagcct ctggccctag gagacccgt agcgactgag ggtcccagca ggccatgcag    188040
cttttgccaag gtacgagccc ctccccagca ggggacagat gtggggaccc tcccaggcag    188100
gagcagctgg gtgcctggtg ctgccatctg ctgcctgcct ggttcttgtc ctcacattgg    188160
aggtcagtgt gagggctctg cctcgggaaa ggccatggag cttgccctgt ccagggcctc    188220
ccatgtgcac tgagcctggg aagagagggt tggagttgag cctttaccc tgggaatgct    188280
gcctggagga tggtgcgggt gtggggtggc accctgccag gcagggccct gcctccctgc    188340
gcccactgga actcgggcag gcaggggtgt aggtgcctcc tctagagccg tccggtgggg    188400
gccccggca gtggtggtgg tgtccactgg ccagcagctg ccccttcagc caggacagta    188460
ggcctgacgc tgtccccagc agctccaagg tggatttgtg gaaggggta gagggcacgt    188520
agaggcccca tgacctcccc agggttctgg gagggctgtg ccccccttagc cagcaccatg    188580
ctgggtgata tagtcagatc ctgttacccc tgttgtggag gtgaggaaac aggttagtgg    188640
ggaggacatg actaaggtcc atgctgagtc gctagagctg cacccagaac cactgctggg    188700
accccatgcc tttctgctta ccccttgtgc cgggagatgc caagagatgc tgggagccag    188760
ccccacctct gcccttggag tcatggctac ggaaagggca ttcggaccgg tccctgacct    188820
caccggggag ggccgaaccc tgttcctgag gagccagggc ttcctagagg aggtaggcct    188880
tctagtcact ccttcatctg caggcactcc acagagctct ctgtgccagc ccccagcacg    188940
gagggctgac cttagtcgag tggagatgcc ccagtgccag gcagtaggga tgatgtctcc    189000
tgaggcccag atggaaggga ctggactagt ctcatgggc tgatggtggg gccaggcctt    189060
gaccaggac ccagtgtagg gggtgcagag acccctctga gttcctcaca catccctggg    189120
gccctcccca tacacttcct atcctgactg cgggcaagag ggagcccag ttcgccttcc    189180
ctatgctggg cacccacagt ggggctgggc accccgccca tgcccctgcc ctgtccttcc    189240
cctgagagcc tcggtcccac ctccaaggtg cctcagagga cagcaggggc agcgggcaga    189300
```

-continued

```
ggccgagatg cctcctcatt ccaggctcag ctgcccttct tggggcagcc cacacctgag 189360
agtctcctgc agttggtcag gcctgaggag ggcaggggggg tgcctgctgt ccctctgctg 189420
accacagtgg catttagcct gggcaccgcg cccagcacag tccatgctgc acaggtgccg 189480
tgggctccac agagccctgc ctgacatgca tgtgttacgt ttcgggtgcc gatgcccttg 189540
ggcggcactt ctccgggcag aaccccagg ccaccgctcc ggttccggtt ccgctgcatc 189600
tggggctctc ggcaggctgt ggtcctccgg ccagcctggg ggcatctcag tcccacagcc 189660
ccacaggggc ctgccccgca gcctgggcct cgagcccgt ctccgcacgc tgtgccgaat 189720
ctggctgccc atcagctccc tgcgtaccca gactgtgccc tgccatgccc gtggctcttc 189780
ccaggagtgc cctgtggcct cccctggct tgctgggctg attccctcct gtgtctcaaa 189840
cagagctcac ctttgccatc actgctgtcc tcaccggccg gtgccagagg cccgtgtctg 189900
tgtaccctgt gtctgcacct ctgggcaggg cctggctctg accaacccgg gcttccagtg 189960
tccacagacc taaggcccag ggcgcctggg ggctggagca agagaagcaa aaggagccaa 190020
gggtgggggt ttggggttct tgtgagggcc cagccccagg accccaggac caggacccc 190080 aggagcccca gggcccagcc ccagttcaga aggcaggggc cttctgaggg agcttaaggg 190140
tcccacagcc caggaccccc accagggcca gtggccagcg ttgggggact cagcctcctc 190200
gtcgctcgtc ctctctgttt ctcccacctt ttgccccctt tctccttgcc tgttcccacc 190260
cgaggccccc tcttggcctg cgtgagccgg ggcggcactg aactgggggc cgatccgcct 190320
gggcggcggt gagaggcagg gccgggagcc gggccgctgg gtttgggcct ggcccgctcg 190380
ccgcaatatt gatggcccgt cagtgcagcc ctgattcctg tgctttcagt taaaaggttt 190440
ctgttgttgt agcttatgca gttgctctgt tgctatggaa acgtgacatc aaaatgacgt 190500
ttcccgttta aaagcttta actaaattcc tgcctgtcag atgtaggccc cattttgagc 190560
gtggagctgc cttcgagcga gcgtgagcgg cgcctcccgc ccatggtgcg tggggccggg 190620 ccgggggccct cgctgagcgc gctctctcac cccacaggcg cctccggcat ggcggcggcc 190680
gaggggcccg gctacctcgt gtctccccag gcggagaagc accggcgggc ccgcaactgg 190740
acggacgccg agatgcgcgg cctcatgctg gtctgggagg agttcttcga cgagctcaag 190800
cagaccaagc gcaacgccaa ggtgtacgag aagatggcca gcaagctctt cgagatgacc 190860
ggcgagcgca ggctgggcga ggagatcaag atcaagatca ccaacatgac cttccagtac 190920
aggtgggcga gcgggcagtg tgggccccac caggacgggc gggcccgggc gtggcgggcc 190980
gctcctgact ttcttggagc tctgagtcgg gacgatgtgt gggtcgtggc ctgcctgtcg 191040
gtctcctctg gccgggtatg ggcagaaccc cacggggtga cgggcccc acggaaaccg 191100 tgtgtgcagc cttccattgg ggaagtgggg aaactgaggc ccagcaaggg caggaaacca 191160
gtctaagagc tgaggggtag caggggtggg gctggtgctg ggcagaggcc aggatggctc 191220
ccaggacgta tgggcggtct gggcactgtc cctcggaggc agcaacactc atggtggtgc 191280
ccactgacct cacaccctgc tcccccatag ggaggcggcg gctgccagtg ccctcccac 191340 caccaagctc ccaagctcag cagggggtttc aggggcctac tgcgtcattg gggaaattga 191400
gactgcaagt gagaaggagg ctcagtgctc tgcgacttgg agcatccact gagcctctgc 191460
catgagccgg tgagccccac tggggctggc cctagggtca cggtggggta tttccagaaa 191520
tcaccaggtg aggtgcagga ccagccagcg catgggtggg gcttacggtg cgaagaagaa 191580
agaggtggag gcctgccctg gcccaggact cccagcgtgg gggctccgg cctgcccca 191640 cctctgctcc tgctacatgg caggtgggcc cttcctgccc tggcaacctg cagggaaggc 191700
```

```
cggaggggac cacccagcca gggagatgtt ggcgtctagg aggggacagg tgtggtccca  191760
cacacccagc atcttaaagt gcgtgggtcc ccagcccatt aggacagggt cccgggtggg  191820
caggggtcat ggtggggtga aggtctcagg cacaggcaag gtcacaggtg cggtgagggt  191880
cttgcagggt gtgaaggtca taggtgtgcg gtgaaggtca caggtgtggg gtgatggttt  191940
tgggtgtggg gagggtcttg cacggagcga gggtggcagc aagagctgga agctgcaggg  192000
ggagaatggc agcagagagc acccggccct gtgggcggcc tggacagggc tgggcctggg  192060
gctgccggag agcctgtcag cttccaggat gggagtggcc tcactcagct gctccacctc  192120
cgggtcaggc aggtgagcct ggggcagaga ggctgagagc acctgagcca cttgtgggag  192180
aggccacccc cactgccccc ctcaggcgag gagccggcct ccagcacagc agaagggaac  192240
ccccagtccc cagccctagt gggagtgggg aagaggccca gcaaggcccc ggacagaccg  192300
ccagcctgtg aggtctccgc tttcagttgc gttgatttga ttttttctga gccttgaagg  192360
aggggtccgg ggcctggccc tgcccaaagg cccctaggca ggcccaaagg ccgggaccta  192420
gggtgctgag catgacggat gttgggtttg agcggctggc ttgcgacgtg agggctgagg  192480
tgtgagcctg ggtatcttca gaggttcggt ggacacaggc agctgcccgc ggccccactg  192540
ttcccgtggc ctcctagtcc tgctcaggca cctggtgagg aagggacgca gagggcagtg  192600
ggaggtggcc acgactgttc cagcaggctc ccctctgact caggaattca cgggcaccac  192660
ctccctggct ggctctggtt ggtgtctggc caggttattc attatttatg ctgaaagcct  192720
cttcagagtc ccaggggagg gtttctgtct ccattcctgg aggctgagag atgagggtgc  192780
agcagagtgg gggcctccac tccagaccct gcagtctggg ctggccaagg gctgcaccgg  192840
tgcactgcac gtcatggctg atgaagcact tccacaccgc agcccctcag agctgccaca  192900
gtcagcctta gttcaccgag ggggaagctg aggcccagag catgagaggg acttgcccag  192960
ggccacatag tccttagcag aggaagctgt ggctgggtga ctcgatcttt gtcctttttc  193020
tttatacccg cagtctcccc atagcagagg cttttctttt ttttttcttt ttcttttttt  193080 ttttttaca agaactcttt atatattaag gctgttgggc tgaagaagcc tgagagggtg  193140
gctggttctg tggagcatgg tttgttgaag tacagtttgg gggcctccta cactgagaat  193200
aggccttttc tcgtttctcc aaagagtggg ctggctcaag tagggcagag agagaagcct  193260
ggggcagagg ttagggatgg gcacccagcg cctgccctca cacgctctgt gctggtgtct  193320
tcacagccac gtgccaccct gggcagcatc ccctgctcac catctggctg tgcctgtttg  193380
ctgggggcac ctcattcaga atccagctta ttgtttccaa cggccaatgg ccacaccctg  193440
gcaggtagca agagtaggag agaggagaca cccactccga gcacaggttg ggtttggagc  193500
ccggccttgg ggcactctgt cactcaaagg cagagtgggg agtgggcact gggccttagg  193560
aggtactggg tccagtgagg cagagatgcc cctgccccac cccacccttg tggcttcttc  193620
cctggcctgg ccagagctgt ctggccgcca tgggccctg tgtctcctgc cttgacctcc  193680
cagagggcag ccgaggccca gggaggcct ggggacttag cctctcaggg caggacctgt  193740
ctgcaggagt aggtgggtgc tgggggtccc agtggtaatg aggcatcagg cagtgtggga  193800
aggggcccat ccgccccacc ccagggcctc tgggcaggtt gcaggttgta gcgctggatc  193860
taggctcctg cccagactgt aggttcaacc aagaatggca tgggagccca gcctgctgtt  193920
tgctttatta aatctgccct gtagctgggg gagggctta ctttgatcat cactatgtca  193980
ttgatataaa aatagaggct cagagaggtg aatgaacctg cccaaagtca cacagcaaag  194040
```

```
tgtggagatg agatactgac tcagggctgt ggacactgaa gcctgtgctc taacgccagt    194100
ggctgtcgct ccctgaggca ttctctcccg aacaacacag ttattatatt acaaaatatt    194160
atcactatat ttatatatct tataataacct tattattaca ataaaaccttt attactctac    194220 cttcaaaat gaattattta aaaagcagta tttgctcatt gcagagagtc tagaaactat    194280
agaaaagcaa gggaaaagca ataggaccag ccccaaggtc ccagcatgca cagataaacct    194340 tagtaatact gggacgtgtg cttccttttt aacatctgag cccgtgtagg tcctgaagcc    194400
cagcttcttt ctaagtccat tgtcatcttg accctggagc ctggccgatt ttgctgggga    194460
ggcccttgcc agccgagagc ggctcctgcc tgtgccggcg tggcgcgccc ctctgctgag    194520
gctgggcagg acagggggctg ggccagctct gtttctcacc cttggctctt gtgtctctcg    194580
tttcaggaaa ttaaaatgca tgacagatag cgagtccgcc ccgcccgact ggccctatta    194640
cctagccatt gatgggattc tggccaaggt ccccgagtcc tgtgatggca aactgccgga    194700
cagccagccg ccgggggccct ccacgtccca gaccgaggcg tccctgtcgc cgcccgctaa    194760
gtccacccct ctgtacttcc cgtataacca gtgctcctac gaaggccgct tcgaggatga    194820
tcgctccgac agctcctcca gcttactgtc ccttaagttc aggtagtgtg tctgcttgtc    194880
cttcccctgc cctggggtat ctcagccccc accatttaga gaaagggact gggagtggca    194940
aggccggcgg cggcggccac agtggttgca gaggccgtgg ctgcgggcag cgcctccagg    195000
gacaggcggc ctcagaccag ggagggcttt agtgtccaca ggcagaccga gtttgtctcc    195060
cagctccatc acttttgagc tgcacggaaa gttccttgac ttctctggcc tcagtctccc    195120
tcctataaaa tggggggtaaa tcagtaccttt tctcagaggg tggctgggag catcacagga    195180
gagaagacgc agcatggggc ccggcacacg gagggagacc aagccccaga ccccagaatg    195240 cgcccctgg cctcccttag cccacacaga ccccacccctc acaggctagc tgccctctca    195300
gcactgggga gggtgtcggg ctgcacctca tcacgtgttg ccgtgggcat gacccgtccc    195360
ctctgccatc catcccacac ctcagacccg tcccgtgctg gccacgtgac tgtgcctgca    195420
agatgctcac agggcagccg ggagccaggc agcatgcagg acagacacct gcggggtggg    195480
cctggggagc ccagagaagg tgcttttgag gaggggacat ttggggtggg ctttcaaggt    195540
aaaatagaag ttggccattt ggaggcaaga acaggaagat tgtggatttg agtcacagct    195600
tctcccctgc cctggtcttc aagtcttttct gacaggaggt gtcagaaaag tatctttagt    195660
agagaaggcg tctccgagga gggtccctct catgccgggg gccgctgctt gactcaggat    195720
ttctcattga agacctgaga caaaaacgct tttgctggca gctagaagga accagcagga    195780
ggcctgagat ttgtggctgt tgttcccgtg gactgagccc agttctcaga ctcagctgcc    195840
tggggccttg cacaggactg gggcgtgggg gctgccctcc ctgatcaggc ccaaagcgcg    195900
gatctcacgc ccctgaggtt ggctgtaccc tctcagctca gagcagagtg tgggccaggg    195960
atgagcaggc actggagcag ggccctgggg tctgtgggtt ttggcagctc cctgcccttc    196020
agggaggtct gctgagacca cggggtggccc ctacccagc agcagagctc tcaggaggcg    196080
cccacagggc tggactgcct ttactcacca cctctaccag agctctgagg tcctggggag    196140
agagcccagg cctcttgtgg gccccacacc ctctaggtgc ctgtccttct gcctctctac    196200
caaggtgtgc cggccccatt tctaggccgc cgggagataa gggggctcac atctcaggcc    196260
cttccttctg ggaccctcagt ttccccatct gcctaaggcc gggtgggggct ggtggtcttg    196320 gcttccctac aggggtcctg agtactctgc actacccagc acccccacacc cctgccttca    196380 tctctccctg gggggtggtct ctccaccccct ggccccaaac tggggctgag cccccacctg    196440
```

```
cccagtttgg tgggtgaagg gtgctccctg gcaggatatg cccctctgca gcccagaaca   196500
tcccacccct tccagaccga aggggtgtgg attgtcctgg gaccctggtc attggggtca   196560
tccgctagtc gcaaaggacg gcaatgcctg tggcctctct ttctttcttt ttcttttttt   196620
ttttttttga gacggagtct cgctcttgtg cagagagcag tggcgcgatc ttggctcact   196680
gcaacctccg cctcgtgggt tcaagcgatt ctcctgcctc agcctcccga gtagctggga   196740
ttacaggcac cgccacaac gcctggctaa tttttgtatt tttagtagag atggggtttc    196800
accatgttgg ccaggctggt cttgaactcc tgacctcagg tgatccacct gcctctgcct   196860
cccaaagtgc tgggattaca ggcataagcc tccacacccg gccacccctg ttactttctg   196920
tcaaaggcgg tgggttctgg cccctccttt gcacatggaa tatgagaccc tgagtaagtg   196980
acctgactcc ctggggcctc agtttcccca tttgcccagt aggattgtcg ggagggtccg   197040
gtgaggcccc tggtgtgccc aggctctgtg ccagcacgt ccacagccgg cactgtcctt    197100
ccaggtcgga ggagcggccg gtgaagaagc gcaaggtgca gagctgccac ctgcagaaga   197160
agcagctgcg gctgctggag gccatggtgg aggagcagcg ccggctgagc cgcgccgtgg   197220
aggagacctg ccgcgaggtg cgccgcgtgc tggaccagca gcacatcctg caggtgcaga   197280
gcctgcagct gcaggagcgc atgatgagtc tgctggagag gatcatcacc aagtccagcg   197340
tctaggccag caggcggcgg cggcggcggg gccgggcggc tggtggtact gctcaggcca   197400
cccagggcag gccactcagg ccaggcgggc aaggggccg ccccgcgagc ggagaccgcc    197460
ttccacctgg cctctggcag gatgtccctt ctgaggggta ttttgaggaa ccccaggcc    197520
ctggggaccg tgaggctcca gtctccagca tgaatgccct cctcggaca caggccaggg    197580
cctctgggt tcactccgag taagaacgtc ctagagccac tctccagtgt cgttactatc    197640
aatgatactt gacgtggctt tgatattaaa cgtatacttt ttcattcttg cctggaacgc   197700
acagtttgct gttgctggct tggtgaggat gccctgattg atggatcccg aaaatgaaag   197760
cagatggaaa cgggttgggg caggctggag ctggggagc tctctcctga agggaaccct    197820
gtgtcctccc tcaccaggac ctctgcgtct ctccttaaat ggcctctgac gcctgatgaa   197880
aaccccagcg accttccagg aggctttat tcagctctgt ttggagcatc aggtgtttcc    197940
actgcctcct tagcaatgac actaataaaa gtcgtaacac ctgttcacat gcacagccct   198000
gttgagtgtt ctgggtgctg gagatatcat ggtggatgac acaaaggccc tggcctcttg   198060
gagcttatgc tcccatgcgg ggaagacaca tgggtcagta gagaaatggt tgcaggttgt   198120
gataagtgct ggaagggagg ggttggcctg aggacacgga ggcagacata cgtggagctg   198180
ggaacagtgg ccacacaggg aacggccagt gcgaaggccc agaggcagag gacactggag   198240
caagcccagc agcagctagg aggctggtgg ccagcagcca ggcacggaa gcccgtgcag    198300
cccgtgggga ggagtgttca tgcttttcaa gcttagtggg agtcttttgg ccagtgcagc   198360
tctgggtctg acatcggtgg gggacagagg ggtggtggag cggccacagc tgcaagctca   198420
cctcactgcc ggcccttcca ccagtttcaa actctttcta gaagctccag ctttcccaaa   198480
gctgaattct ctatgagcct ccttggccgg gactcgggcg tctggttgcc ctggctgcaa   198540
aggaggctgg ggccaggtgt gtttgagtca cctcctggaa ttaggcaagt tgctgcccaa   198600
atagaaggtt gttggcaggt gggtcagcag gtgaacagca tggtttgact cagggttcag   198660
aaaaatctcc ctctggctgc caagcgagca ggccgtggag acaggtgcag aggcaggtgt   198720
ggcagcaggc atcctgccag gcagtgctgc agtcatcctg cgacaagcag cagcagctca   198780
```

```
tcctaccctc tagggggtct tgaggtcagc caggcaagag agcagcttgg actccactgg   198840
gtgtgggacc agcctgtgga ccatggtggt gtggagggtg ccctcggcct gcctgtgtga   198900
aggagaggcc ggcgtgttct gtggagccca aaggggagct gggcaagcag gattcacttc   198960
actctgaggg tcctggagct cccaccctcc tcagccatct ccccagagcc tgtgtgccga   199020
ggactcggcc catgttgctg tgggatgaga ggcagagtgt cgtgagggtg taaggagcgg   199080
cggcagtggt gggaggaggg agcagcagcc agcgctacgg tgccagtttc agctgccag   199140
atgacgccgc tgaccctgtg gttgagaaga gatgcacaga gccagctctt gcaagccagt   199200
gtggctgcca tagcacctgc cgagaagcag aaggaagggt ggcccaggga ggacagagga   199260
tgcgggcaca tctgatgcgg gcctgagttt tgggagcttt tgctctagcc agtttccagc   199320
tccgggaccc acccgcctcg taggcaagac accacccaag aaatcatttg cttaacaaac   199380
acactgggct ccaactggac acctgtgcca ccctagatgc tgggaaccca gccatgacac   199440
aggcacctgc ccccagctgc tgaccactga ggctggctag cagctcccat ggggccagtg   199500
tggggttccc cagcctccta acaggagcc agtcacaagc cctcgagagg gaagggtgcc   199560
cgcggccctg gcaggaaggt taggctggac gctcccacaa gacataacag atggaggttc   199620
taaatgatgt agcaacttct tcaccctgaa actgctgtag agtcagccat gacgcaccgg   199680
tacttcagta actgccaggc atccgggaca gcacaccgcg agtcgctgct gtgcttgggt   199740
tagaagtggt ttggtctgtt ttcttctcgc cctctctaat cagagtcagt gattcatgcc   199800
cttccatcac cttagagaag gggcaggcgc tgcccgacct tctccaggct ggagcagcat   199860
cgcctcatgt cagcagaact cagctgtaga atatcgtggg gttggtgcct ttcatcagca   199920
gcatgtcctt aacaactttc tgatttcttc cttagttgtt ggtccattaa ggagaaaaaa   199980
aatgatctca gccattgcta aaatatttga taagattcag caaagcagca tgttaacatt   200040
gaaaactaga atcaggagcc aggcagatgt gcttgctttt cacctgtagt atttcatgtt   200100
gttttgacgt ttttagctaa tgcattaaga taaataaaca aaagccgggc acggtggttc   200160
acgcctgtaa tcccagcact ttgggaggct gaggcgggag gatcctctga ggtcaggagt   200220
tcaagaccag cctgaccaac atggagaaac ctcgtcatta ctaaaaatac aaaattagct   200280
gggcgtggtg gtgcatgcct gtaatcccag ctacttggga ggctgaggca ggagaatcgc   200340
ttgaacccgg gaggcggagg ttgcagtgag ctgagattgc accactgcac tccagcctgg   200400
gtgacagtga aactcggtct caaaaaaaaa aaaaattaa aaaagataa ataaaataag   200460
caggataaga aatgaagaaa gtagagttac ctttgttttc agatttcatt tttgtatacc   200520
cagaaagcca aatgtacaaa agactgggag ctctttaaac cagcttaaac ttgttgaaaa   200580
tgaggatgaa gaaatatccc attcagagtt ggaatgaatt taacccagaa ggaacaggac   200640
ctctactgaa gagaactatg cagtcttact gaaaaatcta aataatacct gagcgctgga   200700
gaaacttcgc acactcctga aagctccaaa gtcaatgtca tcattttatt aatgtcattc   200760
caaacatagt ctcaataata tcacttcttg gttttgacat ggacgcgatg atgtttaaat   200820
tcatatgaaa aaagaacggg gccaaaagtc caaggccagt cagcgtgaga agaccgctcg   200880
gcctccctcg gagtcgggga gttggaaccg cagactgaga tcatgtggct gctgaggcc   200940
aggacgaacg tcgggaaatg gagactcctg cgttgctggt gggatgtggt gcagccgctt   201000
ccaggagcaa tttggtgtcc cgtcctaaag ctgaagaaac gcatttcctc tggtcagtgc   201060
cactcctaga caggccaccc tgcggcagcc gtcctcaaac tggtctgagg acccctcaac   201120
gctcttaaaa atcattaaaa gtgggccagg tgcggtggct cacacctgta atcccagcac   201180
```

```
tttgggaggc caagacaggc ggatcacgag gtcaggacat tgagatcatc ctggctaaca    201240
cggtgaaacc ccgtctctac taaaaataca aaaaattagc cgggcgtggt ggcgggcgcc    201300
tgtagtccca gctacttggg aggctgagcc aggagaatgg cgtgaaccca ggaggtggag    201360
cttgcagtga gctgagatca ctccactgca ctccagcctg ggcagcagag cgagactctg    201420
tctcaaaaaa aaataataaa taaataaata aaaataaaat aaaataaaat tcattaaaag    201480
tgccaaagaa cttttgctta tgtgagttct aatgaccaat attaatacac attagaatat    201540
cttattagaa attaaacctg agacctttag aaaacatgta ttcatttcaa aatagcaata    201600
aacccatgac atattaacat aaataacaat tgtatgaaaa atatattttc caaaacaaaa    201660
agttttcggg agaagtgtgg catagtttta catggtcgta aatctctggc ttaagagaag    201720
cccactggcc tctcagcagg ctctgggtcc gtccactttg ggggtgtttt ggttgtgaag    201780
tataggagtg aatggagaag ctcattctta cccagatgtg tatttgaaaa gaaaaggaac    201840
attttaataa cctttgcaaa taatcggtat attcttccgt gatcctattc caacactgga    201900
caggtggtgg tttgttttt tttttggag acggagtccc gctctgtcac tcaggctgga    201960
gtgcagtggc gcgatttcag ctcactgcaa gctccgcctc c                        202001

<210> SEQ ID NO 2
<211> LENGTH: 13481
<212> TYPE: DNA
<213> ORGANISM: Homo sapiens
<220> FEATURE:
<221> NAME/KEY: CDS
<222> LOCATION: (146)..(9580)

<400> SEQUENCE: 2
gctgccggga cgggtccaag atggacggcc gctcaggttc tgcttttacc tgcggcccag              60
agccccattc attgccccgg tgctgagcgg cgccgcgagt cggcccgagg cctccgggga             120
ctgccgtgcc gggcgggaga ccgcc atg gcg acc ctg gaa aag ctg atg aag             172
                            Met Ala Thr Leu Glu Lys Leu Met Lys
                              1               5 gcc ttc gag tcc ctc aag tcc ttc cag cag cag cag cag cag cag cag             220
Ala Phe Glu Ser Leu Lys Ser Phe Gln Gln Gln Gln Gln Gln Gln Gln
 10                  15                  20                  25 cag cag cag cag cag cag cag cag cag cag cag cag cag caa cag ccg             268
Gln Gln Gln Gln Gln Gln Gln Gln Gln Gln Gln Gln Gln Gln Gln Pro
                 30                  35                  40 cca ccg ccg ccg ccg ccg ccg ccg cct cct cag ctt cct cag ccg ccg             316
Pro Pro Pro Pro Pro Pro Pro Pro Pro Pro Gln Leu Pro Gln Pro Pro
             45                  50                  55 ccg cag gca cag ccg ctg ctg cct cag ccg cag ccg ccc ccg ccg ccg             364
Pro Gln Ala Gln Pro Leu Leu Pro Gln Pro Gln Pro Pro Pro Pro Pro
         60                  65                  70 ccc ccg ccg cca ccc ggc ccg gct gtg gct gag gag ccg ctg cac cga             412
Pro Pro Pro Pro Pro Gly Pro Ala Val Ala Glu Glu Pro Leu His Arg
     75                  80                  85 cca aag aaa gaa ctt tca gct acc aag aaa gac cgt gtg aat cat tgt             460
Pro Lys Lys Glu Leu Ser Ala Thr Lys Lys Asp Arg Val Asn His Cys
 90                  95                 100                 105 ctg aca ata tgt gaa aac ata gtg gca cag tct gtc aga aat tct cca             508
Leu Thr Ile Cys Glu Asn Ile Val Ala Gln Ser Val Arg Asn Ser Pro
                110                 115                 120 gaa ttt cag aaa ctt ctg ggc atc gct atg gaa ctt ttt ctg ctg tgc             556
Glu Phe Gln Lys Leu Leu Gly Ile Ala Met Glu Leu Phe Leu Leu Cys
            125                 130                 135
```

```
agt gat gac gca gag tca gat gtc agg atg gtg gct gac gaa tgc ctc      604
Ser Asp Asp Ala Glu Ser Asp Val Arg Met Val Ala Asp Glu Cys Leu
        140                 145                 150 aac aaa gtt atc aaa gct ttg atg gat tct aat ctt cca agg tta cag      652
Asn Lys Val Ile Lys Ala Leu Met Asp Ser Asn Leu Pro Arg Leu Gln
155                 160                 165 ctc gag ctc tat aag gaa att aaa aag aat ggt gcc cct cgg agt ttg      700
Leu Glu Leu Tyr Lys Glu Ile Lys Lys Asn Gly Ala Pro Arg Ser Leu
170                 175                 180                 185 cgt gct gcc ctg tgg agg ttt gct gag ctg gct cac ctg gtt cgg cct      748
Arg Ala Ala Leu Trp Arg Phe Ala Glu Leu Ala His Leu Val Arg Pro
                190                 195                 200 cag aaa tgc agg cct tac ctg gtg aac ctt ctg ccg tgc ctg act cga      796
Gln Lys Cys Arg Pro Tyr Leu Val Asn Leu Leu Pro Cys Leu Thr Arg
        205                 210                 215 aca agc aag aga ccc gaa gaa tca gtc cag gag acc ttg gct gca gct      844
Thr Ser Lys Arg Pro Glu Glu Ser Val Gln Glu Thr Leu Ala Ala Ala
        220                 225                 230 gtt ccc aaa att atg gct tct ttt ggc aat ttt gca aat gac aat gaa      892
Val Pro Lys Ile Met Ala Ser Phe Gly Asn Phe Ala Asn Asp Asn Glu
235                 240                 245 att aag gtt ttg tta aag gcc ttc ata gcg aac ctg aag tca agc tcc      940
Ile Lys Val Leu Leu Lys Ala Phe Ile Ala Asn Leu Lys Ser Ser Ser
250                 255                 260                 265 ccc acc att cgg cgg aca gcg gct gga tca gca gtg agc atc tgc cag      988
Pro Thr Ile Arg Arg Thr Ala Ala Gly Ser Ala Val Ser Ile Cys Gln
                270                 275                 280 cac tca aga agg aca caa tat ttc tat agt tgg cta cta aat gtg ctc     1036
His Ser Arg Arg Thr Gln Tyr Phe Tyr Ser Trp Leu Leu Asn Val Leu
        285                 290                 295 tta ggc tta ctc gtt cct gtc gag gat gaa cac tcc act ctg ctg att     1084
Leu Gly Leu Leu Val Pro Val Glu Asp Glu His Ser Thr Leu Leu Ile
        300                 305                 310 ctt ggc gtg ctg ctc acc ctg agg tat ttg gtg ccc ttg ctg cag cag     1132
Leu Gly Val Leu Leu Thr Leu Arg Tyr Leu Val Pro Leu Leu Gln Gln
        315                 320                 325 cag gtc aag gac aca agc ctg aaa ggc agc ttc gga gtg aca agg aaa     1180
Gln Val Lys Asp Thr Ser Leu Lys Gly Ser Phe Gly Val Thr Arg Lys
330                 335                 340                 345 gaa atg gaa gtc tct cct tct gca gag cag ctt gtc cag gtt tat gaa     1228
Glu Met Glu Val Ser Pro Ser Ala Glu Gln Leu Val Gln Val Tyr Glu
                350                 355                 360 ctg acg tta cat cat aca cag cac caa gac cac aat gtt gtg acc gga     1276
Leu Thr Leu His His Thr Gln His Gln Asp His Asn Val Val Thr Gly
        365                 370                 375 gcc ctg gag ctg ttg cag cag ctc ttc aga acg cct cca ccc gag ctt     1324
Ala Leu Glu Leu Leu Gln Gln Leu Phe Arg Thr Pro Pro Pro Glu Leu
        380                 385                 390 ctg caa acc ctg acc gca gtc ggg ggc att ggg cag ctc acc gct gct     1372
Leu Gln Thr Leu Thr Ala Val Gly Gly Ile Gly Gln Leu Thr Ala Ala
        395                 400                 405 aag gag gag tct ggt ggc cga agc cgt agt ggg agt att gtg gaa ctt     1420
Lys Glu Glu Ser Gly Gly Arg Ser Arg Ser Gly Ser Ile Val Glu Leu
410                 415                 420                 425 ata gct gga ggg ggt tcc tca tgc agc cct gtc ctt tca aga aaa caa     1468
Ile Ala Gly Gly Gly Ser Ser Cys Ser Pro Val Leu Ser Arg Lys Gln
                430                 435                 440 aaa ggc aaa gtg ctc tta gga gaa gaa gaa gcc ttg gag gat gac tct     1516
Lys Gly Lys Val Leu Leu Gly Glu Glu Glu Ala Leu Glu Asp Asp Ser
```

-continued

```
                   445                 450                 455
gaa tcg aga tcg gat gtc agc agc tct gcc tta aca gcc tca gtg aag    1564
Glu Ser Arg Ser Asp Val Ser Ser Ser Ala Leu Thr Ala Ser Val Lys
        460                 465                 470 gat gag atc agt gga gag ctg gct gct tct tca ggg gtt tcc act cca    1612
Asp Glu Ile Ser Gly Glu Leu Ala Ala Ser Ser Gly Val Ser Thr Pro
    475                 480                 485 ggg tca gca ggt cat gac atc atc aca gaa cag cca cgg tca cag cac    1660
Gly Ser Ala Gly His Asp Ile Ile Thr Glu Gln Pro Arg Ser Gln His
490                 495                 500                 505 aca ctg cag gcg gac tca gtg gat ctg gcc agc tgt gac ttg aca agc    1708
Thr Leu Gln Ala Asp Ser Val Asp Leu Ala Ser Cys Asp Leu Thr Ser
                510                 515                 520 tct gcc act gat ggg gat gag gag gat atc ttg agc cac agc tcc agc    1756
Ser Ala Thr Asp Gly Asp Glu Glu Asp Ile Leu Ser His Ser Ser Ser
            525                 530                 535 cag gtc agc gcc gtc cca tct gac cct gcc atg gac ctg aat gat ggg    1804
Gln Val Ser Ala Val Pro Ser Asp Pro Ala Met Asp Leu Asn Asp Gly
        540                 545                 550 acc cag gcc tcg tcg ccc atc agc gac agc tcc cag acc acc acc gaa    1852
Thr Gln Ala Ser Ser Pro Ile Ser Asp Ser Ser Gln Thr Thr Thr Glu
    555                 560                 565 ggg cct gat tca gct gtt acc cct tca gac agt tct gaa att gtg tta    1900
Gly Pro Asp Ser Ala Val Thr Pro Ser Asp Ser Ser Glu Ile Val Leu
570                 575                 580                 585 gac ggt acc gac aac cag tat ttg ggc ctg cag att gga cag ccc cag    1948
Asp Gly Thr Asp Asn Gln Tyr Leu Gly Leu Gln Ile Gly Gln Pro Gln
                590                 595                 600 gat gaa gat gag gaa gcc aca ggt att ctt cct gat gaa gcc tcg gag    1996
Asp Glu Asp Glu Glu Ala Thr Gly Ile Leu Pro Asp Glu Ala Ser Glu
            605                 610                 615 gcc ttc agg aac tct tcc atg gcc ctt caa cag gca cat tta ttg aaa    2044
Ala Phe Arg Asn Ser Ser Met Ala Leu Gln Gln Ala His Leu Leu Lys
        620                 625                 630 aac atg agt cac tgc agg cag cct tct gac agc agt gtt gat aaa ttt    2092
Asn Met Ser His Cys Arg Gln Pro Ser Asp Ser Ser Val Asp Lys Phe
    635                 640                 645 gtg ttg aga gat gaa gct act gaa ccg ggt gat caa gaa aac aag cct    2140
Val Leu Arg Asp Glu Ala Thr Glu Pro Gly Asp Gln Glu Asn Lys Pro
650                 655                 660                 665 tgc cgc atc aaa ggt gac att gga cag tcc act gat gat gac tct gca    2188
Cys Arg Ile Lys Gly Asp Ile Gly Gln Ser Thr Asp Asp Asp Ser Ala
                670                 675                 680 cct ctt gtc cat tgt gtc cgc ctt tta tct gct tcg ttt ttg cta aca    2236
Pro Leu Val His Cys Val Arg Leu Leu Ser Ala Ser Phe Leu Leu Thr
            685                 690                 695 ggg gga aaa aat gtg ctg gtt ccg gac agg gat gtg agg gtc agc gtg    2284
Gly Gly Lys Asn Val Leu Val Pro Asp Arg Asp Val Arg Val Ser Val
        700                 705                 710 aag gcc ctg gcc ctc agc tgt gtg gga gca gct gtg gcc ctc cac ccg    2332
Lys Ala Leu Ala Leu Ser Cys Val Gly Ala Ala Val Ala Leu His Pro
    715                 720                 725 gaa tct ttc ttc agc aaa ctc tat aaa gtt cct ctt gac acc acg gaa    2380
Glu Ser Phe Phe Ser Lys Leu Tyr Lys Val Pro Leu Asp Thr Thr Glu
730                 735                 740                 745 tac cct gag gaa cag tat gtc tca gac atc ttg aac tac atc gat cat    2428
Tyr Pro Glu Glu Gln Tyr Val Ser Asp Ile Leu Asn Tyr Ile Asp His
                750                 755                 760 gga gac cca cag gtt cga gga gcc act gcc att ctc tgt ggg acc ctc    2476
Gly Asp Pro Gln Val Arg Gly Ala Thr Ala Ile Leu Cys Gly Thr Leu
```

-continued

```
                        Gly Asp Pro Gln Val Arg Gly Ala Thr Ala Ile Leu Cys Gly Thr Leu
                                        765                 770                 775 atc tgc tcc atc ctc agc agg tcc cgc ttc cac gtg gga gat tgg atg              2524
Ile Cys Ser Ile Leu Ser Arg Ser Arg Phe His Val Gly Asp Trp Met
                780                 785                 790 ggc acc att aga acc ctc aca gga aat aca ttt tct ttg gcg gat tgc              2572
Gly Thr Ile Arg Thr Leu Thr Gly Asn Thr Phe Ser Leu Ala Asp Cys
795                 800                 805 att cct ttg ctg cgg aaa aca ctg aag gat gag tct tct gtt act tgc              2620
Ile Pro Leu Leu Arg Lys Thr Leu Lys Asp Glu Ser Ser Val Thr Cys
810                 815                 820                 825 aag tta gct tgt aca gct gtg agg aac tgt gtc atg agt ctc tgc agc              2668
Lys Leu Ala Cys Thr Ala Val Arg Asn Cys Val Met Ser Leu Cys Ser
                830                 835                 840 agc agc tac agt gag tta gga ctg cag ctg atc atc gat gtg ctg act              2716
Ser Ser Tyr Ser Glu Leu Gly Leu Gln Leu Ile Ile Asp Val Leu Thr
                845                 850                 855 ctg agg aac agt tcc tat tgg ctg gtg agg aca gag ctt ctg gaa acc              2764
Leu Arg Asn Ser Ser Tyr Trp Leu Val Arg Thr Glu Leu Leu Glu Thr
                860                 865                 870 ctt gca gag att gac ttc agg ctg gtg agc ttt ttg gag gca aaa gca              2812
Leu Ala Glu Ile Asp Phe Arg Leu Val Ser Phe Leu Glu Ala Lys Ala
        875                 880                 885 gaa aac tta cac aga ggg gct cat cat tat aca ggg ctt tta aaa ctg              2860
Glu Asn Leu His Arg Gly Ala His His Tyr Thr Gly Leu Leu Lys Leu
890                 895                 900                 905 caa gaa cga gtg ctc aat aat gtt gtc atc cat ttg ctt gga gat gaa              2908
Gln Glu Arg Val Leu Asn Asn Val Val Ile His Leu Leu Gly Asp Glu
                910                 915                 920 gac ccc agg gtg cga cat gtt gcc gca gca tca cta att agg ctt gtc              2956
Asp Pro Arg Val Arg His Val Ala Ala Ala Ser Leu Ile Arg Leu Val
                925                 930                 935 cca aag ctg ttt tat aaa tgt gac caa gga caa gct gat cca gta gtg              3004
Pro Lys Leu Phe Tyr Lys Cys Asp Gln Gly Gln Ala Asp Pro Val Val
                940                 945                 950 gcc gtg gca aga gat caa agc agt gtt tac ctg aaa ctt ctc atg cat              3052
Ala Val Ala Arg Asp Gln Ser Ser Val Tyr Leu Lys Leu Leu Met His
955                 960                 965 gag acg cag cct cca tct cat ttc tcc gtc agc aca ata acc aga ata              3100
Glu Thr Gln Pro Pro Ser His Phe Ser Val Ser Thr Ile Thr Arg Ile
970                 975                 980                 985 tat aga ggc tat aac cta cta cca agc ata aca gac gtc act atg  gaa             3148
Tyr Arg Gly Tyr Asn Leu Leu Pro Ser Ile Thr Asp Val Thr Met Glu
                990                 995                 1000 aat aac ctt tca  aga gtt att gca gca  gtt tct cat gaa cta  atc              3193
Asn Asn Leu Ser  Arg Val Ile Ala Ala  Val Ser His Glu Leu  Ile
                1005                 1010                 1015 aca tca acc acc  aga gca ctc aca ttt  gga tgc tgt gaa gct  ttg              3238
Thr Ser Thr Thr  Arg Ala Leu Thr Phe  Gly Cys Cys Glu Ala  Leu
                1020                 1025                 1030 tgt ctt ctt tcc  act gcc ttc cca gtt  tgc att tgg agt tta  ggt              3283
Cys Leu Leu Ser  Thr Ala Phe Pro Val  Cys Ile Trp Ser Leu  Gly
                1035                 1040                 1045 tgg cac tgt gga  gtg cct cca ctg agt  gcc tca gat gag tct  agg              3328
Trp His Cys Gly  Val Pro Pro Leu Ser  Ala Ser Asp Glu Ser  Arg
                1050                 1055                 1060 aag agc tgt acc  gtt ggg atg gcc aca  atg att ctg acc ctg  ctc              3373
Lys Ser Cys Thr  Val Gly Met Ala Thr  Met Ile Leu Thr Leu  Leu
                1065                 1070                 1075
```

```
tcg tca gct tgg ttc cca ttg gat ctc tca gcc cat caa gat gct      3418
Ser Ser Ala Trp Phe Pro Leu Asp Leu Ser Ala His Gln Asp Ala
            1080                1085                1090 ttg att ttg gcc gga aac ttg ctt gca gcc agt gct ccc aaa tct      3463
Leu Ile Leu Ala Gly Asn Leu Leu Ala Ala Ser Ala Pro Lys Ser
1095                1100                1105 ctg aga agt tca tgg gcc tct gaa gaa gaa gcc aac cca gca gcc      3508
Leu Arg Ser Ser Trp Ala Ser Glu Glu Glu Ala Asn Pro Ala Ala
        1110                1115                1120 acc aag caa gag gag gtc tgg cca gcc ctg ggg gac cgg gcc ctg      3553
Thr Lys Gln Glu Glu Val Trp Pro Ala Leu Gly Asp Arg Ala Leu
            1125                1130                1135 gtg ccc atg gtg gag cag ctc ttc tct cac ctg ctg aag gtg att      3598
Val Pro Met Val Glu Gln Leu Phe Ser His Leu Leu Lys Val Ile
            1140                1145                1150 aac att tgt gcc cac gtc ctg gat gac gtg gct cct gga ccc gca      3643
Asn Ile Cys Ala His Val Leu Asp Asp Val Ala Pro Gly Pro Ala
            1155                1160                1165 ata aag gca gcc ttg cct tct cta aca aac ccc cct tct cta agt      3688
Ile Lys Ala Ala Leu Pro Ser Leu Thr Asn Pro Pro Ser Leu Ser
        1170                1175                1180 ccc atc cga cga aag ggg aag gag aaa gaa cca gga gaa caa gca      3733
Pro Ile Arg Arg Lys Gly Lys Glu Lys Glu Pro Gly Glu Gln Ala
            1185                1190                1195 tct gta ccg ttg agt ccc aag aaa ggc agt gag gcc agt gca gct      3778
Ser Val Pro Leu Ser Pro Lys Lys Gly Ser Glu Ala Ser Ala Ala
Ser Val Pro Leu Ser Pro Lys Lys Gly Ser Glu Ala Ser Ala Ala
    1200                1205                1210 tct aga caa tct gat acc tca ggt cct gtt aca aca agt aaa tcc      3823
Ser Arg Gln Ser Asp Thr Ser Gly Pro Val Thr Thr Ser Lys Ser
        1215                1220                1225 tca tca ctg ggg agt ttc tat cat ctt cct tca tac ctc aaa ctg      3868
Ser Ser Leu Gly Ser Phe Tyr His Leu Pro Ser Tyr Leu Lys Leu
            1230                1235                1240 cat gat gtc ctg aaa gct aca cac gct aac tac aag gtc acg ctg      3913
His Asp Val Leu Lys Ala Thr His Ala Asn Tyr Lys Val Thr Leu
            1245                1250                1255 gat ctt cag aac agc acg gaa aag ttt gga ggg ttt ctc cgc tca      3958
Asp Leu Gln Asn Ser Thr Glu Lys Phe Gly Gly Phe Leu Arg Ser
            1260                1265                1270 gcc ttg gat gtt ctt tct cag ata cta gag ctg gcc aca ctg cag      4003
Ala Leu Asp Val Leu Ser Gln Ile Leu Glu Leu Ala Thr Leu Gln
        1275                1280                1285 gac att ggg aag tgt gtt gaa gag atc cta gga tac ctg aaa tcc      4048
Asp Ile Gly Lys Cys Val Glu Glu Ile Leu Gly Tyr Leu Lys Ser
            1290                1295                1300 tgc ttt agt cga gaa cca atg atg gca act gtt tgt gtt caa caa      4093
Cys Phe Ser Arg Glu Pro Met Met Ala Thr Val Cys Val Gln Gln
            1305                1310                1315 ttg ttg aag act ctc ttt ggc aca aac ttg gcc tcc cag ttt gat      4138
Leu Leu Lys Thr Leu Phe Gly Thr Asn Leu Ala Ser Gln Phe Asp
            1320                1325                1330 ggc tta tct tcc aac ccc agc aag tca caa ggc cga gca cag cgc      4183
Gly Leu Ser Ser Asn Pro Ser Lys Ser Gln Gly Arg Ala Gln Arg
        1335                1340                1345 ctt ggc tcc tcc agt gtg agg cca ggc ttg tac cac tac tgc ttc      4228
Leu Gly Ser Ser Ser Val Arg Pro Gly Leu Tyr His Tyr Cys Phe
        1350                1355                1360 atg gcc ccg tac acc cac ttc acc cag gcc ctc gct gac gcc agc      4273
Met Ala Pro Tyr Thr His Phe Thr Gln Ala Leu Ala Asp Ala Ser
            1365                1370                1375
```

```
ctg agg aac atg gtg cag gcg gag cag gag aac gac acc tcg gga      4318
Leu Arg Asn Met Val Gln Ala Glu Gln Glu Asn Asp Thr Ser Gly
        1380                1385                1390 tgg ttt gat gtc ctc cag aaa gtg tct acc cag ttg aag aca aac      4363
Trp Phe Asp Val Leu Gln Lys Val Ser Thr Gln Leu Lys Thr Asn
        1395                1400                1405 ctc acg agt gtc aca aag aac cgt gca gat aag aat gct att cat      4408
Leu Thr Ser Val Thr Lys Asn Arg Ala Asp Lys Asn Ala Ile His
        1410                1415                1420 aat cac att cgt ttg ttt gaa cct ctt gtt ata aaa gct tta aaa      4453
Asn His Ile Arg Leu Phe Glu Pro Leu Val Ile Lys Ala Leu Lys
        1425                1430                1435 cag tac acg act aca aca tgt gtg cag tta cag aag cag gtt tta      4498
Gln Tyr Thr Thr Thr Thr Cys Val Gln Leu Gln Lys Gln Val Leu
        1440                1445                1450 gat ttg ctg gcg cag ctg gtt cag tta cgg gtt aat tac tgt ctt      4543
Asp Leu Leu Ala Gln Leu Val Gln Leu Arg Val Asn Tyr Cys Leu
        1455                1460                1465 ctg gat tca gat cag gtg ttt att ggc ttt gta ttg aaa cag ttt      4588
Leu Asp Ser Asp Gln Val Phe Ile Gly Phe Val Leu Lys Gln Phe
        1470                1475                1480 gaa tac att gaa gtg ggc cag ttc agg gaa tca gag gca atc att      4633
Glu Tyr Ile Glu Val Gly Gln Phe Arg Glu Ser Glu Ala Ile Ile
        1485                1490                1495 cca aac atc ttt ttc ttg gta tta cta tct tat gaa cgc tat          4678
Pro Asn Ile Phe Phe Leu Val Leu Leu Ser Tyr Glu Arg Tyr
        1500                1505                1510 cat tca aaa cag atc att gga att cct aaa atc att cag ctc tgt      4723
His Ser Lys Gln Ile Ile Gly Ile Pro Lys Ile Ile Gln Leu Cys
        1515                1520                1525 gat ggc atc atg gcc agt gga agg aag gct gtg aca cat gcc ata      4768
Asp Gly Ile Met Ala Ser Gly Arg Lys Ala Val Thr His Ala Ile
        1530                1535                1540 ccg gct ctg cag ccc ata gtc cac gac ctc ttt gta tta aga gga      4813
Pro Ala Leu Gln Pro Ile Val His Asp Leu Phe Val Leu Arg Gly
        1545                1550                1555 aca aat aaa gct gat gca gga aaa gag ctt gaa acc caa aaa gag      4858
Thr Asn Lys Ala Asp Ala Gly Lys Glu Leu Glu Thr Gln Lys Glu
        1560                1565                1570 gtg gtg gtg tca atg tta ctg aga ctc atc cag tac cat cag gtg      4903
Val Val Val Ser Met Leu Leu Arg Leu Ile Gln Tyr His Gln Val
        1575                1580                1585 ttg gag atg ttc att ctt gtc ctg cag cag tgc cac aag gag aat      4948
Leu Glu Met Phe Ile Leu Val Leu Gln Gln Cys His Lys Glu Asn
        1590                1595                1600 gaa gac aag tgg aag cga ctg tct cga cag ata gct gac atc atc      4993
Glu Asp Lys Trp Lys Arg Leu Ser Arg Gln Ile Ala Asp Ile Ile
        1605                1610                1615 ctc cca atg tta gcc aaa cag cag atg cac att gac tct cat gaa      5038
Leu Pro Met Leu Ala Lys Gln Gln Met His Ile Asp Ser His Glu
        1620                1625                1630 gcc ctt gga gtg tta aat aca tta ttt gag att ttg gcc cct tcc      5083
Ala Leu Gly Val Leu Asn Thr Leu Phe Glu Ile Leu Ala Pro Ser
        1635                1640                1645 tcc ctc cgt ccg gta gac atg ctt tta cgg agt atg ttc gtc act      5128
Ser Leu Arg Pro Val Asp Met Leu Leu Arg Ser Met Phe Val Thr
        1650                1655                1660 cca aac aca atg gcg tcc gtg agc act gtt caa ctg tgg ata tcg      5173
Pro Asn Thr Met Ala Ser Val Ser Thr Val Gln Leu Trp Ile Ser
```

```
                    1665              1670              1675
gga att ctg gcc att ttg agg gtt ctg att tcc cag tca act gaa       5218
Gly Ile Leu Ala Ile Leu Arg Val Leu Ile Ser Gln Ser Thr Glu
            1680              1685              1690 gat att gtt ctt tct cgt att cag gag ctc tcc ttc tct ccg tat       5263
Asp Ile Val Leu Ser Arg Ile Gln Glu Leu Ser Phe Ser Pro Tyr
            1695              1700              1705 tta atc tcc tgt aca gta att aat agg tta aga gat ggg gac agt       5308
Leu Ile Ser Cys Thr Val Ile Asn Arg Leu Arg Asp Gly Asp Ser
            1710              1715              1720 act tca acg cta gaa gaa cac agt gaa ggg aaa caa ata aag aat       5353
Thr Ser Thr Leu Glu Glu His Ser Glu Gly Lys Gln Ile Lys Asn
            1725              1730              1735 ttg cca gaa gaa aca ttt tca agg ttt cta tta caa ctg gtt ggt       5398
Leu Pro Glu Glu Thr Phe Ser Arg Phe Leu Leu Gln Leu Val Gly
            1740              1745              1750 att ctt tta gaa gac att gtt aca aaa cag ctg aag gtg gaa atg       5443
Ile Leu Leu Glu Asp Ile Val Thr Lys Gln Leu Lys Val Glu Met
            1755              1760              1765 agt gag cag caa cat act ttc tat tgc cag gaa cta ggc aca ctg       5488
Ser Glu Gln Gln His Thr Phe Tyr Cys Gln Glu Leu Gly Thr Leu
            1770              1775              1780 cta atg tgt ctg atc cac atc ttc aag tct gga atg ttc cgg aga       5533
Leu Met Cys Leu Ile His Ile Phe Lys Ser Gly Met Phe Arg Arg
            1785              1790              1795 atc aca gca gct gcc act agg ctg ttc cgc agt gat ggc tgt ggc       5578
Ile Thr Ala Ala Ala Thr Arg Leu Phe Arg Ser Asp Gly Cys Gly
            1800              1805              1810 ggc agt ttc tac acc ctg gac agc ttg aac ttg cgg gct cgt tcc       5623
Gly Ser Phe Tyr Thr Leu Asp Ser Leu Asn Leu Arg Ala Arg Ser
            1815              1820              1825 atg atc acc acc cac ccg gcc ctg gtg ctg ctc tgg tgt cag ata       5668
Met Ile Thr Thr His Pro Ala Leu Val Leu Leu Trp Cys Gln Ile
            1830              1835              1840 ctg ctg ctt gtc aac cac acc gac tac cgc tgg tgg gca gaa gtg       5713
Leu Leu Leu Val Asn His Thr Asp Tyr Arg Trp Trp Ala Glu Val
            1845              1850              1855 cag cag acc ccg aaa aga cac agt ctg tcc agc aca aag tta ctt       5758
Gln Gln Thr Pro Lys Arg His Ser Leu Ser Ser Thr Lys Leu Leu
            1860              1865              1870 agt ccc cag atg tct gga gaa gag gag gat tct gac ttg gca gcc       5803
Ser Pro Gln Met Ser Gly Glu Glu Glu Asp Ser Asp Leu Ala Ala
            1875              1880              1885 aaa ctt gga atg tgc aat aga gaa ata gta cga aga ggg gct ctc       5848
Lys Leu Gly Met Cys Asn Arg Glu Ile Val Arg Arg Gly Ala Leu
            1890              1895              1900 att ctc ttc tgt gat tat gtc tgt cag aac ctc cat gac tcc gag       5893
Ile Leu Phe Cys Asp Tyr Val Cys Gln Asn Leu His Asp Ser Glu
            1905              1910              1915 cac tta acg tgg ctc att gta aat cac att caa gat ctg atc agc       5938
His Leu Thr Trp Leu Ile Val Asn His Ile Gln Asp Leu Ile Ser
            1920              1925              1930 ctt tcc cac gag cct cca gta cag gac ttc atc agt gcc gtt cat       5983
Leu Ser His Glu Pro Pro Val Gln Asp Phe Ile Ser Ala Val His
            1935              1940              1945 cgg aac tct gct gcc agc ggc ctg ttc atc cag gca att cag tct       6028
Arg Asn Ser Ala Ala Ser Gly Leu Phe Ile Gln Ala Ile Gln Ser
            1950              1955              1960 cgt tgt gaa aac ctt tca act cca acc atg ctg aag aaa act ctt       6073
```

```
                Arg Cys Glu Asn Leu Ser Thr Pro Thr Met Leu Lys Lys Thr Leu
                        1965                1970                1975 cag tgc ttg gag ggg atc cat ctc agc cag tcg gga gct gtg ctc           6118
Gln Cys Leu Glu Gly Ile His Leu Ser Gln Ser Gly Ala Val Leu
            1980                1985                1990 acg ctg tat gtg gac agg ctt ctg tgc acc cct ttc cgt gtg ctg           6163
Thr Leu Tyr Val Asp Arg Leu Leu Cys Thr Pro Phe Arg Val Leu
            1995                2000                2005 gct cgc atg gtc gac atc ctt gct tgt cgc cgg gta gaa atg ctt           6208
Ala Arg Met Val Asp Ile Leu Ala Cys Arg Arg Val Glu Met Leu
            2010                2015                2020 ctg gct gca aat tta cag agc agc atg gcc cag ttg cca atg gaa           6253
Leu Ala Ala Asn Leu Gln Ser Ser Met Ala Gln Leu Pro Met Glu
            2025                2030                2035 gaa ctc aac aga atc cag gaa tac ctt cag agc agc ggg ctc gct           6298
Glu Leu Asn Arg Ile Gln Glu Tyr Leu Gln Ser Ser Gly Leu Ala
            2040                2045                2050 cag aga cac caa agg ctc tat tcc ctg ctg gac agg ttt cgt ctc           6343
Gln Arg His Gln Arg Leu Tyr Ser Leu Leu Asp Arg Phe Arg Leu
            2055                2060                2065 tcc acc atg caa gac tca ctt agt ccc tct cct cca gtc tct tcc           6388
Ser Thr Met Gln Asp Ser Leu Ser Pro Ser Pro Pro Val Ser Ser
            2070                2075                2080 cac ccg ctg gac ggg gat ggg cac gtg tca ctg gaa aca gtg agt           6433
His Pro Leu Asp Gly Asp Gly His Val Ser Leu Glu Thr Val Ser
            2085                2090                2095 ccg gac aaa gac tgg tac gtt cat ctt gtc aaa tcc cag tgt tgg           6478
Pro Asp Lys Asp Trp Tyr Val His Leu Val Lys Ser Gln Cys Trp
            2100                2105                2110 acc agg tca gat tct gca ctg ctg gaa ggt gca gag ctg gtg aat           6523
Thr Arg Ser Asp Ser Ala Leu Leu Glu Gly Ala Glu Leu Val Asn
            2115                2120                2125 cgg att cct gct gaa gat atg aat gcc ttc atg atg aac tcg gag           6568
Arg Ile Pro Ala Glu Asp Met Asn Ala Phe Met Met Asn Ser Glu
            2130                2135                2140 ttc aac cta agc ctg cta gct cca tgc tta agc cta ggg atg agt           6613
Phe Asn Leu Ser Leu Leu Ala Pro Cys Leu Ser Leu Gly Met Ser
            2145                2150                2155 gaa att tct ggt ggc cag aag agt gcc ctt ttt gaa gca gcc cgt           6658
Glu Ile Ser Gly Gly Gln Lys Ser Ala Leu Phe Glu Ala Ala Arg
            2160                2165                2170 gag gtg act ctg gcc cgt gtg agc ggc acc gtg cag cag ctc cct           6703
Glu Val Thr Leu Ala Arg Val Ser Gly Thr Val Gln Gln Leu Pro
            2175                2180                2185 gct gtc cat cat gtc ttc cag ccc gag ctg cct gca gag ccg gcg           6748
Ala Val His His Val Phe Gln Pro Glu Leu Pro Ala Glu Pro Ala
            2190                2195                2200 gcc tac tgg agc aag ttg aat gat ctg ttt ggg gat gct gca ctg           6793
Ala Tyr Trp Ser Lys Leu Asn Asp Leu Phe Gly Asp Ala Ala Leu
            2205                2210                2215 tat cag tcc ctg ccc act ctg gcc cgg gcc ctg gca cag tac ctg           6838
Tyr Gln Ser Leu Pro Thr Leu Ala Arg Ala Leu Ala Gln Tyr Leu
            2220                2225                2230 gtg gtg gtc tcc aaa ctg ccc agt cat ttg cac ctt cct cct gag           6883
Val Val Val Ser Lys Leu Pro Ser His Leu His Leu Pro Pro Glu
            2235                2240                2245 aaa gag aag gac att gtg aaa ttc gtg gtg gca acc ctt gag gcc           6928
Lys Glu Lys Asp Ile Val Lys Phe Val Val Ala Thr Leu Glu Ala
            2250                2255                2260
```

| | | |
|---|---|---|
| ctg tcc tgg cat ttg atc cat gag cag atc ccg ctg agt ctg gat<br>Leu Ser Trp His Leu Ile His Glu Gln Ile Pro Leu Ser Leu Asp<br>2265            2270            2275 | 6973 |
| ctc cag gca ggg ctg gac tgc tgc tgc ctg gcc ctg cag ctg cct<br>Leu Gln Ala Gly Leu Asp Cys Cys Cys Leu Ala Leu Gln Leu Pro<br>2280            2285            2290 | 7018 |
| ggc ctc tgg agc gtg gtc tcc tcc aca gag ttt gtg acc cac gcc<br>Gly Leu Trp Ser Val Val Ser Ser Thr Glu Phe Val Thr His Ala<br>2295            2300            2305 | 7063 |
| tgc tcc ctc atc tac tgt gtg cac ttc atc ctg gag gcc gtt gca<br>Cys Ser Leu Ile Tyr Cys Val His Phe Ile Leu Glu Ala Val Ala<br>2310            2315            2320 | 7108 |
| gtg cag cct gga gag cag ctt ctt agt cca gaa aga agg aca aat<br>Val Gln Pro Gly Glu Gln Leu Leu Ser Pro Glu Arg Arg Thr Asn<br>2325            2330            2335 | 7153 |
| acc cca aaa gcc atc agc gag gag gag gag gaa gta gat cca aac<br>Thr Pro Lys Ala Ile Ser Glu Glu Glu Glu Val Asp Pro Asn<br>2340            2345            2350 | 7198 |
| aca cag aat cct aag tat atc act gca gcc tgt gag atg gtg gca<br>Thr Gln Asn Pro Lys Tyr Ile Thr Ala Ala Cys Glu Met Val Ala<br>2355            2360            2365 | 7243 |
| gaa atg gtg gag tct ctg cag tcg gtg ttg gcc ttg ggt cat aaa<br>Glu Met Val Glu Ser Leu Gln Ser Val Leu Ala Leu Gly His Lys<br>2370            2375            2380 | 7288 |
| agg aat agc ggc gtg ccg gcg ttt ctc acg cca ttg cta agg aac<br>Arg Asn Ser Gly Val Pro Ala Phe Leu Thr Pro Leu Leu Arg Asn<br>2385            2390            2395 | 7333 |
| atc atc atc agc ctg gcc cgc ctg ccc ctt gtc aac agc tac aca<br>Ile Ile Ile Ser Leu Ala Arg Leu Pro Leu Val Asn Ser Tyr Thr<br>2400            2405            2410 | 7378 |
| cgt gtg ccc cca ctg gtg tgg aag ctt gga tgg tca ccc aaa ccg<br>Arg Val Pro Pro Leu Val Trp Lys Leu Gly Trp Ser Pro Lys Pro<br>2415            2420            2425 | 7423 |
| gga ggg gat ttt ggc aca gca ttc cct gag atc ccc gtg gag ttc<br>Gly Gly Asp Phe Gly Thr Ala Phe Pro Glu Ile Pro Val Glu Phe<br>2430            2435            2440 | 7468 |
| ctc cag gaa aag gaa gtc ttt aag gag ttc atc tac cgc atc aac<br>Leu Gln Glu Lys Glu Val Phe Lys Glu Phe Ile Tyr Arg Ile Asn<br>2445            2450            2455 | 7513 |
| aca cta ggc tgg acc agt cgt act cag ttt gaa gaa act tgg gcc<br>Thr Leu Gly Trp Thr Ser Arg Thr Gln Phe Glu Glu Thr Trp Ala<br>2460            2465            2470 | 7558 |
| acc ctc ctt ggt gtc ctg gtg acg cag ccc ctc gtg atg gag cag<br>Thr Leu Leu Gly Val Leu Val Thr Gln Pro Leu Val Met Glu Gln<br>2475            2480            2485 | 7603 |
| gag gag agc cca cca gaa gaa gac aca gag agg acc cag atc aac<br>Glu Glu Ser Pro Pro Glu Glu Asp Thr Glu Arg Thr Gln Ile Asn<br>2490            2495            2500 | 7648 |
| gtc ctg gcc gtg cag gcc atc acc tca ctg gtg ctc agt gca atg<br>Val Leu Ala Val Gln Ala Ile Thr Ser Leu Val Leu Ser Ala Met<br>2505            2510            2515 | 7693 |
| act gtg cct gtg gcc ggc aac cca gct gta agc tgc ttg gag cag<br>Thr Val Pro Val Ala Gly Asn Pro Ala Val Ser Cys Leu Glu Gln<br>2520            2525            2530 | 7738 |
| cag ccc cgg aac aag cct ctg aaa gct ctc gac acc agg ttt ggg<br>Gln Pro Arg Asn Lys Pro Leu Lys Ala Leu Asp Thr Arg Phe Gly<br>2535            2540            2545 | 7783 |
| agg aag ctg agc att atc aga ggg att gtg gag caa gag att caa<br>Arg Lys Leu Ser Ile Ile Arg Gly Ile Val Glu Gln Glu Ile Gln<br>2550            2555            2560 | 7828 |

-continued

```
gca atg gtt tca aag aga gag aat att gcc acc cat cat tta tat       7873
Ala Met Val Ser Lys Arg Glu Asn Ile Ala Thr His His Leu Tyr
            2565                2570                2575 cag gca tgg gat cct gtc cct tct ctg tct ccg gct act aca ggt       7918
Gln Ala Trp Asp Pro Val Pro Ser Leu Ser Pro Ala Thr Thr Gly
            2580                2585                2590 gcc ctc atc agc cac gag aag ctg ctg cta cag atc aac ccc gag       7963
Ala Leu Ile Ser His Glu Lys Leu Leu Leu Gln Ile Asn Pro Glu
    2595                2600                2605 cgg gag ctg ggg agc atg agc tac aaa ctc ggc cag gtg tcc ata       8008
Arg Glu Leu Gly Ser Met Ser Tyr Lys Leu Gly Gln Val Ser Ile
        2610                2615                2620 cac tcc gtg tgg ctg ggg aac agc atc aca ccc ctg agg gag gag       8053
His Ser Val Trp Leu Gly Asn Ser Ile Thr Pro Leu Arg Glu Glu
            2625                2630                2635 gaa tgg gac gag gaa gag gag gag gag gcc gac gcc cct gca cct       8098
Glu Trp Asp Glu Glu Glu Glu Glu Glu Ala Asp Ala Pro Ala Pro
            2640                2645                2650 tcg tca cca ccc acg tct cca gtc aac tcc agg aaa cac cgg gct       8143
Ser Ser Pro Pro Thr Ser Pro Val Asn Ser Arg Lys His Arg Ala
            2655                2660                2665 gga gtt gac atc cac tcc tgt tcg cag ttt ttg ctt gag ttg tac       8188
Gly Val Asp Ile His Ser Cys Ser Gln Phe Leu Leu Glu Leu Tyr
            2670                2675                2680 agc cgc tgg atc ctg ccg tcc agc tca gcc agg agg acc ccg gcc       8233
Ser Arg Trp Ile Leu Pro Ser Ser Ser Ala Arg Arg Thr Pro Ala
            2685                2690                2695 atc ctg atc agt gag gtg gtc aga tcc ctt cta gtg gtc tca gac       8278
Ile Leu Ile Ser Glu Val Val Arg Ser Leu Leu Val Val Ser Asp
            2700                2705                2710 ttg ttc acc gag cgc aac cag ttt gag ctg atg tat gtg acg ctg       8323
Leu Phe Thr Glu Arg Asn Gln Phe Glu Leu Met Tyr Val Thr Leu
            2715                2720                2725 aca gaa ctg cga agg gtg cac cct tca gaa gac gag atc ctc gct       8368
Thr Glu Leu Arg Arg Val His Pro Ser Glu Asp Glu Ile Leu Ala
            2730                2735                2740 cag tac ctg gtg cct gcc acc tgc aag gca gct gcc gtc ctt ggg       8413
Gln Tyr Leu Val Pro Ala Thr Cys Lys Ala Ala Ala Val Leu Gly
            2745                2750                2755 atg gac aag gcc gtg gcg gag cct gtc agc cgc ctg ctg gag agc       8458
Met Asp Lys Ala Val Ala Glu Pro Val Ser Arg Leu Leu Glu Ser
            2760                2765                2770 acg ctc agg agc agc cac ctg ccc agc agg gtt gga gcc ctg cac       8503
Thr Leu Arg Ser Ser His Leu Pro Ser Arg Val Gly Ala Leu His
            2775                2780                2785 ggc gtc ctc tat gtg ctg gag tgc gac ctg ctg gac gac act gcc       8548
Gly Val Leu Tyr Val Leu Glu Cys Asp Leu Leu Asp Asp Thr Ala
            2790                2795                2800 aag cag ctc atc ccg gtc atc agc gac tat ctc ctc tcc aac ctg       8593
Lys Gln Leu Ile Pro Val Ile Ser Asp Tyr Leu Leu Ser Asn Leu
            2805                2810                2815 aaa ggg atc gcc cac tgc gtg aac att cac agc cag cag cac gta       8638
Lys Gly Ile Ala His Cys Val Asn Ile His Ser Gln Gln His Val
            2820                2825                2830 ctg gtc atg tgt gcc act gcg ttt tac ctc att gag aac tat cct       8683
Leu Val Met Cys Ala Thr Ala Phe Tyr Leu Ile Glu Asn Tyr Pro
            2835                2840                2845 ctg gac gta ggg ccg gaa ttt tca gca tca ata ata cag atg tgt       8728
Leu Asp Val Gly Pro Glu Phe Ser Ala Ser Ile Ile Gln Met Cys
```

-continued

```
                 2850                2855                2860
     ggg gtg atg ctg tct gga agt gag gag tcc acc ccc tcc atc att        8773
     Gly Val Met Leu Ser Gly Ser Glu Glu Ser Thr Pro Ser Ile Ile
                 2865                2870                2875
     tac cac tgt gcc ctc aga ggc ctg gag cgc ctc ctg ctc tct gag        8818
     Tyr His Cys Ala Leu Arg Gly Leu Glu Arg Leu Leu Leu Ser Glu
                 2880                2885                2890
     cag ctc tcc cgc ctg gat gca gaa tcg ctg gtc aag ctg agt gtg        8863
     Gln Leu Ser Arg Leu Asp Ala Glu Ser Leu Val Lys Leu Ser Val
                 2895                2900                2905
     gac aga gtg aac gtg cac agc ccg cac cgg gcc atg gcg gct ctg        8908
     Asp Arg Val Asn Val His Ser Pro His Arg Ala Met Ala Ala Leu
                 2910                2915                2920
     ggc ctg atg ctc acc tgc atg tac aca gga aag gag aaa gtc agt        8953
     Gly Leu Met Leu Thr Cys Met Tyr Thr Gly Lys Glu Lys Val Ser
                 2925                2930                2935
     ccg ggt aga act tca gac cct aat cct gca gcc ccc gac agc gag        8998
     Pro Gly Arg Thr Ser Asp Pro Asn Pro Ala Ala Pro Asp Ser Glu
                 2940                2945                2950
     tca gtg att gtt gct atg gag cgg gta tct gtt ctt ttt gat agg        9043
     Ser Val Ile Val Ala Met Glu Arg Val Ser Val Leu Phe Asp Arg
                 2955                2960                2965
     atc agg aaa ggc ttt cct tgt gaa gcc aga gtg gtg gcc agg atc        9088
     Ile Arg Lys Gly Phe Pro Cys Glu Ala Arg Val Val Ala Arg Ile
                 2970                2975                2980
     ctg ccc cag ttt cta gac gac ttc ttc cca ccc cag gac atc atg        9133
     Leu Pro Gln Phe Leu Asp Asp Phe Phe Pro Pro Gln Asp Ile Met
                 2985                2990                2995
     aac aaa gtc atc gga gag ttt ctg tcc aac cag cag cca tac ccc        9178
     Asn Lys Val Ile Gly Glu Phe Leu Ser Asn Gln Gln Pro Tyr Pro
                 3000                3005                3010
     cag ttc atg gcc acc gtg gtg tat aag gtg ttt cag act ctg cac        9223
     Gln Phe Met Ala Thr Val Val Tyr Lys Val Phe Gln Thr Leu His
                 3015                3020                3025
     agc acc ggg cag tcg tcc atg gtc cgg gac tgg gtc atg ctg tcc        9268
     Ser Thr Gly Gln Ser Ser Met Val Arg Asp Trp Val Met Leu Ser
                 3030                3035                3040
     ctc tcc aac ttc acg cag agg gcc ccg gtc gcc atg gcc acg tgg        9313
     Leu Ser Asn Phe Thr Gln Arg Ala Pro Val Ala Met Ala Thr Trp
                 3045                3050                3055
     agc ctc tcc tgc ttc ttt gtc agc gcg tcc acc agc ccg tgg gtc        9358
     Ser Leu Ser Cys Phe Phe Val Ser Ala Ser Thr Ser Pro Trp Val
                 3060                3065                3070
     gcg gcg atc ctc cca cat gtc atc agc agg atg ggc aag ctg gag        9403
     Ala Ala Ile Leu Pro His Val Ile Ser Arg Met Gly Lys Leu Glu
                 3075                3080                3085
     cag gtg gac gtg aac ctt ttc tgc ctg gtc gcc aca gac ttc tac        9448
     Gln Val Asp Val Asn Leu Phe Cys Leu Val Ala Thr Asp Phe Tyr
                 3090                3095                3100
     aga cac cag ata gag gag gag ctc gac cgc agg gcc ttc cag tct        9493
     Arg His Gln Ile Glu Glu Glu Leu Asp Arg Arg Ala Phe Gln Ser
                 3105                3110                3115
     gtg ctt gag gtg gtt gca gcc cca gga agc cca tat cac cgg ctg        9538
     Val Leu Glu Val Val Ala Ala Pro Gly Ser Pro Tyr His Arg Leu
                 3120                3125                3130
     ctg act tgt tta cga aat gtc cac aag gtc acc acc tgc tga            9580
     Leu Thr Cys Leu Arg Asn Val His Lys Val Thr Thr Cys
                 3135                3140 gcgccatggt gggagagact gtgaggcggc agctggggcc ggagcctttg gaagtctgcg  9640
```

```
cccttgtgcc ctgcctccac cgagccagct tggtccctat gggcttccgc acatgccgcg    9700
ggcggccagg caacgtgcgt gtctctgcca tgtggcagaa gtgctctttg tggcagtggc    9760
caggcaggga gtgtctgcag tcctggtggg gctgagcctg aggccttcca gaaagcagga    9820
gcagctgtgc tgcacccat gtgggtgacc aggtcctttc tcctgatagt cacctgctgg     9880
ttgttgccag gttgcagctg ctcttgcatc tgggccagaa gtcctccctc ctgcaggctg    9940
gctgttggcc cctctgctgt cctgcagtag aaggtgccgt gagcaggctt tgggaacact   10000
ggcctgggtc tccctggtgg ggtgtgcatg ccacgccccg tgtctggatg cacagatgcc   10060
atggcctgtg ctgggccagt ggctgggggt gctagacacc cggcaccatt ctcccttctc   10120
tcttttcttc tcaggattta aaatttaatt atatcagtaa agagattaat tttaacgtaa   10180
ctctttctat gcccgtgtaa agtatgtgaa tcgcaaggcc tgtgctgcat gcgacagcgt   10240
ccggggtggt ggacagggcc cccggccacg ctccctctcc tgtagccact ggcatagccc   10300
tcctgagcac ccgctgacat ttccgttgta catgttcctg tttatgcatt cacaaggtga   10360
ctgggatgta gagaggcgtt agtgggcagg tggccacagc aggactgagg acaggccccc   10420
attatcctag gggtgcgctc acctgcagcc cctcctcctc gggcacagac gactgtcgtt   10480
ctccacccac cagtcaggga cagcagcctc cctgtcactc agctgagaag gccagccctc   10540
cctggctgtg agcagcctcc actgtgtcca gagacatggg cctcccactc ctgttccttg   10600
ctagccctgg ggtggcgtct gcctaggagc tggctggcag gtgttgggac ctgctgctcc   10660
atggatgcat gccctaagag tgtcactgag ctgtgttttg tctgagcctc tctcggtcaa   10720
cagcaaagct tggtgtcttg gcactgttag tgacagagcc cagcatccct tctgcccccg   10780
ttccagctga catcttgcac ggtgacccct tttagtcagg agagtgcaga tctgtgctca   10840
tcggagactg ccccacggcc ctgtcagagc cgccactcct atccccaggc caggtccctg   10900
gaccagcctc ctgtttgcag gcccagagga gccaagtcat taaaatgaa gtggattctg    10960 gatggccggg ctgctgctga tgtaggagct ggatttggga gctctgcttg ccgactggct   11020
gtgagacgag gcaggggctc tgcttcctca gccctagagg cgagccaggc aaggttggcg   11080
actgtcatgt ggcttggttt ggtcatgccc gtcgatgttt gggtattga atgtggtaag    11140 tggaggaaat gttggaactc tgtgcaggtg ctgccttgag accccaagc ttccacctgt     11200 ccctctccta tgtggcagct ggggagcagc tgagatgtgg acttgtatgc tgcccacata   11260
cgtgaggggg agctgaaagg gagcccctcc tctgagcagc ctctgccagg cctgtatgag   11320
gcttttccca ccagctccca acagaggcct ccccagcca ggaccactc gtcctcgtgg     11380 cggggcagca ggagcggtag aaaggggtcc gatgtttgag gaggccctta agggaagcta   11440
ctgaattata acacgtaaga aaatcaccat tccgtattgg ttgggggctc ctgtttctca   11500
tcctagcttt ttcctggaaa gcccgctaga aggtttggga acgaggggaa agttctcaga   11560
actgttggct gctccccacc cgcctcccgc ctccccgca ggttatgtca gcagctctga    11620
gacagcagta tcacaggcca gatgttgttc ctggctagat gtttacattt gtaagaaata   11680
acactgtgaa tgtaaaacag agccattccc ttggaatgca tatcgctggg ctcaacatag   11740
agtttgtctt cctcttgttt acgacgtgat ctaaaccagt ccttagcaag gggctcagaa   11800
caccccgctc tggcagtagg tgtcccccac ccccaaagac ctgcctgtgt gctccggaga   11860
tgaatatgag ctcattagta aaatgacctt cacccacgca tatacataaa gtatccatgc   11920
atgtgcatat agacacatct ataattttac acacacacct ctcaagacgg agatgcatgg   11980
```

```
cctctaagag tgcccgtgtc ggttcttcct ggaagttgac tttccttaga cccgccaggt   12040
caagttagcc gcgtgacgga catccaggcg tgggacgtgg tcagggcagg gctcattcat   12100
tgcccactag gatcccactg gcgaagatgg tctccatatc agctctctgc agaagggagg   12160
aagactttat catgttccta aaatctgtg gcaagcaccc atcgtattat ccaaattttg     12220
ttgcaaatgt gattaatttg gttgtcaagt tttggggtg ggctgtgggg agattgcttt    12280
tgttttcctg ctggtaatat cgggaaagat tttaatgaaa ccagggtaga attgtttggc   12340
aatgcactga agcgtgtttc tttcccaaaa tgtgcctccc ttccgctgcg ggcccagctg   12400
agtctatgta ggtgatgttt ccagctgcca agtgctcttt gttactgtcc accctcattt   12460
ctgccagcgc atgtgtcctt tcaaggggaa aatgtgaagc tgaaccccct ccagacaccc   12520
agaatgtagc atctgagaag gccctgtgcc ctaaaggaca cccctcgccc ccatcttcat   12580
ggaggggtc atttcagagc cctcggagcc aatgaacagc tcctcctctt ggagctgaga   12640
tgagccccac gtggagctcg ggacggatag tagacagcaa taactcgtg tgtggccgcc    12700
tggcaggtgg aacttcctcc cgttgcgggg tggagtgagg ttagttctgt gtgtctggtg   12760
ggtggagtca ggcttctctt gctacctgtg agcatccttc ccagcagaca tcctcatcgg   12820
gctttgtccc tccccgctt cctccctctg cggggaggac ccgggaccac agctgctggc    12880
cagggtagac ttggagctgt cctccagagg ggtcacgtgt aggagtgaga agaaggaaga   12940
tcttgagagc tgctgaggga ccttggagag ctcaggatgg ctcagacgag gacactcgct   13000
tgccgggcct gggcctcctg ggaaggaggg agctgctcag aatgccgcat gacaactgaa   13060
ggcaacctgg aaggttcagg ggccgctctt cccccatgtg cctgtcacgc tctggtgcag   13120
tcaaaggaac gccttcccct cagttgtttc taagagcaga gtctcccgct gcaatctggg   13180
tggtaactgc cagccttgga ggatcgtggc caacgtggac ctgcctacgg agggtgggct   13240
ctgacccaag tggggcctcc ttgtccaggt ctcactgctt tgcaccgtgg tcagagggac   13300
tgtcagctga gcttgagctc ccctggagcc agcagggctg tgatgggcga gtcccggagc   13360
cccacccaga cctgaatgct tctgagagca agggaagga ctgacgagag atgtatattt    13420
aattttttaa ctgctgcaaa cattgtacat ccaaattaaa ggaaaaaaat ggaaaccatc   13480
a                                                                   13481
```

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

```
<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 10
taaattgtca tcacc                                                    15

<210> SEQ ID NO 11
<211> LENGTH: 15
<212> TYPE: DNA
<213> ORGANISM: Artificial Sequence
<220> FEATURE:
<223> OTHER INFORMATION: Synthetic olignucleotide
<220> FEATURE:
<221> NAME/KEY: misc_feature
<222> LOCATION: (8)..(8)
<223> OTHER INFORMATION: bases at these positions are RNA

<400> SEQUENCE: 11
taaattguca tcacc                                                    15

<210> SEQ ID NO 12
<211> LENGTH: 15
<212> TYPE: DNA
<213> ORGANISM: Artificial Sequence
<220> FEATURE:
<223> OTHER INFORMATION: Synthetic olignucleotide
<220> FEATURE:
<221> NAME/KEY: misc_feature
<222> LOCATION: (8)..(8)
<223> OTHER INFORMATION: n = A,T,C or G

<400> SEQUENCE: 12
taaattgnca tcacc                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic olignucleotide
<220> FEATURE:
<221> NAME/KEY: misc_feature
<222> LOCATION: (5)..(5)
<223> OTHER INFORMATION: bases at these positions are RNA

<400> SEQUENCE: 13
```
taaautgtca tcacc                           15

<210> SEQ ID NO 14
<211> LENGTH: 16
<212> TYPE: DNA
<213> ORGANISM: Artificial Sequence
<220> FEATURE:
<223> OTHER INFORMATION: Synthetic olignucleotide

<400> SEQUENCE: 14
taaattgtca tcacca                          16

<210> SEQ ID NO 15
<211> LENGTH: 18
<212> TYPE: DNA
<213> ORGANISM: Artificial Sequence
<220> FEATURE:
<223> OTHER INFORMATION: Synthetic olignucleotide

<400> SEQUENCE: 15
taaattgtca tcaccta                         18

<210> SEQ ID NO 16
<211> LENGTH: 20
<212> TYPE: DNA
<213> ORGANISM: Artificial Sequence
<220> FEATURE:
<223> OTHER INFORMATION: Synthetic olignucleotide

<400> SEQUENCE: 16
taaattgtca tcaccattta                      20

<210> SEQ ID NO 17
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 17
taaattgtca tcaccta                         17

<210> SEQ ID NO 18
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 18
taaattgtca tcaccttta                       19

<210> SEQ ID NO 19
<211> LENGTH: 16
<212> TYPE: DNA
<213> ORGANISM: Artificial Sequence
<220> FEATURE:
<223> OTHER INFORMATION: Synthetic olignucleotide

<400> SEQUENCE: 19
gtaaattgtc atcacc                          16

<210> SEQ ID NO 20
<211> LENGTH: 17
<212> TYPE: DNA

```
<213> ORGANISM: Artificial Sequence
<220> FEATURE:
<223> OTHER INFORMATION: Synthetic olignucleotide

<400> SEQUENCE: 20
ggtaaattgt catcacc                                                      17

<210> SEQ ID NO 21
<211> LENGTH: 18
<212> TYPE: DNA
<213> ORGANISM: Artificial Sequence
<220> FEATURE:
<223> OTHER INFORMATION: Synthetic olignucleotide

<400> SEQUENCE: 21
ggttaaattg tcatcacc                                                     18

<210> SEQ ID NO 22
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 22
ggtgtaaatt gtcatcacc                                                    19

<210> SEQ ID NO 23
<211> LENGTH: 20
<212> TYPE: DNA
<213> ORGANISM: Artificial Sequence
<220> FEATURE:
<223> OTHER INFORMATION: Synthetic olignucleotide

<400> SEQUENCE: 23
ggtgataaat tgtcatcacc                                                   20

<210> SEQ ID NO 24
<211> LENGTH: 21
<212> TYPE: DNA
<213> ORGANISM: Artificial Sequence
<220> FEATURE:
<223> OTHER INFORMATION: Synthetic olignucleotide

<400> SEQUENCE: 24
ggctaaattg tcatcaccgc c                                                 21

<210> SEQ ID NO 25
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 25
gctaaattgt catcaccgc                                                    19

<210> SEQ ID NO 26
<211> LENGTH: 21
<212> TYPE: DNA
<213> ORGANISM: Artificial Sequence
<220> FEATURE:
<223> OTHER INFORMATION: Synthetic olignucleotide

<400> SEQUENCE: 26
taataaattg tcatcacctt a                                                 21
```

```
<210> SEQ ID NO 27
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 27
aataaattgt catcacctt                                                  19

<210> SEQ ID NO 28
<211> LENGTH: 21
<212> TYPE: DNA
<213> ORGANISM: Artificial Sequence
<220> FEATURE:
<223> OTHER INFORMATION: Synthetic olignucleotide

<400> SEQUENCE: 28
tcttaaattg tcatcaccag a                                               21

<210> SEQ ID NO 29
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 29
cttaaattgt catcaccag                                                  19

<210> SEQ ID NO 30
<211> LENGTH: 18
<212> TYPE: DNA
<213> ORGANISM: Artificial Sequence
<220> FEATURE:
<223> OTHER INFORMATION: Synthetic olignucleotide

<400> SEQUENCE: 30
taataaattg tcatcacc                                                   18

<210> SEQ ID NO 31
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 31
aataaattgt catcacc                                                    17

<210> SEQ ID NO 32
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 32
ataaattgtc atcacca                                                    17

<210> SEQ ID NO 33
<211> LENGTH: 17
<212> TYPE: DNA
<213> ORGANISM: Artificial Sequence
<220> FEATURE:
```

<223> OTHER INFORMATION: Synthetic olignucleotide

<400> SEQUENCE: 33
ataaattctc atcacca                                                            17

<210> SEQ ID NO 34
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 34
ataaatagtc atcacca                                                            17

<210> SEQ ID NO 35
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 35
ataaattgtg atcacca                                                            17

<210> SEQ ID NO 36
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 36
ataaattgtc ttcacca                                                            17

<210> SEQ ID NO 37
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 37
ataaattgtc aacacca                                                            17

<210> SEQ ID NO 38
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 38
taaattctca tcacc                                                              15

<210> SEQ ID NO 39
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 39
taaaatgtca tcacc                                                              15

```
<210> SEQ ID NO 40
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 40
taaattgtga tcacc                                                        15

<210> SEQ ID NO 41
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 41
taaattgtct tcacc                                                        15

<210> SEQ ID NO 42
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 42
taaattgtca acacc                                                        15

<210> SEQ ID NO 43
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 43
ttaaattgtc atcacca                                                      17

<210> SEQ ID NO 44
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 44
aaaaattgtc atcacca                                                      17

<210> SEQ ID NO 45
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 45
attaattgtc atcacca                                                      17

<210> SEQ ID NO 46
<211> LENGTH: 17
<212> TYPE: DNA
<213> ORGANISM: Artificial Sequence
<220> FEATURE:
<223> OTHER INFORMATION: Synthetic olignucleotide
```

-continued

<400> SEQUENCE: 46
atatattgtc atcacca                                                  17

<210> SEQ ID NO 47
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 47
ataatttgtc atcacca                                                  17

<210> SEQ ID NO 48
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 48
ataaattgtc atgacca                                                  17

<210> SEQ ID NO 49
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 49
ataaattgtc atctcca                                                  17

<210> SEQ ID NO 50
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 50
ataaattgtc atcagca                                                  17

<210> SEQ ID NO 51
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 51
ataaattgtc atcacga                                                  17

<210> SEQ ID NO 52
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 52
ataaattgtc atcacct                                                  17

<210> SEQ ID NO 53
<211> LENGTH: 15

```
<212> TYPE: DNA
<213> ORGANISM: Artificial Sequence
<220> FEATURE:
<223> OTHER INFORMATION: Synthetic olignucleotide

<400> SEQUENCE: 53
taagttgtca tcacc                                                      15

<210> SEQ ID NO 54
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 54
taaagtgtca tcacc                                                      15

<210> SEQ ID NO 55
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 55
taaatggtca tcacc                                                      15

<210> SEQ ID NO 56
<211> LENGTH: 20
<212> TYPE: DNA
<213> ORGANISM: Artificial Sequence
<220> FEATURE:
<223> OTHER INFORMATION: Synthetic olignucleotide

<400> SEQUENCE: 56
tctctattgc acattccaag                                                 20

<210> SEQ ID NO 57
<211> LENGTH: 20
<212> TYPE: DNA
<213> ORGANISM: Artificial Sequence
<220> FEATURE:
<223> OTHER INFORMATION: Synthetic olignucleotide

<400> SEQUENCE: 57
ccttccctga aggttcctcc                                                 20

<210> SEQ ID NO 58
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 58
aattgtcatc accagaa                                                    17

<210> SEQ ID NO 59
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 59
```
aattgtcatc accagaa                                                    17

<210> SEQ ID NO 60
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 60
aaattgtcat caccaga                                                    17

<210> SEQ ID NO 61
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 61
taaattgtca tcaccag                                                    17

<210> SEQ ID NO 62
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 62
aataaattgt catcacc                                                    17

<210> SEQ ID NO 63
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 63
taataaattg tcatcac                                                    17

<210> SEQ ID NO 64
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 64
ttaataaatt gtcatca                                                    17

<210> SEQ ID NO 65
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 65
attgtcatca ccaga                                                      15

<210> SEQ ID NO 66
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 66
ttaataaatt gtcat                                                        15

<210> SEQ ID NO 67
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 67
ttgtcatcac cagaa                                                        15

<210> SEQ ID NO 68
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 68
aattgtcatc accag                                                        15

<210> SEQ ID NO 69
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 69
aaattgtcat cacca                                                        15

<210> SEQ ID NO 70
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 70
aataaattgt catca                                                        15

<210> SEQ ID NO 71
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 71
attaataaat tgtca                                                        15

<210> SEQ ID NO 72
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 72
tattaataaa ttgtc                                                        15

```
<210> SEQ ID NO 73
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 73
gtcatcacca gaaaa                                                          15

<210> SEQ ID NO 74
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 74
tgtcatcacc agaaa                                                          15

<210> SEQ ID NO 75
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 75
ataaattgtc atcac                                                          15

<210> SEQ ID NO 76
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 76
taataaattg tcatc                                                          15

<210> SEQ ID NO 77
<211> LENGTH: 17
<212> TYPE: DNA
<213> ORGANISM: Artificial Sequence
<220> FEATURE:
<223> OTHER INFORMATION: Synthetic olignucleotide

<400> SEQUENCE: 77
ataaaatgtc atcacca                                                        17

<210> SEQ ID NO 78
<211> LENGTH: 15
<212> TYPE: DNA
<213> ORGANISM: Artificial Sequence
<220> FEATURE:
<223> OTHER INFORMATION: Synthetic olignucleotide

<400> SEQUENCE: 78
taaatagtca tcacc                                                          15

<210> SEQ ID NO 79
<211> LENGTH: 20
<212> TYPE: DNA
<213> ORGANISM: Artificial Sequence
<220> FEATURE:
<223> OTHER INFORMATION: Synthetic olignucleotide
```

```
<400> SEQUENCE: 79
ctcgactaaa gcaggatttc                                              20

<210> SEQ ID NO 80
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 80
aataaattgt catcaccag                                               19

<210> SEQ ID NO 81
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 81
cacagtgcta cccaacctt                                               19

<210> SEQ ID NO 82
<211> LENGTH: 19
<212> TYPE: DNA
<213> ORGANISM: Artificial Sequence
<220> FEATURE:
<223> OTHER INFORMATION: Synthetic olignucleotide

<400> SEQUENCE: 82
tcacagctat cttctcatc                                               19
```